United States Patent
Kim

(10) Patent No.: US 10,007,764 B2
(45) Date of Patent: Jun. 26, 2018

(54) MEDICINE DISPENSING SYSTEM AND CONTROL METHOD THEREOF

(71) Applicant: JVM CO., LTD., Daegu (KR)

(72) Inventor: Jun Ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 117 days.

(21) Appl. No.: 14/395,413

(22) PCT Filed: Apr. 17, 2013

(86) PCT No.: PCT/KR2013/003256
§ 371 (c)(1),
(2) Date: Oct. 17, 2014

(87) PCT Pub. No.: WO2013/157851
PCT Pub. Date: Oct. 24, 2013

(65) Prior Publication Data
US 2015/0127145 A1    May 7, 2015

(30) Foreign Application Priority Data

| Apr. 18, 2012 | (KR) | 10-2012-0040537 |
| Apr. 18, 2012 | (KR) | 10-2012-0040539 |
| Apr. 18, 2012 | (KR) | 10-2012-0040540 |
| Feb. 13, 2013 | (KR) | 10-2013-0015366 |

(51) Int. Cl.
G07F 17/00 (2006.01)
G06F 19/00 (2018.01)
A61J 7/00 (2006.01)

(52) U.S. Cl.
CPC ........ G06F 19/3462 (2013.01); A61J 7/0084 (2013.01); G07F 17/0092 (2013.01); A61J 2205/10 (2013.01); A61J 2205/60 (2013.01)

(58) Field of Classification Search
CPC ......................... G07F 17/0092; G07F 11/165
USPC ................................................ 700/236, 237
See application file for complete search history.

(56) References Cited

U.S. PATENT DOCUMENTS

| 5,713,487 A * | 2/1998 | Coughlin | G07F 17/0092 221/2 |
| 6,330,491 B1 | 12/2001 | Lion | |
| 6,636,780 B1 | 10/2003 | Haitin et al. | |
| 7,040,077 B2 * | 5/2006 | Yasuoka | B65B 5/103 53/493 |

(Continued)

FOREIGN PATENT DOCUMENTS

| CN | 201584017 U | 9/2010 |
| CN | 102069920 A | 5/2011 |

(Continued)

*Primary Examiner* — Timothy R Waggoner
(74) *Attorney, Agent, or Firm* — Birch, Stewart, Kolasch & Birch, LLP

(57) ABSTRACT

Disclosed in the present invention is a medicine dispensing device comprising: a medicine storage portion for storing a medicine; a medicine discharge portion for discharging the medicine stored at the medicine storage portion; a communication module for communicating with a hospital server; and a control portion for controlling the operation of the medicine storage portion and the medicine discharge portion so as to allow the medicine to be discharged on the basis of prescription information of a prescription received from the hospital server through the communication module.

18 Claims, 191 Drawing Sheets

(56) References Cited

U.S. PATENT DOCUMENTS

| | | | | |
|---|---|---|---|---|
| 7,263,411 | B2* | 8/2007 | Shows | G06F 19/3462 |
| | | | | 221/2 |
| 7,809,470 | B2* | 10/2010 | Shoenfeld | G08B 13/14 |
| | | | | 221/123 |
| 8,165,929 | B2* | 4/2012 | Chudy | G06F 19/3462 |
| | | | | 700/213 |
| 8,434,641 | B2* | 5/2013 | Coughlin | G07F 11/16 |
| | | | | 221/174 |
| 8,620,472 | B2* | 12/2013 | Mockus | G07F 11/165 |
| | | | | 221/127 |
| 9,117,016 | B2* | 8/2015 | Carson | G06Q 30/018 |
| 9,122,783 | B2* | 9/2015 | Carson | G06Q 30/018 |
| 9,251,641 | B2* | 2/2016 | Kim | G07F 17/0092 |
| 2004/0182044 | A1 | 9/2004 | Kim | |
| 2010/0300041 | A1* | 12/2010 | Kim | G07F 11/165 |
| | | | | 53/281 |
| 2011/0168733 | A1 | 7/2011 | Yuyama et al. | |
| 2011/0251850 | A1 | 10/2011 | Stephens | |
| 2012/0239186 | A1* | 9/2012 | Kim | G07F 17/0092 |
| | | | | 700/232 |

FOREIGN PATENT DOCUMENTS

| | | |
|---|---|---|
| CN | 102159172 A | 8/2011 |
| EP | 1 122 194 A1 | 8/2001 |
| EP | 1 598 748 A2 | 11/2005 |
| EP | 1 684 203 A2 | 7/2006 |
| JP | 2001-301930 A | 10/2001 |
| JP | 2007-7443 A | 1/2007 |
| KR | 10-2004-0082567 A | 9/2004 |
| KR | 10-2011-0112085 A | 10/2011 |
| KR | 10-2012-0026285 A | 3/2012 |

\* cited by examiner

【FIG.1】
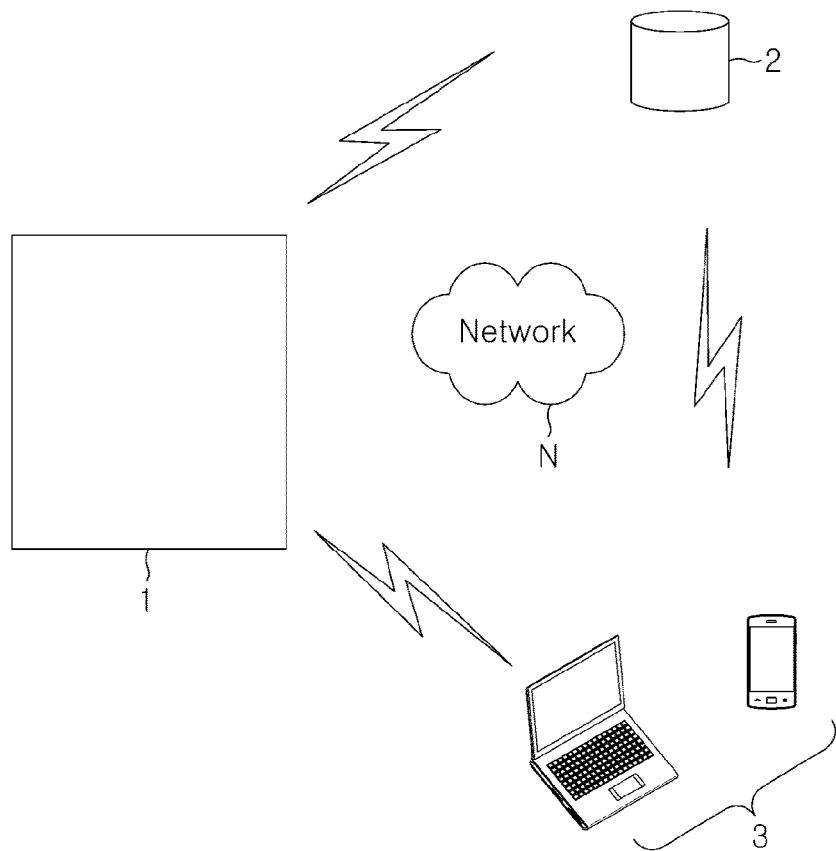
【FIG.2】
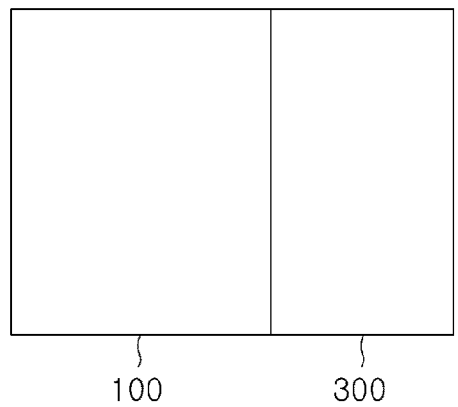

[FIG.3]
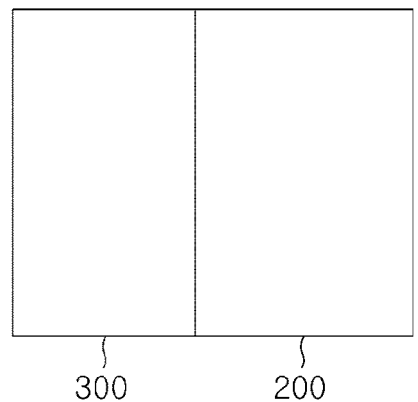
300    200
[FIG.4]
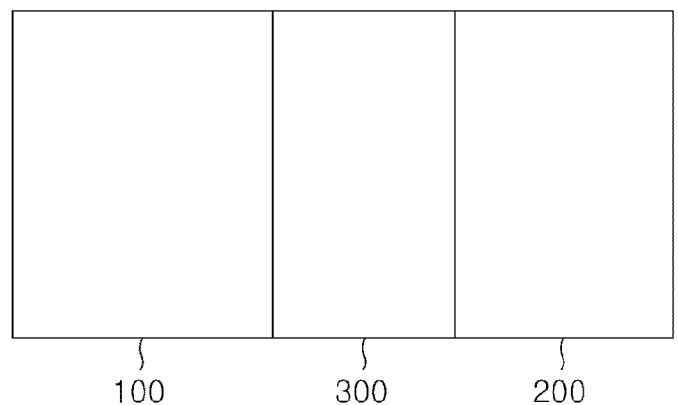
100    300    200

[FIG.5]
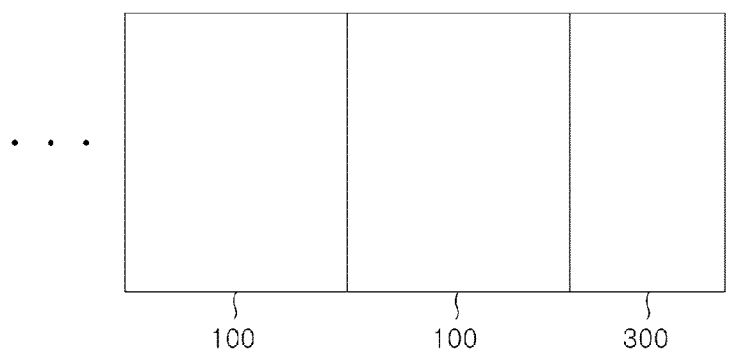
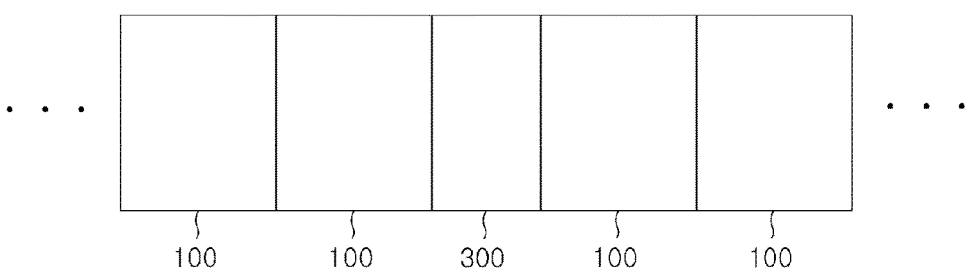

【FIG.6】
(a)
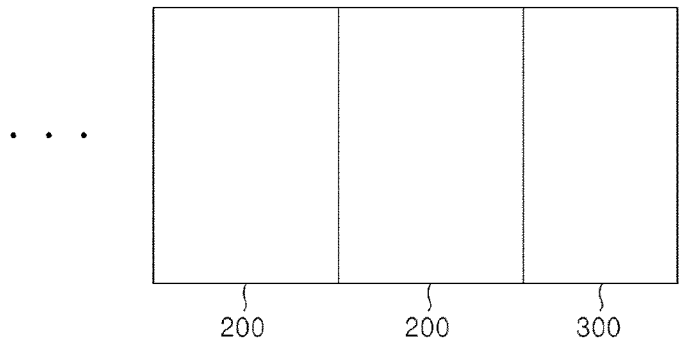
(b)
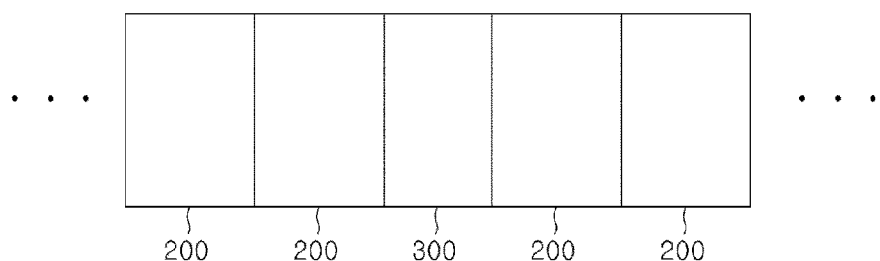
【FIG.7】
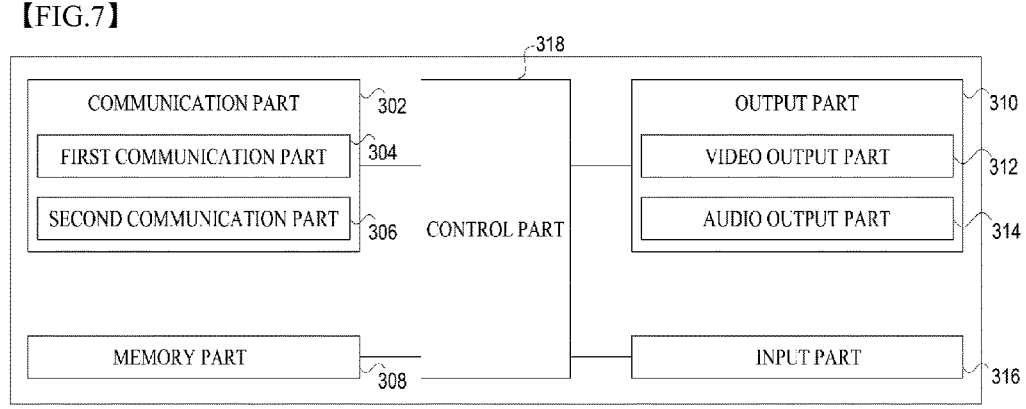

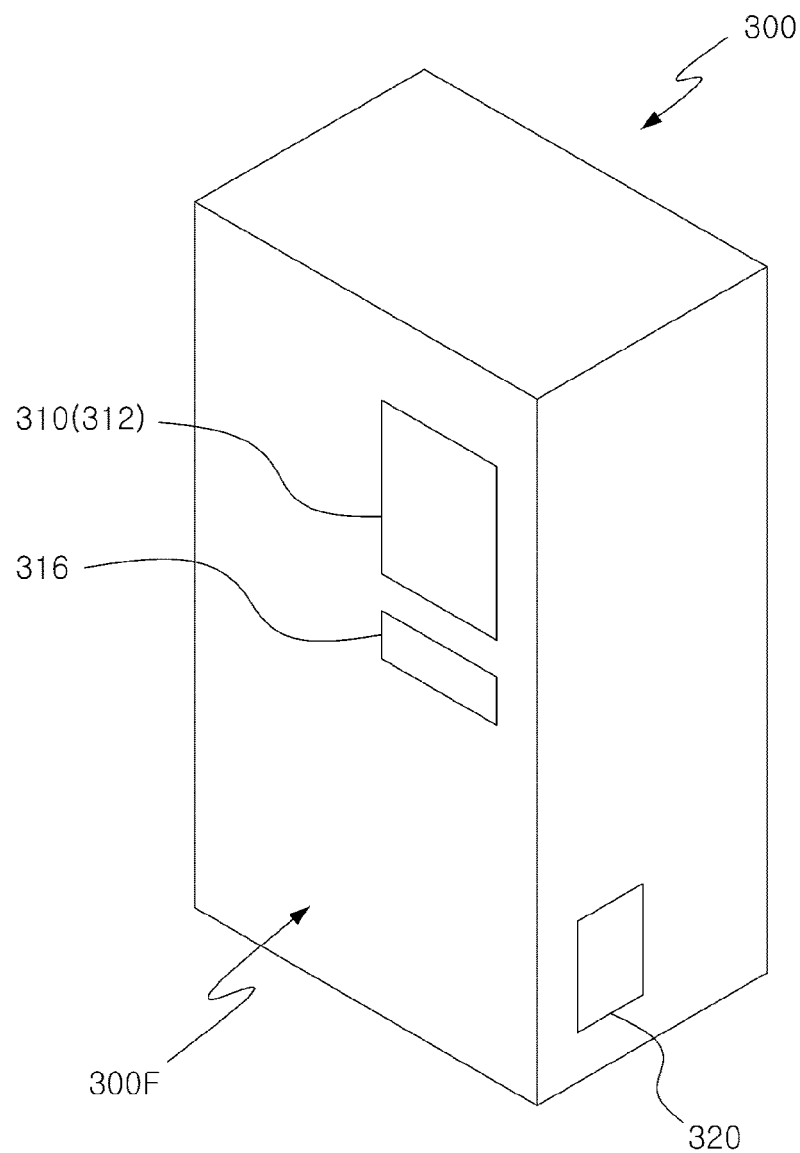
[FIG.8]

【FIG.9】
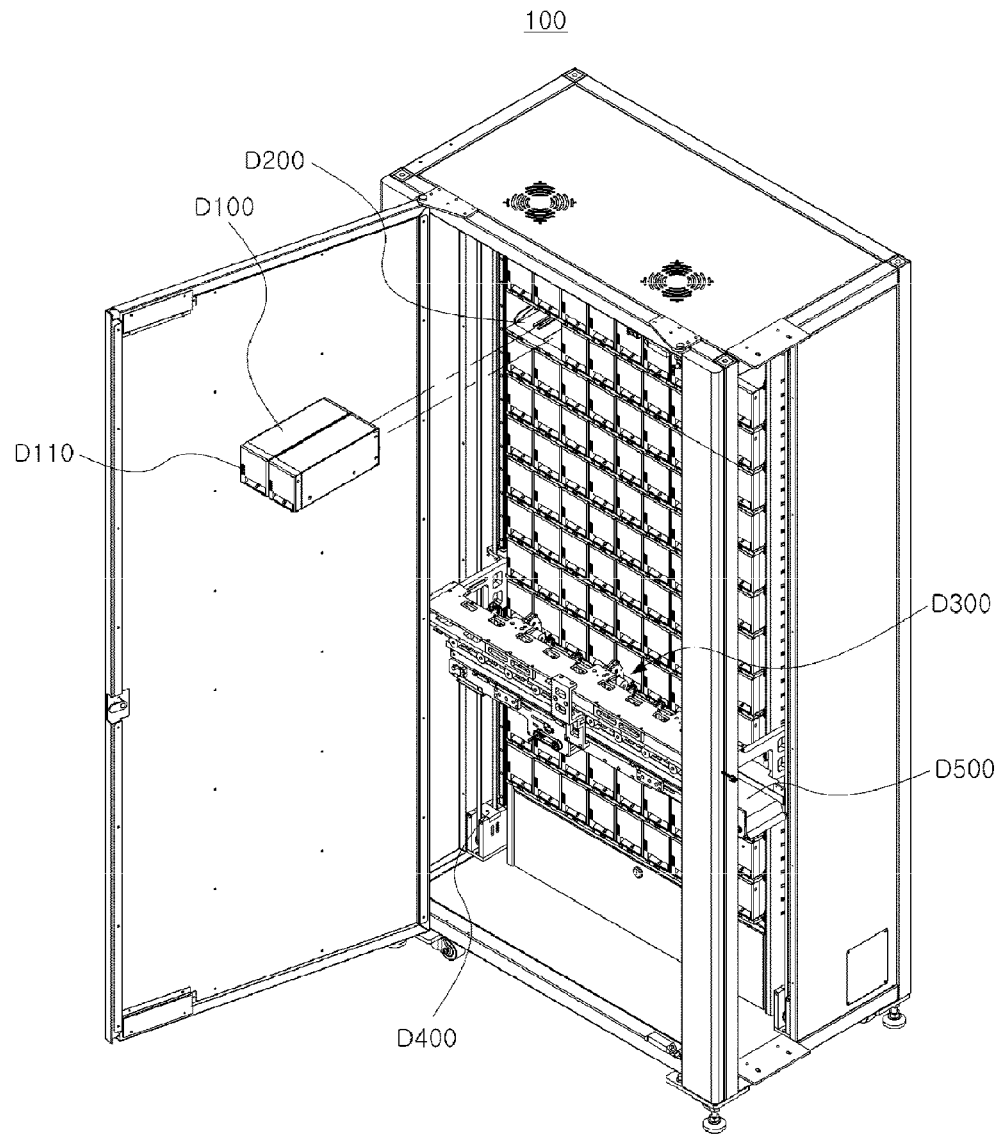

[FIG.10]
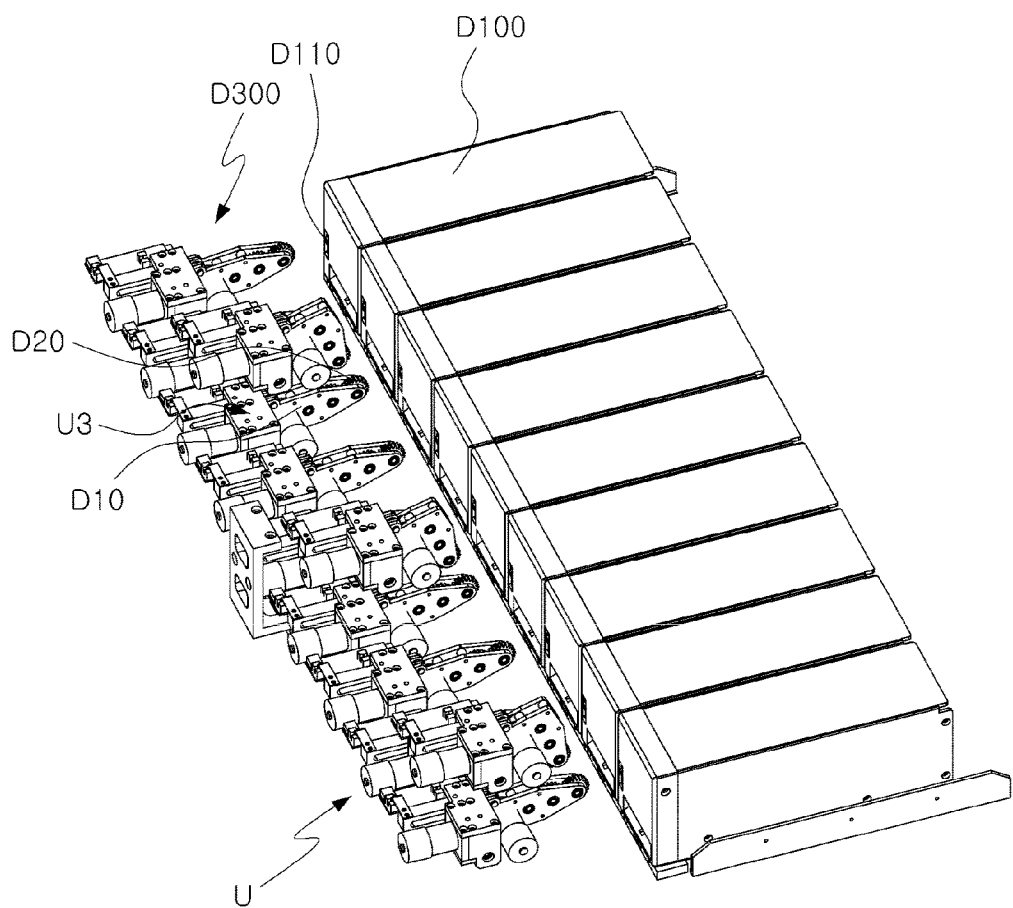

【FIG.11】
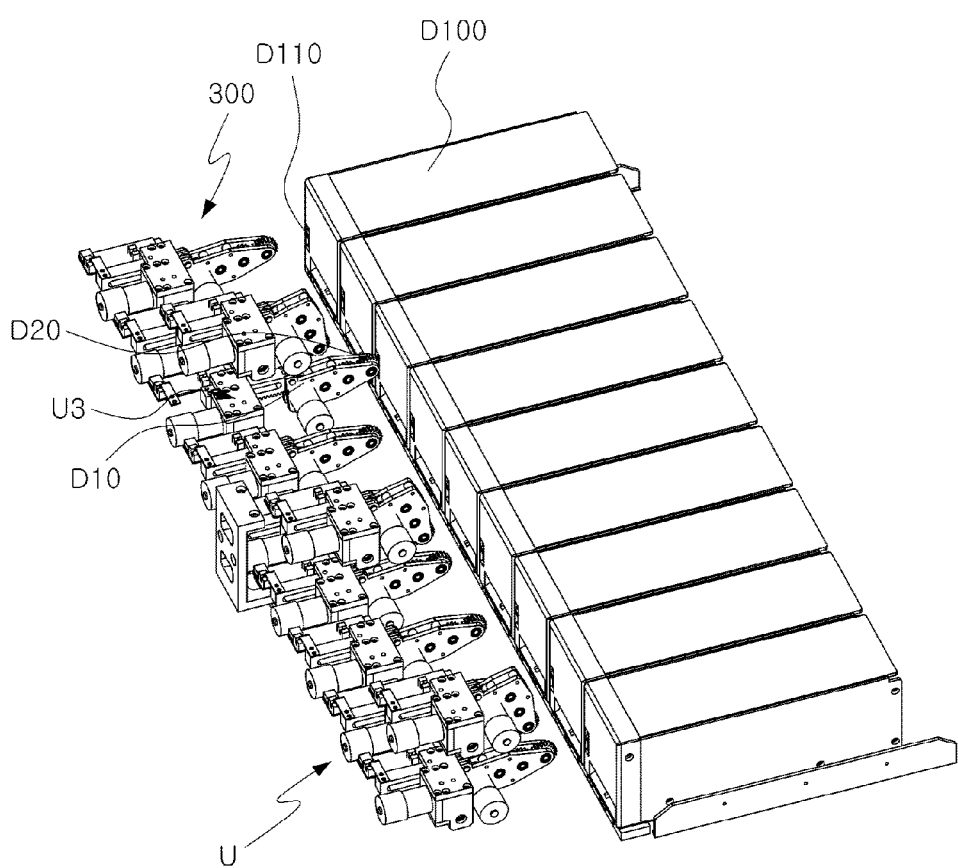

[FIG.12]
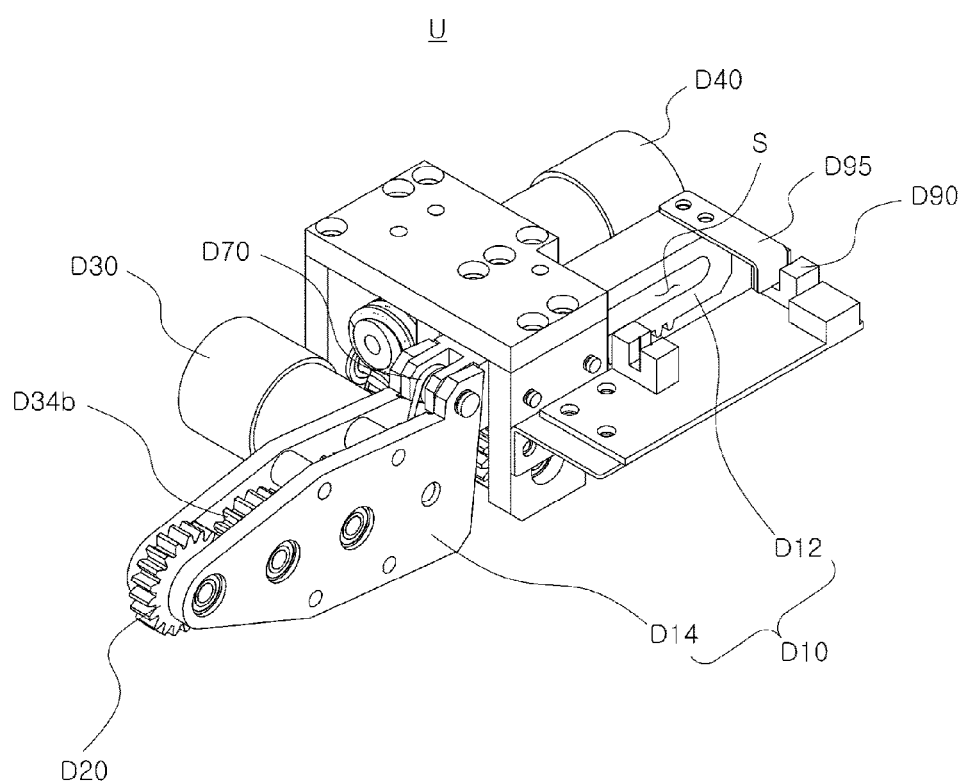

[FIG.13]
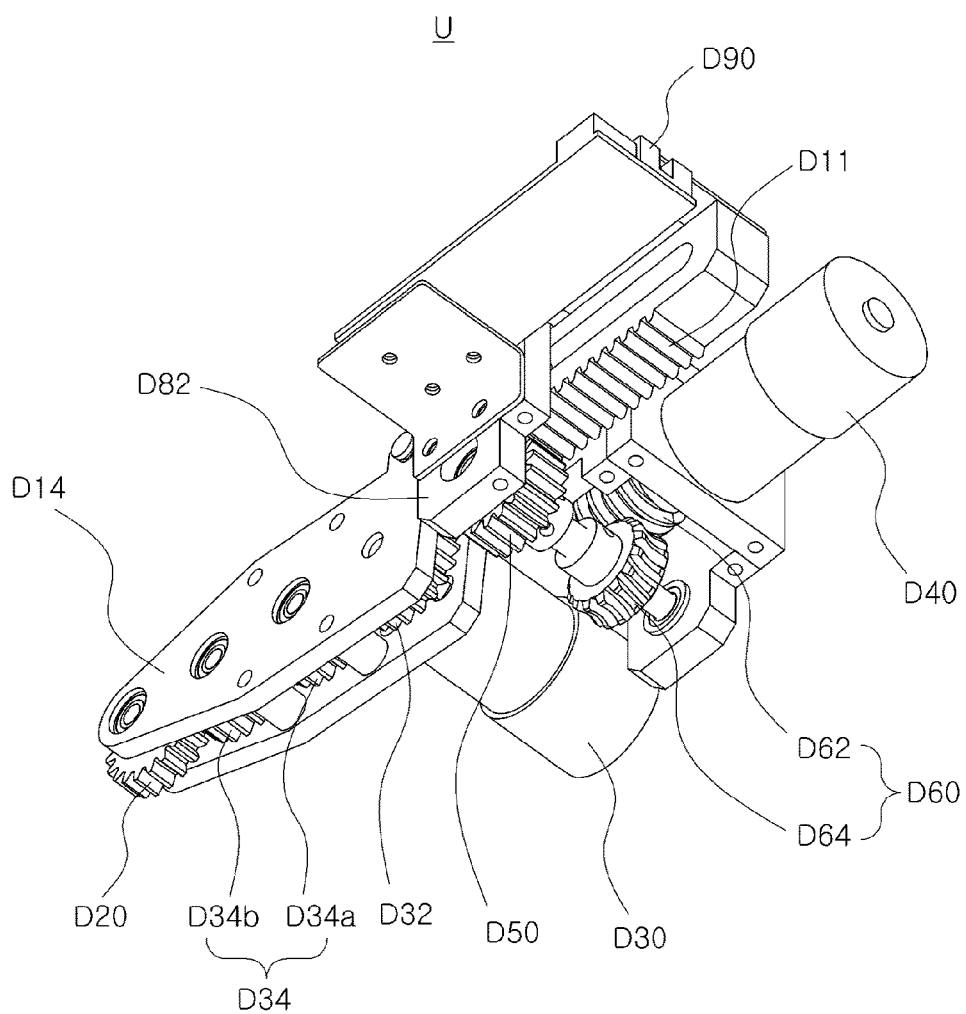

【FIG.14】
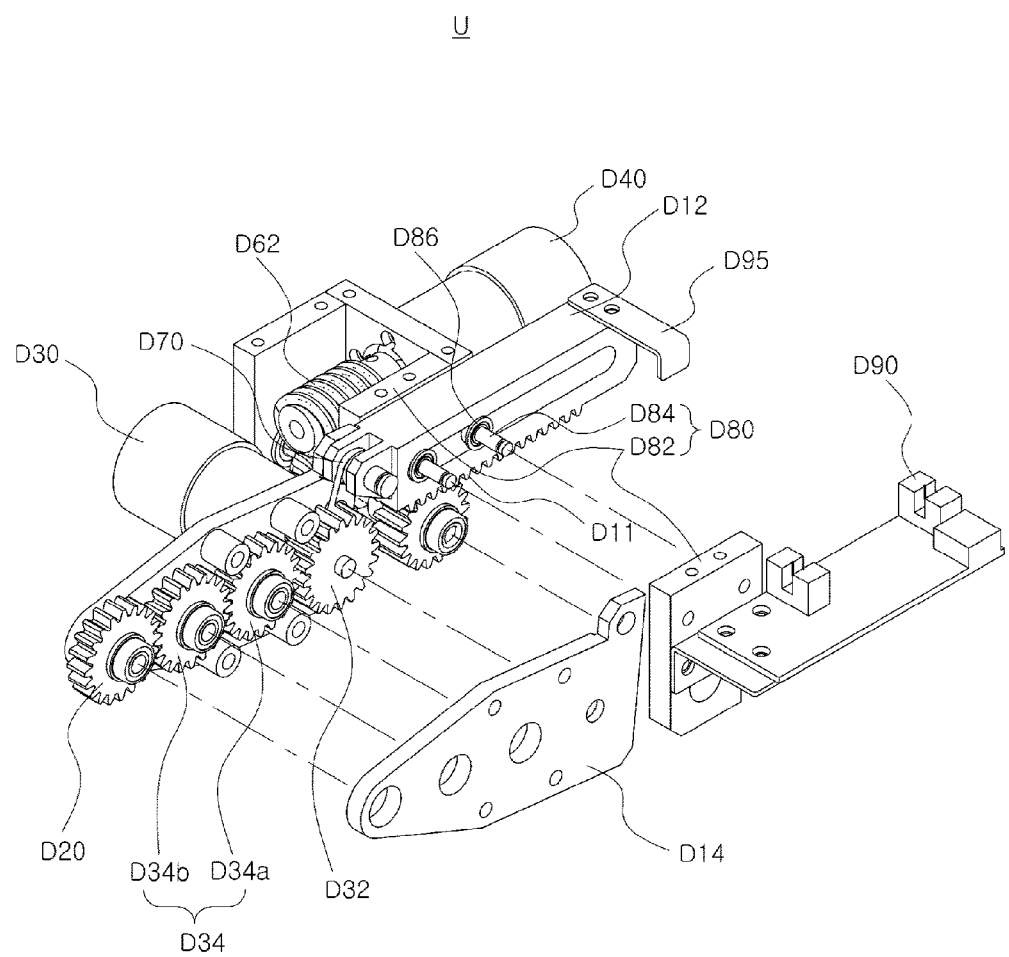

【FIG.15】
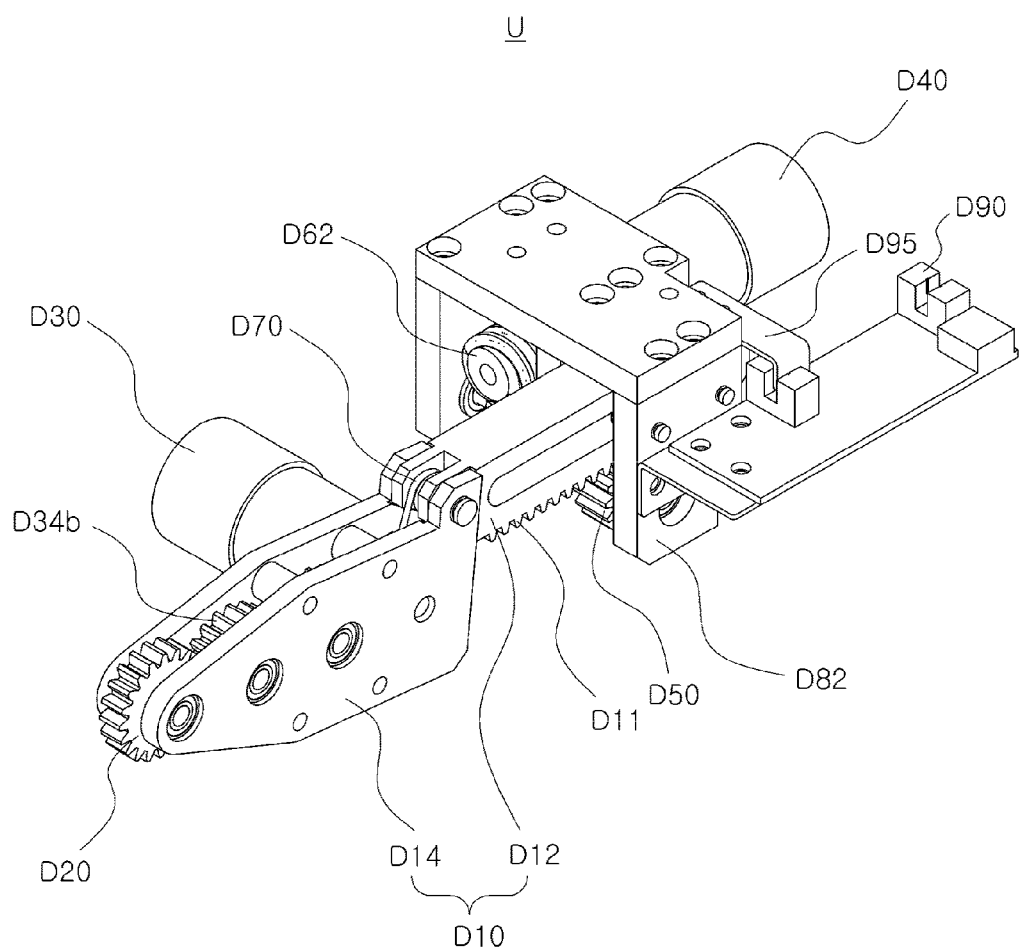

[FIG.16]
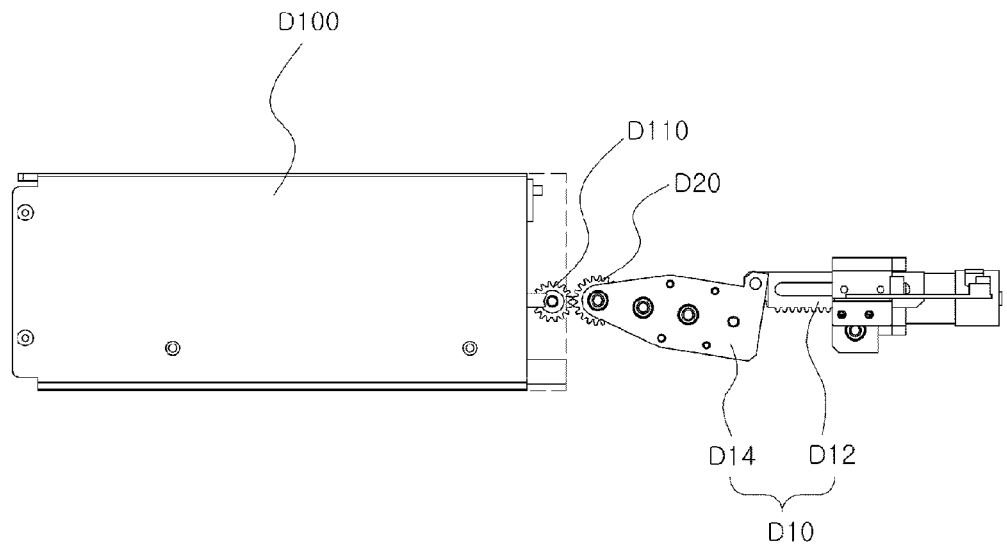
[FIG.17]
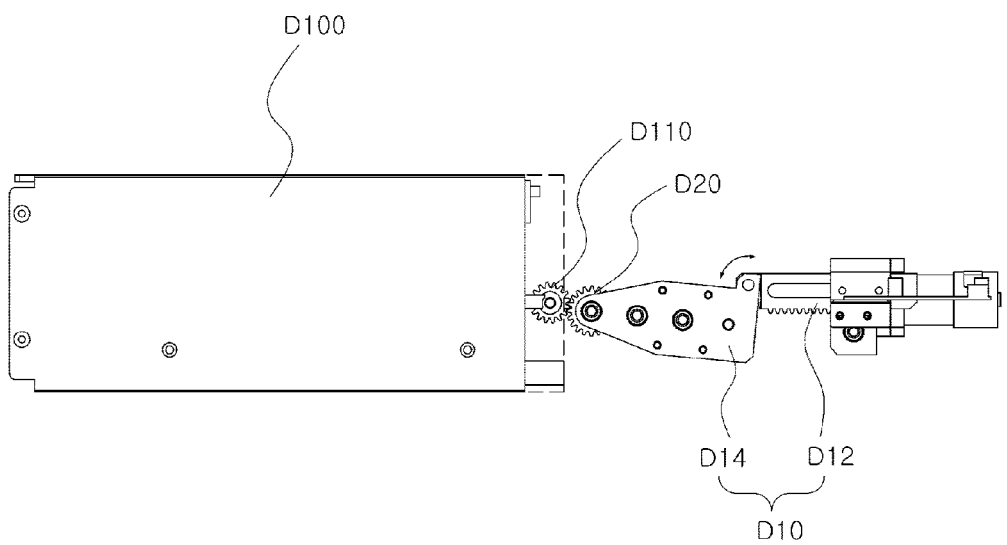

[FIG.18]
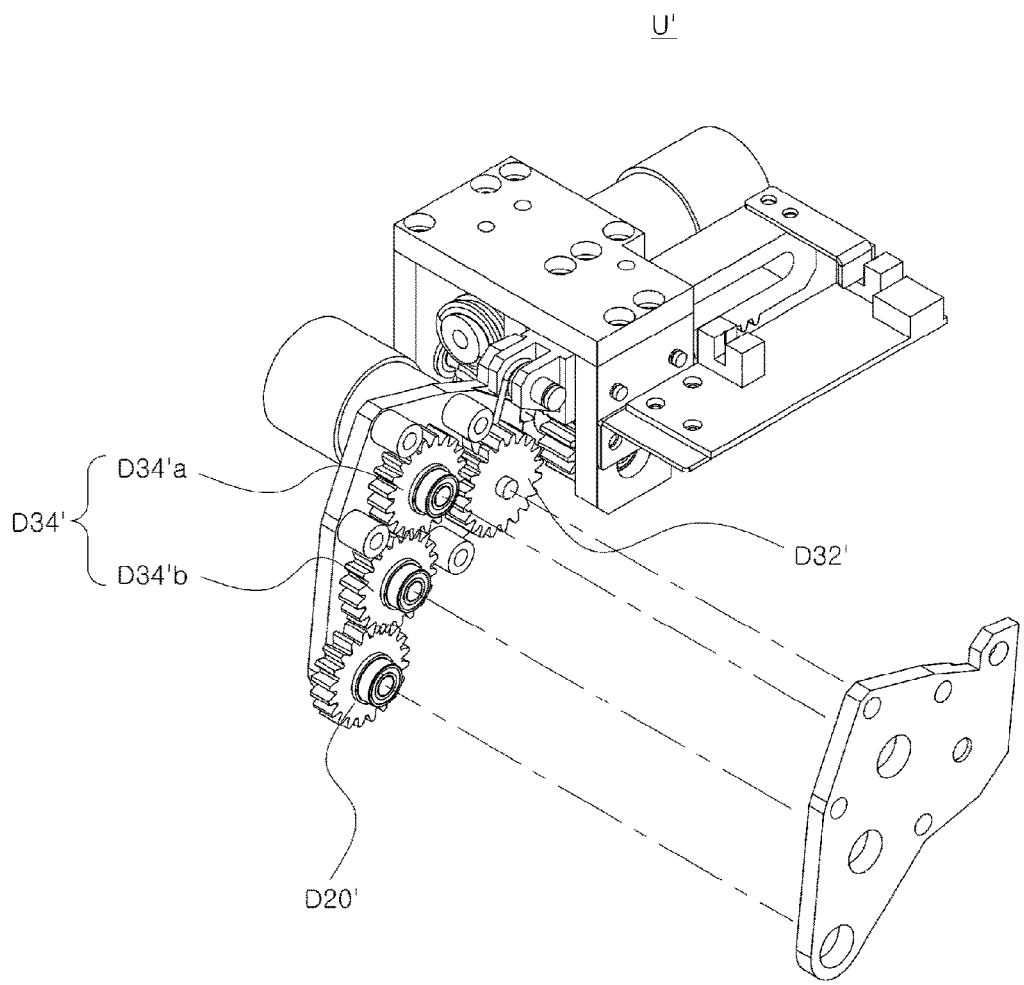

[FIG.19]
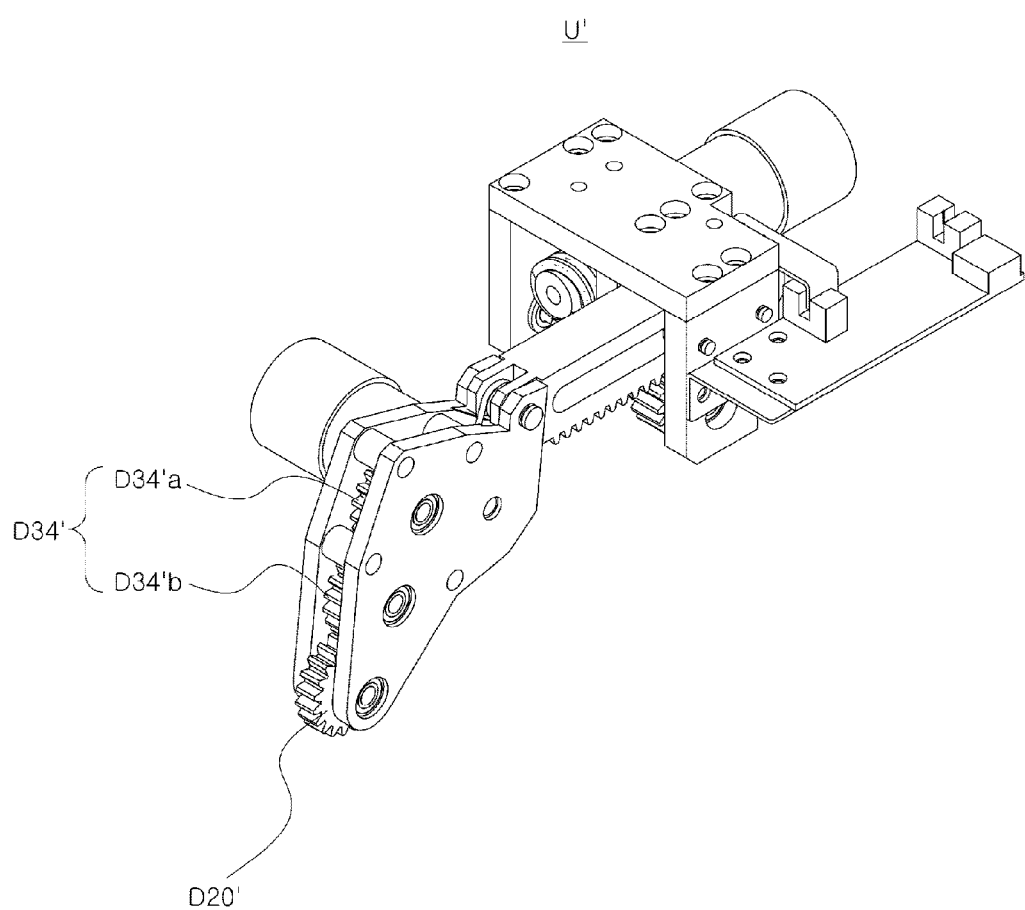

[FIG.20]
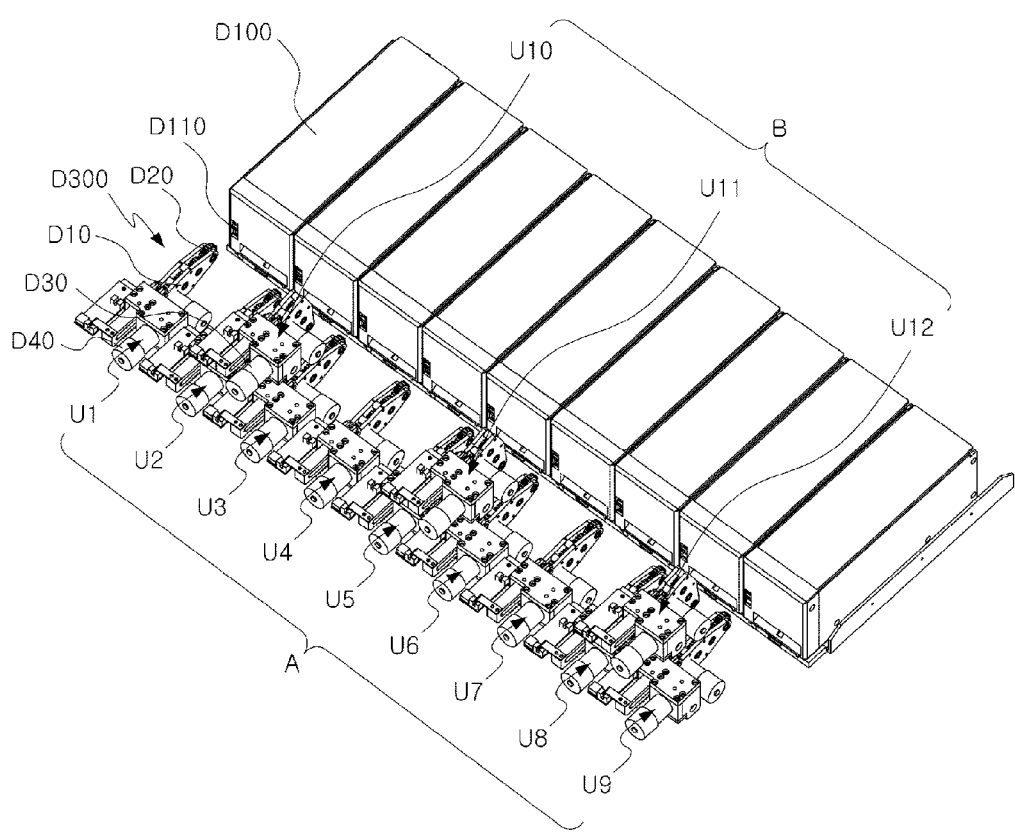

【FIG.21】
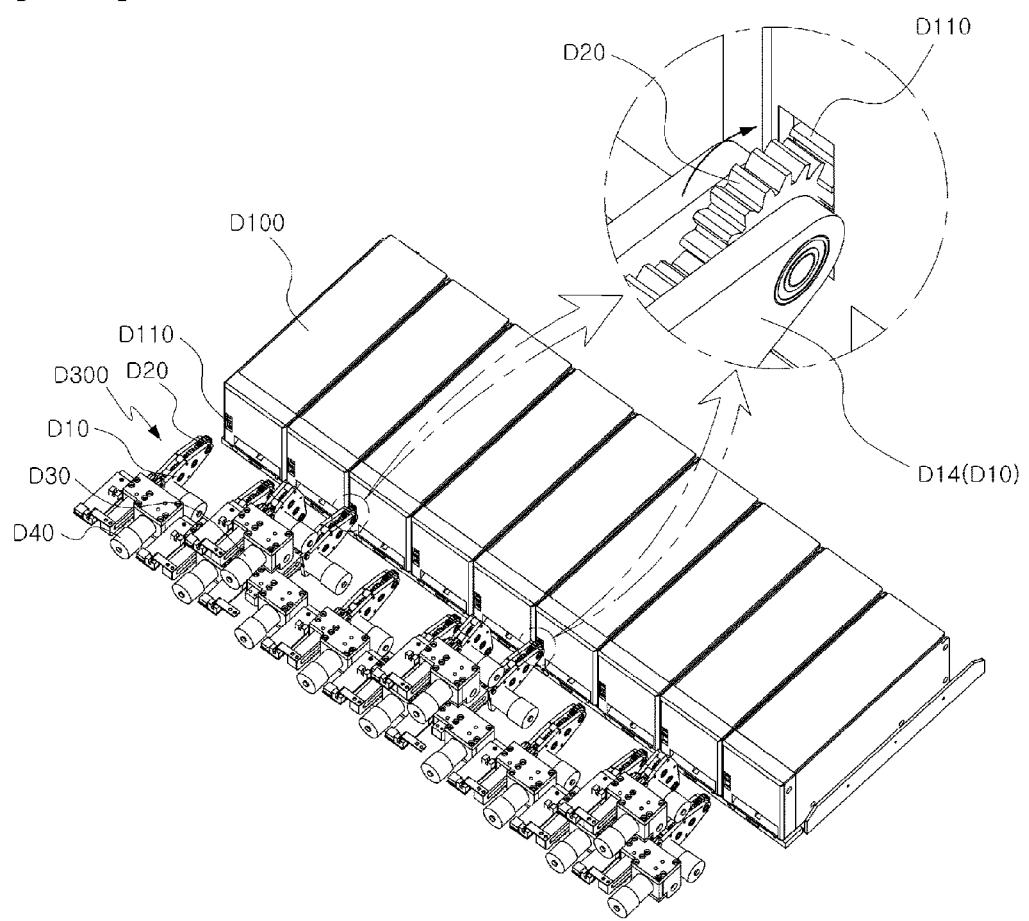

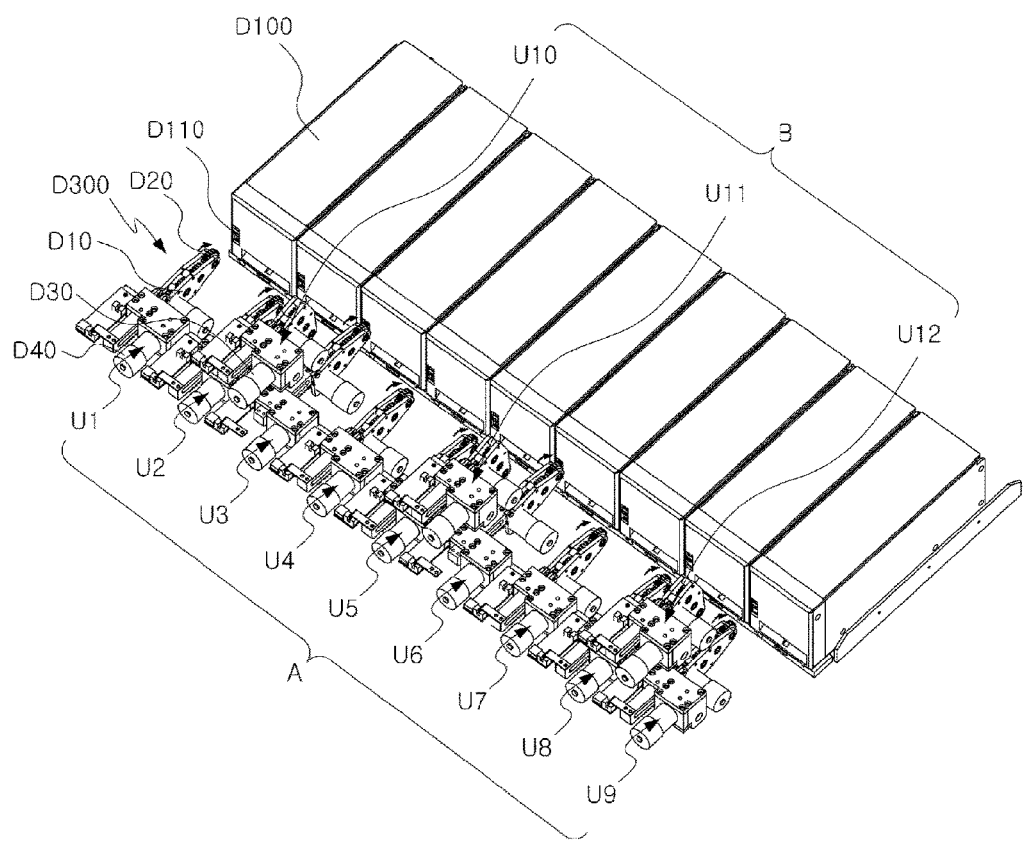
[FIG.22]

[FIG.23]
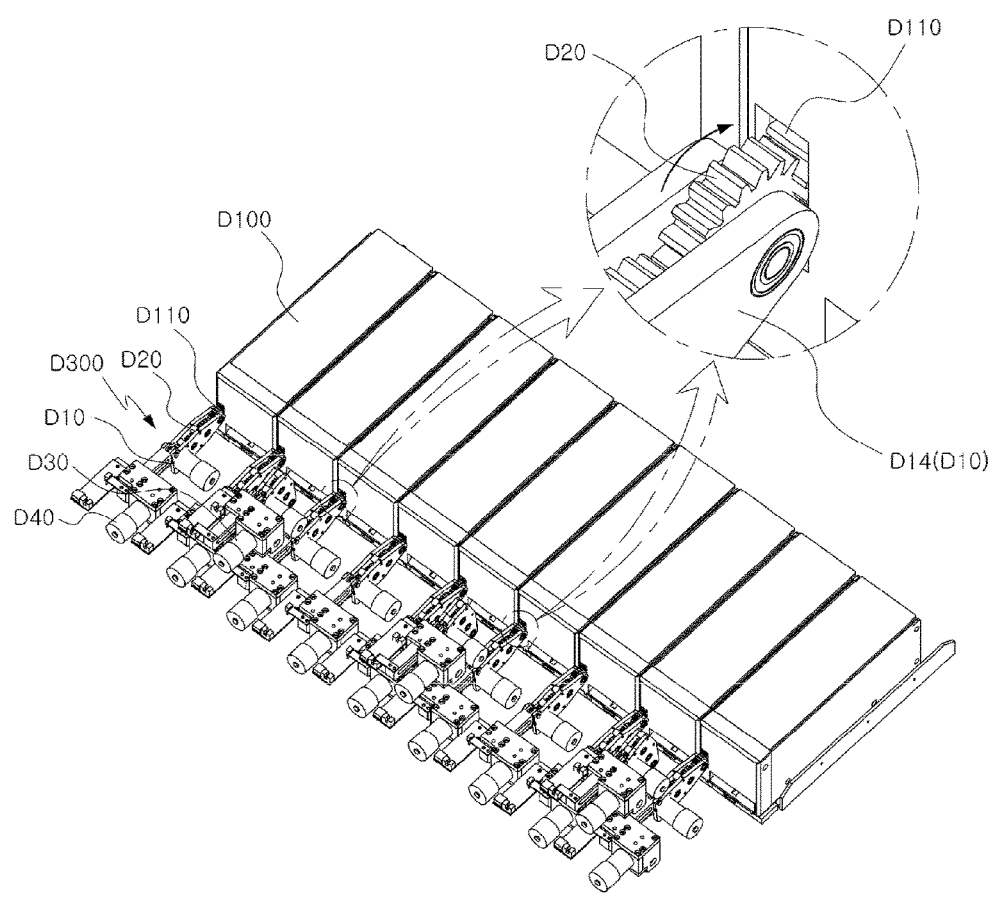

[FIG.24]
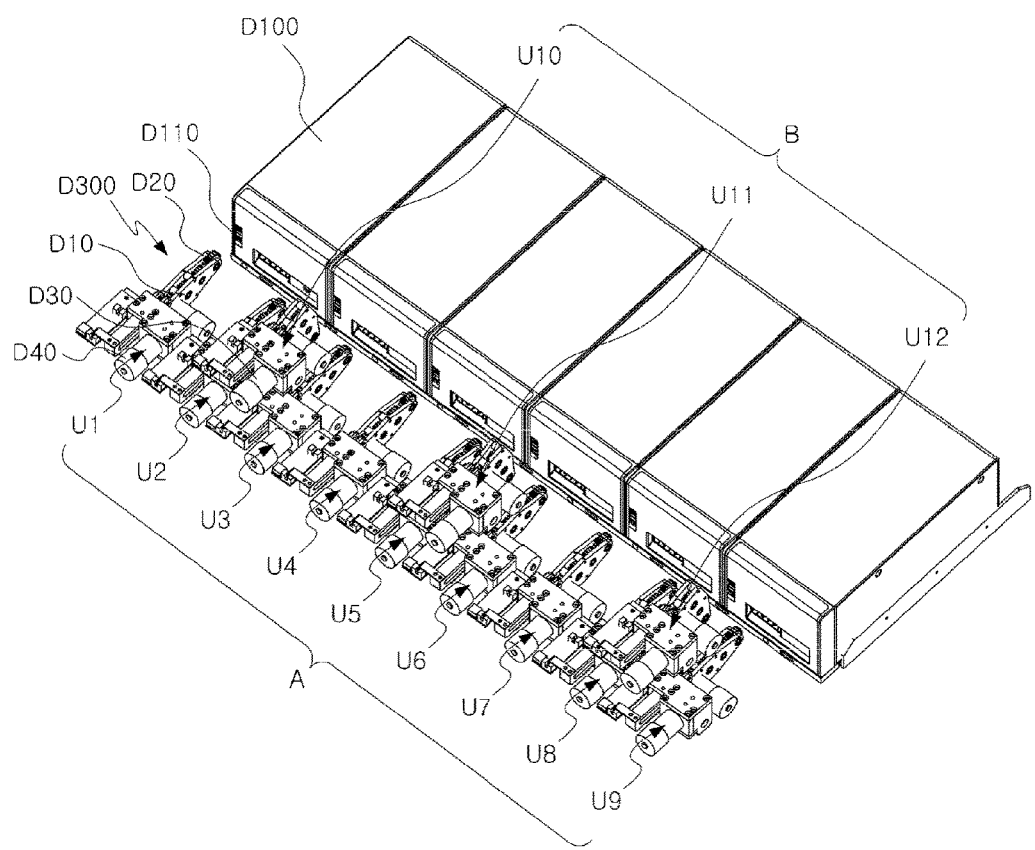

【FIG.25】
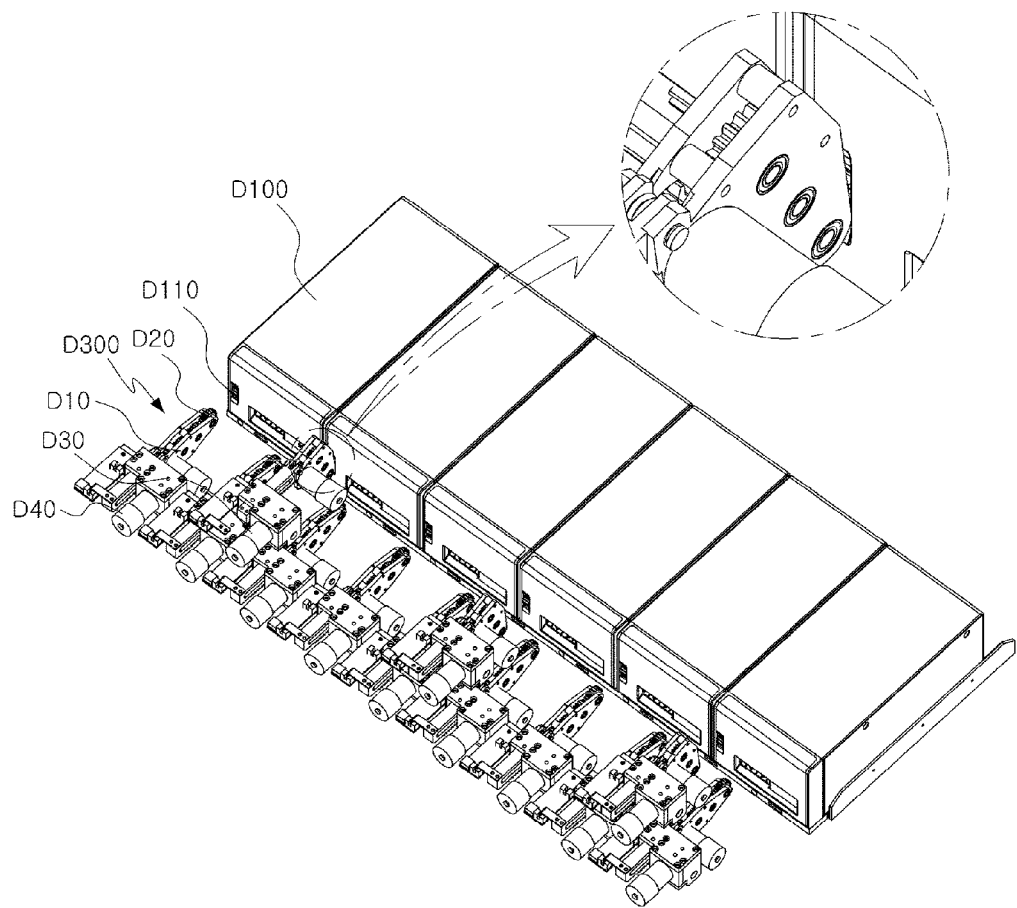
【FIG.26】
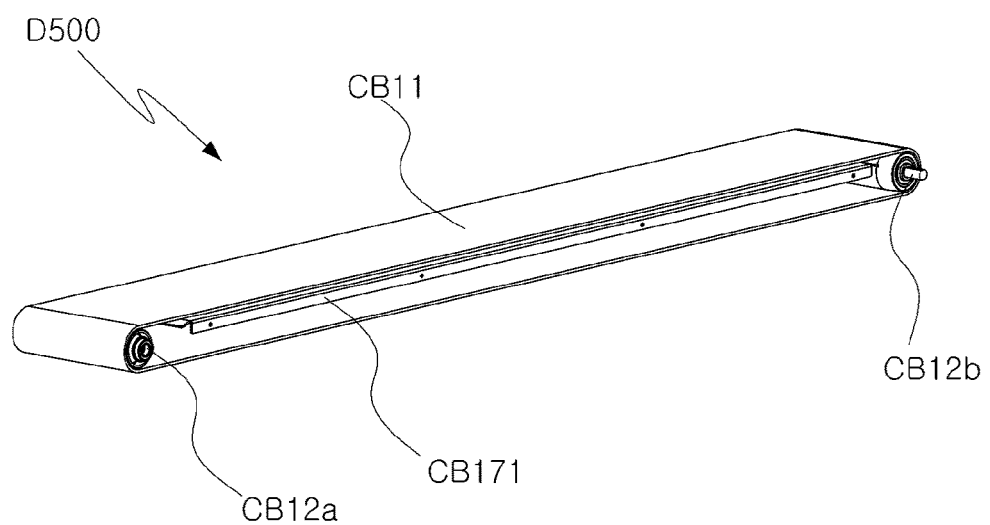

[FIG.27]
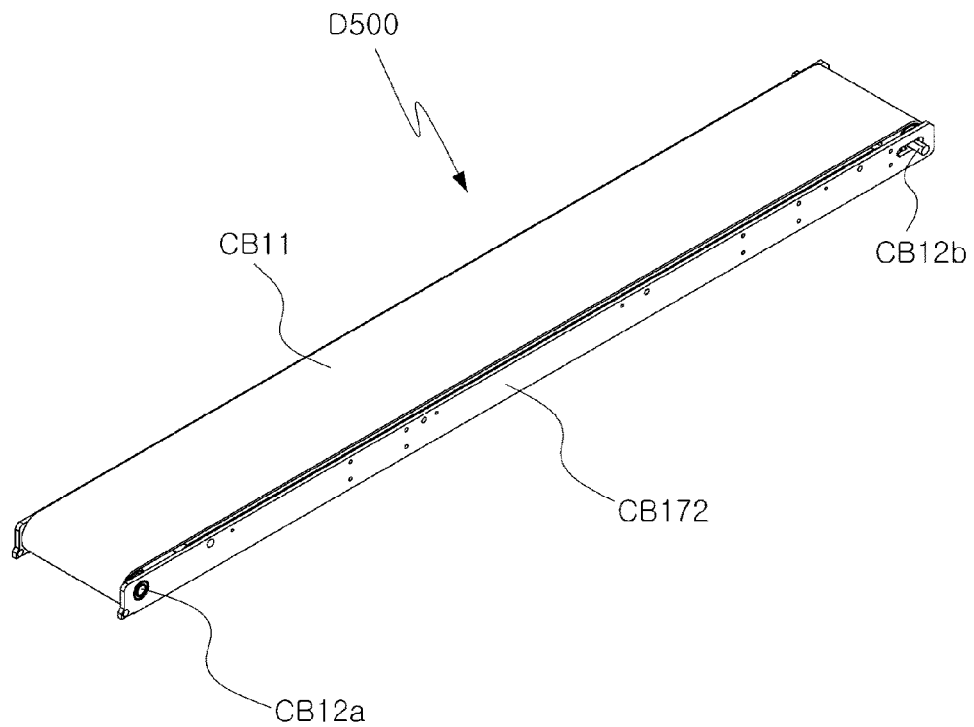
[FIG.28]
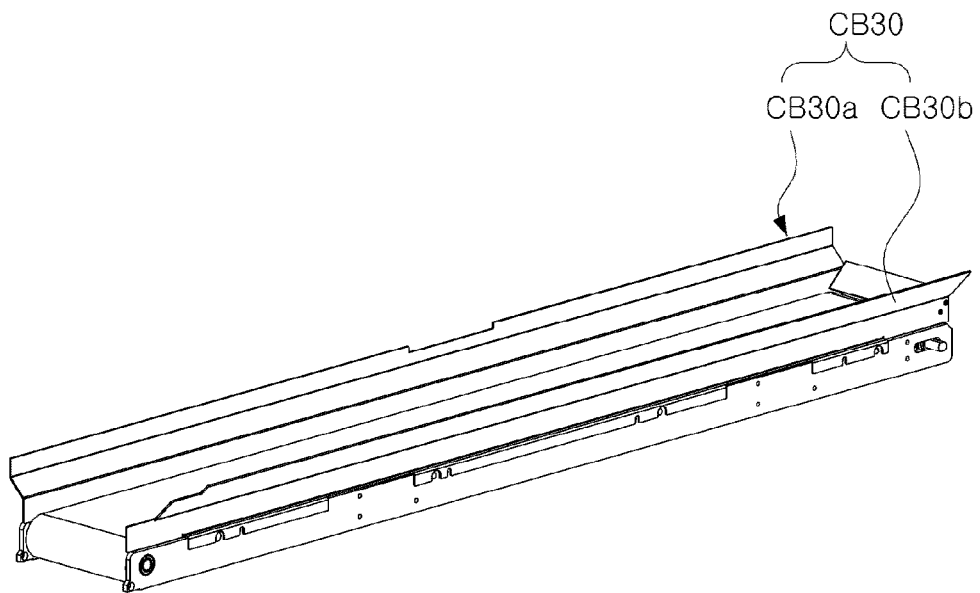

【FIG.29】
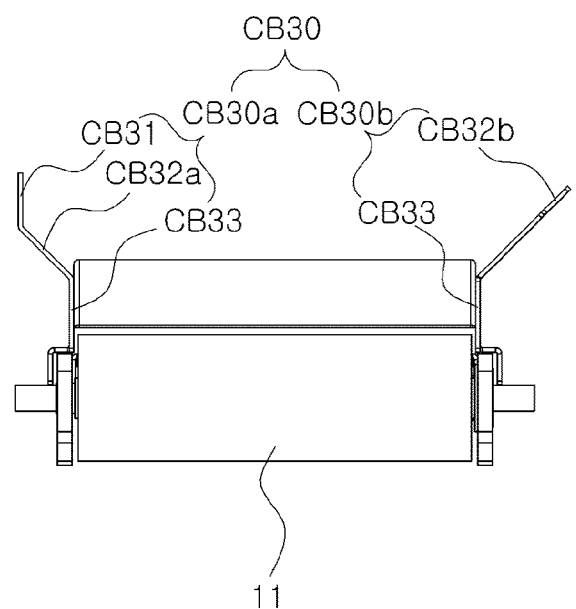
【FIG.30】
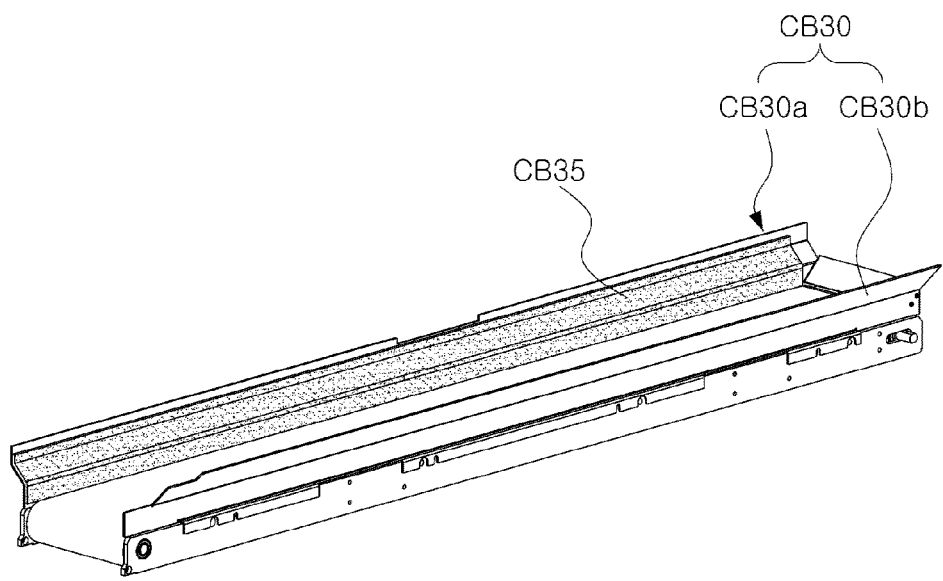

[FIG.31]
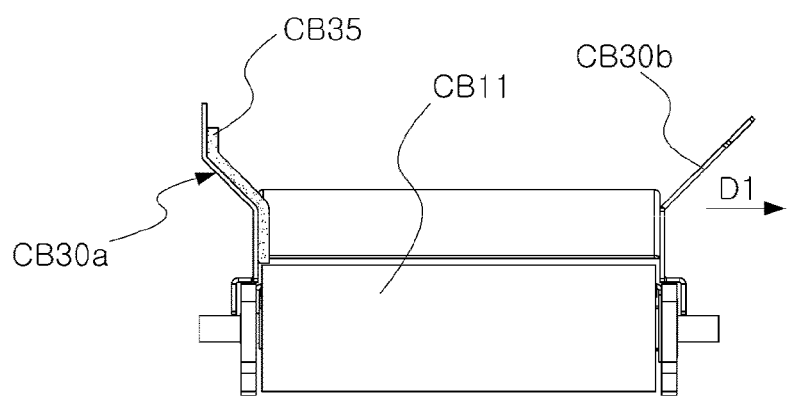
[FIG.32]
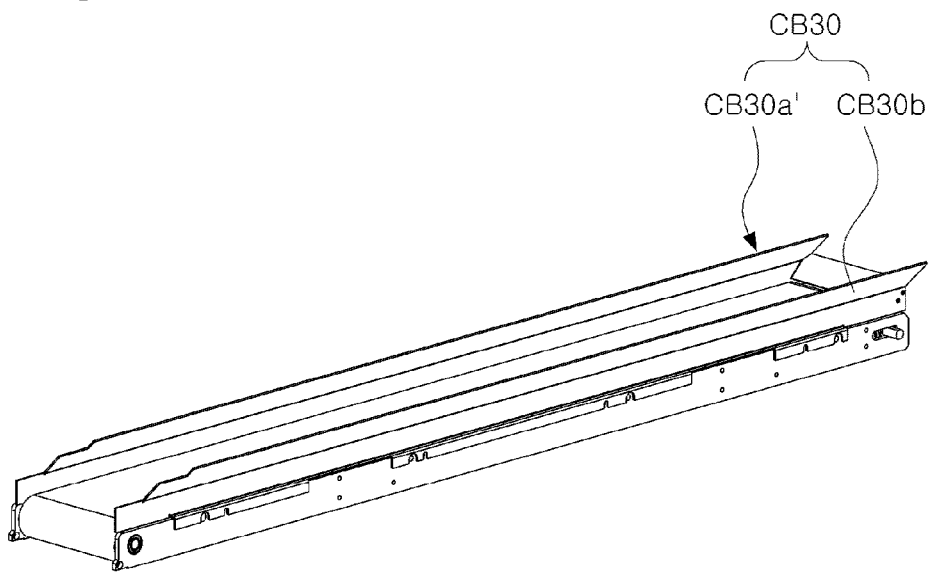

[FIG.33]
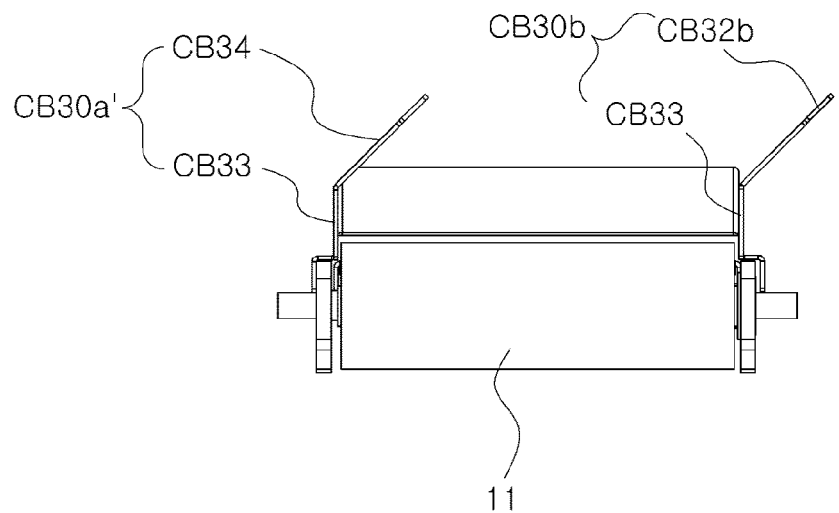
[FIG.34]
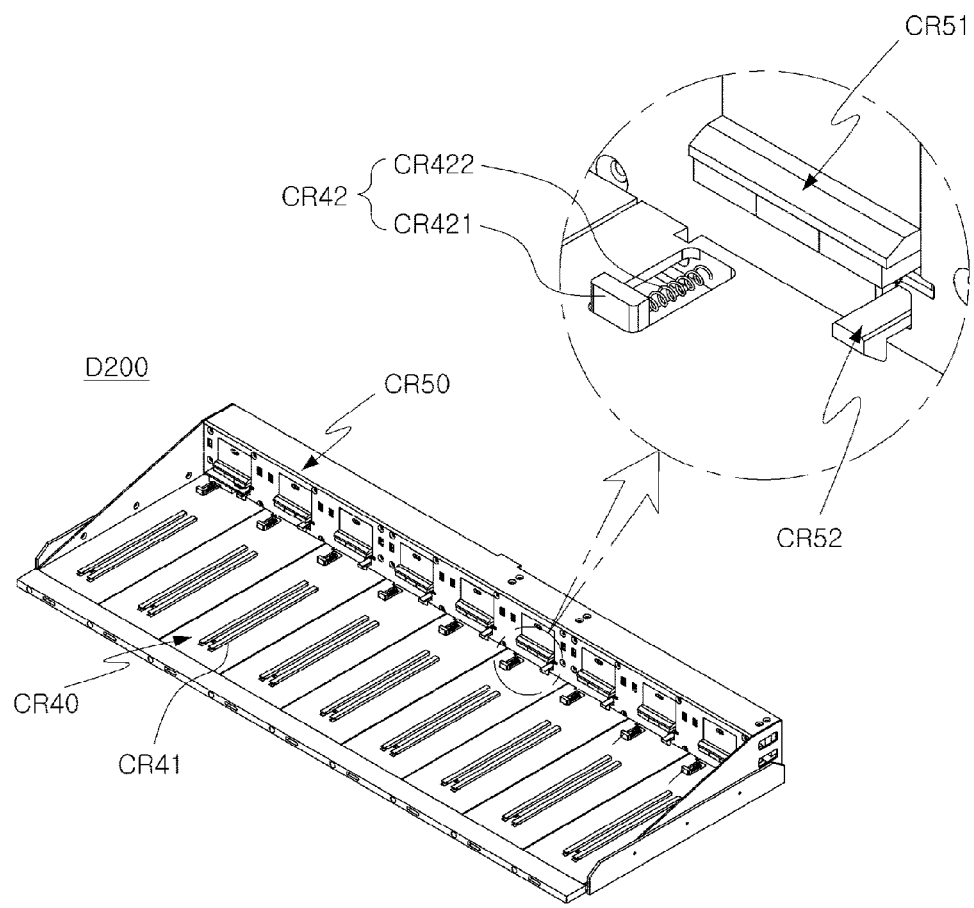

【FIG.35】
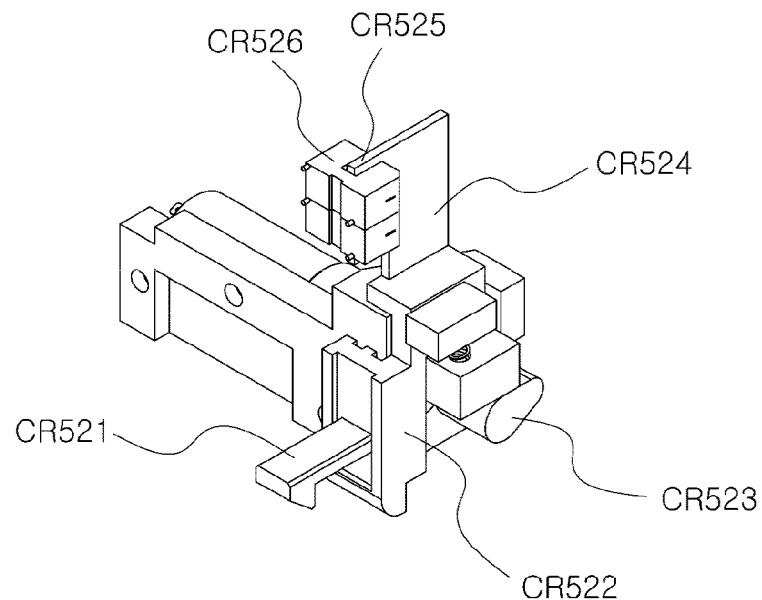
【FIG.36】
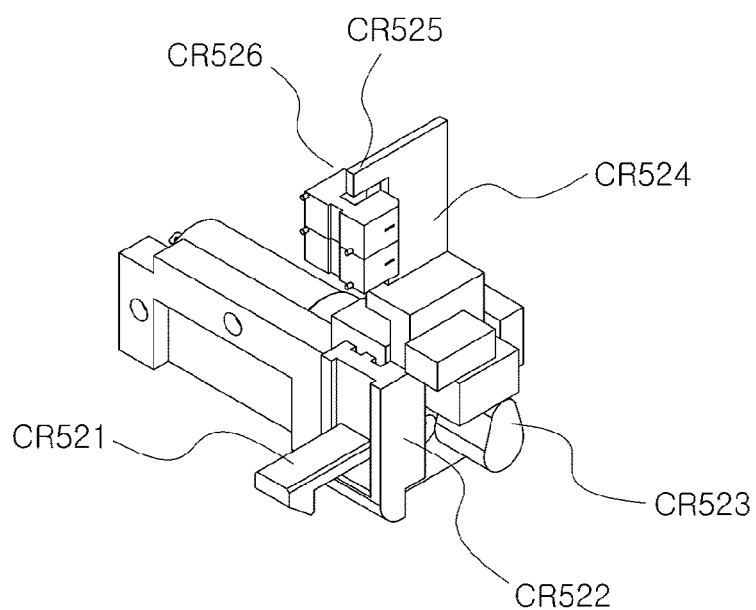

【FIG.37】
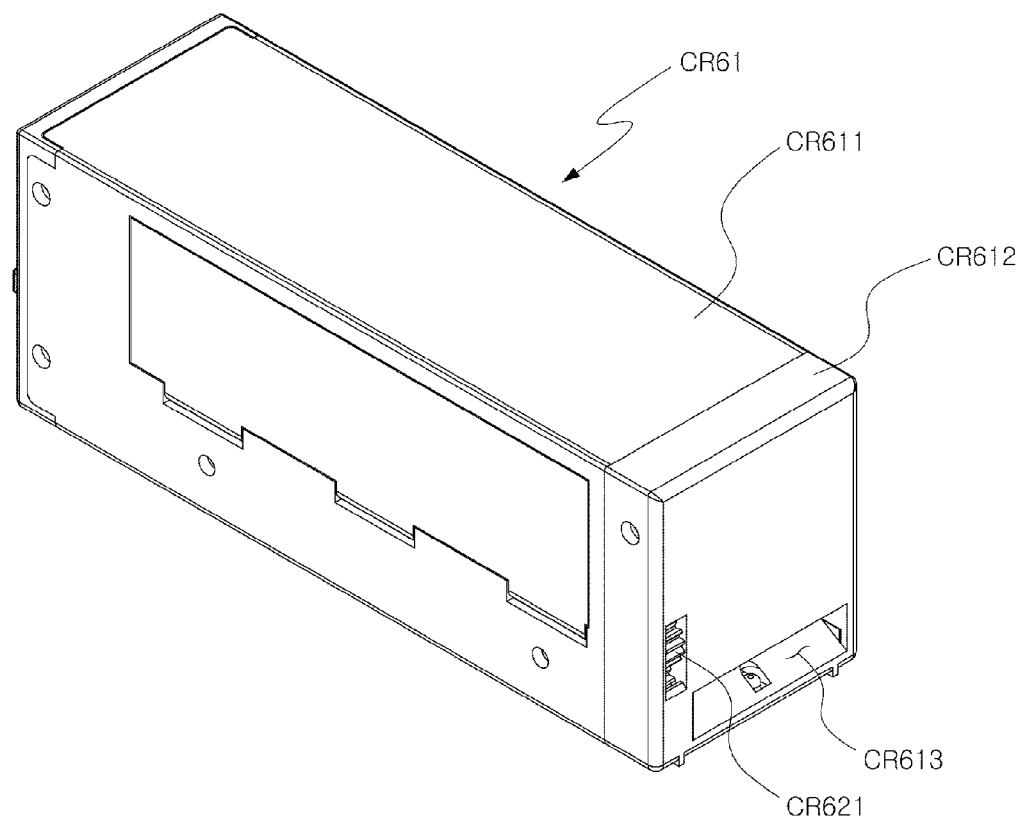

[FIG.38]
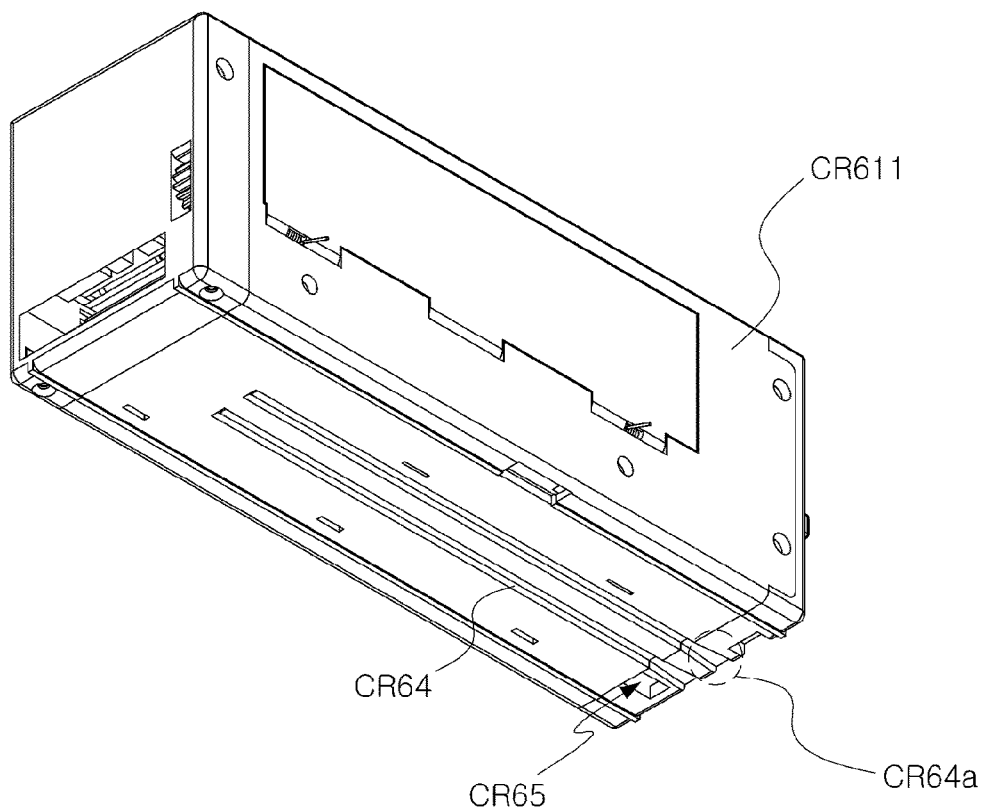

[FIG.39]
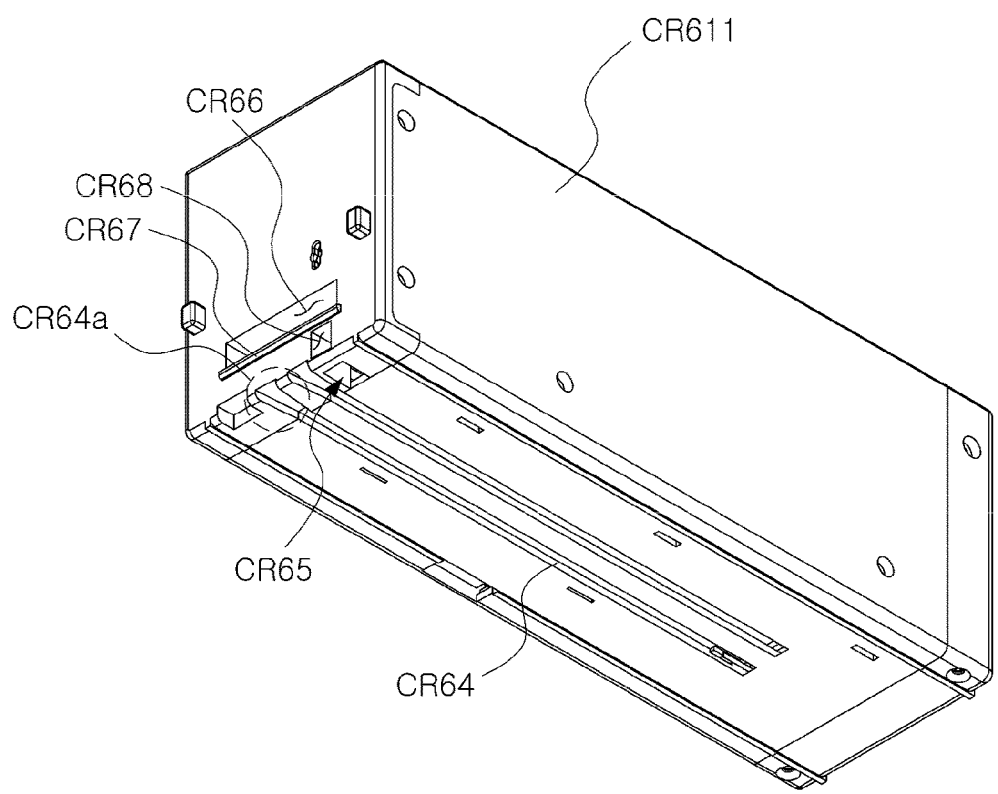

[FIG.40]
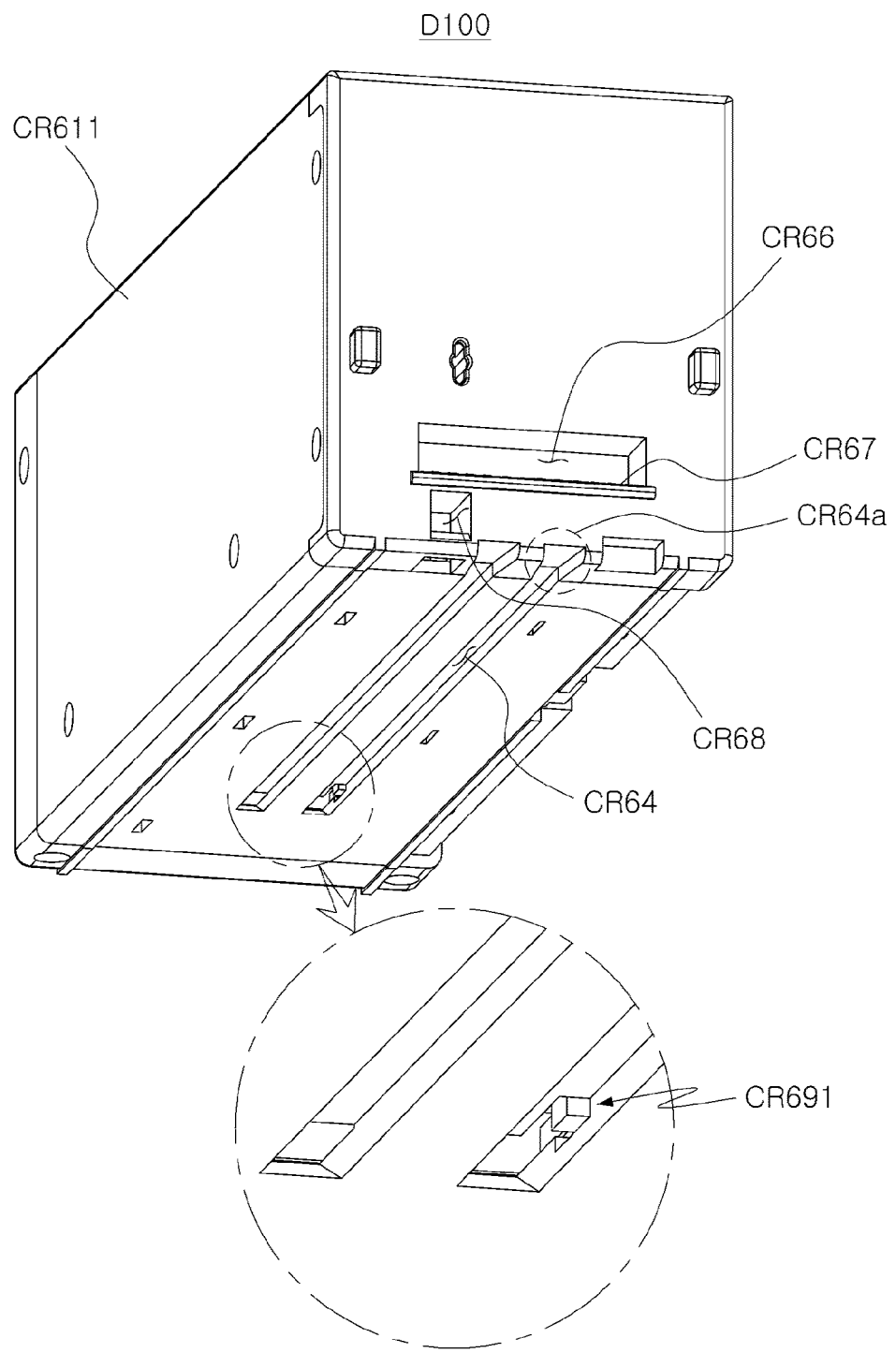

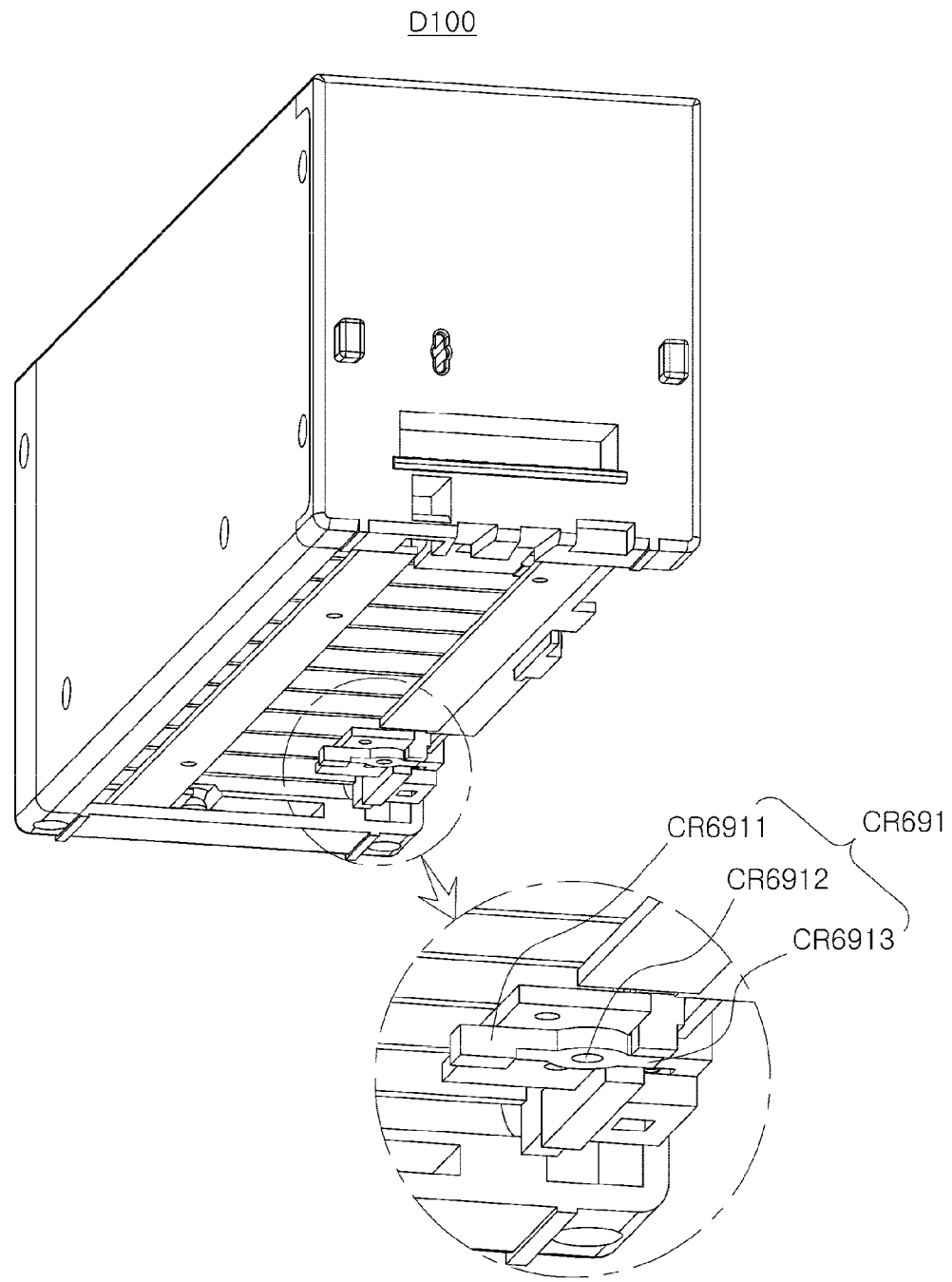
【FIG.41】

【FIG.42】
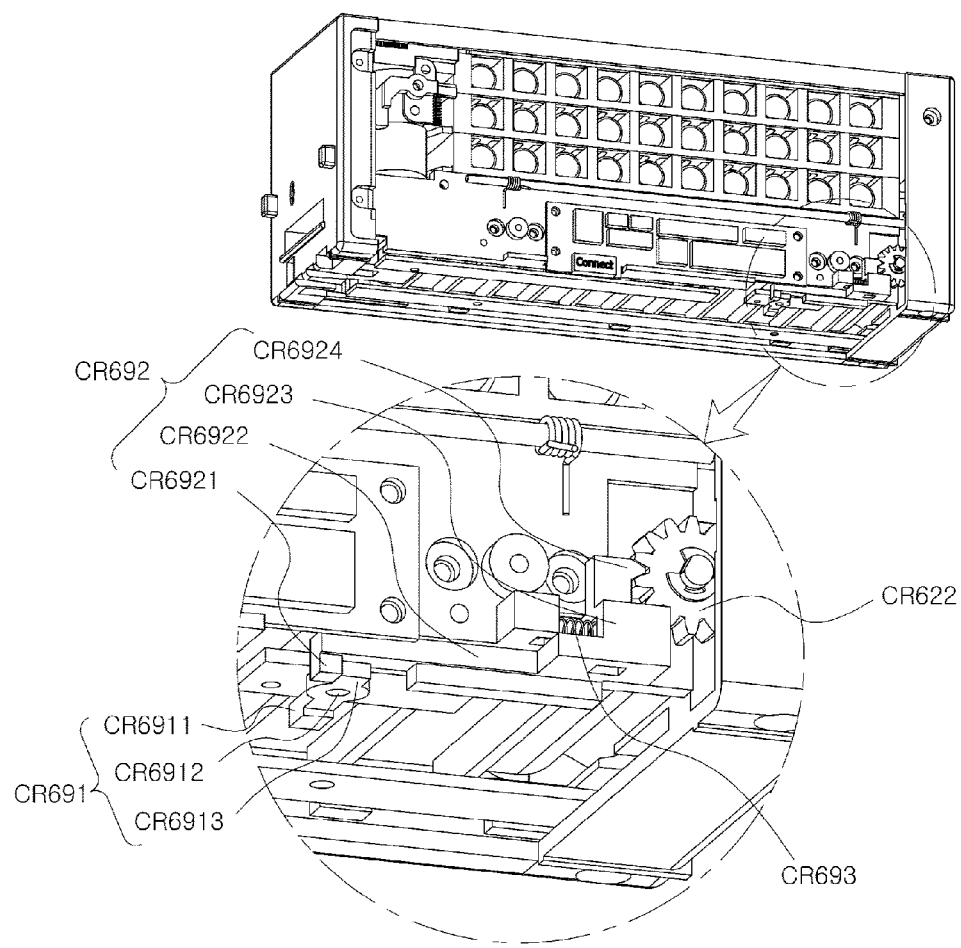

[FIG.43]
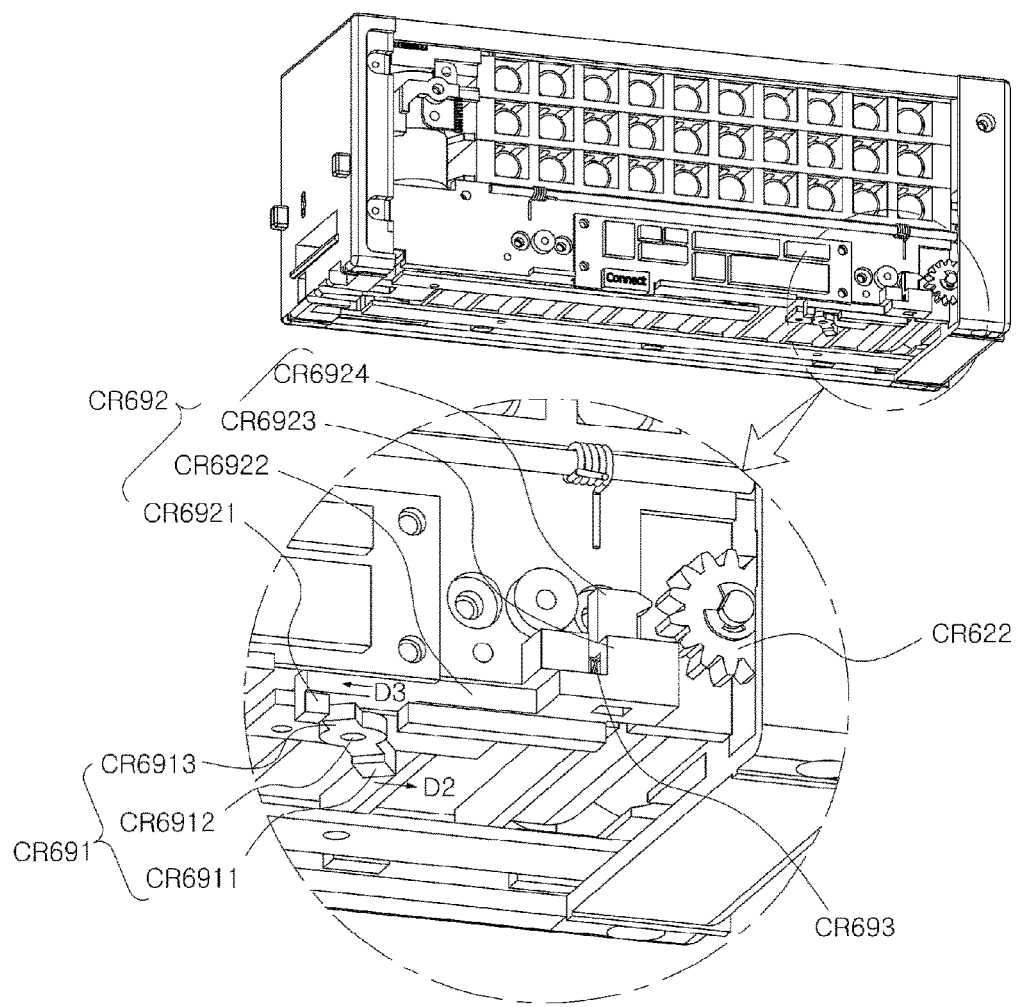

【FIG.44】
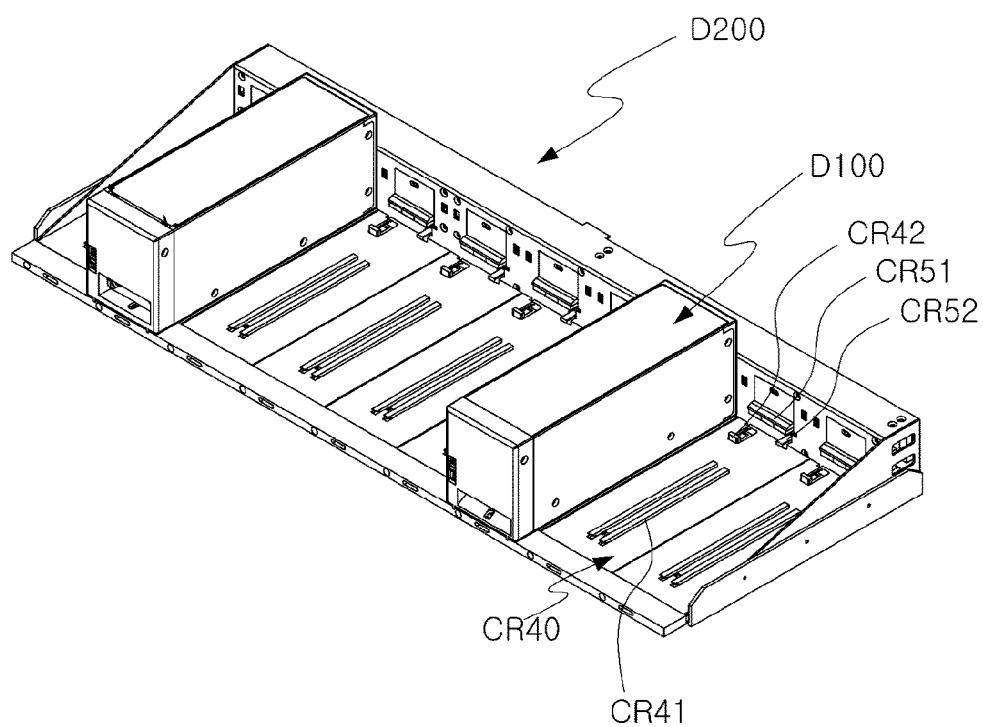
【FIG.45】
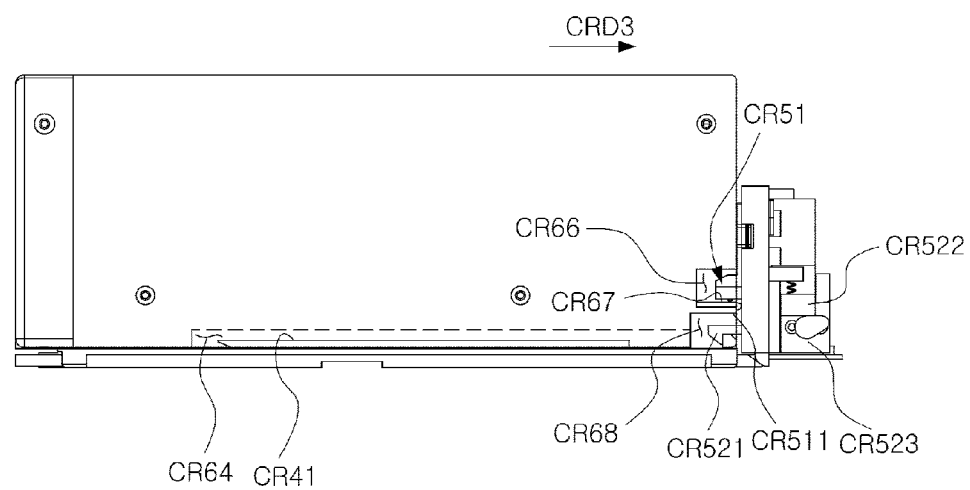

【FIG.46】
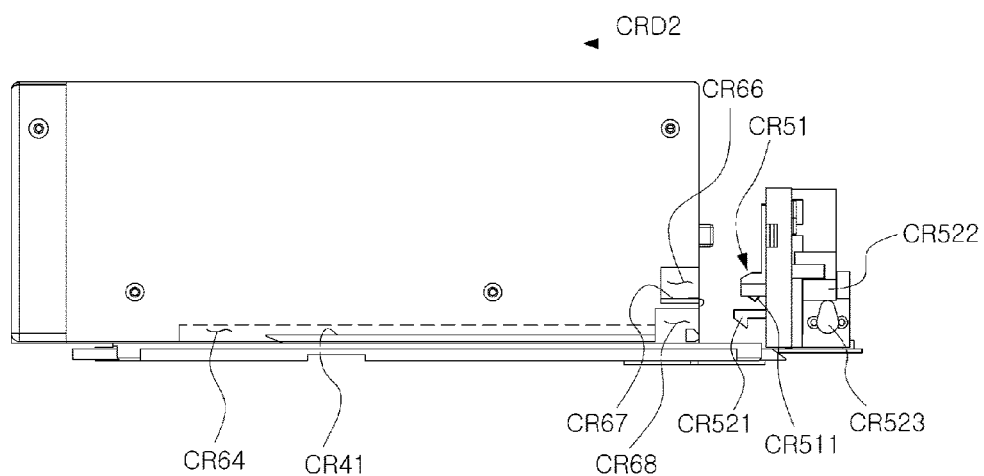

[FIG.47]
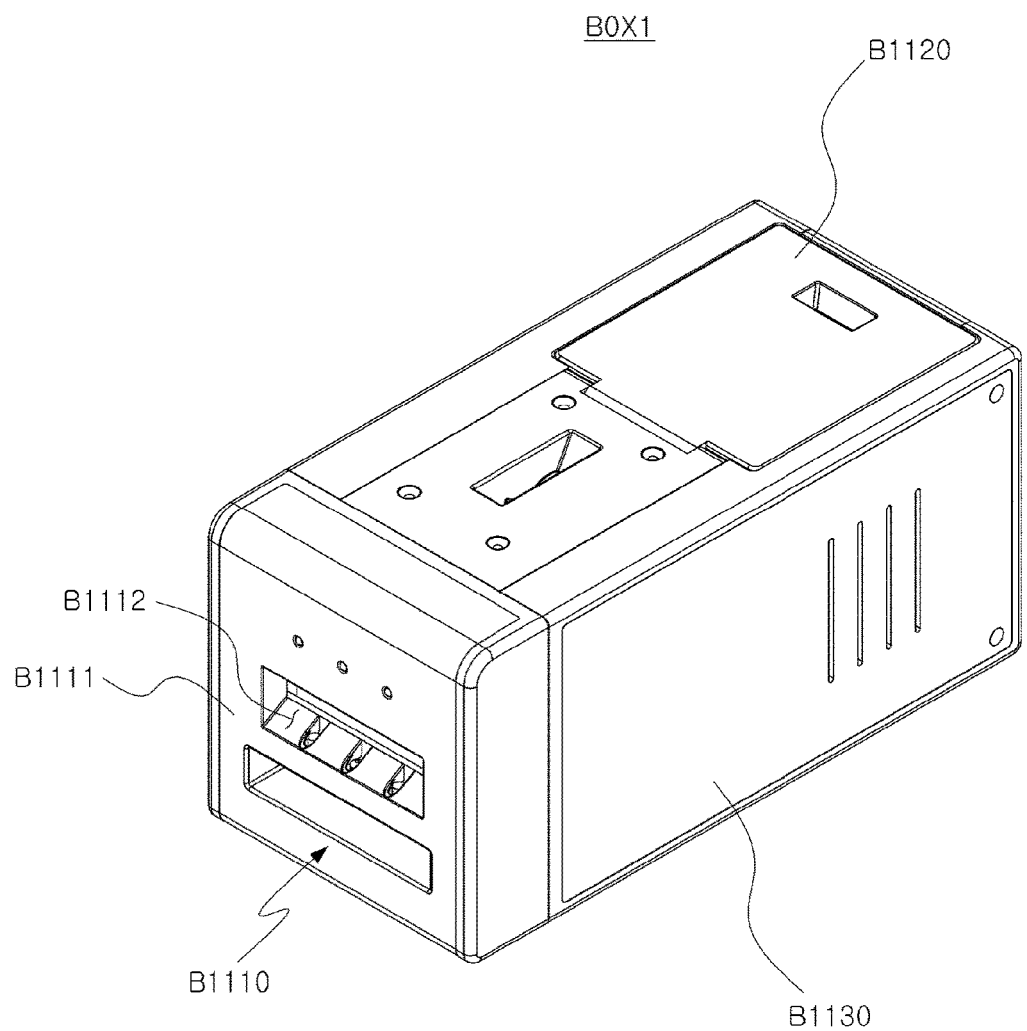

[FIG.48]
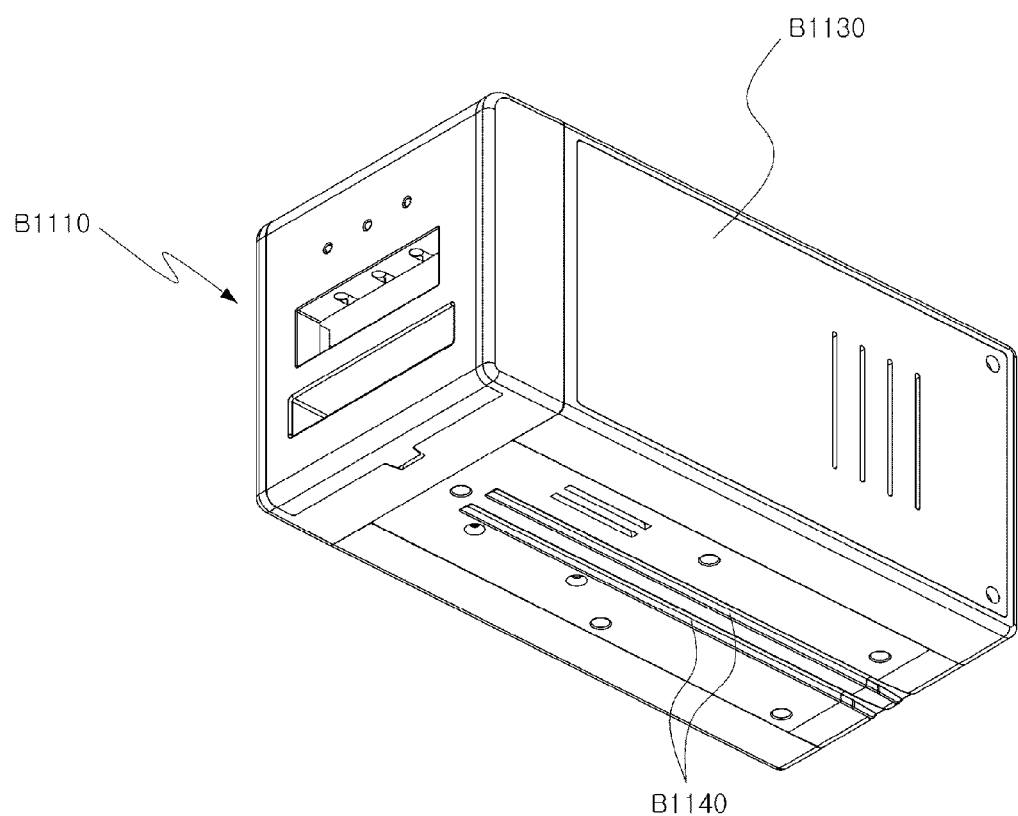

[FIG.49]
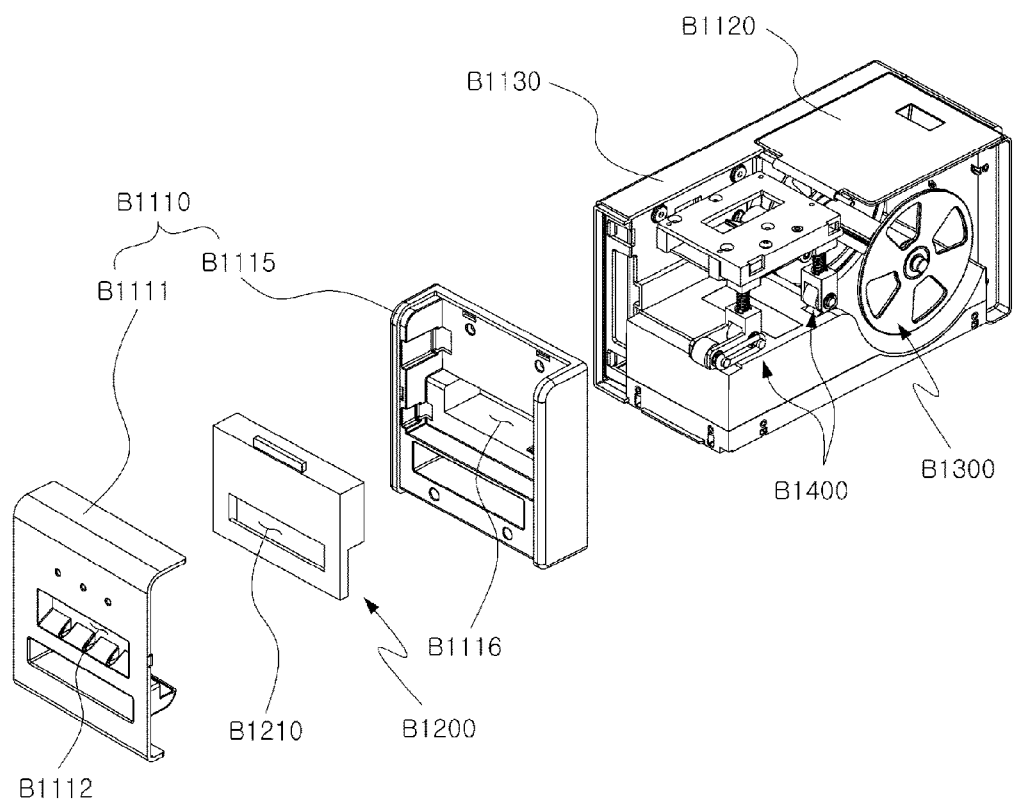

[FIG.50]
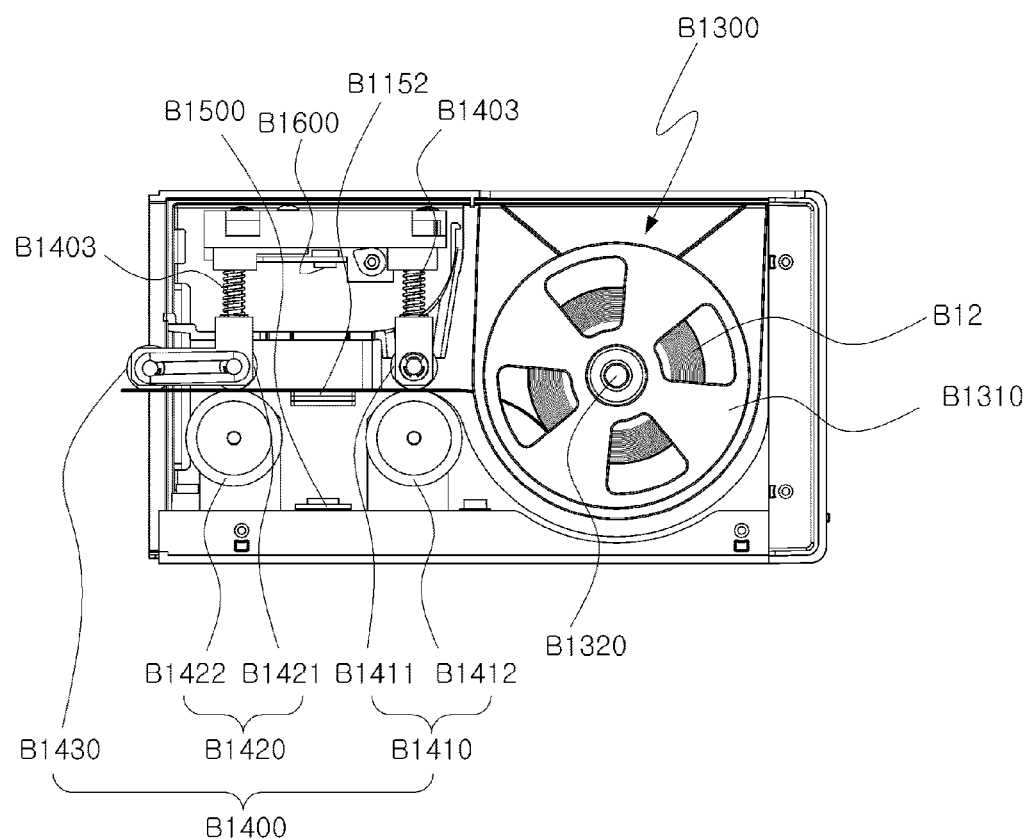

【FIG.51】
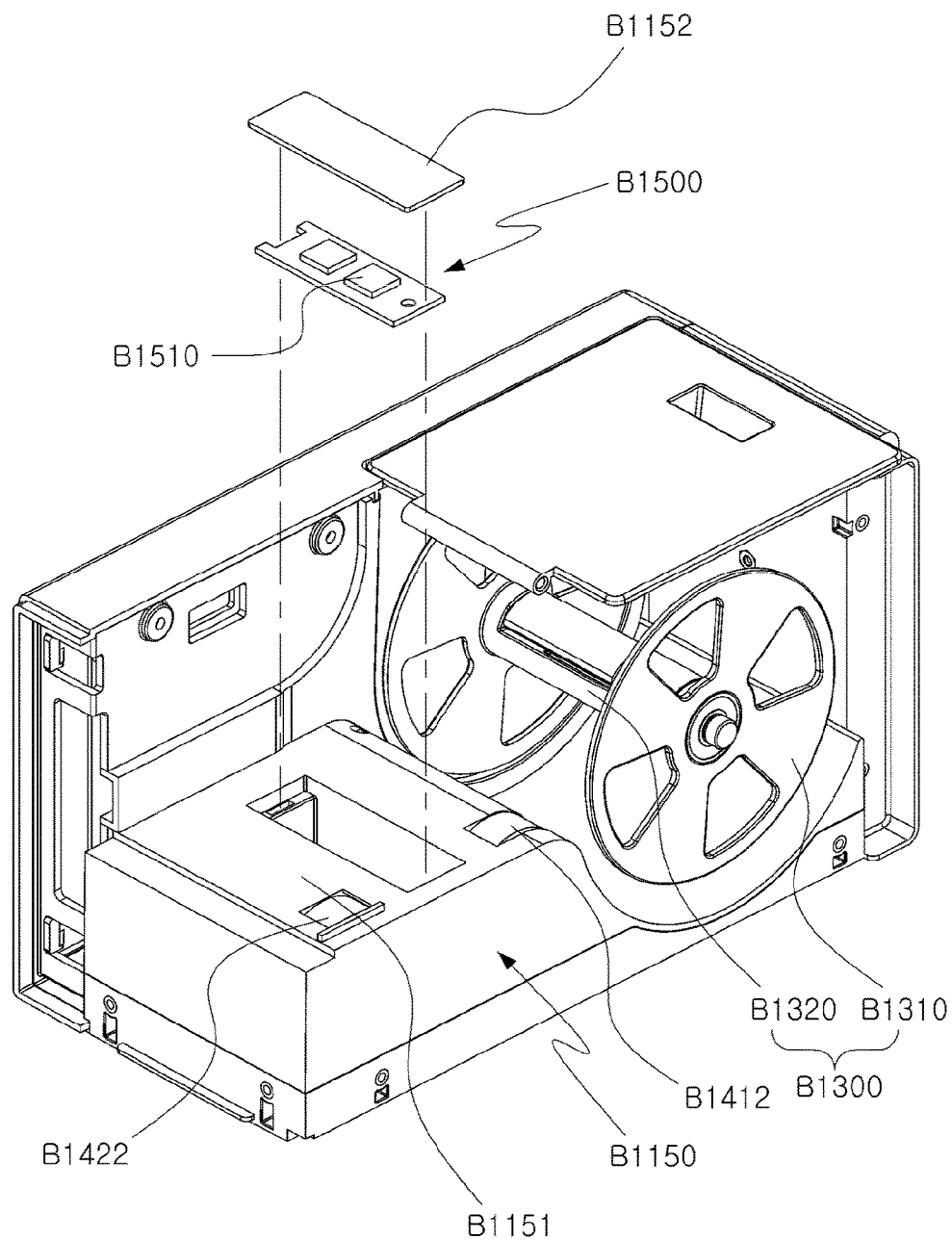

[FIG.52]
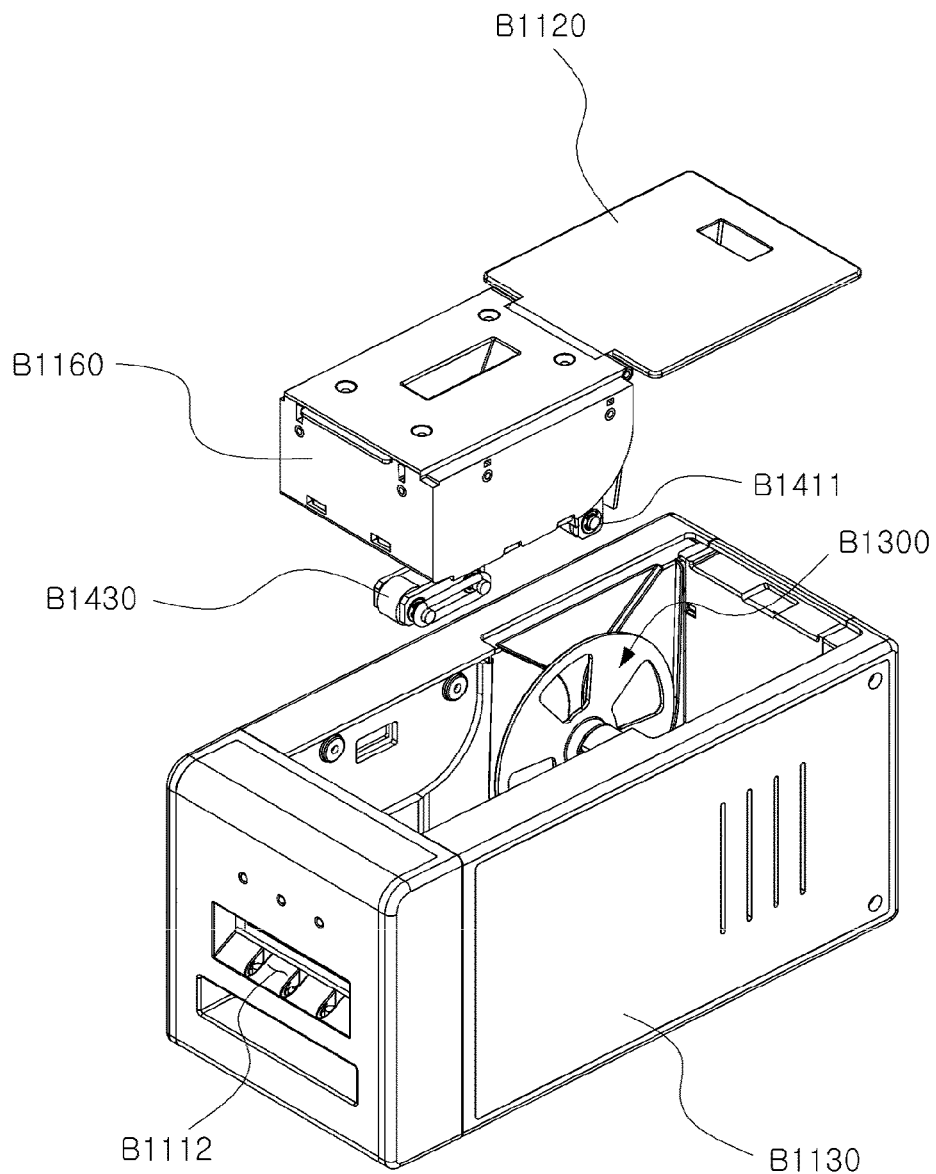

[FIG.53]
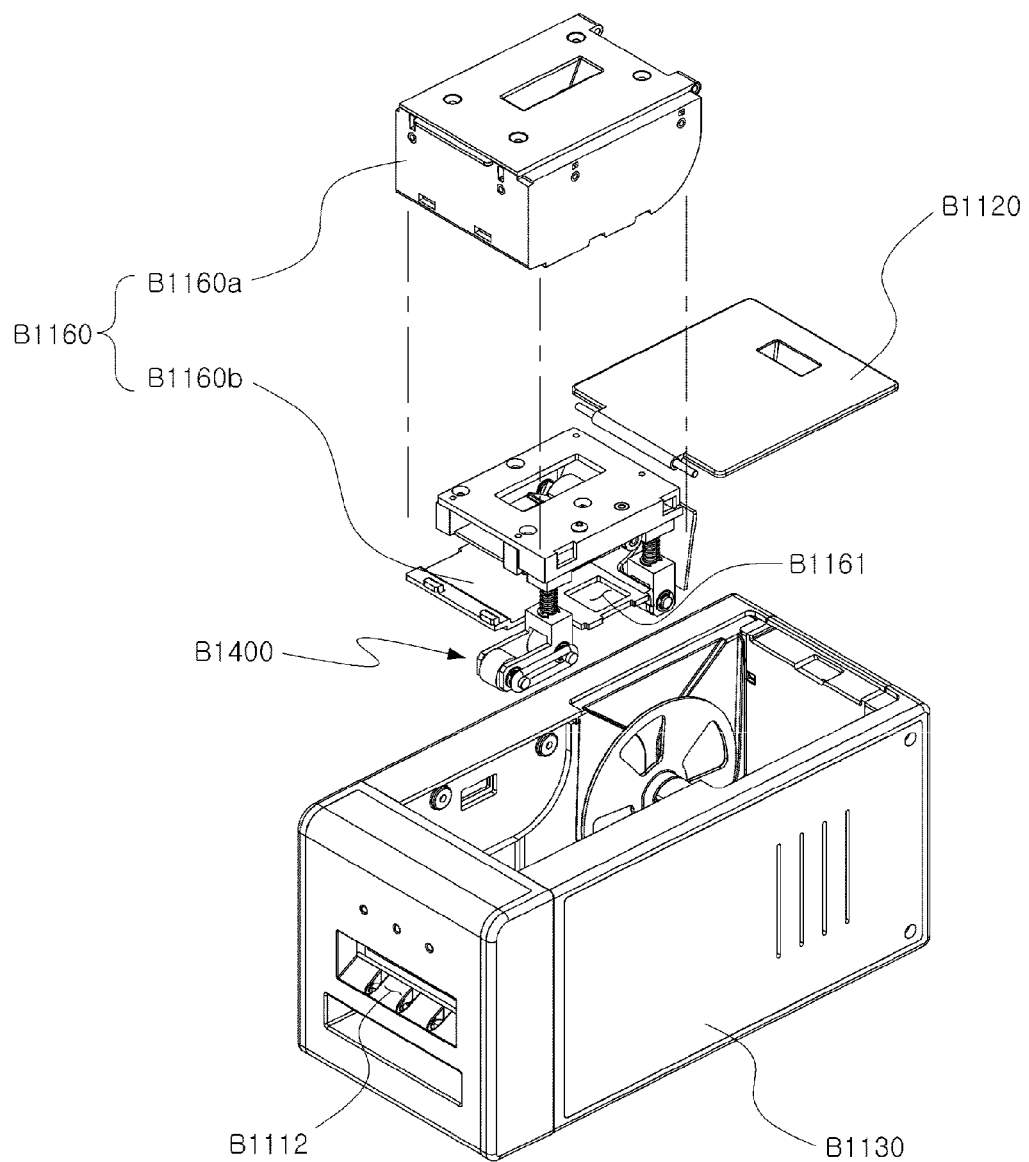

[FIG.54]
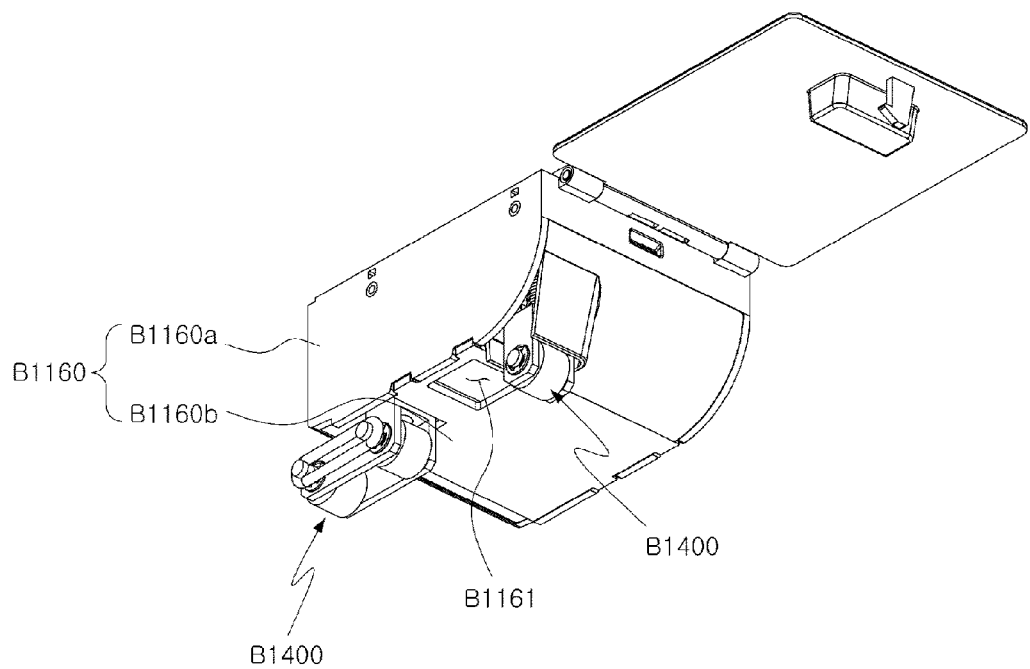

[FIG.55]
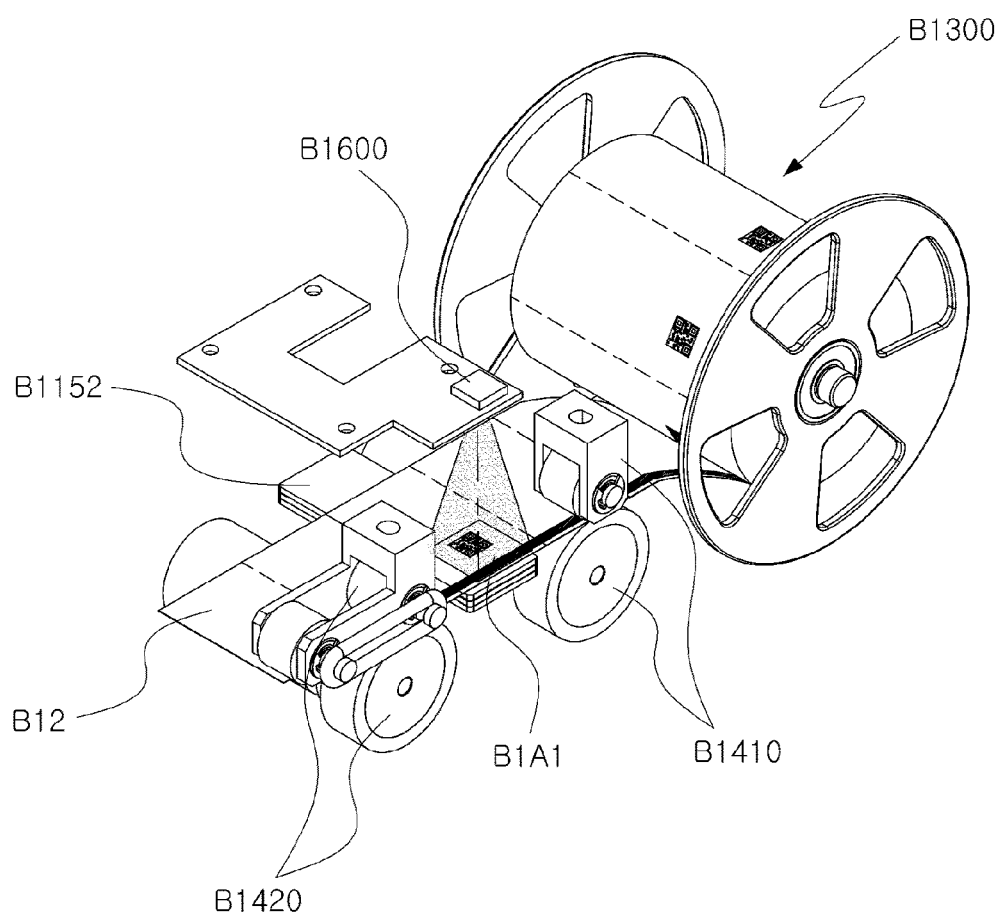

[FIG.56]
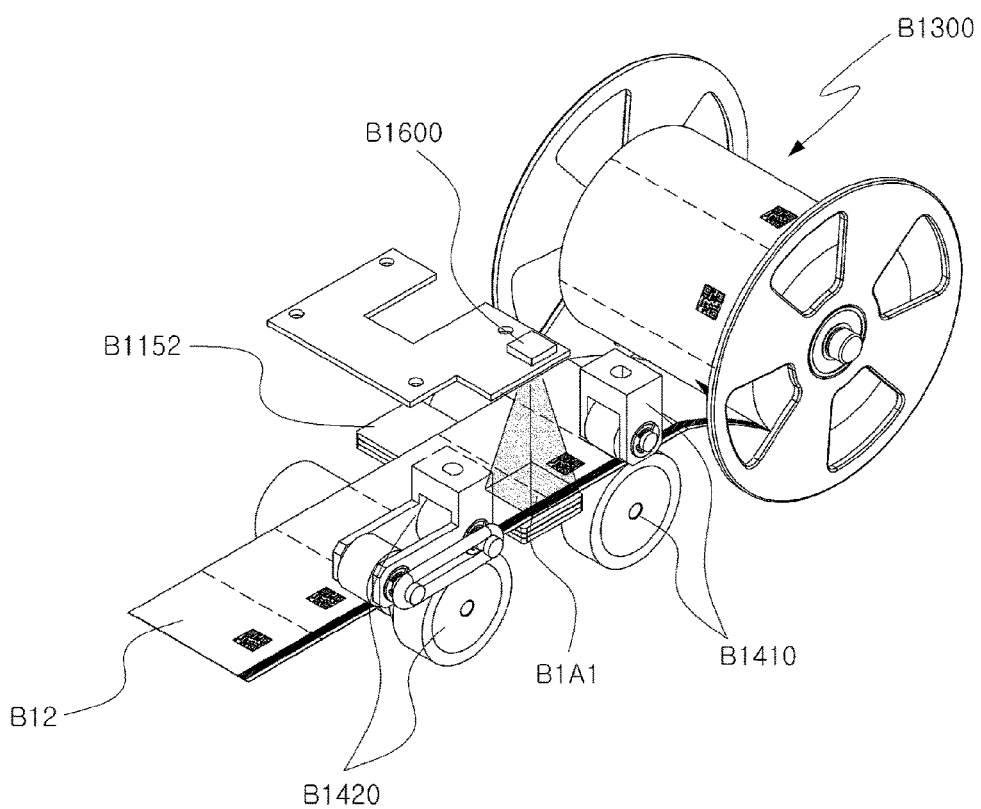
[FIG.57]
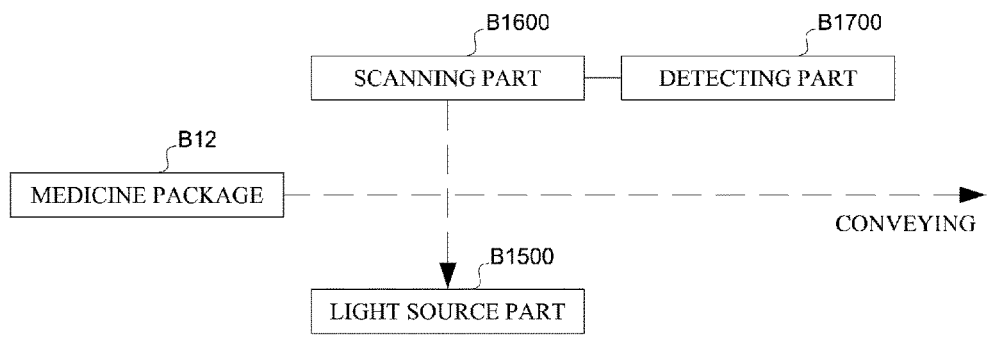

[FIG.58]
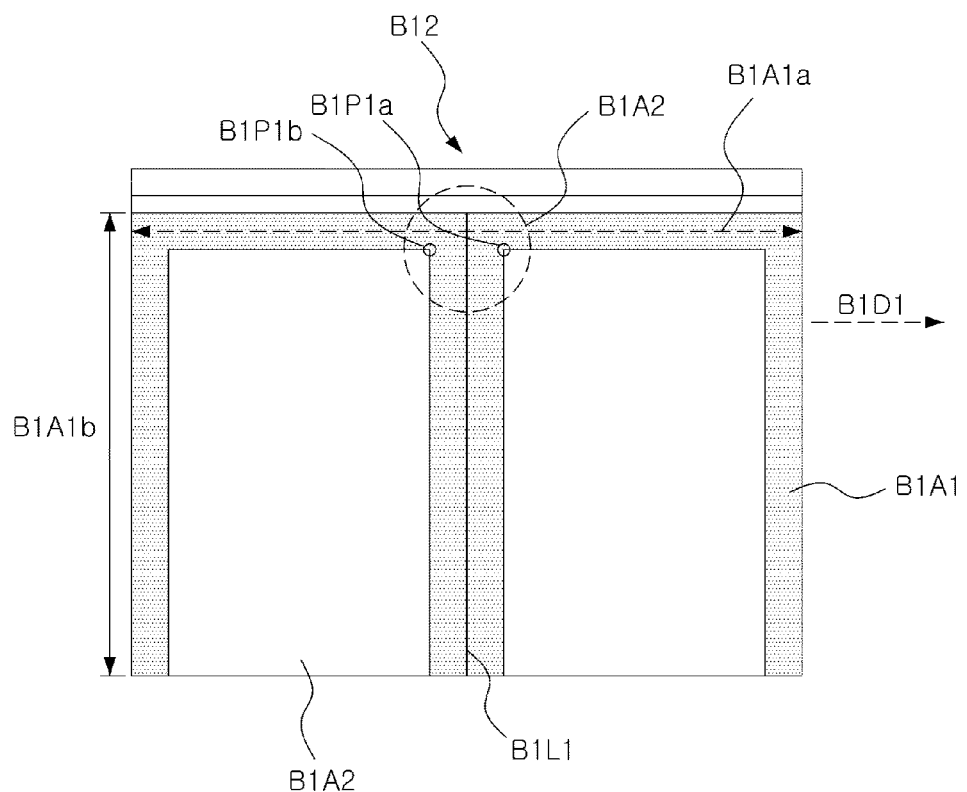

[FIG.59]
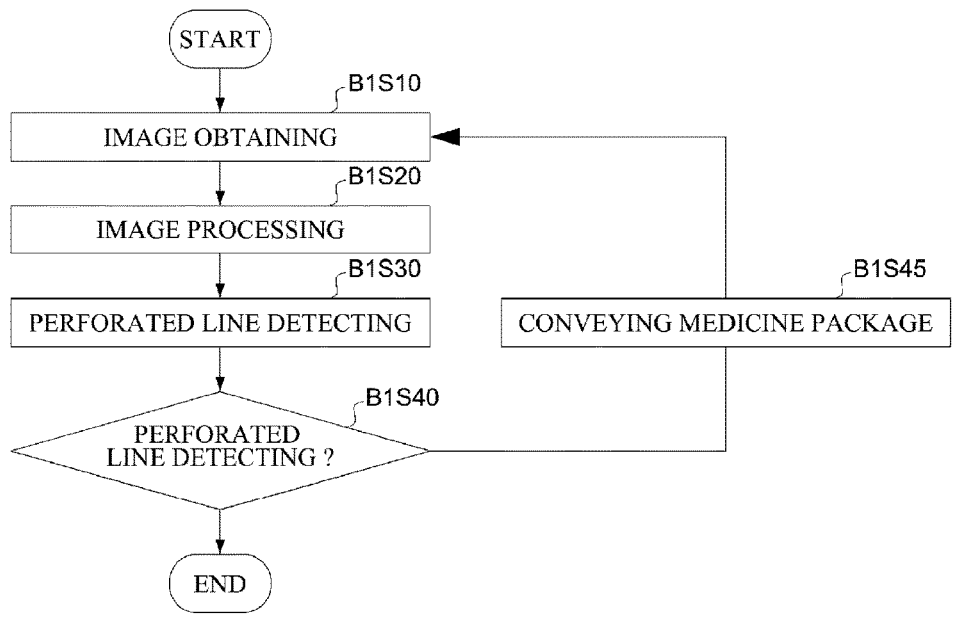
[FIG.60]
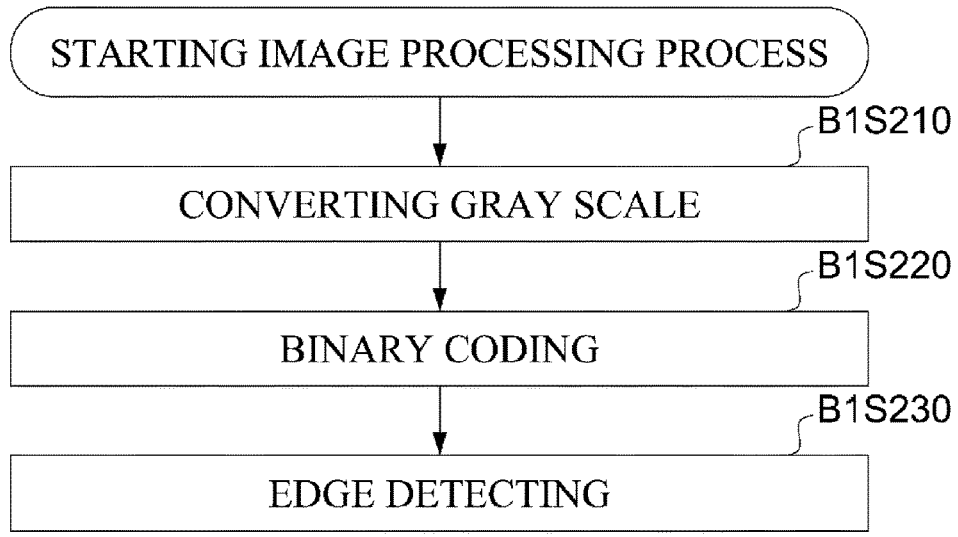

[FIG.61]
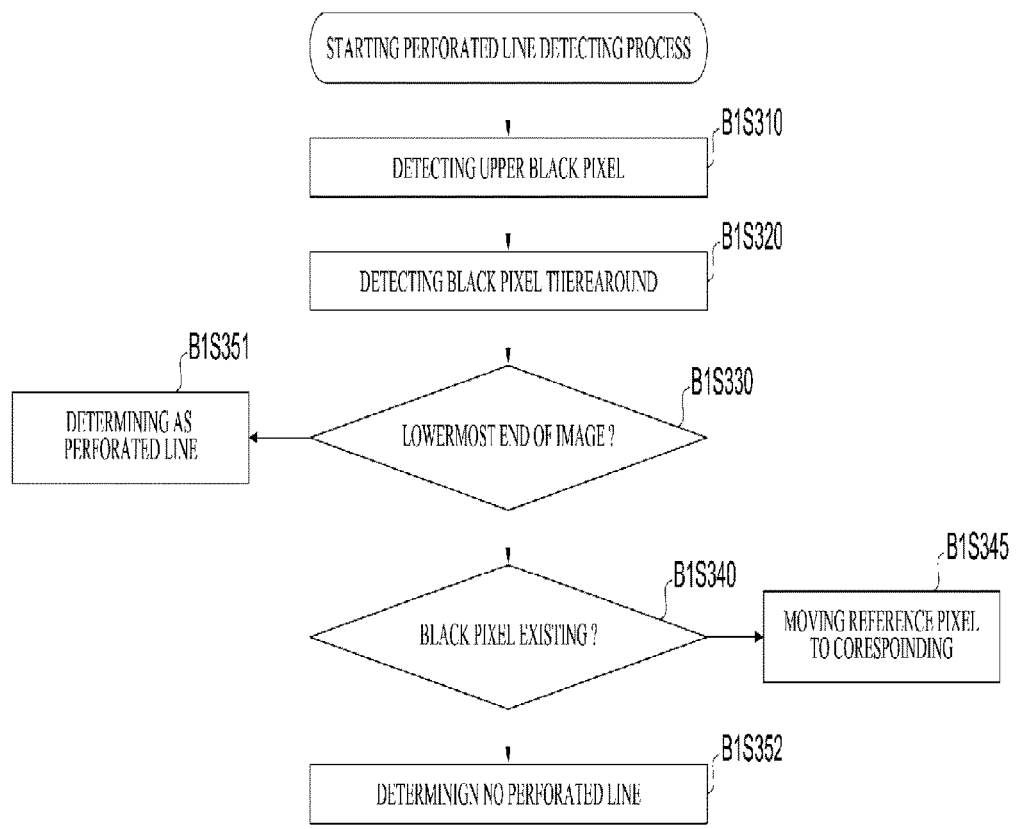

[FIG.62]
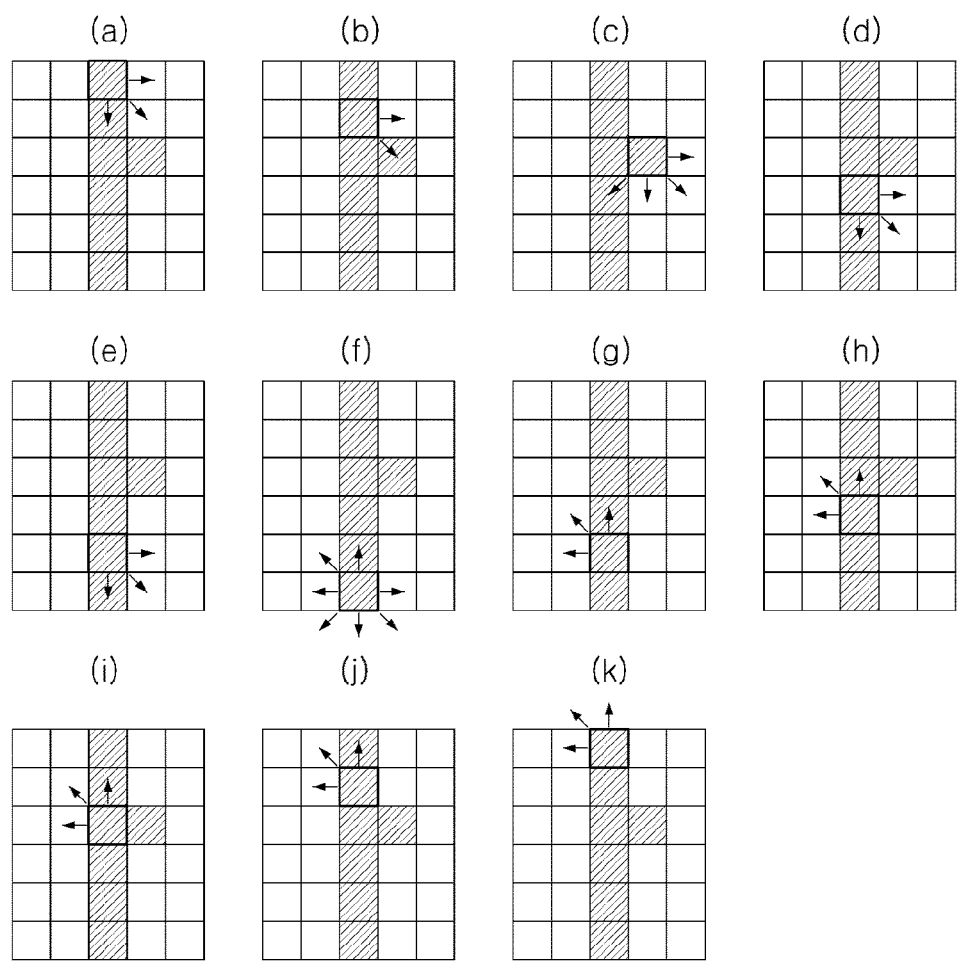

【FIG.63】
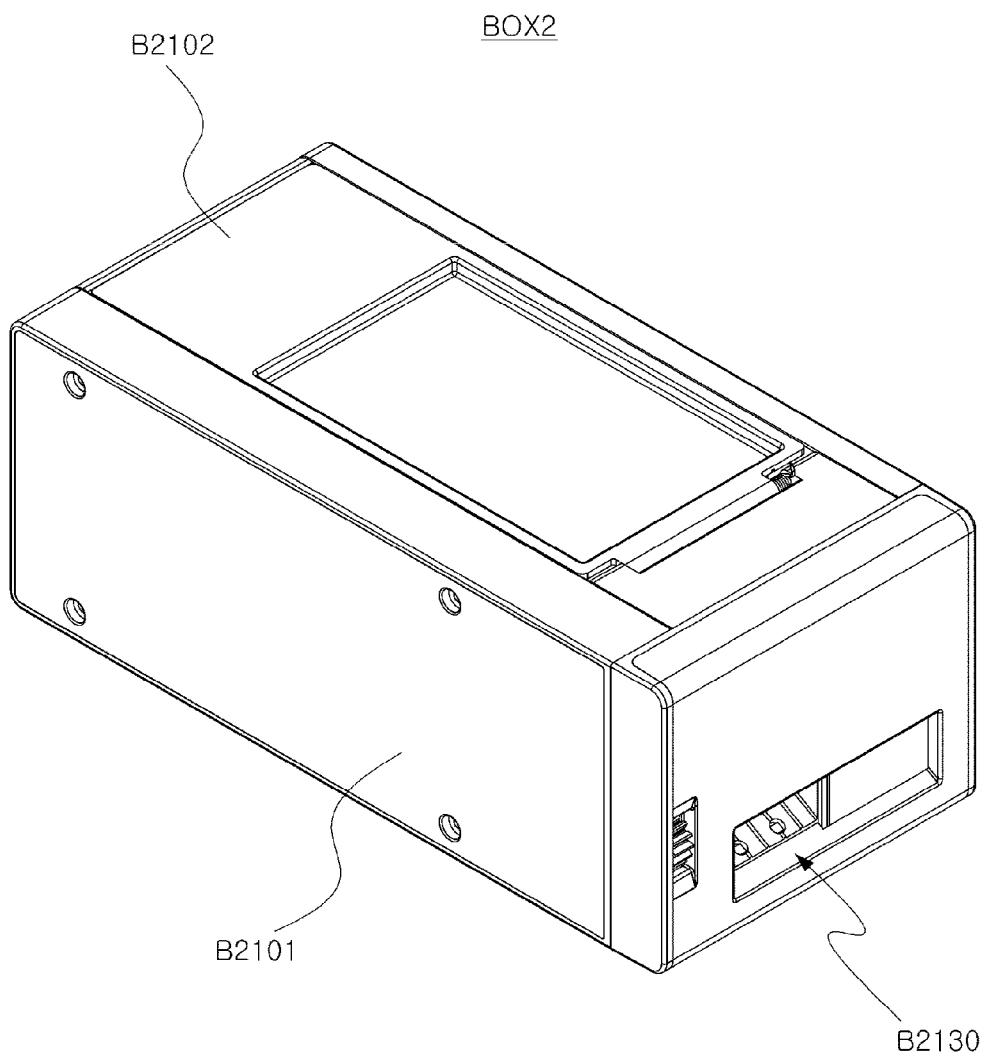

【FIG.64】
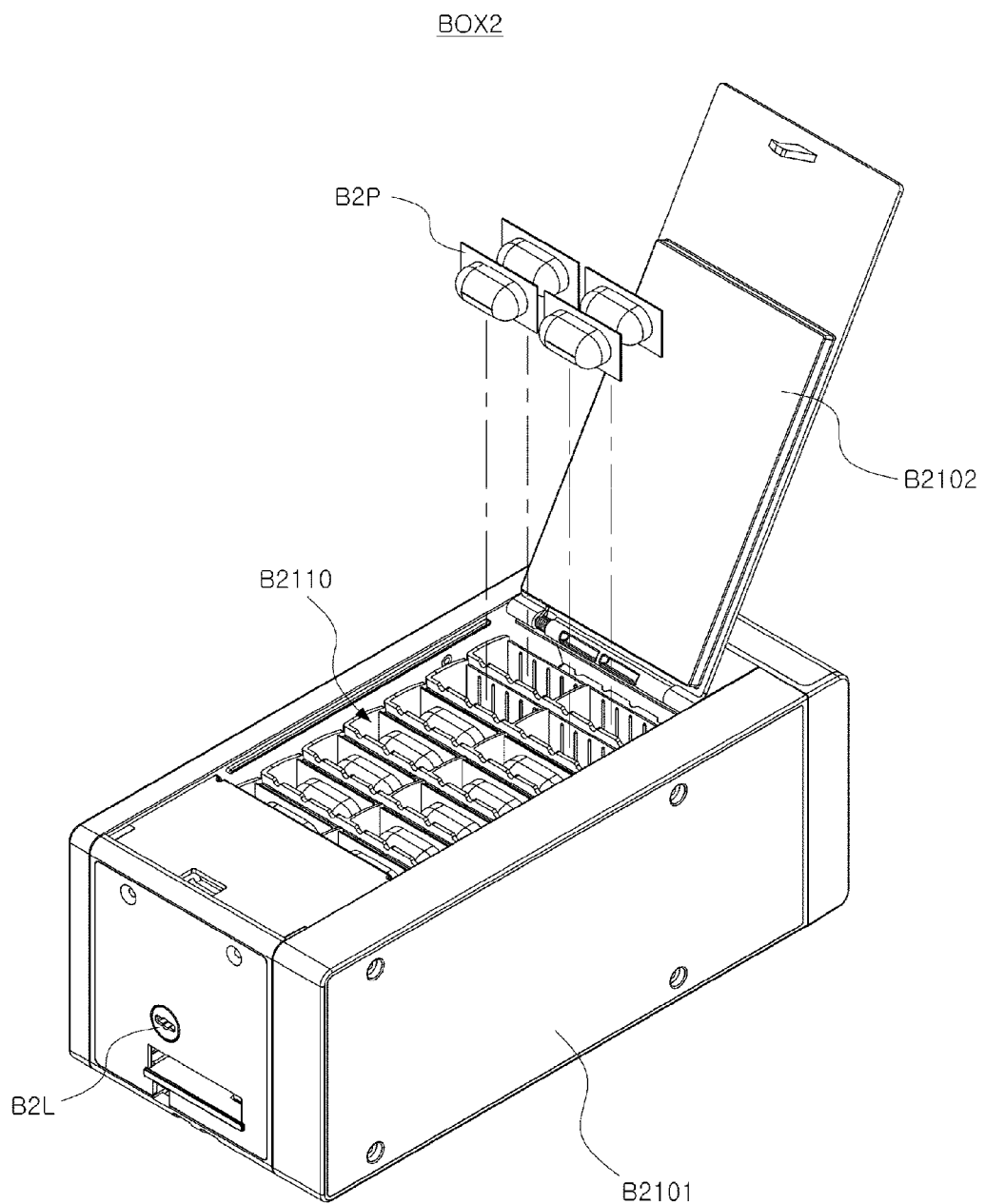

[FIG.65]
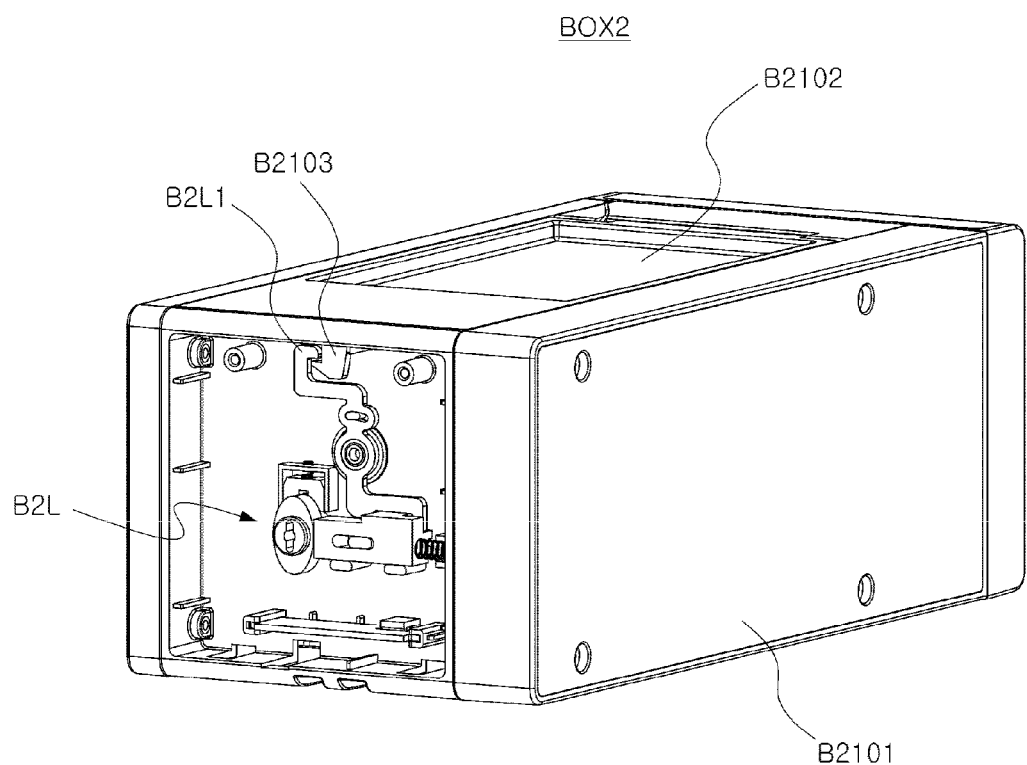

【FIG.66】
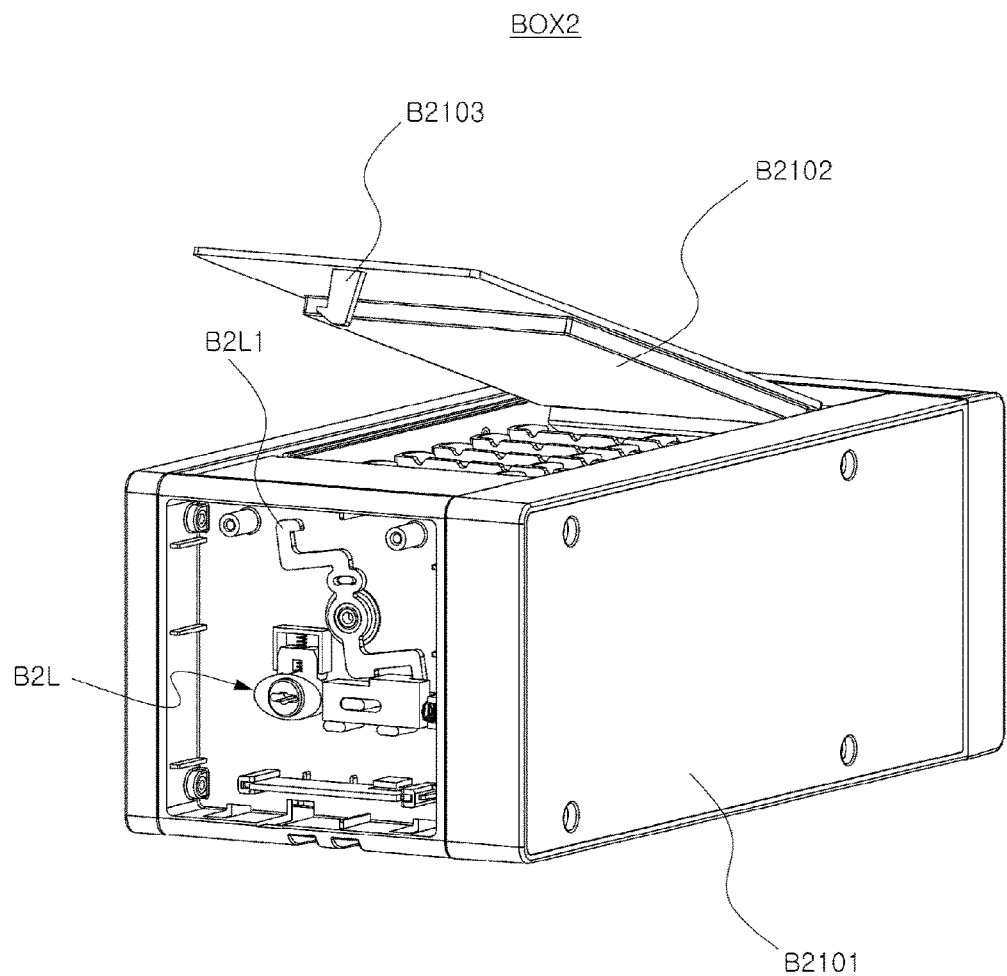

[FIG.67]
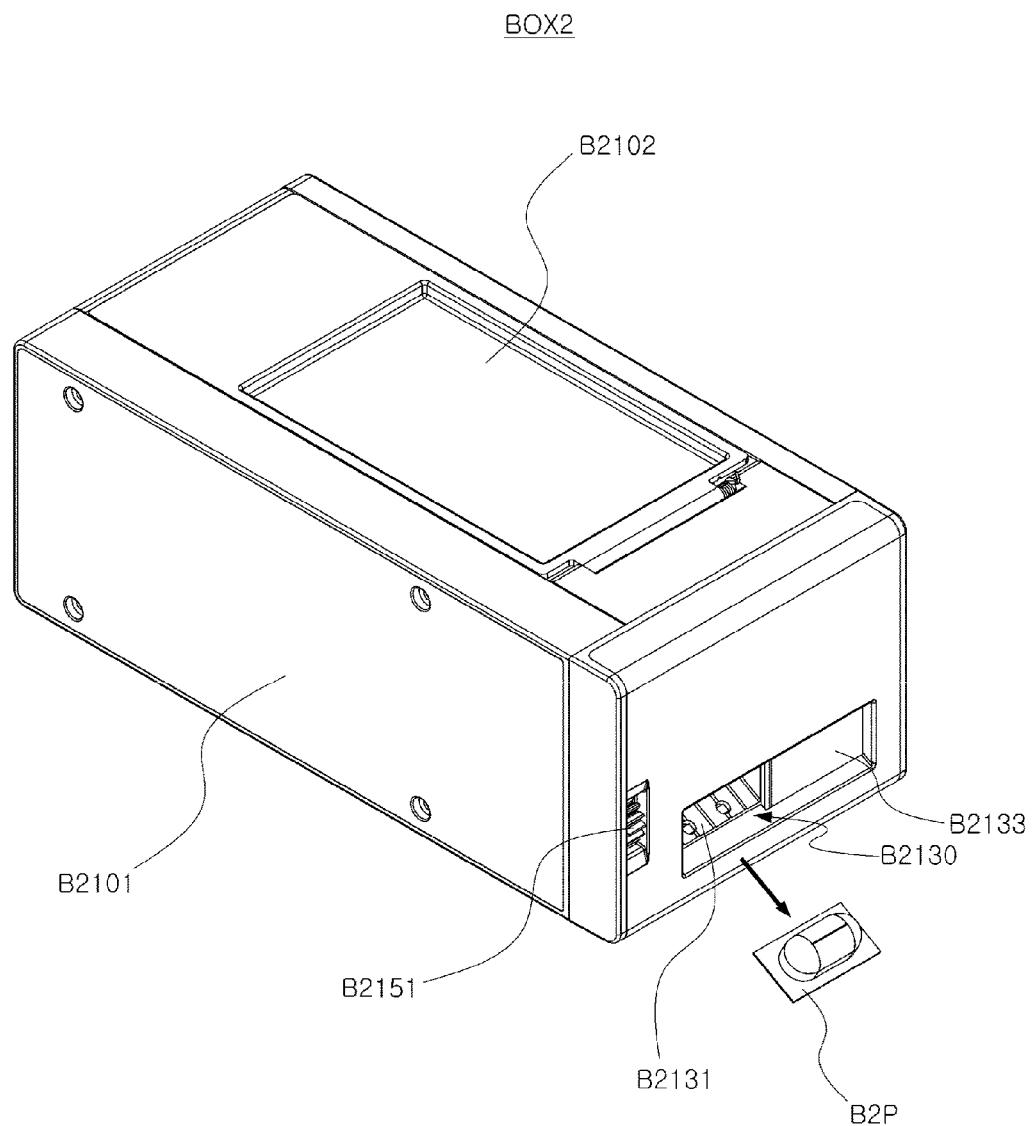

[FIG.68]
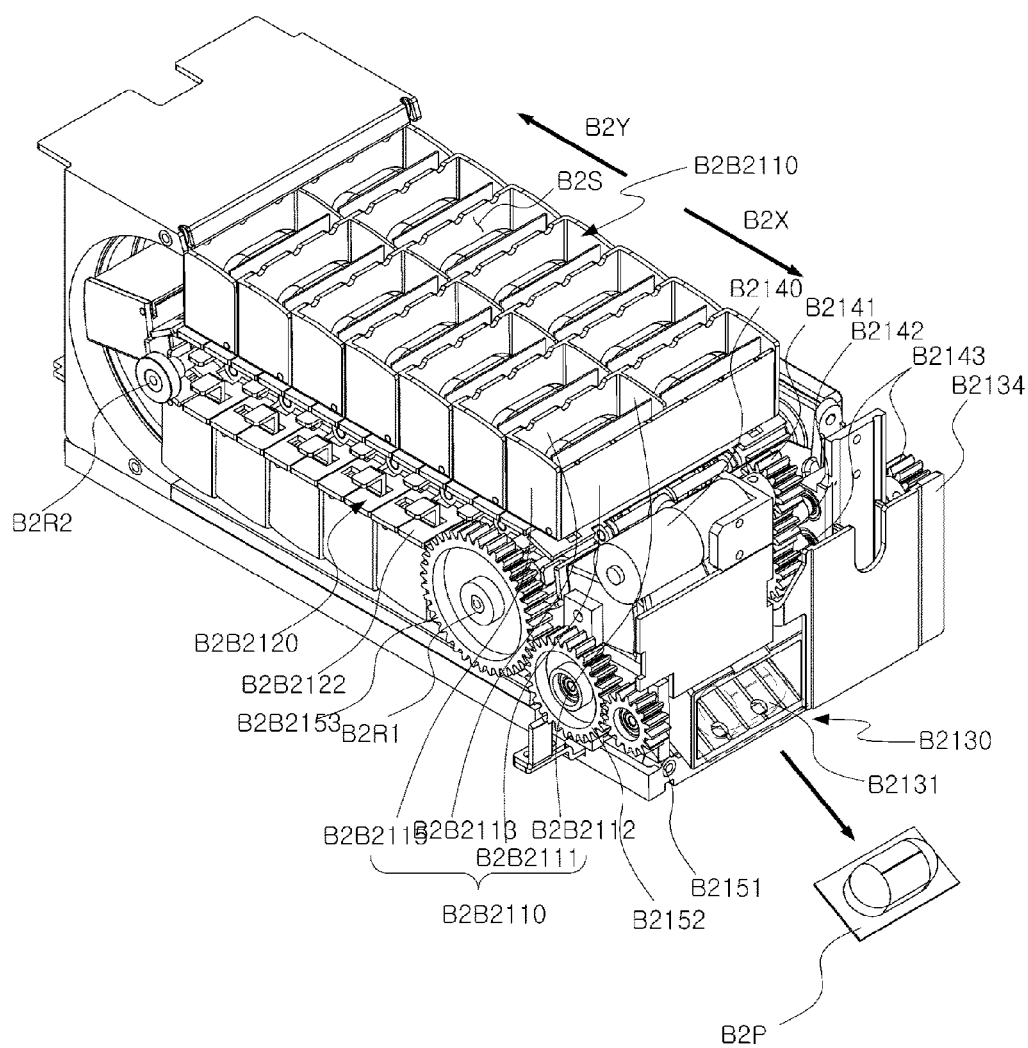

[FIG.69]
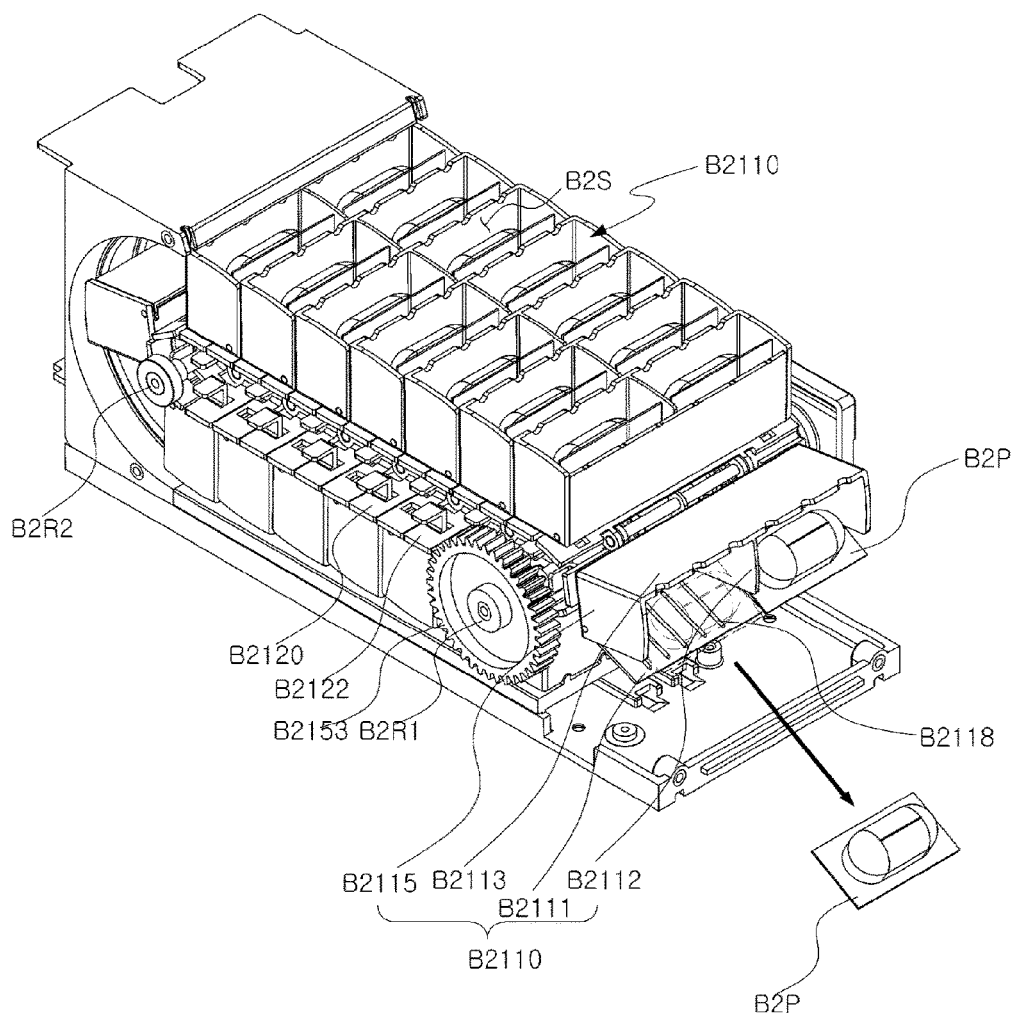

[FIG.70]
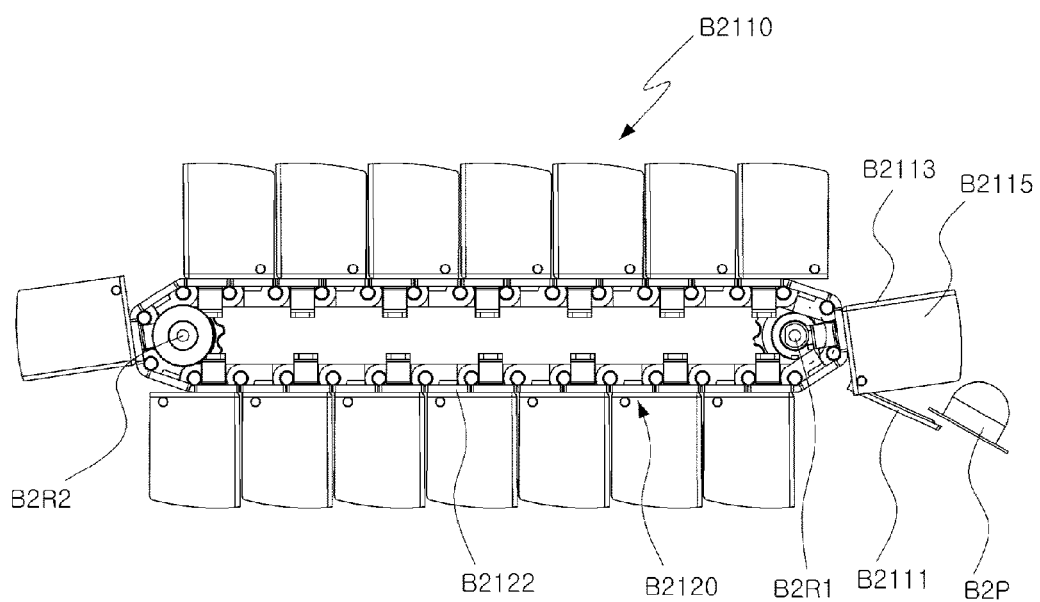

【FIG.71】
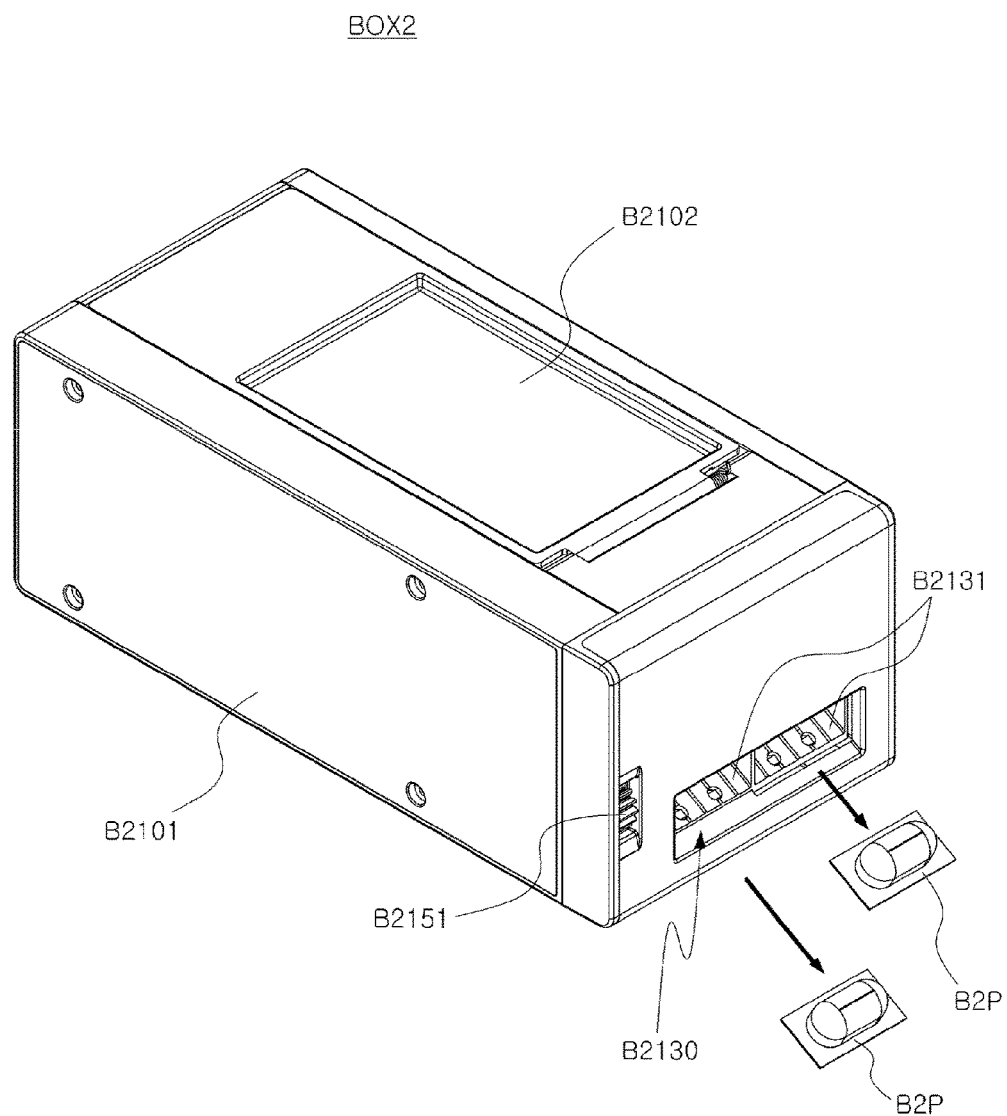

[FIG.72]
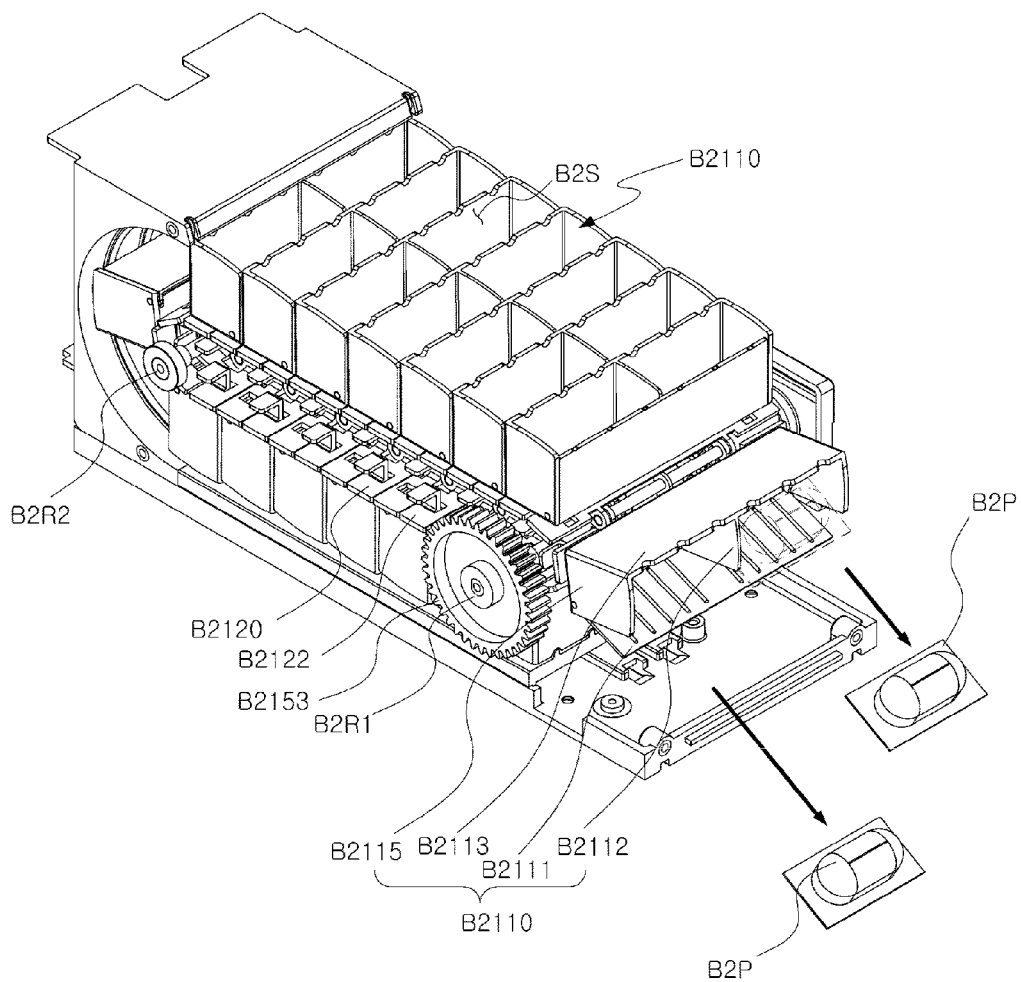

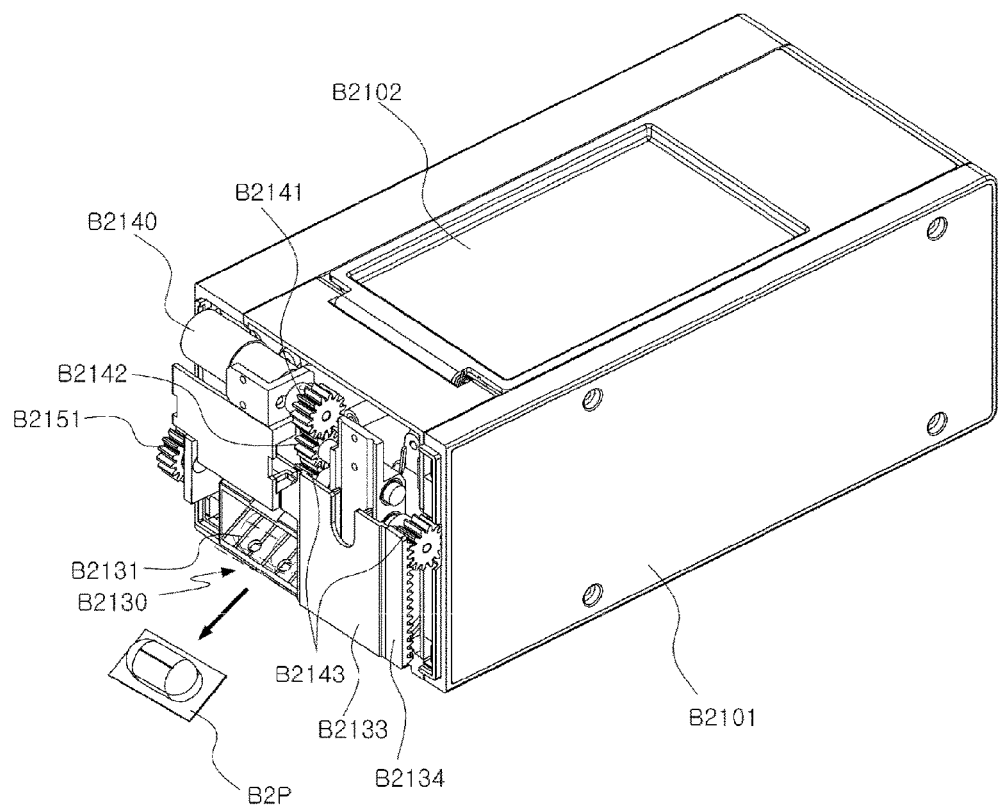
[FIG.73]

[FIG.74]
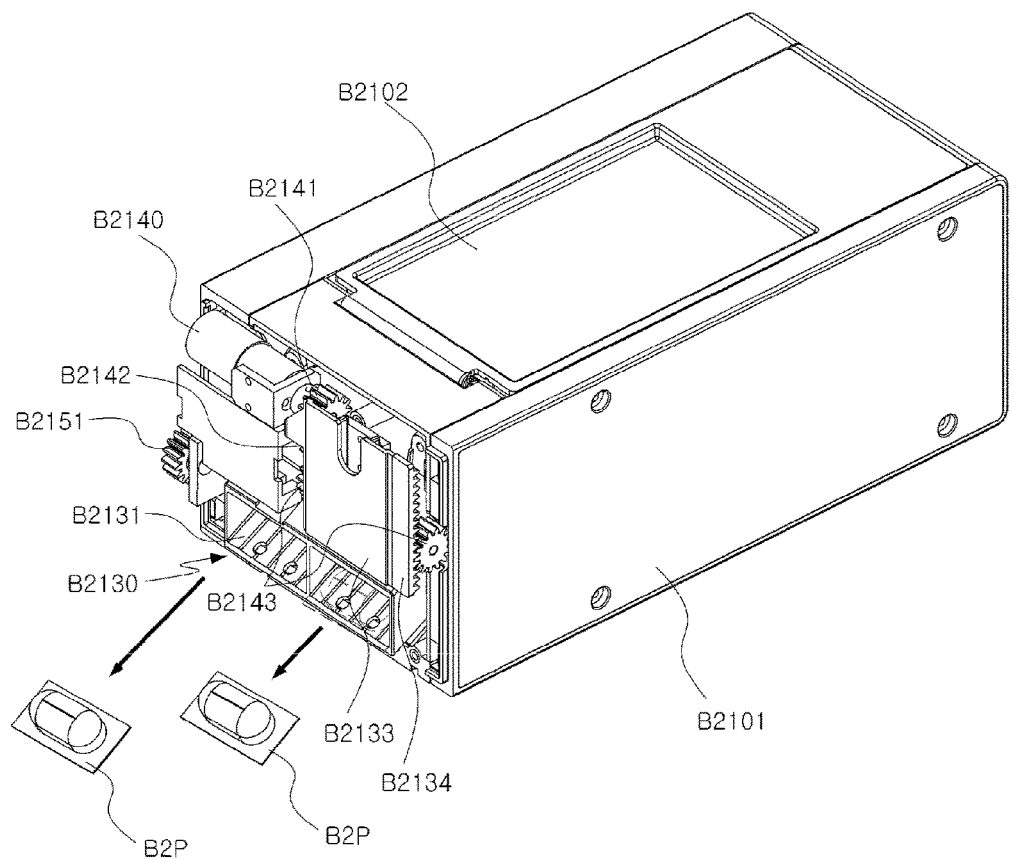

[FIG.75]
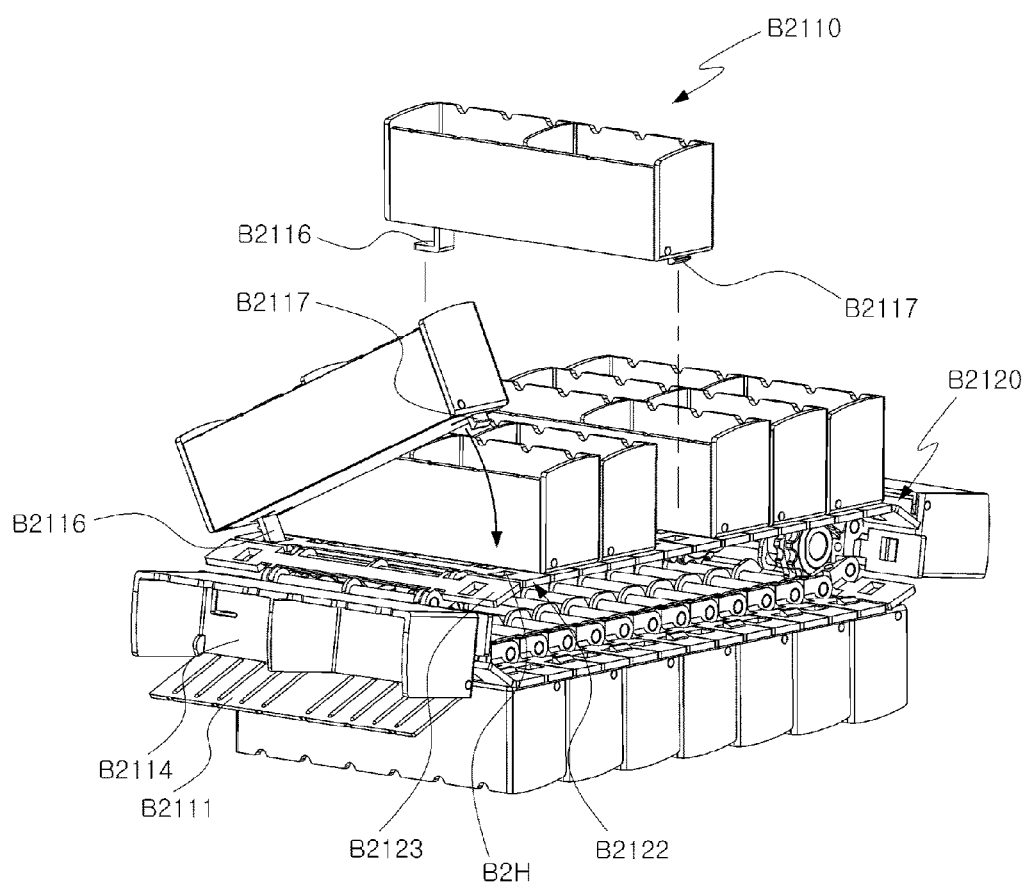

【FIG.76】
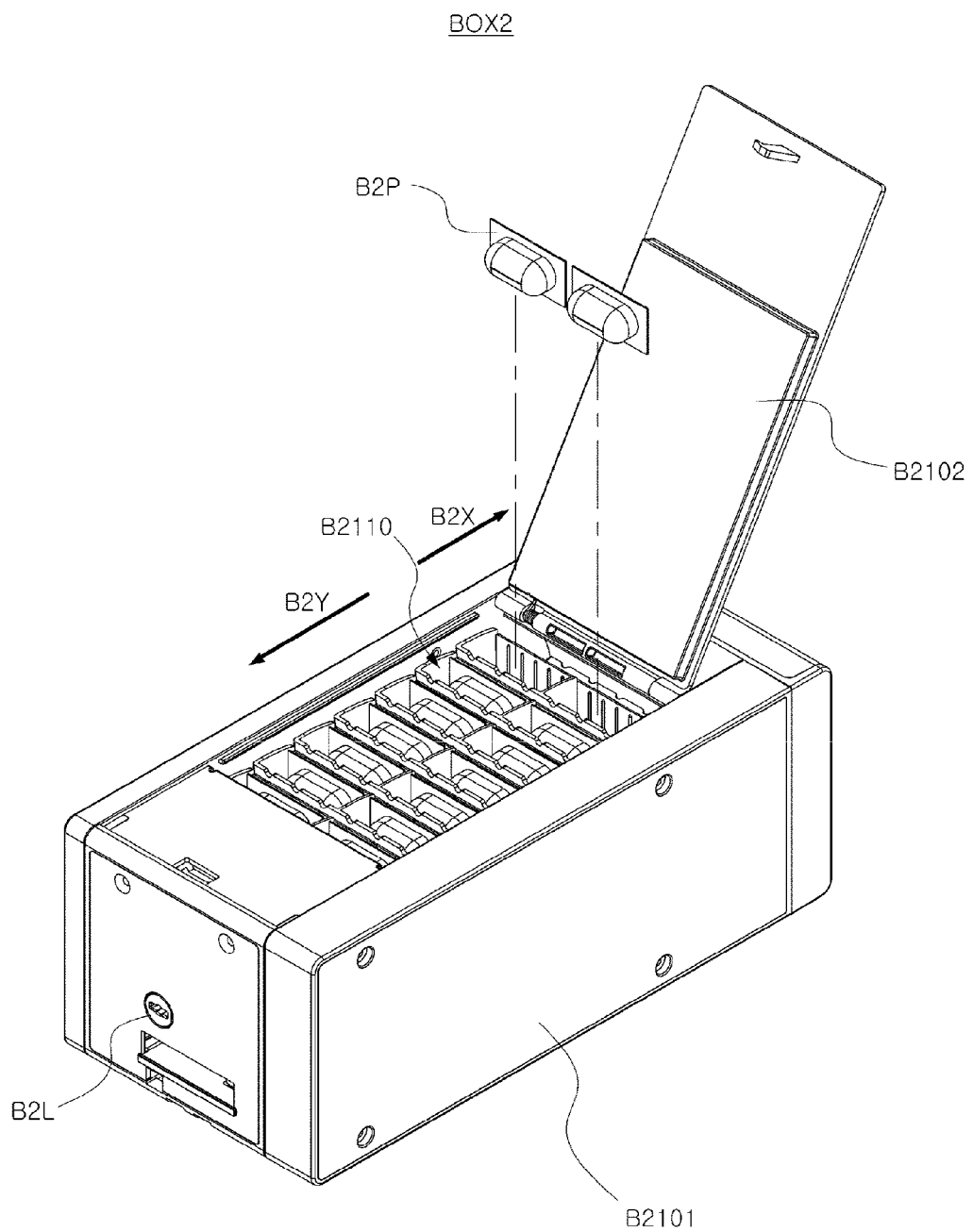

【FIG.77】
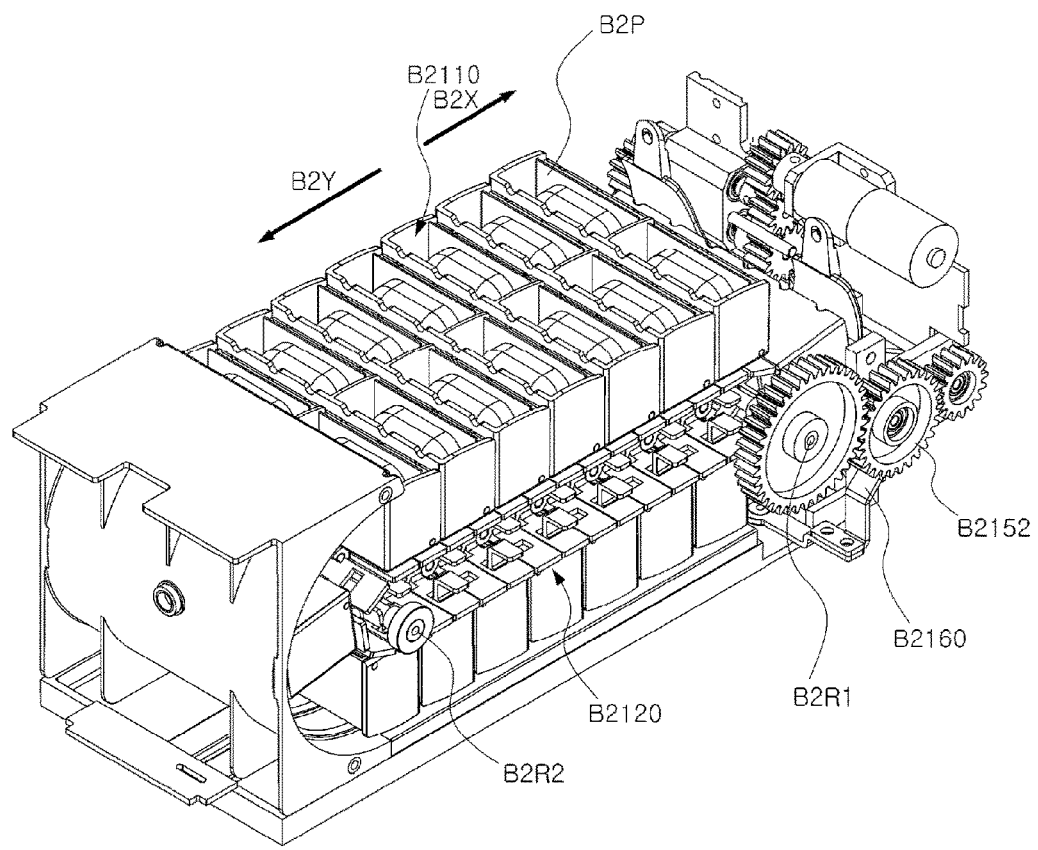

[FIG.78]
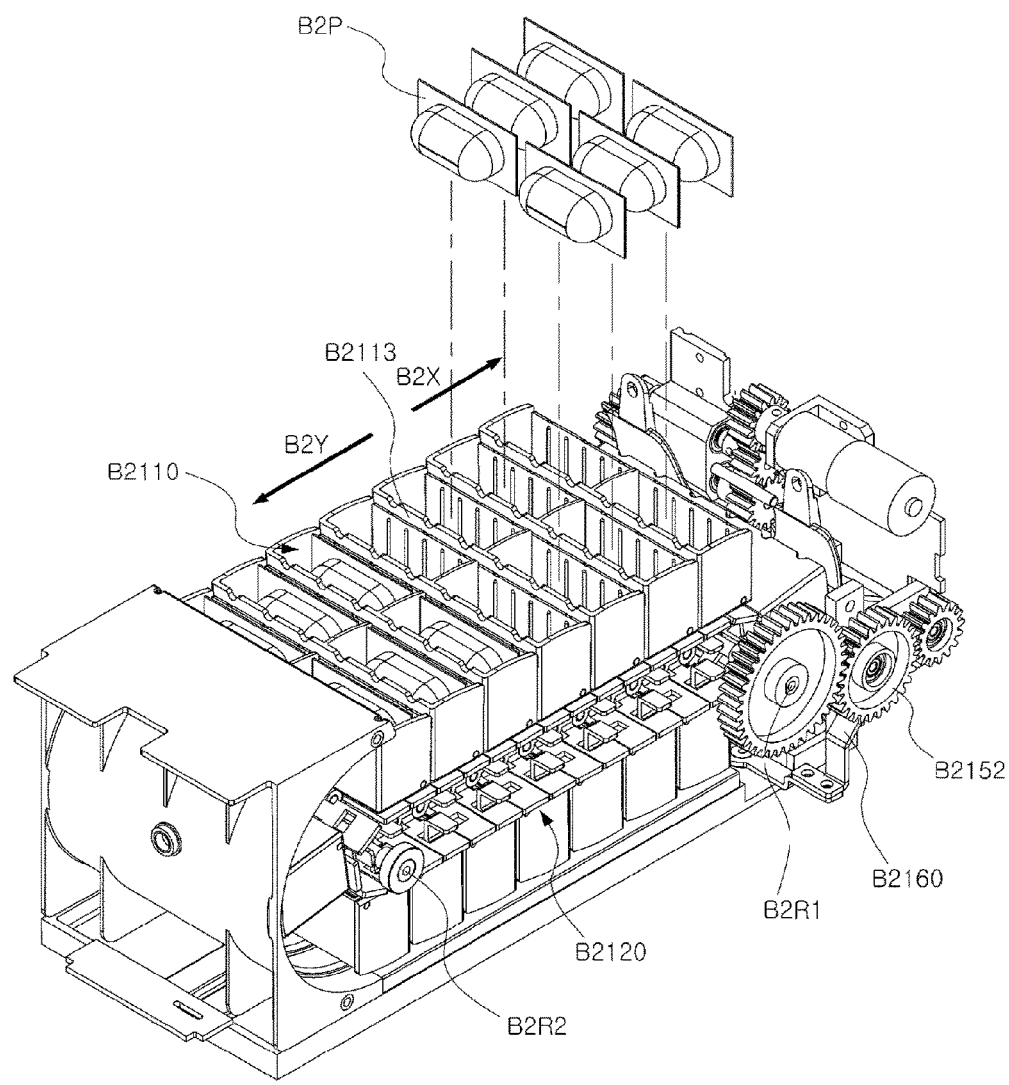

[FIG.79]
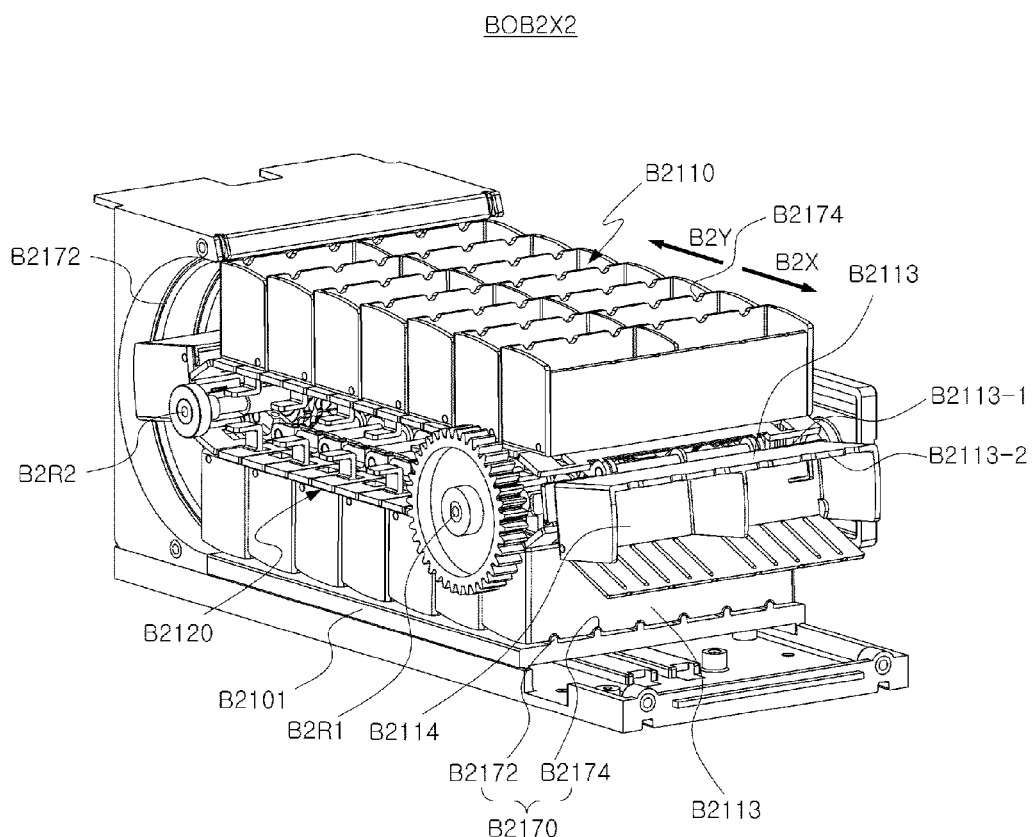

[FIG.80]
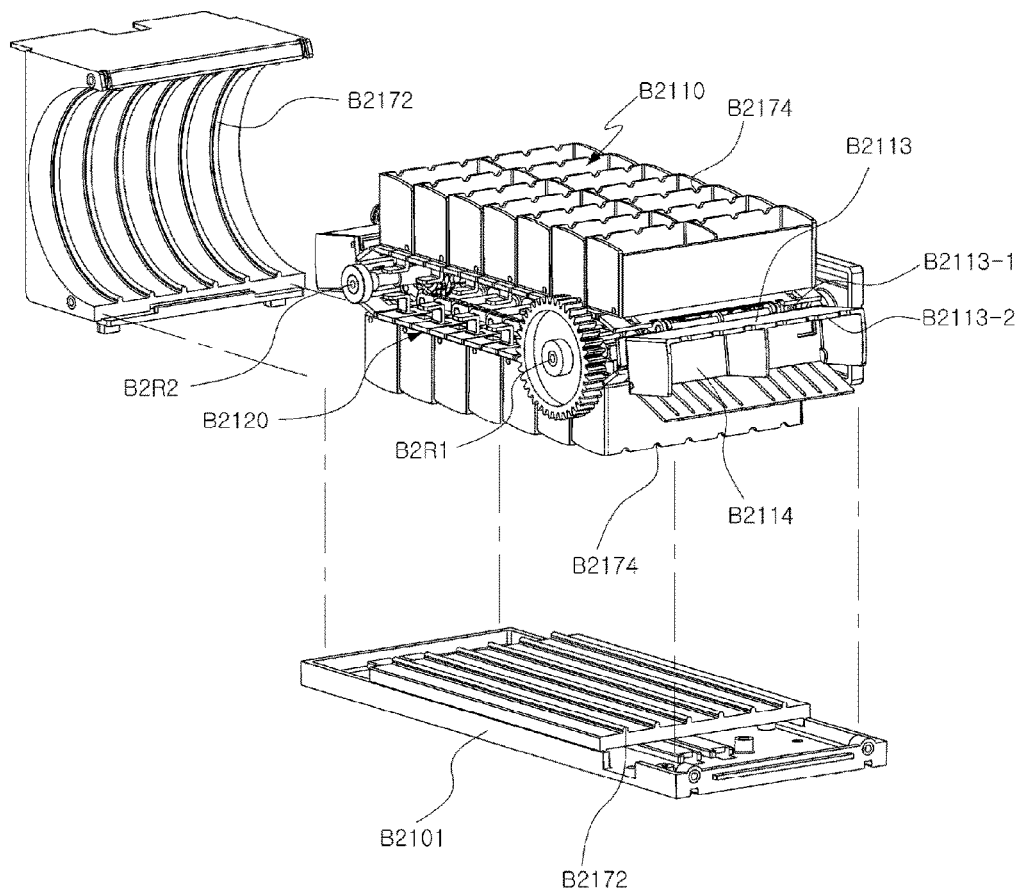

【FIG.81】
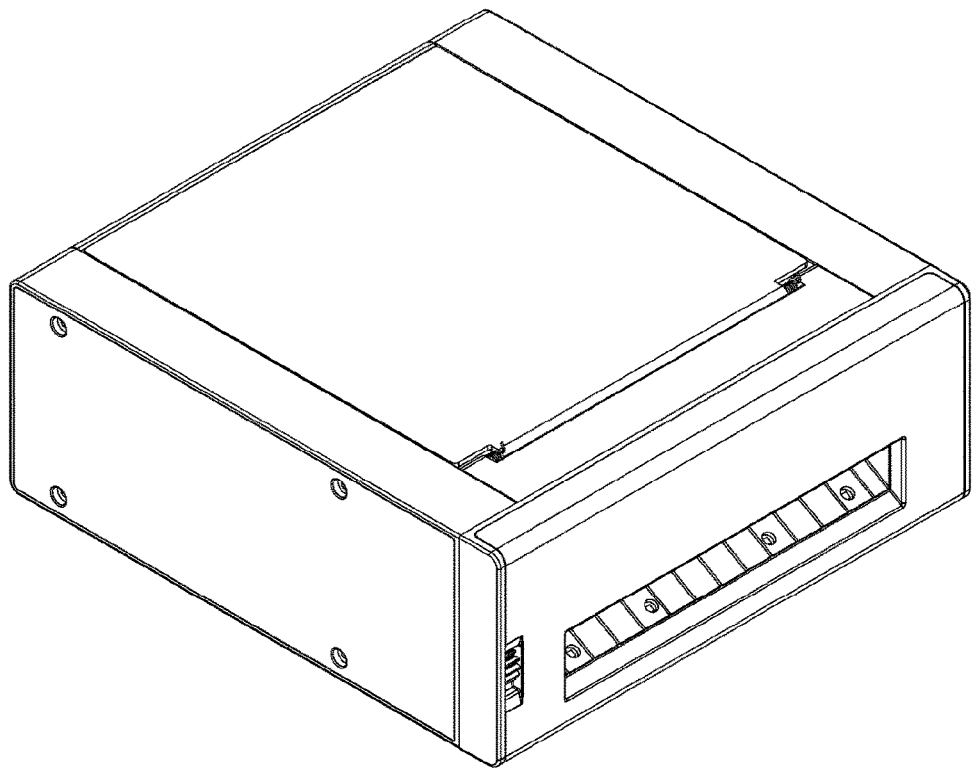

【FIG.82】
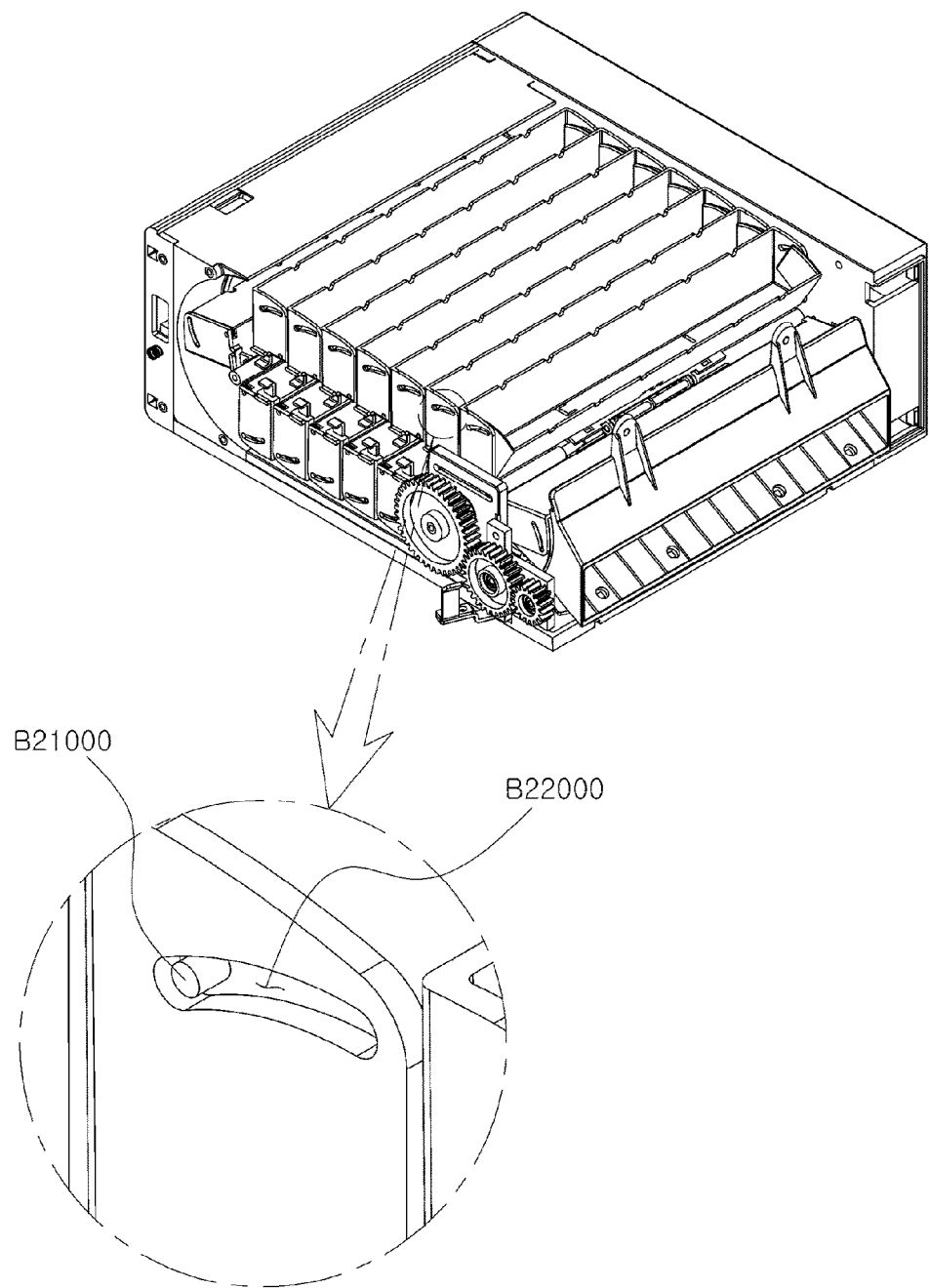

【FIG.83】
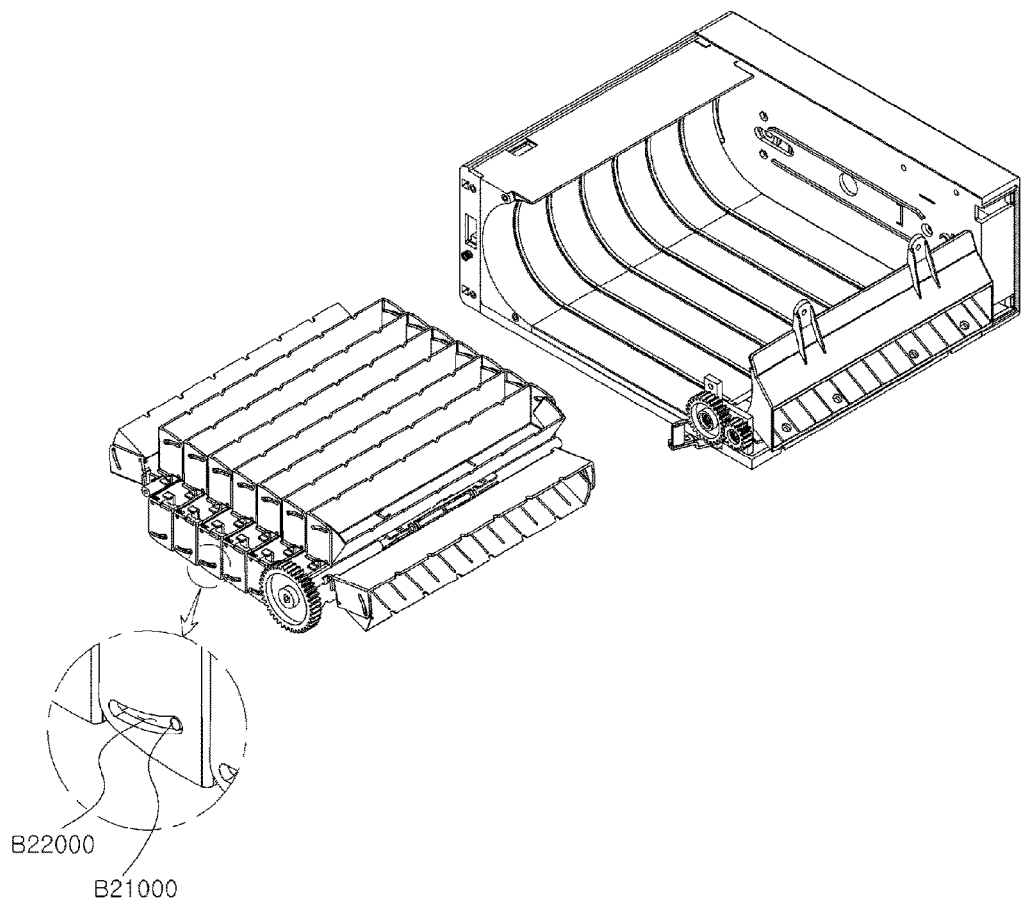

【FIG.84】
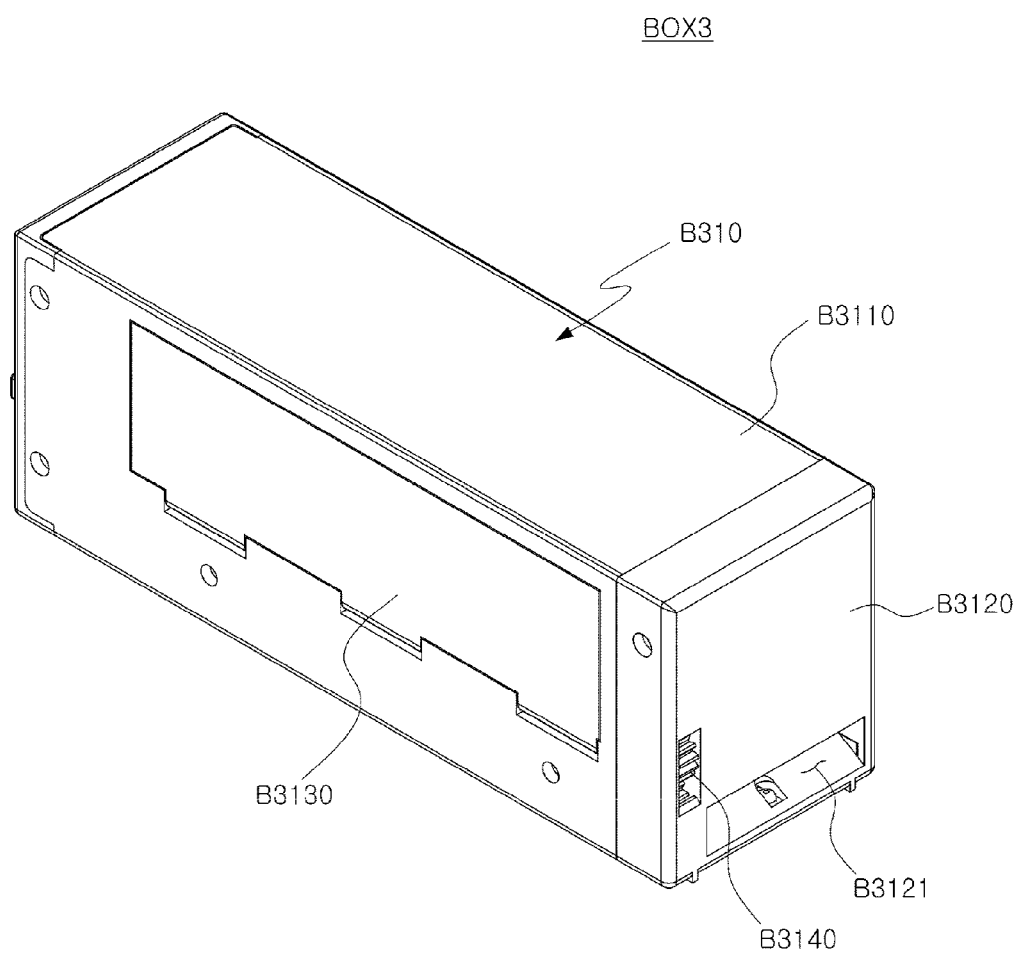

【FIG.85】
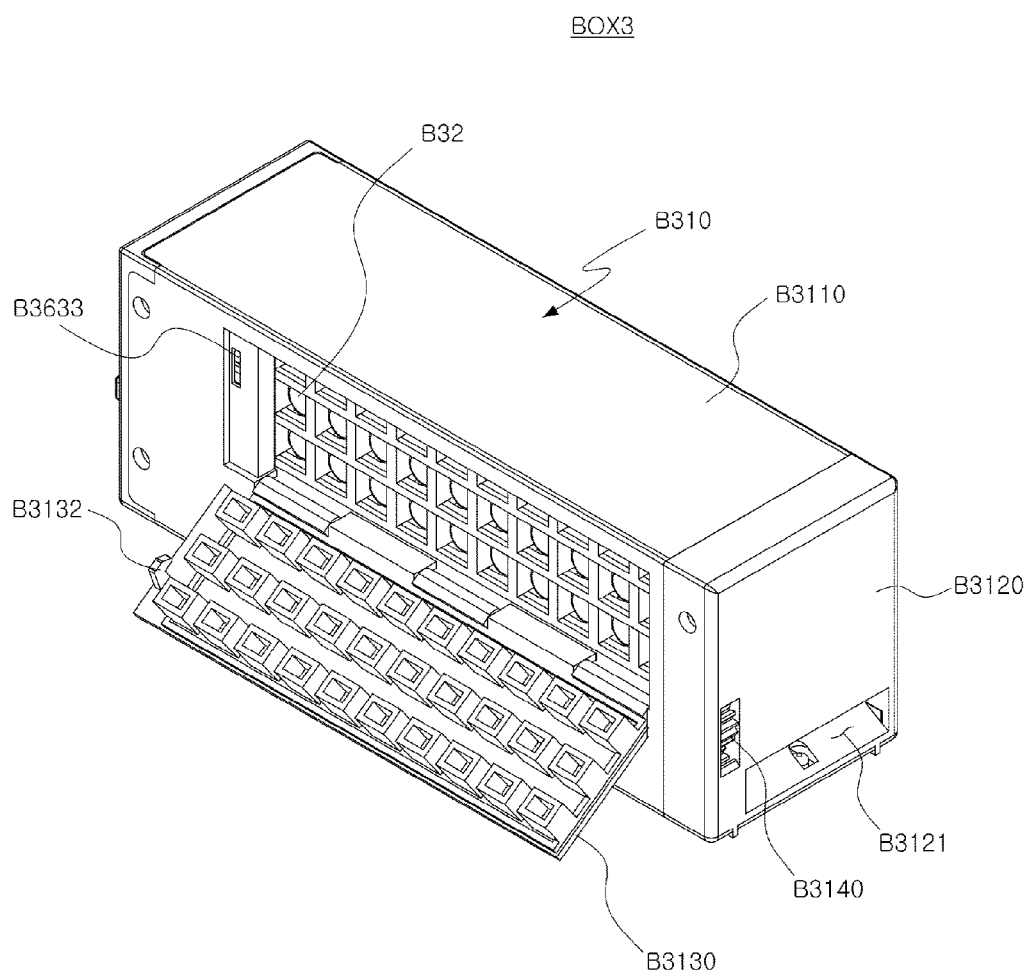

[FIG.86]
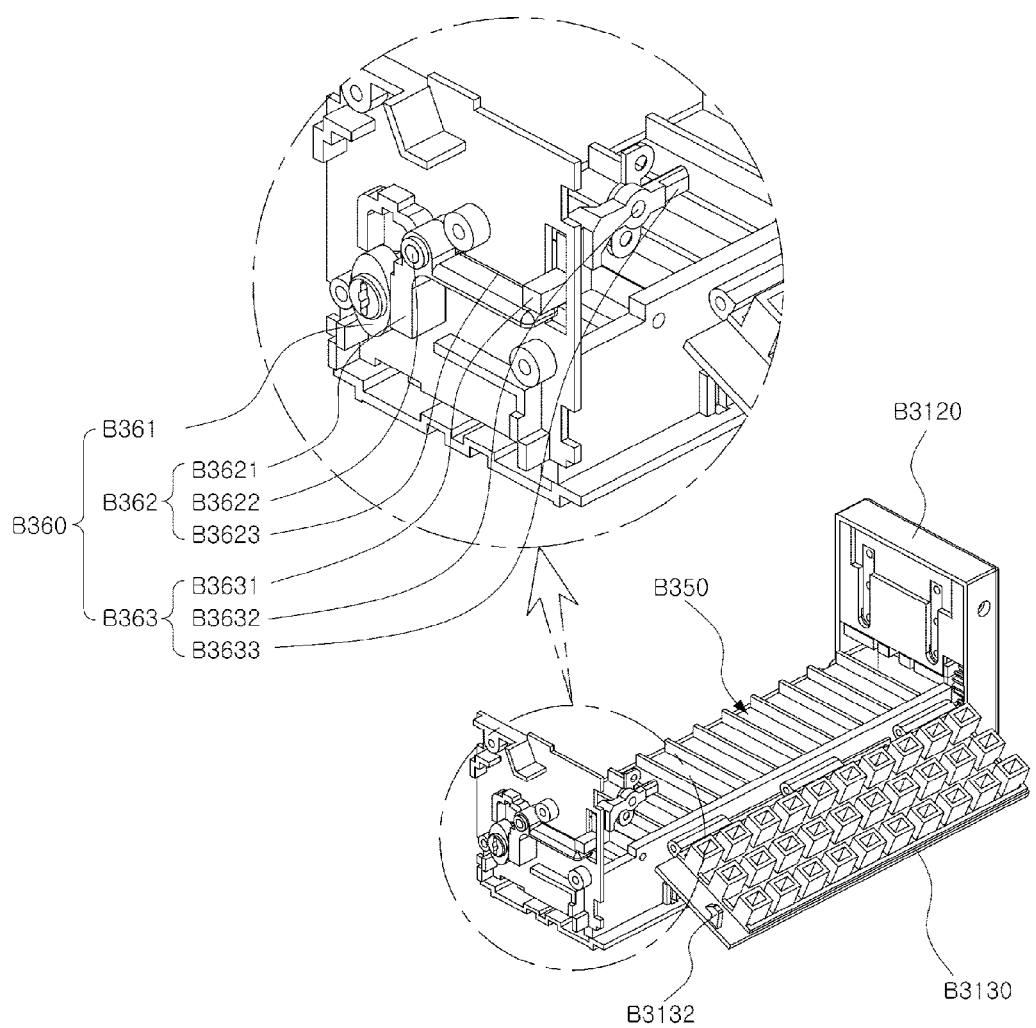

【FIG.87】
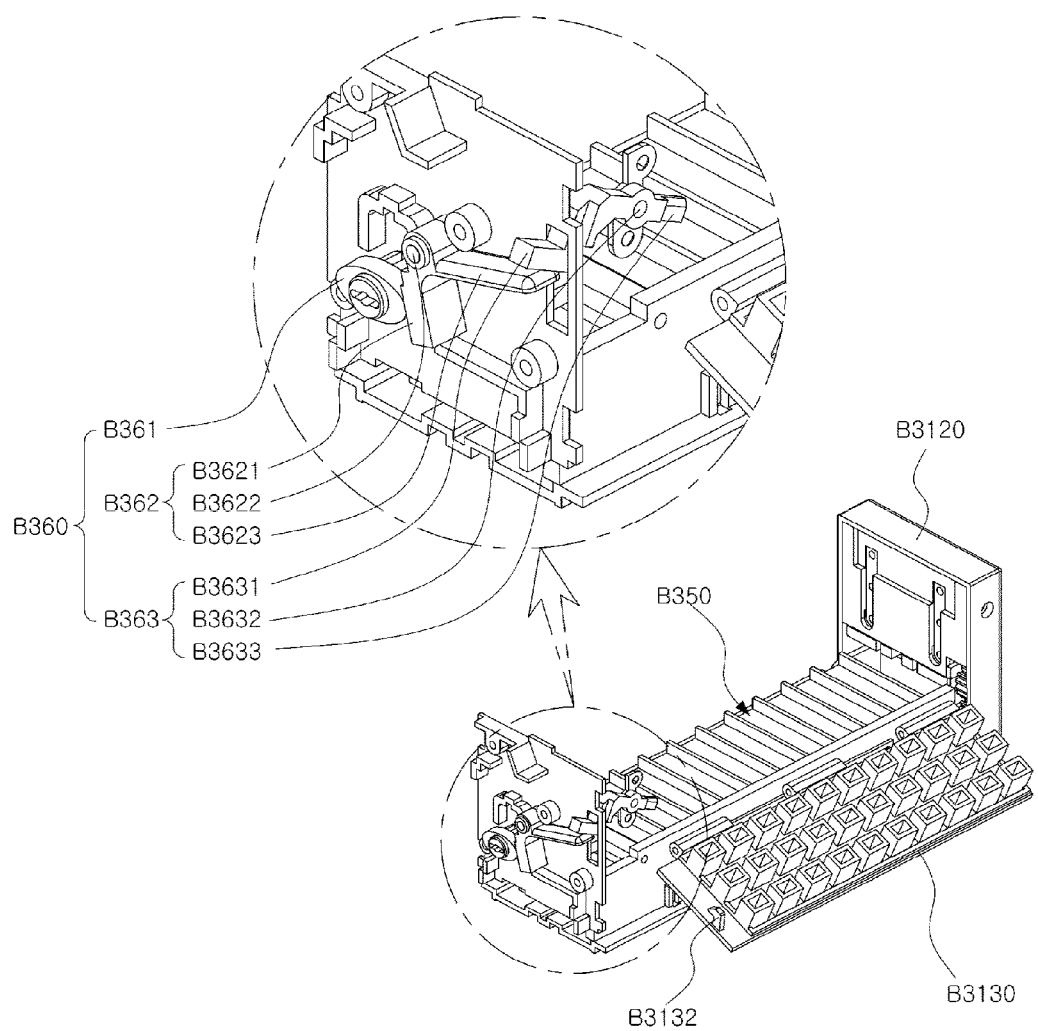

【FIG.88】
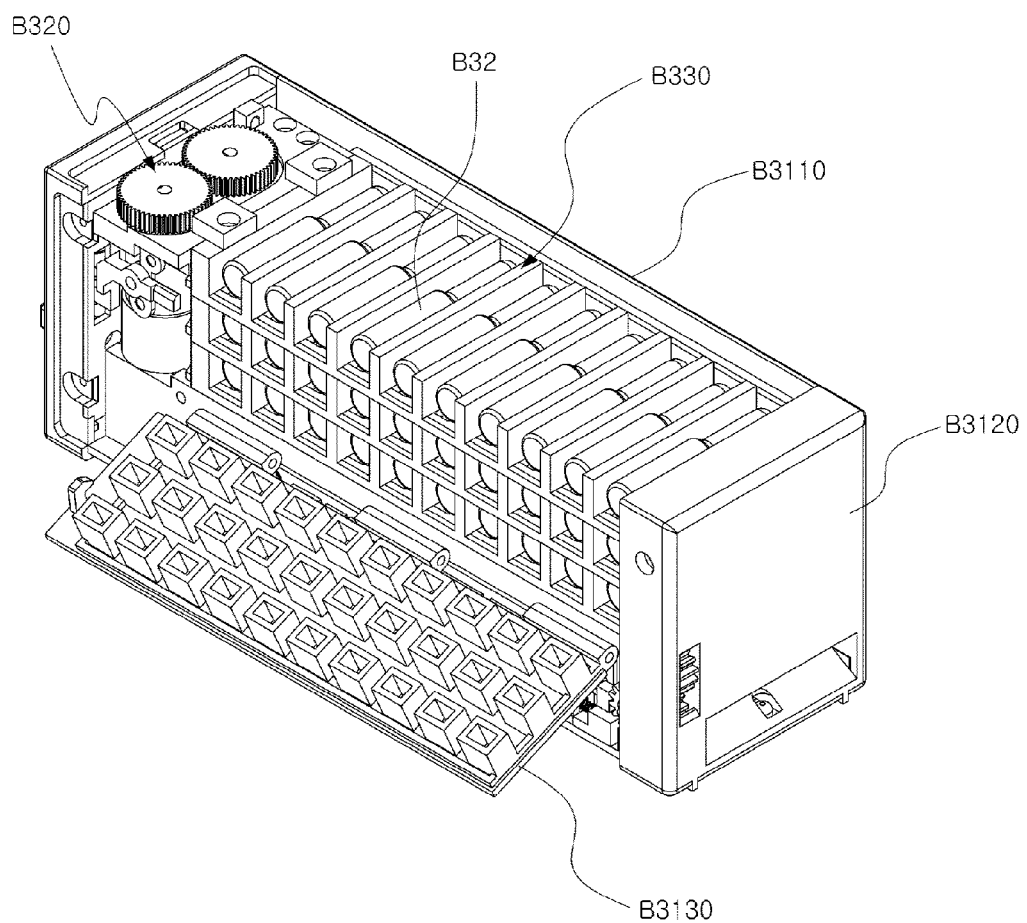

[FIG.89]
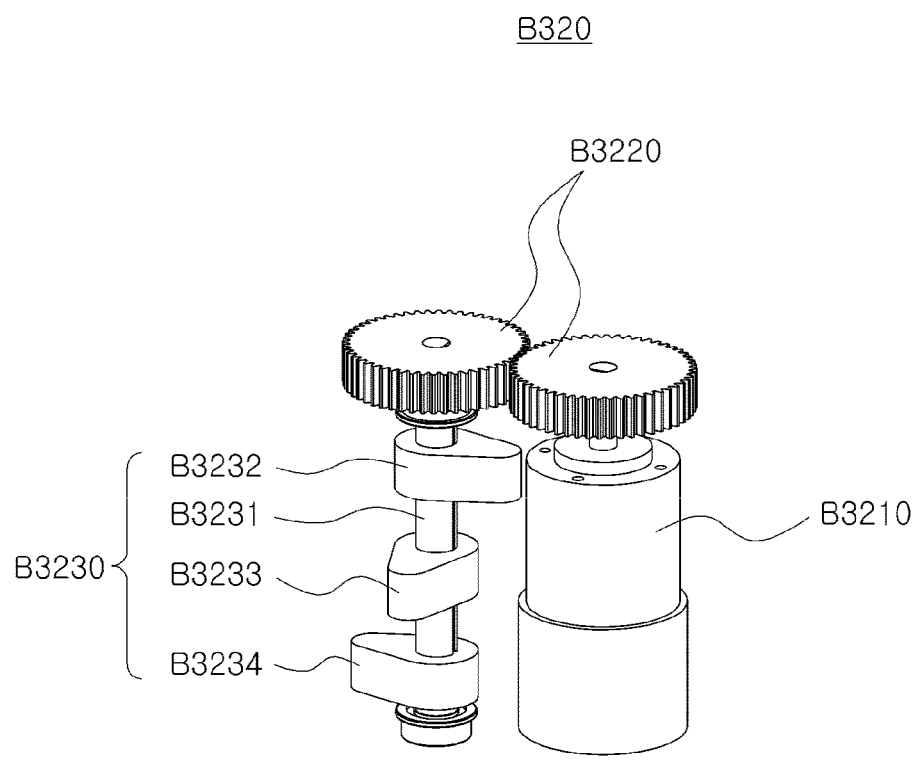

[FIG.90]
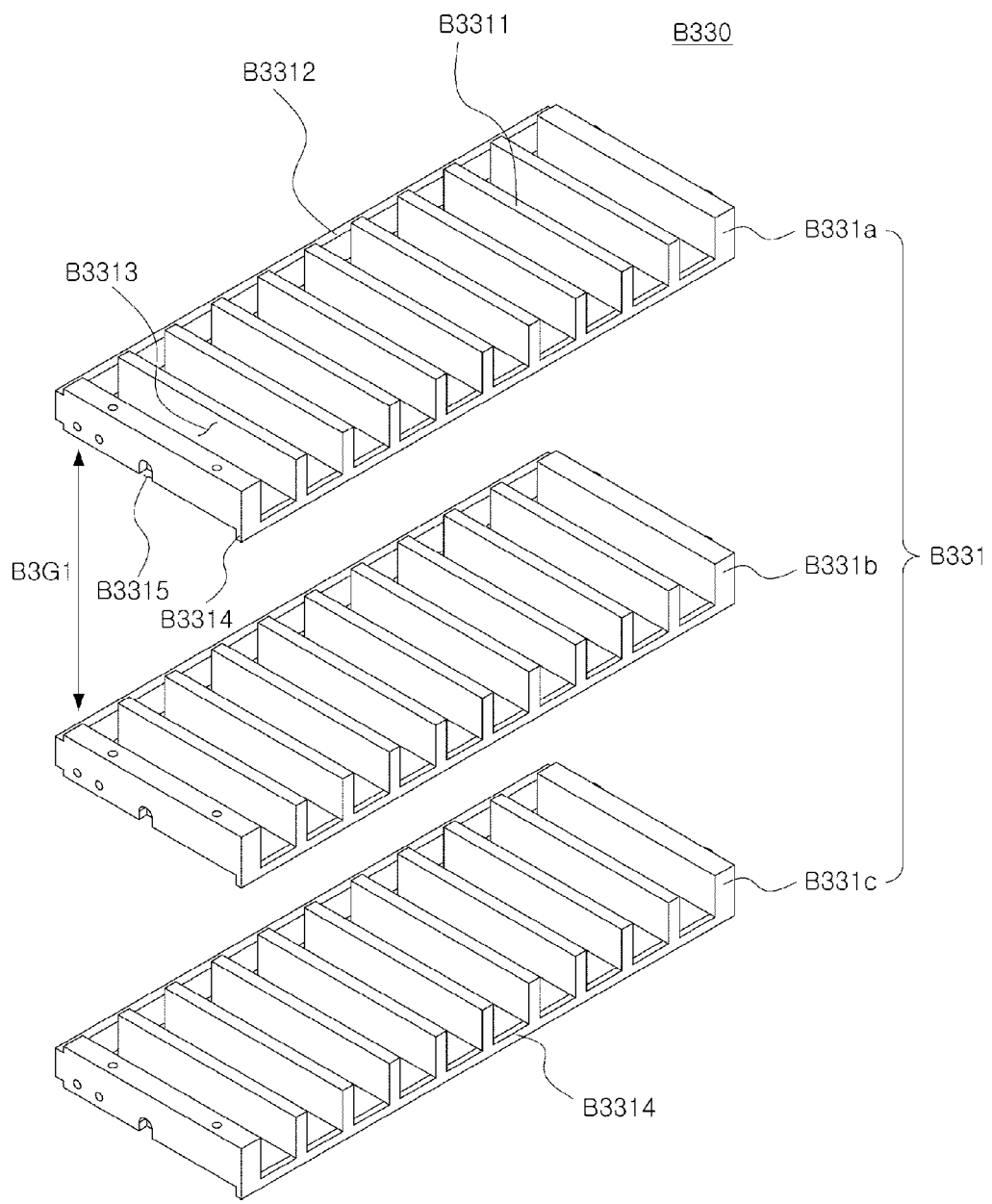

【FIG.91】
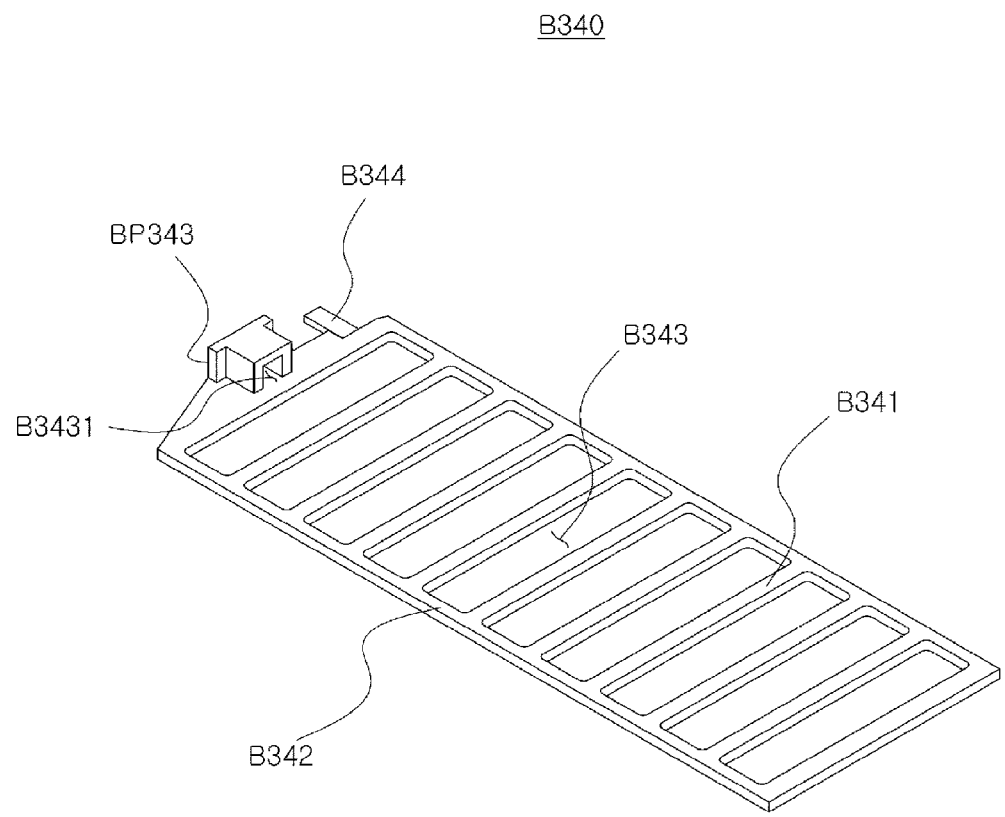

【FIG.92】
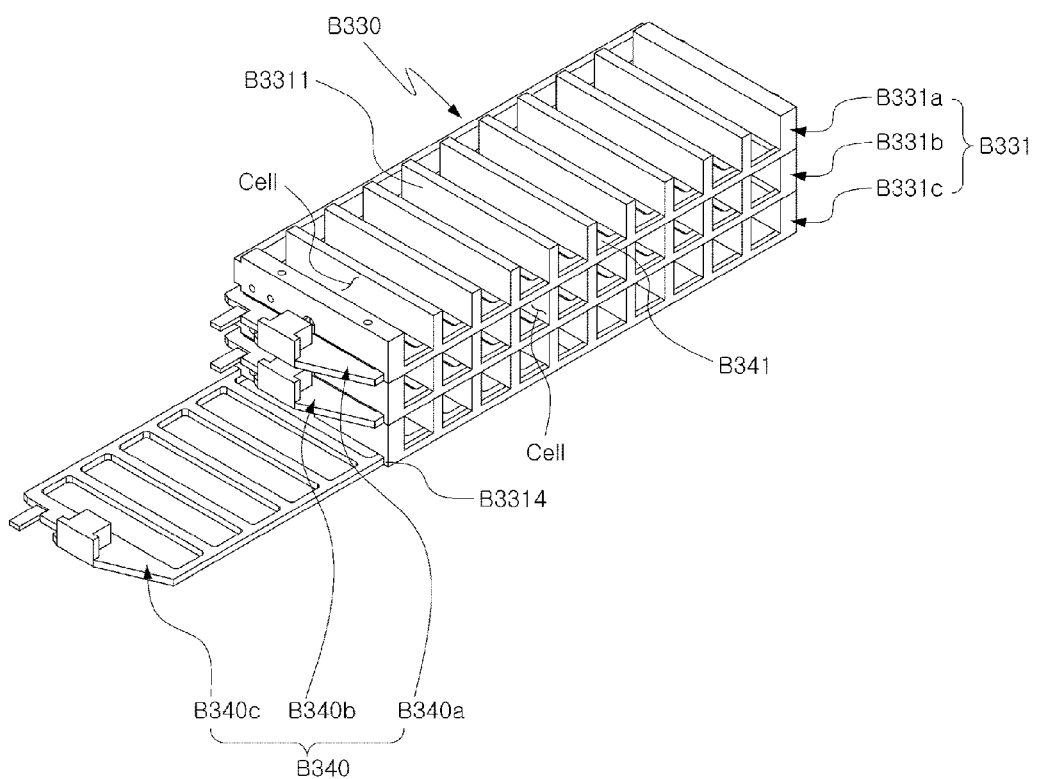

【FIG.93】
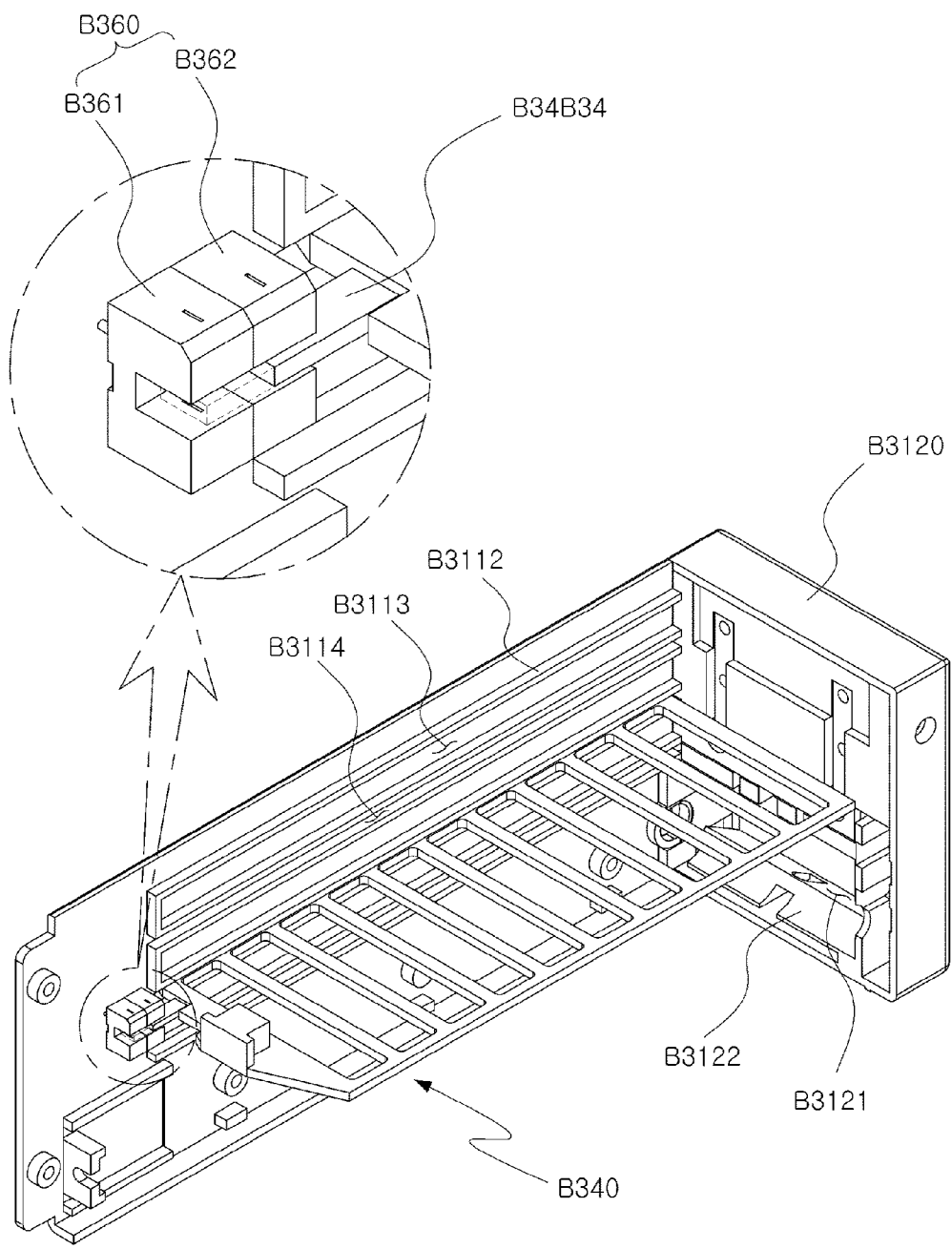

[FIG.94]
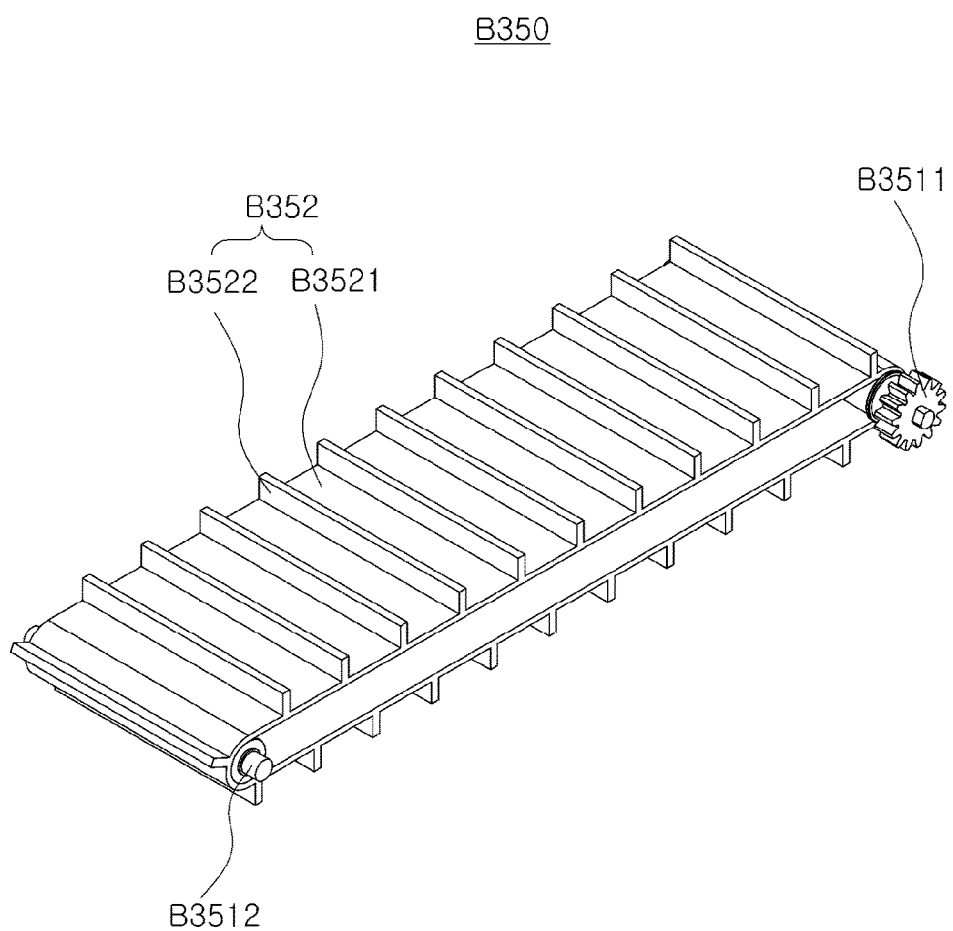

[FIG.95]
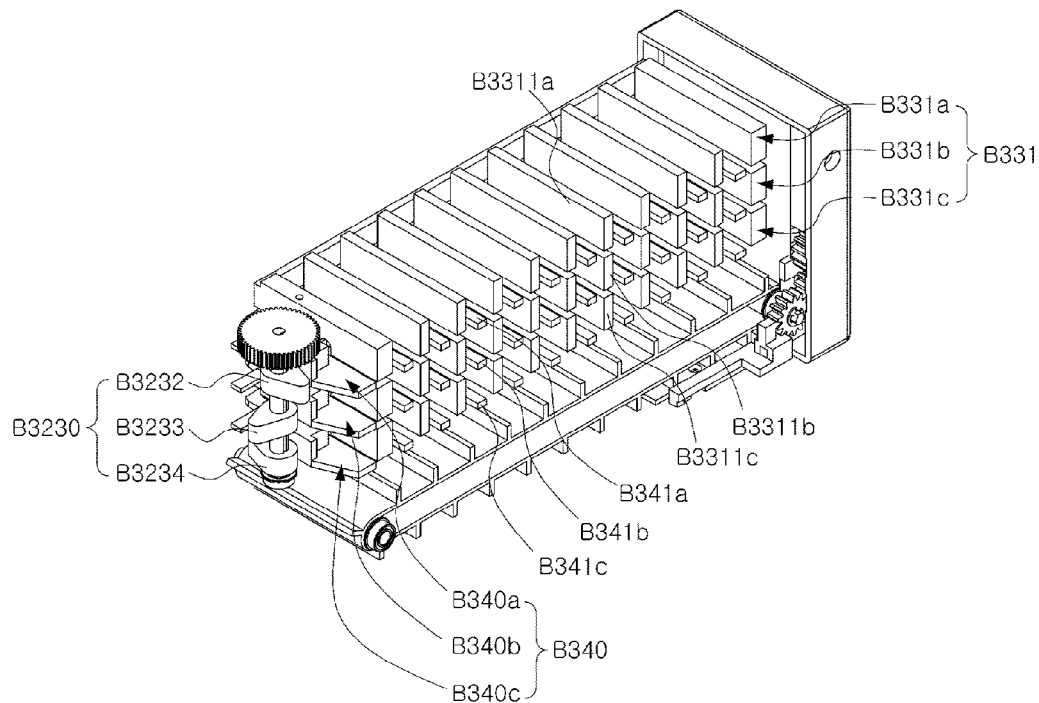
[FIG.96]
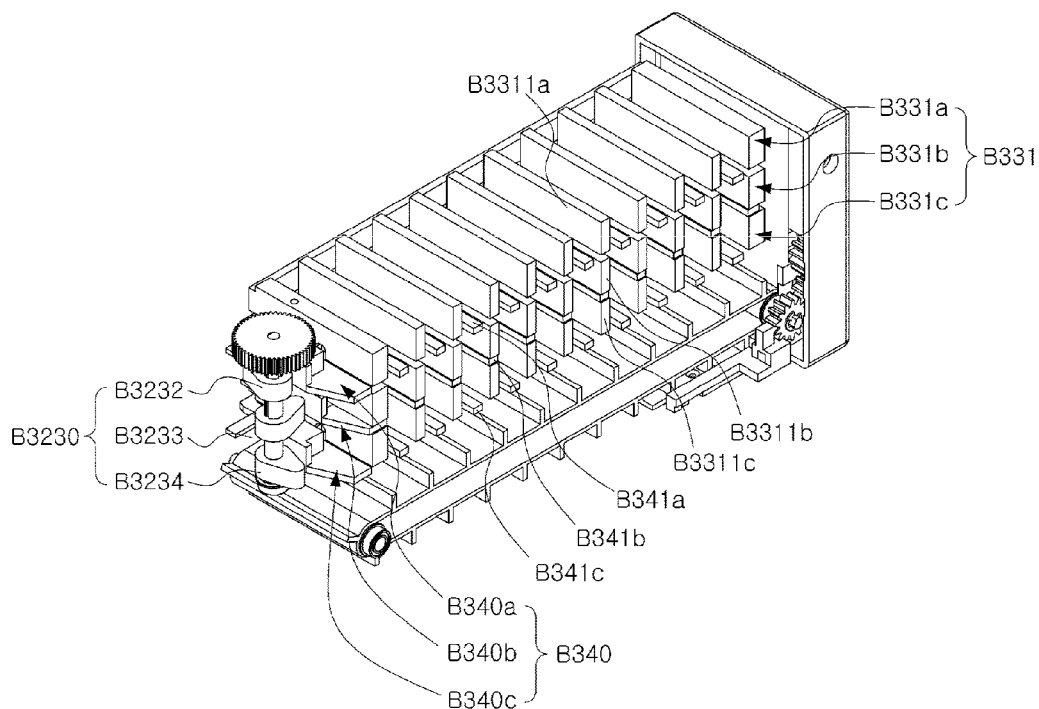

[FIG.97]
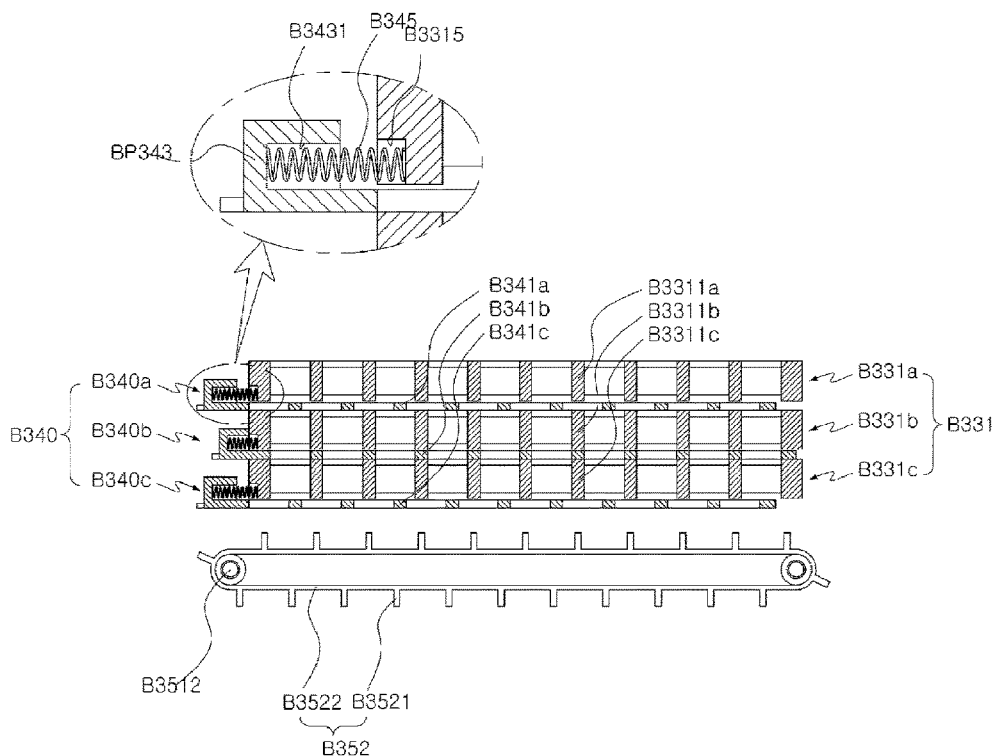
[FIG.98]
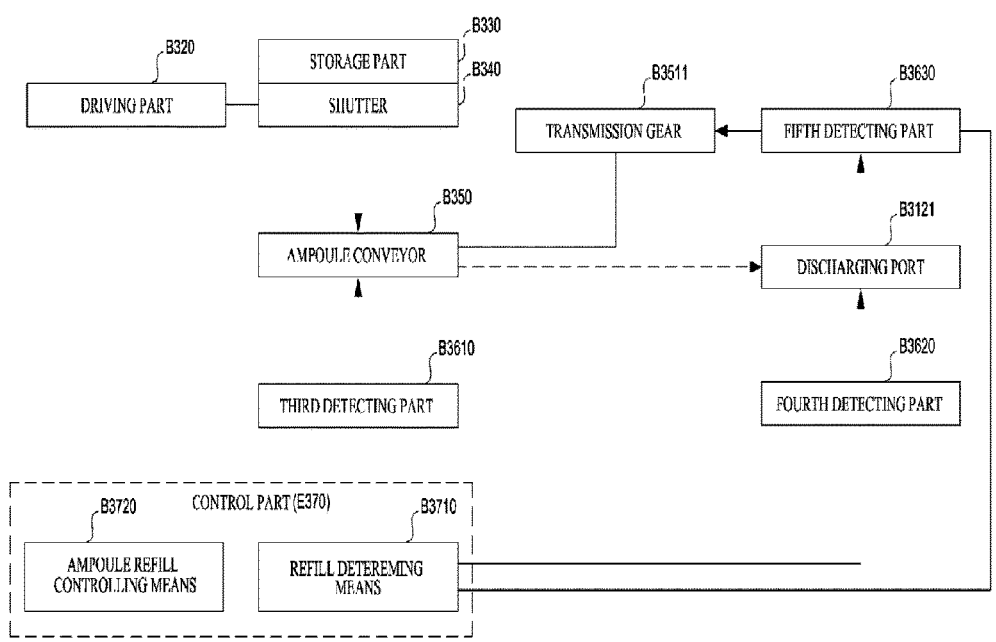

[FIG.99]
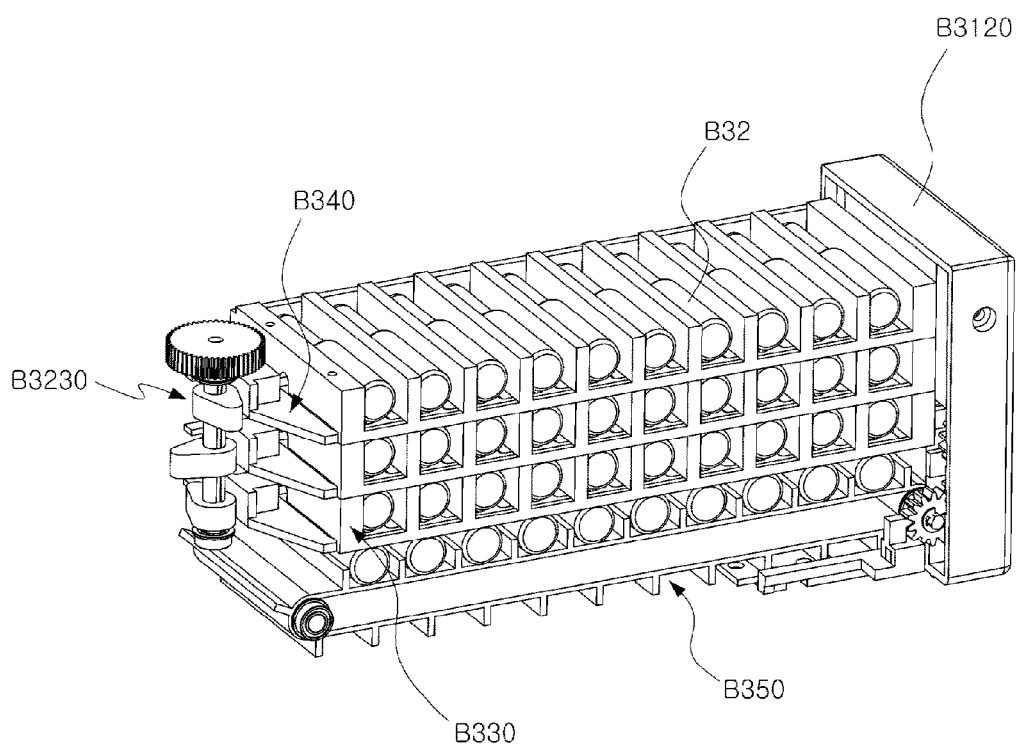

【FIG.100】
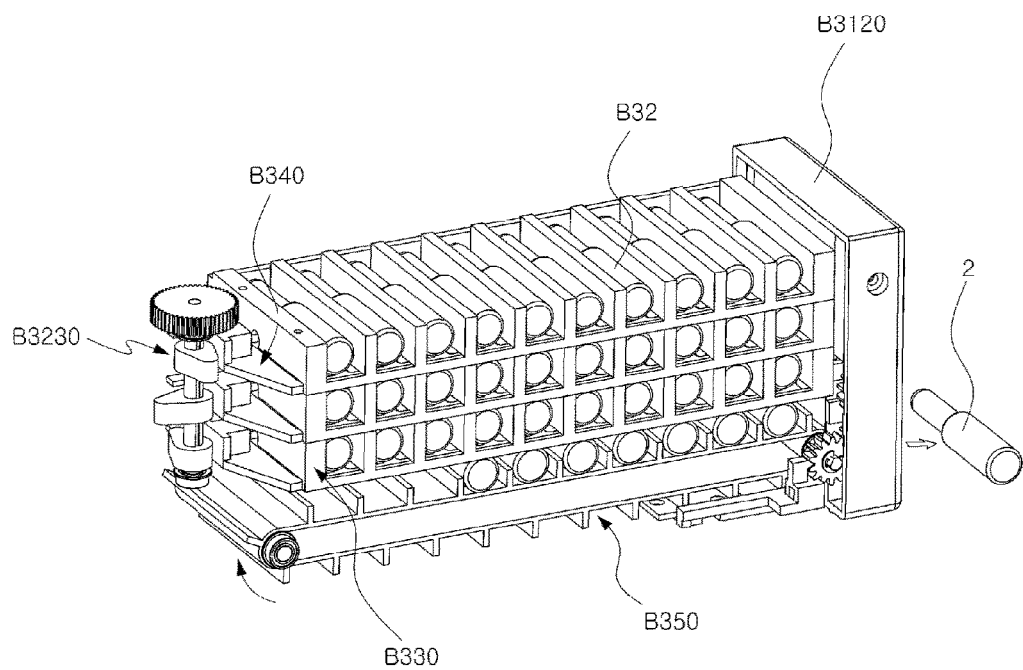

【FIG.101】
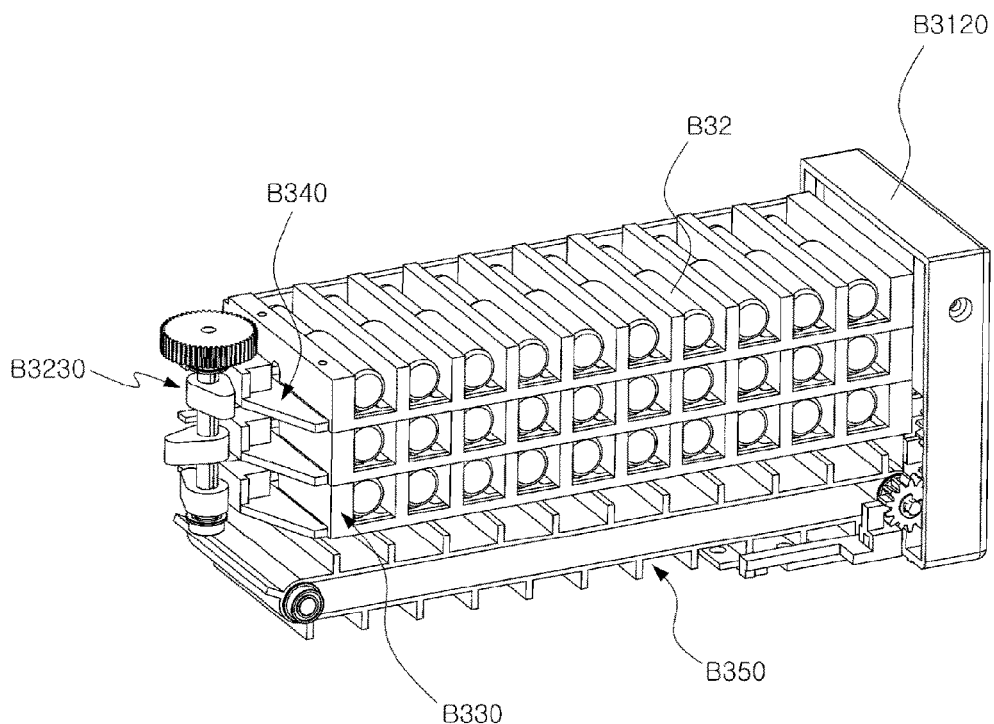
【FIG.102】
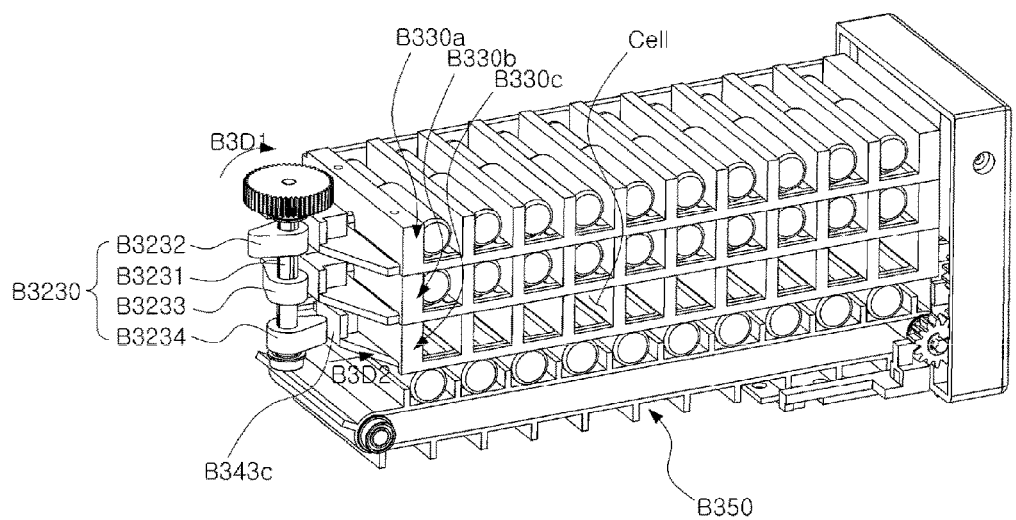

【FIG.103】
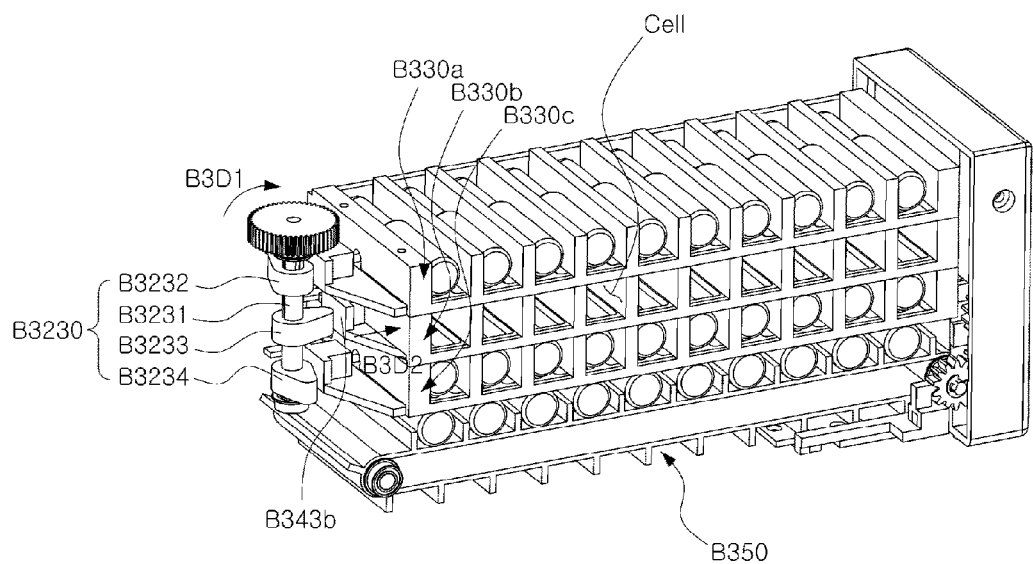
【FIG.104】
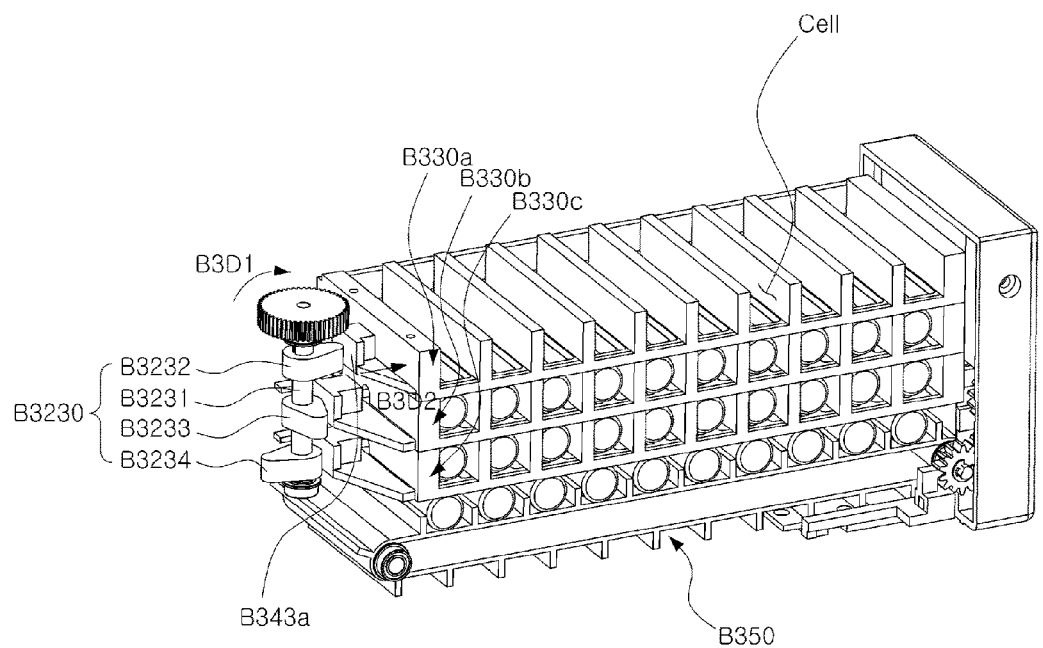

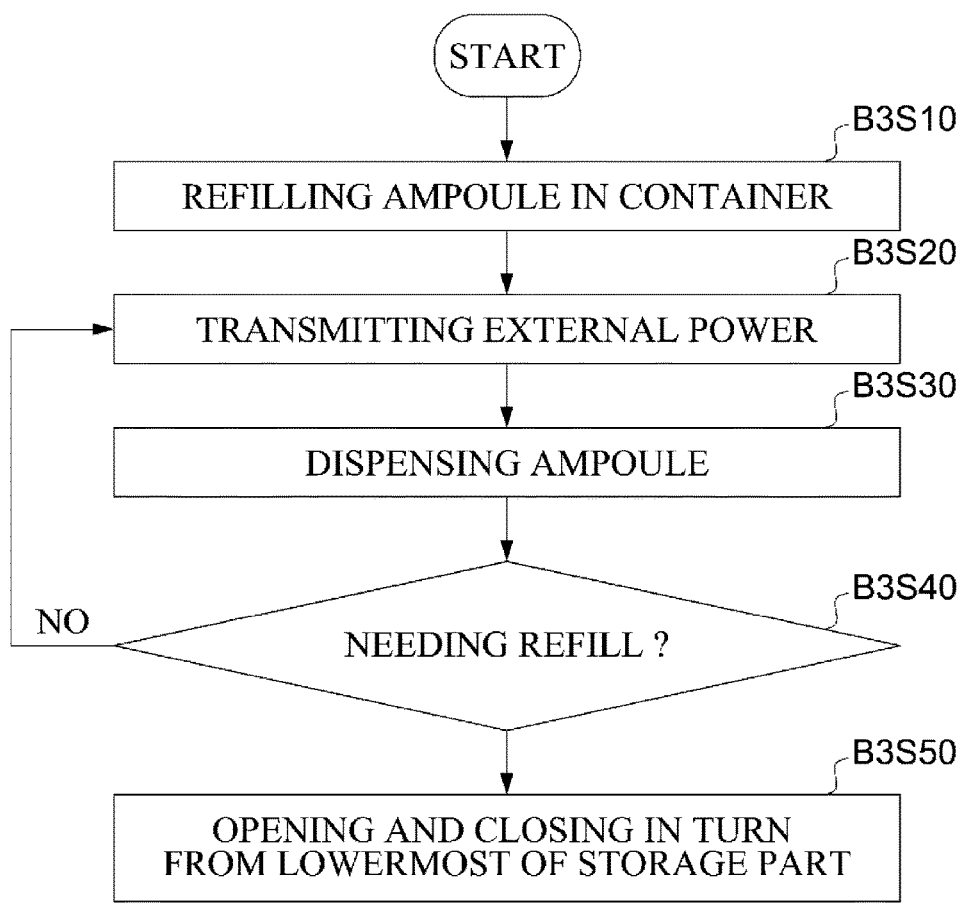
[FIG.105]

[FIG.106]
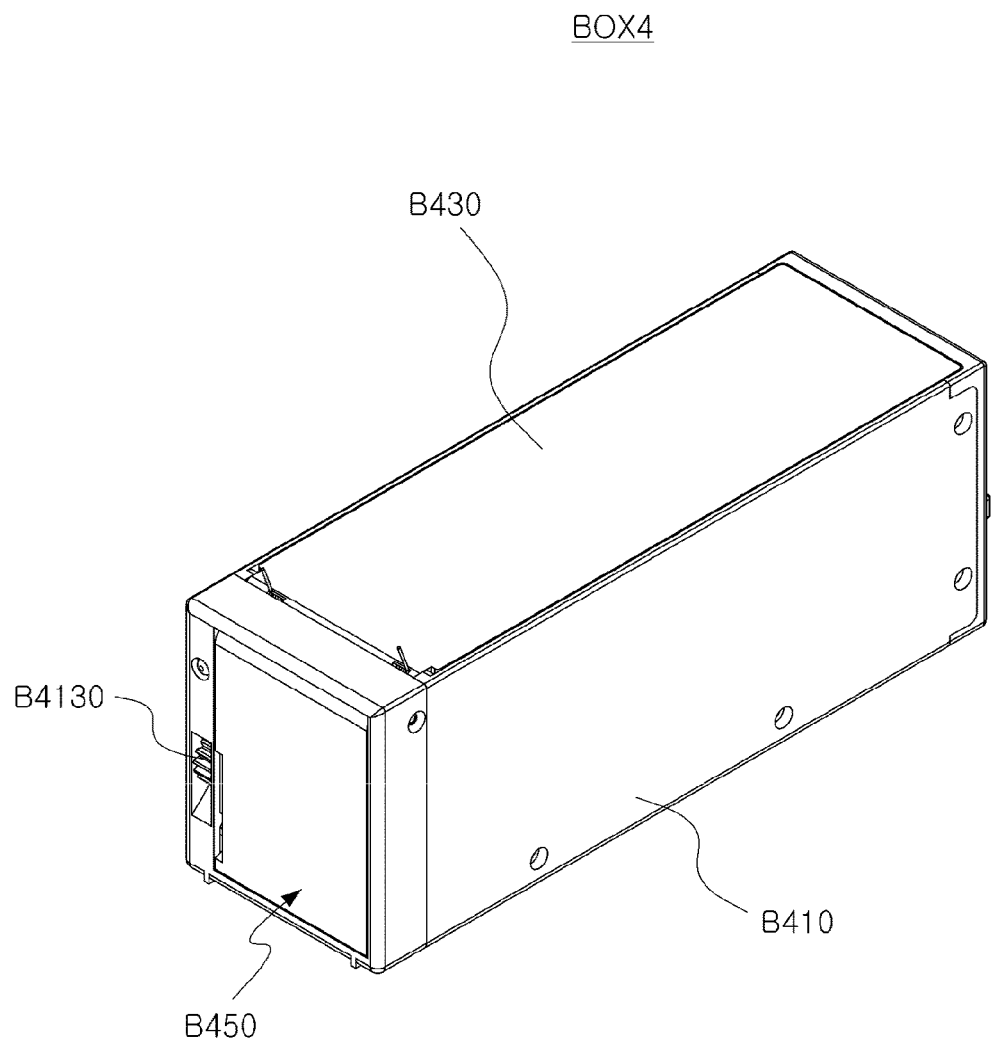

【FIG.107】
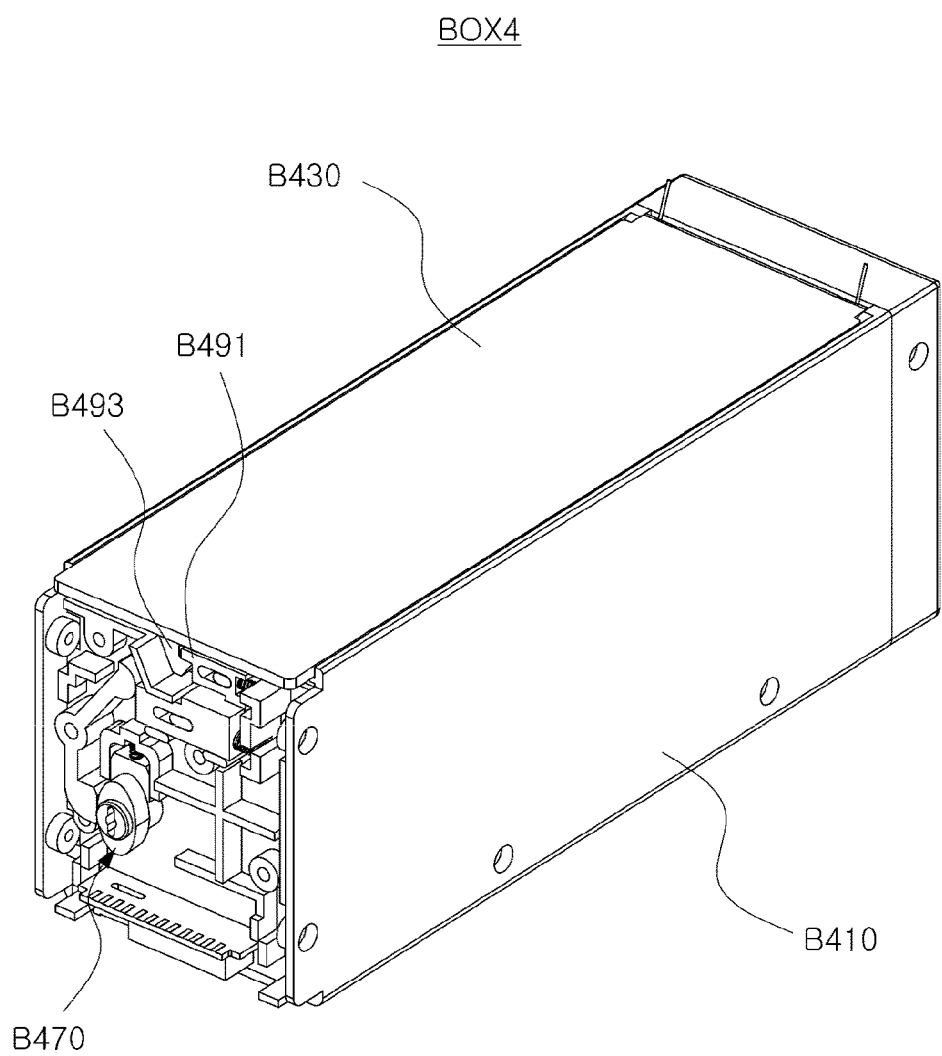

[FIG.108]
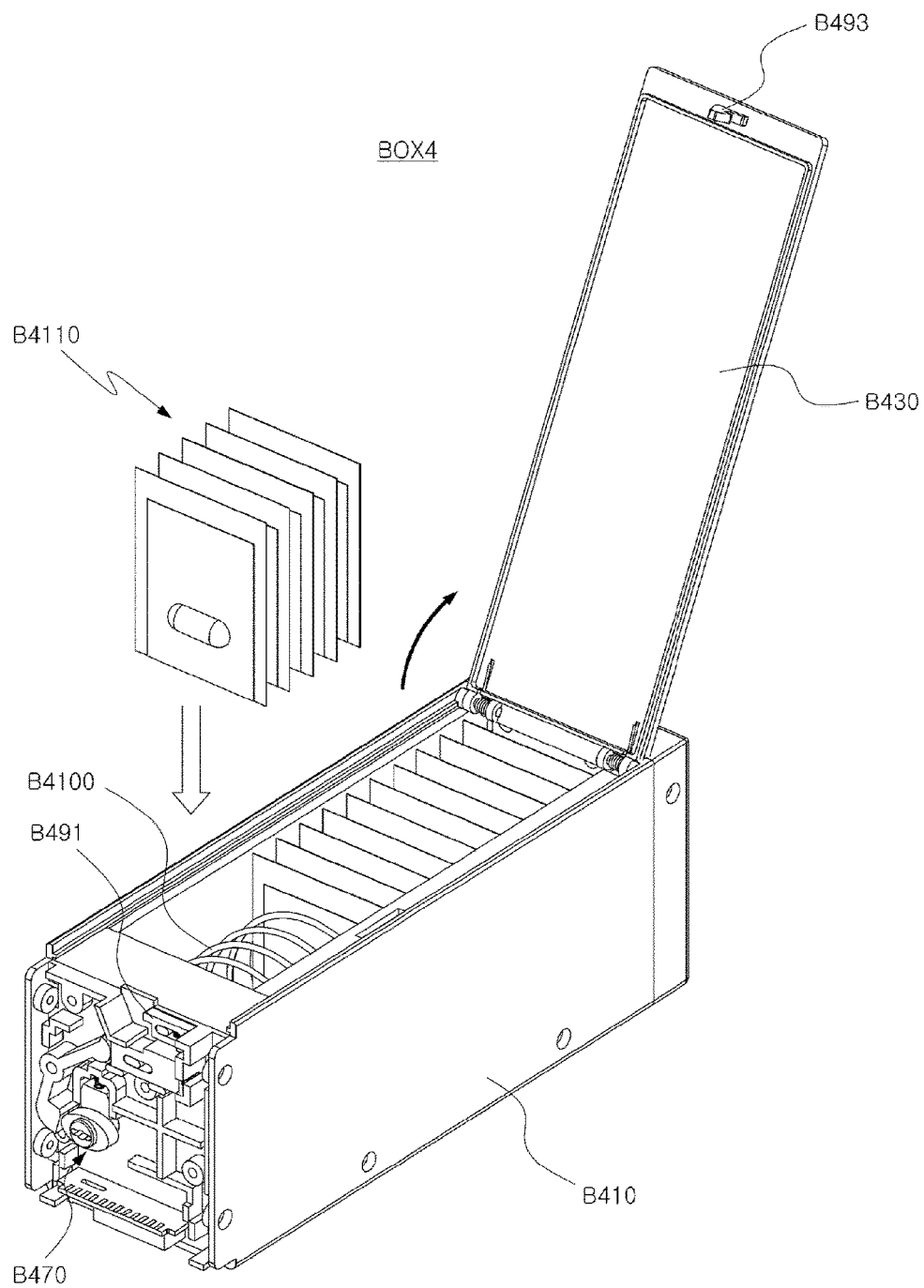

【FIG.109】
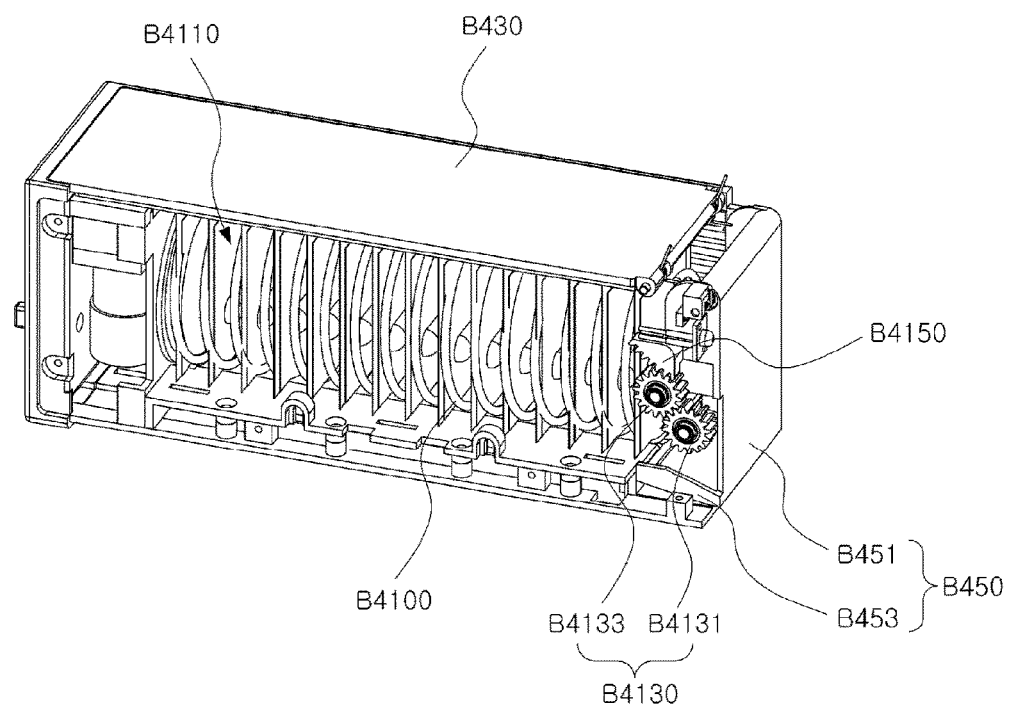

[FIG.110]
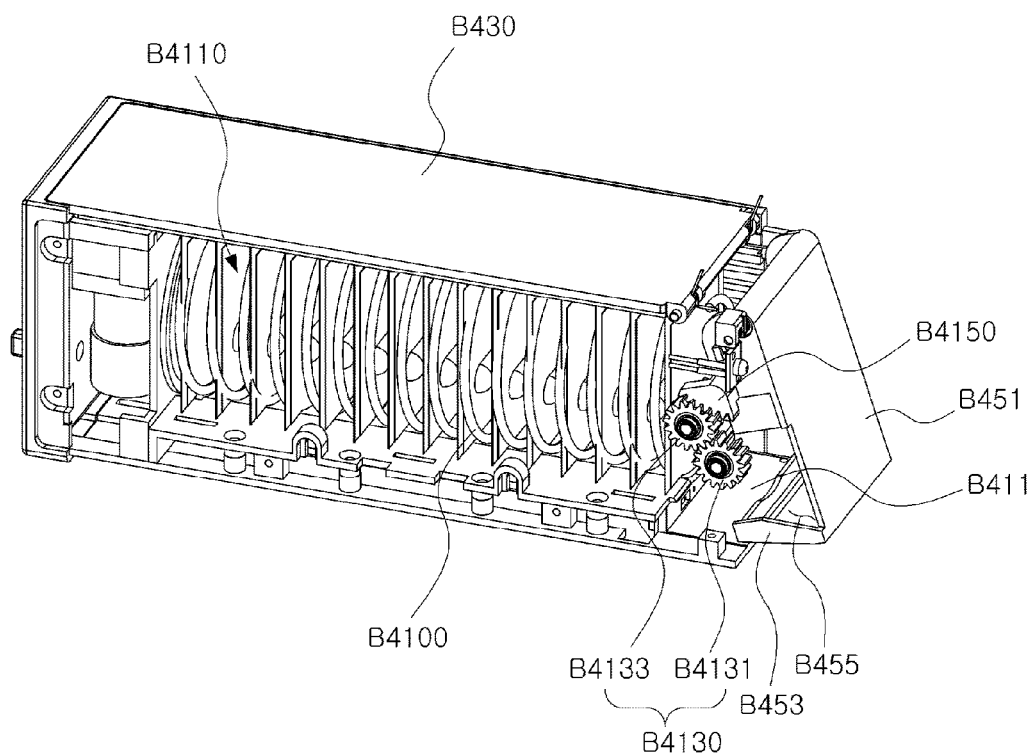

【FIG.111】
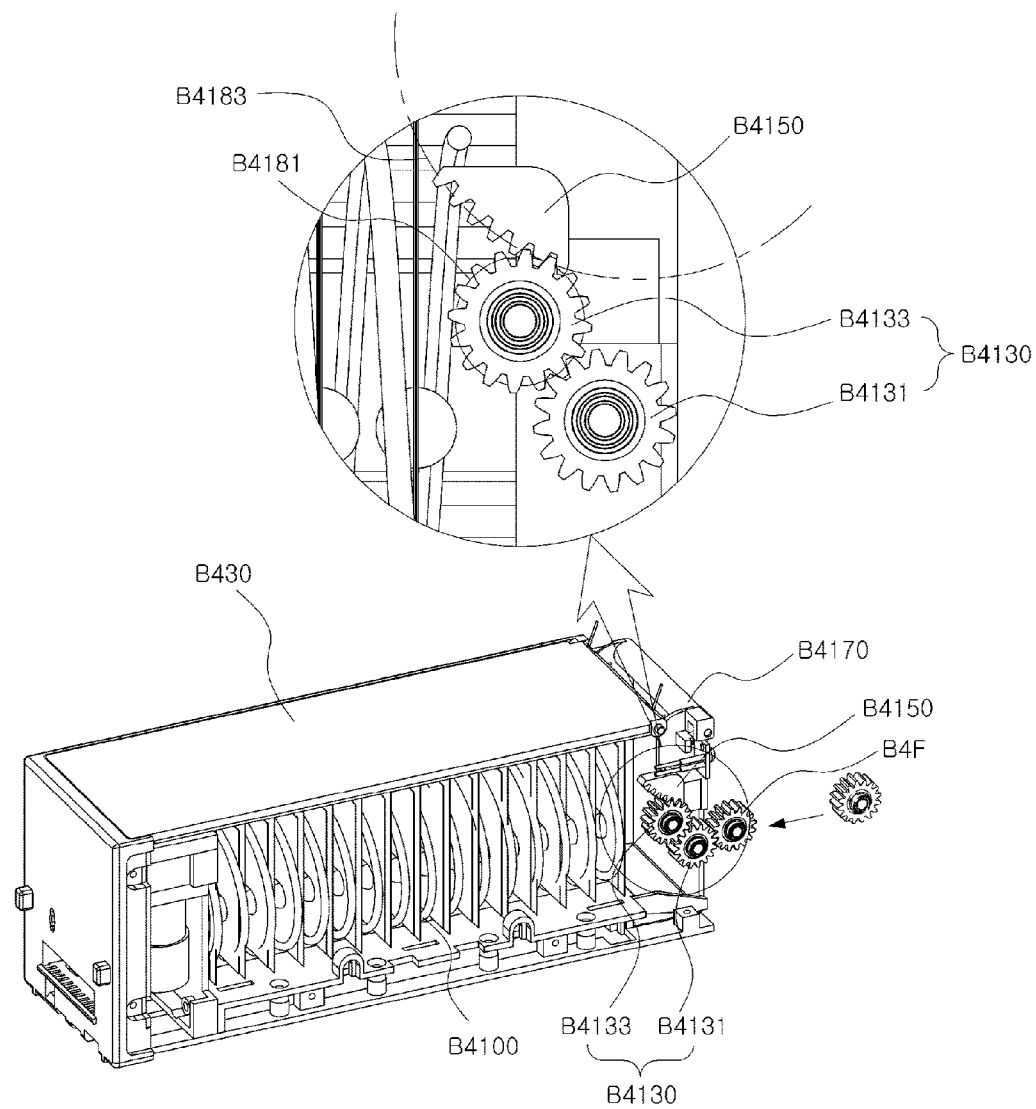

【FIG.112】
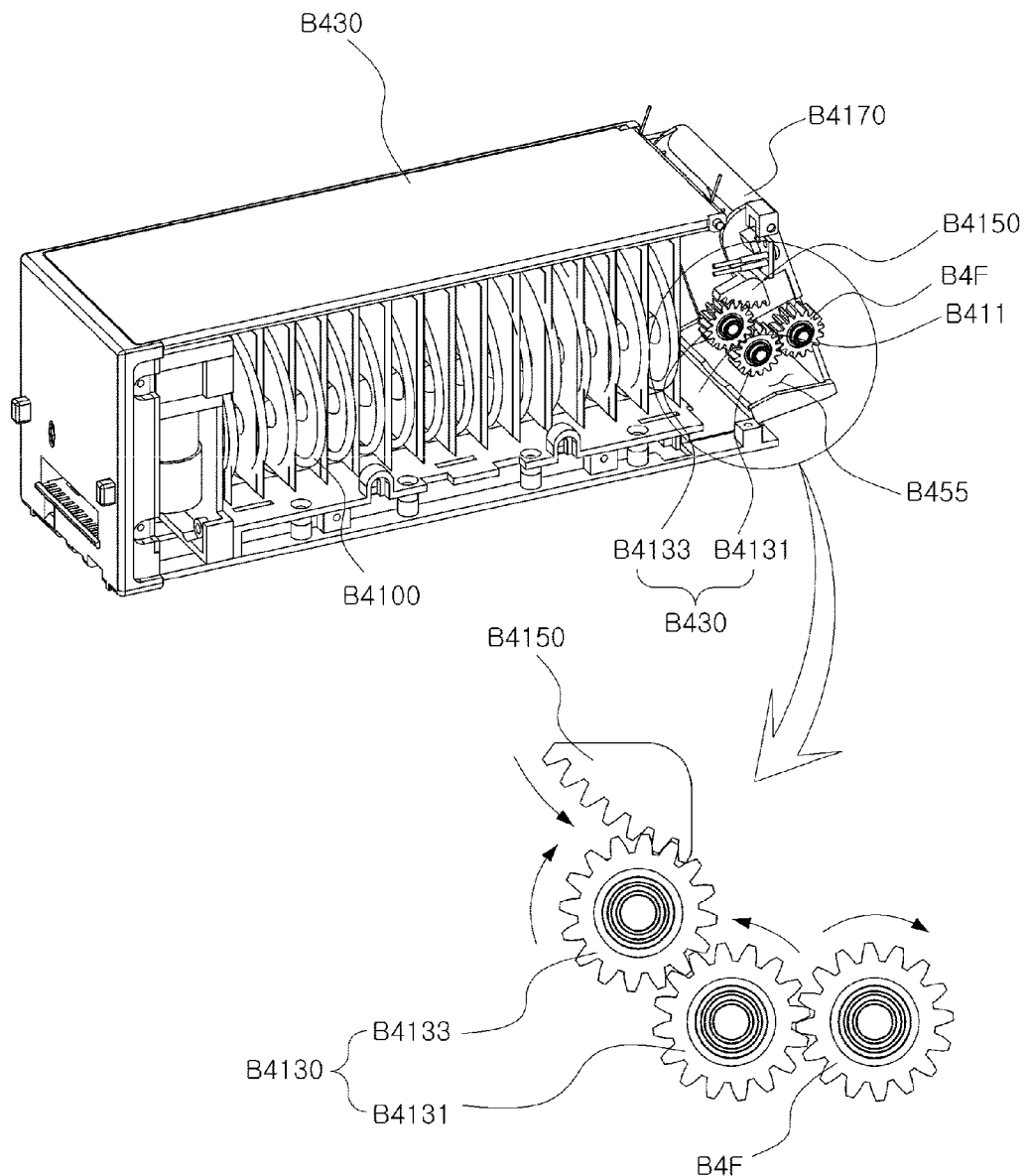

【FIG.113】
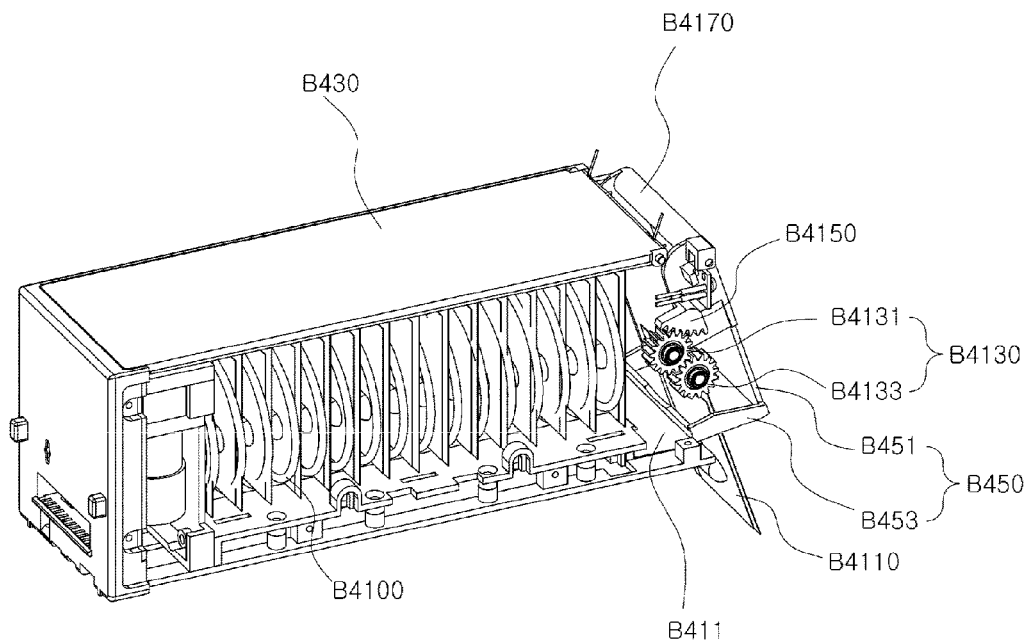

【FIG.114】
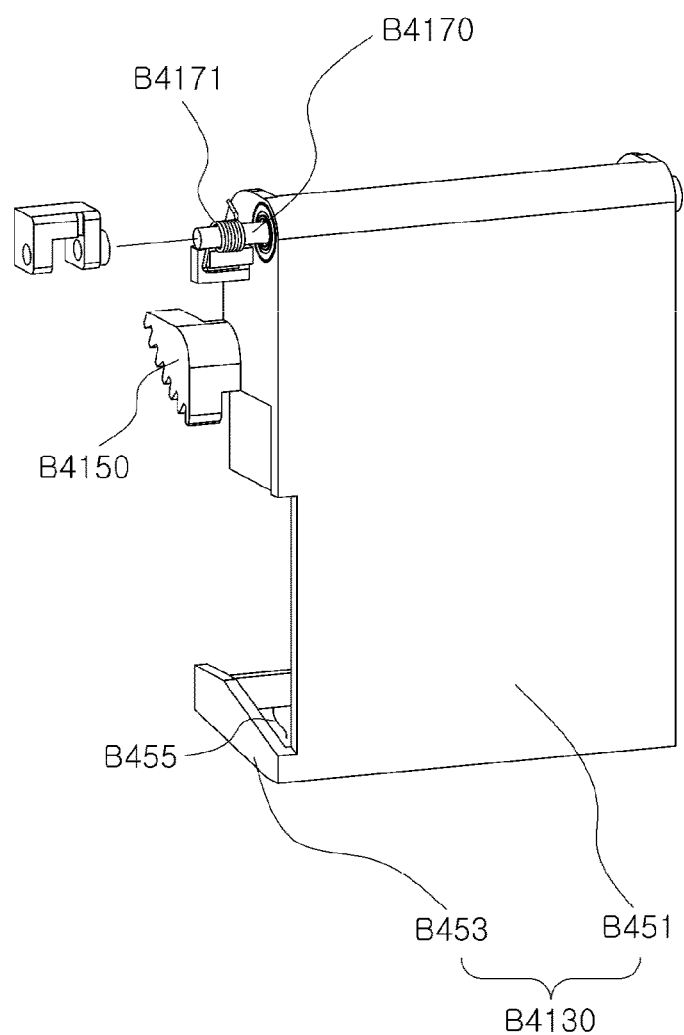

【FIG.115】
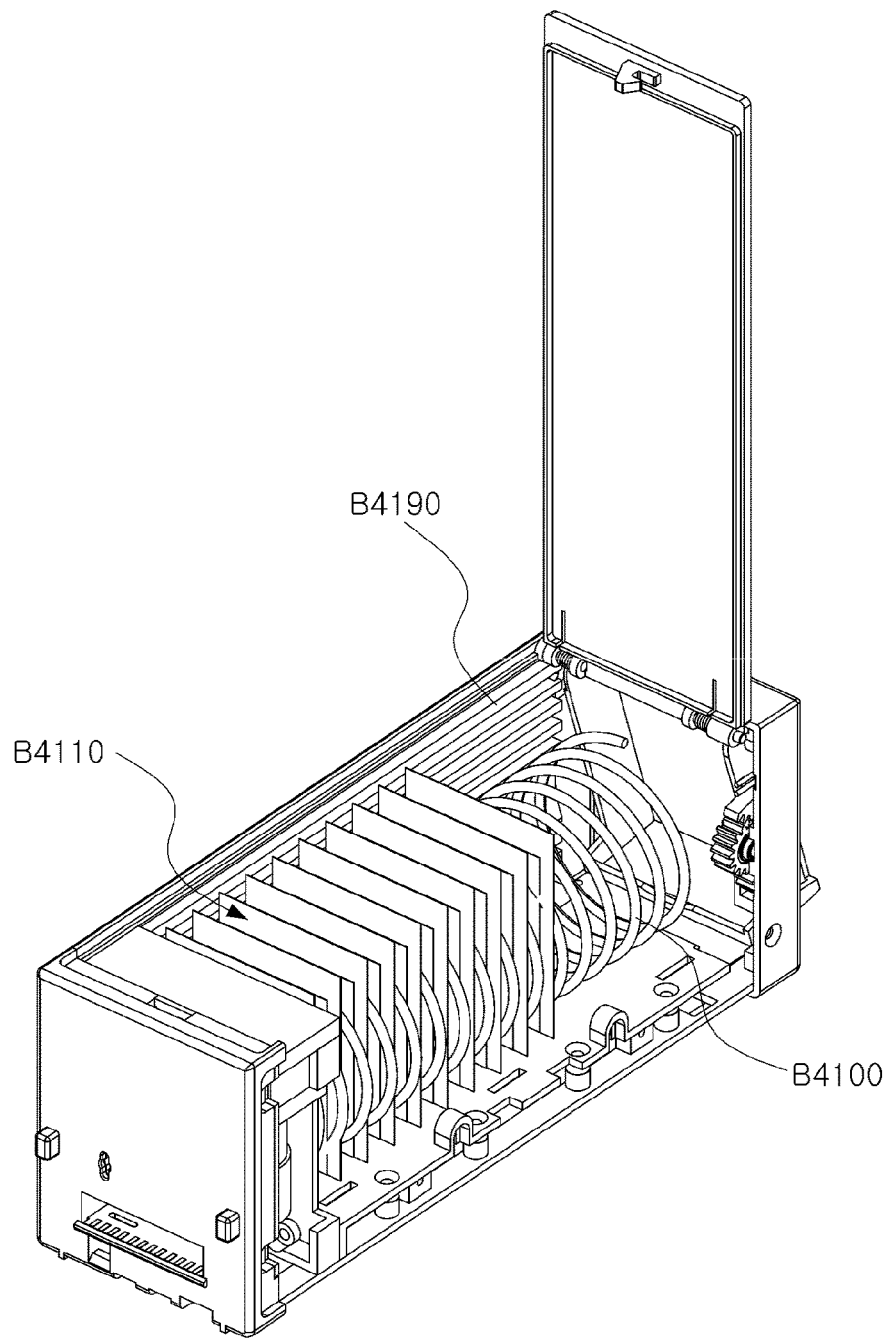

【FIG.116】
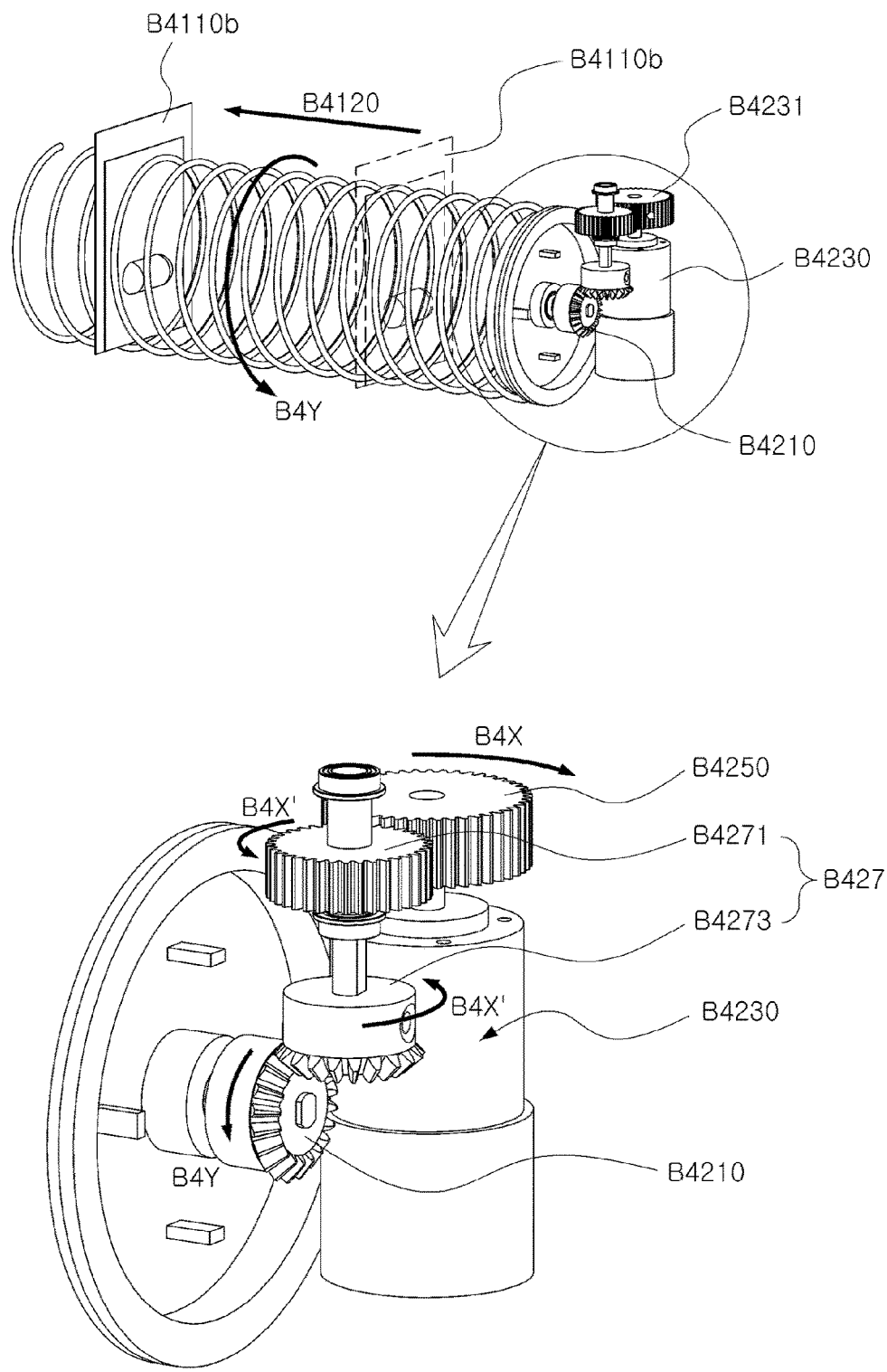

[FIG.117]
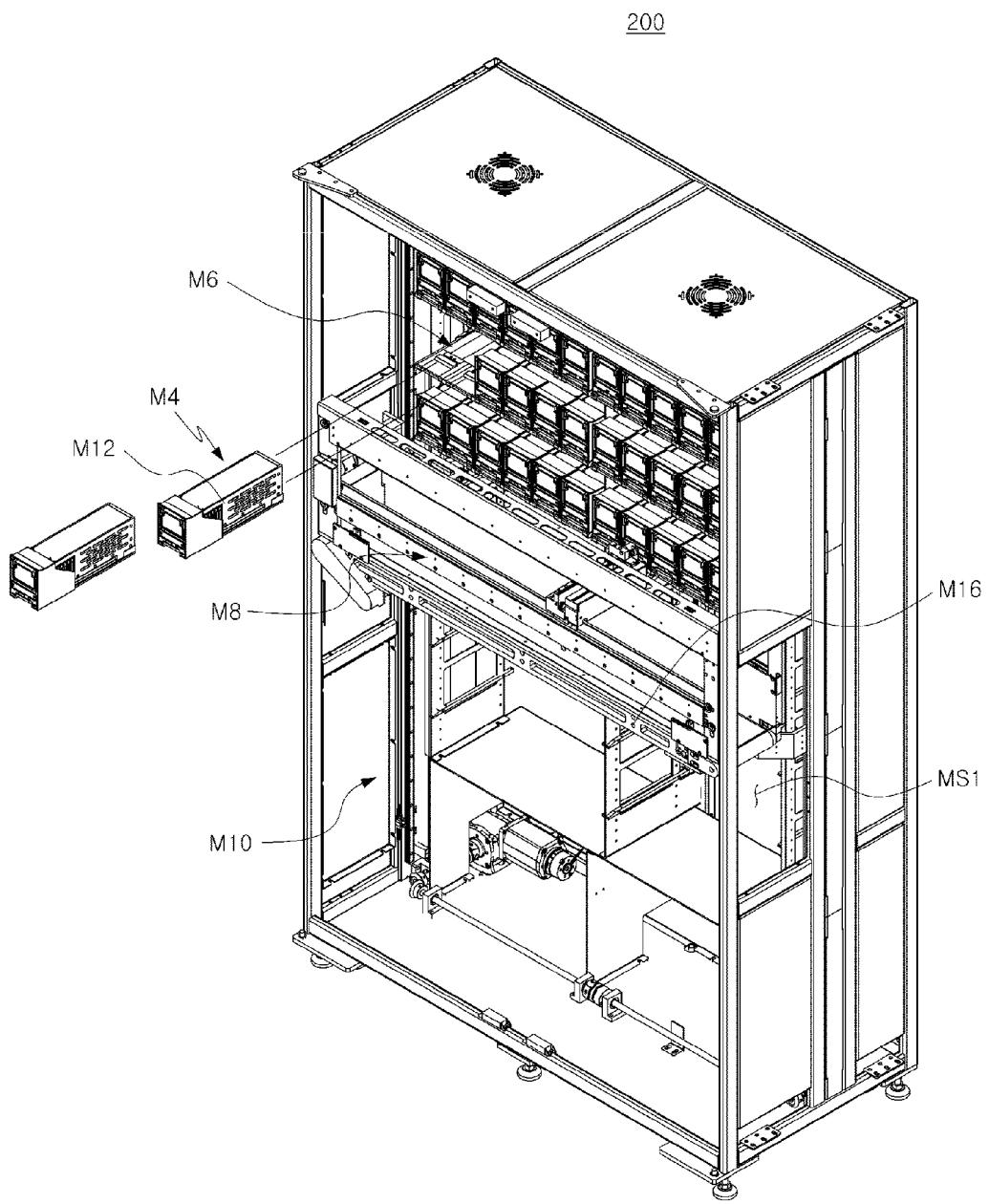

[FIG.118]
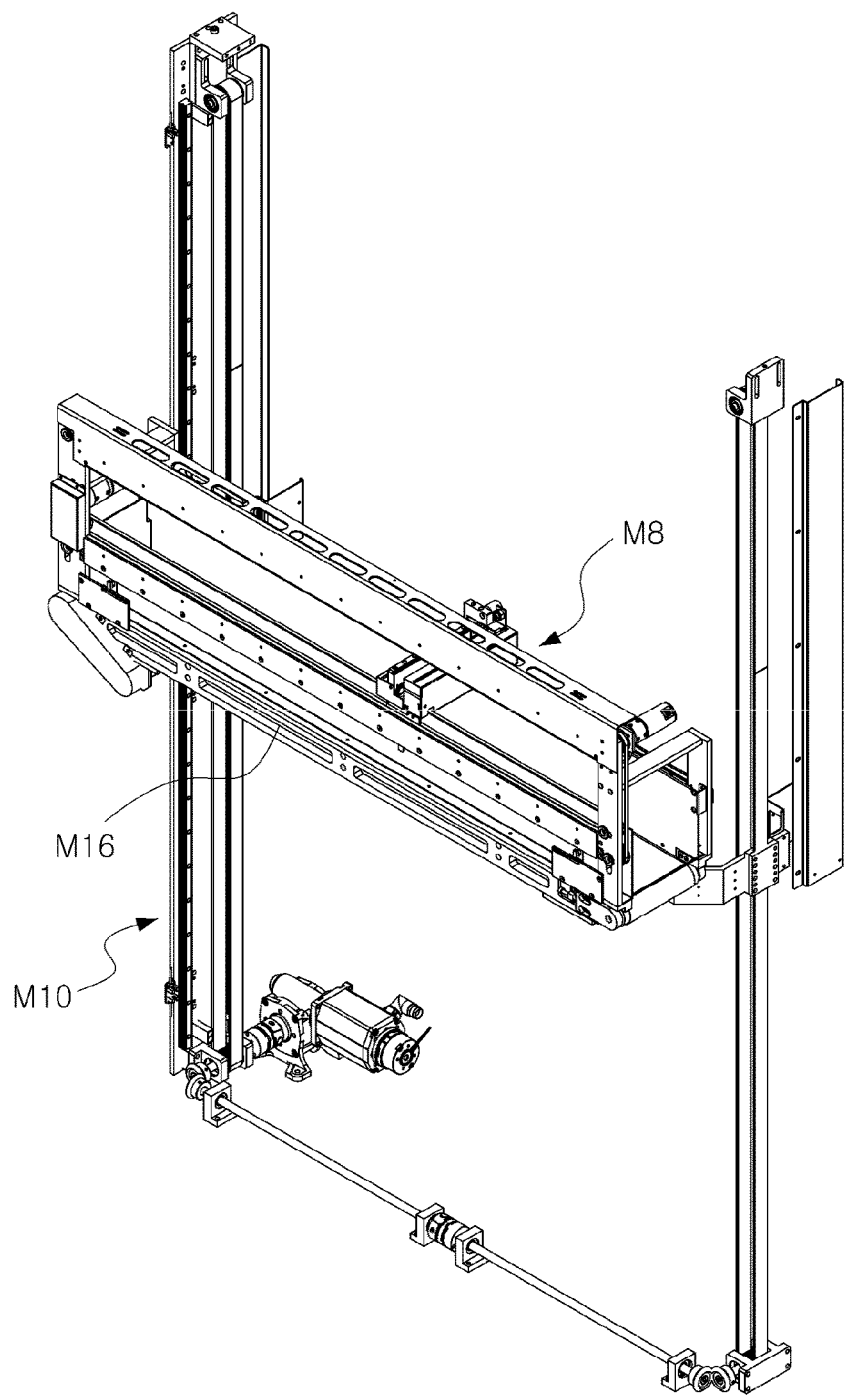

【FIG.119】
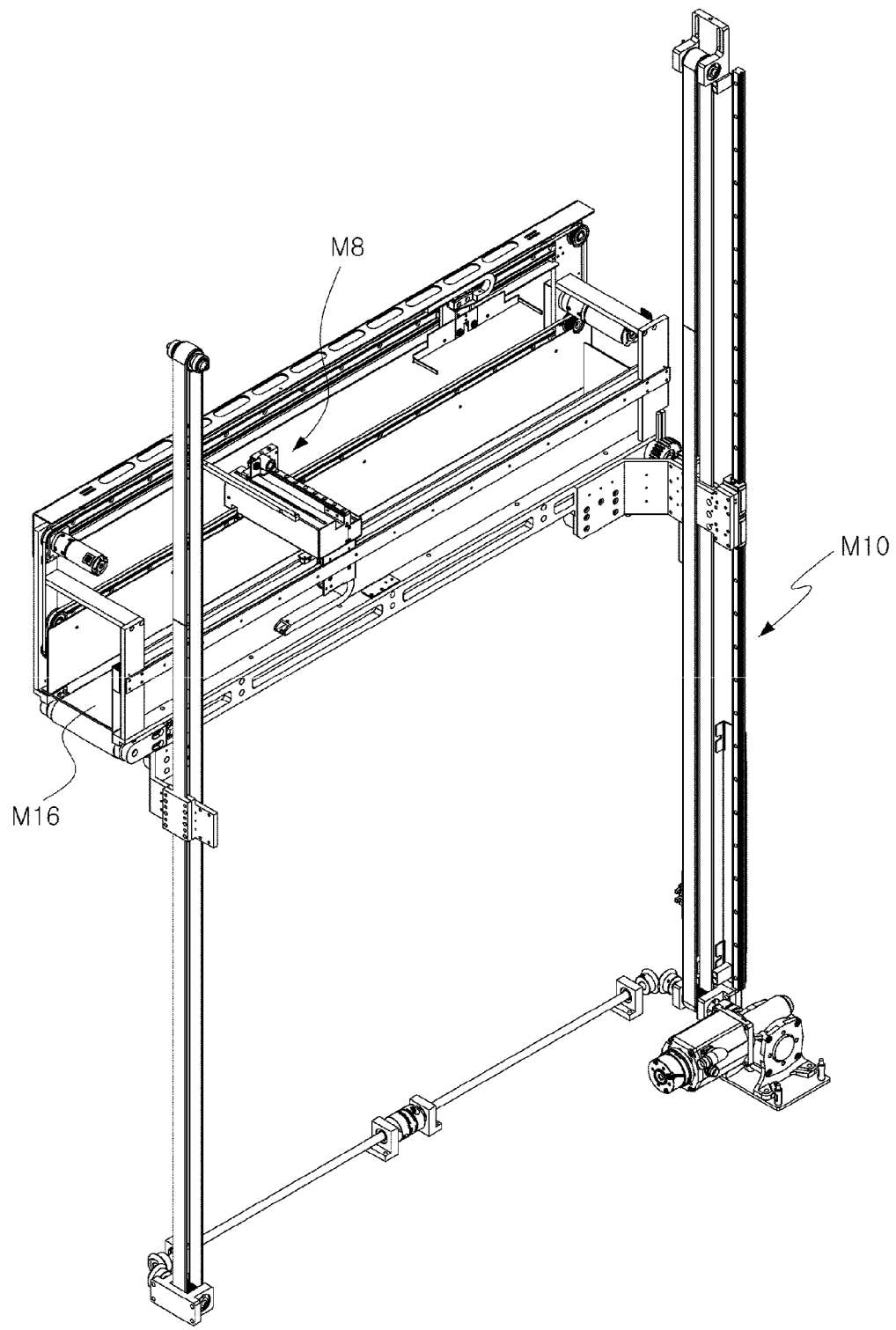

【FIG.120】
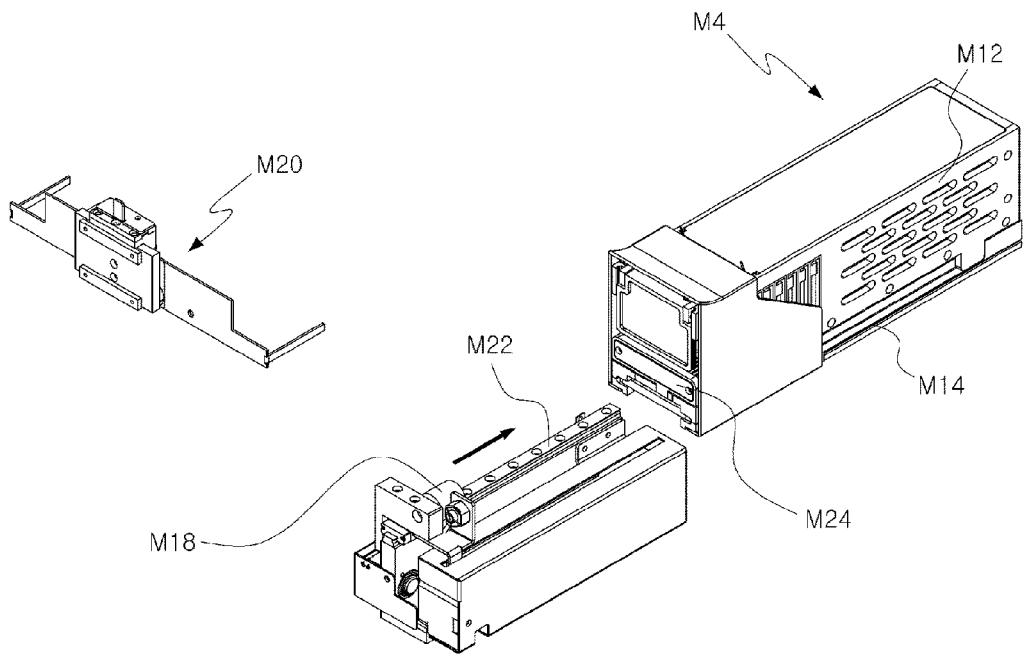
【FIG.121】
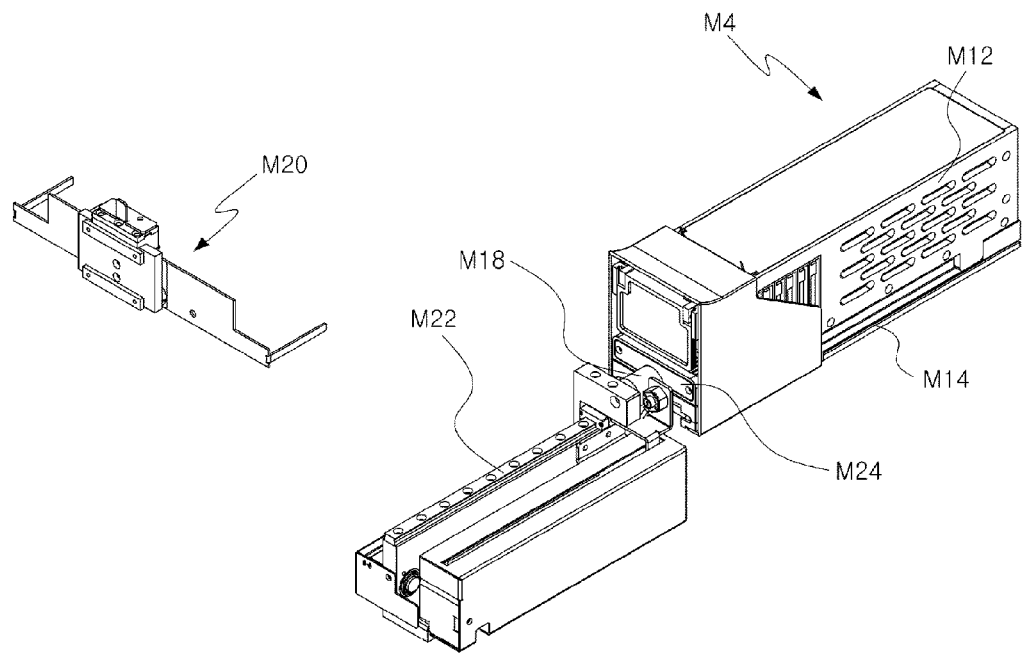

[FIG.122]
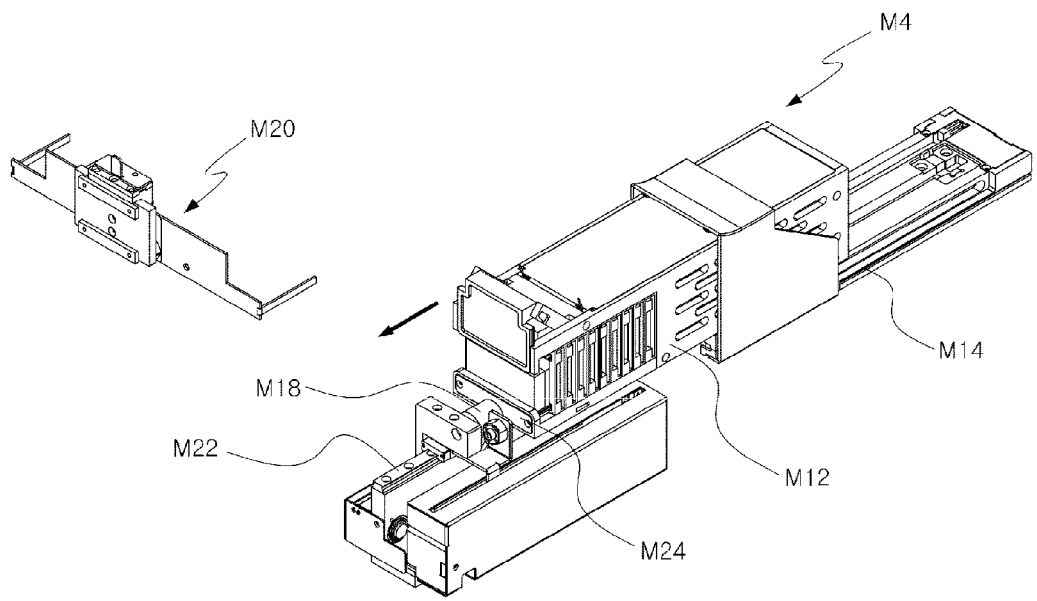
[FIG.123]
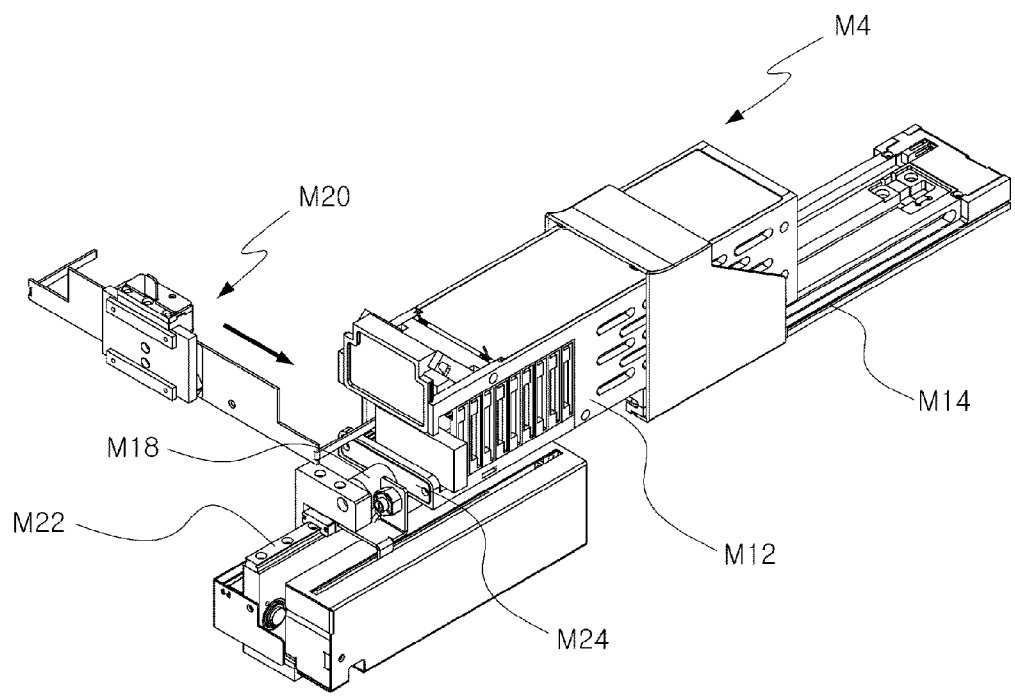

[FIG.124]
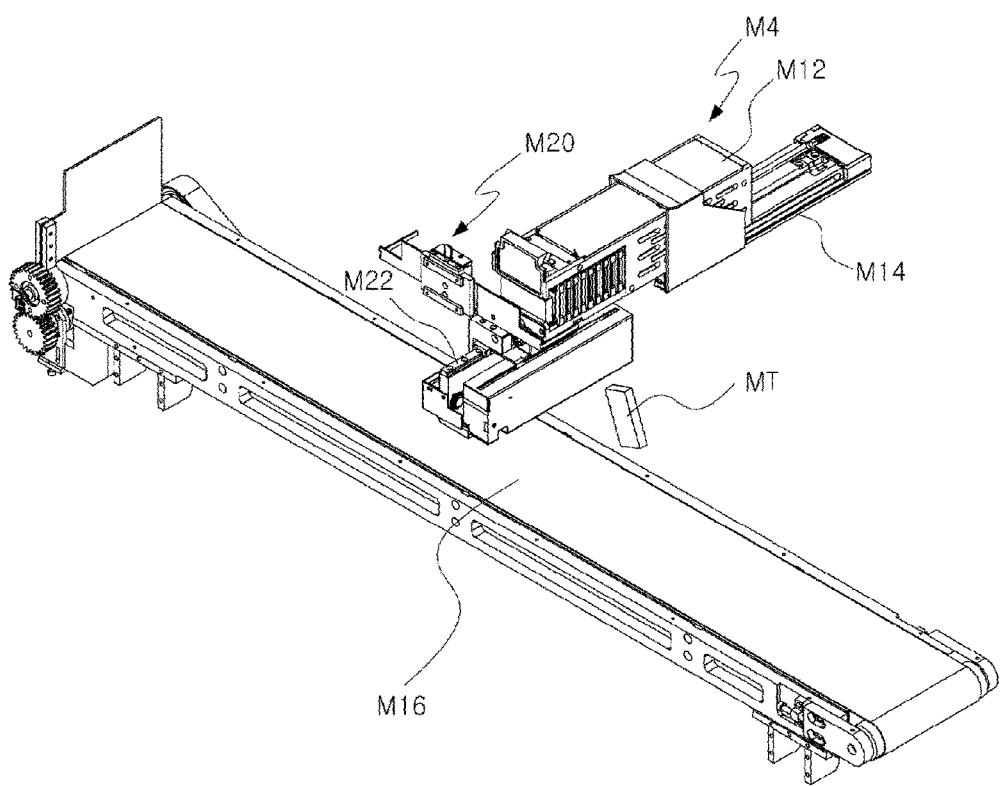

[FIG.125]
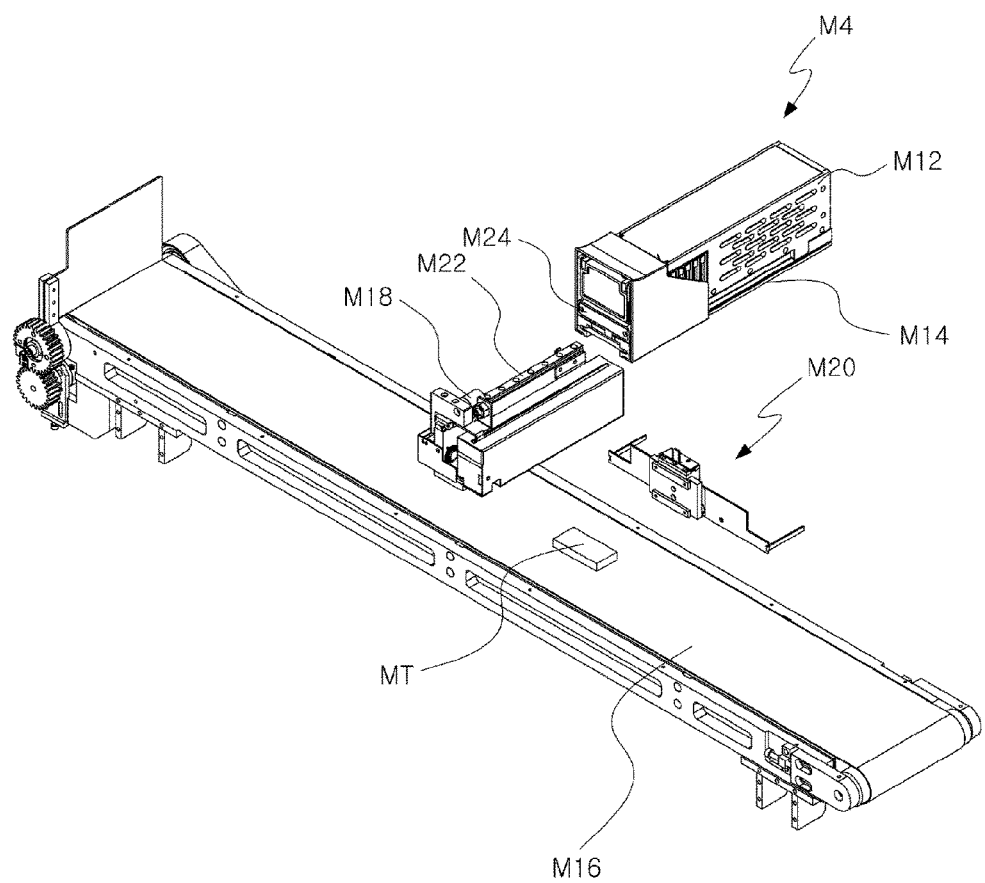

[FIG.126]
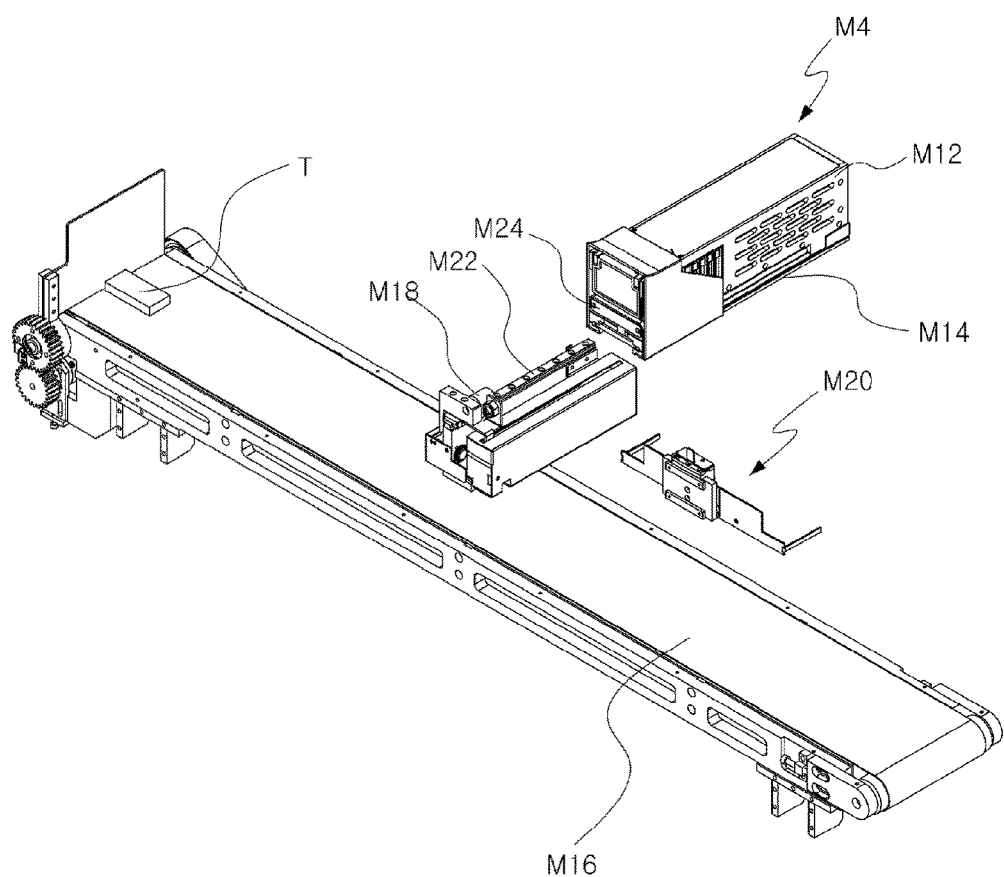

【FIG.127】
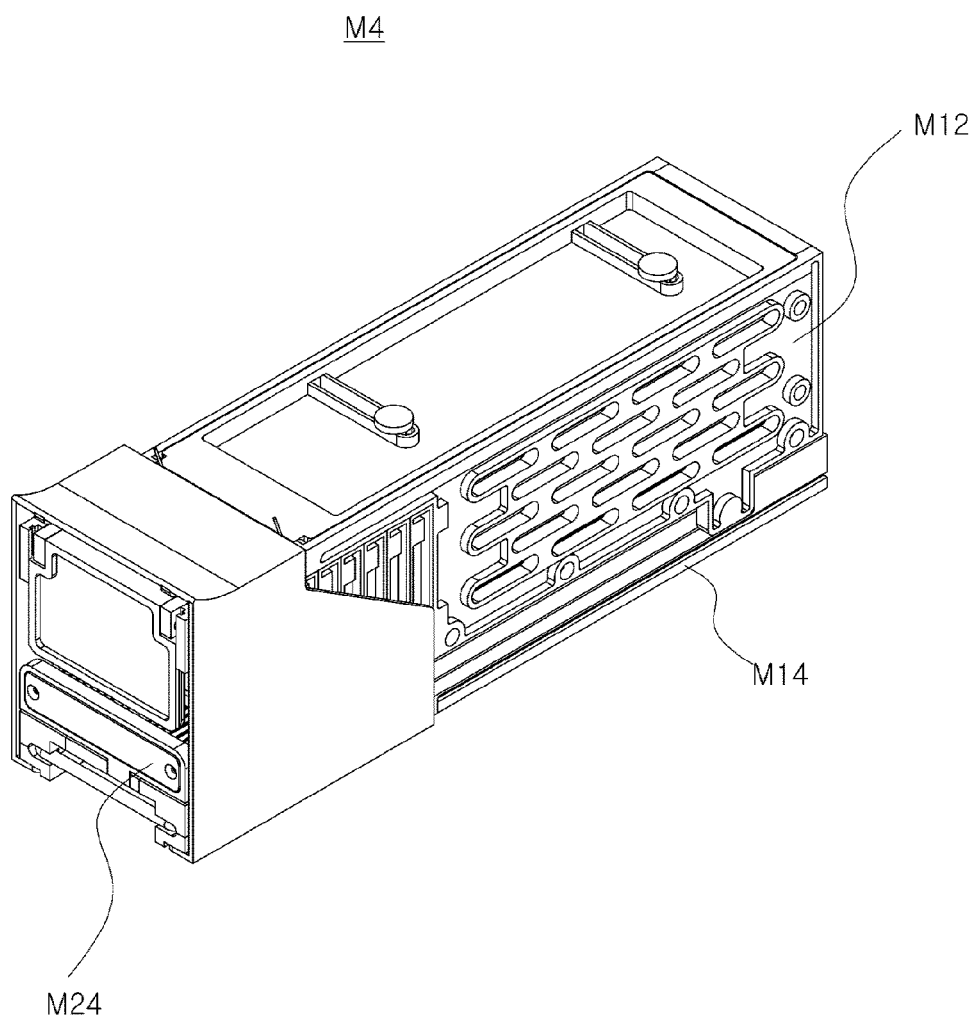

【FIG.128】
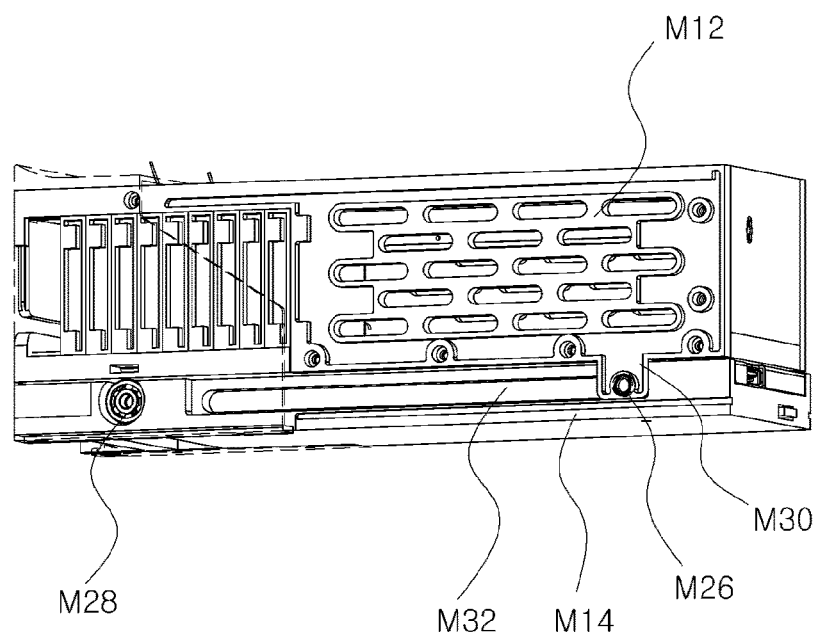

【FIG.129】
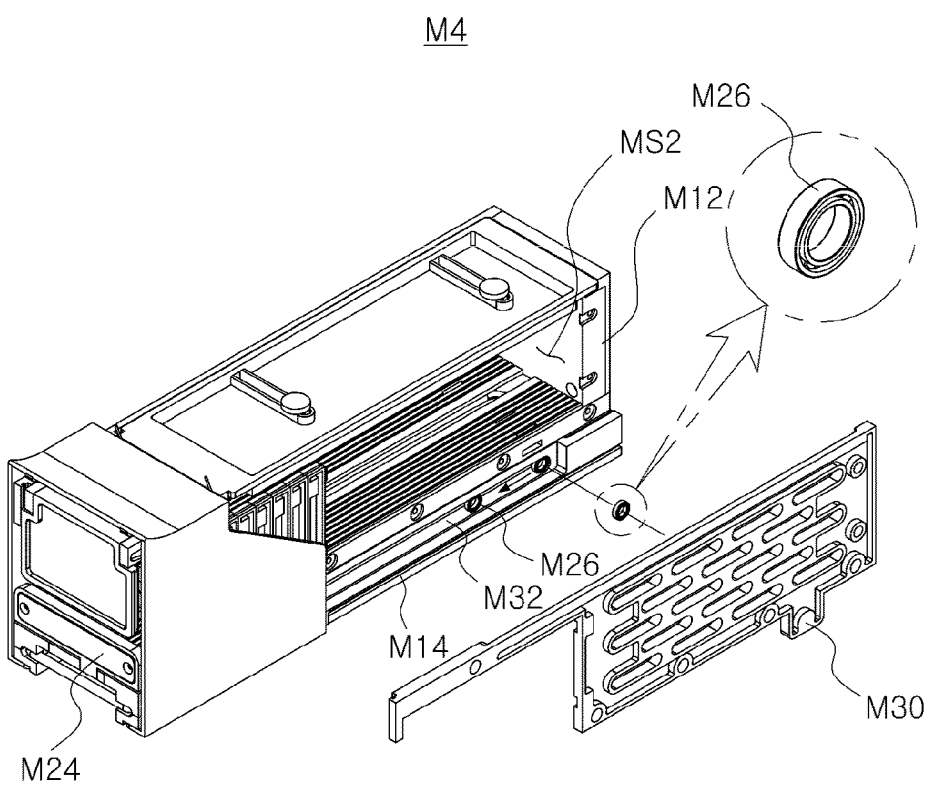

[FIG.130]
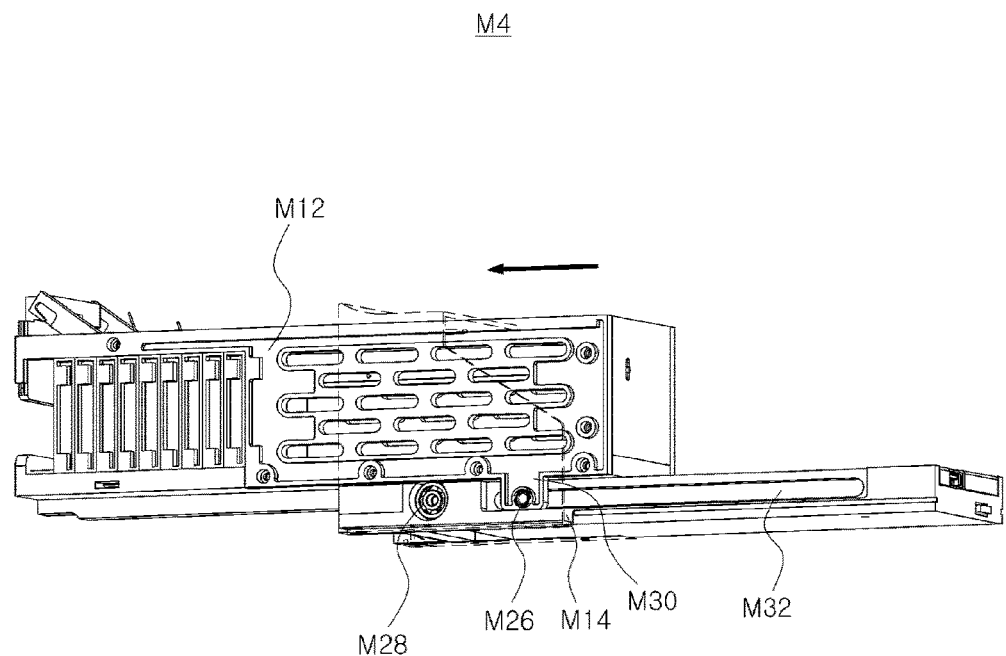

【FIG.131】
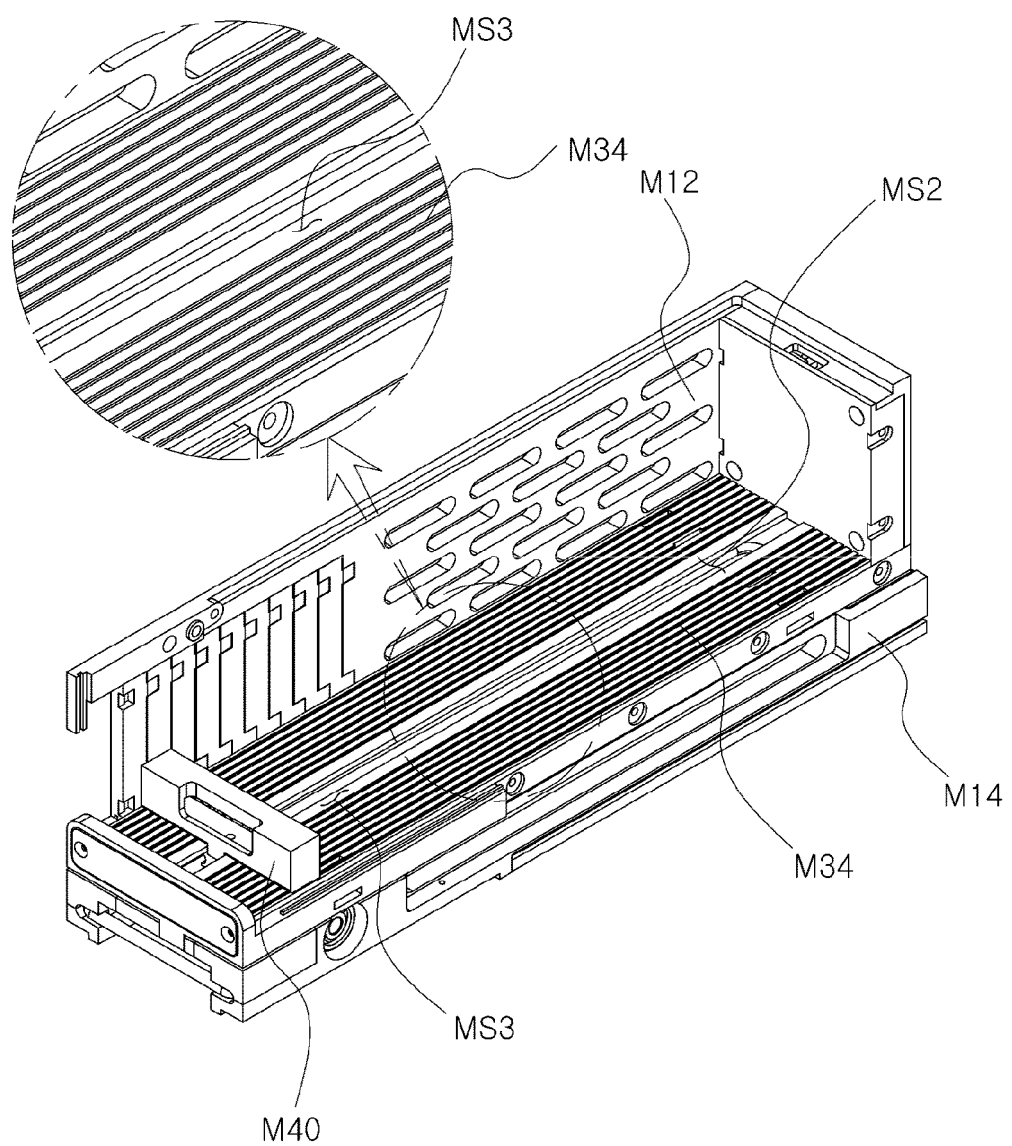

[FIG.132]
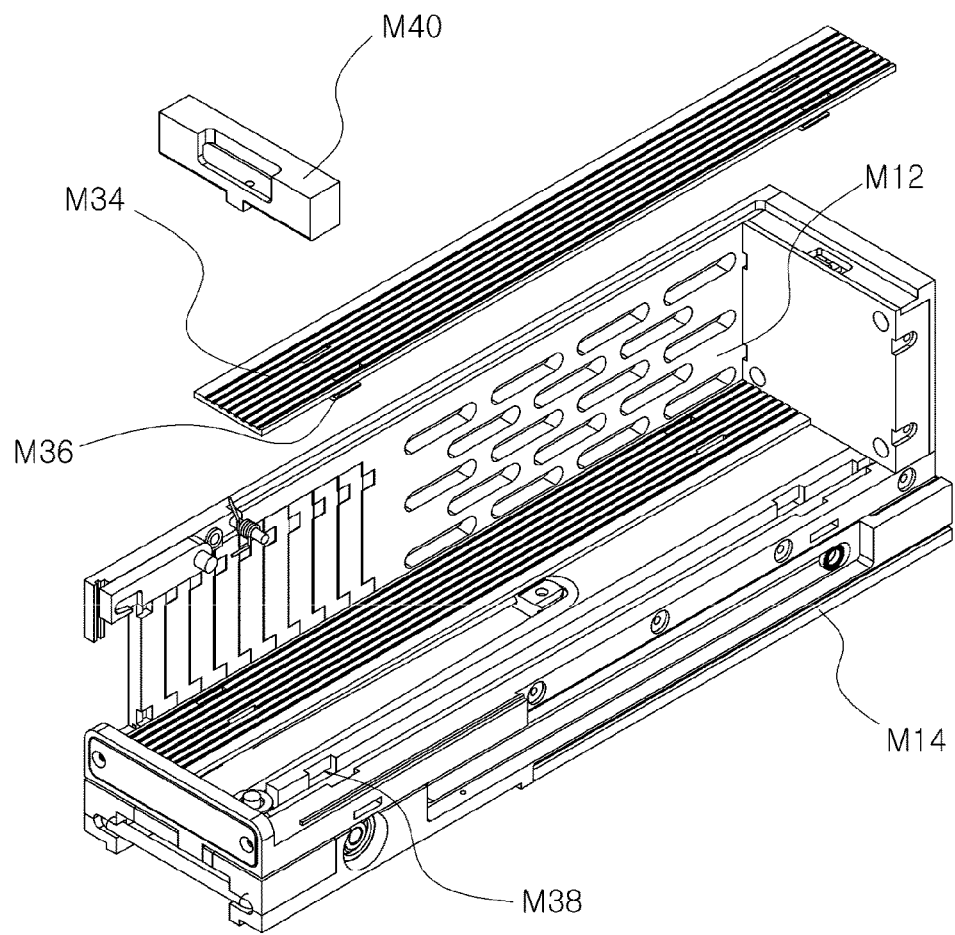

[FIG.133]
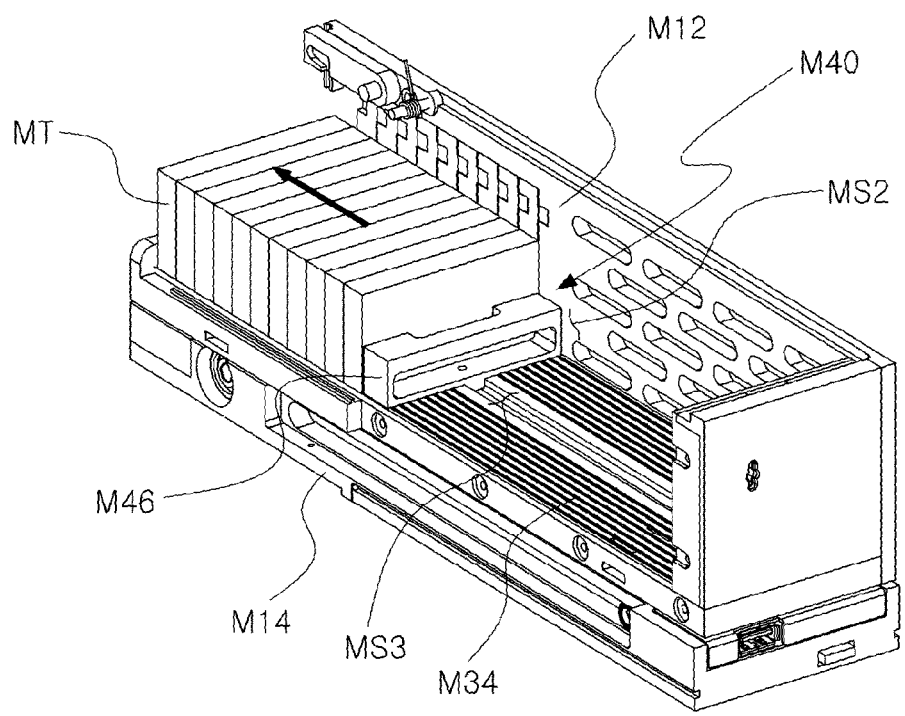

[FIG.134]
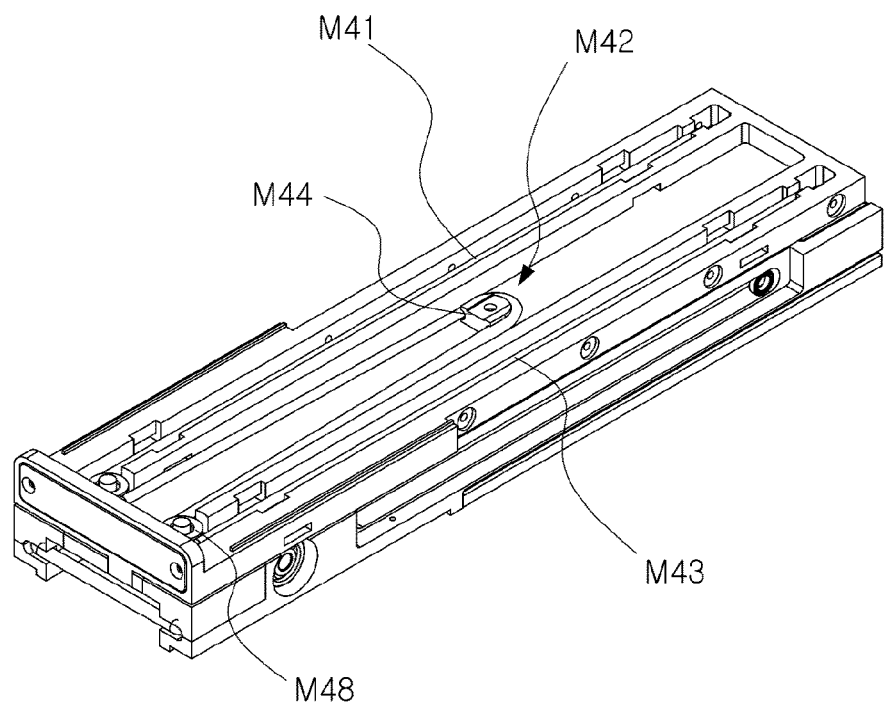

[FIG.135]
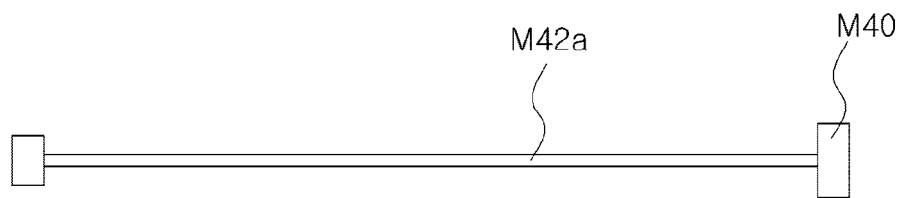
[FIG.136]
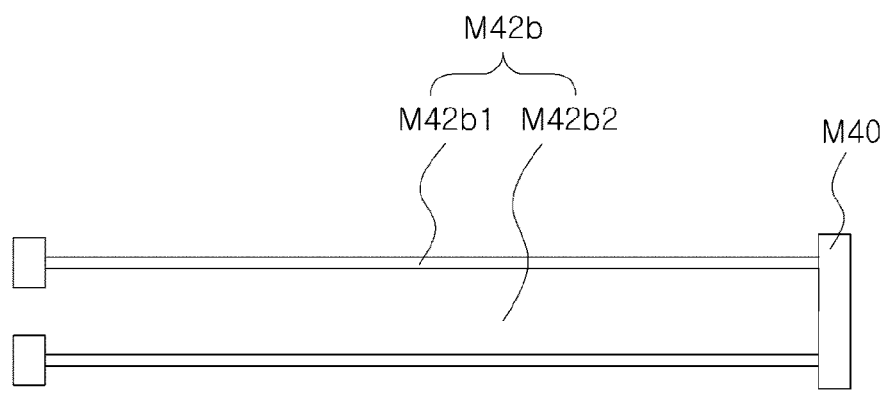
[FIG.137]
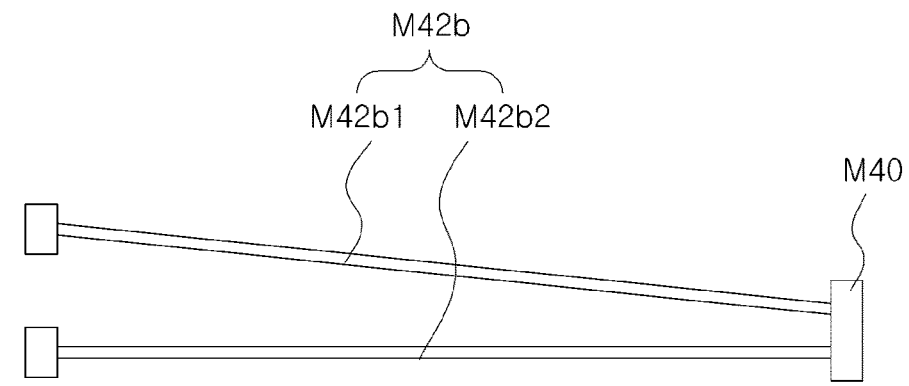

[FIG.138]
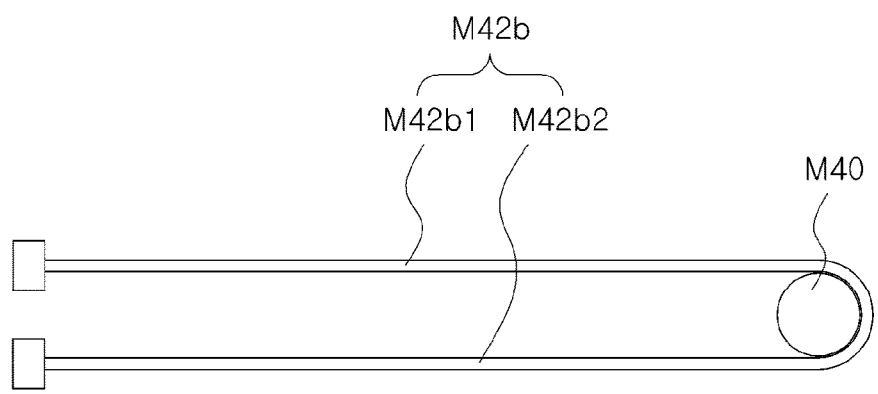

[FIG.139]
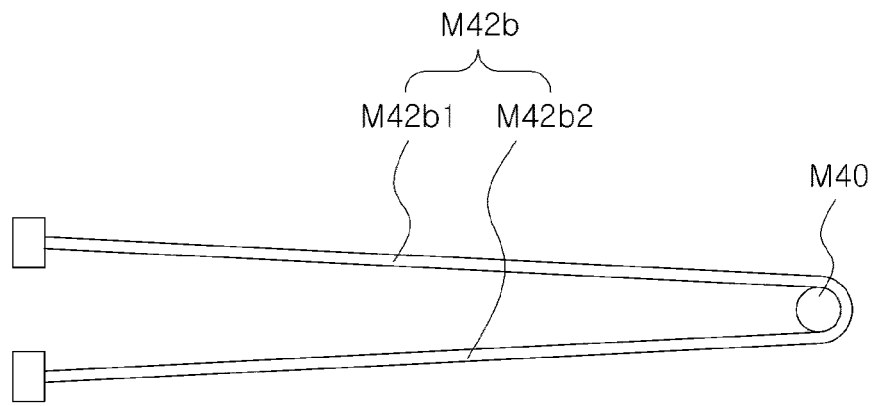
[FIG.140]
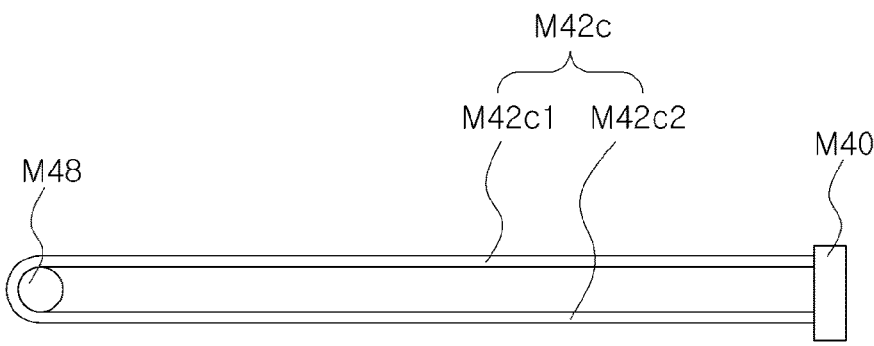
[FIG.141]
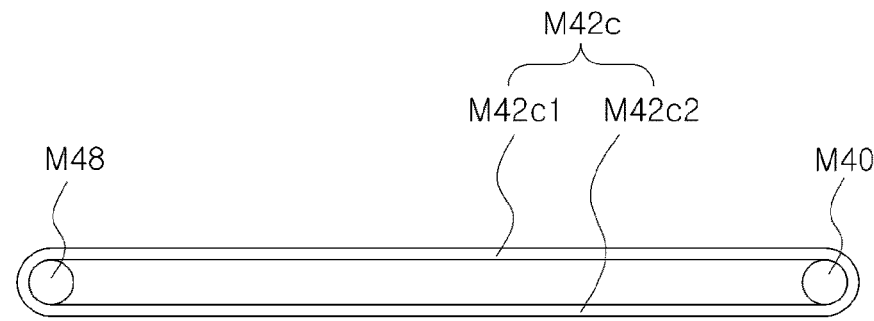

[FIG.142]
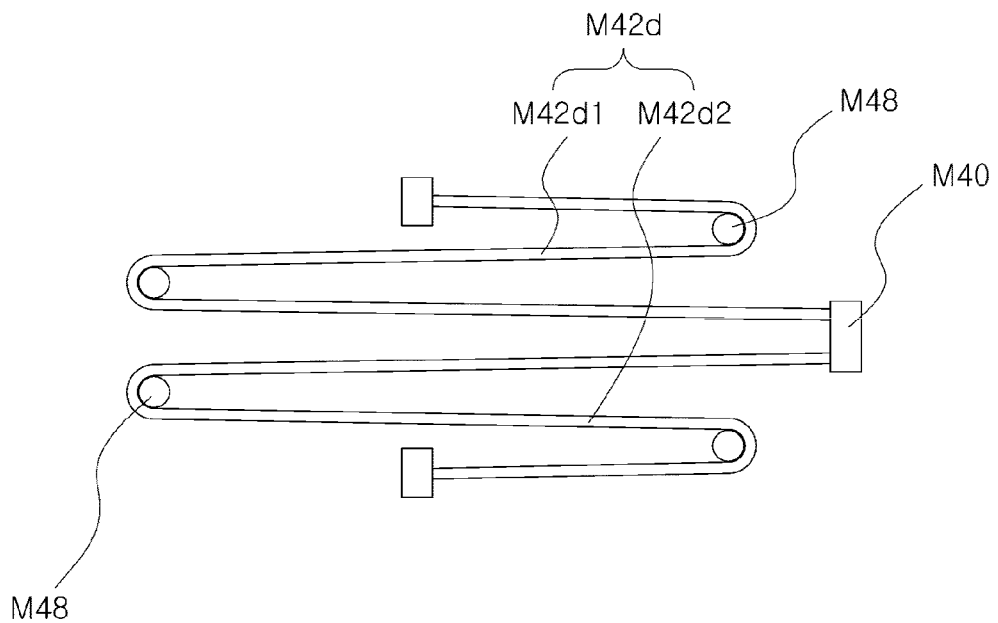
[FIG.143]
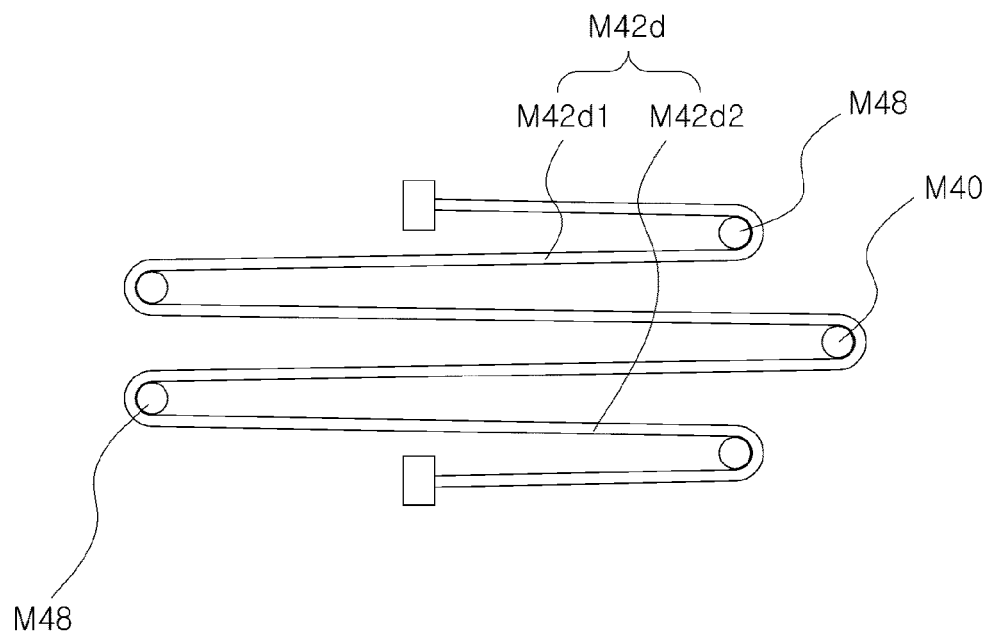

[FIG.144]
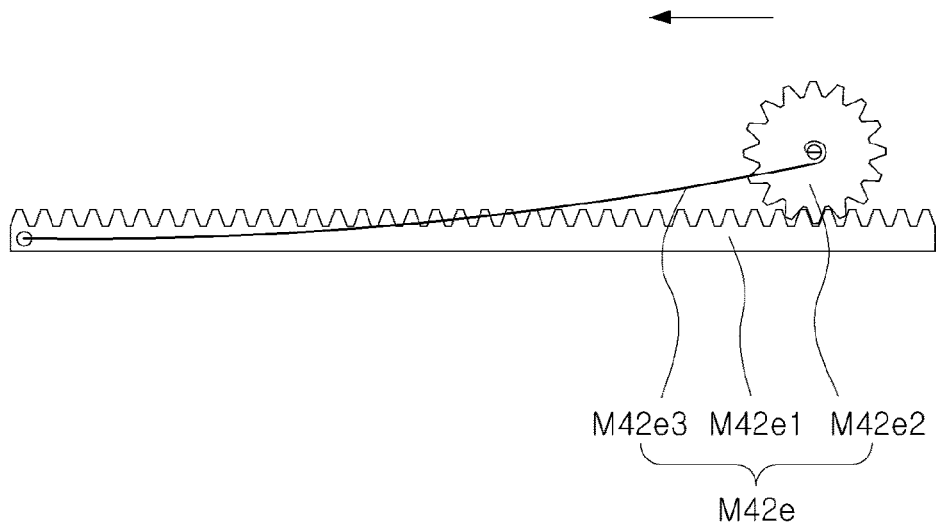
[FIG.145]
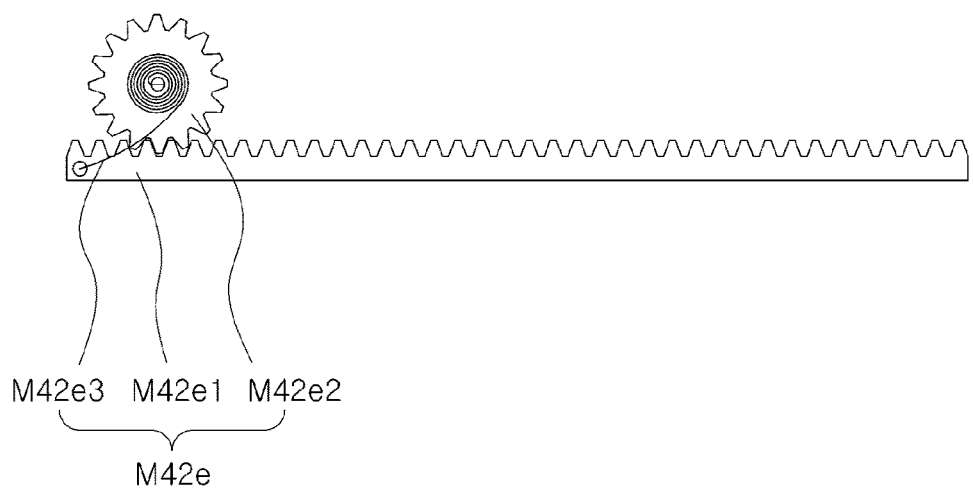

【FIG.146】
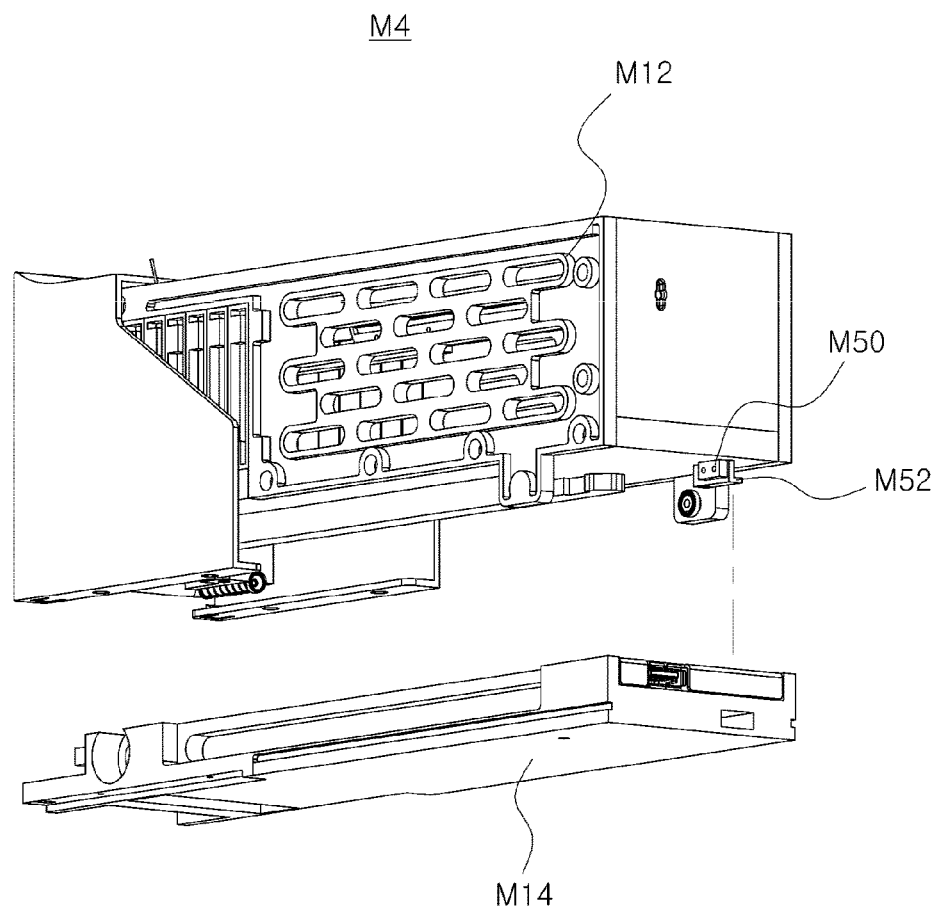

[FIG.147]
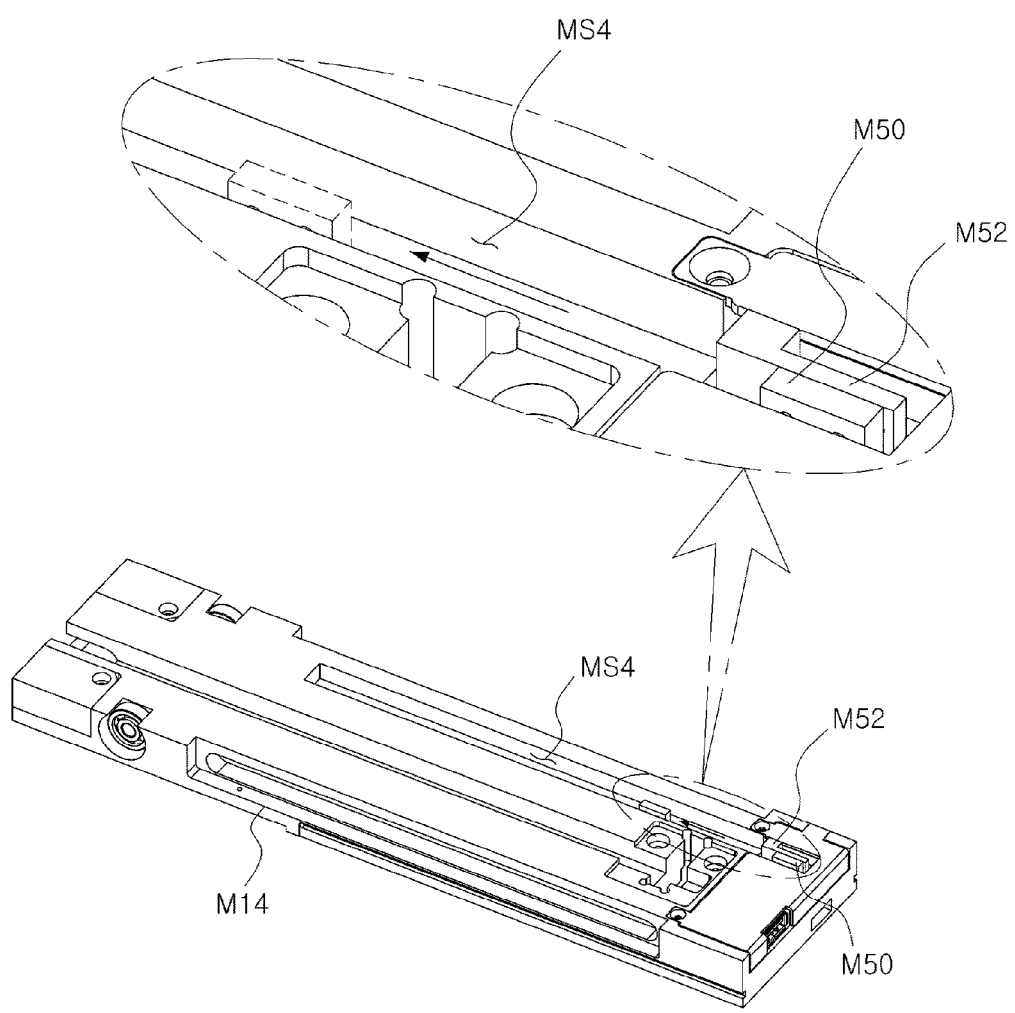

【FIG.148】
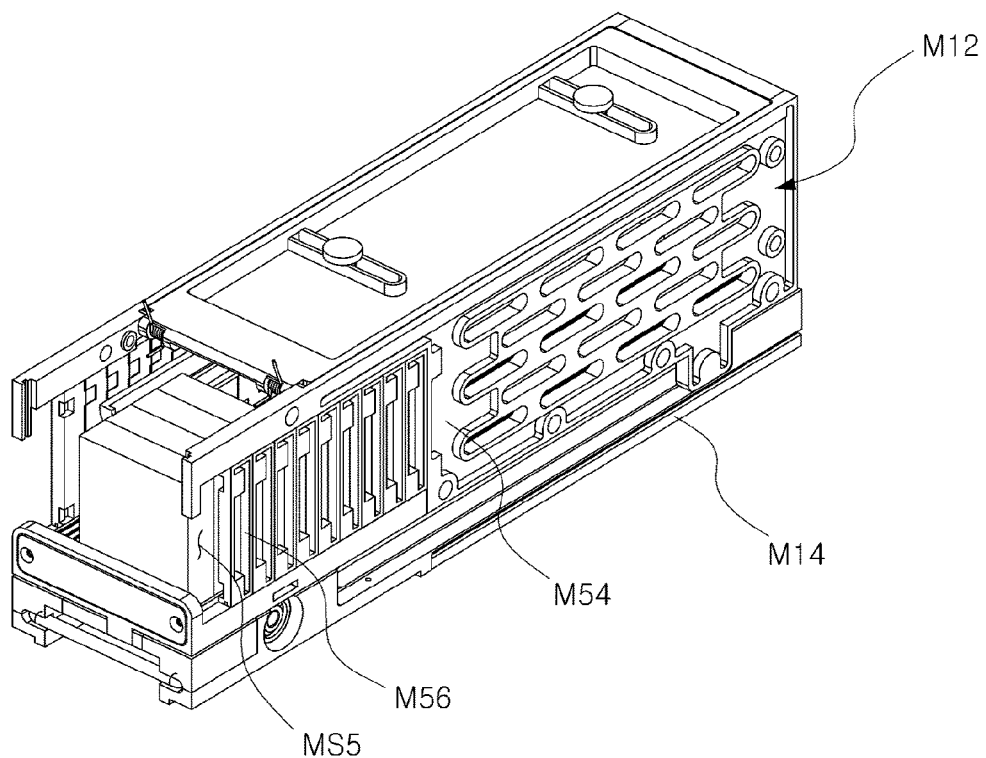

[FIG.149]
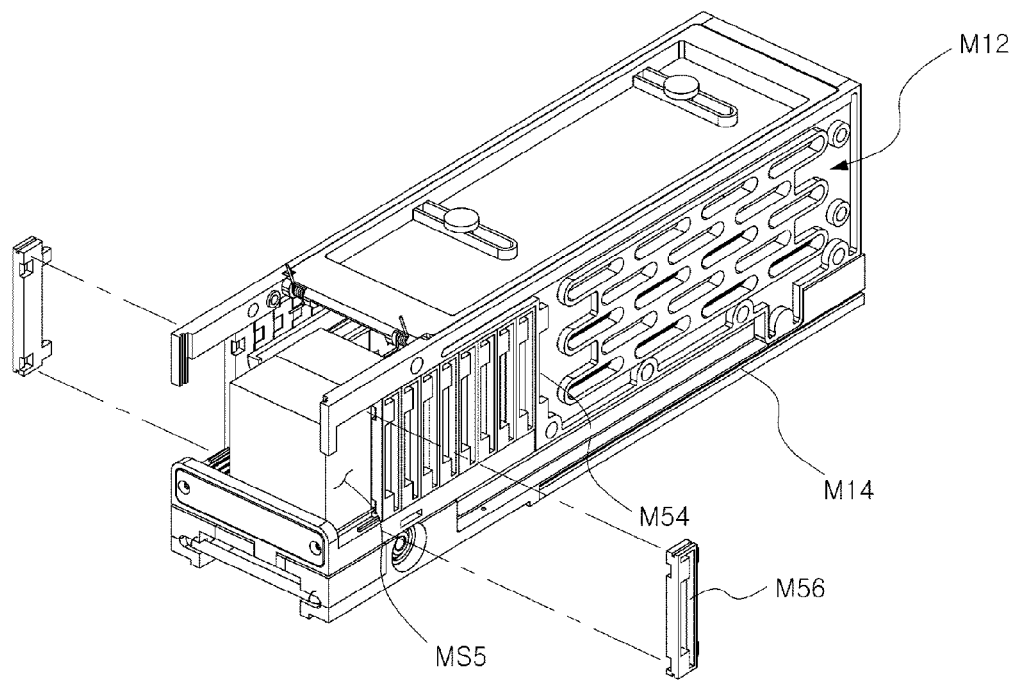

【FIG.150】
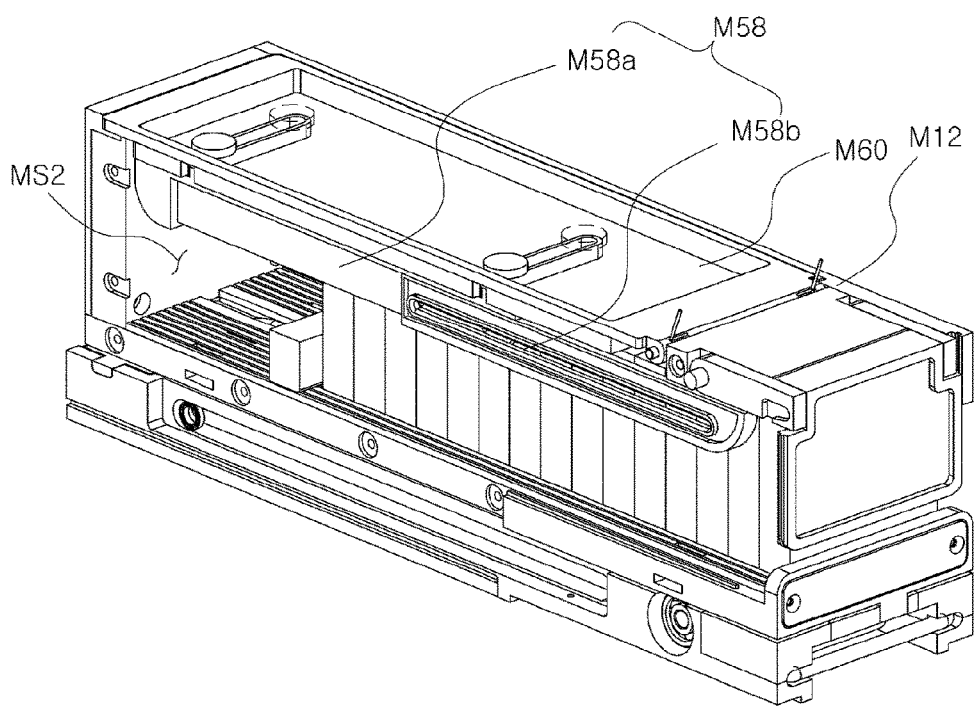

[FIG.151]
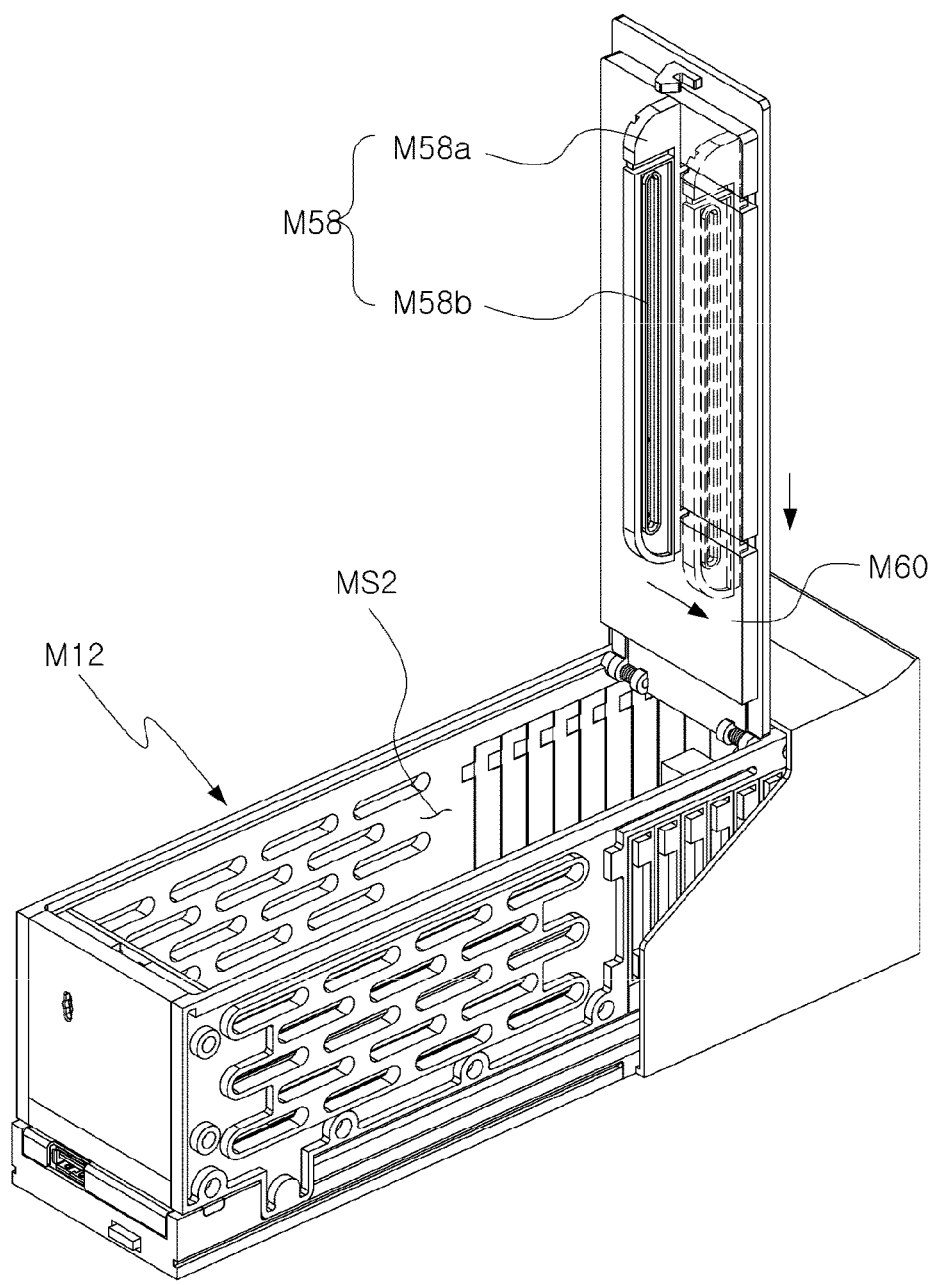

【FIG.152】
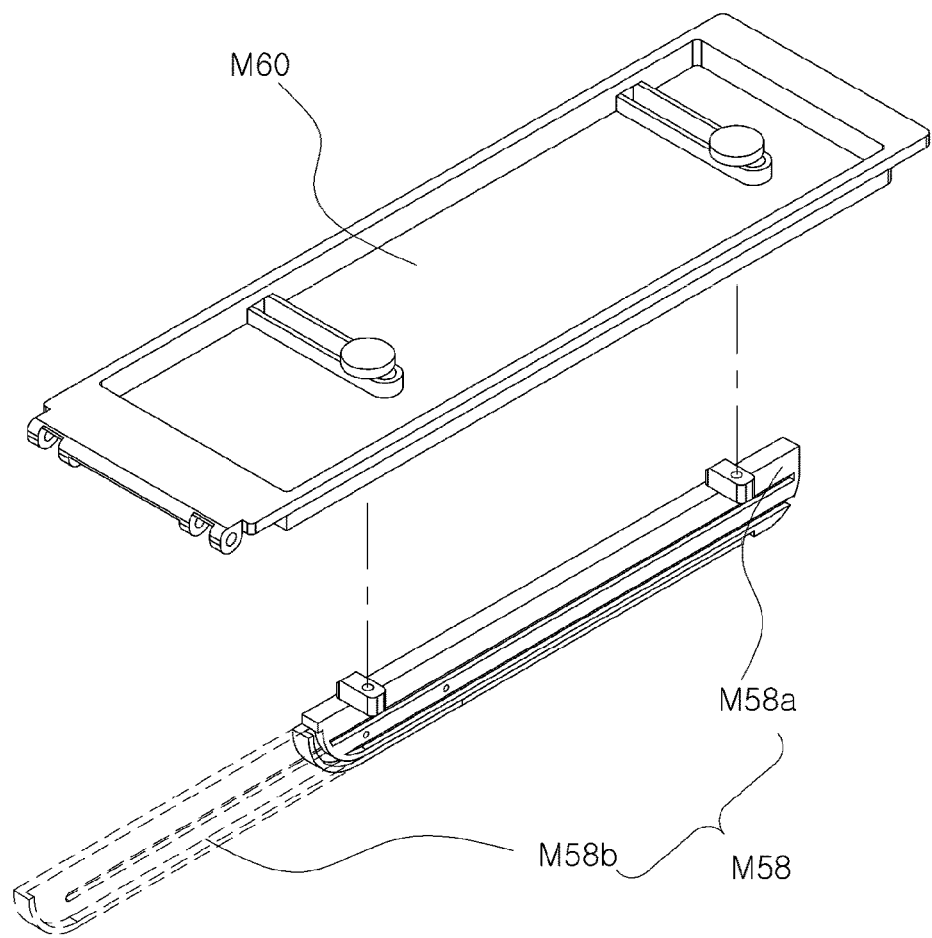

[FIG.153]
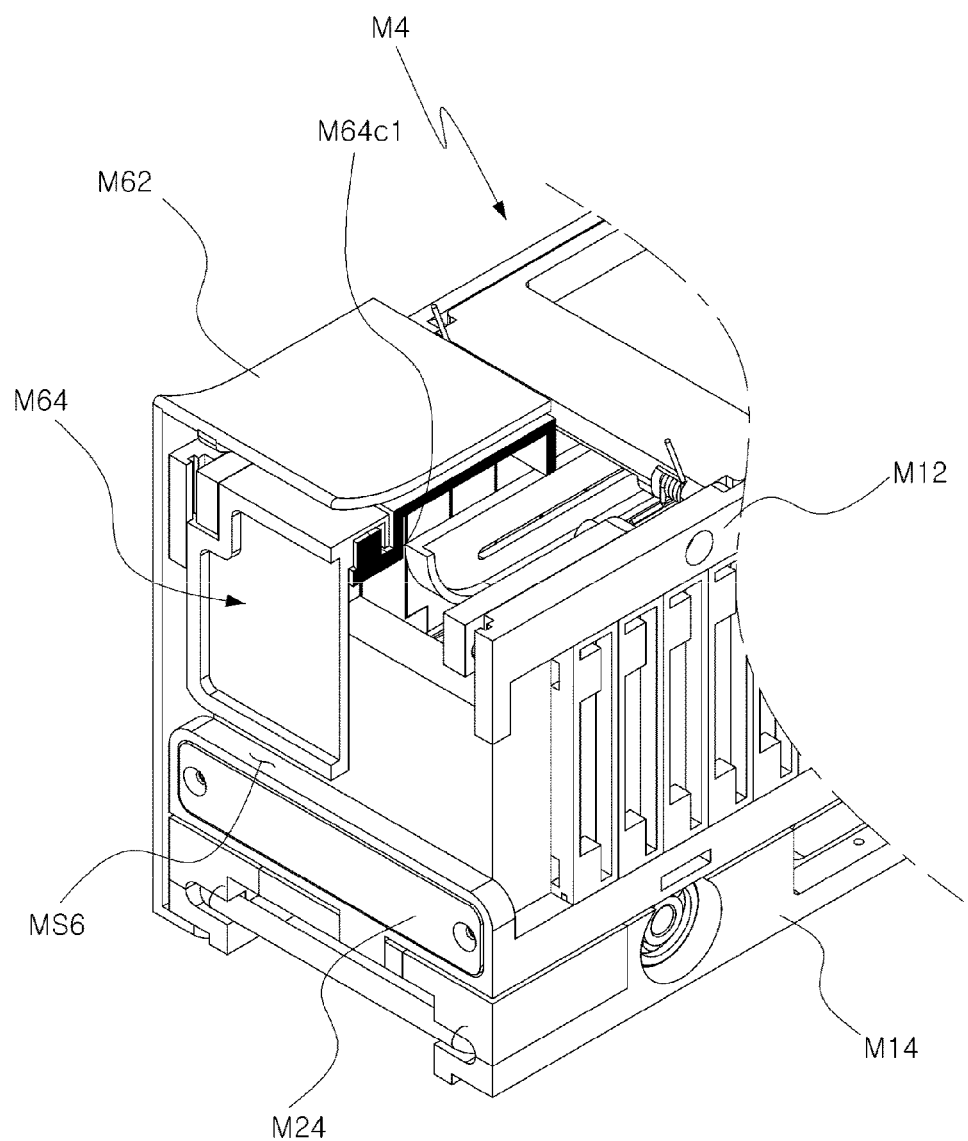

[FIG.154]
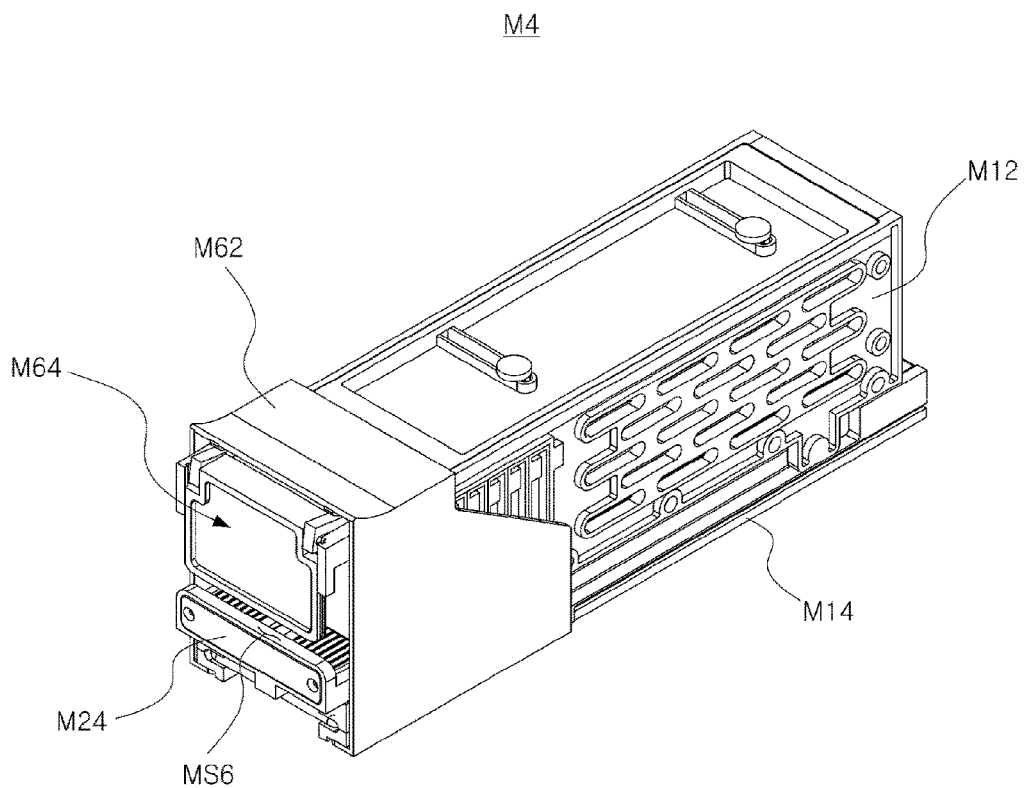

【FIG.155】
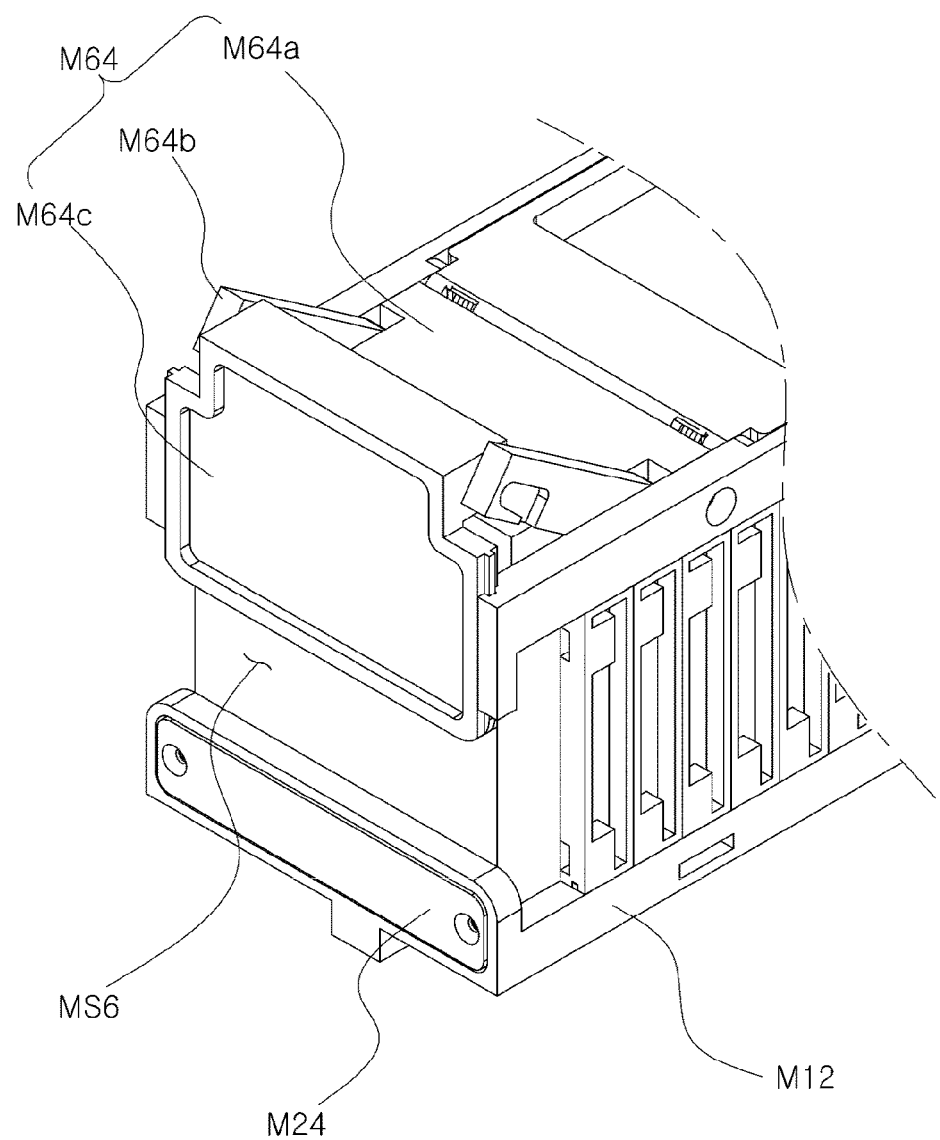

[FIG.156]
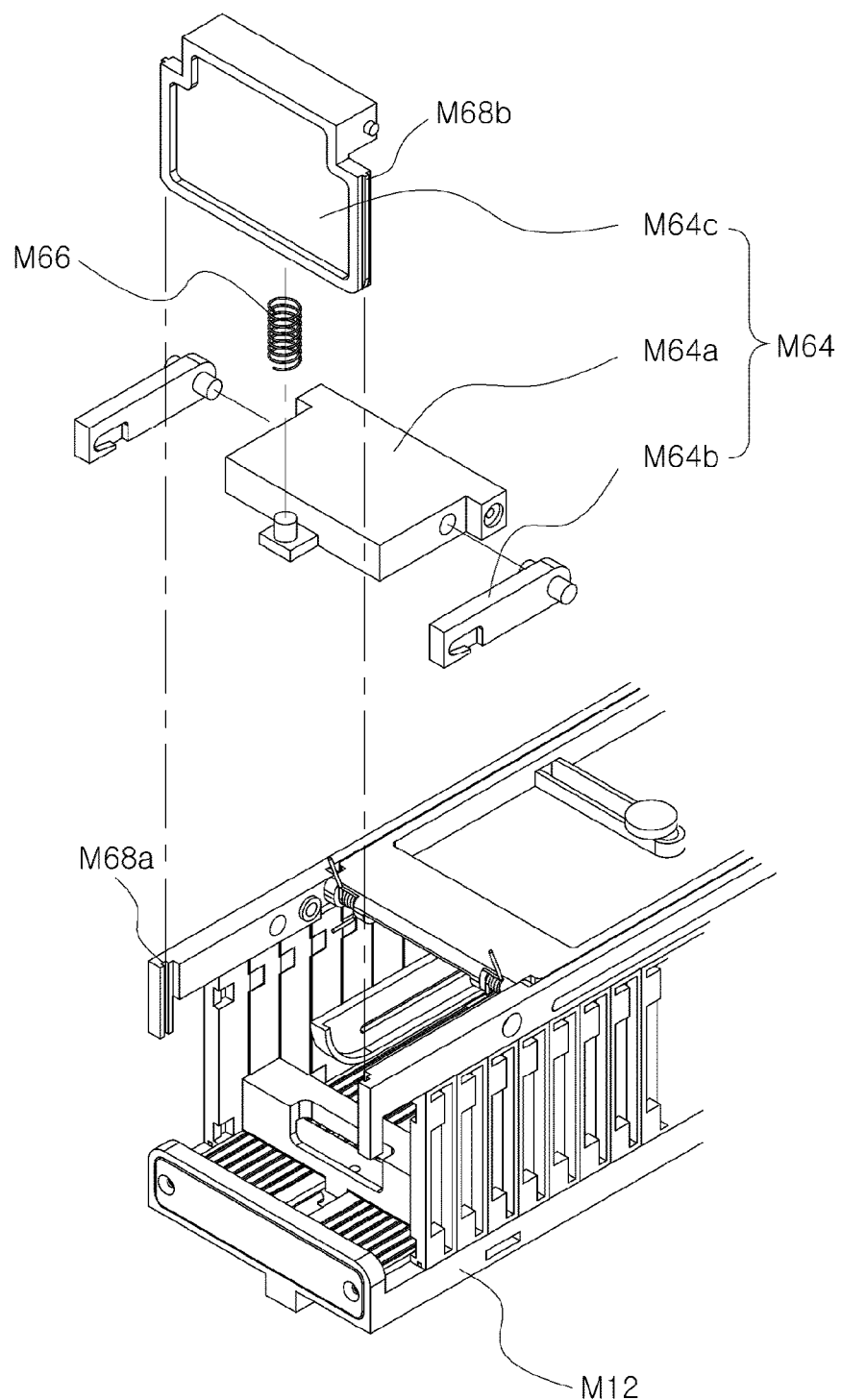

【FIG.157】
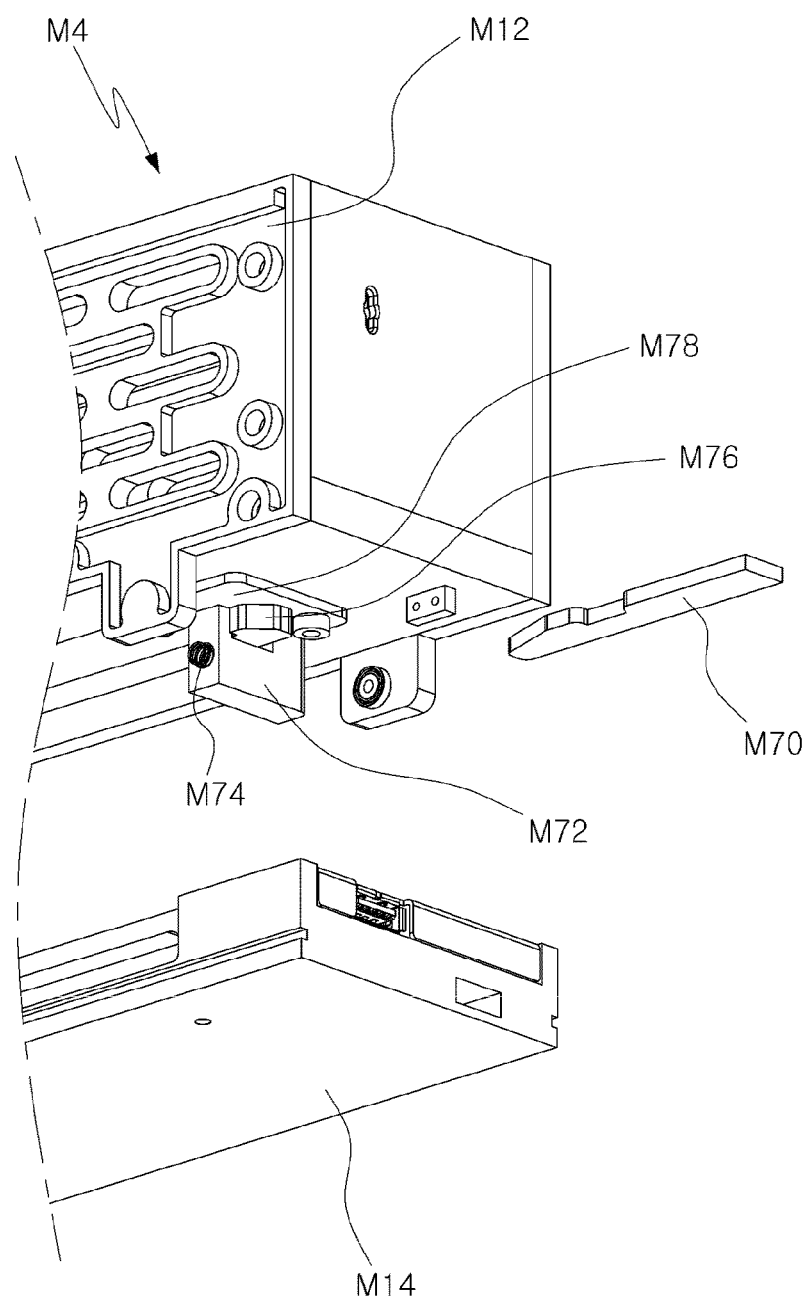

【FIG.158】
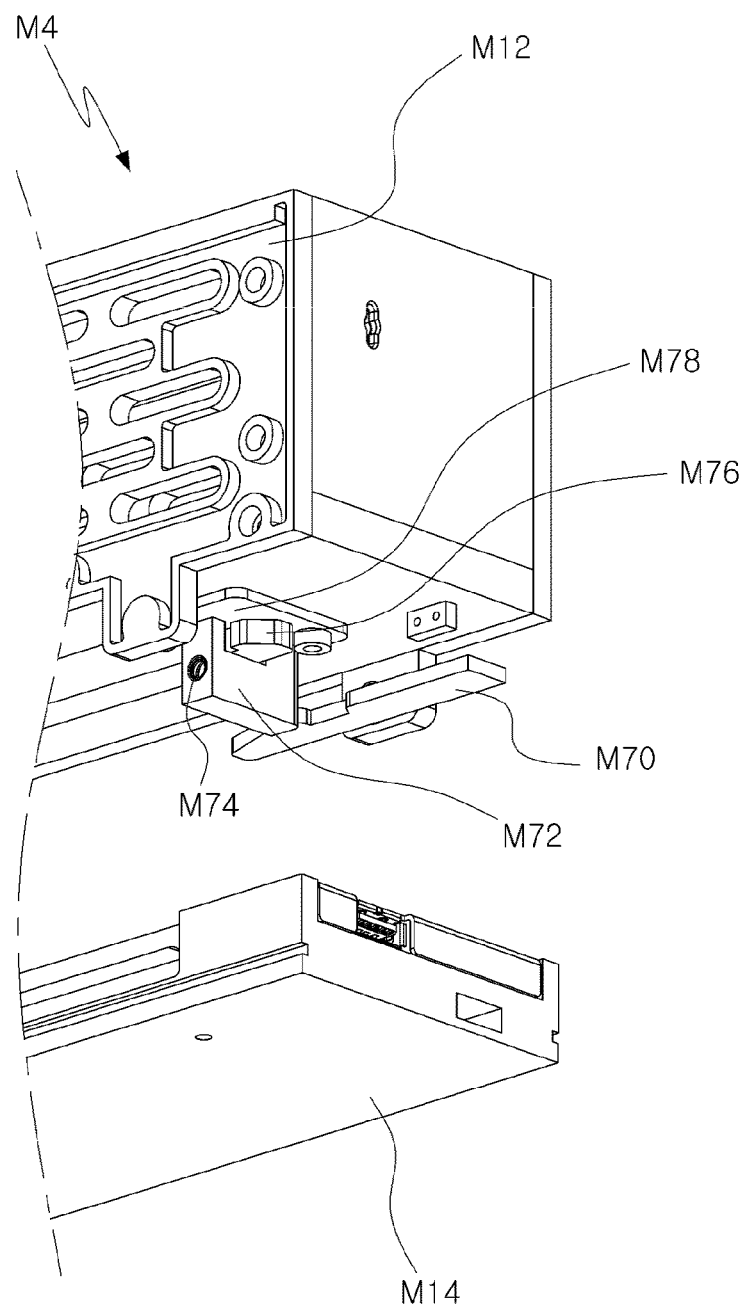

[FIG.159]
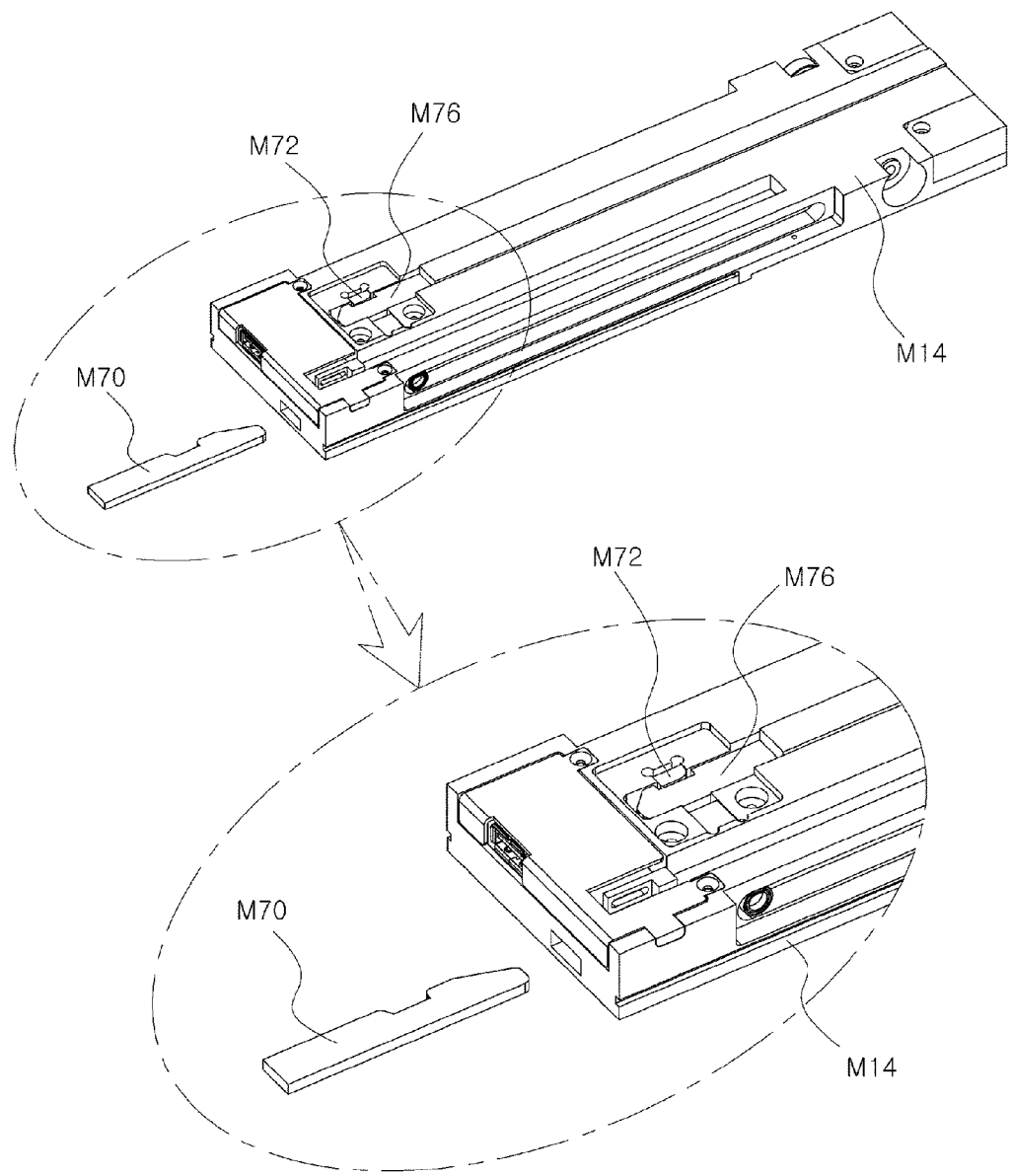

[FIG.160]
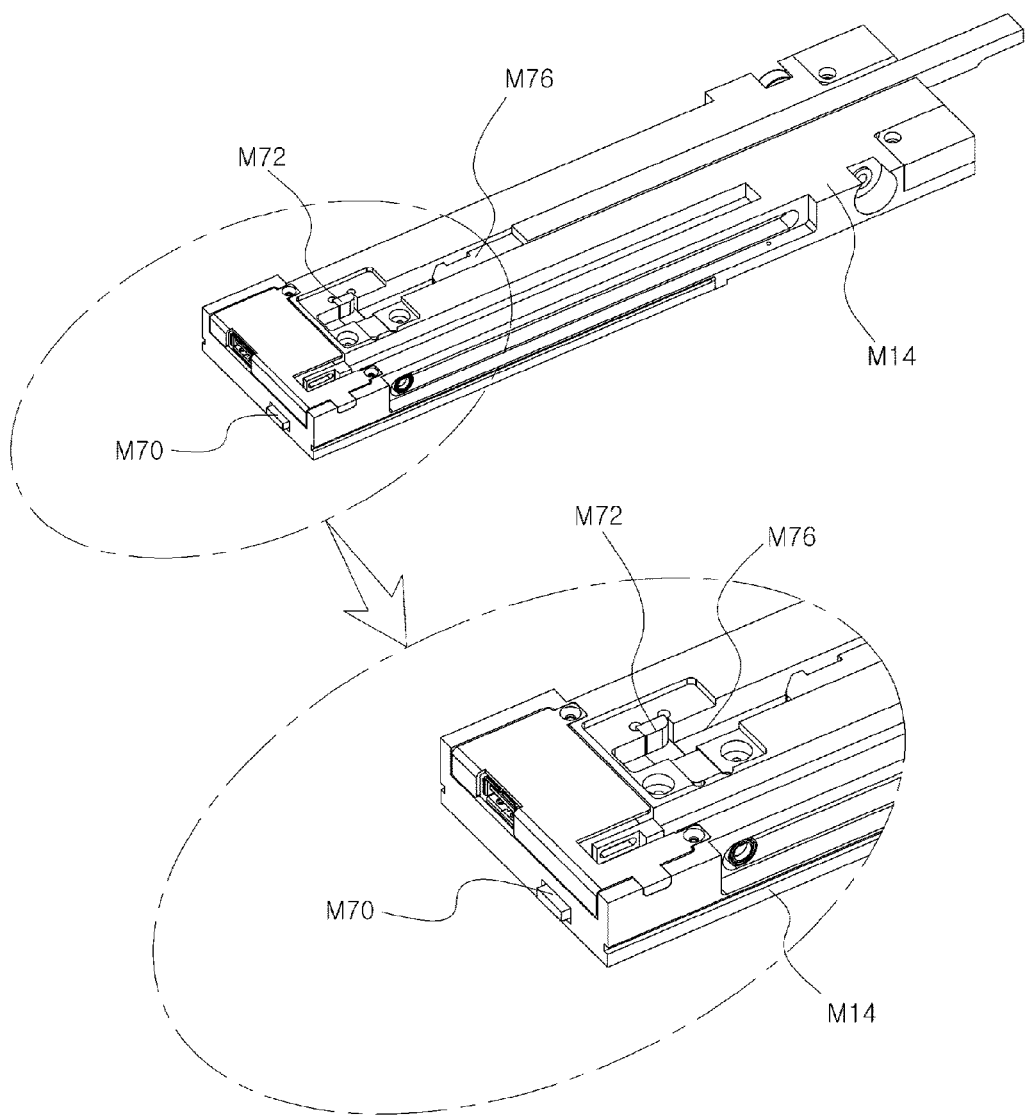

[FIG.161]
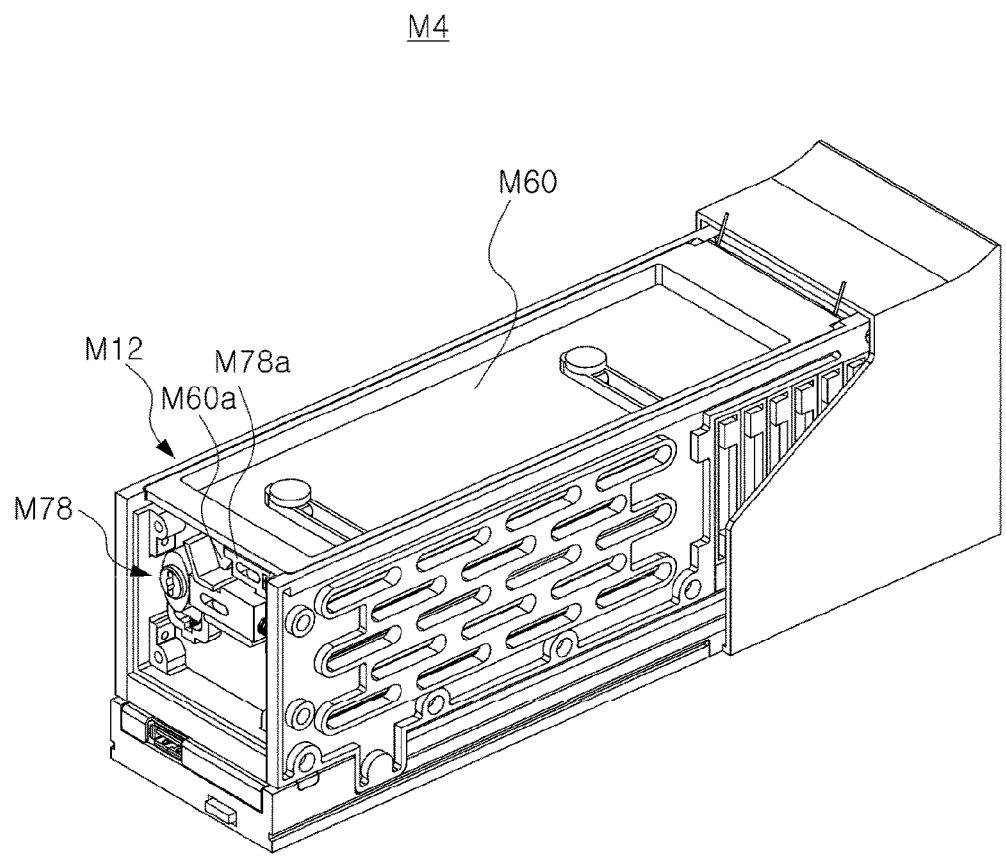

[FIG.162]
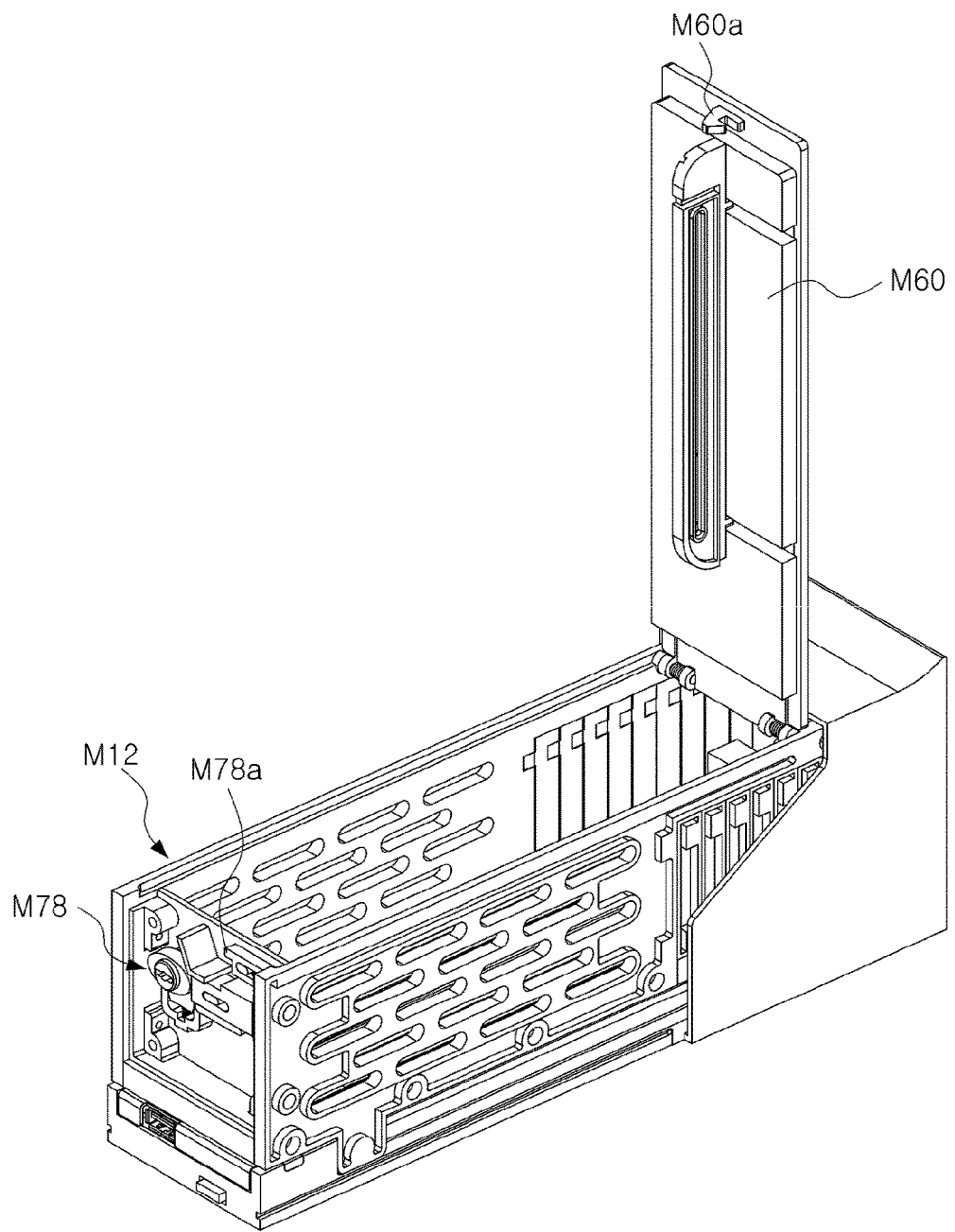

【FIG.163】
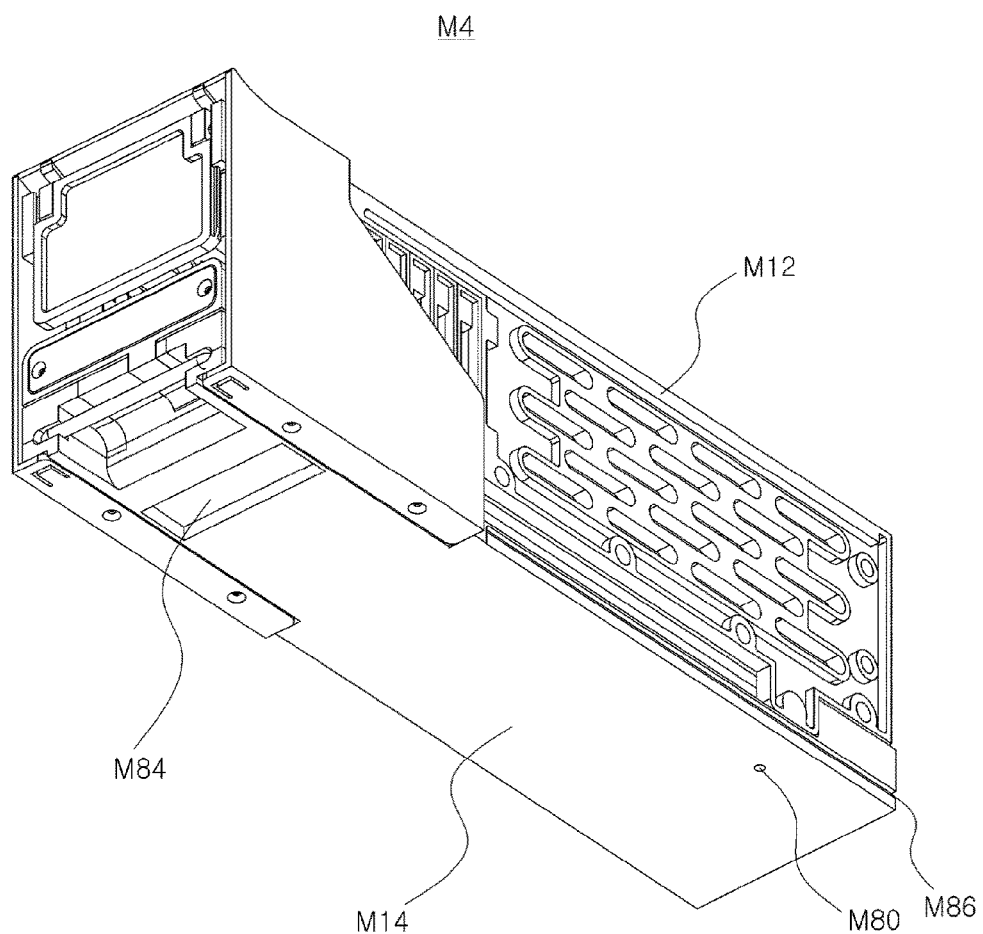

[FIG.164]
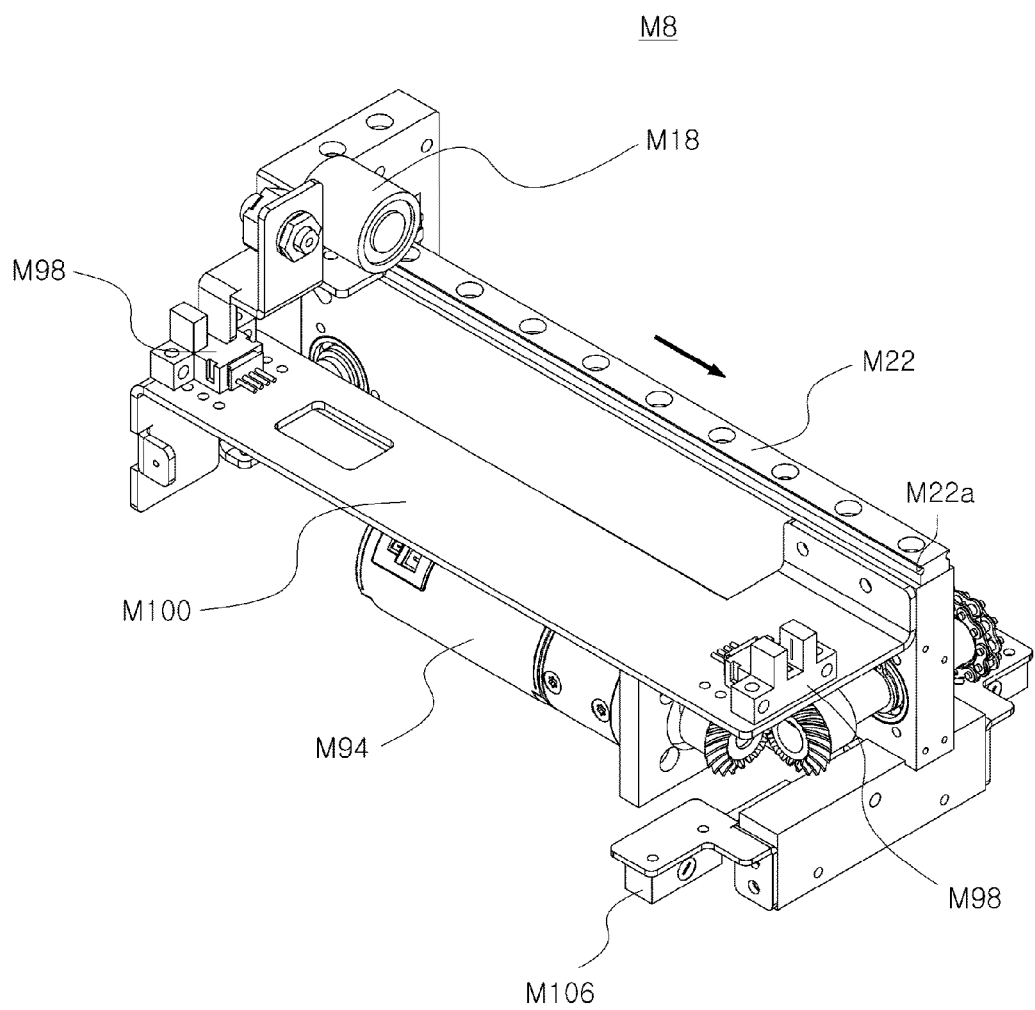

【FIG.165】
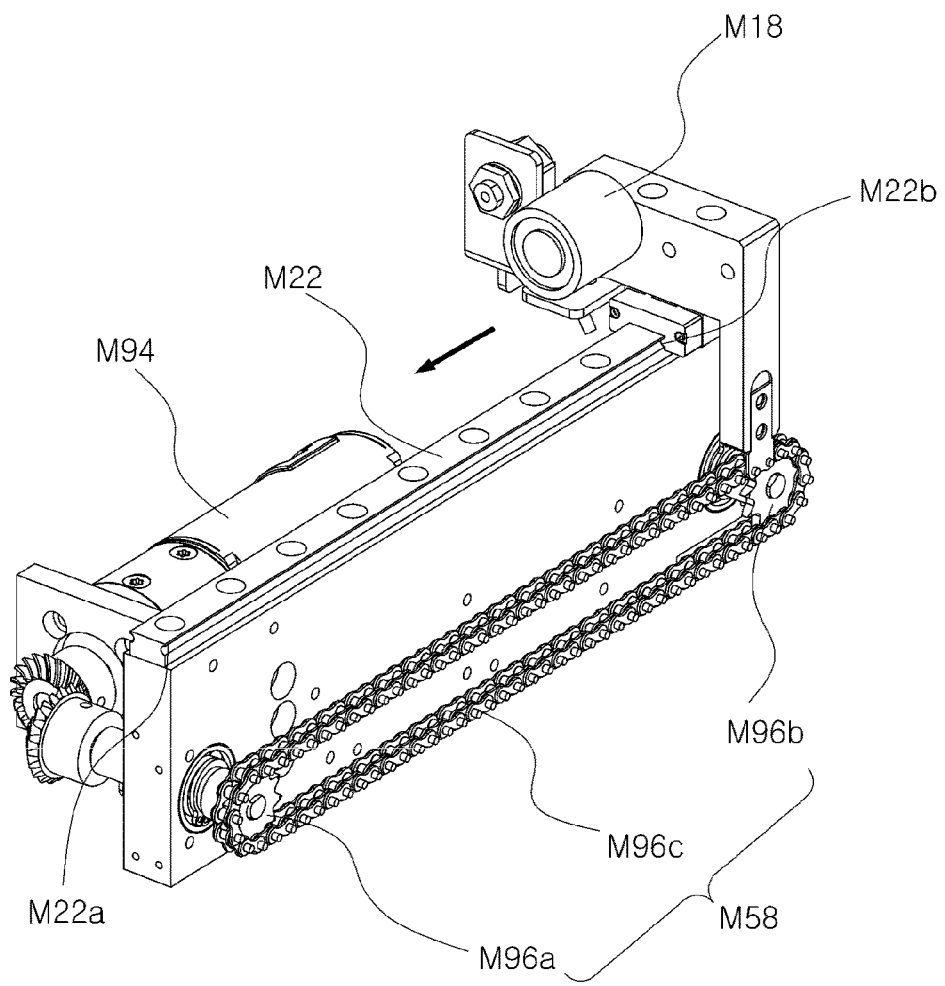

[FIG.166]
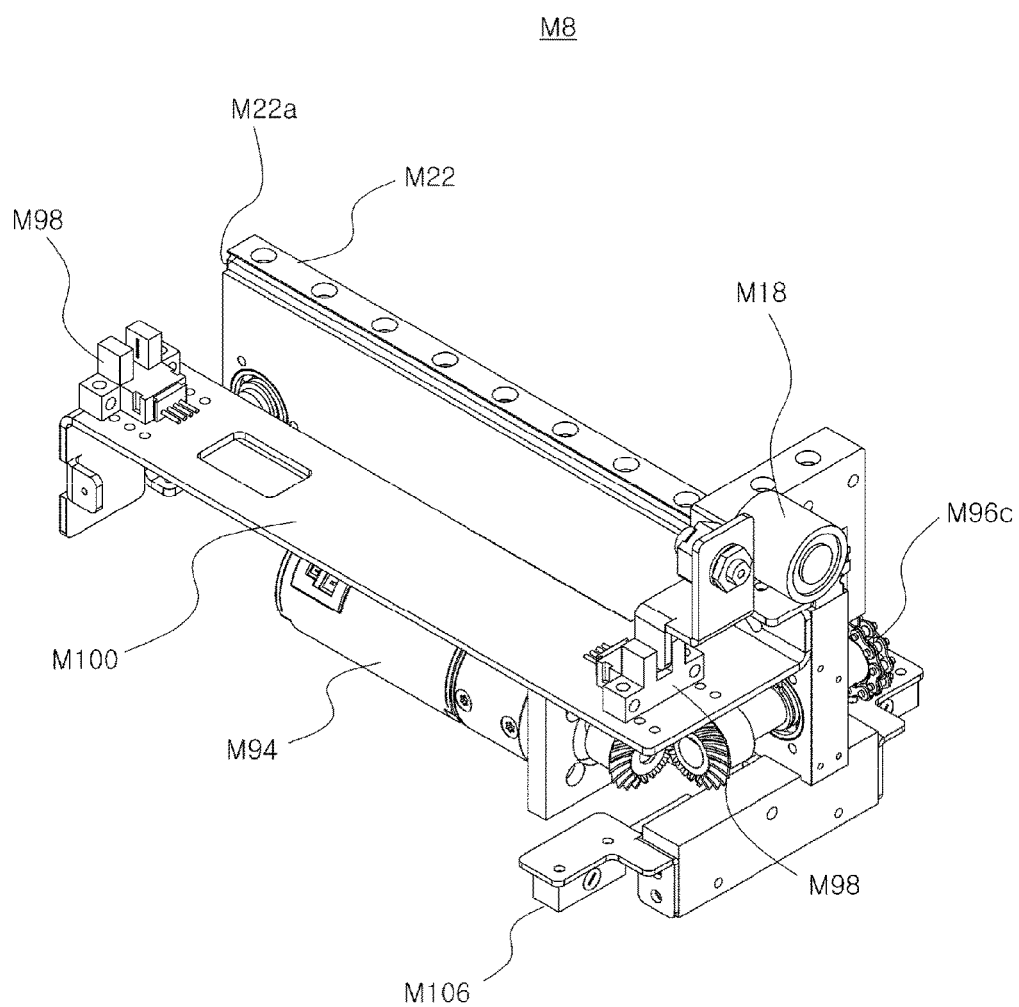

[FIG.167]
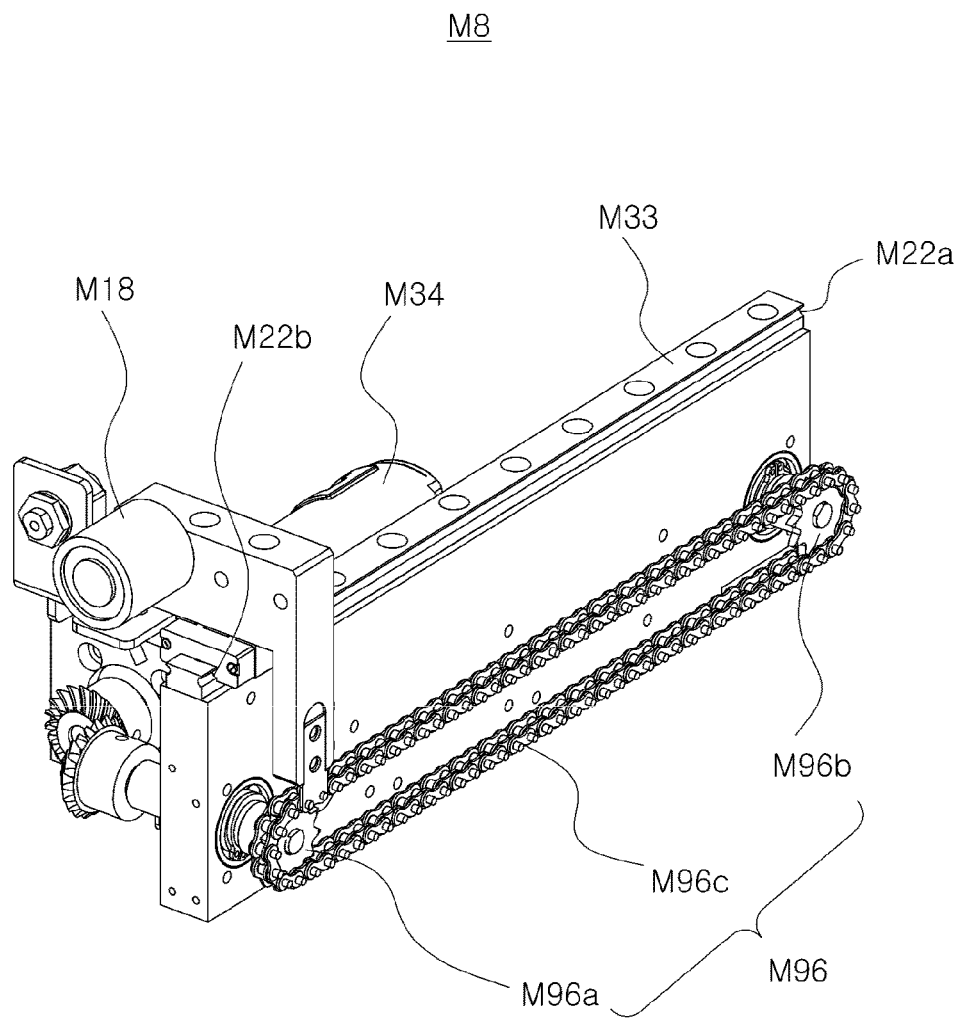

[FIG.168]
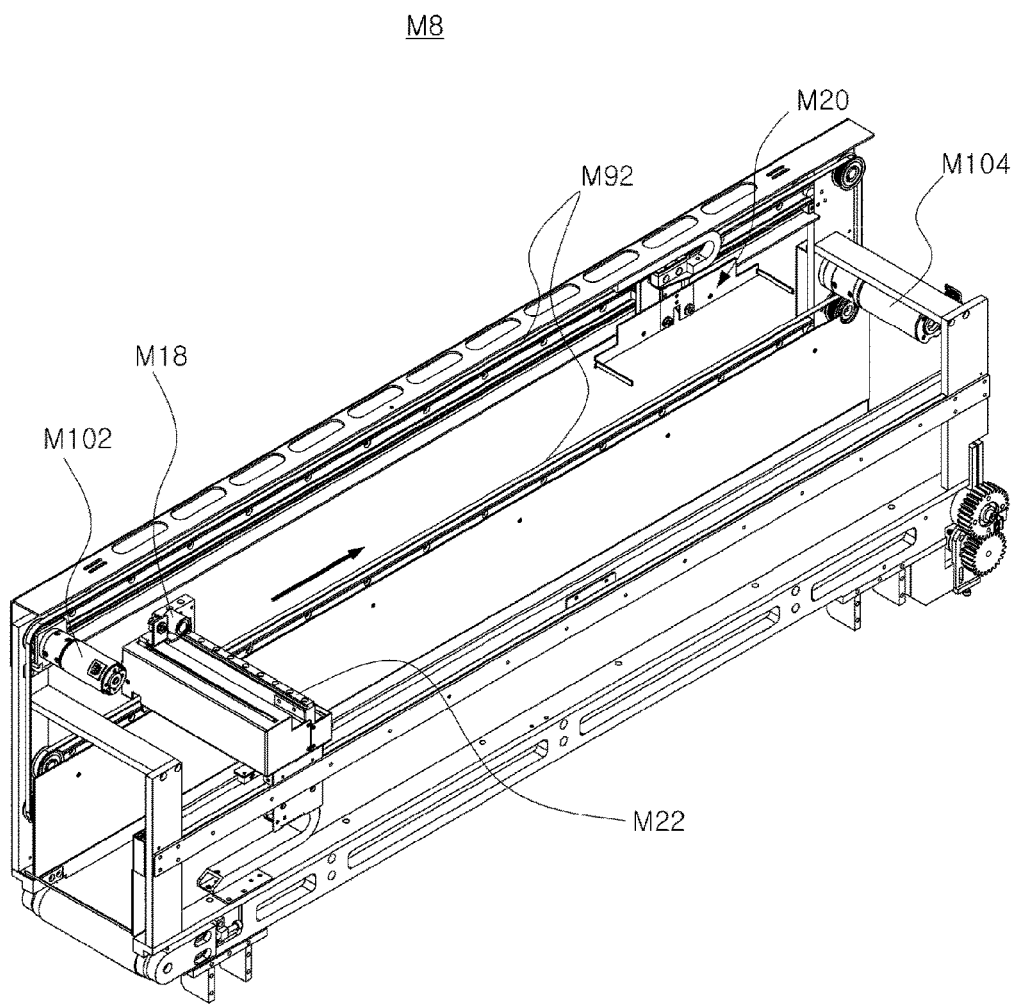

[FIG.169]
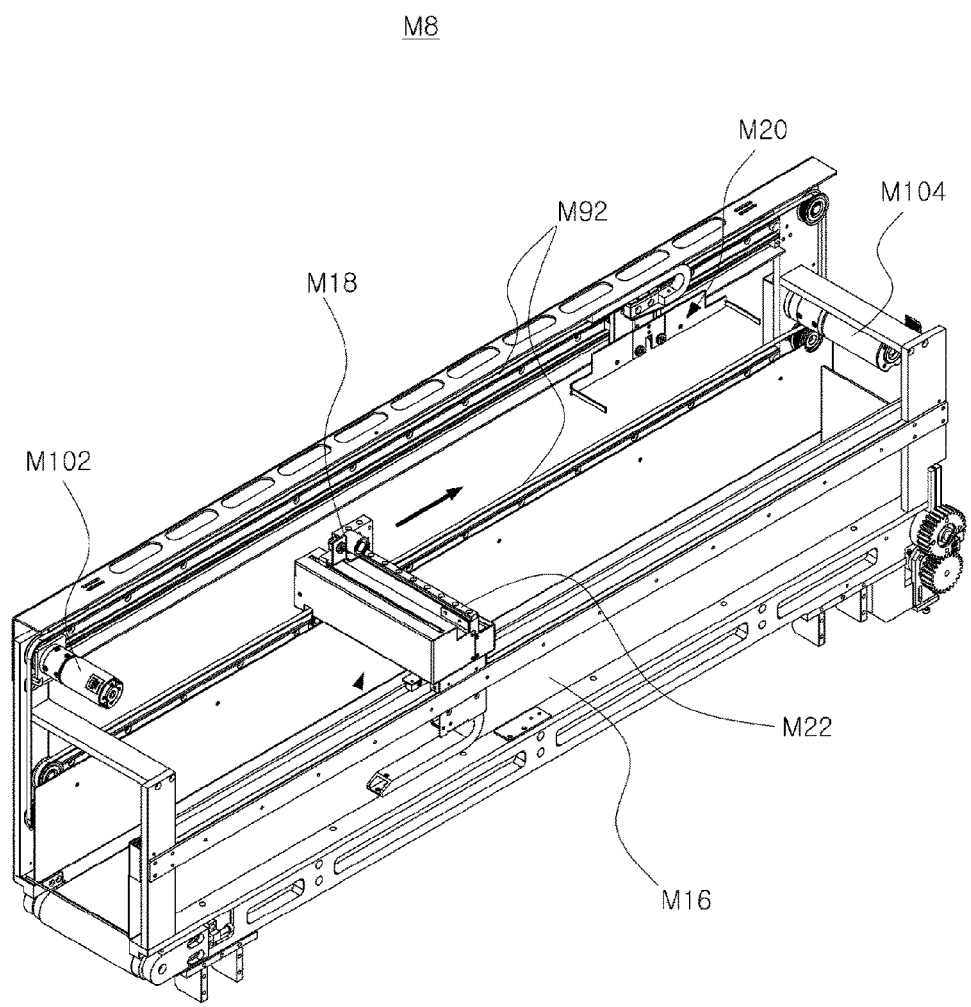

【FIG.170】
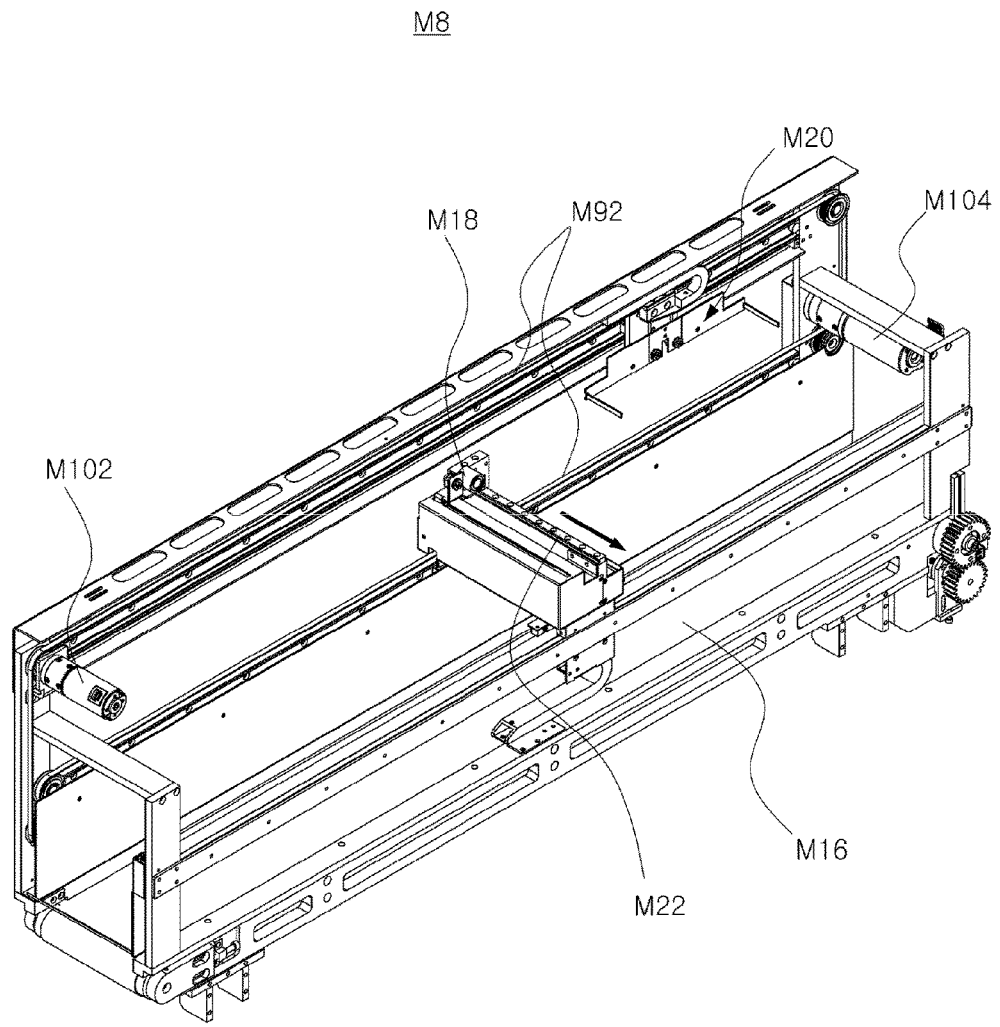

[FIG.171]
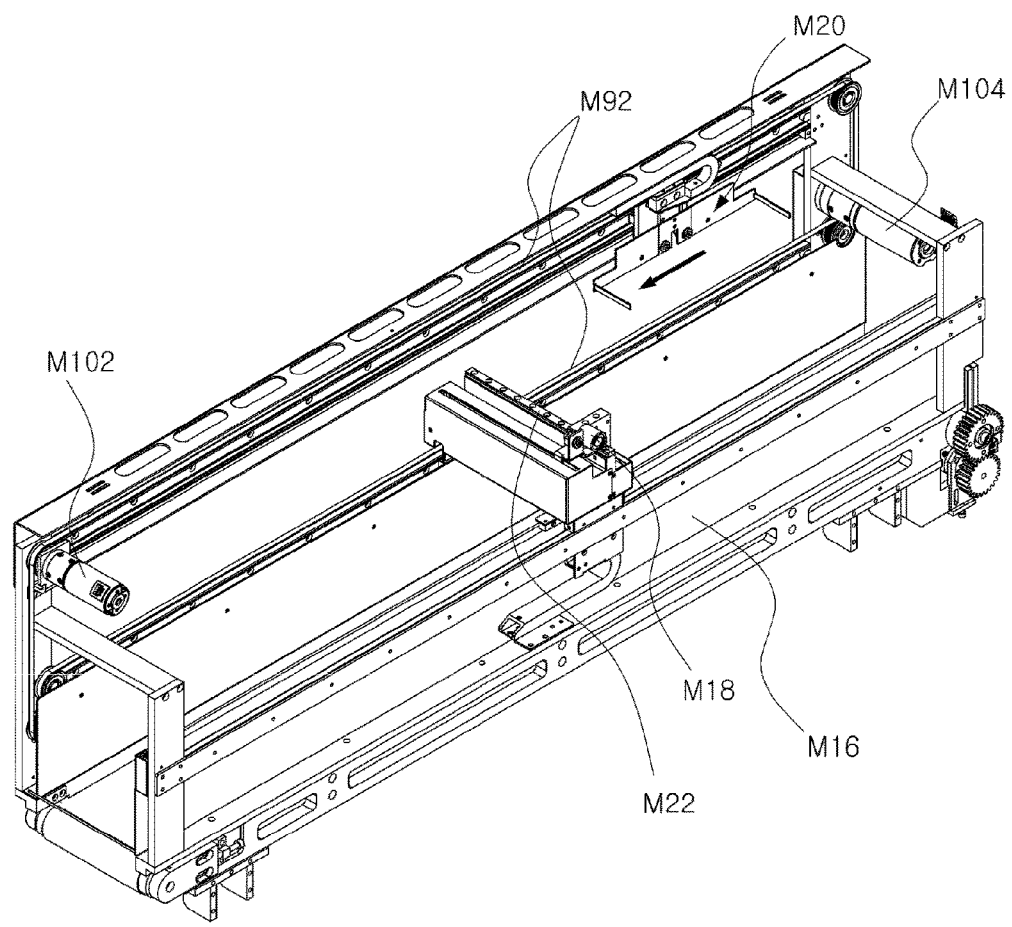

【FIG.172】
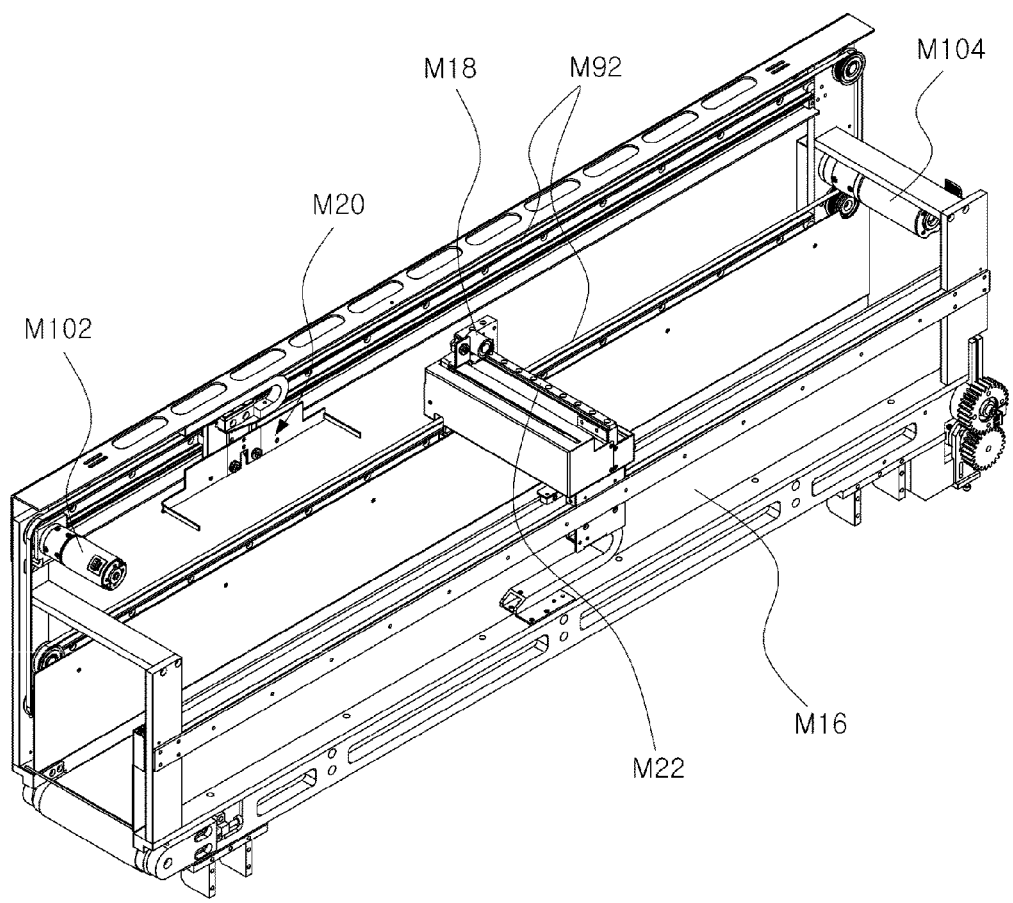

[FIG.173]
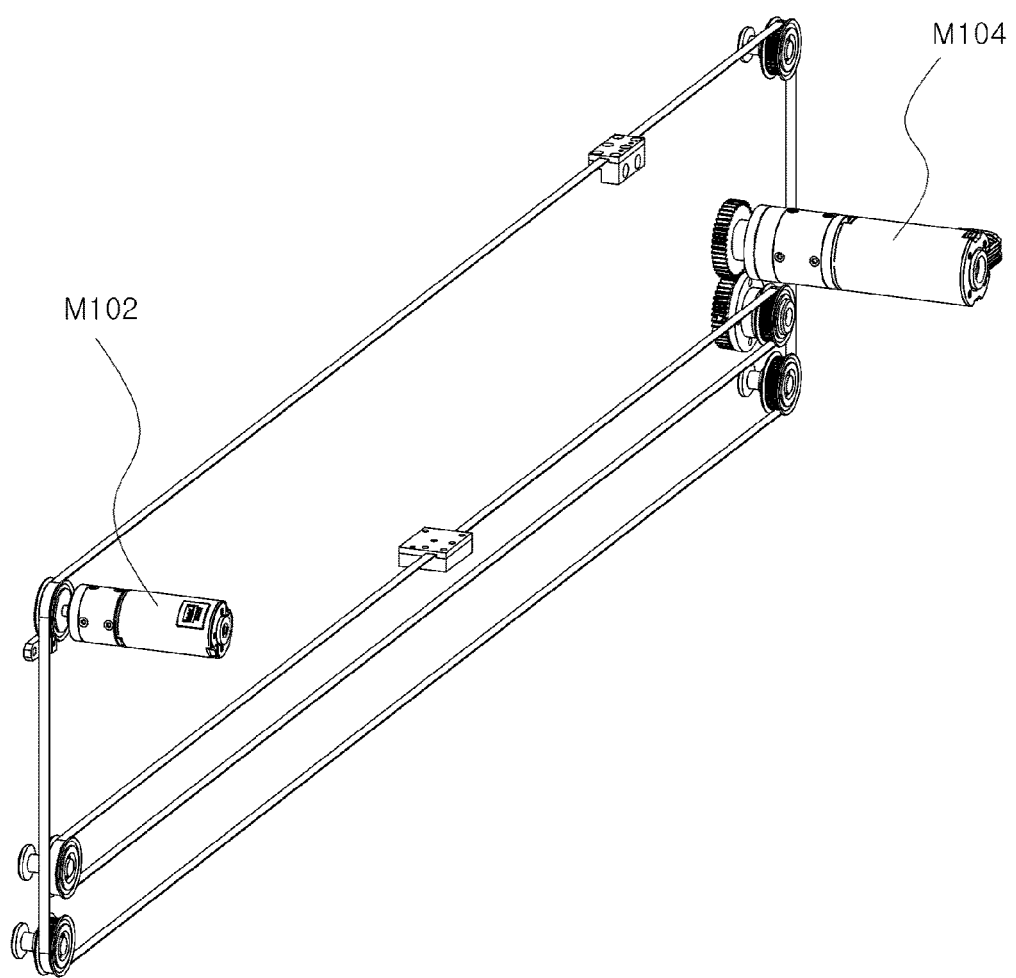

【FIG.174】
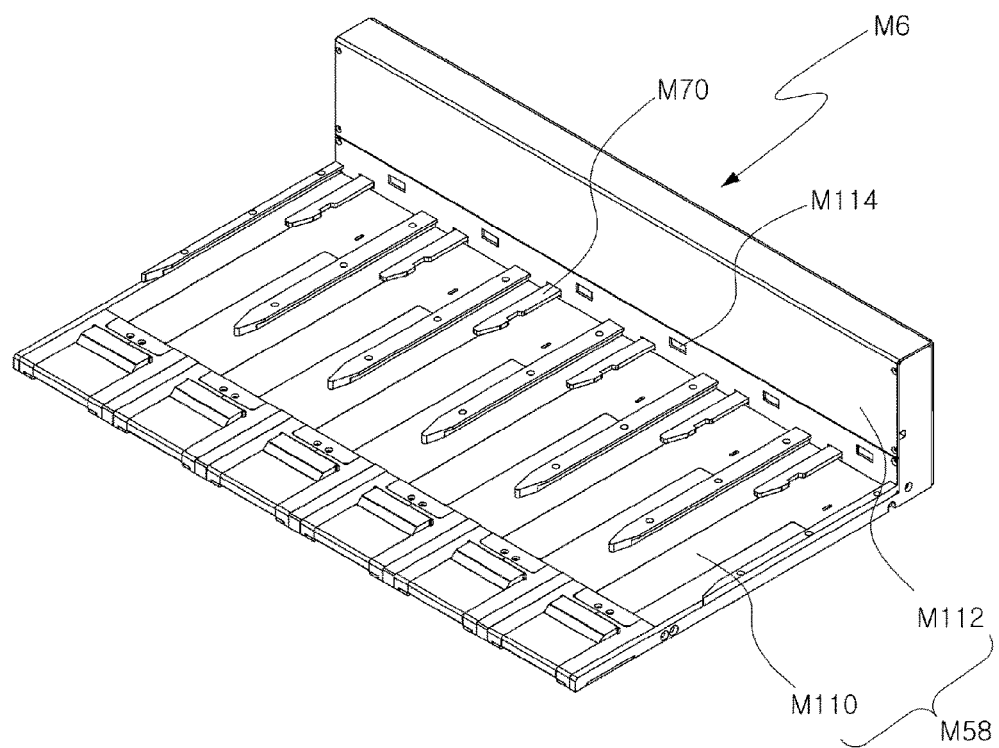

[FIG.175]
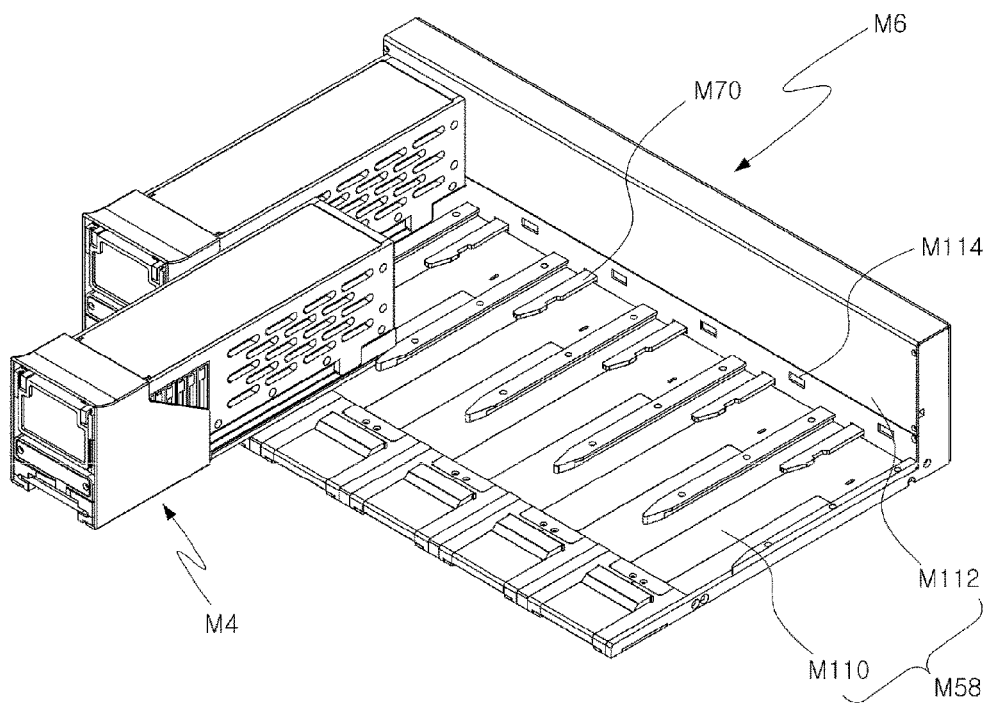

[FIG.176]
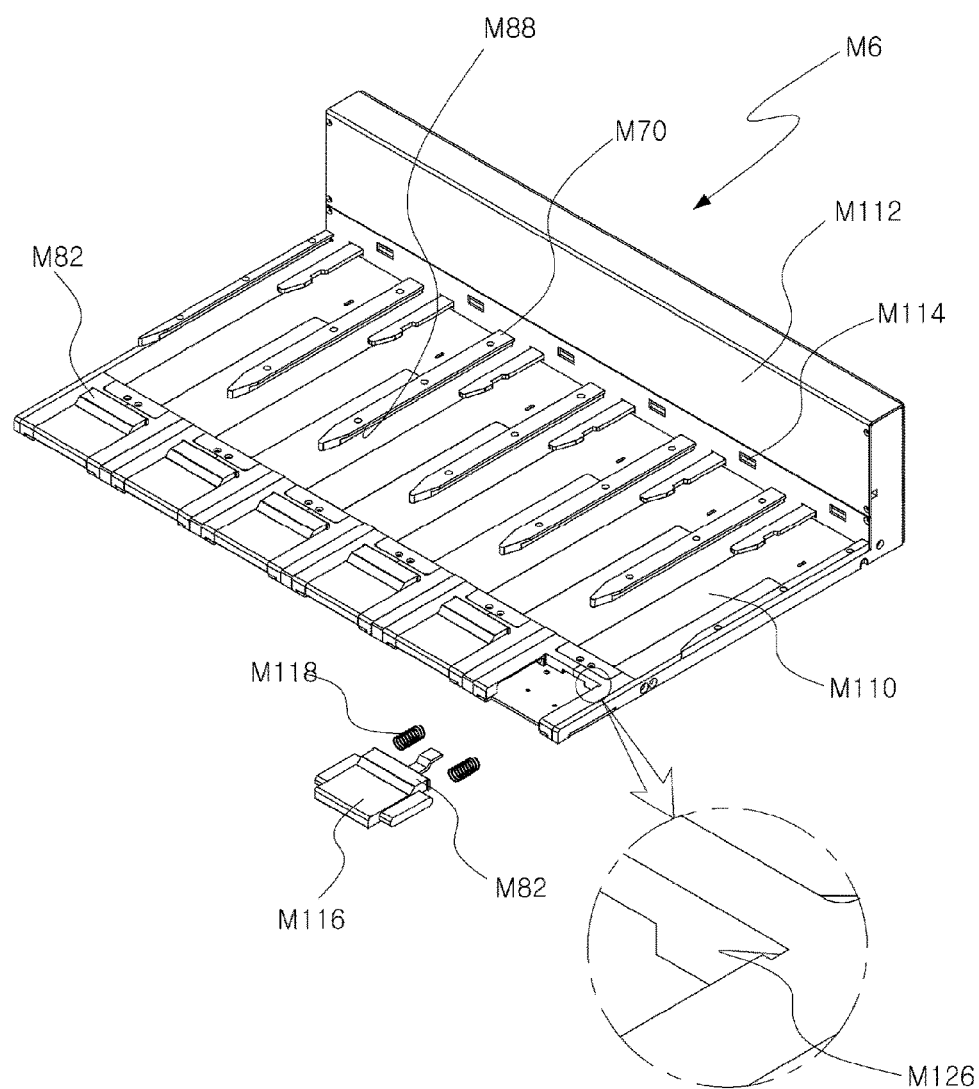

[FIG.177]
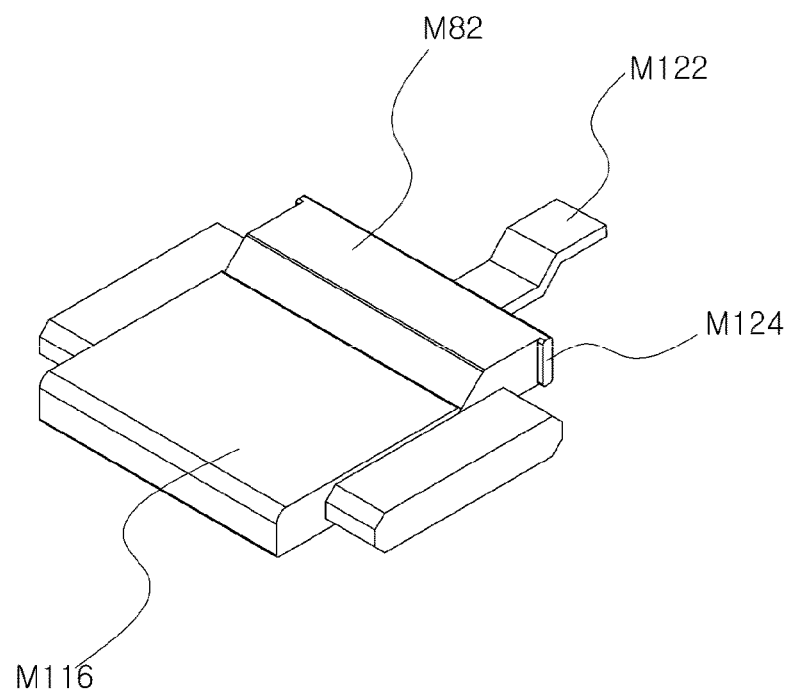

[FIG.178]
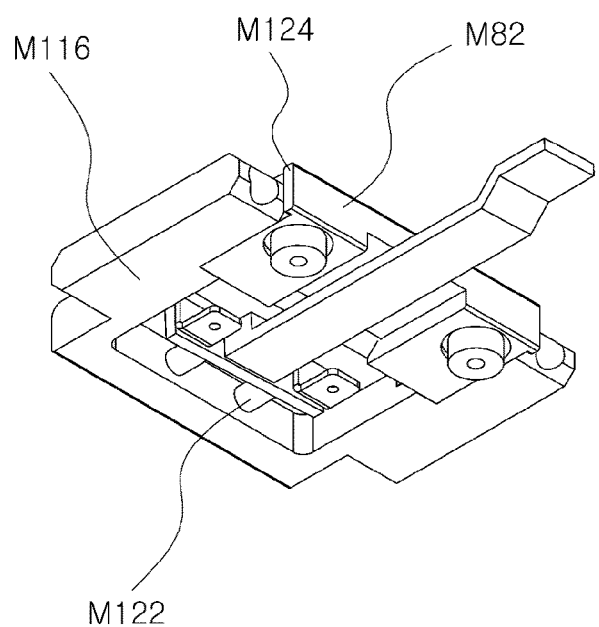

【FIG.179】
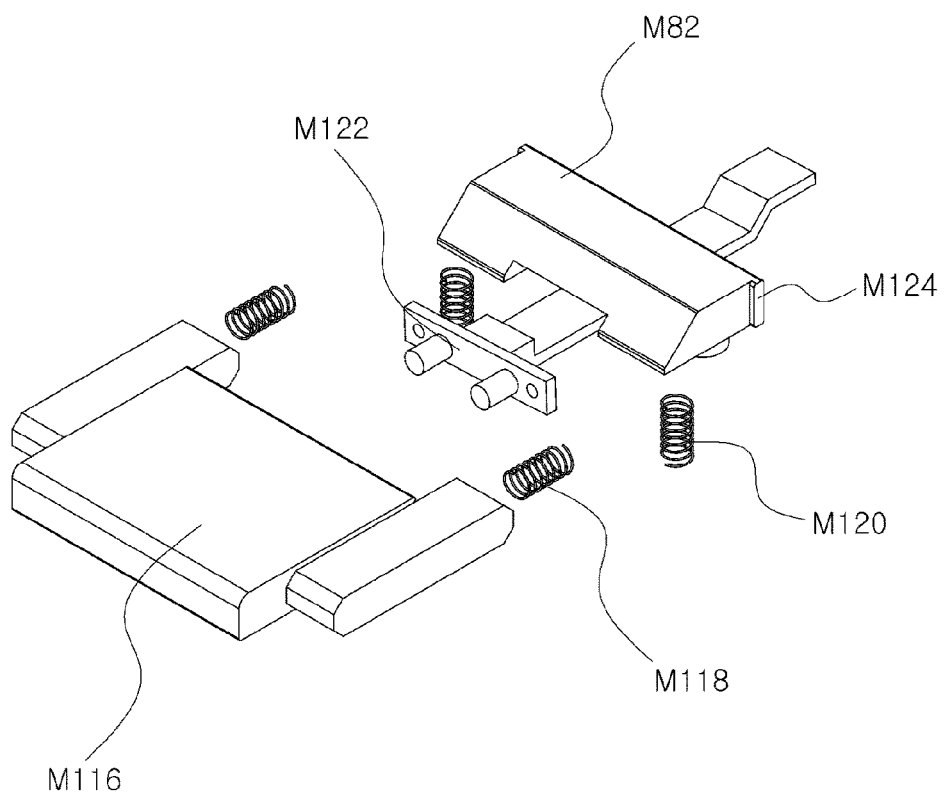

[FIG.180]
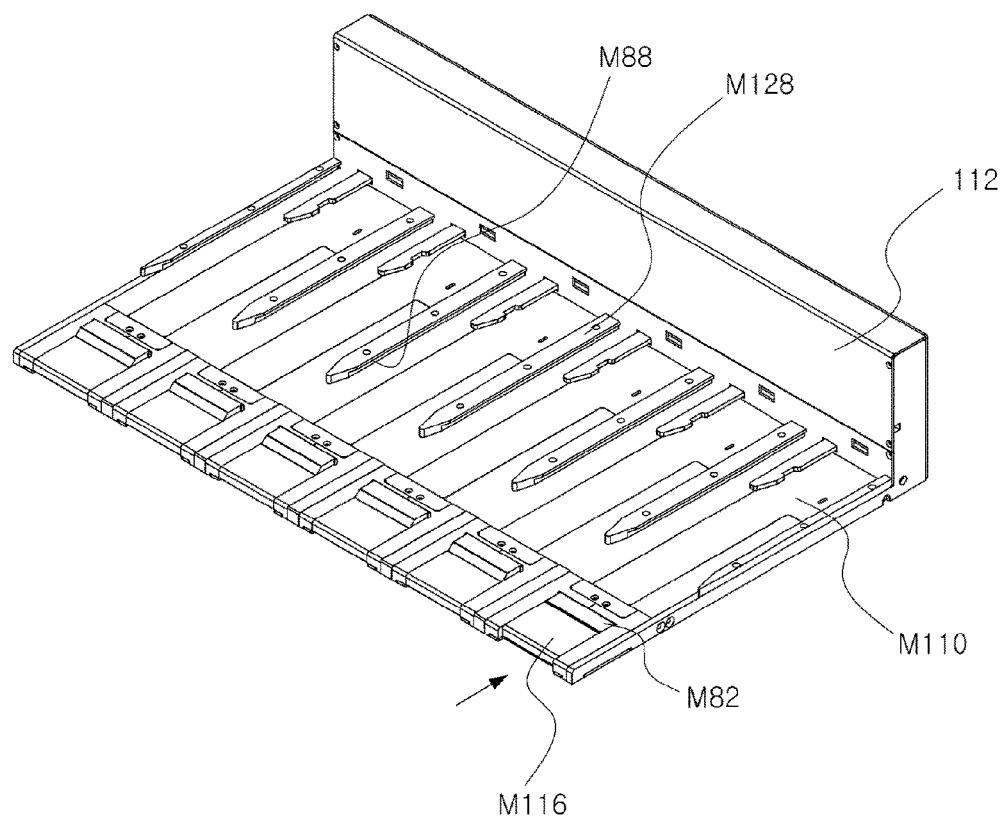

[FIG.181]
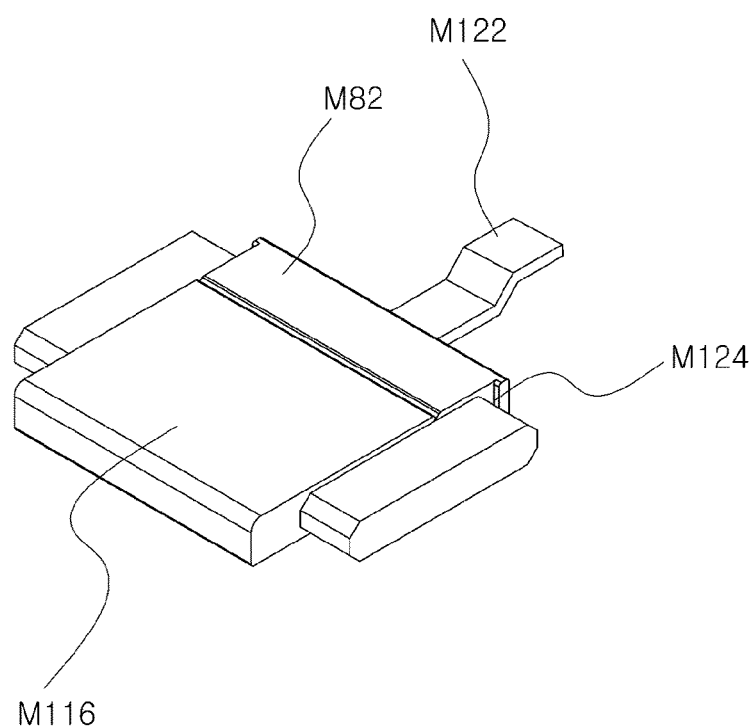

[FIG.182]
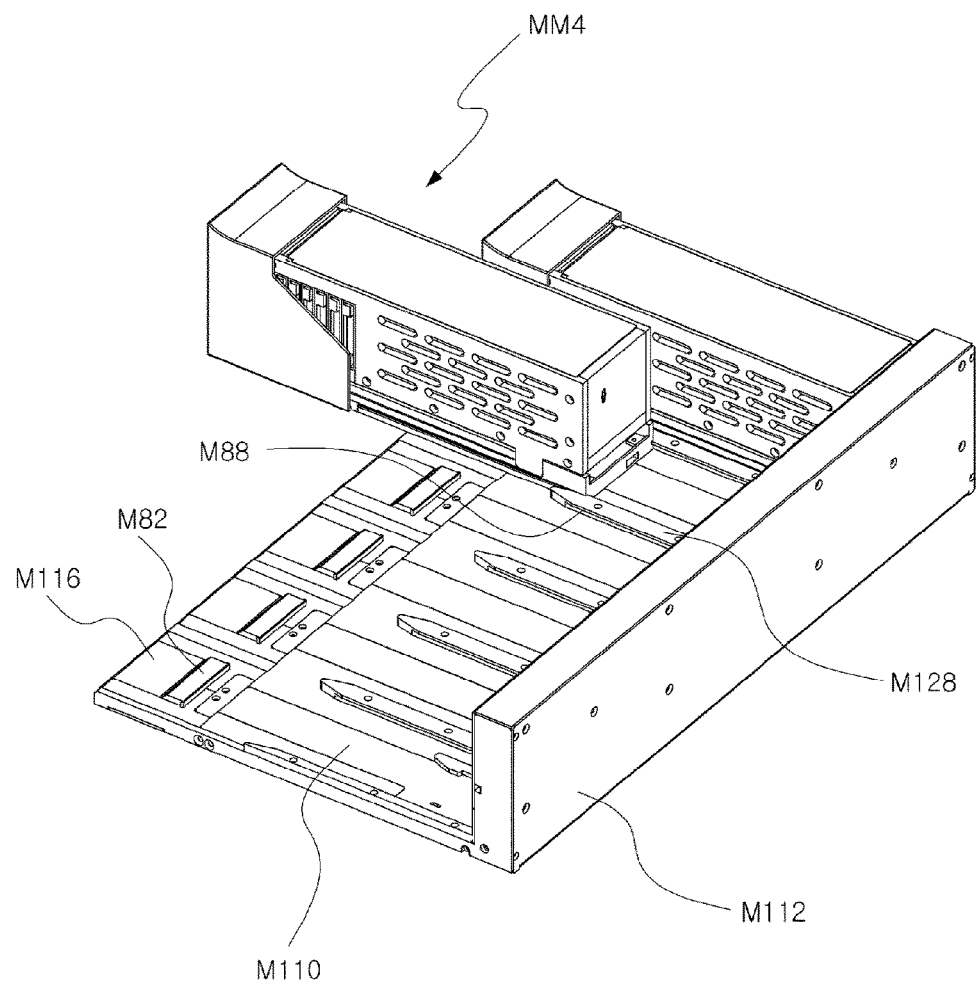

[FIG.183]
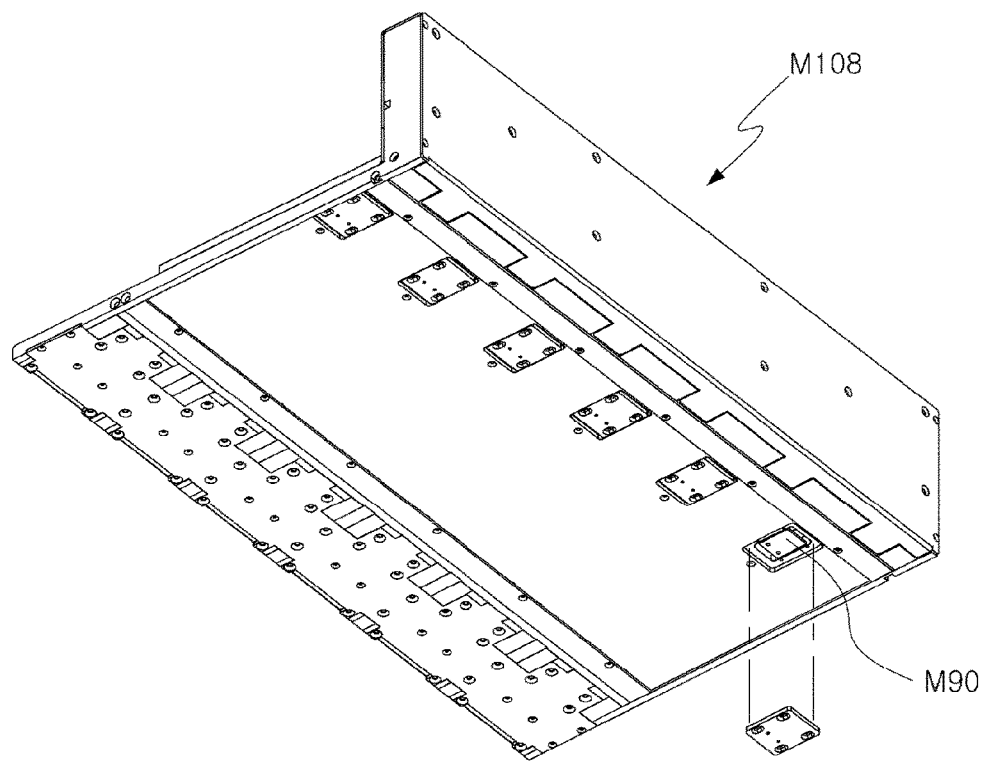

[FIG.184]
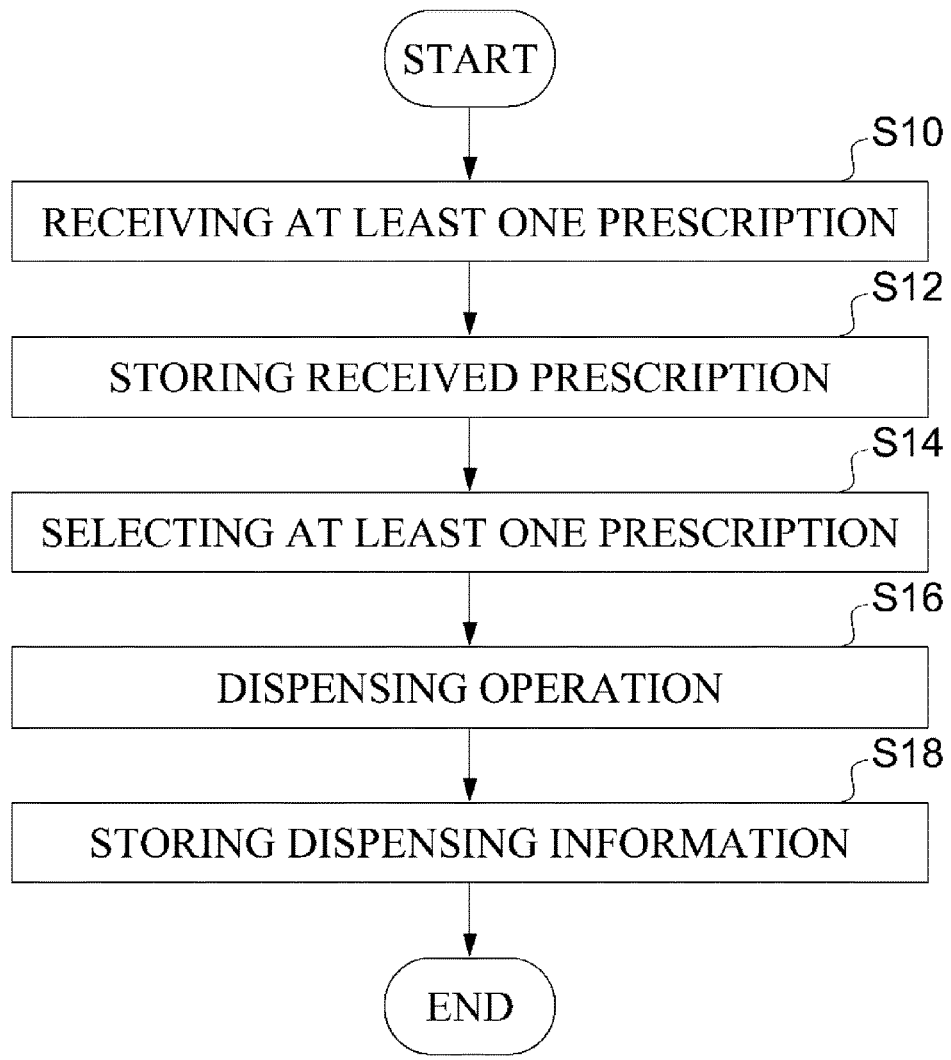

【FIG.185】
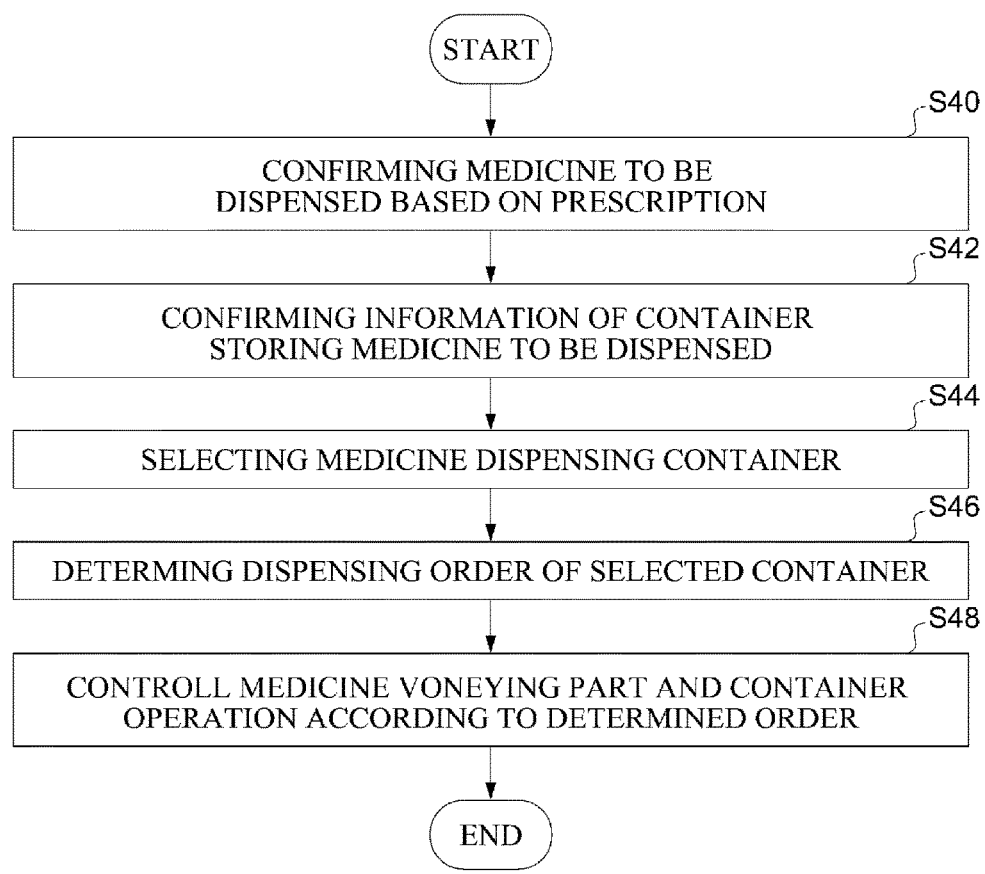

【FIG.186】
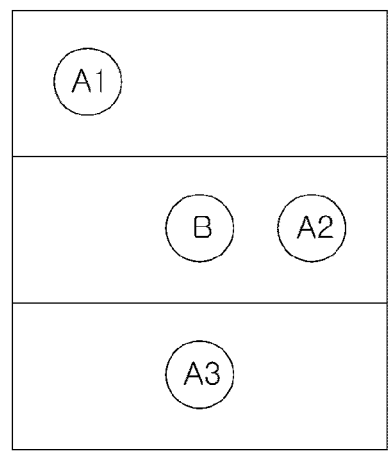

【FIG.187】
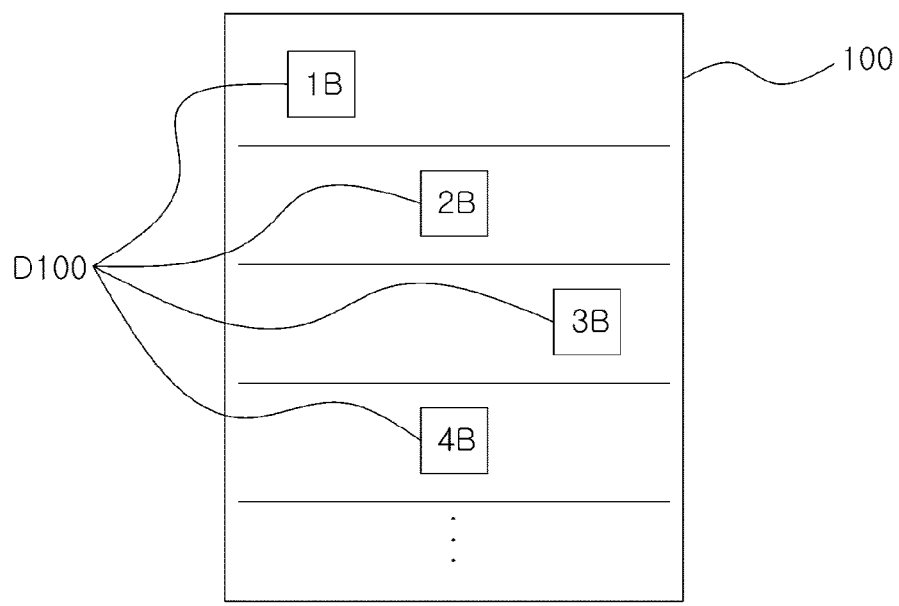
【FIG.188】
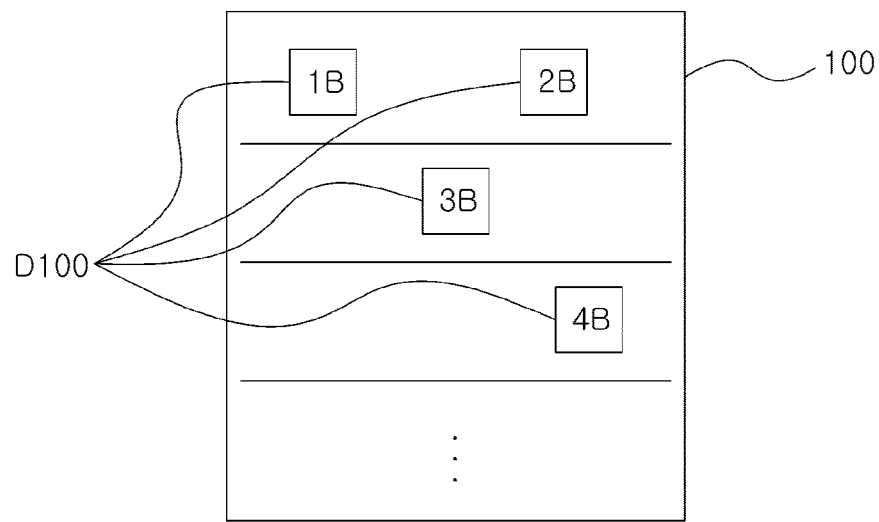

[FIG.189]
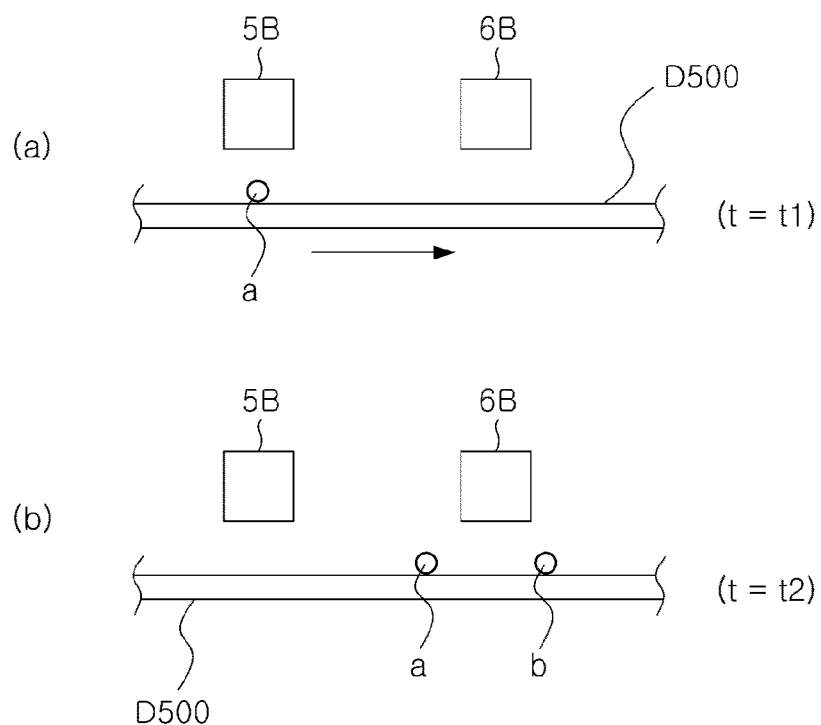

[FIG.190]
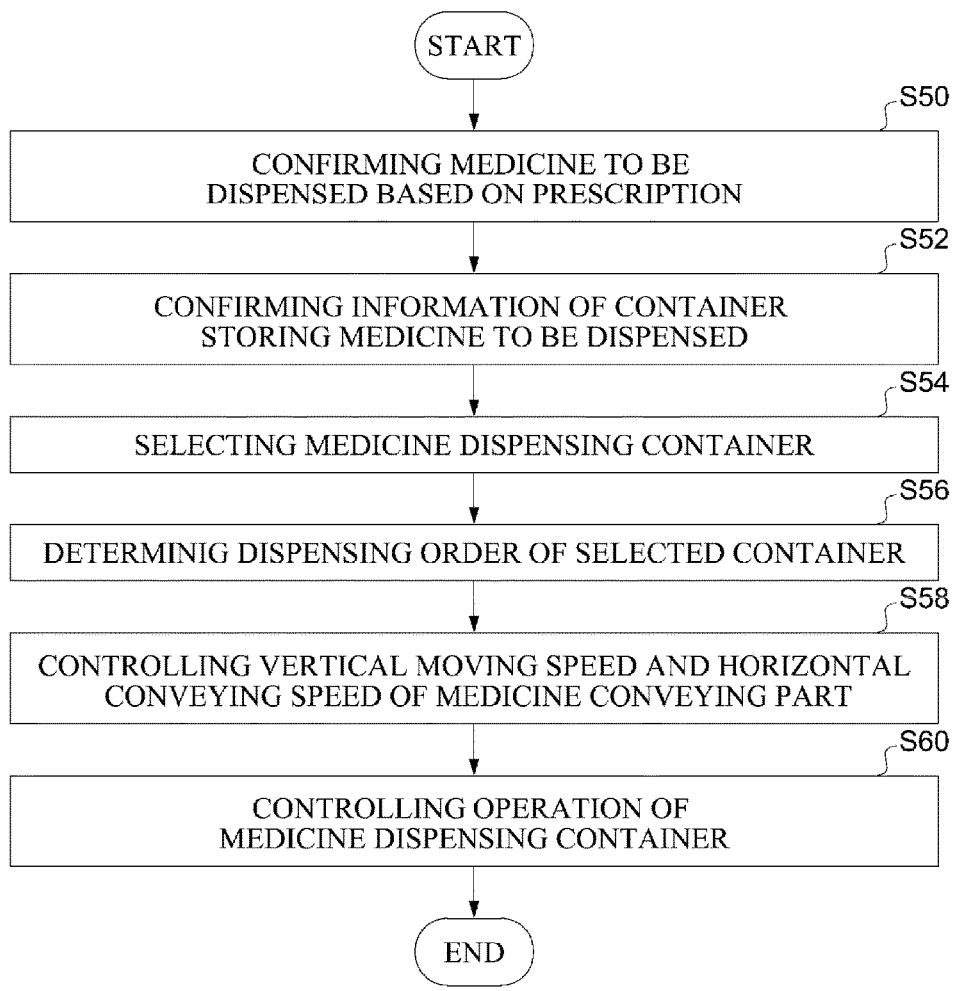

[FIG.191]
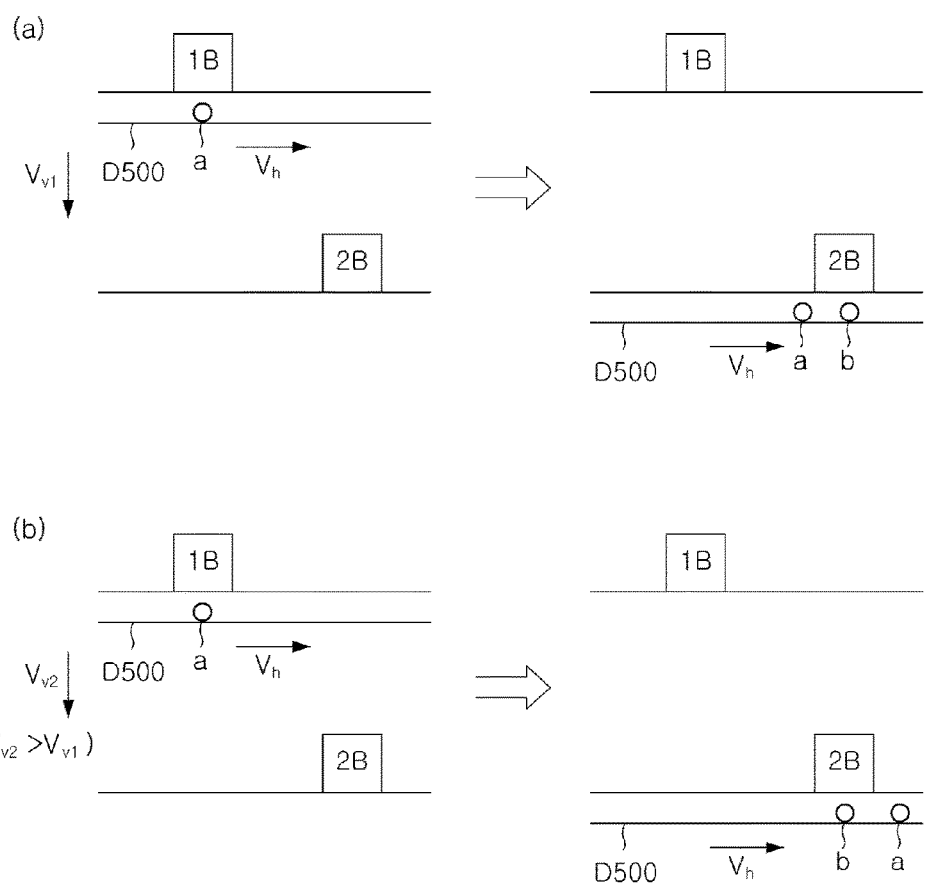

[FIG.192]
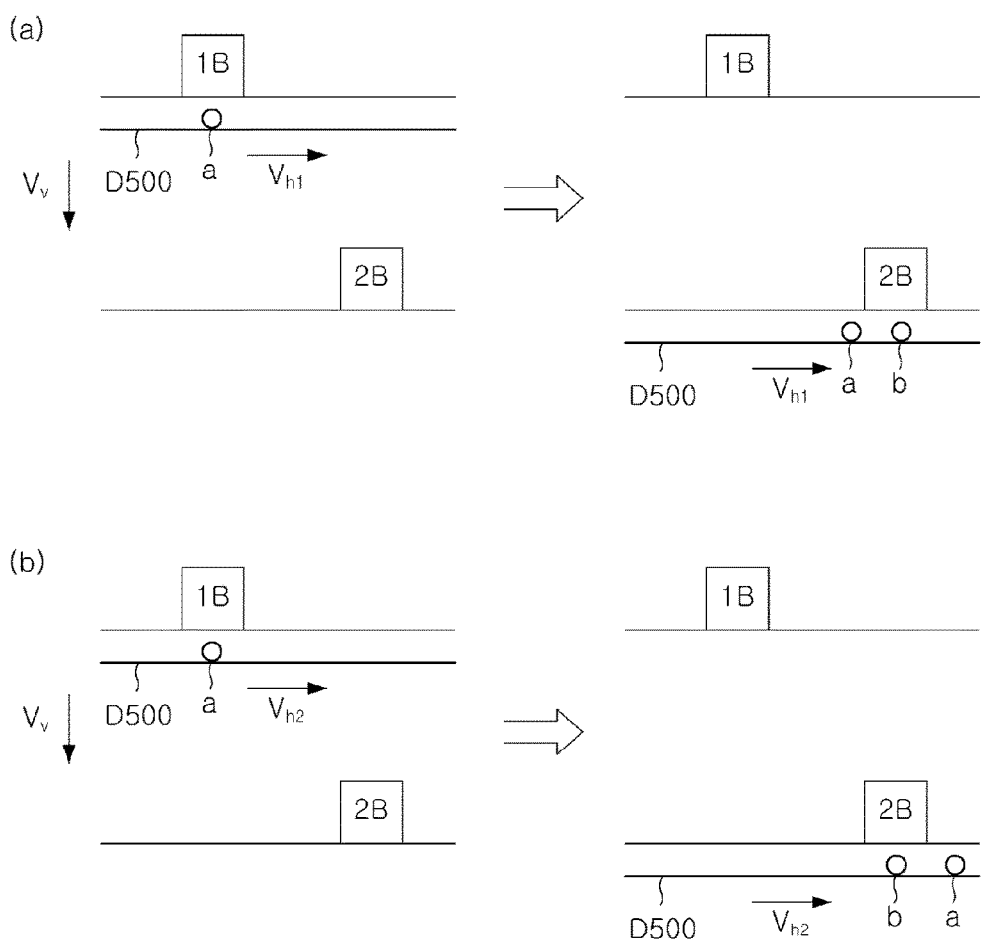

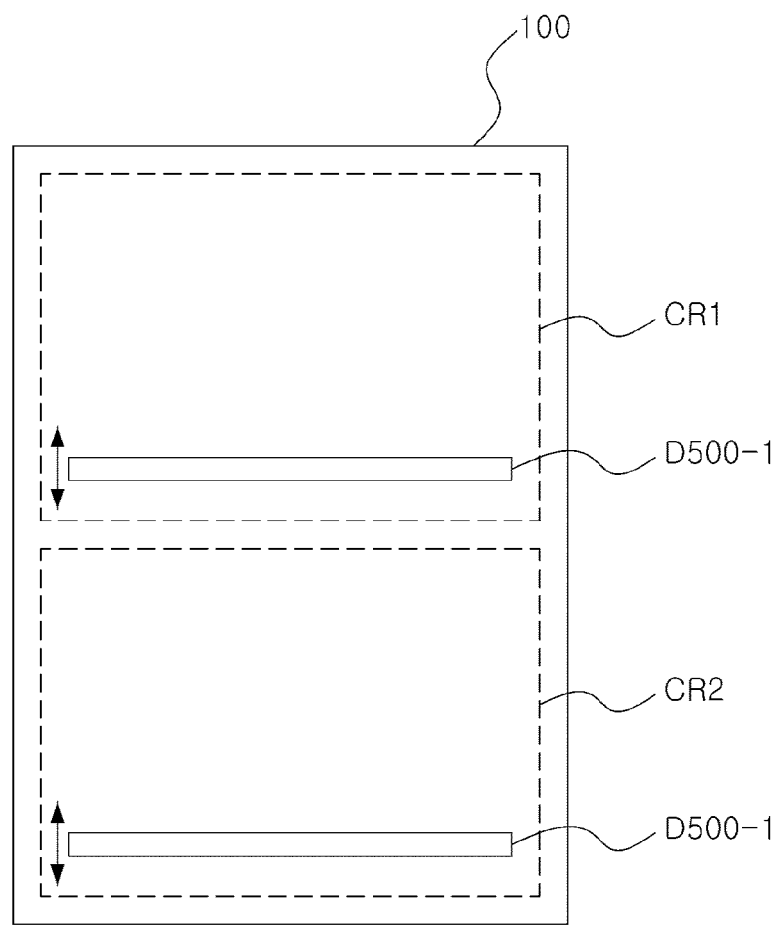
[FIG.193]

[FIG.194]
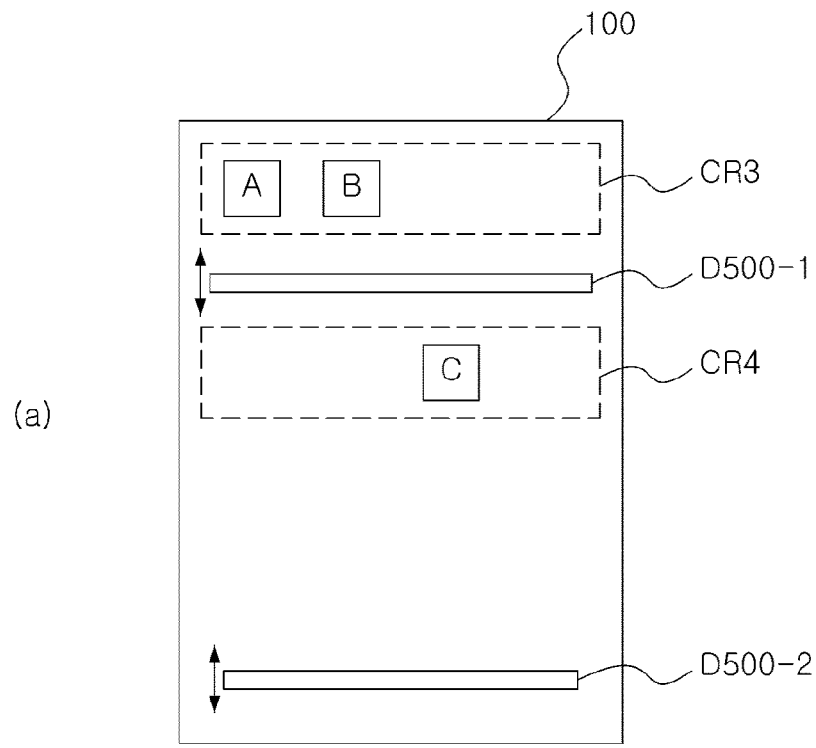
(a)
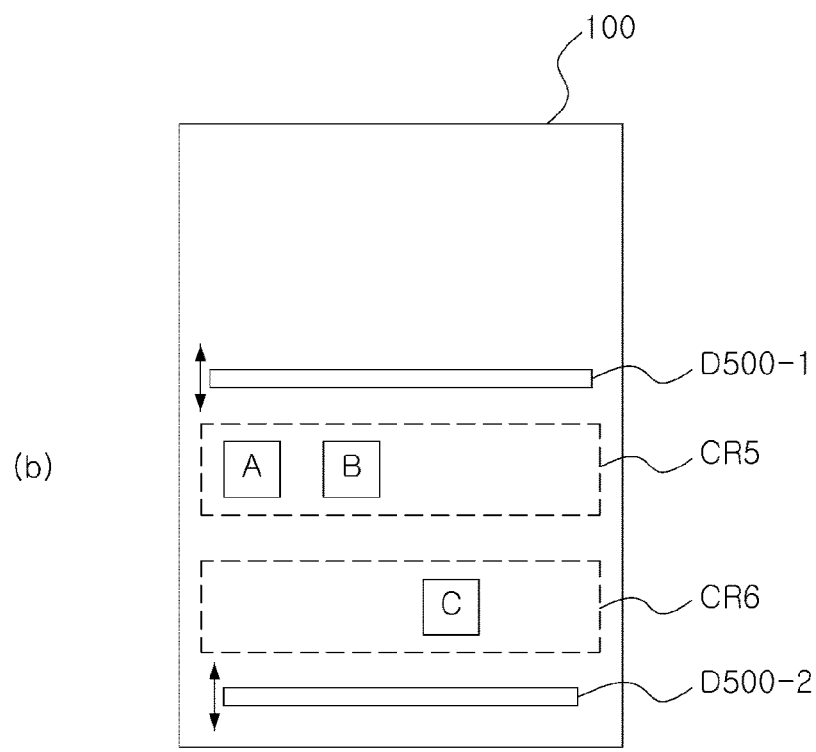
(b)

【FIG.195】
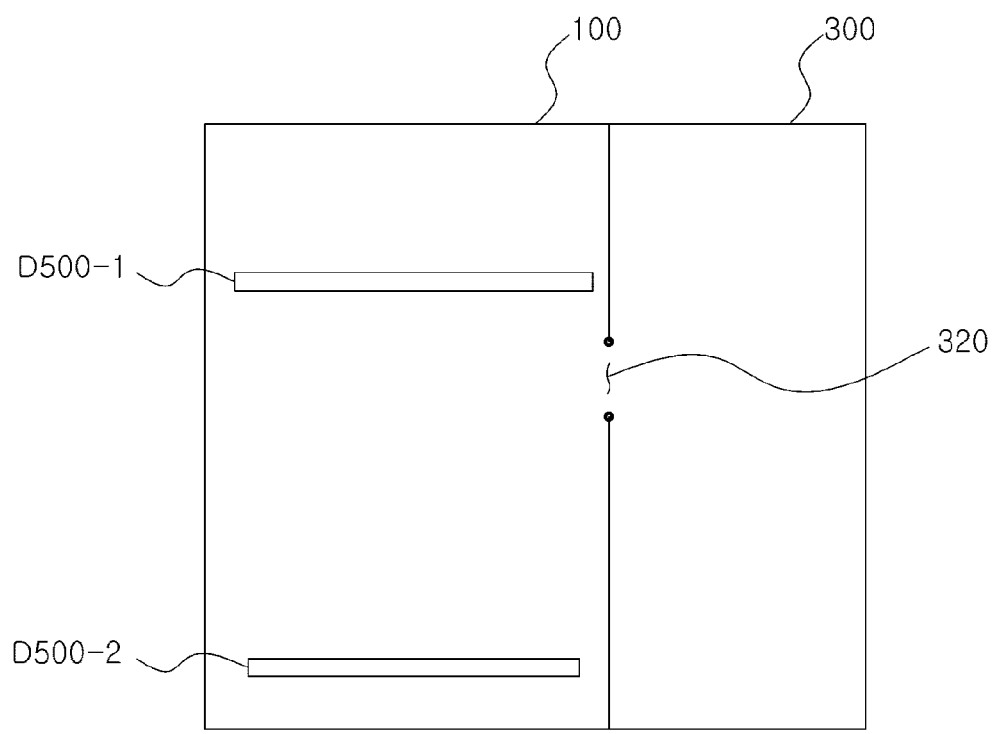

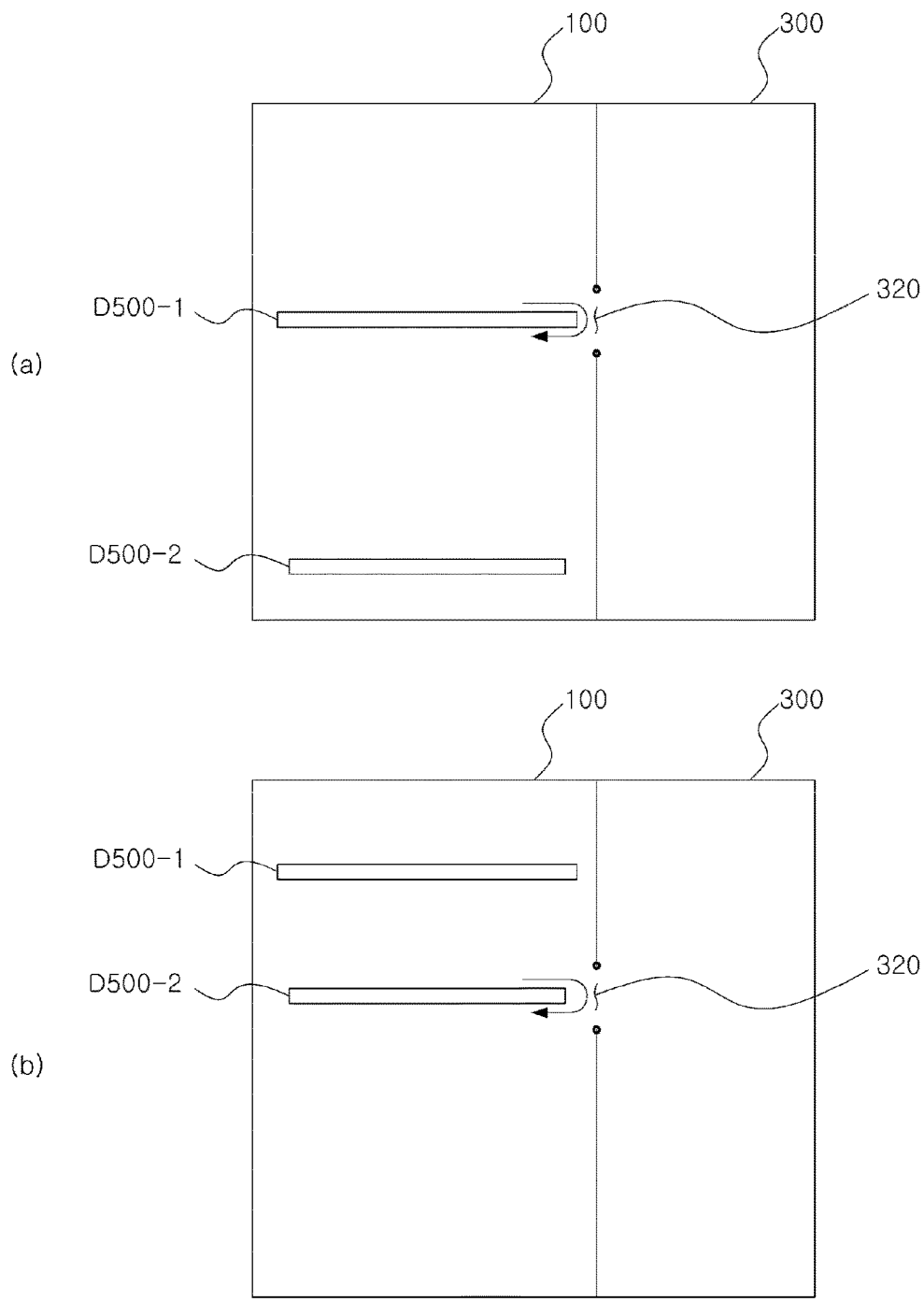
[FIG.196]

[FIG.197]
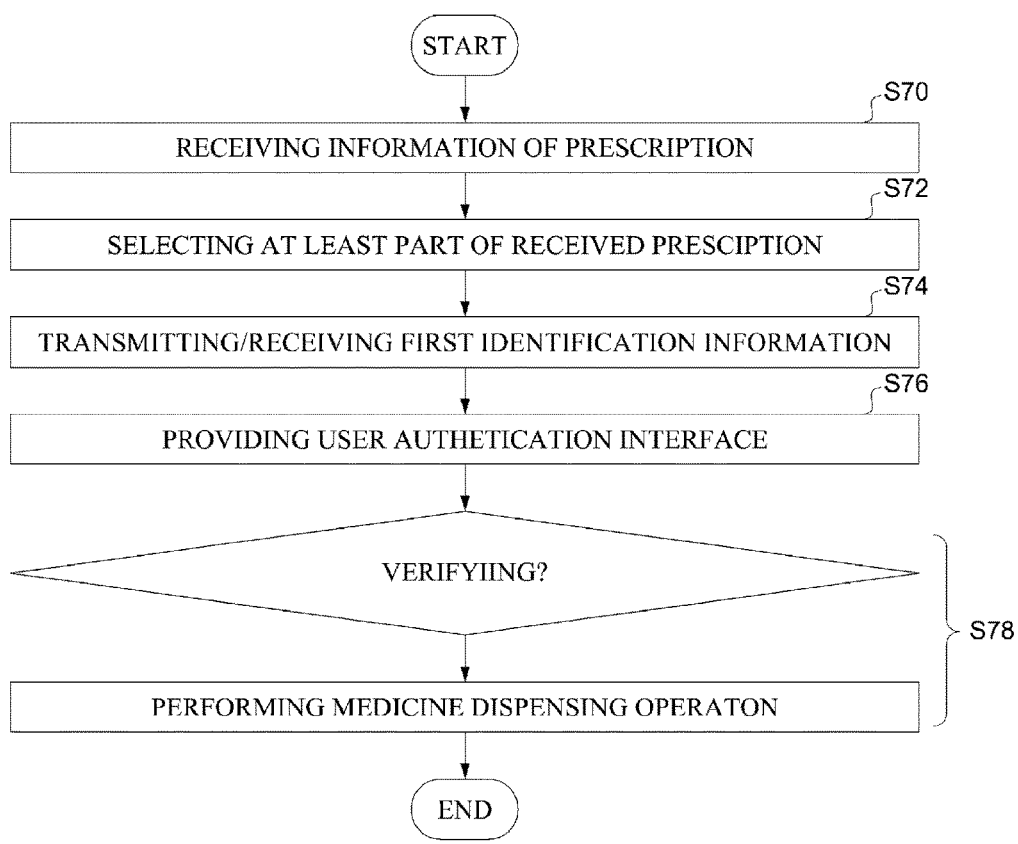

[FIG.198]
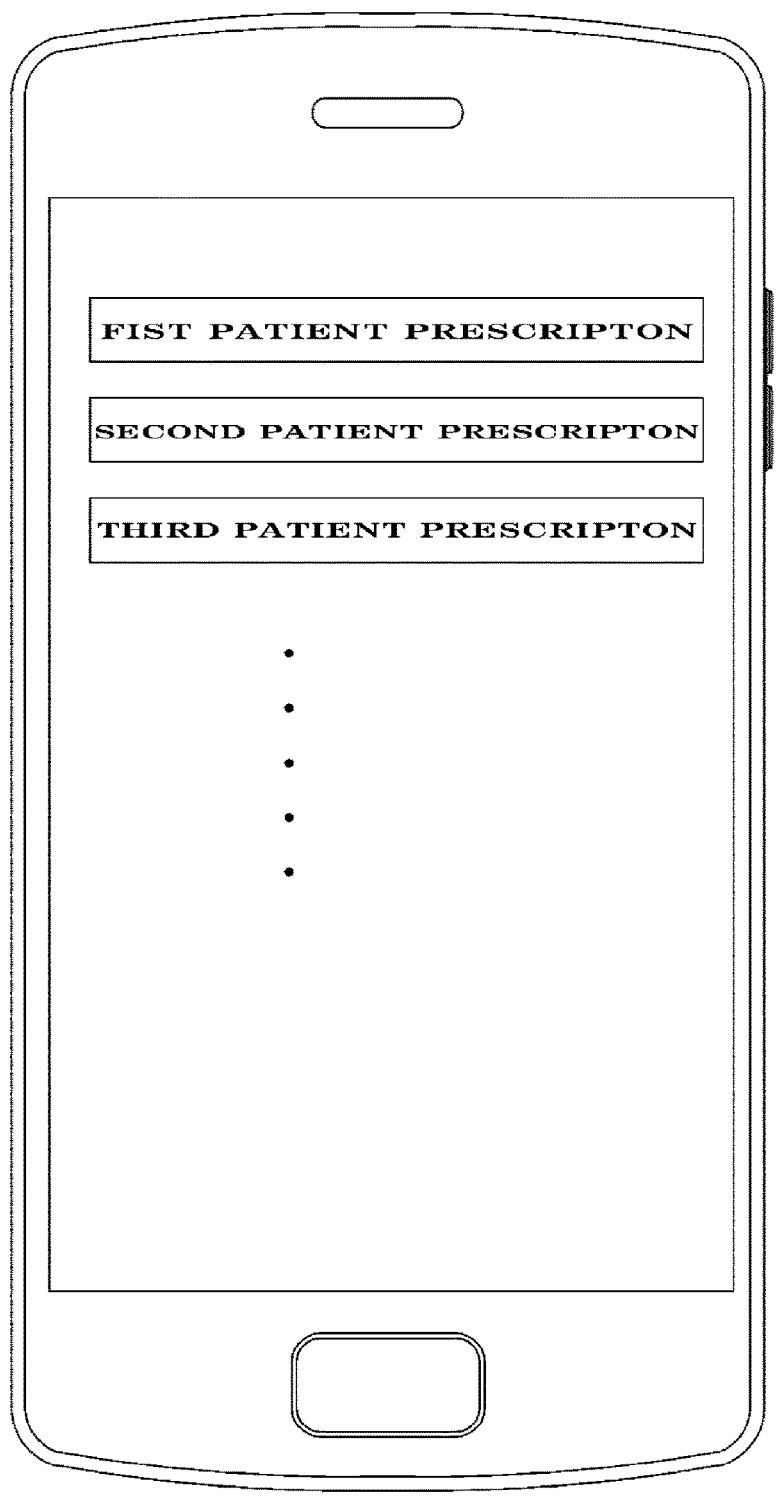

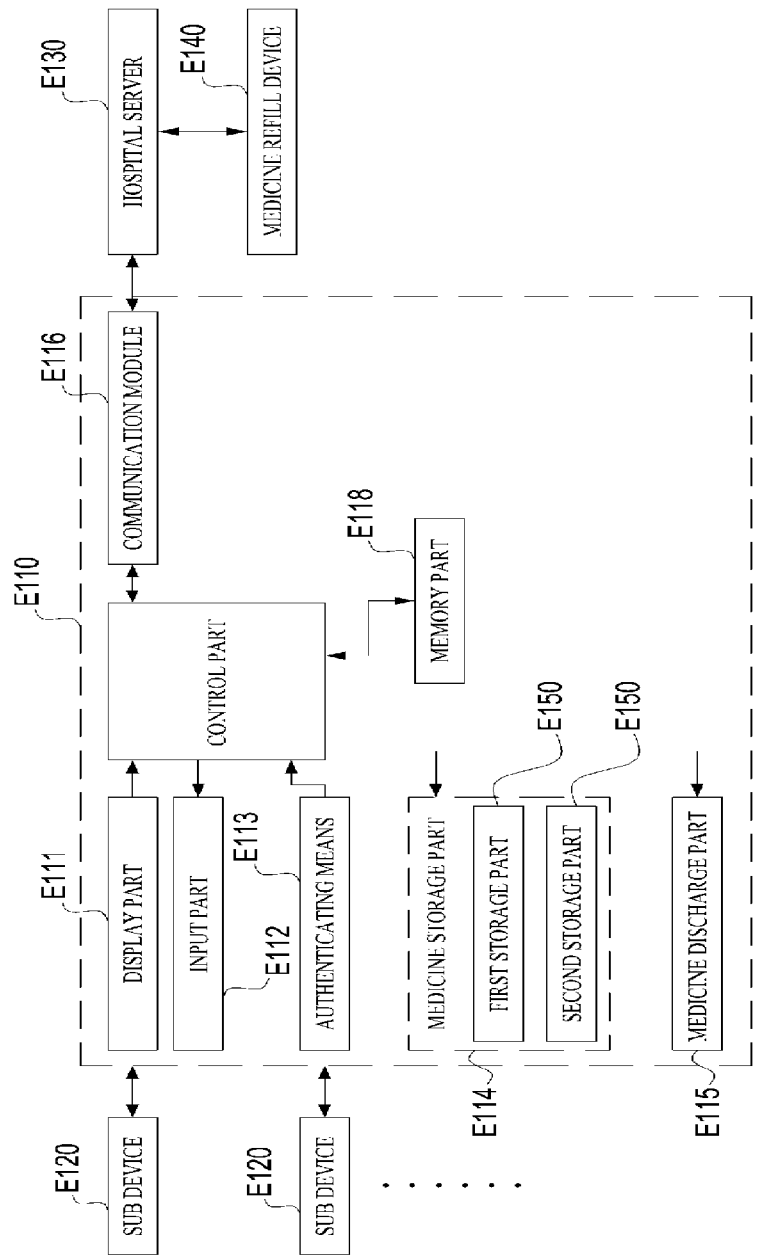
[FIG.199]

[FIG.200]
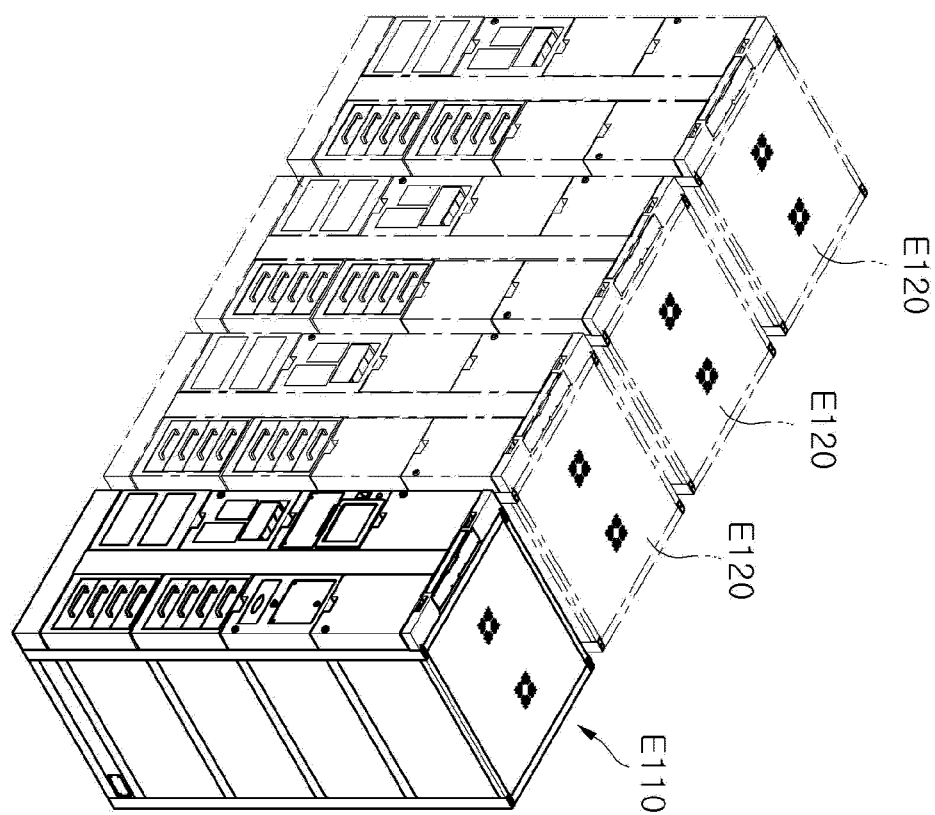

[FIG.201]
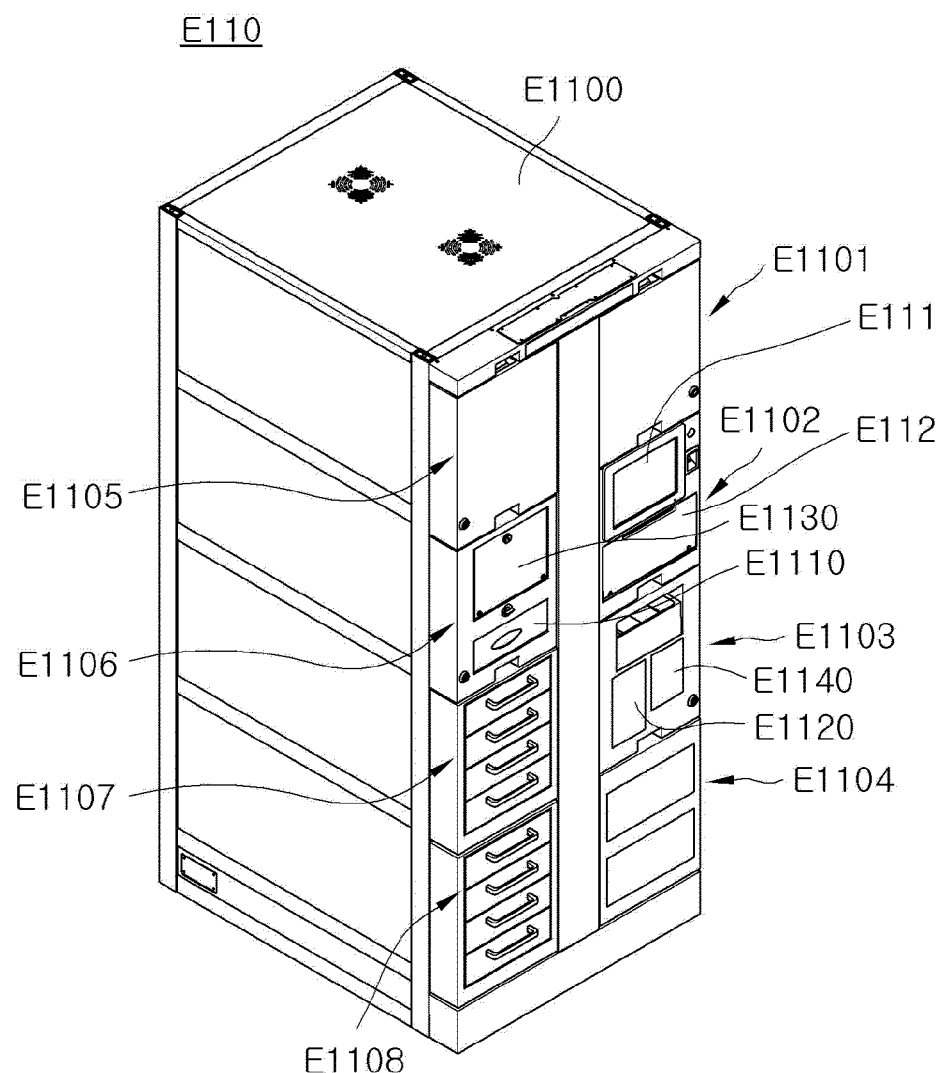

[FIG.202]
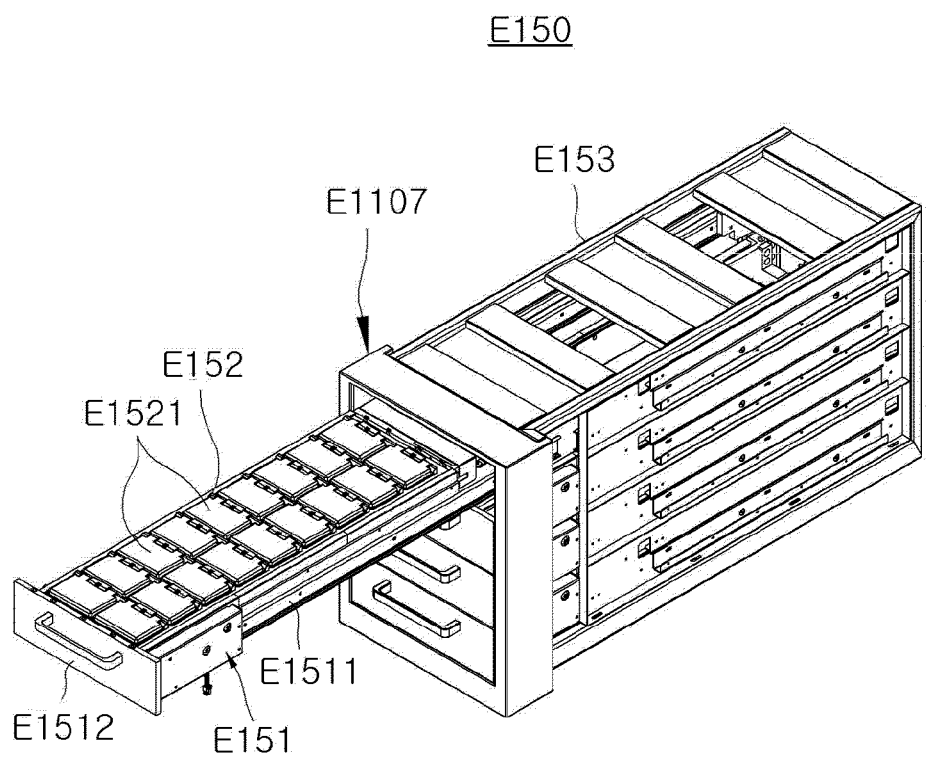

[FIG.203]
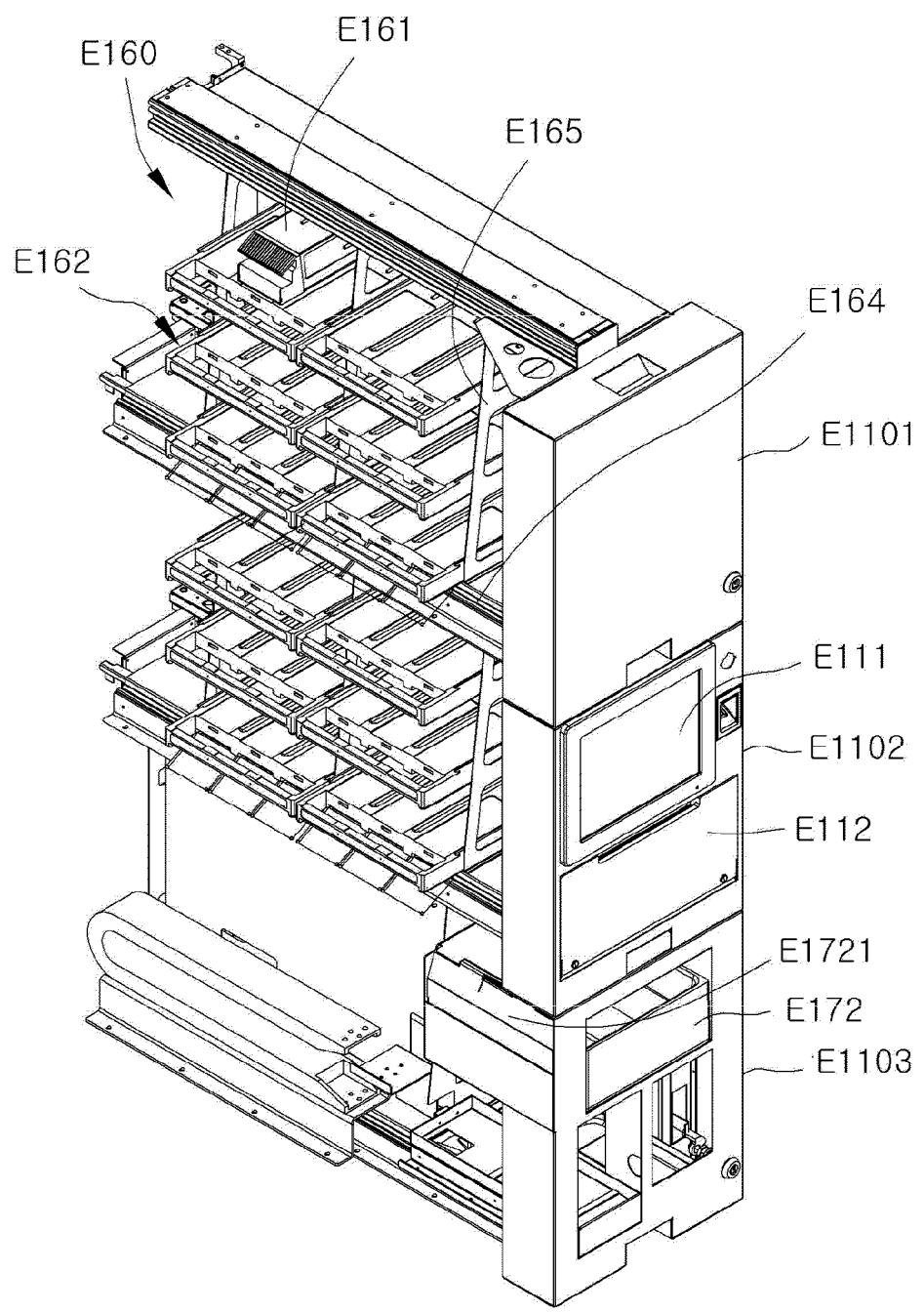

【FIG.204】
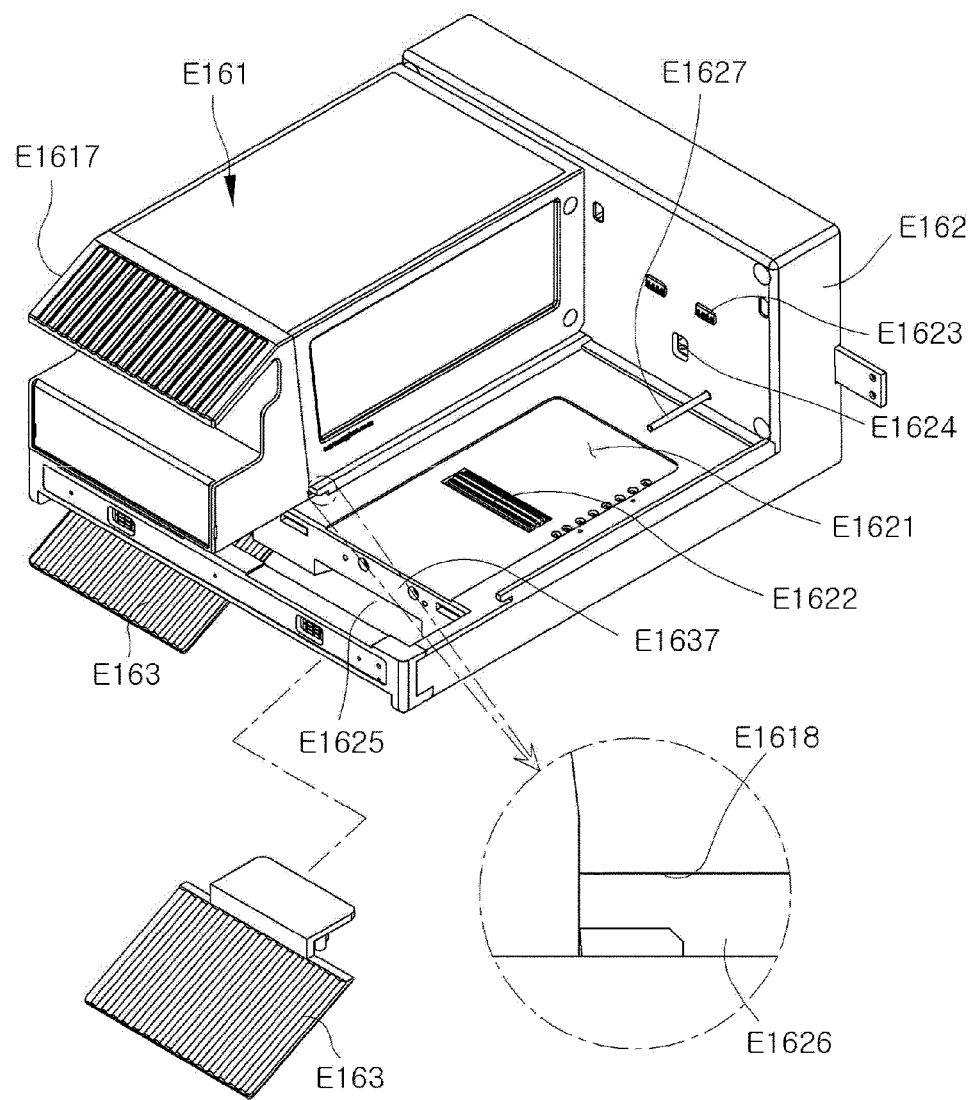

【FIG.205】
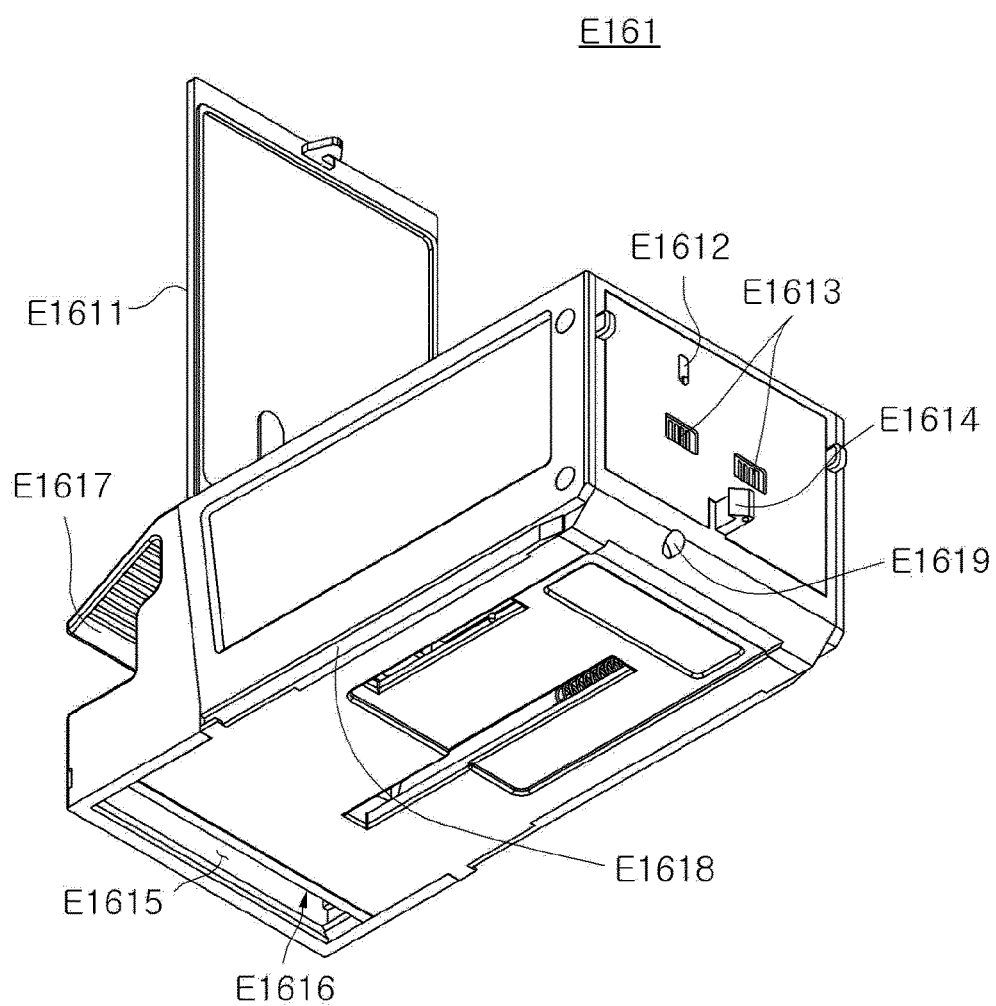

[FIG.206]
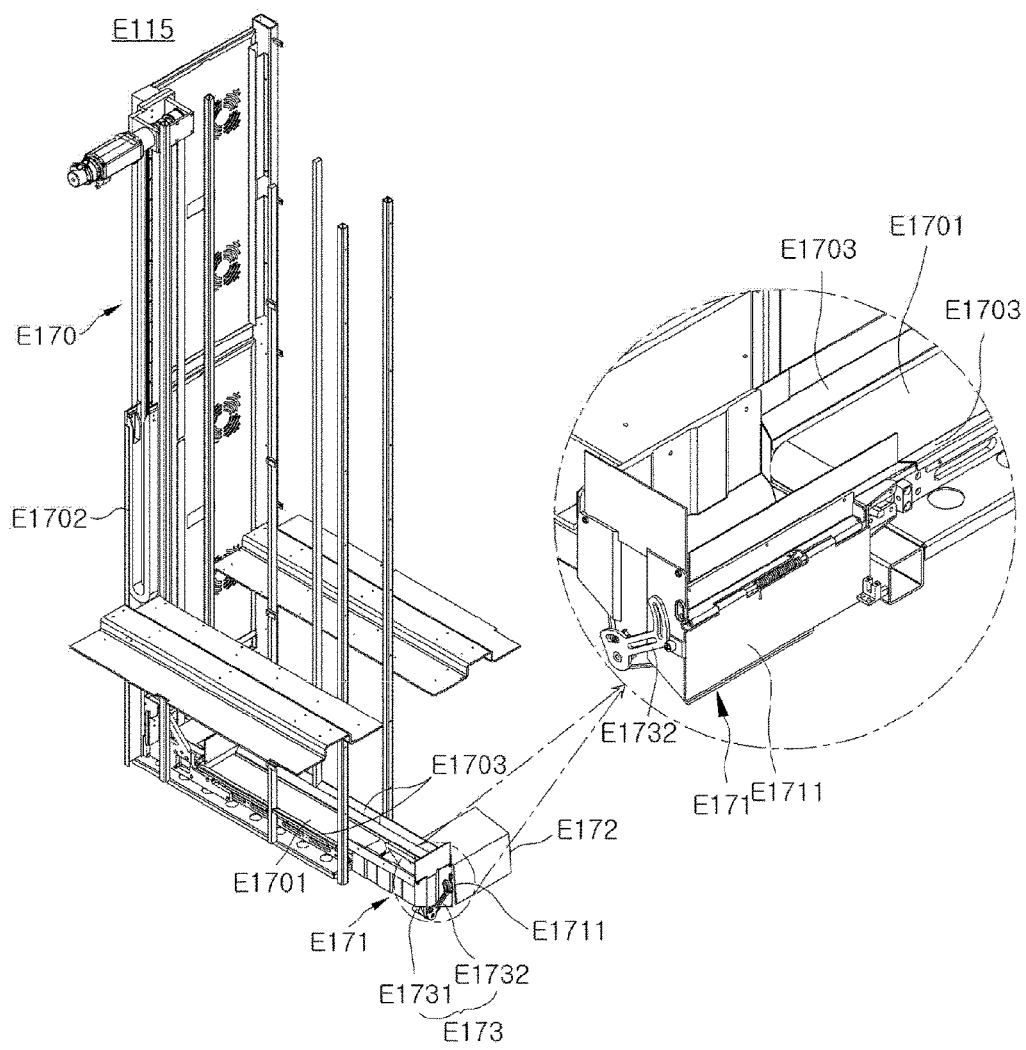

【FIG.207】
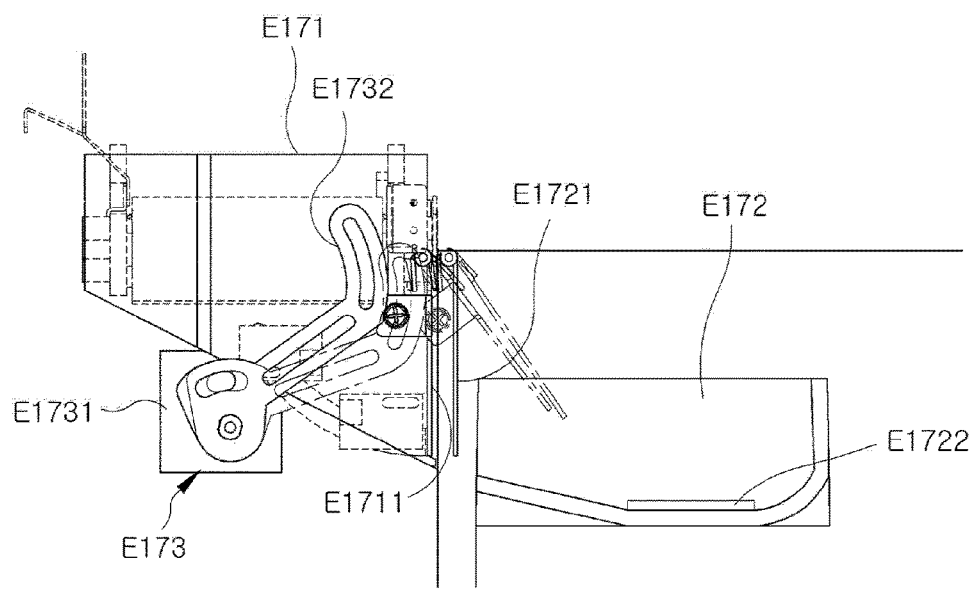

[FIG.208]
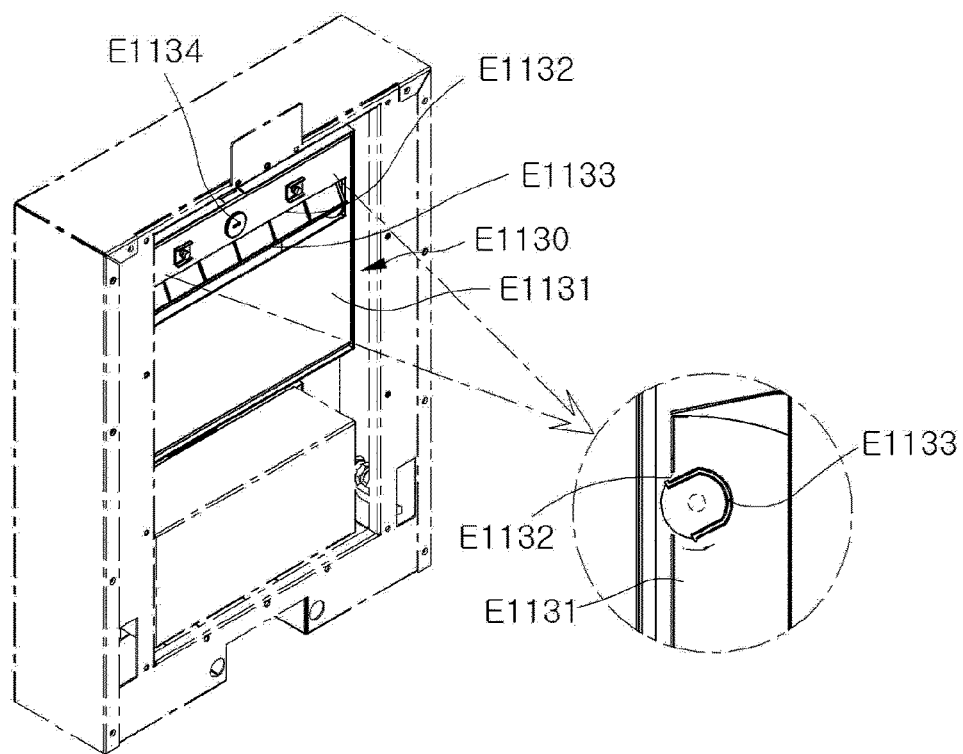

[FIG.209]
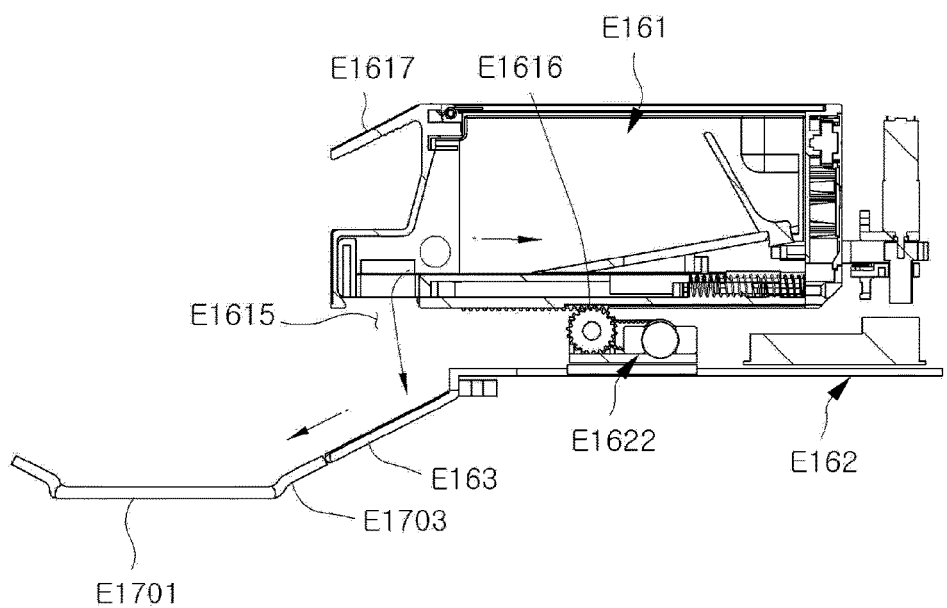

【FIG.210】
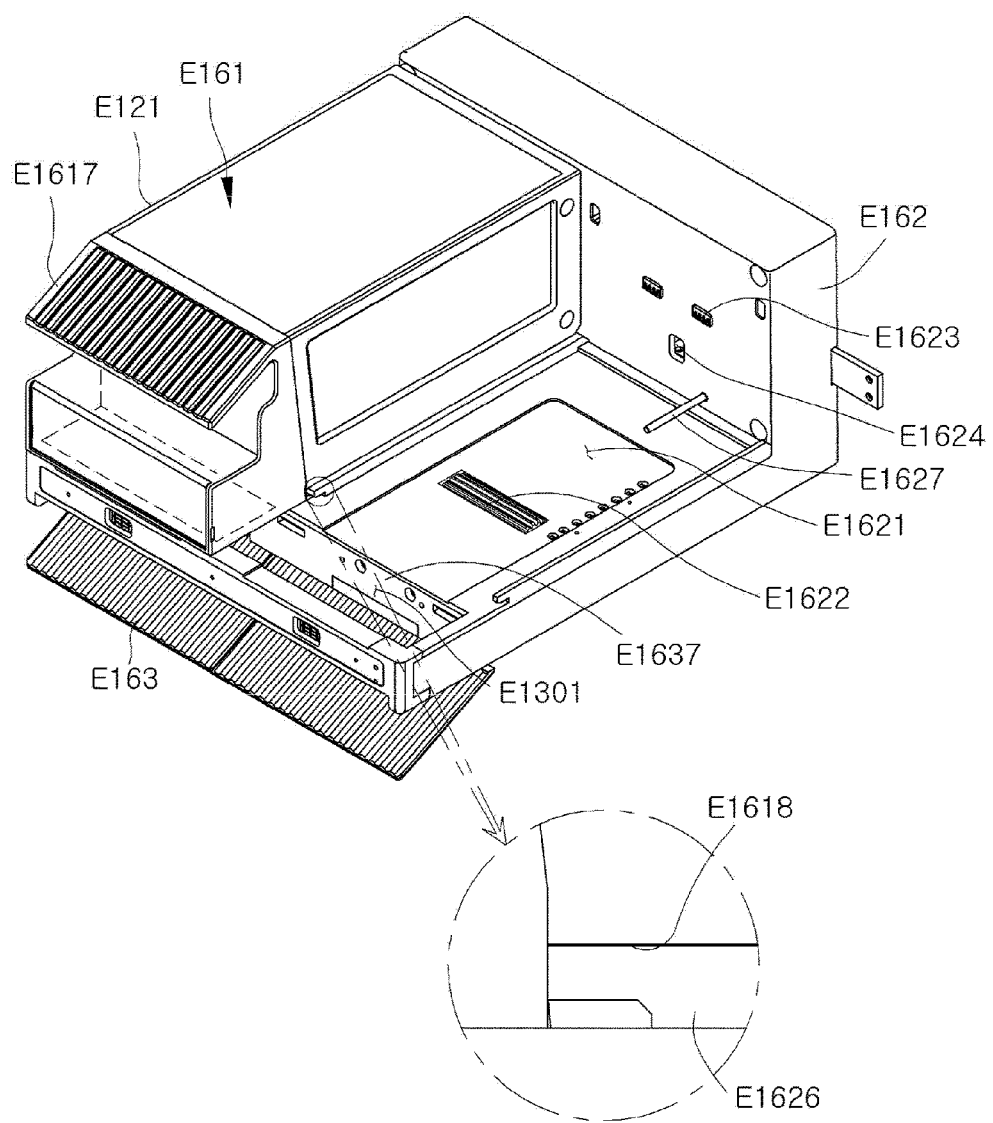

【FIG.211】
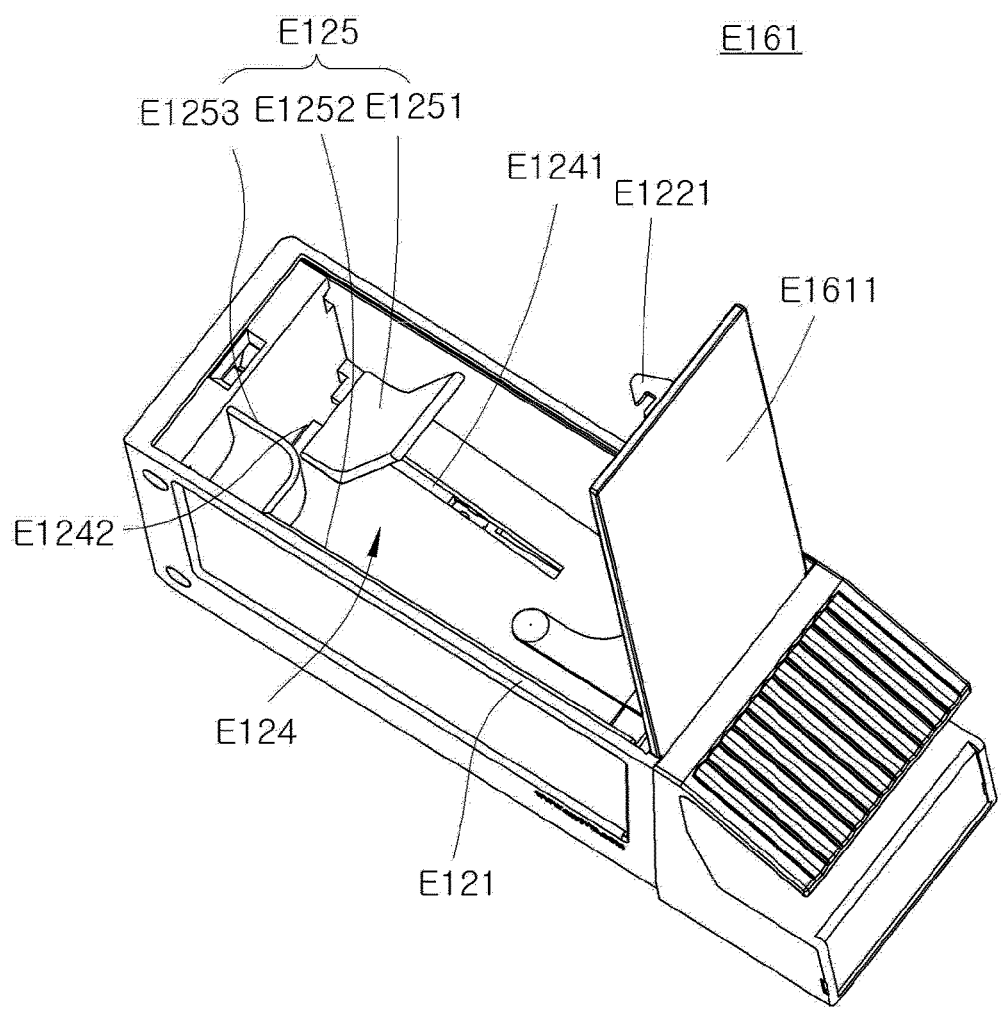

【FIG.212】
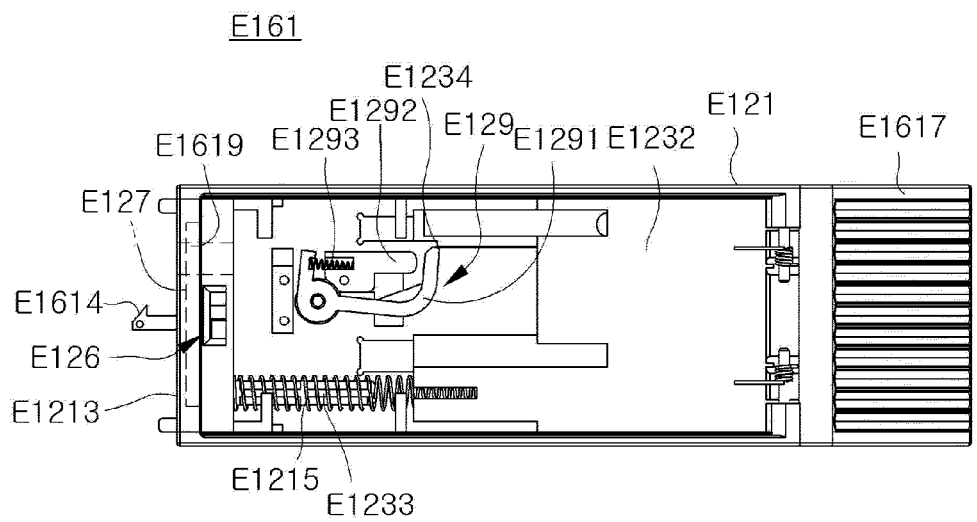
【FIG.213】
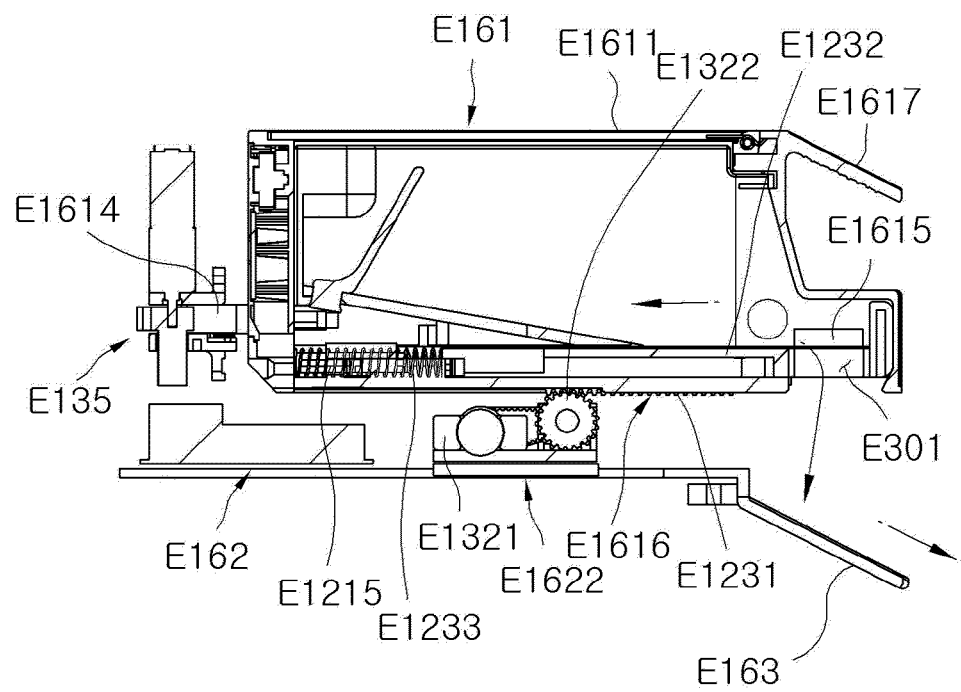

[FIG.214]
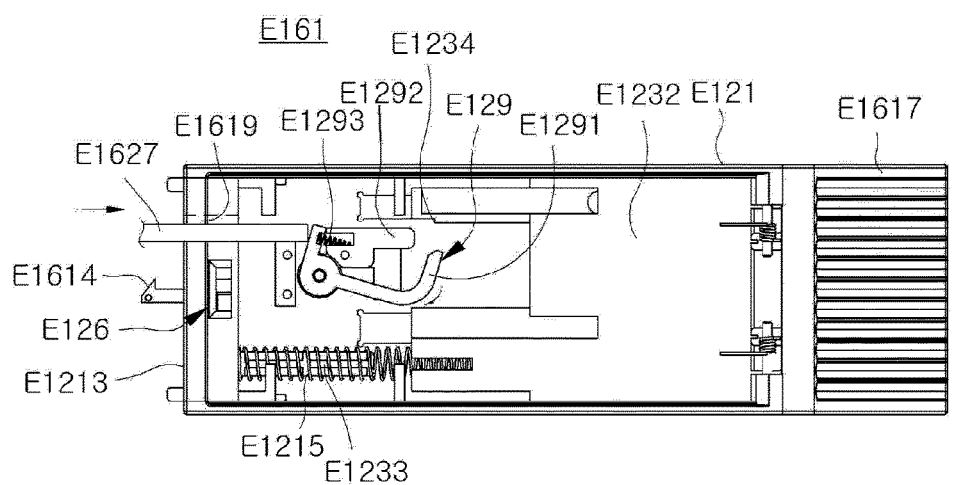

[FIG.215]
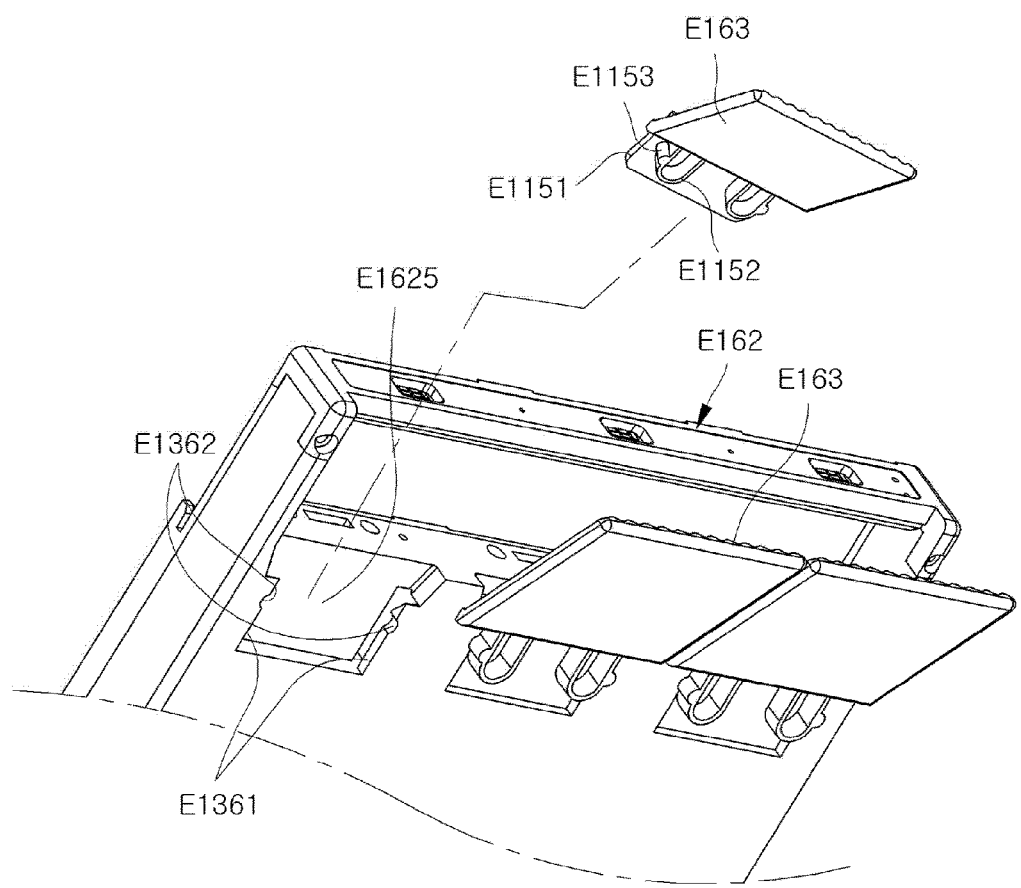

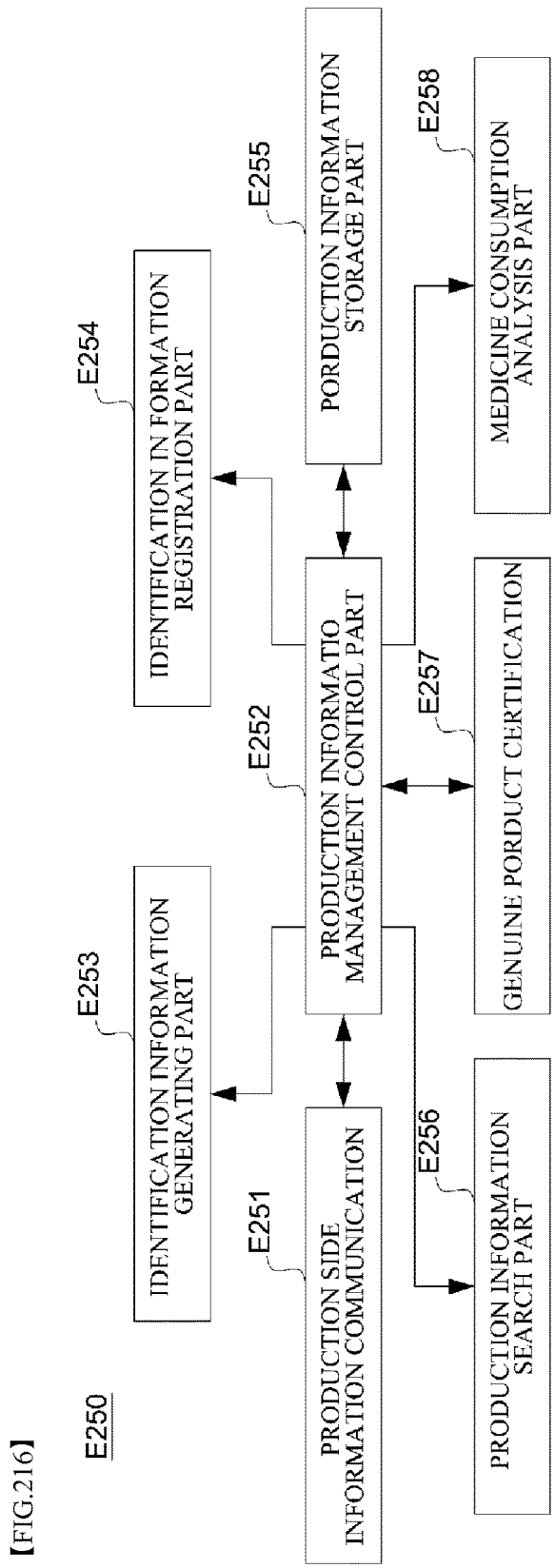
[FIG.216]

[FIG.217]
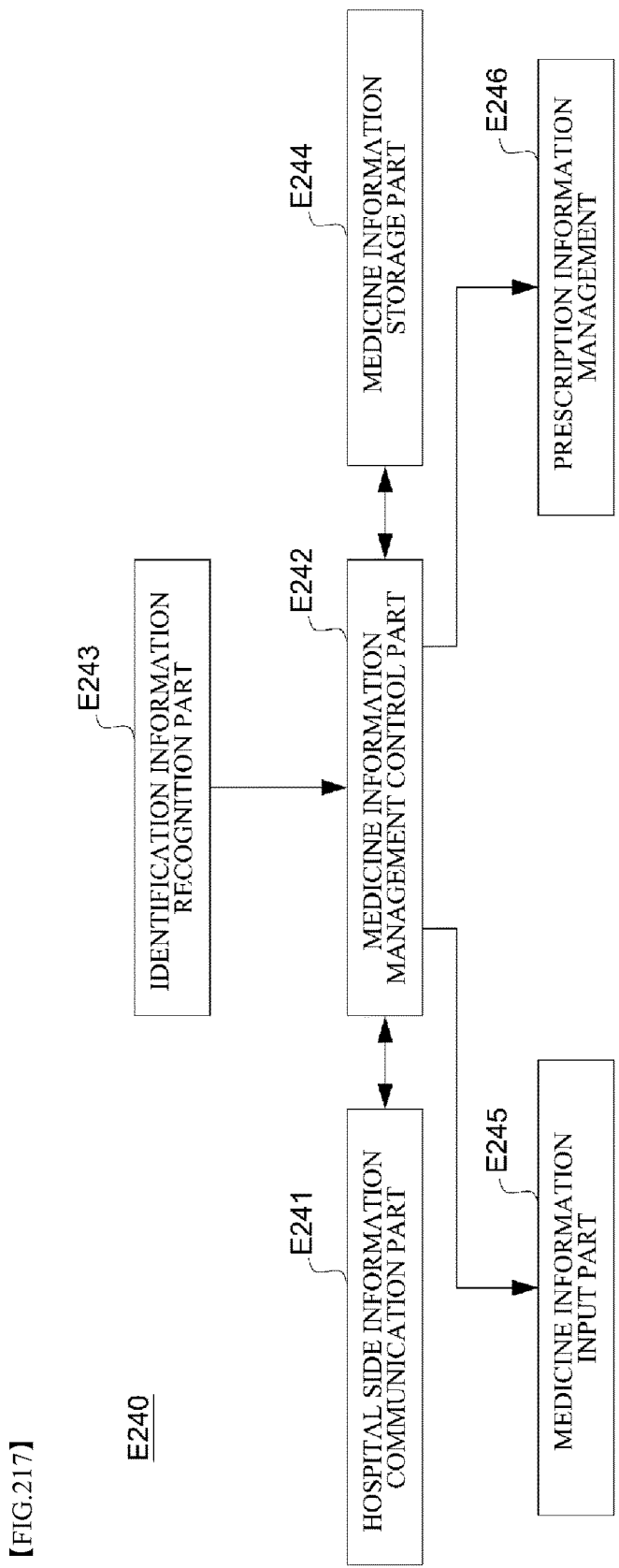

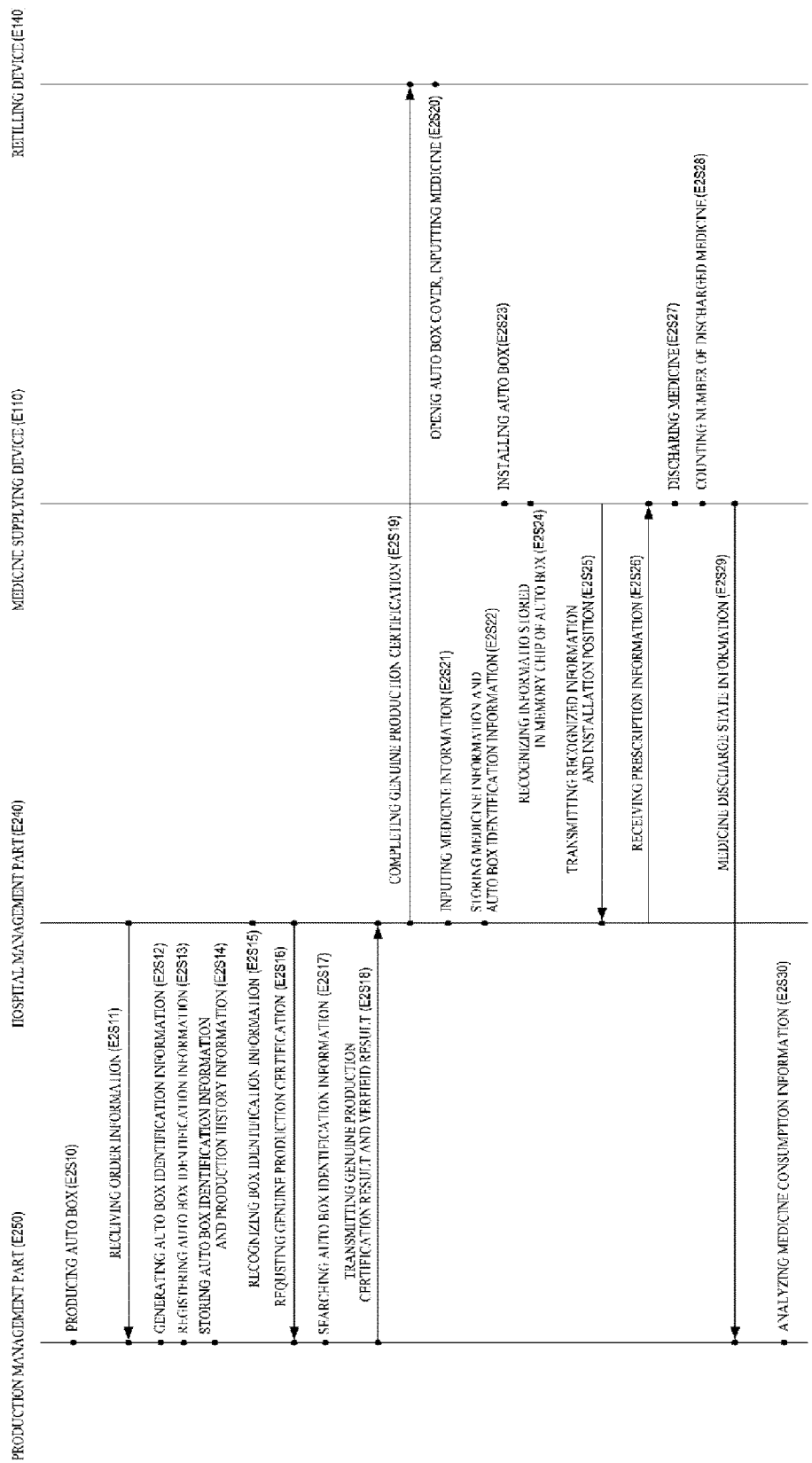
[FIG.218]

MEDICINE DISPENSING SYSTEM AND CONTROL METHOD THEREOF

TECHNICAL FIELD

The present invention relates to a medicine dispensing system, and more particularly, to a medicine storing and supplying apparatus which safely stores medicines having various forms and sizes and automatically supplies the stored medicines according to a request of an administrator having an authorization.

Further, the present invention relates to a medicine dispensing system and a control method thereof, and more particularly, to a medicine management system which may record inherent identification information on a medicine receiving container storing the medicine, may distinguish whether the medicine receiving container is a genuine one, when the medicine receiving container is installed in a cabinet of a hospital or a pharmacy, and may manage information of a stock and supply of the medicine through communication with the cabinet, a hospital server, and a producer server, and a control method thereof.

Furthermore, the present invention relates to a medicine dispensing system and a control method thereof, and more particularly, to a medicine dispensing system which discharges the medicine from a medicine dispensing container in which the medicine is received, and a control method thereof.

BACKGROUND ART

Generally, medicines of various kinds and forms may be included in a unit dose of medication according to a prescription for a patient, and the unit dose of medication is put in a basket and delivered to the patient.

The various medicines in one basket are gathered from containers storing each kind of medicine according to the kind and the number of medicines written on the prescription, and the basket in which the medicines are gathered is delivered to the patient, and the patient takes the medicines gathered in the basket.

Meanwhile, conventionally, to gather the various medicines in the one basket, a medicine specialist such as a pharmacist should manually take out each of the medicines from bottles or the like, in which the medicines are stored, according to the prescription for the patient, and then should put the gathered medicines in the basket. Therefore, a confirmation work which checks again accuracy of the gathered medicines is essentially required.

In such an operation, it is difficult to ensure the accuracy of administration of the medicine, and thus there is always possibility of medication accidents. In addition to the medication accidents, since a medicine gathering process itself is very complicated, it takes a long time to gather the medicines according to the prescription for the patient, and thus there is another problem that work efficiency is deteriorated.

Therefore, in gathering the medicines by a unit dose according to the prescription for the patient, a study on methods and techniques which may enhance the accuracy and the efficiency to provide convenience to a user such as the pharmacist and also may prevent the medication accidents in advance is required.

In addition, the medicines are manufactured to contain ingredients for treating a corresponding disease and to have various kinds and dosage forms such as tablets, powders, and injections.

To automatically store and supply the medicines of such various forms and kinds, medicine storing and supplying apparatuses have been developed.

In particular, since the injections in which liquid medicines are stored are manufactured using glass containers, there is a problem that the containers bump against each other during a storage and supply process and thus the injections are damaged.

Therefore, it is necessary to develop a medicine storing and supplying system which may complexly store the medicines of different forms and kinds from each other, such as the injections and the tablets, may supply the accurate medicines to the patient, and may check a storing and supplying state of each medicine in real time.

Meanwhile, if a specific medicine of the medicines is erroneously supplied to other patient, the patient who has taken the wrong medicine may be seriously harmed. Therefore, it is necessary to establish an access right to each medicine and to allow only an administrator having the authorization to store and supply the corresponding medicine.

Further, conventionally, there was no means for confirming whether a medicine receiving container storing the medicine is a genuine one, and thus the medication accidents occurred due to an unjustifiable use of the medicine receiving container.

DISCLOSURE

Technical Problem

The present invention is directed to providing a medicine dispensing system which may rapidly and accurately dispense medicines from a medicine dispensing container, when gathering the medicines to be provided to a patient, and a control method thereof.

Also, the present invention is directed to providing a medicine dispensing system which may prevent fragile medicines from being damaged in a medicine gathering process, when gathering the medicines to be provided to the patient, and a control method thereof.

Also, the present invention is directed to providing a medicine dispensing system which may allow an administrator and/or a user to conveniently and effectively operate, when gathering the medicines to be provided to the patient, and a control method thereof.

Also, the present invention is directed to providing a medicine dispensing system which may store many more medicines and may rapidly and accurately dispense the medicines, when gathering the medicines to be provided to the patient, and a control method thereof.

Also, the present invention is directed to providing a medicine dispensing system which may safely store the medicines of various forms and sizes and may automatically supply the stored medicines according to a request of an administrator having a valid authorization, and a control method thereof.

Also, the present invention is directed to providing a medicine dispensing system which may safely discharge the stored medicine, and a control method thereof.

Also, the present invention is directed to providing a medicine dispensing system which may provide storing and supplying information of the medicines and thus may allow stock management of the medicines to be easily performed, and a control method thereof.

Also, the present invention is directed to providing a medicine dispensing system which may provide inherent identification information to a medicine receiving container configured to store the medicines and discharge the medicines according to prescription information and thus may effectively manage the medicines using the medicine receiving container, and a control method thereof.

Also, the present invention is directed to providing a medicine dispensing system which may transmit information of the medicine receiving container installed in a cabinet to a hospital server in real time, and thus may manage a medicine discharge state in real time, and a control method thereof.

Also, the present invention is directed to providing a medicine dispensing system which may establish an access right of an administrator to the medicine receiving container and may allow only the administrator having a valid authorization to discharge and replenish the medicines, and a control method thereof.

Also, the present invention is directed to providing a medicine dispensing system which may store information of discharged medicines and information of the administrator who discharges the corresponding medicines and thus may trace the discharged medicines using the stored information, when the medicines are erroneously discharged, and a control method thereof.

DISCLOSURE

Technical Problem

The present invention is directed to providing a medicine dispensing system which may rapidly and accurately dispense medicines from a medicine dispensing container, when gathering the medicines to be provided to a patient, and a control method thereof.

Also, the present invention is directed to providing a medicine dispensing system which may prevent fragile medicines from being damaged in a medicine gathering process, when gathering the medicines to be provided to the patient, and a control method thereof.

Also, the present invention is directed to providing a medicine dispensing system which may allow an administrator and/or a user to conveniently and effectively operate, when gathering the medicines to be provided to the patient, and a control method thereof.

Also, the present invention is directed to providing a medicine dispensing system which may store much more medicines and may rapidly and accurately dispense the medicines, when gathering the medicines to be provided to the patient, and a control method thereof.

Also, the present invention is directed to providing a medicine dispensing system which may safely store the medicines of various forms and sizes and may automatically supply the stored medicines according to a request of an administrator having an authorization, and a control method thereof.

Also, the present invention is directed to providing a medicine dispensing system which may safely discharge the stored medicine, and a control method thereof.

Also, the present invention is directed to providing a medicine dispensing system which may provide storing and supplying information of the medicines and thus may allow stock management of the medicines to be easily performed, and a control method thereof.

Also, the present invention is directed to providing a medicine dispensing system which may provide inherent identification information to a medicine receiving container configured to store the medicines and discharge the medicines according to prescription information and thus may effectively manage the medicines using the medicine receiving container, and a control method thereof.

Also, the present invention is directed to providing a medicine dispensing system which may transmit information of the medicine receiving container installed in a cabinet to a hospital server in real time, and thus may manage a medicine discharge state in real time, and a control method thereof.

Also, the present invention is directed to providing a medicine dispensing system which may establish an access right of an administrator to the medicine receiving container and may allow only the administrator having an authorization to discharge and replenish the medicines, and a control method thereof.

Also, the present invention is directed to providing a medicine dispensing system which may store information of discharged medicines and information of the administrator who discharges the corresponding medicines and thus may trace the discharged medicines using the stored information, when the medicines are erroneously discharged, and a control method thereof.

Technical Solution

One aspect of the present invention provides a medicine dispensing device including a medicine storage part configured to store a medicine, a medicine discharge part configured to discharge the medicine stored in the medicine storage part, a communication module configured to communicate with a hospital server, and a control part configured to control an operation of the medicine storage part and the medicine discharge part to discharge the medicine based on prescription information of a prescription received from the hospital server through the communication module.

The medicine dispensing device may further include an identification means configured to verify an access authorization of an administrator and to allow the administrator having the verified access authorization to access the prescription information of the prescription to discharge the medicine stored.

The medicine dispensing device may further include a display part configured to display an operation state and various menus for performing a medicine storing operation and a supplying operation, an input part configured to input a command to select a menu displayed on the display part and to perform a desired operation, and a memory part configured to discharge information and store stock information of the medicine stored in the medicine storage part, and access information of the administrator. At this time, the medicine dispensing device may be communicably connected with one or more sub device having the medicine storage part therein. The medicine storage part may be a receiving container which is removably installed to be slid forwardly from a cabinet forming an exterior of the medicine dispensing device.

The medicine dispensing device may further includes a wrapper providing part configured to provide a wrapper packing the discharged medicine, a printing part configured to print a notice informing an administration method of the discharged medicine on a sticker, a collection container configured to collect erroneously discharged medicine, and a bar code recognition part configured to recognize information of the collected medicine.

The medicine storage part may include a medicine cartridge formed in a box shape of which an upper portion is opened to store the medicine therein and having a discharging port through which the medicine is discharged, and a cartridge installing part having a plurality of installation spaces in which the medicine cartridge is installed, and the medicine cartridge may be removably installed in an installation space of the cartridge installing part to be stacked, and may include a discharging portion opening/closing part provided at a lower side thereof to open and close the discharging port. The medicine cartridge may include a cover installed at an opened upper surface to perform an opening/closing operation, a locking means installed at a rear surface of the medicine cartridge to lock and release the cover, and a discharging port opening/closing locking part configured to lock the discharging port opening/closing part and to release the discharging port opening/closing part when being installed at the cartridge installing part so that a locking release member installed at a front surface of the cartridge installing part is inserted therein, and an insertion hole in which the locking release member is inserted may be formed in the rear surface of the medicine cartridge. The medicine cartridge may further include a locking member configured to pass through a coupling hole formed in the cartridge installing part and to be coupled to a cartridge installation locking part provided at the cartridge installing part.

The medicine dispensing device may further include a medicine refill device separately manufactured from the medicine dispensing device, and configured to open the cover of the medicine cartridge after the valid access authorization of the administrator is verified, when it is necessary to refill the medicine into the medicine cartridge, and the locking means may perform a locking release operation only when installed in the medicine refill device.

The medicine cartridge may have a memory chip configured to store a serial number assigned when the medicine cartridge was first manufactured and information of the stored medicine, and the cartridge installing part may have a memory recognition part installed at a position corresponding to the memory chip of the medicine cartridge, and the memory chip may have a read-only-memory to prevent initially stored information from being deleted or changed.

The medicine discharge part may include a conveying part which is moved up and down to convey the medicine discharged from the storage container to a predetermined discharge position, a gathering part configured to primarily gather the medicine conveyed by the conveying part, a take-out container configured to deliver the medicine delivered from the gathering part to the administrator, and a shutter opening/closing part configured to open and close a shutter. The conveying part may include a conveyor configured to convey the medicine discharged from the medicine cartridge toward the gathering part, and an up and down moving part which moves up and down the conveyor belt, and a seat guide may be installed at both sides of the conveyor belt to guide the medicine discharged from the medicine cartridge and to seat the medicine on the conveyor belt.

A buffer member may be provided at at least one of an upper surface of the seat guide and an upper surface of the conveyor belt.

A opening may be formed at one side surface of the gathering part to receive the medicine from the conveyor belt and to deliver the medicine into the take-out container, and a transmitting shutter configured to perform an opening/closing operation by the shutter opening/closing part may be installed at the opened one side surface of the gathering part, and a take-out shutter configured to perform an opening/closing operation together with the opening/closing operation of the transmitting shutter may be at one side of the take-out container.

The medicine storage part may include a drawer in which medicine storage cases having different shapes according to types of the medicine are received, and a drawer installing part having a loading space in which the drawers are arranged on a plurality of levels to be stacked.

A plurality of cells formed according to a shape of the received medicine may be provided at the medicine storage case, and the plurality of cells may include a door installed at an upper surface of each cell to selectively open and close the upper surface, a door detecting part configured to detect whether the door is opened, a door opening/closing part installed at each cell to open and close the door, and a memory chip configured to store a serial number assigned to each cell when the cell was first manufactured and information of the medicine stored therein, and the memory chip may have a read-only-memory to prevent initially stored information from being deleted or changed.

A withdrawal detecting part configured to detect a withdrawing state of the drawer may be installed at a rear end of the drawer or a front surface of the drawer installing part, and a fixing means configured to fix the drawer in a withdrawn state may be installed at the front surface of the drawer installing part, and the control part may control the door opening/closing part to open the door of the cell storing the medicine to be discharged, among the cells provided at the medicine storage case according to a detecting signal of the withdrawal detecting part, and may control the fixing means so that the drawer is slid into the drawer installing part, only when all of the doors are closed.

The medicine dispensing device may further include a medicine refill device separately manufactured from the medicine dispensing device, and configured to open a door provided at each cell of the medicine storage case after the valid access authorization of the administrator is verified, when it is necessary to refill the medicine into the medicine cartridge.

Advantageous Effects

According to the present invention, the following effects may be obtained.

According to the present invention, the necessary medicines can be accurately dispensed from the medicine dispensing container according to the prescription for the patient. In particular, even when dispensing the plurality of necessary medicines, it is possible to control the medicines to be more rapidly and accurately dispensed, and thus to allow the medicine dispensing operation to be effectively and rapidly performed.

According to the present invention, in the cartridge coupled with the medicine dispensing body, since the guide rail configured to guide the medicine dispensing container when the medicine dispensing body is connected with the cartridge is provided, the connection can be achieved at a right position. Further, since a cutoff device of power transmission is provided to allow external power for dispensing the medicine to be transmitted to the medicine dispensing container or to restrict the external power from being transmitted to the medicine dispensing container, the medicine can be dispensed at only a suitable time.

According to the present invention, in the medicine conveying part which conveys the medicine to the medicine gathering device, since the side guide part is provided at both side surfaces of the medicine conveying part, it is possible to prevent the dispensed medicine from being bounced and separated to the outer side. Further, since the buffer member is provided at the side guide part, even though the medicine is bounced and collides with the side guide part, the shock can be minimized and thus the damage of the medicine can be prevented.

According to the present invention, in an ampoule type medicine dispensing device, since a medicine storing matrix which stores an ampoule type medicine is provided, and a shutter device is provided, it is easy to automatically dispense the ampoule type medicine. Further, the ampoule type medicines stored therein can fall down, in turn, on the conveyor in a shutter drop manner, and the fallen ampoule type medicine can be dispensed in turn by the operation of the conveyor. Further, since various types of cams can be provided to operate the shutters provided in multiple layers, it is possible to provide the dispensing device corresponding to various environments and requirements. Furthermore, the stored ampoule type medicines can be dispensed at various timings and in various manners, it is possible to prevent the damage of the medicine due to collision with each other, and to stably dispense the medicine.

According to the present invention, in a blister-packed medicine dispensing container, since the dispensing of the blister-packed medicines can be simply performed by the movement of the medicine receiving part, it is possible to provide a simple structure. Further, in loading of the blister-packed medicines, the interference between the blister-packed medicine and other elements can be prevented, and thus the blister-packed medicine can be precisely put into the medicine receiving part.

According to the present invention, in a packaging type medicine dispensing container, as an essential precondition for individual cutting the medicine package, a perforated line of the medicine package can be easily detected. Further, by minimizing an image taking area or obtaining area, it is possible to minimize a resource of a computing system, which is required in continuously image processing of a series of images, and thus the perforated line can be effectively and rapidly detected. Furthermore, since only a camera module is used to detect the perforated line of the medicine package without any sensor, the configuration for detecting the perforated line of the medicine package can be minimized, and it is possible to get advantage in the economic aspect.

According to the present invention, in a pouch type medicine dispensing container, when the pouch type medicine is dispensed, it is possible to prevent the damage of the pouch type medicine, and thus it is possible to improve work efficiency.

According to the present invention, in order to prevent a damage of the medicines to be dispensed, the dispensing timing of each medicine is controlled in various methods, and thus it is possible to rapidly, effectively and also safely dispense the medicines.

According to the present invention, even when part of the medicines are previously dispensed, the medicine dispensing information is separately stored. Therefore, in the medicine dispensing operation, the medicines are dispensed in consideration of the medicine dispensing information, and thus it is possible to prevent the repeated dispensing by which the same medicines are repeatedly provided to the same patient.

According to the present invention, it is possible to safely store various types of medicines such as injections and tablets. Further the stored medicine can be automatically dispensed to an administrator having a just access right, and thus this allows the safety prescription and administration.

According to the present invention, in a process of storing and discharging the medicine formed of a glass container, it is possible to the damage of the medicine and also to enhance the storage efficiency.

According to the present invention, a door of each cell of the medicine storage case, which stores the medicine to be dispensed, can be opened only when the access right of the administrator is identified. Further, only when all of the doors are closed, the drawer can be slid into the drawer installing part, and thus the damage or the breakdown of the storage case and the door can be prevented.

According to the present invention, since prescription information of a prescription provided from a hospital server is provided to only the administrator having the just access right, the prescribed medicines can be precisely administered to the corresponding patient, and thus medication accidents due to erroneous administration can be prevented.

According to the present invention, since storage information of the medicine stored in the medicine storage part and discharge information of the discharged medicine are synchronized with the hospital server in real time, the stock of the medicine can be integrally managed.

According to the present invention, since a medicine storage case and a medicine cartridge of a medicine storage part are opened in only a separate medicine refill device, and then the medicines are refilled, a loss of the medicine and an erroneous administration can be prevented.

According to the present invention, since the erroneously discharged medicine is collected through a collection container, and information of the collected medicine is transmitted to the hospital server in real time, it is possible to precisely manage the discharge information of the medicine.

According to the present invention, a locking device is installed at front and rear sides of the collection container, and only the administrator having the just access right is allowed to put the medicine into the collection container, to release the locking device, and to take out the collected medicines.

According to the present invention, a rotational member is installed at an inner side of the collecting port of the collection container, and thus the collected medicine is prevented from being discharged through the collecting port.

According to the present invention, since a storage container in which internal shapes have different shapes according to the stored medicine is formed in the same unit size, and the storage container is selectively installed at a cabinet of a main device and a sub device, the efficiency in medicine storage can be enhanced.

According to the present invention, the medicine cartridge storing the medicines having various shapes and sizes is easily installed at the cartridge installing part, and also the medicine can be exactly supplied to the administrator having the identified access right according to the prescription information of the prescription.

According to the present invention, when the damage or the breakdown of the storage container or the cartridge installing part occurs, the corresponding storage container can slid forwardly, and then separated from the main body, and replace or repaired. Therefore, the maintenance can be performed without space restriction, and also workability can be increased.

According to the present invention, since the cartridge installing part is formed in a shelf structure having multi-stage, and the medicine cartridge can be removably installed at the installation space of the cartridge installing part to be stacked, the plurality of medicines can be effectively stored. When all of the stored medicines are discharged, the medicine cartridge can be easily separated from the cartridge installing part, and then the medicines can be easily refilled.

According to the present invention, when the medicine cartridge is installed at the cartridge installing part, the locking release member of the cartridge installing part is inserted through an insertion hole formed in the cartridge body, such that a pressing end of the hinge rotating member is pressed. Therefore, the hinge rotating member is rotated, and the engaging with the opening/closing member is released.

According to the present invention, the discharging portion is opened and closed, only when the medicine cartridge is installed at the cartridge installing part. And when the medicine cartridge is separated from the cartridge installing part, the discharging port is always closed by the opening/closing member, and the discharge of the medicine is blocked. Therefore, the medicine can be prevented from being discharged due to vibration in a moving process According to the present invention, since the medicine is naturally moved along an inclined surface of the inclined member, a separate deriving device for moving the medicine in the medicine cartridge is not required, and thus the manufacturing cost can be reduced, and the workability can be also enhanced.

According to the present invention, the second guide is moved according to a height of the medicine stored in the medicine cartridge, such that the medicine is pushed toward one side, and thus the medicine is prevented from being damaged or broken, and also the medicines having various sizes may be safely stored.

According to the present invention, when a medicine discharging operation is performed, the stock of the medicine stored in the medicine cartridge is transmitted to the hospital management part in real time, the stock management of the medicine in the hospital can be enhanced.

According to the present invention, since identification information is provided to the medicine receiving container in which the stored medicine is discharged according to the prescription information of the prescription, the management of the medicine receiving container and the medicine can be easily performed, and unjustifiable use of the medicine receiving container and the medicine can be prevented.

According to the present invention, since the cover provided at the medicine receiving container is opened only when the access right of the administrator is identified, the erroneous administration of the medicine can be prevented, and the safety of special medicines is further increased.

According to the present invention, inherent medicine receiving container identification information is generated and registered to each medicine receiving container, and thus medicine receiving container identification information can be systematically managed.

According to the present invention, the medicine receiving container can be distinguished and driven by installation positions of the cartridge installing part.

According to the present invention, the consumption state of the medicine received in the medicine receiving container may be variously analyzed by hospitals, regional groups and lengths of time using the medicine consumption analysis part, may be reflected to the medicine production, and thus efficiency in the production and the stock management of the medicine may be enhanced.

According to the present invention, the discharge state of the medicine is checked in real time using the medicine receiving container, and the consumption information is analyzed using the discharge state of the medicine, and thus the efficiency of the stock management and the production management is enhanced.

DESCRIPTION OF DRAWINGS

FIG. 1 is an environmental view schematically illustrating an operating environment of a medicine dispensing system according to one embodiment of the present invention.

FIGS. 2 to 6 are views illustrating various configuration examples of the medicine dispensing system according to one embodiment of the preset invention.

FIG. 7 is a block diagram illustrating a medicine gathering device according to one embodiment of the present invention.

FIG. 8 is a schematic perspective view of the medicine gathering device according to one embodiment of the present invention.

FIG. 9 is a schematic perspective view of a first medicine dispensing device according to present invention.

FIGS. 10 and 11 are schematic views illustrating a principle of dispensing a medicine from a medicine dispensing container through a medicine dispensing driving means according to the present invention.

FIGS. 12 and 13 are schematic perspective views illustrating a medicine dispensing unit according to one embodiment of the present invention.

FIG. 14 is a schematic exploded perspective view illustrating the medicine dispensing unit according to one embodiment of the present invention.

FIG. 15 is a schematic perspective views illustrating a state in which a position moving part of the medicine dispensing unit according to one embodiment of the present invention is moved.

FIGS. 16 and 17 are schematic views illustrating a state in which a rotation supporting part of the medicine dispensing unit according to one embodiment of the present invention is rotated.

FIG. 18 is a schematic partially-exploded perspective view illustrating a medicine dispensing unit according to another embodiment of the present invention.

FIG. 19 is a schematic perspective view illustrating a state in which a position moving part of the medicine dispensing unit according to another embodiment of the present invention is moved.

FIG. 20 is a schematic perspective view illustrating the medicine dispensing driving means according to the present invention.

FIG. 21 is a schematic perspective view illustrating an operation state of the medicine dispensing driving means according to the present invention.

FIG. 22 is a schematic perspective view illustrating another operation state of the medicine dispensing driving means according to the present invention.

FIG. 23 is a schematic perspective view illustrating still another operation state of the medicine dispensing driving means according to the present invention.

FIG. 24 is a schematic perspective view illustrating a state in which the medicine dispensing driving means according to the present invention may be applied to the medicine dispensing containers of various sizes.

FIG. 25 is a schematic perspective view illustrating an operation state in the case of FIG. 24.

FIG. 26 is a perspective view illustrating a partially cut-away state of a medicine conveying part according to one embodiment of the present invention.

FIG. 27 is a perspective view illustrating the medicine conveying part according to one embodiment of the present invention.

FIG. 28 is a perspective view illustrating a shape of the medicine conveying part with a side guide part according to one embodiment of the present invention.

FIG. 29 is a side view illustrating the shape of the medicine conveying part of FIG. 28.

FIG. 30 is a perspective view illustrating a shape of the medicine conveying part with a side guide part according to another embodiment of the present invention.

FIG. 31 is a side view illustrating the shape of the medicine conveying part of FIG. 30.

FIG. 32 is a perspective view illustrating a shape of the medicine conveying part with a side guide part according to still another embodiment of the present invention.

FIG. 33 is a side view illustrating the shape of the medicine conveying part of FIG. 32.

FIG. 34 is a perspective view illustrating a shape of a cartridge according to one embodiment of the present invention.

FIGS. 35 and 36 are perspective views illustrating a configuration and an operation state of a fixing part according to one embodiment.

FIG. 37 is a perspective view illustrating a shape of the medicine dispensing container according to one embodiment.

FIG. 38 is a front side bottom perspective view illustrating the shape of the medicine dispensing container of FIG. 37.

FIG. 39 is a rear side bottom perspective view illustrating the shape of the medicine dispensing container of FIG. 37.

FIG. 40 is a rear side bottom perspective view illustrating the medicine dispensing container of FIG. 37, when seen from another angle.

FIGS. 41 to 43 are cut-away perspective views illustrating the shape of the medicine dispensing container of FIG. 37.

FIG. 44 is a perspective view illustrating a connection state between the medicine dispensing container and the cartridge according to one embodiment.

FIGS. 45 and 46 are schematic views illustrating the connection state between the medicine dispensing container and the cartridge according to one embodiment.

FIG. 47 is a perspective view illustrating a shape of a packaging type medicine dispensing container according to one embodiment of the present invention.

FIG. 48 is a bottom perspective view illustrating the shape of the packaging type medicine dispensing container according to one embodiment.

FIG. 49 is a partially cut-away exploded perspective view illustrating the shape of the packaging type medicine dispensing container according to one embodiment.

FIG. 50 is a cross-sectional view illustrating the shape of the packaging type medicine dispensing container according to one embodiment.

FIG. 51 is a partially cut-away perspective view of the packaging type medicine dispensing container according to one embodiment.

FIG. 52 is an exploded perspective view of the packaging type medicine dispensing container according to one embodiment.

FIG. 53 is another exploded perspective view of the packaging type medicine dispensing container according to one embodiment.

FIG. 54 is a bottom perspective view illustrating a shape of a light shielding part according to one embodiment.

FIGS. 55 and 56 are schematic views illustrating an operation state of a scanning part according to one embodiment.

FIG. 57 is a block diagram illustrating construction elements related to detection of a perforated line of a medicine package according to one embodiment.

FIG. 58 is schematic view schematically illustrating the medicine package.

FIG. 59 is a flowchart illustrating a method of detecting the perforated line according to one embodiment.

FIG. 60 is a flowchart illustrating an image processing process according to one embodiment.

FIG. 61 is a flowchart illustrating a perforated line detecting process according to one embodiment.

FIG. 62 is a view explaining the method of detecting the perforated line according to one embodiment.

FIG. 63 is a schematic perspective view illustrating a blister-packed medicine dispensing container according to one embodiment of the present invention.

FIG. 64 is a schematic perspective view illustrating a state in which a rotating part provided at the blister-packed medicine dispensing container according to one embodiment of the present invention is rotated from a main body.

FIGS. 65 and 66 are schematic perspective views explaining a principle in which the rotating part provided at the blister-packed medicine dispensing container according to one embodiment of the present invention is rotated from the main body.

FIG. 67 is a schematic perspective view illustrating a state in which a blister-packed medicine is dispensed from a first row medicine receiving part provided at the blister-packed medicine dispensing container according to one embodiment of the present invention.

FIG. 68 is an internal configuration view explaining the state in which the blister-packed medicine is dispensed from the first row medicine receiving part provided at the blister-packed medicine dispensing container according to one embodiment of the present invention.

FIGS. 69 and 70 are internal configuration views illustrating a state in which a dispensing part is omitted to explain a principle in which the blister-packed medicine is dispensed from the first row medicine receiving part provided at the blister-packed medicine dispensing container according to one embodiment of the present invention.

FIG. 71 is a schematic perspective view illustrating a state in which the blister-packed medicine is dispensed from a second row medicine receiving part provided at the blister-packed medicine dispensing container according to one embodiment of the present invention.

FIG. 72 is an internal configuration view explaining the state in which the blister-packed medicine is dispensed from the second row medicine receiving part provided at the blister-packed medicine dispensing container according to one embodiment of the present invention.

FIGS. 73 and 74 are schematic views explaining an operation principle of an opening/closing part through which the blister-packed medicine is dispensed from the second row medicine receiving part provided at the blister-packed medicine dispensing container according to one embodiment of the present invention.

FIG. 75 is a schematic exploded perspective view explaining a principle in which a medicine receiving part provided at the blister-packed medicine dispensing container according to one embodiment of the present invention is fixed to a rail part.

FIG. 76 is a schematic perspective view explaining a process in which the blister-packed medicine is put into the blister-packed medicine dispensing container according to one embodiment of the present invention.

FIGS. 77 and 78 are internal configuration views explaining the process in which the blister-packed medicine is put into the blister-packed medicine dispensing container according to one embodiment of the present invention.

FIG. 79 is an internal configuration view explaining a jam preventing part provided at the blister-packed medicine dispensing container according to one embodiment of the present invention.

FIG. 80 is a schematic exploded perspective view explaining the jam preventing part provided at the blister-packed medicine dispensing container according to one embodiment of the present invention.

FIG. 81 is a schematic perspective view illustrating a modified example of the blister-packed medicine dispensing container according to one embodiment of the present invention.

FIG. 82 is an internal configuration view illustrating the modified example of the blister-packed medicine dispensing container according to one embodiment of the present invention.

FIG. 83 is an internal exploded perspective view illustrating the modified example of the blister-packed medicine dispensing container according to one embodiment of the present invention.

FIG. 84 is a perspective view illustrating an ampoule type medicine dispensing container according to one embodiment of the present invention.

FIG. 85 is a perspective view illustrating a state in which a side surface of the ampoule type medicine dispensing container according to one embodiment of the present invention is opened.

FIGS. 86 and 87 are cut-away perspective views illustrating, in turn, an operation state of a locking device according to one embodiment.

FIG. 88 is a cut-away perspective view illustrating the ampoule type medicine dispensing container according to one embodiment of the present invention.

FIG. 89 is a perspective view illustrating a shape of a driving part according to one embodiment.

FIG. 90 is an exploded perspective view illustrating a shape of a partition member according to one embodiment.

FIG. 91 is a perspective view illustrating a shape of a shutter according to one embodiment.

FIG. 92 is a perspective view illustrating a state in which the partition member is coupled with the shutter according to one embodiment.

FIG. 93 is a partially cut-away perspective view illustrating shapes of a detecting part and a to-be-detected part according to one embodiment.

FIG. 94 is a perspective view illustrating a shape of a conveyor of the ampoule type medicine dispensing container according to one embodiment.

FIGS. 95 and 96 are partially cut-away perspective views illustrating a state in which each unit cell is opened or closed.

FIG. 97 is a longitudinal cross-sectional view of FIG. 96.

FIG. 98 is a block diagram illustrating an entire shape of the ampoule type medicine dispensing container according to one embodiment.

FIGS. 99 to 104 are partially cut-away perspective views illustrating, in turn, a state in which an ampoule type medicine is dispensed.

FIG. 105 is a flowchart illustrating, in turn, an operation sequence of the ampoule type medicine dispensing container.

FIG. 106 is a schematic perspective view illustrating a pouch type medicine dispensing container according to one embodiment of the present invention.

FIGS. 107 and 108 are schematic perspective views explaining a principle in which a rotating part provided at the pouch type medicine dispensing container according to one embodiment of the present invention is rotated from a housing.

FIGS. 109 and 110 are internal configuration views explaining an internal configuration of the pouch type medicine dispensing container according to one embodiment of the present invention.

FIGS. 111 to 114 are schematic perspective views explaining a principle in which a pouch type medicine is dispensed from a medicine receiving part provided at the pouch type medicine dispensing container according to one embodiment of the present invention.

FIG. 115 is a schematic perspective view explaining a state in which the pouch type medicine is moved by the medicine receiving part provided at the pouch type medicine dispensing container according to one embodiment of the present invention.

FIG. 116 is a schematic view explaining a principle in which the pouch type medicine is moved by the medicine receiving part provided at the pouch type medicine dispensing container according to one embodiment of the present invention.

FIG. 117 is a schematic perspective view illustrating a second medicine dispensing device according to the present invention.

FIGS. 118 and 119 are schematic perspective views illustrating a packed medicine dispensing means and a packed medicine dispensing means moving part provided at the second medicine dispensing device according to the present invention.

FIGS. 120 to 126 are schematic perspective views illustrating an operation relationship between the packed medicine dispensing means and the packed medicine dispensing means moving part provided at the second medicine dispensing device according to the present invention.

FIGS. 127 and 128 are schematic perspective views illustrating a packed medicine dispensing container provided at the second medicine dispensing device according to the present invention.

FIG. 129 is a partial exploded perspective view illustrating the packed medicine dispensing container provided at the second medicine dispensing device according to the present invention.

FIG. 130 is a schematic perspective view illustrating a state after a medicine receiving part of the packed medicine dispensing container provided at the second medicine dispensing device according to the present invention is withdrawn.

FIG. 131 is a schematic perspective view illustrating an inner side of the packed medicine dispensing container provided at the second medicine dispensing device according to the present invention.

FIG. 132 is a schematic exploded perspective view illustrating the inner side of the packed medicine dispensing container provided at the second medicine dispensing device according to the present invention.

FIGS. 133 and 134 are internal configuration views explaining an operation principle of a pressing part of the packed medicine dispensing container provided at the second medicine dispensing device according to the present invention.

FIGS. 135 to 145 are schematic views illustrating a modified example of a pressing source part of the packed medicine dispensing container provided at the second medicine dispensing device according to the present invention.

FIGS. 146 and 147 are a schematic exploded perspective view and a partial view explaining a principle of detecting a movement of the packed medicine dispensing container provided at the second medicine dispensing device according to the present invention.

FIGS. 148 and 149 are partial views explaining a principle of increasing and reducing an external communication space of the packed medicine dispensing container provided at the second medicine dispensing device according to the present invention.

FIGS. 150 to 152 are partial views explaining an operation principle of an aligning part of the packed medicine dispensing container provided at the second medicine dispensing device according to the present invention.

FIGS. 153 to 156 are schematic views explaining an operating principle of a dispensing space increasing part of the packed medicine dispensing container provided at the second medicine dispensing device according to the present invention.

FIGS. 157 to 160 are schematic views explaining an operation principle of a withdrawal realizing part and a movement blockade part of the packed medicine dispensing container provided at the second medicine dispensing device according to the present invention.

FIGS. 161 and 162 are schematic views explaining an operation principle of a locking part of the packed medicine dispensing container provided at the second medicine dispensing device according to the present invention.

FIG. 163 is a schematic view explaining a principle of installing the packed medicine dispensing container provided at the second medicine dispensing device according to the present invention to the cartridge.

FIGS. 164 to 167 are schematic views explaining an operation principle of a withdrawal external force applying part of a packed medicine dispensing means provided at the second medicine dispensing device according to the present invention.

FIGS. 168 to 173 are schematic views explaining an operation principle of the packed medicine dispensing means provided at the second medicine dispensing device according to the present invention.

FIGS. 174 and 175 are schematic perspective views illustrating a cartridge for installing a packed medicine storage container provided at packed medicine dispensing equipment.

FIGS. 176 to 182 are schematic views explaining an operation principle of a position fixing part of the cartridge for installing the packed medicine storage container provided at the packed medicine dispensing equipment.

FIG. 183 is a schematic view explaining an operation principle of a separation detecting sensor of the cartridge for installing the packed medicine storage container provided at the packed medicine dispensing equipment.

FIG. 184 is a flowchart explaining a method of controlling the medicine dispensing system according to one embodiment of the present invention.

FIG. 185 is a flowchart explaining an operation state in which the medicine is dispensed in the medicine dispensing system according to one embodiment of the present invention.

FIG. 186 is a view explaining a method of selecting the medicine dispensing container in the medicine dispensing system according to one embodiment of the present invention.

FIGS. 187 and 188 are views explaining a medicine dispensing order according to one embodiment of the present invention.

FIG. 189 is a view explaining a method of controlling medicine dispensing timing of the medicine dispensing containers according to one embodiment of the present invention.

FIG. 190 is a flowchart explaining a method of controlling a dispensing operation of the medicine dispensing system according to another embodiment of the present invention.

FIGS. 191 and 192 are views explaining a method of controlling the dispensing timing of the medicine dispensing container according to another embodiment of the present invention.

FIGS. 193 to 196 are views explaining a method of controlling the medicine conveying part when two or more medicine conveying parts are provided to the medicine dispensing device according to one embodiment of the present invention.

FIG. 197 is a flowchart explaining a method of selecting a prescription according to one embodiment of the present invention.

FIG. 198 is an exemplary view explaining the method of selecting the prescription according to one embodiment of the present invention.

FIG. 199 is a block diagram of a medicine integrated management system using a medicine storing and supplying device according to one embodiment of the present invention.

FIG. 200 is a perspective view of a main device and a sub device illustrated in FIG. 199.

FIG. 201 is a perspective view of the main device illustrated in FIG. 200.

FIG. 202 is a perspective view of a first storage part illustrated in FIG. 201.

FIG. 203 is a partially-enlarged perspective view of a second storage part illustrated in FIG. 201.

FIG. 204 is a partially-enlarged perspective view of the second storage part illustrated in FIG. 203.

FIG. 205 is a perspective view of a medicine cartridge illustrated in FIG. 203.

FIG. 206 is a perspective view of a medicine discharge part illustrated in FIG. 201.

FIG. 207 is an enlarged perspective view of a main portion of the medicine discharge part illustrated in FIG. 206.

FIG. 208 is a perspective view of a collection container illustrated in FIG. 201.

FIG. 209 is an operation state diagram illustrating an medicine discharging action.

FIG. 210 is another perspective view of a cartridge installing part and the medicine cartridge illustrated in FIG. 203.

FIG. 211 is a perspective view illustrating a state in which a cover is opened from the medicine cartridge illustrated in FIG. 210 to show an internal configuration.

FIG. 212 is a plan view illustrating a state in which an inclined part and the cover are removed in FIG. 211 to show the internal configuration.

FIG. 213 is an operation state diagram illustrating a state in which the medicine cartridge illustrated in FIG. 212 is installed at the cartridge installing part.

FIG. 214 is an operation state diagram illustrating an operation state of an opening/closing blocking part when a locking release member illustrated in FIG. 212 is coupled.

FIG. 215 is an enlarged perspective view of a main portion of the cartridge installing part illustrated in FIG. 210.

FIG. 216 is a block diagram of a production management part according to one embodiment of the present invention.

FIG. 217 is a block diagram of a hospital management part according to one embodiment of the present invention.

FIG. 218 is a flowchart explaining a method of controlling each process of a medicine management system according to one embodiment of the present invention.

MODES OF THE INVENTION

The terms used herein are merely to easily describe the present invention, and thus the present invention is not limited to them.

It will be understood that when an element is referred to as being "connected" or "coupled" to another element, it can be directly connected or coupled to the other element or intervening elements may be present. Further, the term "module" or "part" are used for just convenience of explanation, and thus it does not have particular distinguishing meaning or function.

The present invention may be modified or changed without departing from the principles and spirit of the invention. At this time, the modification or change within the principles and spirit of the invention would be obvious to those skilled in the art. Therefore, the present invention includes a modified or changed example without departing from the principles and spirit of the invention. Further, the present invention is not limited to the embodiments to be described below.

Hereinafter, the present invention will be described in detail the accompanying drawings. However, the drawings are to help understanding of the present invention, and thus the technical spirit of the present invention is not limited by the accompanying drawings. Meanwhile, like reference numerals refer to like or corresponding elements regardless of reference numerals and a detailed description thereof will be omitted. However, for convenience of explanation, separate reference numerals may be further provided to the like or corresponding elements.

1. Operating Environment

FIG. 1 is an environmental view schematically illustrating an operating environment of a medicine dispensing system according to one embodiment of the present invention.

Referring to FIG. 1, the medicine dispensing system 1 according to one embodiment of the present invention may be communicated with various external electronic devices 2 and 3. For example, if the medicine dispensing system 1 is disposed in a hospital, it may be connected with a server 2 (hereinafter, called as "server") installed at the hospital, and/or a PC, a smart phone and/or a terminal 3 having similar functions (hereinafter, called as "terminal") provided to employees (e.g., a doctor, a pharmacist, a nurse or the like, hereinafter, called as "user") of the hospital. For convenience of explanation, an environment in which the medicine dispensing system according to one embodiment of the present invention is operated may be called as a medicine management system.

The medicine dispensing system 1 may be connected with the server 2 and/or the terminal 3 through a predetermined network N. The network N may include all of wire and radio networks.

The server 2 may store a variety of information of patients, identification information and/or authentication information of users, or the like. For example, the variety of information of patients may be personal information such as each patient's name and sex, medical history information such as each patient's disease records, prescription information of medicines to be provided at the corresponding patient, or the like. Further, the identification information and authentication information of the users are inherent identification information of the users, which may establish an access right of each user to the server 2, and may be an ID and password, a registration number, a certificate, and biometric information such as fingerprint information, face recognition information, voice recognition information, and iris recognition information.

The terminal 3 allows the users to be connected with the medicine dispensing system 1 and/or the server 2 and thus to obtain necessary information or to perform an input for operating the medicine dispensing system 1 and/or the server 2.

2. Entire System

FIGS. 2 to 6 are views illustrating various configuration examples of the medicine dispensing system according to one embodiment of the preset invention.

The medicine dispensing system 1 according to one embodiment of the preset invention may include various sub-devices. The various sub-devices may include at least one of a first medicine dispensing device 100, a second medicine dispensing device 200, and a medicine gathering device 300.

The first medicine dispensing device 100 is a comparatively standardized device which may store medicine having a relatively small size, and then, if necessary, may dispense corresponding medicine.

The second medicine dispensing device 200 is a comparatively non-standardized device which may store medicine having a relatively large size, and/or a medical appliance, and then, if necessary, may dispense it. Hereinafter, for convenience of explanation, the medication dispensed through the second medicine dispensing device 200 includes the medical appliance as well as the medication.

The medicine gathering device 300 may gather the medicines dispensed from the first and second medicine dispensing devices 100 and 200, and then may deliver the gathered medications to a user.

The detailed configuration of the first and second medication dispensing devices 100 and 200 and the medicine gathering device 300 will be described later.

The medicine dispensing system 1 according to one embodiment of the present invention may be configured by various combinations of the sub-devices 100, 200, and 300.

As an example, referring to FIG. 2, the medicine dispensing system 1 may include one first medicine dispensing device 100 and one medicine gathering device 300.

As another example, referring to FIG. 3, the medicine dispensing system 1 may include one second medicine dispensing device 200 and one medicine gathering device 300.

As still another example, referring to FIG. 4, the medicine dispensing system 1 may include one first medicine dispensing device 100, one second medicine dispensing device 200, and one medicine gathering device 300.

As yet another example, referring to FIG. 5, the medicine dispensing system 1 may include a plurality of first medicine dispensing devices 100 and one medicine gathering device 300.

As yet still another example, referring to FIG. 6, the medicine dispensing system 1 may include a plurality of second medicine dispensing devices 200 and one medicine gathering device 300.

Although not shown in the drawings, the medicine dispensing system 1 may include a combination of one first medicine dispensing device 100, the plurality of second medicine dispensing devices 200, and one medicine gathering device 300, a combination of the plurality of first medicine dispensing devices 100, one second medicine dispensing device 200, and one medicine gathering device 300, or a combination of the plurality of first medicine dispensing devices 100, the plurality of second medicine dispensing devices 200, and one medicine gathering device 300.

Further, although not shown in the drawings, a plurality of medicine gathering devices 300 may be provided in each of the combinations.

Hereinafter, the detailed configuration of the medicine dispensing system 1, the first medicine dispensing device 100, and the second medicine dispensing device 200 will be specifically described.

3. Structure of Medicine Gathering Device

FIG. 7 is a block diagram illustrating the medicine gathering device according to one embodiment of the present invention, and FIG. 8 is a schematic perspective view of the medicine gathering device according to one embodiment of the present invention.

Referring to FIGS. 7 and 8, the medicine gathering device 300 may include a communication part 302, an output part 310, an input part 316, a memory part 308, a control part 318, and a medicine feeding port 320. Meanwhile, although not specifically shown in the drawings, a medicine gathering space may be provided in the medicine gathering device 300. The medicines gathered in the medicine gathering space may be provided to the user through one side surface (e.g., a front surface 300F) of the medicine gathering device 300. Preferably, the medicine feeding port 320 is located at an upper side than the medicine gathering space.

Meanwhile, in FIG. 8, the medicine feeding port 320 is located at a right side of the medicine gathering device 300, but, if necessary, may be located at a left side thereof, and may also be located at both of the left and right sides.

The communication part 302 may be communicated with another electronic device, and may include a plurality of communication modules which are optimized for a plurality of communication protocols. For example, the communication part 302 may include an Internet module part, a local area network module part, and the like capable of being communicated with the above-described server 2 and/or terminal 3. The Internet module part 304 may be a module for Internet connection, and may be installed at an inner side or an outer side of the medicine gathering device 300. The local area network module part 306 is a module for a local area network, and may use various local area network technologies such as Bluetooth, radio frequency identification (RFID), near field communication (NFC), infrared data association (IrDa), ultra wideband (UWB), and ZigBee. The communication part 302 may further include a separate communication module which performs communication with the first and second medicine dispensing devices.

The memory part 308 may store information.

The memory part 308 may store information necessary for an operation of the medicine gathering device 300, and information produced by the operation of the medicine gathering device 300. Further, the memory part 308 may also store information necessary for an operation of the first and second medicine dispensing devices 100 and 200, and information produced by the operation thereof.

The memory part 308 may include various storage media. For example, the memory part 308 may include at least one of a flash memory, a random access memory (RAM), a static random access memory (SRAM), a read only memory (ROM), an electrically erasable programmable read only memory (EEPROM), a hard disk, a magnetic memory, a magnetic disc, an optical disc such as an CD and a blue-ray disc, a card type memory such as an SD card, and another storage medium which is obvious to those skilled in the art.

The memory part 308 may be formed to be installed at the inner side of the medicine gathering device 300, to be separately located at the outer side thereof, or to be attachable and detachable. The memory part 308 formed to be separately located at the outer side may include an external hard disk and a web storage which performs a storing function of the memory part 308 on the Internet or in the server 2.

The output part 310 may output information. The user may receive a variety of information through the output part 310.

The output part 310 may output the information using at least one of an acoustic signal and a visual signal. The output part 310 may include at least one of a display, a speaker, and another output device which is obvious to those skilled in the art.

The output part 310 may include at least one of a video output part 312 and an audio output part 314.

The video output part 312 may output the visual signal. That is, the video output part 312 may display video information. For example, the video output part 312 may display a user UI or a graphic user interface (GUI).

The video output part 312 may be at least one of a liquid crystal display (LCD), a thin film transistor liquid crystal display, an organic light-emitting diode display, a flexible display, a 3D display, and another display which is obvious to those skilled in the art.

The audio output part 314 may output the acoustic signal, i.e., an audio signal. For example, the audio output part 314 may output the audio signal related to various functions performed in the medicine dispensing system 1.

The audio output part 314 may include a receiver, a speaker, a buzzer, or the like.

The input part 316 may receive an input necessary for the operation of the medicine gathering device 300 and/or the medicine dispensing devices 100 and 200 from the user. The user may directly operate the operation of the medicine gathering device 300 and/or the medicine dispensing devices 100 and 200. The input part 316 may include at least one of a key pad, a dome switch, a jog wheel, a jog switch, a touch pad, and another input device which is obvious to those skilled in the art.

Meanwhile, the output part 310 (particularly, the video output part 312) and the input part 316 may be integrally formed with each other.

For example, the output part 310 and the input part 316 may be configured with a touchscreen which may display the information and, at the same time, may receive a touch input. The touchscreen may include a display for displaying the information and a touch panel for detecting the touch input, which are arranged to be layered with each other. Here, the touch panel may detect the touch input, and thus may detect at least one of a touched position, a touched area, and a touched strength of the touch input.

The touchscreen may display the information and may receive the touch input at the same time.

The medicine feeding port 320 may be a passage which receives the medicine from the medicine dispensing devices 100 and 200.

The control part 318 may control an entire operation of the medicine dispensing system 1 including the medicine gathering device 300 and/or the medicine dispensing devices 100 and 200, and other construction elements included therein. For example, the control part 318 serves to connect a variety of information, and to process the information to be usable.

The control part 318 may be configured with a computer or a similar device using software, hardware, or a combination thereof.

In the hardware, the control part 318 may be configured with at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and other electric devices which are obvious to those skilled in the art.

In the software, the control part 318 may be configured with a software code or a software application which is written by one or more program languages. The software may be stored in the memory part 308, and then may be executed by the hardware configuration of the control part 318. Also, for example, the software may be transmitted from an external device, for example, the server 2 to the medicine dispensing system 1 and then installed therein.

4. First Medicine Dispensing Device

FIG. 9 is a schematic perspective view of the first medicine dispensing device according to present invention.

Referring to FIG. 9, the first medicine dispensing device 100 according to the present invention may include a medicine dispensing container D100 which receives at least one medicine, a cartridge D200 which allows the medicine dispensing container D100 to be installed in the first medicine dispensing device 100, a medicine dispensing driving means D300 which allows the medicine received in the medicine dispensing container D100 to be dispensed, and a medicine dispensing driving means moving part D400 which moves the medicine dispensing driving means D300 between layers in the first medicine dispensing device 100.

In the first medicine dispensing device 100 according to the present invention, a plurality of medicine dispensing containers D100 may be installed at the cartridge D200, and the cartridge D200 may be provided at each layer of the first medicine dispensing device 100.

At least one cartridge D200 may be installed at each layer of the first medicine dispensing device 100. The number of the medicine dispensing containers D100 installed at one cartridge D200 may be variously changed according to intention of those skilled in the art.

Here, the first medicine dispensing device 100 rotates a dispensing part D110 of the medicine dispensing container D100, which receives at least one medicine, using the medicine dispensing driving means D300, and thus dispenses the medicine. The medicine dispensing container D100 may be removably inserted and installed into the cartridge D200.

The medicine dispensed to an outside by the medicine dispensing driving means D300 may be seated on a medicine conveying part D500. For example, the medicine conveying part D500 may be a construction element including a conveyor belt. Hereinafter, for convenience for explanation, the medicine conveying part D500 may be referred to as a conveyor part D500. The medicine seated on the conveyor part D500 may be moved by a belt rotational displacement of the conveyor part D500, and may be gathered in a predetermined external space.

The medicine conveying part D500 may horizontally transport the dispensed medicine, while a medicine dispensing operation is performed.

A speed of the dispensed medicine horizontally transported by the medicine conveying part D500 may be constant or may be variable.

Meanwhile, an interlayer movement of the medicine dispensing driving means D300 may be performed by the medicine dispensing driving means moving part D400. The medicine dispensing driving means moving part D400 may move the medicine dispensing driving means D300 to a layer, in which the medicine dispensing container D100 receiving the necessary packed medicine is disposed, according to an external signal (e.g., a control signal generated from the control part provided at the first medicine dispensing device 100, and/or a control signal generated from the control part provided at the medicine gathering device 300).

In other words, if a signal according a prescription for a patient is applied to the first medicine dispensing device 100, the medicine dispensing driving means moving part D400 moves the medicine dispensing driving means D300 to the desired layer according to the signal, and the dispensing part D110 of the medicine dispensing container D100 is rotated by the medicine dispensing driving means D300, and thus the necessary packed medicine may be dispensed from the medicine dispensing container D100.

The dispensed medicine may be seated on the conveyor part D500, and the conveyor part D500 on which the medicine is seated is moved to a position corresponding to a predetermined dispensing space by the medicine dispensing driving means moving part D400, and then the seated medicine may be gathered in the predetermined external space by the belt rotational displacement of the conveyor part D500. For example, the first medicine dispensing device 100 may have a medicine discharging port at a position corresponding to the medicine feeding port 320 of the medicine gathering device 300. The medicine dispensed from the medicine dispensing container D100 may be moved to the medicine discharging port and the medicine feeding port 320 by a driving of the conveyor part D500, and the moved medicine may be transmitted to the medicine gathering space through the medicine discharging port and the medicine feeding port 320.

However, the conveyor part D500 is not limited to a state in which the belt rotational displacement thereof is performed after the conveyor part D500 is moved to the position corresponding to the predetermined dispensing space. The belt rotational displacement thereof may be performed before the conveyor part D500 is moved to the position corresponding to the dispensing space.

Meanwhile, when the medicines according to the prescription for the patient are received in the plurality of medicine dispensing containers D100 disposed at each layer and the medicine dispensing containers D100 disposed at multiple layers, the medicine dispensing driving means D300 may be located at one certain layer by the medicine dispensing driving means moving part D400 and then may dispense the packed medicines from the plurality of medicine dispensing containers D100, in turn, or at the same time. When the dispensing at the one certain layer is completed, the medicine dispensing driving means D300 may be moved to another layer, and then may dispense again the medicines.

As described above, when the dispensing of the medicines from the plurality of medicine dispensing containers D100 according to the prescription for the patient is completed, the conveyor part D500 on which the plurality of medicines are seated is moved to the position corresponding to the predetermined dispensing space by the medicine dispensing driving means moving part D400, and the plurality of seated medicines may be gathered in the predetermined external space by the belt rotational displacement of the conveyor part D500.

4-1. Dispensing Principle of Medicine from Medicine Dispensing Container

FIGS. 10 and 11 are schematic views illustrating a principle of dispensing the medicine from the medicine dispensing container through the medicine dispensing driving means according to the present invention.

Referring to FIGS. 10 and 11, the dispensing of the medicine from the medicine dispensing container D100 may be performed by a rotation of the dispensing part D110 exposed to a front side of the medicine dispensing container D100, and the rotation of the dispensing part D110 may be performed by a position movement of a medicine dispensing unit U of the medicine dispensing driving means D300.

The medicine dispensing unit U may be one element included in the medicine dispensing driving means D300, and a plurality of medicine dispensing units U may be provided together and thus may form one medicine dispensing driving means D300. At this time, the medicine dispensing driving means D300 may include at least two medicine dispensing units U.

Hereinafter, assuming the medicine to be dispensed is received in one medicine dispensing container D100 located at a certain layer, the dispensing principle of the medicine will be described.

The medicine dispensing driving means D300 may be moved to a position corresponding to the medicine dispensing container D100, in which the medicine to be dispensed is received, by the medicine dispensing driving means moving part D400. When the movement is completed, a position moving part D10 (referring to FIG. 12) of one medicine dispensing unit U3 (hereinafter, called as "third medicine dispensing unit") of the plurality of medicine dispensing units U, which corresponds to the medicine dispensing container D100 in which the medicine to be dispensed is received, may be moved.

The position moving part D10 of the third medicine dispensing unit U3 may be moved to the medicine dispensing container D100 according to the external signal, and then a dispensing-part-rotating part D20 provided at the position moving part D10 is engaged with the dispensing part D110.

In this case, the dispensing-part-rotating part D20 is rotated, and the dispensing part D110 is interlocked and rotated by the rotation of the dispensing-part-rotating part D20.

The medicine received in the medicine dispensing container D100 may be dispensed to the conveyor part D500 by the rotation of the dispensing part D110, and the medicine seated on the conveyor part D500 may be gathered in the predetermined external space by the belt rotational displacement.

Here, the position moving part D10 of which a position is moved is not limited to the third medicine dispensing unit U3, and the detailed description thereof will be described later with reference to FIGS. 20 to 25.

4-2. Medicine Dispensing Unit

FIGS. 12 and 13 are schematic perspective views illustrating the medicine dispensing unit according to one embodiment of the present invention, FIG. 14 is a schematic exploded perspective view illustrating the medicine dispensing unit according to one embodiment of the present invention, FIG. 15 is a schematic perspective view illustrating a state in which the position moving part of the medicine dispensing unit according to one embodiment of the present invention is moved, and FIGS. 16 and 17 are schematic views illustrating a state in which a rotation supporting part of the medicine dispensing unit according to one embodiment of the present invention is rotated.

Referring to FIGS. 12 to 15, the medicine dispensing unit U may be one element included in the medicine dispensing driving means D300, and may include the position moving part D10 having the dispensing-part-rotating part D20 of which the position is moved to be in contact with the dispensing part D110 of the medicine dispensing container D100 and thus to allow the dispensing part D110 to be rotatable, a rotational force providing part D30 which generates a driving force to provide a rotational force to the dispensing-part-rotating part D20, and a position moving force providing part D40 which provides a driving force for the position movement of the position moving part.

Here, the rotational force providing part D30 and the position moving force providing part D40 may be disposed adjacent to the position moving part D10, and may be a kind of small motor which generates the rotational force.

Here, the position moving force providing part D40 may be driven by an external signal to generate the rotational force, and the rotational force may rotate a pinion gear D50.

The position movement of the position moving part D10 may be performed by a rotation of the pinion gear D50.

Specifically, the position moving part D10 may have a rack gear D11 which is linearly moved by the rotation of the pinion gear D50 so that the dispensing-part-rotating part D20 is in contact with the dispensing part D110 of the medicine dispensing container D100, and the rack gear D11 may be a kind of linear gear.

The rack gear D11 may be formed on a lower surface of the position moving part D10, and the rack gear D11 is linearly moved by the rotation of the pinion gear D50, and thus the position moving part D10 may be moved.

Here, the rotation of the pinion gear D50 may be performed by a worm gear D60, and the worm gear may include a worm D62 and a worm wheel D64.

In other words, the position moving force providing part D40 may include the worm gear D60 and the pinion gear D50, and a rotational direction thereof may be changed by the worm gear D60 including the worm D62 and the worm wheel D64.

A rotational direction of the worm 62 and a rotational direction of the worm wheel D64 may be different from each other, and the worm wheel D64 may be interlocked and rotated in the same direction as a rotational direction of the pinion gear D50. This is because the same rotating shaft is shared.

Finally, the rotational force generated by the position moving force providing part D40 rotates the worm D62, the worm wheel D64 is rotated by the rotation of the worm D62, and the pinion gear D50 is rotated by the rotation of the worm wheel D64.

The rotation of the pinion gear D50 may linearly move the rack gear D11 of the position moving part D11, and the dispensing-part-rotating part D20 may be in contact with the dispensing part D110 of the medicine dispensing container D100 by the linear movement of the position moving part D10.

Meanwhile, the position moving part D10 may include a rack gear part D12 having the rack gear D11, and a rotation supporting part D14 which is connected with the rack gear part D12 and rotatably supports the dispensing-part-rotating part D20.

The rotation supporting part D14 may be rotatably connected with the rack gear part D12, and thus transmission of the rotational force due to the contacting from the dispensing-part-rotating part D20 to the dispensing part D110 may be enhanced.

Referring to FIGS. 16 and 17, the dispensing-part-rotating part D20 and the dispensing part D110 may be formed as a kind of gear. The dispensing-part-rotating part D20 and the dispensing part D110 should be coupled so as to be engaged with each other when the dispensing part D110 is rotated by the rotation of the dispensing-part-rotating part D20.

Here, if the position moving part D10 is moved toward the medicine dispensing container D100 by the driving force of the position moving force providing part D40, there is a possibility in which teeth of the gear of the dispensing-part-rotating part D20 may collide with teeth of the gear of the dispensing part D110.

In this case, the dispensing-part-rotating part D20 and the dispensing part D110 should be engaged with each other by up and down movement of the dispensing-part-rotating part D20. In the present invention, they may be engaged with each other by a rotation of the rotation supporting part D14 from the rack gear part D12.

Meanwhile, the rotation of the rotation supporting part D14 from the rack gear part D12 may be performed within a limited range by a restoring member D70 provided at a rotating shaft thereof, and the rotation generated while the dispensing-part-rotating part D20 is engaged with the dispensing part D110 may be restored to its original position by the restoring member D70 when the dispensing-part-rotating part D20 rotates the dispensing part D110 to dispense the medicine and then is separated.

The rotation of the dispensing-part-rotating part D20 may be performed by the rotational force providing part D30 disposed adjacent to the position moving part D10, and the driving force of the rotational force providing part D30 may be transmitted to the dispensing-part-rotating part D20 by a rotational force interlocking part D32.

The rotational force interlocking part D32 which is one element of the rotation supporting part D14 may be a kind of gear. A rotational force of the rotational force interlocking part D32 may be transmitted to the dispensing-part-rotating part D20 by a rotational force transmitting part D34.

The rotational force transmitting part D34 may be one element of the rotation supporting part D14, which is disposed to be in contact with the rotational force interlocking part D32, and may be a kind of gear which may transmit the rotational force of the rotational force interlocking part D32 to the dispensing-part-rotating part D20.

The rotational force transmitting part D34 may include a first rotational force transmitting part D34a disposed to be in contact with the rotational force interlocking part D32, and a second rotational force transmitting part D34b disposed to be in contact with the first rotational force transmitting part D34a and the dispensing-part-rotating part D20.

Finally, the rotational force interlocking part D32, the rotational force transmitting part D34, and the dispensing-part-rotating part D20 are disposed to be engaged with each other, and the rotational force of the rotational force providing part D30 may be finally transmitted to the dispensing-part-rotating part D20.

However, the rotational force providing part D30 is not limited to a state in which the rotational force thereof is transmitted to the dispensing-part-rotating part D20 by the above-mentioned plurality of gears. The rotational force providing part D30 may directly rotate the dispensing-part-rotating part D20, and also the rotational force interlocking part D32 may be engaged with the dispensing-part-rotating part D20 without the rotational force transmitting part D34.

Further, the rotational force interlocking part D32, the rotational force transmitting part D34, and the dispensing-part-rotating part D20 are not limited to the gears, and may be belts, chains, or the like.

Meanwhile, the position movement of the position moving part D10 by the position moving force providing part D40 may be supported by a position movement supporting part D80, and the position movement supporting part D80 may be disposed at both sides of the position moving part D10.

The position movement supporting part D80 may be a kind of fixing structure from the point of view of the position moving part D10, which supports the displacement of the position moving part D10, and may include position fixing parts D82 and at least one supporting shaft D84.

The position fixing parts D82 may be a kind of separation preventing wall which prevents separation of the position moving part D10, and the supporting shaft D84 may be a connection shaft which connects the position fixing parts D82.

Here, the position moving part D10 may have a passing-through portion S which allows the supporting shaft D84 to pass through such that the supporting shaft D84 is disposed between the position fixing parts D82. The passing-through portion S may be continuously formed along a position movement direction of the position moving part D10.

The passing-through portion S may define a position movement range of the position moving part D11, and the position moving part D10 may be moved to the medicine dispensing container D100 in a state in which the supporting shaft D84 passes through the passing-through portion S.

Here, the displacement of the position moving part D10 may be guided by a guide part D86 coupled to the supporting shaft D84, and the guide part D86 may be one element of the position movement supporting part D80 which is in contact with a wall defining the passing-through portion S to guide the position movement of the position moving part D10.

The position moving part D10 may be slid in a state of being in contact with the guide part D86. However, the guide part D86 may be formed in a ball bearing shape, and the position movement may be guided by a rotation of the ball bearing.

Meanwhile, the medicine dispensing unit U according to one embodiment of the present invention may detect whether the position movement of the position moving part D10 is performed using a movement detecting part D90, and the movement detecting part D90 may be disposed at one side of the position moving part D10.

Here, the movement detecting part D90 may detect whether an extending part D95 of the position moving part D10, which is formed to extend toward the movement detecting part D90, is moved. At least two or more movement detecting parts D90 are provided within a moving range of the position moving part D10 to detect whether the extending part D95, i.e., the position moving part D10 is moved.

FIG. 18 is a schematic partially-exploded perspective view illustrating a medicine dispensing unit according to another embodiment of the present invention, and FIG. 19 is a schematic perspective view illustrating a state in which a position moving part of the medicine dispensing unit according to another embodiment of the present invention is moved.

Referring to FIGS. 18 and 19, the medicine dispensing unit U' according to another embodiment of the present invention, as illustrated in FIG. 18, has the same configuration and effect as the medicine dispensing unit U according to one embodiment of the present invention, as illustrated in FIGS. 12 to 17, except an arrangement relationship of a rotational force interlocking part D32', a rotational force transmitting part D34', and a dispensing-part-rotating part D20'. Therefore, the description thereof, except the arrangement relationship of the rotational force interlocking part D32', the rotational force transmitting part D34', and the dispensing-part-rotating part D20', will be omitted.

The rotational force transmitting part D34' may include a first rotational force transmitting part D34'a and a second rotational force transmitting part D34'b. The rotational force interlocking part (D32), the first rotational force transmitting part D34'a and the second rotational force transmitting part D34'b, and the dispensing-part-rotating part D20' may be arranged to entirely form a " ⌐ " shape.

This is because of a height of the medicine dispensing unit U' arranged in the first medicine dispensing device 100, and because a second medicine dispensing unit layer B is formed. This will be described below.

4-3. Medicine Dispensing Driving Means

FIG. 20 is a schematic perspective view illustrating the medicine dispensing driving means according to the present invention, and FIG. 21 is a schematic perspective view illustrating an operation state of the medicine dispensing driving means according to the present invention.

Further, FIG. 22 is a schematic perspective view illustrating another operation state of the medicine dispensing driving means according to the present invention.

Referring to FIG. 20, the medicine dispensing driving means D300 may have at least one layer, may be installed at the first medicine dispensing device 100 in which the plurality of medicine dispensing containers D100 receiving the medicine are installed at the layer, and may be a kind of medicine dispensing structure which rotates the dispensing part D110 of the medicine dispensing container D100 and dispenses at least one medicine.

Specifically, the medicine dispensing driving means D300 may include first to N-th medicine dispensing units which are disposed to correspond to the medicine dispensing containers installed at the one layer, and the first to N-th medicine dispensing units may rotate the dispensing part D110 of the corresponding medicine dispensing container D100 receiving the necessary medicine to dispense the necessary medicine (N is a natural number).

Further, when the necessary medicines to be dispensed are received in the plurality of medicine dispensing containers D100, the first to N-th medicine dispensing units may rotate the dispensing parts D110 of the plurality of medicine dispensing containers D100 receiving the necessary medicines, in turn, or at the same time to dispense the necessary medicines from the plurality of medicine dispensing containers D100.

In the one layer, when the number of medicine dispensing units U provided at the medicine dispensing driving means D300 is smaller than that of medicine dispensing containers D100 provided at the medicine dispensing driving means D300, from which the medicines should be dispensed (for example, in the one layer, when the number of medicine dispensing containers D100 from which the medicines should be dispensed is 3, and the number of medicine dispensing units U provided at the medicine dispensing driving means D300 is 2), the medicines may be dispensed according to medicine dispensing order assigned to the medicine dispensing containers D100, while the positions of the medicine dispensing units U are moved left and right to dispense the medicines in turn.

Therefore, the medicine dispensing driving means D300 according to the present invention may precisely dispense the necessary medicine according to the prescription for the patient, and also may enhance medicine dispensing efficiency.

Meanwhile, part of the first to N-th medicine dispensing units may be disposed to have the same height to form a first medicine dispensing unit layer A, and the rest of them may be disposed at one side of the first medicine dispensing unit layer A to have the same height and thus to form a second medicine dispensing unit layer B.

Here, the dispensing-part-rotating parts of the medicine dispensing units forming the second medicine dispensing unit layer B may be formed to have the same height as those of the medicine dispensing units forming the first medicine dispensing unit layer A.

This may be embodied by arranging the rotational force interlocking part D32', the first rotational force transmitting part D34'a, the second rotational force transmitting part D34'b, and the dispensing-part-rotating part D20', which form the second medicine dispensing unit layer B, to entirely form a " ⌐ " shape (referring to FIGS. 18 and 19).

The first and second medicine dispensing unit layers A and B disposed to have the different heights from each other are to correspond to various widths of the medicine dispensing container D100. When the medicine is dispensed from the medicine dispensing container D100 having a relatively large width, the medicine dispensing unit forming the first medicine dispensing unit layer A and the medicine dispensing unit forming the second medicine dispensing unit layer B may be applied at the same time.

However, when the medicine is dispensed from the medicine dispensing container D100 having a relatively small width, only the medicine dispensing unit forming the first medicine dispensing unit layer A may dispense the medicines.

In other words, as illustrated in the drawing, the medicine dispensing unit corresponding to the case in which the medicine dispensing container D100 has the relatively small width may be the medicine dispensing unit included in the first medicine dispensing unit layer A.

Hereinafter, as an example, when the N is 12 and the medicine dispensing containers D100 are relatively small, and when the medicines received in the medicine dispensing containers D100 respectively corresponding to a third medicine dispensing unit U3 and a sixth medicine dispensing unit U6 by the medicine dispensing driving means D300 according to the present invention are dispensed, the operation state thereof will be described.

Referring to FIG. 21, the medicine dispensing driving means D300 may be moved to positions corresponding to the medicine dispensing containers D100 receiving the necessary medicines by the medicine dispensing driving means moving part D400. When the movement is completed, the position moving force providing parts D40 of the third and sixth medicine dispensing units U3 and U6 may be driven by the external signal.

The position moving part D10 of the third medicine dispensing unit U3 and the position moving part D10 of the sixth medicine dispensing unit U6 may be respectively moved to the corresponding medicine dispensing containers D100 by the driving force from the position moving force providing parts D40 of the third and sixth medicine dispensing units U3 and U6, and the dispensing-part-rotating parts D20 may be respectively engaged with the dispensing parts D110 of the medicine dispensing containers D100.

Here, when the teeth of the gear of the dispensing-part-rotating part D20 collide with the teeth of the gear of the dispensing part D110, the engagement may be ensured by the rotation of the rotation supporting part D14 from the rack gear part D12 (referring to FIGS. 16 and 17).

Then, the rotational force providing part D30 of the third medicine dispensing unit U3 and the rotational force providing part D30 of the sixth medicine dispensing unit U6 generate the driving force to rotate each of the dispensing-part-rotating part D20, and thus the corresponding dispensing parts D110 of the medicine dispensing containers D100 are rotated, and the necessary medicines may be dispensed to the conveyor part D500.

However, referring to FIG. 22, the driving of the rotational force providing part D30, which generates the driving force, is not limited to the third and sixth medicine dispensing units U3 and U6, and the rotational force providing part D30 of at least one of the medicine dispensing units U1, U2, U4, U5, and U7 to U12 other than the third and sixth medicine dispensing units U3 and U6 may be driven.

When the dispensing of the necessary medicines is completed, the rotational force providing parts D30 of the third and sixth medicine dispensing units U3 and U6 stop their rotations and thus the driving force, and each of the position moving parts D10 may be returned to its original position by the driving force from the position moving force providing parts D40 of the third and sixth medicine dispensing units U3 and U6.

Here, the position movement direction of the third and sixth medicine dispensing units U3 and U6 by the position moving force providing parts D40 may be determined by a change of a rotational direction of the position moving force providing parts D40.

As described above, when two or more necessary medicines are received in the same layer, the corresponding position moving parts D10 are respectively moved, and the medicines may be dispensed at the same time by the driving force of the corresponding rotational force providing parts D30.

However, the movement of the position moving parts D10 and the generation of the driving force of the rotational force providing parts D30 do not have to be performed at the same time, and may be performed in turn.

FIG. 23 is a schematic perspective view illustrating still another operation state of the medicine dispensing driving means according to the present invention.

Referring to FIG. 23, the medicine dispensing driving means D300 may be moved to the position corresponding to the medicine dispensing container D100 receiving the necessary medicine by the medicine dispensing driving means moving part D400, and when the movement is completed, the position moving force providing part D40 of at least one of the medicine dispensing units U1, U2, U4, U5, and U7 to U12 other than the third and sixth medicine dispensing units U3 and U6, as well as the position moving force providing parts D40 of the third and sixth medicine dispensing units U3 and U6 may be driven by the external signal.

Hereinafter, for example, a case in which the position moving force providing parts D40 of the first to ninth medicine dispensing units U1 to U9 are driven will be described.

The position moving parts D10 of the first to ninth medicine dispensing units U1 to U9 may be respectively moved to the corresponding medicine dispensing containers D100 by the driving force from the position moving force providing parts D40 of the first to ninth medicine dispensing units U1 to U9, and the dispensing-part-rotating parts D20 may be respectively engaged with the dispensing parts D110 of the medicine dispensing containers D100.

Then, the rotational force providing parts D30 of the third and sixth medicine dispensing units U3 and U6 generate the driving force to rotate each of the dispensing-part-rotating parts D20, and thus the dispensing parts D110 of the corresponding medicine dispensing containers D100 are rotated so that the necessary medicines are dispensed on the conveyor part D500.

That is, all of the moved dispensing-part-rotating parts D20 are respectively engaged with the corresponding dispensing parts D110. However, since the dispensing-part-rotating parts D20 to be rotated are limited to those of the third and sixth medicine dispensing units U3 and U6, the dispensing parts D110 to be rotated may be also limited thereto.

When the dispensing of the necessary medicines is completed, the rotational force providing parts D30 of the third and sixth medicine dispensing units U3 and U6 stop their rotations and thus the driving force, and each of the position moving parts D10 may be returned to its original position by the driving force from the position moving force providing parts D40 of the first to ninth medicine dispensing units U1 to U9.

The generation of the driving force of the rotational force providing parts D30 in the third and sixth medicine dispensing units U3 and U6 does not have to be performed at the same time, and may be performed in turn.

FIG. 24 is a schematic perspective view illustrating a state in which the medicine dispensing driving means according to the present invention may be applied to the medicine dispensing containers of various sizes, and FIG. 25 is a schematic perspective view illustrating an operation state in the case of FIG. 24.

Referring to FIGS. 24 and 25, the medicine dispensing driving means D300 may include the first medicine dispensing unit layer A and the second medicine dispensing unit layer B. The dispensing-part-rotating parts of the medicine dispensing units forming the second medicine dispensing unit layer B may be formed to have the same height as those of the medicine dispensing units forming the first medicine dispensing unit layer A.

Here, as described above, when the medicine dispensing unit corresponding to the medicine dispensing container D100 having a relatively large width may be included in all of the first medicine dispensing unit layer A and the second medicine dispensing unit layer B.

Specifically, the medicine dispensing unit corresponding to the medicine dispensing container D100 having a relatively large width may be the first medicine dispensing unit U1, the tenth medicine dispensing unit U10, the fourth medicine dispensing unit U4, the eleventh medicine dispensing unit U11, the seventh medicine dispensing unit U7, and the twelfth medicine dispensing unit U12.

Therefore, the medicine dispensing driving means D300 according to the present invention may be applied to all of the medicine dispensing containers D100 having various widths due to the first medicine dispensing unit layer A and the second medicine dispensing unit layer B.

Meanwhile, a process of dispensing the medicine from the medicine dispensing container D100 may be the same as that described with reference to FIGS. 20 to 23.

4-4. Structure of Medicine Conveying Part (Conveyor Part)

The medicine conveying part according to one embodiment will be described with reference to FIGS. 26 and 27. FIG. 26 is a perspective view illustrating a partially cutaway state of the medicine conveying part according to one embodiment of the present invention, and FIG. 27 is a perspective view illustrating the medicine conveying part according to one embodiment of the present invention.

The medicine conveying part D500 (the conveyor part) is an element on which the dispensed medicine is seated. The medicine conveying part D500 includes a conveyor belt CB11, one pair of track shafts CB12a and CB12b, one pair of path conversion rolls CB13a and CB13b, and a driving roll CB14.

The conveyor belt CB11 is rotated along a track. The dispensed medicine is seated on the conveyor belt CB11. Further, the one pair of track shafts CB12a and CB12b serve as both shafts of the track in which the conveyor belt CB11 is rotated. That is, the conveyor belt CB11 is rotated along the track via outer circumferential surfaces of the one pair of track shafts CB12a and CB12b.

Meanwhile, as illustrated in FIG. 26, the conveyor belt CB11 may be rotated via the one pair of path conversion rolls CB13a and CB13b and the driving roll CB14. The driving roll CB14 is connected with a motor CB15 and a timing belt CB16 to be rotated, and thus transmits a driving force which rotates the conveyor belt CB11. At this time, the one pair of path conversion rolls CB13a and CB13b is provided to be in contact with an outer circumferential surface of the conveyor belt CB11, and the driving roll CB14 is provided to be in contact with an inner circumferential surface of the conveyor belt CB11. Further, the driving roll CB14 is disposed between the one pair of path conversion rolls CB13a and CB13b, and also provided at a position lower than the one pair of path conversion rolls CB13a and CB13b, i.e., at an outer side of the one pair of path conversion rolls CB13a and CB13b based on the conveyor belt CB11. A support plate CB171 is provided under an upper surface of the conveyor belt CB11. The support plate CB171 supports the upper surface of the conveyor belt CB11 and receives an falling impact of the medicine through the upper surface of the conveyor belt CB11, when the medicine is dispensed. Further, as illustrated in FIG. 27, the medicine conveying part D500 according to the embodiment includes a side member CB172. The support plate CB171 is fixed to the side member CB172.

A side guide part according to one embodiment will be described with reference to FIGS. 28 and 29. FIG. 28 is a perspective view illustrating a shape of the medicine conveying part with the side guide part according to one embodiment of the present invention, and FIG. 29 is a side view illustrating the shape of the medicine conveying part of FIG. 28.

As illustrated in FIG. 28, at least one side guide part CB30 which is provided to have a predetermined height and thus to prevent the medicine from being separated to an outer side, when the medicine is seated, may be provided at a side surface of the medicine conveying part.

Specifically, as illustrated in FIG. 29, the side guide part CB30 may include a fixing part CB33, a first inclined part CB32a, CB32b, and a height reinforcing part CB31. The fixing part CB33 is an element which fixes the side guide parts CB30a and CB30b to the side member CB172. The first inclined part CB32a, CB32b is formed upwardly to be inclined toward an outer side. The first inclined part CB32a, CB32b serves to expand an area in which the dispensed medicine may be seated, and also to minimize the falling impact when medicine is fallen. The height reinforcing part CB31 serves to secure a height of the side guide part CB30 and thus to prevent the dispensed medicine from being bounced and separated to the outer side.

A side guide part according to another embodiment will be described with reference to FIGS. 30 and 31. FIG. 30 is a perspective view illustrating a shape of the medicine conveying part with the side guide part according to another embodiment of the present invention, and FIG. 31 is a side view illustrating the shape of the medicine conveying part of FIG. 30.

As illustrated in FIGS. 30 and 31, the side guide part CB30 may have a buffer member CB35 provided at an inner surface thereof to absorb the impact generated by collision of the dispensed medicine. As illustrated in FIG. 31, the buffer member CB35 is provided at inner sides of the side guide parts CB30a and CB30b and formed of a material which may absorb the impact. In particular, the buffer member CB35 is preferably provided at at least the side guide part CB30a opposite to a direction CBD1 of the medicine dispensing container.

A side guide part according to still another embodiment will be described with reference to FIGS. 32 and 33. FIG. 32 is a perspective view illustrating a shape of the medicine conveying part with the side guide part according to still another embodiment of the present invention, and FIG. 33 is a side view illustrating the shape of the medicine conveying part of FIG. 32.

As illustrated in FIGS. 32 and 33, a side guide part CB30a' opposite to a direction CBD1 of the medicine dispensing container D100 may have a second inclined part CB34 which is inclined in a direction same to an inclined direction of the first inclined part CB32a, CB32b. The second inclined part CB34 is formed to be inclined toward an inner side, and thus to more actively prevent the falling medicine from being bounced and separated to the outer side, when the medicine is dispensed.

4-5. Structure of Cartridge

The cartridge according to one embodiment will be described with reference to FIGS. 34 to 36. FIG. 34 is a perspective view illustrating a shape of the cartridge according to one embodiment of the present invention, and FIGS. 35 and 36 are perspective views illustrating a configuration and an operation state of a fixing part according to one embodiment.

The cartridge D200 includes a cartridge housing having a lower housing CR40 and a rear housing CR50. As described below, when the medicine dispensing container to be connected enters, the lower housing CR40 supports the medicine dispensing container, and the rear housing CR50 restricts the medicine dispensing container from entering over a predetermined distance. A rail CR41 is provided along an entering course of the medicine dispensing container D100, which will be described later, on the lower housing CR40. The rail CR41 serves to guide the entering of the medicine dispensing container D100 along the entering course. The rail CR41 is formed to have a predetermined length and to protrude upwardly. Further, two or more rails CR41 may protrude so as to be parallel with each other.

A first data transmitting and receiving terminal CR51 may be provided at the rear housing CR50. The first data transmitting and receiving terminal CR51 is connected with the medicine dispensing container to transmit and receive data to/from a control means provided in the medicine dispensing container. As an example, the medicine dispensing device may receive UUID or the like of the medicine dispensing container through the first data transmitting and receiving terminal CR51, and thus may obtain information of the kind and the number of the medicines stored in the corresponding medicine dispensing container.

In the embodiment, the first data transmitting and receiving terminal CR51 is formed to protrude from the rear housing CR50 to a front surface and thus to have a step difference, and a plurality of connector pins which are electrically connected with the medicine dispensing container are provided at a lower end thereof.

A separation promoting part CR42 is provided at the lower housing CR40. The separation promoting part CR42 serves to exert a force to the medicine dispensing container D100 in a separation direction, when the medicine dispensing container is separated. Specifically, the separation promoting part CR42 includes a first protruding part CR421 and a first elastic member CR422. The first protruding part CR421 protrudes above the lower housing CR40 and is exposed to an outer side. The first elastic member CR422 is pressed while the medicine dispensing container D100 is connected, and then provides a restoring force due to an elastic force thereof to the medicine dispensing container D100, when the medicine dispensing container D100 is separated.

Further, a locking part CR52 which fixes or separably releases the medicine dispensing container D100 is provided at the rear housing CR50. As illustrated in FIG. 35, the locking part CR52 includes a cam CR523, a locking part body CR522, a hooking part CR521, an extending part CR524, a to-be-detected part CR525, and a detecting part CR526.

The cam CR523 is rotated about a predetermined axis, and has a long radius portion and a short radius portion which may be divided with respect to the axis as a rotational center. The locking part body CR522 forms a body of the locking part, and as illustrated in FIGS. 35 and 36, is provided to be in contact with an outer circumferential surface of the cam CR523. Thus, according to a rotation of the cam CR523, the locking part body CR522 is operated to be moved up when being in contact with the long radius portion, and moved down when being in contact with the short radius portion. The hooking part CR521 is formed to extend from a front surface of the locking part body CR522 and to be move up and down together according to the up and down movement of the locking part body CR522. Meanwhile, the locking part CR52 further includes the extending part CR524 which is formed to extend upwardly from an upper end of the locking part body CR522, and the detecting part CR526 is provided to be adjacent to the extending part CR524. The detecting part CR526 may be a sensor having a light receiving part and a light emitting part, for example, an infrared sensor. The to-be-detected part CR525 is formed to extend from one side of the extending part CR524. The to-be-detected part CR525 is provided to be moved up and down between the light receiving part and the light emitting part of the detecting part CR526, and determines whether the locking part CR52 is moved up or down, i.e., whether the locking part CR52 is in a fixing position or a releasing position.

The medicine dispensing container according to one embodiment will be described with reference to FIGS. 37 to 39. FIG. 37 is a perspective view illustrating a shape of the medicine dispensing container according to one embodiment, FIG. 38 is a front side bottom perspective view illustrating the shape of the medicine dispensing container of FIG. 37, and FIG. 39 is a rear side bottom perspective view illustrating the shape of the medicine dispensing container of FIG. 37.

The medicine dispensing container D100 includes a dispensing container housing CR61. Specifically, the dispensing container housing CR61 includes a housing body CR611 and a front part CR612. The front part CR612 has a discharging port CR613, and a gear CR621 is provided to be exposed to an outer side. For example, the gear CR621 may be the same element as the dispensing part D110 (referring to FIGS. 16 and 17) of the medicine dispensing container D100.

As illustrated in FIG. 38, a rail receiving part CR64 is formed in a lower surface of the housing body CR611. The rail is inserted into the rail receiving part CR64 to be guided along the entering course. The rail receiving part CR64 is formed to a rear surface of the housing body CR611. Further, when the medicine dispensing container is connected with the cartridge, the rail is received in the rail receiving part CR64 from a rear surface side, and then gradually received along the rail receiving part CR64 toward a front surface side. At this time, the rail receiving part CR64 may have a starting portion CR64a formed at the rear surface side of the dispensing container housing CR61. The starting portion CR64a is a part of the rail receiving part CR64, and is formed so that a width thereof is gradually increased toward the rear surface side. Since the width of starting portion CR64a in which the rail is received is expanded, the rail may be easily received. The starting portion CR64a may be formed to have various lengths. That is, the entire rail receiving part CR64 may be formed so that a width thereof is gradually increased toward the rear surface side.

Meanwhile, a separation promoting part receiving groove CR65 which receives the separation promoting part is formed in the lower surface of the housing body CR611. As described above, the separation promoting part is pressed while received in the separation promoting part receiving groove CR65, when the medicine dispensing container is connected to the cartridge, or exerts the force due to the elastic force thereof to the housing body CR611 in the separation direction.

A data terminal part CR66, CR67 may be provided at a rear surface of the housing body CR611. Specifically, the data terminal part includes a terminal receiving groove CR66 and a second data transmitting and receiving terminal CR67. The terminal receiving groove CR66 receives the data transmitting and receiving terminal of the cartridge, and the second data transmitting and receiving terminal CR67 is electrically connected with the data transmitting and receiving terminal of the cartridge.

Further, a catching part CR68 is formed at the rear surface of the housing body CR611. The catching part CR68 is formed in a stepped groove shape in which the hooking part of the locking part of the cartridge may be hooked.

A power cut-off part of the medicine dispensing container according to one embodiment will be described with reference to FIGS. 40 to 43. FIG. 40 is a rear side bottom perspective view illustrating the medicine dispensing container of FIG. 37, when seen from another angle, and FIGS. 41 to 43 are cut-away perspective views illustrating the shape of the medicine dispensing container of FIG. 37.

Meanwhile, a rotating part CR691 is exposed at a front surface side of the rail receiving part CR64 formed in the lower surface of the housing body CR611. As illustrated in FIGS. 40 and 41, the rotating part CR691 is one element of the power cut-off part which is pressed by the rail when the rail is received. As described above, the medicine dispensing container D100 has at least one gear which receives the power from the outer side. The power cut-off part is a mechanical element which controls the gears to be restricted and thus not to be rotated, or to be released.

Specifically, as illustrated in FIG. 42, the power cut-off part includes the rotating part CR691 and a cut-off part body CR692. The rotating part CR691 includes a first end CR6911, a rotating shaft CR6912, and a second end CR6913. The first end CR6911 is rotated about the rotating shaft CR6912, and the second end CR6913 is provided at another side of the first end CR6911 with respect to the rotating shaft CR6912 to be rotated in the same direction as a rotational direction of the first end CR6911.

The cut-off part body CR692 includes a contacting part CR6921, a first extending part CR6922, a second extending part CR6923, and a second protruding part CR6924. The contacting part CR6921 is provided to be in contact with the second end CR6913. The first extending part CR6922 is formed to extend from the contacting part CR6921 toward a gear CR622 side, and the second extending part CR6923 is formed to extend upwardly from an end of the gear CR622 side. The second protruding part CR6924 protruding toward the gear CR622 side is formed at an end of the second extending part CR6923. The second protruding part CR6924 is inserted between teeth of the gear CR622 to restrict a rotation of the gear CR622, or separated from between the teeth of the gear CR622 and released so that the gear CR622 may be rotated. Meanwhile, a second elastic member CR693 may be provided to be in contact with the second extending part CR6923. The second elastic member CR693 serves to push the second extending part CR6923 toward the gear CR622 using an elastic force thereof.

Referring to FIG. 43, when the first end CR6911 is pushed by the rail and rotated in a direction CRD2 toward the gear CR622, the second end CR6913 is rotated in an opposite direction CRD3 to the gear CR622. At this time, the contacting part CR6921 is pushed back in the opposite direction CRD3 to the gear CR622 by the second end CR6913, and the second protruding part CR6924 connected with the contacting part CR6921 via the first and second connecting parts CR6922 and CR6923 is also pushed back in the opposite direction CRD3 to the gear CR622 and thus separated from between the teeth of the gear CR622. In this state, the gear CR622 is released to be rotatable.

A connection state between the medicine dispensing container and the cartridge according to one embodiment will be described with respect to FIGS. 44 to 46. FIG. 44 is a perspective view illustrating the connection state between the medicine dispensing container and the cartridge according to one embodiment, and FIGS. 45 and 46 are schematic views illustrating the connection state between the medicine dispensing container and the cartridge according to one embodiment.

As illustrated in FIG. 44, the medicine dispensing container D100 enters along the rail C41 provided on the lower housing CR40 of the cartridge D200, and is coupled to the cartridge D200. At this time, as described above, the separation promoting part CR42, the first transmitting and receiving terminal CR51, and the locking part C52 are respectively inserted into the corresponding construction parts of the medicine dispensing container D100.

Specifically, when the medicine dispensing container D100 is coupled, the rail CR41 is received in the rail receiving part CR64, and the hooking part CR521 is inserted and caught into the catching part CR68 formed in the rear surface of the medicine dispensing container D100. Further, the first data transmitting and receiving terminal CR51 is received in the data terminal part CR66 and electrically connected with the medicine dispensing container D100. At this time, the short radius portion of the cam CR523 is in contact with the locking part body CR522.

Further, when the medicine dispensing container D100 is separated, the long radius portion of the cam CR523 is in contact with the locking part body CR522, and thus the hooking part CR521 is moved up. If the hooking part CR521 is moved up, the hooking part CR521 is released from the catching part CR68 formed in the rear surface of the medicine dispensing container D100, and thus medicine dispensing container D100 may be separable. When the medicine dispensing container D100 is separated, the rail CR41 is gradually separated from the rail receiving groove CR64, and the first data transmitting and receiving terminal CR51 is also separated from the data terminal part CR66.

Hereinafter, various types of medicine dispensing containers D100 which may be installed at the first medicine dispensing device 100 will be described. Here, a packaging type medicine dispensing container BOX1, a blister-packed medicine dispensing container BOX2, an ampoule type medicine dispensing container BOX3 and a pouch type medicine dispensing container BOX4, which will be described, may include the structure of the dispensing part D110 which allows the medicine to be dispensed by the driving of the medicine dispensing driving means D300, the coupling structure which is coupled to the cartridge D200, and the like. However, hereinafter, for convenience of explanation, the detailed description thereof will be omitted.

4-6. Medicine Dispensing Container #1—Packaging Type Medicine Dispensing Container The packaging type medicine dispensing container according to the present invention is a device for dispensing the medicine which is stored in a package type. The packaging type medicine dispensing container according to one embodiment of the present invention includes a storage part, a conveying part, a cutting part, a light source part, and a scanning part. Hereinafter, each element will be described in detail with reference to the drawings.

A housing forming an exterior will be described with reference to FIGS. 47 and 48. FIG. 47 is a perspective view illustrating a shape of the packaging type medicine dispensing container according to one embodiment of the present invention, and FIG. 48 is a bottom perspective view illustrating the shape of the packaging type medicine dispensing container according to one embodiment.

The housing forming an exterior of the packaging type medicine dispensing container BOX1 includes a housing body B1130, a front end B1110, and a housing cover B1120. The housing body B1130 is entirely formed in a rectangular parallelepiped shape. The housing cover B1120 is provided at an upper end of the housing body B1130. One side of the housing cover B1120 is rotatably fixed so as to be opened and closed. A discharging port B1112 through which a cut medicine package is discharged is formed at the front end B1110. The discharging port B1112 is provided to pass through a front end cover B1111 and thus to be exposed to an outer side. Meanwhile, a sensor (not shown) which detects the discharged medicine package may be provided at the discharging port B1112. In this case, a counting means for counting the number of medicine packages detected by the sensor may be provided so as to count the number of discharged medicine packages.

As illustrated in FIG. 48, a rail receiving part B1140 is provided in a lower end of the housing body B1130. The rail receiving part B1140 serves to receive the rail formed at the cartridge D200 in which the packaging type medicine dispensing container BOX1 according to the embodiment is received, and thus to guide an insertion of the packaging type medicine dispensing container.

The front end and the cutting part of the housing will be described with reference to FIG. 49. FIG. 49 is a partially cut-away exploded perspective view illustrating the shape of the packaging type medicine dispensing container according to one embodiment.

The front end B1110 of the housing includes a front end body B1115 and the front end cover B1111. A first medicine package moving port B1116 connected with and in communication with the discharging port B1112 is formed in the front end body B1115. A cutting part B1200 is provided at an inner side of the front end body B1115. The cutting part B1200 has a second medicine package moving port B1210 so as to cut a medicine package moved through the second medicine package moving port B1210. The second medicine package moving port B1210 is connected with and in communication with the first medicine package moving port B1116 of the front end body B1115 and the discharging port B1112 of the front end cover B1111.

A conveying part, a storage part, and a light source part will be described with reference to FIGS. 50 and 51. FIG. 50 is a cross-sectional view illustrating the shape of the packaging type medicine dispensing container according to one embodiment, and FIG. 51 is a partially cut-away perspective view of the packaging type medicine dispensing container according to one embodiment.

A storage part B1300 is formed in a wheel shape in which a medicine package B12 is stored in a wound state. The storage part B1300 includes a winding core B1320 and a side case B1310. The medicine package B12 is wound on the winding core B1320 and unrolled by a conveying part B1400. The side case B1310 serves to prevent the medicine package B12 from being deviated through a side surface, when the medicine package B12 is wound on or unrolled from the winding core B1320. Meanwhile, the storage part B1300 may be formed to have only a space part which may simply store the medicine package. That is, only the simple space may be formed without the construction element such as the wheel, and the medicine package may be simply folded in the space part.

The conveying part B1400 includes one pair of first rolls B1410, one pair of second rolls B1420, and a discharging roll B1430. The one pair of first rolls B1410 includes a first upper roll B1411 and a first lower roll B1412. The first upper roll B1411 is located above the first lower roll B1412 to be in contact with the first lower roll B1412. Outer circumferential surfaces of the first upper roll B1411 and the first lower roll B1412 may be formed of an elastic material, particularly, a porous material. Since the outer circumferential surfaces of the first upper roll B1411 and the first lower roll B1412 are formed of the elastic material, a pressing force applied to the medicines in the medicine package located therebetween may be minimized. In the embodiment, the first lower roll B1412 is driven by a motor, preferably, a step motor, and the first upper roll B1411 is passively rotated according to a rotational direction of the first lower roll B1412. The one pair of first rolls B1410 guides the medicine package B12 toward the discharging roll B1430, when a distal front end of the medicine package B12 is initially positioned.

The one pair of second rolls B1420 conveys the front end of the medicine package B12 transferred from the one pair of first rolls B1410 toward the discharging roll B1430. The one pair of second rolls B1420 includes a second upper roll B1421 and a second lower roll B1422. The second upper roll B1421 is located above the second lower roll B1422 to be in contact with the second lower roll B1422. Outer circumferential surfaces of the second upper roll B1421 and the second lower roll B1422 may be formed of an elastic material, particularly, a porous material. Since the outer circumferential surfaces of the second upper roll B1421 and the second lower roll B1422 are formed of the elastic material, a pressing force applied to the medicines in the medicine package located therebetween may be minimized. In the embodiment, the second lower roll B1422 is driven by a motor, preferably, a step motor, and the second upper roll B1421 is passively rotated according to a rotational direction of the second lower roll B1422. The one pair of second rolls B1420 guides the distal front end of the medicine package B12 toward the discharging roll B1430.

Meanwhile, the first lower roll B1412 and the second lower roll B1422 are preferably driven by independent driving motors. When the medicine package B12 disposed between the first lower roll B1412 and the second lower roll B1422 is folded or loosed, it may not be easy to detect a perforated line of the medicine package B12. In this case, one of the first lower roll B1412 and the second lower roll B1422 is driven in a direction which generates tension, and an error which may occur when detecting the perforated line may be minimized. At this time, each roll is driven using the step motor, and thus the tension may be precisely applied.

Meanwhile, the first upper roll B1411 and the second upper roll B1421 are connected with each other through an elastic member B1403. Since the first upper roll B1411 and the second upper roll B1421 are fixed by the elastic member B1403, a predetermined operating range may be provided in a vertical direction, and the first upper roll B1411 and the second upper roll B1421 may be lifted up by a user, when an initial setting operation is performed or when an error occurs. Even when the medicine package B12 is conveyed in a state of being interposed between the first and second rolls B1410 and B1420, the force applied to the medicines in the medicine package may be minimized.

The discharging roll B1430 may be provided at a distal end of a conveying direction. The discharging roll B1430 serves to discharge the medicine package B12 conveyed from the one pair of second rolls B1420 to an outer side. The discharging roll B1430 is connected with the second upper roll B1421 using a timing belt to receive a driving force.

As illustrated in FIG. 51, a supporting part B1150 which supports the medicine package conveyed via the first and second lower rolls B1412 and B1422 is further provided. The medicine package is conveyed in a state of being supported by a conveying plate B1151 formed in a flat plate shape at an upper end of the supporting part B1150. At this time, the first lower roll B1412 and the second lower roll B1422 are provided to be exposed to the conveying plate B1151. A light transmission member B1152 serves to transmit light emitted from a light source part B1500 which is disposed under the light transmission member B1152. The light source part B1500 emits the light using a light emitting device B1510. The light emitted from the light source part B1500 is used as illumination light, when taking a photograph of the medicine package using the scanning part to be described later. Meanwhile, the light source part B1500 may provide the illumination light in an indirect lighting manner. In the embodiment, the light transmission member B1152 is used in the indirect lighting manner. The light transmission member B1152 may serve to scatter or diffuse the light emitted from the light source part B1500, to uniformalize an illumination distribution, and also to prevent the light from being concentrated to other elements. Meanwhile, unlike the embodiment, the light source part B1500 may be provided so that the light emitting device B1510 is directed downwardly and thus reflected light may be directed upwardly. In the embodiment, the light source part B1500 is provided at an opposite side to the scanning part to be described below based on the medicine package.

The scanning part and a light shielding part will be described with reference to FIGS. 52 to 56. FIG. 52 is an exploded perspective view of the packaging type medicine dispensing container according to one embodiment, FIG. 53 is another exploded perspective view of the packaging type medicine dispensing container according to one embodiment, FIG. 54 is a bottom perspective view illustrating a shape of the light shielding part according to one embodiment, and FIGS. 55 and 56 are schematic views illustrating an operation state of the scanning part according to one embodiment.

As illustrated in FIG. 52, the light shielding part B1160 is included. As illustrated in FIG. 53, the light shielding part B1160 includes a light shielding part upper case B1160a and a light shielding part lower case B1160b. The upper case B1160a and the lower case B1160b of the light shielding part B1160 define a predetermined space in which the scanning part may be provided. As illustrated in FIG. 54, a scanning window B1161 is formed at the light shielding part lower case B1160b. The scanning part to be described later may take a photograph of the medicine package located under the scanning window B1161 through the scanning window B1161. At this time, the light shielding part B1160 prevents other optical noise from being introduced into a corresponding image. Further, a light absorbing layer (not shown) which minimizes reflection of the light may be provided at an inner side of the light shielding part B1160. At this time, a matte black coating layer may be used as the light absorbing layer. Further, the upper construction elements of the conveying part B1400, such as the first upper roll, may be exposed to the light shielding part lower case B1160b.

The scanning part B1600 is located above the light transmission member B1152, and takes a series of images of the medicine package B12 which is unrolled from the storage part B1300 and conveyed on the light transmission member B1152, as illustrated in FIGS. 55 and 56. At this time, preferably, the scanning part B1600 takes the images with a bonded portion of the medicine package B12, which is formed when the medicine package B12 is sealed, in the center.

A method of detecting the perforated line of the medicine package according to one embodiment will be described with reference to FIGS. 57 to 61. FIG. 57 is a block diagram illustrating construction elements related to detection of the perforated line of the medicine package according to one embodiment, FIG. 58 is schematic view schematically illustrating the medicine package. Further, FIG. 59 is a flowchart illustrating the method of detecting the perforated line according to one embodiment, FIG. 60 is a flowchart illustrating an image processing process according to one embodiment, and FIG. 61 is a flowchart illustrating a perforated line detecting process according to one embodiment.

Referring to FIG. 57, as described above, the scanning part B1600 takes the series of images of the conveyed medicine package B12 using the illumination light provided by the illumination part B1500. At this time, a detecting part B1700 receives the series of images taken by the scanning part B1600, and detects the perforated line. Hereinafter, the method of detecting the perforated line of the medicine package B12 using the scanning part B1600 and the detecting part B1700 will be described in detail.

Firstly, as illustrated in FIG. 58, the medicine package B12 is generally fabricated by folding a piece of sheet material in half, forming a thermal bonded portion B1A1 by a thermal bonding operation, and then forming the perforated line B1L1. A medicine receiving portion B1A2 in which the medicine is received is provided at an inner side of each medicine package due to the thermal bonded portion B1A1. At this time, the thermal bonded portion B1A1 may be divided into a transverse thermal bonded portion B1A1a and a longitudinal thermal bonded portion B1A1b. The transverse thermal bonded portion B1A1a serves to seal an entrance of the medicine package B12, and the longitudinal thermal bonded portion B1A1b serves to partition the medicine receiving portion B1A2 formed between the medicine packages. Meanwhile, for convenience of explanation, terms of a crossed portion B1A2 of the transverse thermal bonded portion B1A1a and the longitudinal thermal bonded portion B1A1b, and an internal crossing point B1P1a, P1b of the transverse thermal bonded portion B1A1a and the longitudinal thermal bonded portion B1A1b will be used. The crossed portion B1A2 of the transverse thermal bonded portion B1A1a and the longitudinal thermal bonded portion B1A1b means a portion on which the transverse thermal bonded portion B1A1a and the longitudinal thermal bonded portion B1A1b meet and are crossed, and as illustrated in FIG. 58, the internal crossing point B1P1a, P1b of the transverse thermal bonded portion B1A1a and the longitudinal thermal bonded portion B1A1b means a crossing point which is located at the innermost of the crossed portion B1A2. Further, when the medicine package is conveyed in a certain direction B1D1, the internal crossing point B1P1a, P1b is divided into a first internal crossing point B1P1a and a second internal crossing point B1P1b according to an order taken by the scanning part.

As illustrated in FIG. 59, the method of detecting the perforated line of the medicine package according to the embodiment includes an image obtaining process B1S10, an image processing process B1S20, and a perforated line detecting process B1S30. In the image obtaining process B1S10, an image of the medicine package, which includes a crossed portion of a transverse thermal bonded portion and a longitudinal thermal bonded portion, is obtained. In the image processing process B1S20, an image processing operation of the obtained image is performed as a previous process for detecting the perforated line. In the perforated line detecting process B1S30, the perforated line of the medicine package is detected using the processed image.

At this time, in a case B1S40 in which the perforated line is not detected in the perforated line detecting process B1S30, the image obtaining process B1S10, the image processing process B1S20, and the perforated line detecting process B1S30 are repeated in a state B1S45 in which the medicine package is further conveyed.

Specifically, the image obtaining process may be divided into a first image obtaining process of taking the image of the medicine package, and a second image obtaining process of cutting off only the image including the crossed portion of the transverse thermal bonded portion and the longitudinal thermal bonded portion of the medicine package. That is, the image of the medicine package is taken using a camera, and only a necessary portion of the image is remained, and thus a size of the image for detecting the perforated line may be reduced.

The medicine package is variously formed using a transparent material and an opaque material. However, in the case of the thermal bonded portion, a property of the material is changed to be transparent by high heat. Therefore, if the corresponding image is taken by the scanning part while the illumination light is provided from a rear surface of the medicine package by the illumination part, light and shade on the image of the thermal bonded portion is considerably different from those on the image of another portion.

Meanwhile, to detect the cross portion of the transverse thermal bonded portion and the longitudinal thermal bonded portion, there are a method in which the scanning part is located at a corresponding position and then the image is taken, and a method in which the image is taken, the internal crossing point of the transverse thermal bonded portion and the longitudinal thermal bonded portion is detected, and then a position of the crossed portion of the transverse thermal bonded portion and the longitudinal thermal bonded portion is estimated.

Referring to FIG. 60, in the image processing process B1S20, the firstly obtained image is converted into a gray scale to remove color information (B1S210). Meanwhile, if necessary, before the converting into the gray scale, noise may be removed from the image using a median filter.

Then, the image converted into the gray scale is binary-coded to be displayed with only white and black colors (B1S220). In a last process of the image processing, an edge of the binary-coded image is extracted (B1S230). An edge-extracted image output is converted so that a boundary between the white and black colors is indicated by the black color. Further, the noise removing may be performed by the median filter.

The perforated line detecting process may be performed in various methods. For example, the perforated line of the medicine package may be extracted by an outline tracing method using an edge-extracted image, or a pattern recognizing method.

In the pattern recognizing method, a pattern of black pixels in the edge-extracted image is grasped, and when there is a linear pattern which traverses an image in the corresponding image, the pixels corresponding to the corresponding pattern may be determined as the perforated line of the medicine package.

As illustrated in FIG. 61, in the outline tracing method, an operation of finding the black pixels located at the uppermost portion of the edge-extracted image is performed (B1S310). When the black pixels located at the uppermost portion are found, the corresponding pixels are regarded as reference pixels, and the black pixels therearound are detected (B1S320). At this time, various methods may be used. However, in the embodiment, when the outline is traced toward a lower end of the image, it is determined whether there are the black pixels therearound in a clockwise direction from the 3 o'clock direction. When there are the black pixels therearound (B1S340), the corresponding pixels are regarded again as the reference pixels, and a movement is performed (B1S345), and the black pixels therearound are detected in the same method. At this time, when the black pixels are not found until the lowermost portion of the image, it is determined that the perforated line is not present in the corresponding image (B1S352), and when the detecting of the black pixels therearound is repeated, and the reference pixels arrive the lowermost portion of the image, it is determined that there is the perforated line in the corresponding image, and a moving route of the reference pixels corresponds to the perforated line. Meanwhile, in the embodiment, only a unidirectional tacking method from an upper portion of the image to a lower portion thereof is used, but the tacking may be continuously performed from the lower portion thereof to the upper portion thereof. In this case, whether it is the black pixel is determined from a pixel located in the 9 o'clock direction of the reference pixel, and when the corresponding pixel does not have information of the black color, the movement is performed in the clockwise direction, and it is determined whether the pixel therearound has the information of the black color. When there is the black pixel therearound, the movement is performed, while the corresponding pixel is regarded as the reference pixel, and then it is determined again whether there is the black pixel therearound.

When the outline is traced as described above, and the moving route of the reference pixels is formed in a linear shape from the upper portion of the image to the lower portion thereof, it may be determined that a position of the moving route of the corresponding reference pixel corresponds to a position of the perforated line of the medicine package.

The detailed description thereof will be provided with reference to FIG. 62. As illustrated in FIG. 62a, firstly, the black pixel located at the uppermost of the image is detected, and the corresponding pixel is regarded as the reference pixel. Then, the black pixel therearound is detected in the clockwise direction from the pixel in the 3 o'clock direction of the reference pixel. In this case, illustrated in FIG. 62b, since the pixel located just thereunder is the black pixel, the reference pixel is moved to the below pixel, and the black pixel therearound is traced again in the clockwise direction from the 3 o'clock direction. If the black pixels therearound are traced in such a method, the reference pixels form a route which arrives at a lower end of the image along a right outline of the black pixels, as illustrated in FIGS. 62c to 62f. In this case, when the black pixels which transversely protrude arrive at a transverse end of the image, or do not arrive at the lower end of the image and are cut off, it is determined that the corresponding pixels are not the perforated line. In the case of FIGS. 62a to 62f, since there are the black pixels which traverse the image, the black pixels may be determined as the perforated line. Meanwhile, as illustrated in FIGS. 62f to 62k, to increase accuracy thereof, the outline may be further traced from the lower end to the upper end. In this case, the black pixel is traced in the clockwise direction from the pixel located in the 9 o'clock direction of the reference pixel. As a result, when the tracing of the image is performed from the lower end to the upper end, a left outline of the black pixels is traced. The outline of the pixels included in the image is traced in such a method, and it is determined whether the moving route of the reference pixels traverses the image, and thus the position of the perforated line is detected.

4-7. Medicine Dispensing Container #2—Blister-Packed Medicine Dispensing Container (용이 봉일)

FIG. 63 is a schematic perspective view illustrating a blister-packed medicine dispensing container according to one embodiment of the present invention, FIG. 64 is a schematic perspective view illustrating a state in which a rotating part provided at the blister-packed medicine dispensing container according to one embodiment of the present invention is rotated from a main body, and FIGS. 65 and 66 are schematic perspective views explaining a principle in which the rotating part provided at the blister-packed medicine dispensing container according to one embodiment of the present invention is rotated from the main body.

Referring to FIGS. 63 to 66, the blister-packed medicine dispensing container BOX2 according to one embodiment of the present invention may include medicine receiving parts B2110 which receive a plurality of blister-packed medicines B2P and are arranged in at least one row, a position moving part B2120 (referring to FIG. 68) which moves the position of the medicine receiving parts B2110, and a dispensing part B2130 which dispenses the blister-packed medicines B2P received in the medicine receiving parts B2110 to an outer side.

That is, the medicine receiving parts B2110 are coupled to the position moving part B2120 to be rotationally moved according to a rotational movement of the position moving part B2120. The medicine receiving parts B2110 which are located at a predetermined position according to the rotational movement may dispense the received blister-packed medicines B2P to the outer side through the dispensing part B2130.

Meanwhile, the blister-packed medicine dispensing container BOX2 according to one embodiment of the present invention may be a container which dispenses the blister-packed medicines B2P one by one according to a prescription for a patient, and may be fixed to the cartridge of the medicine dispensing device together with the ampoule type medicine dispensing container, the pouch type medicine dispensing container, or the like.

In other words, the blister-packed medicine dispensing container BOX2 is fixed to the cartridge D200 of the medicine dispensing device 100, and may dispense the blister-packed medicines B2P to order, when the blister-packed medicines B2P are included in medication according to the prescription for the patient.

Here, when all of the blister-packed medicines B2P received in the blister-packed medicine dispensing container BOX2 are dispensed to the outer side through the dispensing part B2130, new blister-packed medicines B2P may be put into the medicine receiving parts B2110, and thus the blister-packed medicine dispensing container BOX2 may be semi-permanently used.

That is, the blister-packed medicine dispensing container BOX2 may include a body part B2101 providing a predetermined inner space in which the medicine receiving parts B2110, the position moving part B2120, and the dispensing part B2130 are disposed. A rotating part B2102 which is coupled so as to be rotatable from the body part B2101 and thus to expose the medicine receiving parts B2110 to the outer side may be coupled to the body part B2101.

Therefore, to put the new blister-packed medicines B2P into the medicine receiving parts B2110, the rotating part B2102 may be rotated from the body part B2101, and the rotation of the rotating part B2102 may be determined by a locking part B2L coupled to an opposite side to the dispensing part B2130.

In other words, as illustrated in FIGS. 65 and 66, to rotate the rotating part B2102 and thus to put the new blister-packed medicines B2P into the medicine receiving parts B2110, the locking part B2L may be rotated using a separate releasing member, and if the locking part B2L is rotated by the separate releasing member, a hook B2103 of the rotating part B2102 is separated from a hook corresponding part B2L1 which is interlocked with the locking part B2L and moved, and thus the rotating part B2102 may be rotated from the body part B2101.

Meanwhile, the releasing member may be configured with a kind of key which is inserted into the locking part B2L to rotate the rotating part B2102 when necessary. However, to ensure medication expertise and prevent medication accidents, a separate refill station with a key may be used.

That is, when the new blister-packed medicines B2P are put into the medicine receiving parts B2110 of the blister-packed medicine dispensing container BOX2, the blister-packed medicine dispensing container BOX2 is separated from the medicine dispensing device, and then inserted into the refill station, and thus the locking part B2L may be rotated.

At this time, the key as the releasing member provided at the refill station is automatically inserted into the locking part B2L to rotate the locking part B2L.

Therefore, using of the refill station to rotate the locking part B2L may more enhance safety than using of the releasing member configured with only the existing key, and the medication accidents due to loading of wrong medicines may be previously prevented.

FIG. 67 is a schematic perspective view illustrating a state in which the blister-packed medicine is dispensed from a first row medicine receiving part provided at the blister-packed medicine dispensing container according to one embodiment of the present invention, and FIG. 68 is an internal configuration view explaining the state in which the blister-packed medicine is dispensed from the first row medicine receiving part provided at the blister-packed medicine dispensing container according to one embodiment of the present invention.

Further, FIGS. 69 and 70 are internal configuration views illustrating a state in which the dispensing part is omitted to explain a principle in which the blister-packed medicine is dispensed from the first row medicine receiving part provided at the blister-packed medicine dispensing container according to one embodiment of the present invention.

Referring to FIGS. 67 to 70, the blister-packed medicine dispensing container BOX2 according to one embodiment of the present invention may include the medicine receiving parts B2110 which separately store the plurality of blister-packed medicines B2P, and the position moving part B2120 which is coupled to the medicine receiving parts B2110 to move the position of the medicine receiving parts B2110.

Firstly, terms of rotational directions will be described. A dispensing direction B2X may be a direction in which the medicine receiving parts B2110 disposed above rotating shafts B2R1 and B2R2 are rotated toward the dispensing part B2130, and a loading direction B2Y may be a direction which is rotated in an opposite direction to the dispensing direction B2X.

The medicine receiving parts B2110 may respectively have a receiving space B2S which separately stores the plurality of blister-packed medicines B2P, and may be arranged in at least one row.

Here, the position moving part B2120 may rotate a track and thus may move the medicine receiving parts B2110. As the position of the medicine receiving parts B2110 are moved by the position moving part B2120, the blister-packed medicine dispensing container BOX2 according to one embodiment of the present invention may dispense the blister-packed medicines B2P one by one to the outer side.

In other words, the blister-packed medicine dispensing container BOX2 may dispense the blister-packed medicines B2P one by one to the outer side by a rotational movement of the medicine receiving parts B2110 due to the position moving part B2120, regardless of the number of rows of the medicine receiving parts B2110.

However, when the number of rows of the medicine receiving parts B2110 is two or more, an opening/closing part B2133 to be described later may be provided so as to dispense the blister-packed medicines B2P one by one. The medicine receiving parts B2110 forming each row may be alternately arranged without the opening/closing part B2133, and thus each of the blister-packed medicines B2P may be dispensed in order.

That is, the medicine receiving parts B2110 according to the present invention are arranged in at least one row to dispense the blister-packed medicines B2P one by one to the outer side whenever required. Hereinafter, for convenience of explanation, a case in which the medicine receiving parts B2110 are arranged, for example, in two rows will be described.

The medicine receiving parts B2110 may be arranged in two rows, and may be symmetrically arranged with respect to a boundary of each row.

Therefore, the medicine receiving parts B2110 adjacent to each other may simultaneously dispense the blister-packed medicines B2P to the dispensing part B2130.

This may be realized by a position change of the medicine receiving parts B2110 due to the position moving part B2120, and the final dispensing of the blister-packed medicines B2P may be performed by passing one of the rotating shafts B2R1 and B2R2 of the position moving part B2120.

Here, the position moving part B2120 may include two or more rotating shafts B2R1 and B2R2, and a rail part B2122 which is wound on the two or more rotating shafts B2R1 and B2R2 and enables the position of the medicine receiving parts B2110 to be changed in a track manner by rotation of the two or more rotating shafts B2R1 and B2R2. The dispensing of the blister-packed medicines B2P from the medicine receiving parts B2110 to the dispensing part B2130 may be performed by gravity according to the position change of the medicine receiving parts B2110, while the medicine receiving parts B2110 pass the rotating shaft B2R1 which is close to the dispensing part B2130.

Meanwhile, the position moving part B2120 may have a pitch sensor which detects the position change. The pitch sensor may detect the position change of the medicine receiving parts B2110 with respect to the rotational movement of the position moving part B2120.

Therefore, the blister-packed medicines B2P are dispensed to the dispensing part B2130 by the rotational movement of the medicine receiving parts B2110, and then whether the next rotational movement is performed may be controlled.

Meanwhile, the dispensing of the blister-packed medicines B2P according to the position change of the medicine receiving parts B2110 may be realized by a rotation of a rotating wall B2111 which partitions the receiving space B2S and is rotatable, and this will be described later.

The position moving part B2120 may move the medicine receiving parts B2110 toward the dispensing part B2130 by the rotation of the two or more rotating shafts B2R1 and B2R2, may dispense the blister-packed medicines B2P to the dispensing part B2130, and then may be returned to its original position.

Here, the dispensing part B2130 may be disposed in a moving direction of the medicine receiving parts B2110 so that the blister-packed medicines B2P received in the medicine receiving parts B2110 are dispensed one by one to the outer side, and may include a storing part B2131 and the opening/closing part B2133.

The storing part B2131 may temporarily store the blister-packed medicines B2P simultaneously dispensed from the medicine receiving parts B2110 forming each row before the blister-packed medicines B2P are dispensed to the outer side. The opening/closing part B2133 may be a kind of opening/closing door which dispenses the blister-packed medicines B2P one by one to the outer side.

In other words, the dispensing part B2130 may be formed to correspond to the medicine receiving parts B2110 forming each row. When the medicine receiving parts B2110 are arranged in two rows, two dispensing parts B2130 may be provided.

Here, the opening/closing part B2133 may block one of two storing parts B2131 from the outer side, and this is to dispense the blister-packed medicines B2P one by one.

That is, when the blister-packed medicines B2P are dispensed from the storing part B2131, which is not blocked, to the outer side, the opening/closing part B2133 may allow one of the blocked storing parts B2131 to be in communication with the outer side, such that the blister-packed medicines B2P are dispensed one by one.

Specifically, since the medicine receiving parts B2110 may be symmetrically arranged with respect to the boundary of each row, the blister-packed medicines B2P received in the medicine receiving part B2110 of the adjacent row may be simultaneously dispensed together with the blister-packed medicines B2P received in the medicine receiving part B2110 by the position change due to the position moving part B2120. If the one of the storing parts B2131 is not blocked by the opening/closing part B2133, the two blister-packed medicines B2P are simultaneously dispensed to the outer side.

Therefore, in order to dispense the blister-packed medicines B2P one by one to the outer side, when the blister-packed medicines B2P are dispensed from the unblocked storing part B2131 to the outer side, the opening/closing part B2133 is opened to dispense the blister-packed medicines B2P from the blocked storing part B2131.

Here, power for opening and closing the opening/closing part B2133 may be provided by an opening/closing power providing part B2140, and the opening/closing power providing part B2140 may be a kind of small motor disposed in the body part B2101 of the blister-packed medicine dispensing container BOX2 according to the present invention.

An opening/closing power rotating part B2141 which is a kind of spur gear may be coupled to a rotating shaft rotated by the opening/closing power providing part B2140. The opening/closing power rotating part B2141 may be interlocked via an opening/closing power intermediation part B2142 with an opening/closing power transmitting part B2143 for opening and closing the opening/closing part B2133.

In other words, the opening/closing power rotating part B2141, the opening/closing power intermediation part B2142, and the opening/closing power transmitting part B2143 which are the spur gears may be engaged with each other. When the opening/closing power rotating part B2141 is rotated by the opening/closing power providing part B2140, the opening/closing power intermediation part B2142 is also rotated, and thus the opening/closing power transmitting part B2143 is rotated.

Therefore, when the opening/closing power transmitting part B2143 is rotated, an opening/closing moving part B2134 coupled to one end of the opening/closing part B2133 is moved upwardly by the rotation of the opening/closing power transmitting part B2143, and thus the opening/closing part B2133 is opened.

Here, the opening/closing moving part B2134 may be a rack gear which is a kind of a linear gear to be moved upwardly by the rotation of the opening/closing power transmitting part B2143 which is a kind of spur gear. The opening/closing part B2133 may be opened and then may be closed again by a change of the rotational direction of the opening/closing power providing part B2140.

Therefore, the opening and closing of the opening/closing part B2133 may be realized by an automatic control using the opening/closing power providing part B2140. This may be different from a dispensing power providing part B2151 which provides power for rotating the position moving part B2120.

Here, the dispensing power providing part B2151 is a kind of spur gear. When the blister-packed medicine dispensing container BOX2 according to the present invention is fixed to the cartridge of the medicine dispensing device, the dispensing power providing part B2151 may be automatically engaged with one construction element of the medicine dispensing device according to the prescription of the patient to receive external power and thus to be rotated by the received external power.

When the dispensing power providing part B2151 is rotated by the external power, rotational force of the dispensing power providing part B2151 rotates a dispensing power transmitting part B2153 which is coupled with the rotating shaft B2R1 of the position moving part B2120 to be interlocked and rotated with the rotating shaft B2R1.

Here, the rotation of the dispensing power transmitting part B2153 by the rotational force of the dispensing power providing part B2151 may be mediated by a dispensing power intermediation part B2152 which is engaged between the construction elements. This may realized by arranging the construction elements configured with the spur gears to be engaged with each other.

Therefore, the power for the rotational movement of the position moving part B2120 and the power for opening and closing the opening/closing part B2133 may be different from each other in the aspect of the external power and the internal power.

Meanwhile, the dispensing of the blister-packed medicines B2P from the medicine receiving part B2110 which is rotationally moved by the dispensing power providing part B2151 may be performed by the rotation of the rotating wall B2111 which partitions the receiving space B2S. The rotating wall B2111 may be rotated when the medicine receiving part B2110 is disposed at a predetermined position by the position moving part B2120.

Here, the medicine receiving part B2110 may include a plurality of walls which partition the receiving space B2S. Specifically, the plurality of walls may include a bottom wall B2114 (referring to FIG. 79) which is coupled with the rail part B2122 and on which the blister-packed medicines B2P are seated, a partition wall B2113 which extends from another edge of the bottom wall B2114 to an outer side of the rail part B2122, a boundary wall B2112 which partitions the medicine receiving part B2110 of the row adjacent to one medicine receiving part B2110 and establishes a boundary, and a side wall B2115 which forms an outer wall of the medicine receiving part B2110 of the row adjacent to one medicine receiving part B2110.

The rotating wall B2111 may be rotated about one edge of the bottom wall B2114 which is used as a rotating shaft.

The rotating wall B2111 may be rotated about the rotating shaft by gravity due to its own weight, and the rotation of the rotating wall B2111 may be performed while passing one of the two or more rotating shafts of the position moving part B2120.

In other words, the rotating wall B2111 is not rotated when passing upper and lower sides of the two or more rotating shafts B2R1 and B2R2 and also passing the rotating shaft B2R2 other than the rotating shaft B2R1 adjacent to the dispensing part B2130 among the two or more rotating shafts B2R1 and B2R2. The rotating wall B2111 is rotated only when passing the rotating shaft B2R1 adjacent to the dispensing part B2130.

That is, assuming that the medicine receiving part B2110 is moved in the dispensing direction B2X by the rotational movement of the position moving part B2120, when the medicine receiving part B2110 is disposed at the upper sides of the two or more rotating shafts B2R1 and B2R2, the rotating wall B2111 of each medicine receiving part B2110 may not be rotated in the dispensing direction B2X by the partition wall B2113 of the adjacent medicine receiving part B2110 which is disposed in the same row.

Further, the rotating wall B211 of the medicine receiving part B2110 may be in contact with the boundary wall B2112, and thus may be prevented from being rotated into the receiving space B2S of the medicine receiving part B2110.

By the same reason, when the medicine receiving part B2110 is disposed at the lower sides of the two or more rotating shafts B2R1 and B2R2 to be moved, the rotation of the rotating wall B2111 may be prevented.

Further, when the medicine receiving part B2110 is moved in the dispensing direction B2X, and moved from the lower sides of the two or more rotating shafts B2R1 and B2R2 toward the upper sides thereof, the rotating wall B2111 is in contact with the boundary wall B2112 and thus prevented from being rotated into the receiving space B2S.

Finally, the rotating wall B211 of the medicine receiving part B2110 may be rotated only when moved to the rotating shaft B2R1 adjacent to the dispensing part B2130, i.e., from the upper sides of the two or more rotating shafts B2R1 and B2R2 toward the lower sides thereof. The blister-packed medicines B2P may be free-fallen by the rotation of the rotating wall B2111, and then may be dispensed to the dispensing part B2130.

Meanwhile, a predetermined area of the bottom wall B2114 of the medicine receiving part B2110 may be spaced apart from the rail part B2122, while passing at least one rotating shaft B2R1 of the two or more rotating shafts B2R1 and B2R2.

That is, the predetermined area of the bottom wall B2114 of the medicine receiving part B2110 may be spaced apart from the rail part B2122, when moved from the upper sides of the two or more rotating shafts B2R1 and B2R2 toward the lower sides thereof.

This is because of a coupling manner between the rail part B2122 and the position moving part B2120. The coupling manner between the rail part B2122 and the position moving part B2120 may be a manner in which a coupling protrusion B2116 (referring to FIG. 75) and a removal protrusion B2117 (referring to FIG. 75) protruding from the bottom wall B2114 of the medicine receiving part B2110 are inserted and coupled into a coupling hole B2H formed in the rail part B2122.

This will be described later with reference to FIG. 75.

Meanwhile, when the medicine receiving part B2110 is moved from the upper sides of the two or more rotating shafts B2R1 and B2R2 toward the lower sides thereof by the position change due to the position moving part B2120, the blister-packed medicines B2P may be dispensed. At this time, a frictional force between the rotating wall B2111 and the blister-packed medicines B2P is reduced, and thus the blister-packed medicines B2P may be effectively dispensed to the dispensing part B2130.

That is, at least one friction reducing part B2118 may be protrudingly formed at one surface of the rotating wall B2111. The at least one friction reducing part B2118 may be continuously formed in the dispensing direction B2X of the blister-packed medicines B2P.

Therefore, when the blister-packed medicines B2P are dispensed, the blister-packed medicines B2P are in line contact with the rotating wall B2111, and thus a minimum frictional force may be applied when the blister-packed medicines B2P are dispensed to the dispensing part B2130.

Further, the friction reducing part B2118 may be also formed at the storing part B2131. Thus, when the blister-packed medicines B2P are dispensed, a frictional force between the storing part B2131 and the blister-packed medicines B2P is reduced, and thus the blister-packed medicines B2P may be effectively dispensed to the outer side.

However, the friction reducing part B2118 is not limited to a state of being continuously formed in the dispensing direction B2X of the blister-packed medicines B2P, but may be configured with a plurality of protrusions.

FIG. 71 is a schematic perspective view illustrating a state in which the blister-packed medicine is dispensed from a second row medicine receiving part provided at the blister-packed medicine dispensing container according to one embodiment of the present invention, and FIG. 72 is an internal configuration view explaining the state in which the blister-packed medicine is dispensed from the second row medicine receiving part provided at the blister-packed medicine dispensing container according to one embodiment of the present invention.

Further, FIGS. 73 and 74 are schematic views explaining an operation principle of the opening/closing part through which the blister-packed medicine is dispensed from the second row medicine receiving part provided at the blister-packed medicine dispensing container according to one embodiment of the present invention.

Referring to FIGS. 71 to 74, the dispensing part B2130 for dispensing the blister-packed medicines B2P may include the storing part B2131 and the opening/closing part B2133, as described above referring to FIGS. 67 to 70.

Here, when the medicine receiving parts B2110 of the blister-packed medicine dispensing container BOX2 according the present invention are arranged in two rows, the blister-packed medicines B2P received in one medicine receiving part B2110 and the adjacent row medicine receiving part B2110 are simultaneously dispensed by the rotation of the medicine receiving parts B2110 due to the position moving part B2120.

At this time, the blister-packed medicines B2P should be dispensed one by one in order, and this may be realized by the opening and closing of the opening/closing part B2133, as described above.

That is, among the blister-packed medicines B2P simultaneously dispensed to the storing part B2131 of the dispensing part B2130, the blister-packed medicines B2P dispensed to the storing part B2131 in which the opening/closing part B2133 is not disposed may be naturally dispensed to the outer side. After the dispensing, when the dispensing of another blister-packed medicine B2P is required, the dispensing should be performed from the storing part B2131 which is closed by the opening/closing part B2133.

In this case, the opening/closing part B2133 may be opened to dispense the other blister-packed medicine B2P to the outer side. The power for opening and closing the opening/closing part B2133 may be provided by the opening/closing power providing part B2140.

Meanwhile, the opening/closing power rotating part B2141 may be coupled to the opening/closing power providing part B2140. The opening/closing power rotating part B2141 may be interlocked with the opening/closing power transmitting part B2143 for opening and closing the opening/closing part B2133 by the opening/closing power intermediation part B2142.

That is, if the opening/closing power rotating part B2141 is rotated by the opening/closing power providing part B2140, the opening/closing power intermediation part B2142 is also rotated, and thus the opening/closing power transmitting part B2143 is rotated.

Therefore, if the opening/closing power transmitting part B2143 is rotated, the opening/closing moving part B2134 coupled to one end of the opening/closing part B2133 is moved upwardly by the rotation of the opening/closing power transmitting part B2143, and thus the opening/closing part B2133 is opened.

FIG. 75 is a schematic exploded perspective view explaining a principle in which the medicine receiving part provided at the blister-packed medicine dispensing container according to one embodiment of the present invention is fixed to the rail part.

Referring to FIG. 75, the coupling between the rail part B2122 and the medicine receiving part B2110 may be performed by inserting the coupling protrusion B2116 and the removal protrusion B2117, which protrude from the bottom wall B2114 of the medicine receiving part B2110, into each coupling hole B2H formed in both sides of the rail part B2122.

That is, the coupling protrusion B2116 may be formed to protrude from one side of a lower surface of the bottom wall B2114 and then to be bent to an outer side, and thus entirely formed in an "L" shape. The removal protrusion B2117 may be formed in a semi-arrowhead shape which may be fitted into the coupling hole B2H.

Therefore, when the coupling protrusion B2116 is inserted into the coupling hole B2H, and then the removal protrusion B2117 is fitted into the coupling hole B2H by exerting external force, the medicine receiving part B2110 may be stably fixed to the rail part B2122.

Meanwhile, the rail part B2122 may be formed by connecting a plurality of rail elements B2123, and the bottom wall B2114 of the medicine receiving part B2110 may correspond to two rail elements B2123.

However, the coupling protrusion B2116 and the removal protrusion B2117 protruding from the bottom wall B2114 may be coupled into the coupling holes B2H formed at both sides of one rail element B2123.

Therefore, when the medicine receiving part B2110 is rotated in the dispensing direction B2X, the predetermined area of the bottom wall B2114 of the medicine receiving part B2110 may be spaced apart from the rail part B2122, while passing at least one rotating shaft B2R1 of the two or more rotating shafts B2R1 and B2R2.

In other words, the predetermined area of the bottom wall B2114 of the medicine receiving part B2110 may be spaced apart from the rail part B2122, when moved from the upper sides of the two or more rotating shafts B2R1 and B2R2 toward the lower sides thereof.

FIG. 76 is a schematic perspective view explaining a process in which the blister-packed medicine is put into the blister-packed medicine dispensing container according to one embodiment of the present invention, and FIGS. 77 and 78 are internal configuration views explaining the process in which the blister-packed medicine is put into the blister-packed medicine dispensing container according to one embodiment of the present invention.

Further, FIG. 79 is an internal configuration view explaining a jam preventing part provided at the blister-packed medicine dispensing container according to one embodiment of the present invention, and FIG. 80 is a schematic exploded perspective view explaining the jam preventing part provided at the blister-packed medicine dispensing container according to one embodiment of the present invention.

Referring to FIGS. 76 to 80, in the blister-packed medicine dispensing container BOX2, when all of the blister-packed medicines B2P received in the medicine receiving parts B2110 are dispensed to the outer side through the dispensing part B2130, the rotating part B2102 may be rotated from the body part B2101, and new blister-packed medicines B2P may be put into the empty medicine receiving parts B2110.

Here, the rotation of the rotating part B2102 may be performed by separating the blister-packed medicine dispensing container BOX2 from the medicine dispensing device, inserting it into the refill station, and rotating the locking part B2L as described above with reference to FIGS. 63 to 65.

At this time, the key as the releasing member provided at the refill station may be automatically inserted into the locking part B2L, and then may rotate the locking part B2L.

Meanwhile, if the rotating part B2102 is rotated from the body part B2101, and the medicine receiving part B2110 is exposed to the outer side, the new blister-packed medicines B2P are put into the medicine receiving part B2110, and the medicine receiving part B2110 is automatically or manually is rotated in the loading direction B2Y opposite to the dispensing direction B2X, and thus the loading into the medicine receiving part B2110 may be completed.

Here, for the rotational movement of the medicine receiving part B2110, i.e., the rotation of the position moving part B2120 in the loading direction B2Y, a movement blocking part B2160 which is in contact with the dispensing power intermediation part B2152 to prevent the medicine receiving part B2110 from being moved by the position moving part B2120 should be separated from the dispensing power intermediation part B2152, and this may be performed by a separation providing part provided at the refill station.

Also, in performing the dispensing of the blister-packed medicines B2P from the medicine receiving part B2110 due to the rotational movement of the position moving part B2120, the movement blocking part B2160 may be separated from the dispensing power intermediation part B2152 by the separation providing part provided at the cartridge of the medicine dispensing device.

Meanwhile, when the blister-packed medicines B2P are dispensed from the medicine receiving part B2110 and when the blister-packed medicines B2P are put into the medicine receiving part B2110, the blister-packed medicine B2P may be prevented from being jammed between the partition wall B2113 and the body part B2101 by the jam preventing part B2170.

Hereinafter, possibility in which the blister-packed medicine B2P may be jammed between the partition wall B2113 and the body part B2101 according to the position and the rotational direction of the medicine receiving part B2110 will be described.

Firstly, when the blister-packed medicines B2P are received in all of the medicine receiving parts B2110, and dispensed from the medicine receiving parts B2110 by the rotational movement of the position moving part B2120, there is no possibility in which the blister-packed medicines B2P in the medicine receiving part B2110 passing the upper sides of the two or more rotating shafts B2R1 and B2R2 are jammed between the partition wall B2113 and the body part B2101.

This is because, when the medicine receiving part B2110 passes the upper sides of the two or more rotating shafts B2R1 and B2R2, the blister-packed medicines B2P are moved in a state of being seated on the bottom wall B2114 of the medicine receiving part B2110 by gravity.

And there is no problem when the blister-packed medicines B2P are dispensed, while the medicine receiving part B2110 passes the rotating shaft B2R1 adjacent to the dispensing part B2130 and then the medicine receiving part B2110 passes the lower sides of the two or more rotating shafts B2R1 and B2R2.

However, when the medicine receiving part B2110 in which the blister-packed medicines B2P are received passes the lower sides of the two or more rotating shafts B2R1 and B2R2 before the blister-packed medicines B2P are dispensed from the medicine receiving part B2110, and when the medicine receiving part B2110 passes the rotating shaft B2R2 other than the rotating shaft B2R1 adjacent to the dispensing part B2130 among the two or more rotating shafts B2R1 and B2R2, the blister-packed medicine B2P may be seated on an inner surface of the body part B2101 by gravity, and thus may be jammed between the partition wall B2113 and the body part B2101.

Further, in the case in which all of the blister-packed medicines B2P are dispensed from the medicine receiving part B2110, and the medicine receiving part B2110 is rotated in the loading direction B2Y and the new blister-packed medicines B2P are loaded, when the medicine receiving part B2110 in which the new blister-packed medicines B2P are loaded passes the rotating shaft B2R2 other than the rotating shaft B2R1 adjacent to the dispensing part B2130 among the two or more rotating shafts B2R1 and B2R2, and when the medicine receiving part B2110 passes the lower sides of the two or more rotating shafts B2R1 and B2R2, there is the possibility in which the blister-packed medicine B2P is jammed between the partition wall B2113 and the body part B2101 due to the above-mentioned reason.

Finally, in order to reduce the possibility in which the blister-packed medicine B2P is jammed between the partition wall B2113 and the body part B2101, and also to minimize an interference with the inner surface of the body part B2101 of the partition wall B2113, and thus to smoothly perform the rotational movement, the partition wall B2113 and the body part B2101 should be formed to correspond to each other. To this end, an opened end B2113-2 of the partition wall B2113 should be maintained in a state in contact with the body part B2101, or the opened end B2113-2 of the partition wall B2113 should be close to the inner surface of the body part B2101 so as to minimize a distance therebetween.

Therefore, since a moving route in which the partition wall B2113 of the medicine receiving part B2110 passes the rotating shaft B2R2 other than the rotating shaft B2R1 adjacent to the dispensing part B2130 among the two or more rotating shafts B2R1 and B2R2 is formed to be rounded, the inner surface of the body part B2101 corresponding to the moving route may be also formed to be rounded, and thus the opened end B2113-2 of the partition wall B2113 may be in contact with or close to the inner surface of the body part B2101.

Further, even when the medicine receiving part B2110 passes the lower sides of the two or more rotating shafts B2R1 and B2R2, the opened end B2113-2 of the partition wall B2113 and the inner surface of the body part B2101 may be formed to be in contact with or close to each other.

Here, when the opened end B2113-2 of the partition wall B2113 and the inner surface of the body part B2101 may be formed to correspond to each other and thus to be in contact with or close to each other, it is possible to reduce the possibility in which the blister-packed medicine B2P is jammed between the partition wall B2113 and the body part B2101, but it is impossible to completely remove the possibility due to a property of a blister package.

Therefore, in order to completely prevent the possibility in which the blister-packed medicine B2P is jammed between the partition wall B2113 and the body part B2101, and also to minimize an interference with the inner surface of the body part B2101 of the partition wall B2113, and thus to smoothly perform the rotational movement, the present invention may have the jam preventing part B2170.

Specifically, the jam preventing part B2170 may be formed on the moving route of the medicine receiving part B2110 due to the position moving part B2120, and may include a protruding part B2172 formed at one of the partition wall B2113 and the body part B2101, and a receiving part B2174 formed at the other one to receive the protruding part B2172.

The jam preventing part B2170 may form at least one curve between the partition wall B2113 and the body part B2101, and thus prevent the blister-packed medicine B2P from being jammed therebetween. The protruding part B2172 and the receiving part B2174 forming the jam preventing part B2170 may be formed to correspond to each other.

However, the protruding part B2172 and the receiving part B2174 are not limited to a corresponding state to each other. Any other states may be applied, as long as the curve may be formed between partition wall B2113 and the body part B2101.

Here, the partition wall B2113 may include a fixing end B2113-1 coupled to the rail part B2122, and the opened end B2113-2 adjacent to the body part B2101. The receiving part B2174 may be formed to be recessed from the opened end B2113-2 of the partition wall B2113.

Further, a plurality of receiving parts B2174 may be formed to be spaced apart from each other, and also a plurality of protruding parts B2172 may be formed in the same way.

Meanwhile, the protruding part B2172 may be formed on all areas of the inner surface of the body part B2101, and may be also formed at only a portion having the possibility in which the blister-packed medicine B2P is jammed between the partition wall B2113 and the body part B2101.

That is, the protruding part B2172 may be formed on the moving route of the medicine receiving part B2110 corresponding to the lower sides of the two or more rotating shafts B2R1 and B2R2 in the inner surface of the body part B2101, and may be formed on the moving route of the medicine receiving part B2110 which passes the rotating shaft B2R2 other than the rotating shaft B2R1 through which the blister-packed medicines pass to be dispensed.

In other words, when the position moving part B2120 is rotationally moved in the loading direction B2Y opposite to the dispensing direction B2X to load the blister-packed medicines B2P into the medicine receiving part B2110, and thus the medicine receiving part B2110 is also rotationally moved, the protruding part B2172 may be formed on only the moving route of the inner surface of the body part B2101, in which the position of the medicine receiving part B2110 is moved from the upper sides of the two or more rotating shafts B2R1 and B2R2 to the lower sides thereof, and also only the moving route thereof, in which the medicine receiving part B2110 passes the lower sides thereof.

Therefore, when the position moving part B2120 is rotationally moved in the loading direction B2Y, and the blister-packed medicines B2P are put into the medicine receiving part B2110, the problem that the blister-packed medicine B2P is caught or jammed between the partition wall B2113 and the body part B2101 may be previously prevented by the jam preventing part B2170.

Further, even when all of the blister-packed medicines B2P are received in the medicine receiving part B2110, and then the medicine receiving part B2110 is rotationally moved to dispense the blister-packed medicines B2P, the above description may be applied as it is.

Finally, the jam preventing part B2170 may serve to previously prevent the jamming phenomenon of the blister-packed medicine B2P, and also to guide the smooth rotation of the medicine receiving part B2110.

Meanwhile, in at least one of a case in which the medicine receiving part B2110 in which the blister-packed medicines B2P are received passes the lower sides of the two or more rotating shafts B2R1 and B2R2 before the blister-packed medicines B2P are dispensed from the medicine receiving part B2110, and a case in which the medicine receiving part B2110 passes the rotating shaft B2R2 other than the rotating shaft B2R1 adjacent to the dispensing part B2130 among the two or more rotating shafts B2R1 and B2R2, the blister-packed medicine B2P may be seated on the protruding part B2172. In this case, the blister-packed medicine B2P is moved on the protruding part B2172.

Further, in the case in which all of the blister-packed medicines B2P are dispensed from the medicine receiving part B2110, and the medicine receiving part B2110 is rotated in the loading direction B2Y, and the new blister-packed medicines B2P are loaded, when the medicine receiving part B2110 in which the new blister-packed medicines B2P are loaded passes the rotating shaft B2R2 other than the rotating shaft B2R1 adjacent to the dispensing part B2130 among the two or more rotating shafts B2R1 and B2R2, and/or when the medicine receiving part B2110 passes the lower sides of the two or more rotating shafts B2R1 and B2R2, the protruding part B2172 may be applied in the same way.

Therefore, the protruding part B2172 may reduce a frictional force generated while the blister-packed medicine B2P is seated thereon and moved, and thus it is possible to allow the movement to be performed with minimum noise and vibration.

FIG. 81 is a schematic perspective view illustrating a modified example of the blister-packed medicine dispensing container according to one embodiment of the present invention, FIG. 82 is an internal configuration view illustrating the modified example of the blister-packed medicine dispensing container according to one embodiment of the present invention, and FIG. 83 is an internal exploded perspective view illustrating the modified example of the blister-packed medicine dispensing container according to one embodiment of the present invention.

Referring to FIGS. 81 to 83, since the blister-packed medicine dispensing container BOX2' has the same configuration and effect as the above-mentioned embodiment, except a guide hole B22000 formed in a side wall, and a guide protrusion B21000 formed on a rotating wall, description thereof, except the guide hole B22000 and the guide protrusion B21000, will be omitted.

The rotating wall may be rotated by free-fall by gravity. In this case, a rotating range thereof may be limited.

That is, since the guide protrusion B21000 formed on the rotating wall is inserted into the guide hole B22000 formed in the side wall, the range in which the rotating wall is free-fallen and rotated may be limited within a length range of the guide hole B22000.

Until now, the configurations and characteristics of the present invention have been described on the basis of the embodiments according to the present invention, but the present invention is not limited thereto. Various modifications or changes within the spirit of the invention would be obvious to those skilled in the art. Therefore, the modifications or changes belong to the claims.

That is, in the drawings, the medicine receiving part B2110 is illustrated to have a rectangular parallelepiped, but is not limited thereto. The medicine receiving part B2110 may have a trapezoidal shape of which a width becomes narrower toward the position moving part B2120.

Further, in the aspect of the arrangement of the medicine receiving parts B2110, the medicine receiving parts B2110 are not limited to the two-row symmetric structure, and may be alternately arranged, and also may be arranged in two or more rows.

Also, the driving force for the rotation of the position moving part B2120, the driving of the opening/closing part B2133, or the like may be provided by a driving device such as an internal or external motor of the blister-packed medicine dispensing container BOX2 according to the present invention.

4-8. Medicine Dispensing Container #3—Ampoule Type Medicine Dispensing Container An ampoule type medicine dispensing container according to the present invention is a device which dispenses an ampoule type medicine (hereinafter, called as "ampoule" for convenience of explanation), which is formed of a glass material such an ampoule and a vial. The ampoule type medicine dispensing container according to one embodiment of the present invention includes a storage part, a shutter, a driving part, a conveyor, a discharging port, and so on. The storage part is an element in which a space is partitioned into multi-layers and multi-rows to store a plurality of ampoules, the shutter is an element which is operated to vertically open and close each storage compartment, and the driving part is an element which drives the shutter. The conveyor is an element which is provided at a lower end of the storage part so that the fallen ampoule is seated thereon, and which conveys the seated elements. Hereinafter, each element will be described in detail with reference to the drawings.

The construction elements related to a housing and a locking device will be described with reference to FIGS. 84 to 87. FIG. 84 is a perspective view illustrating the ampoule type medicine dispensing container according to one embodiment of the present invention, and FIG. 85 is a perspective view illustrating a state in which a side surface of the ampoule type medicine dispensing container according to one embodiment of the present invention is opened. Also, FIGS. 86 and 87 are cut-away perspective views illustrating, in turn, an operation state of a locking device according to one embodiment.

The ampoule type medicine dispensing container BOX3 according to the embodiment includes a housing B310 defining an exterior. In the embodiment, the housing B310 is formed in a rectangular parallelepiped shape. The housing B310 includes a housing body B3110, a front part B3120, and an ampoule loading gate B3130. A discharging port B3121 which discharges the ampoule, and a driving gear B3140 which transmits power from an outer side to the conveyor to be described later, or the like are provided at the front part B3120 provided at a front surface of the housing B310. Meanwhile, the discharging port B3121 is preferably formed to be inclined downwardly toward an outer side. By such a structure, an impact due to a step difference of the discharging port B3121 may be minimized so as to prevent damage of the ampoule or the vial formed of the glass material. The ampoule loading gate B3130 through which the ampoule is supplied is provided at one side surface of the housing B310. In the embodiment, the ampoule loading gate B3130 is provided to be opened, while one side thereof is fixed by a hinge or the like. Meanwhile, as illustrated in FIG. 85, a hooking part B3132 having a hook shape is formed at an inner side of the ampoule loading gate B3130. The hooking part B3132 is an element corresponding to a catching part B3633 provided at an inner side of the housing B310. The catching part B3633 will be fully described in the description of FIG. 86. Further, a plurality of ampoules B32 are received in the housing B310. Meanwhile, as described above, all medicines which are formed of the glass material, such as the vial and the ampoule, or other alternative materials to have a similar shape to an ampoule shape, may be received in the housing B310.

As illustrated in FIG. 86, a locking device B360 corresponding to the hooking part B3132 is provided at the inner side of the housing. The locking device B360 is an element which fixes or releases the hooking part B3132 to lock or unlock the ampoule loading gate B3130.

Specifically, the locking device B360 includes a locking part B361, a first rotating part B362, and a second rotating part B363. The locking part B361 is provided at an inner side of a rear surface of the housing. The locking part B361 is provided to be rotated using an effective key or the like. Further, an outer circumferential surface of the locking part B361 is provided to radially have a long radius portion and a short radius portion with a rotating shaft in the center.

The first rotating part B362 is provided at the inner side of the rear surface of the housing. The first rotating part B362 is fixed so that a first end B3621 and a second end B3623 may be rotated about a first rotating shaft B3622 within a predetermined range. Further, the first end B3621 of the first rotating part B362 is provided to be in contact with the outer circumferential surface of the locking part B361. In a locking state, as illustrated in FIG. 86, first end B3621 of the first rotating part B362 is provided to be in contact with the short radius portion of the locking part B361.

The second rotating part B363 is provided at an inner side of a side surface of the housing, and a first end B3631 of the second rotating part B363 is provided to be in contact with an upper portion of the second end B3623 of the first rotating part B362. The first end B3631 and a second end B3633 of the second rotating part B363 are also provided to be rotated about a second rotating shaft B3632. In the locking state, while the ampoule loading gate B3130 is in a closed state, the hooking part B3132 is caught by the second end B3633 of the second rotating part B363. Hereinafter, the first rotating part B362 and the second rotating part B363 are commonly defined as a rotational force transmitting part, and the second end B3633 of the second rotating part B363 is defined as a catching part.

An operating method of an opened state will be described with reference to FIG. 87. As the locking part B361 is rotated, the long radius portion of the locking part B361 is in contact with the first end B3621 of the first rotating part B362, and the first end B3621 is pushed back to one side. When the first end B3621 of the first rotating part B362 is pushed back by the long radius portion of the locking part B361 and thus rotated about the first rotating shaft B3622 in a counterclockwise direction, the second end B3623 of the first rotating part B362 is also rotated in the same direction, i.e., the counterclockwise direction. When the first end B3631 of the second rotating part B363 is lifted up by the second end B3623 of the first rotating part B362, the catching part B3633 is rotated about the second rotating shaft B3632 in a clockwise direction. In this case, the catching part B3633 is rotated and moved downwardly, and thus the hooking part B3132 is released from the locking state.

The driving part will be described with reference to FIGS. 88 and 89. FIG. 88 is a cut-away perspective view illustrating the ampoule type medicine dispensing container according to one embodiment of the present invention, and FIG. 89 is a perspective view illustrating a shape of the driving part according to one embodiment.

A driving part B320 is an element which drives the shutter to be described later. As illustrated in FIG. 88, the driving part B320 is provided to be adjacent to one end of a storage part B330. Referring to FIG. 89, a cam part B3230 includes a cam shaft B3231, a first cam B3232, a second cam B3233, and a third cam B3234. The first cam B3232, the second cam B3233, and the third cam B3234 are respectively provided to have a long radius portion and a short radius portion with the cam shaft B3231 in the center, and rotated together about the cam shaft B3231. A motor B3210 generates a physical rotational force using electric power, and gears B3220 transmit the rotational force generated from the motor B3210 to the cam part B3230. An outer circumferential surface of each of the first cam B3232, the second cam B3233, and the third cam B3234 is provided to be in contact with one end of each shutter to be described later. The cams B3232, B3233, and B3234 are operated to push the shutters, in turn, from the lowermost layer to the uppermost layer, while rotated.

The storage part, the shutter, and related elements will be described with reference to FIGS. 90 to 93. FIG. 90 is an exploded perspective view illustrating a shape of a partition member according to one embodiment, and FIG. 91 is a perspective view illustrating a shape of the shutter according to one embodiment. Further, FIG. 92 is a perspective view illustrating a state in which the partition member is coupled with the shutter according to one embodiment, and FIG. 93 is a partially cut-away perspective view illustrating shapes of a detecting part and a to-be-detected part according to one embodiment.

The storage part B330 according to the embodiment includes a plurality of partition members B331. The plurality of partition members B331 are provided to form a plurality of layers. Each partition member B331a, B331b, B331c is partitioned into a plurality of spaces B3313 to store the ampoules. At this time, a member between the spaces B3313 is referred to as a partition wall B3311 by which the spaces B3313 are partitioned. Further, a partition wall supporting part B3314 which protrudes downwardly and connects each partition member B3331 is formed at a lower end of one side of the partition wall B3311. A partition member side wall B3312 which connects the partition walls B3311 is provided at the other side surface of the partition wall B3311. The partition member side wall B3312 is formed to have a predetermined thickness and to protrude laterally from the partition member B331.

A receiving groove B3315 is formed at one end of the partition member B331. The receiving groove B3315 is formed so that one end of an elastic member to be described later is received and/or fixed therein.

Meanwhile, when the partition members B331a, B331b, and B331c are stacked, a predetermined space is formed among the partition members B331a, B331b, and B331c by the partition wall supporting part B3314. A space defined by the partition wall supporting part B3314 and the partition members B331a, B331b, and B331c is formed, and the shutter to be described later is inserted through the space. Hereinafter, the space is referred to as a shutter receiving part.

As illustrated in FIG. 91, a shutter B340 is formed in a plate shape in which a plurality of up-and-down through-holes are formed. The shutter B340 has perforated gates B343 which are formed in a lengthwise direction so that the plurality of ampoules pass therethrough. A cross-section of each gate B343 is preferably formed to have a size larger than a width of the ampoule and equal to or smaller than a width of the space B3313 of the partition member. At this time, a member which partitions the gates B343 is referred to as an ampoule supporting part B341. The ampoule supporting part B341 connects between side members of the shutter B340, and partitions the gate B343. A protrusion BP343 is formed at one end of the shutter B340. A receiving groove B3431 is formed at an inner side of the protrusion BP343 to receive and/or fix an elastic member to be described later. The other side surface of the protrusion BP343 is in contact with the outer circumferential surfaces of the cams B3232, B3233, and B3234 of the cam part B3230. That is, when the cams B3232, B3233, and B3234 are rotated, the protrusion BP343 is pushed by the long radius portions of the cams B3232, B3233, and B3234, and the entire shutter B340 is pushed and moved.

Meanwhile, a to-be-detected part B344 is formed at one end of the shutter B340. The to-be-detected part B344 is formed to protrude by a predetermined length in a lengthwise direction of the shutter. The to-be-detected part B344 is an element which is detected by a detecting part, which is described later, to determine whether the shutter B340 is moved or a current position of the shutter B340.

Referring to FIG. 92, the plurality of partition members B331 are stacked. Each shutter B340a, B340b, B340c is inserted into the shutter receiving part defined by the distance among the partition members B331a, B331b, and B331c and the partition member supporting part B3314. At this time, the adjacent partition walls B3311 of the partition member B331 and the ampoule supporting parts B341 of the adjacent shutters B340 form a predetermined space in which the single ampoule is stored. Hereinafter, the space is referred to as a unit cell.

A length of one side of the unit cell is preferably formed to correspond to that of one side of the shutter 340.

Meanwhile, a side wall inserting groove B3113 is formed at one inner side surface of the housing. The partition member side wall B3312 (referring to FIG. 90) is inserted and fixed into the side wall inserting groove B3113. The side wall inserting groove B3113 may be formed in a groove formed in the inner side surface of the housing to have a predetermined depth. However, the side wall inserting groove B3113 is preferably formed by forming a stepped part B3112 therearound and thus providing the predetermined depth at an inner side of the stepped part B3112. Further, a guide groove B3114 may be formed between the side wall inserting grooves B3113 in a lengthwise direction. The guide groove B3114 serves to receive a side surface of the shutter B340 and to guide a movement of the shutter B340 in the lengthwise direction.

Meanwhile, a detecting part B360 is provided at the inner side surface of the housing. The detecting part B360 detects whether the to-be-detected part B344 of the shutter B340 is moved. In the embodiment, one pair of detecting parts B360 is provided. A first detecting part B361 detects the to-be-detected part B344 when the shutter B340 is moved and located toward the detecting part B360, and a second detecting part B362 detects the to-be-detected part B344 when the shutter B340 is located at the detecting part B360 side or moved in an opposite direction, and thus it is possible to confirm whether the shutter B340 is normally provided. Meanwhile, an infrared sensor having a light emitting part and a light receiving part may be used as the detecting part B360.

The conveyor of the ampoule type medicine dispensing container will be described with reference to FIG. 94. FIG. 94 is a perspective view illustrating a shape of the conveyor of the ampoule type medicine dispensing container according to one embodiment.

An ampoule conveyor B350 is an element on which the fallen ampoule is seated and then discharged to an outer side. The ampoule conveyor B350 includes a conveyor belt B352, a track shaft B3512, and at least one transmission gear B3511. The conveyor belt B352 includes a belt body B3521 and a belt partition wall B3522. The belt body B3521 is rotated on a track via an outer circumferential surface of the track shaft B3512. The belt partition wall B3522 is provided on the belt body B3521 to partition and form a space on which each ampoule is seated. A distance between the belt partition walls B3522 is preferably formed to be the same as that between the ampoule supporting parts B341 (referring to FIG. 91) of the shutter.

One pair of track shafts B3512 is provided and used as two rotating shafts of the track of the ampoule conveyor B350. The transmission gear B3511 receives a rotational force from the driving gear B3140 provided at the front surface of the housing to be exposed, and then transmits the rotational force to one of the track shafts B3512.

A structure of each unit cell of the storage part and an operating method of opening and closing the unit cell will be described with reference to FIGS. 95 to 97. FIGS. 95 and 96 are partially cut-away perspective views illustrating a state in which each unit cell is opened or closed, and FIG. 97 is a longitudinal cross-sectional view of FIG. 96.

Referring to FIG. 95, while the cam part B3230 is not rotated, the ampoule supporting parts B341a, B341b, and B341c of the shutter B340 block between unit cells adjacent to each other up and down. This state is defined as a closed state of each unit cell or each layer.

Referring to FIGS. 96 and 97, the shutter B340b in a second layer from the bottom is pushed back by the cam B3233, and the ampoule supporting parts B341b of the shutter B340b in the second layer are pushed and located among the partition walls B3311b and B3311c in second and third layers. At this time, the second layer is defined as an opened state. The first and third layers are still maintained in the closed state.

Meanwhile, as illustrated in FIG. 97, an elastic member B345 is provided at one end of the partition member B331 adjacent to the protrusion BP343 of the shutter B340. The elastic member B345 is provided so that both ends thereof are received and/or fixed to the receiving groove B3431 of the protrusion BP343 and the receiving groove B3315 of the partition member B331. By an elastic force of the elastic member B345, the shutter B340 may be returned to an initial position from the above-mentioned state pushed to one side by the cam. That is, the elastic member B345 provides the restoring force which restores the position of the shutter B340.

The entire shape of the ampoule type medicine dispensing container including electrical construction elements will be described with reference to FIG. 98. FIG. 98 is a block diagram illustrating the entire shape of the ampoule type medicine dispensing container according to one embodiment.

In the embodiment, the ampoule conveyor B350 may further include various detecting parts which determines whether it is necessary to additionally refill the ampoules, and a control part which controls the refilling of the ampoules.

A third detecting part B3610 directly senses whether the ampoule is on the ampoule conveyor B350 using an infrared sensor, a proximity sensor, or the like. At this time, the third detecting part B3610 is preferably provided to detect the ampoule at a distal end of the ampoule conveyor B350 in the dispensing direction. When the ampoule does not exist at the distal end of the ampoule conveyor B350 in the dispensing direction, it may be determined that the ampoule does not exist on the ampoule conveyor B350. When the ampoule is not detected any more, the third detecting part B3610 transmits a signal indicating non-existence of the ampoule to a control part B370.

A fourth detecting part B3620 directly senses the ampoule dispensed through the discharging port B3121. The fourth detecting part B3620 senses the dispensed ampoule, and transmits a signal indicating the dispensing of the ampoule to the control part B370 whenever the ampoule is dispensed.

A fifth detecting part B3630 senses the number of revolutions of the power transmission part B3511, i.e., the gears or the track shafts for transmitting power. In order to dispense one ampoule, the gear or the track shaft should be rotated by a predetermined number of revolutions. The number of revolutions necessary to dispense one ampoule is defined as one step. The fifth detecting part B3630 senses the number of steps and transmits it to the control part B370.

Only one of the third to fifth detecting parts B3610, B3620, and B3630 may be selectively provided to determine whether it is necessary to additionally refill the ampoule on the ampoule conveyor B350. To ensure the accuracy, two or more detecting parts may be provided.

The control part B370 includes a refill determining means B3710 and an ampoule refill controlling means B3720. The refill determining means B3710 may determine that it is necessary to refill the ampoules, when receiving the signal indicating the non-existence of the ampoule on the ampoule conveyor B350 from the third detecting part B3610. Further, the refill determining means B3710 may receive the signal from the fourth detecting part B3620, may calculate the total number of the dispensed ampoules, and then may determine that it is necessary to additionally refill the ampoules, when the number of the dispensed ampoules reaches the total number of the refilled ampoules. Further, the refill determining means B3710 may receive the signal or the number of steps from the fifth detecting part B3630, whenever the step is performed, may calculate the number of the dispensed ampoules, and thus may determine whether it is necessary to refill the ampoules.

When it is determined by the refill determining means B3710 that the ampoule does not exist on the conveyor, the ampoule refill controlling means B3720 controls the driving part B320 to fall the ampoule on the ampoule conveyor B350. Hereinafter, the controlling method of the ampoule type medicine dispensing container will be described in detail on the basis of the ampoule refill controlling means B3720.

The controlling method of the ampoule type medicine dispensing container will be described with reference to FIGS. 99 to 105. FIGS. 99 to 104 are partially cut-away perspective views illustrating, in turn, a state in which an ampoule type medicine is dispensed, and FIG. 105 is a flowchart illustrating, in turn, an operation sequence of the ampoule type medicine dispensing container.

FIG. 99 illustrates an initial state in which the ampoules B32 are received. As illustrated in FIG. 99, at the initial stage, the ampoules B32 may be loaded on the ampoule conveyor B350. As described previously, the ampoule conveyor B350 is operated using the external power. As illustrated in FIG. 100, when the power is transferred to the ampoule conveyor B350 to dispense the ampoule, the dispensing is performed from the ampoule located at the distal end in the dispensing direction. If all of the ampoules on the ampoule conveyor B350 are discharged, the control part determines that it is necessary to refill the ampoule, and starts a controlling operation for refilling the ampoules.

When the refilling of the ampoules is started, the control part controls the driving part B3230 to open the first layer of the storage part B330. As illustrated in FIG. 102, when the third cam B3234 is rotated in one direction B3D1, and the third shutter B343c is pushed in the dispensing direction B3D2, the first layer B330c of the storage part B330 is opened. If the first layer B330c of the storage part B330 is opened, the ampoules stored in the first layer B330c are fallen on the ampoule conveyor B350, and thus the ampoules are refilled. When the refilling of the ampoules is completed, the number of steps or the number of the dispensed ampoules, which is calculated to determine whether it is necessary to refill the ampoules, is initialized.

Then, the control part may set the storage part B330 in a refill standby state. In the refill standby state, the ampoules are filled in each layer from the lowermost layer to refill the ampoules. As illustrated in FIG. 103, the control part controls the cam part B3230 to be further rotated in the one direction B3D1, such that the second layer B330b of the storage part B330 is pushed in the dispensing direction B3D2 to be opened. If the second layer B343b is opened, the ampoules stored in the second layer B343b are fallen down. Then, as illustrated in FIG. 104, the control part controls the cam part B3230 to be further rotated in the one direction B3D1, such that the third layer B330a of the storage part B330 is pushed in the dispensing direction B3D2 to be opened. If the third layer B343a is opened, the ampoules stored in the third layer B343a are fallen down.

Meanwhile, the ampoules received in the first layer should be fallen only when the ampoule does not exist on the conveyor any more. However, the ampoules of the second or more layers may be fallen on various timings. Regardless of whether the conveyor is operated, the cam may be rotated in a constant speed to open the first, second, and third layers in turn. When the ampoule does not exist on the conveyor, the ampoules of the second or more layers may be controlled to be fallen down in turn.

In brief, as illustrated in FIG. 105, in a state in which the ampoules are refilled in the dispensing container (B3S10), if the external power is applied (B3S20), the dispensing of the ampoules seated on the conveyor are stated (B3S30). As described above, whenever each ampoule is dispensed, it is determined whether it is necessary to refill the ampoule on the conveyor (B3S40). When it is necessary to refill the ampoule on the conveyor, the storage part is opened and closed in turn from the lowermost layer (B3S50), and thus the ampoule is refilled on the conveyor, and the ampoules are controlled to be located at the lower layer of the storage part.

4-9. Medicine Dispensing Container #4—Pouch Type Medicine Dispensing Container

Hereinafter, the configuration related to a pouch type medicine dispensing container according to one embodiment of the present invention will be described in detail with reference to drawings.

FIG. 106 is a schematic perspective view illustrating the pouch type medicine dispensing container according to one embodiment of the present invention, and FIGS. 107 and 108 are schematic perspective views explaining a principle in which a rotating part provided at the pouch type medicine dispensing container according to one embodiment of the present invention is rotated from a housing.

The pouch type medicine dispensing container BOX4 according to one embodiment of the present invention may be a container which may dispense pouch type medicines B4110 one by one to an outer side according to a prescription for a patient, and may be fixed to the cartridge of the medicine dispensing device together with the blister-packed medicine dispensing container and the ampoule type medicine dispensing container.

In other words, the pouch type medicine dispensing container BOX4 may be a kind of pouch type medicine dispensing container which is fixed to the cartridge of the medicine dispensing device and dispenses the pouch type medicine B4110 when the pouch type medicine B4110 is included in a medication according to the prescription for the patient.

Specifically, the pouch type medicine dispensing container BOX4 may include a medicine receiving part B4100 which stores a plurality of pouch type medicines B4110, a housing B410 which receives the medicine receiving part B4100, and a medicine dispensing part B450 which dispenses the pouch type medicines B4110 stored in the medicine receiving part B4100 to the outer side.

Meanwhile, when all of the pouch type medicines B4110 stored in the pouch type medicine dispensing container BOX4 are dispensed through the medicine dispensing part B450 to the outer side, the new pouch type medicines B4110 may be loaded in the medicine receiving part B4100, and thus the pouch type medicine dispensing container BOX4 may be semi-permanently used.

Hereinafter, a state in which a rotating part provided at the pouch type medicine dispensing container BOX4 according to one embodiment of the present invention is rotated from a body part will be described in detail with reference to FIGS. 106 to 108.

As illustrated in FIGS. 106 to 108, the pouch type medicine dispensing container BOX4 may include the housing B410 which receives the medicine receiving part B4100, and a rotating part B430 which is coupled so as to be rotated from the housing B410. A power providing part B4130 for providing power supplied from an outer side may be provided to be exposed.

The rotating part B430 may be coupled so as to be rotated from the housing B410 and thus to expose the medicine receiving part B4100 to the outer side, and also may load the new pouch type medicines B4110 in the medicine receiving part B4100 by rotation.

Meanwhile, the rotation of the rotating part B430 may be determined by a locking part B470 provided at a side surface of a rear side of the housing B410.

In other words, as illustrated in FIGS. 107 and 108, in order to rotate the rotating part B430 and to load the new pouch type medicines B4110 in the medicine receiving part B4100, the locking part B470 may be rotated using a separate releasing member. If the locking part B470 is rotated by the releasing member, a hooking part B493 of the rotating part B430 is separated from a hooking-part-corresponding part B491 interlocked and moved with the locking part B470, and thus the rotating part B430 may be smoothly rotated from the housing B410. Therefore, as illustrated in FIG. 108, the hooking part B493 of the rotating part B430 may be released form the hooking-part-corresponding part B491.

Further, referring to FIG. 107, in a locking state, the hooking part B493 may be caught by the hooking-part-corresponding part B491, and the rotating part B430 is in a closed state.

Meanwhile, the releasing member may be configured with a kind of key which is inserted into the locking part B470 to rotate the rotating part B430, when necessary. However, to ensure medication expertise and prevent medication accidents, a separate refill station with a key may be used.

That is, as illustrated in FIG. 108, when the new pouch type medicines B4110 is loaded into the medicine receiving parts B4100 of the pouch type medicine dispensing container BOX4, the pouch type medicine dispensing container BOX4 is separated from the medicine dispensing device, and then inserted into the refill station, and thus the locking part B470 may be rotated. At this time, the key as the releasing member provided at the refill station is automatically inserted into the locking part B470 to rotate the locking part B470.

Therefore, using of the refill station to rotate the locking part B470 may more enhance safety than using of the releasing member configured with only the existing key, and the medication accidents due to loading of wrong medicines may be previously prevented.

Hereinafter, a state in which the pouch type medicine is dispensed from the medicine receiving part provided at the pouch type medicine dispensing container according to one embodiment of the present invention will be described in detail with reference to FIGS. 109 to 114.

FIGS. 109 and 110 are internal configuration views explaining an internal configuration of the pouch type medicine dispensing container according to one embodiment of the present invention, and FIGS. 111 to 114 are schematic perspective views explaining a principle in which the pouch type medicine is dispensed from the medicine receiving part provided at the pouch type medicine dispensing container according to one embodiment of the present invention.

Referring to FIGS. 109 and 110, the pouch type medicine dispensing container BOX4 may include the medicine receiving part B4100 which movably stores the plurality of pouch type medicines B4110, the housing B410 which receives the medicine receiving part B4100, and the medicine dispensing part B450 configured to provide a dispensing space B455 which dispenses the pouch type medicine B4110 located at a predetermined position, among the pouch type medicines B4110 stored in the medicine receiving part B4100, to the outer side.

Specifically, the medicine dispensing part B450 may include a closing part B451 and a dispensing space forming part B453. That is, the closing part B451 may close one side of the housing B410 formed to be opened, and the dispensing space forming part B453 may be formed to extend from one side of the closing part B451 while having the dispensing space B455.

In other words, the closing part B451 may be rotatably coupled to an upper edge of one side of the housing B410, and the dispensing space forming part B453 may be formed to extend from a lower end of the closing part B451 toward the medicine receiving part B4100.

Therefore, the pouch type medicine B4110 located at a distal end of the medicine receiving part B4100 in a dispensing direction B4120, among the pouch type medicines B4110 stored in the medicine receiving part B4100, may be dispensed to the outer side through the dispensing space B455 provided at the dispensing space forming part B453 which is in communication with the outer side by the rotation of the closing part B451.

Here, the dispensing space forming part B453 may provide the dispensing space B455 having a sufficient size to prevent the pouch type medicine B4110 from being damaged during a dispensing process. Further, the pouch type medicine B4110 may be dispensed by gravity, preferably free-fall.

Hereinafter, a principle in which the medicine dispensing part B450 is rotated will be described in detail with reference to FIGS. 111 to 113.

The medicine dispensing part B450 may be rotated about a rotating shaft B4170 disposed at an upper portion of one side of the opened housing B410, and the rotation of the medicine dispensing part B450 may be performed by a driving force provided from the outer side.

Referring to FIGS. 111 and 112, the pouch type medicine dispensing container BOX4 may further include a power providing part B4130 which provides the driving force to rotate the medicine dispensing part B450. The power providing part B4130 is coupled to the housing B410 and rotated by the driving force provided from the outer side.

Further, the medicine dispensing part B450 may include a rotation providing part B4150 which is formed to be in contact with the power providing part B4130 and to receive the driving force from the power providing part B4130.

Further, the power providing part B4130 may include a driving gear B4131 which is directly rotated by the driving force provided from the outer side, and a power transmitting gear B4133 which is coupled to be engaged with the driving gear B4131 and to transmit the driving force for the rotation of the medicine dispensing part B450 to the rotation providing part B4150. Preferably, the driving gear B4131 and the power transmitting gear B4133 may be spur gears, and the rotation providing part B4150 may be coupled to be engaged with the power transmitting gear B4133.

When the driving gear B4131 is engaged with a gear B4F for supplying the external driving force to the driving gear B4131, the rotation providing part B4150 may be engaged with the power transmitting gear B4133 to be rotated.

Specifically, the rotation providing part B4150 may have a pitch circle B4183 which is larger than a pitch circle B4181 of the power transmitting gear B4133, such that the medicine dispensing part B450 is rotated at a predetermined angle by the rotation of the power transmitting gear B4133. That is, as the rotation providing part B4150 is interlocked and rotated with the power providing part B4130, the medicine dispensing part B450 may be rotated at the predetermined angle, and the dispensing space B455 may or may not be in communication with the outer side according to the rotation of the medicine dispensing part B450.

Here, the predetermined angle is an angle in which the dispensing space B455 may be in communication with the outer side to dispense the pouch type medicine B4110. The predetermined angle may be a predetermined certain value. If the medicine dispensing part B450 is rotated at an angle which is less than the predetermined angle, the dispensing of the pouch type medicine B4110 located at a predetermined position may be blocked.

Meanwhile, as described above, the dispensing space B455 may be provided by the rotation of the medicine dispensing part B450, and the dispensing of the pouch type medicine B4110 located at a predetermined position may be dispensed to the outer side through the dispensing space B455.

That is, the medicine dispensing part B450 may be rotated from a first position in which the dispensing space B455 is not allowed to be in communication with the outer side to a second position in which the dispensing space B455 is allowed to be in communication with the outer side.

The first position may be a position before the medicine dispensing part B450 is rotated, and the second position may be a position after the medicine dispensing part B450 is rotated.

Referring to FIG. 113, when the medicine dispensing part B450 is rotated, the dispensing space B455 may be moved from a lower side B411 of the housing toward the outer side to be in communication with the outer side. That is, if the medicine dispensing part B450 is rotated, the pouch type medicine B4110 located at a predetermined position, among the pouch type medicines B4110 received in the medicine receiving part B4100, may be dispensed to the outer side through the dispensing space B455.

On the contrary, as illustrated in FIG. 111, before the medicine dispensing part B450 is rotated, the dispensing space B455 may not be allowed to be in communication with the outer side by the lower side B411 of the housing. That is, before the medicine dispensing part B450 is rotated, the dispensing to the outer side may be blocked by the lower side B411 of the housing, even though the pouch type medicine B4110 is located at the predetermined position.

Meanwhile, as described above, if the pouch type medicine B4110 located at the predetermined position is dispensed to the outer side, the medicine dispensing part B450 may be automatically rotated in an opposite direction by a restoring member B4171 coupled to the rotating shaft B4170.

Referring to FIG. 114, the restoring member B4171 may be inserted into the rotating shaft B4170, and one end of the restoring member B4171 may be in contact with the housing B410, and the other end thereof may be in contact with the medicine dispensing part B450. Further, the restoring member B4171 may be an elastic member, preferably a spring, which provides an elastic force so that the medicine dispensing part B450 is automatically rotated in the opposite direction.

In other words, since the pouch type medicine B4110 located at the predetermined position is dispensed to the outer side and then the dispensing space B455 is automatically rotated in the opposite direction by the elastic force of the restoring member B4171, the dispensing space B455 may be in a state before the medicine dispensing part B450 is rotated and thus may not be allowed to be in communication with the outer side, as illustrated in FIG. 111.

Therefore, when the pouch type medicine B4110 located at the predetermined position is dispensed to the outer side through the dispensing space B455 provided by the rotation of the medicine dispensing part B450, the pouch type medicine B4110 may be prevented from being damaged during the dispensing process, and also may be simply and precisely dispensed one by one.

FIG. 115 is a schematic perspective view explaining a state in which the pouch type medicine is moved by the medicine receiving part provided at the pouch type medicine dispensing container according to one embodiment of the present invention, and FIG. 116 is a schematic view explaining a principle in which the pouch type medicine is moved by the medicine receiving part provided at the pouch type medicine dispensing container according to one embodiment of the present invention.

Hereinafter, a process in which the pouch type medicine B4110 received in the medicine receiving part B4100 is moved to the predetermined position will be described in detail with reference to the drawings. The pouch type medicines B4110 may be moved in the dispensing direction B4120, while received in all of receiving spaces. However, for convenience of explanation, the drawings illustrate that the pouch type medicines B4110 are received at only part of the receiving spaces.

Referring to FIG. 115, the medicine receiving part B4100 may provide the receiving space such that a plurality of the pouch type medicines B4110 may be received therein to be spaced apart from each other. Therefore, the plurality of the pouch type medicines B4110 may be received in the receiving space to be spaced apart from each other.

Further, referring to FIG. 116, the medicine receiving part B4100 may be in a coil spring shape, and the movement of the pouch type medicines B4110 in the dispensing direction B4120 may be performed by the rotation of the medicine receiving part B4100.

Power for the rotation of the medicine receiving part B4100 may be provided by a rotational force providing part B4230 which is a kind of small motor. The rotational force provided by the rotational force providing part B4230 is transmitted to a rotating part B4210 coupled to be interlocked with the medicine receiving part B4100, and thus the medicine receiving part B4100 may be rotated.

Specifically, the rotational force generated by the rotational force providing part B4230 may be transmitted to the rotating part B4210 through a rotational force transmitting part B4250 and a rotational force intermediation part B4270. The rotational force transmitting part B4250 may be a kind of spur gear which is coupled to a rotating shaft of the rotational force providing part B4230.

And the rotational force intermediation part B4270 may include a spur gear part B4271 and a bevel gear part B4273 which are engaged with the rotational force transmitting part B4250 and the rotating part B4210, respectively. A rotational direction of the rotating part B4210 and a rotational direction of the rotational force transmitting part B4250 may be different from each other by the bevel gear part B4273.

In other words, when the rotational force transmitting part B4250 is rotated in a first direction B4X by the rotational force providing part B4230, the spur gear part B4271 and the bevel gear part B4273 of the rotational force intermediation part B4270 are rotated in a second direction B4X', and the rotating part B4210 may be rotated in a third direction B4Y by the bevel gear part B4273.

Therefore, the pouch type medicine B4100b received in the medicine receiving part B4100 may be moved in the dispensing direction B4120, which is the same as a direction of the rotating shaft, by the rotational movement of the rotating part B4210 in the third direction B4Y.

Therefore, in the pouch type medicine dispensing container B410 according to the present invention, the dispensing of the pouch type medicine B4110 is performed by a linear movement of the pouch type medicine B4110 caused by the rotational movement of the medicine receiving part B4100, and thus the configuration of the container may be simplified.

Meanwhile, as illustrated in FIG. 115, at least one of inner surfaces of the housing B410 may have at least one concavo-convex part B4190. That is, due to the concavo-convex part B4190, a frictional force with an inner side wall of the housing B410 may be reduced, when the pouch type medicine B4110 is moved by the rotation of the medicine receiving part B4100.

As described above with reference to FIGS. 106 to 116, the plurality of pouch type medicines B4110 may be received in the medicine receiving part B4100 disposed in the pouch type medicine dispensing container BOX4 to be spaced apart from each other, and the pouch type medicines B4110 may be located at the predetermined position by the rotational movement of the medicine receiving part B4100. Therefore, the pouch type medicines B4110 located at the predetermined position may be dispensed one by one to the outer side through the dispensing space provided by the rotation of the medicine dispensing part B450.

Here, the pouch type medicine dispensing container BOX4 may include a control part which may control the rotational movement of the medicine receiving part B4100 and the rotation of the medicine dispensing part B450, and a sensing part which detects whether the pouch type medicines B4110 are located at the predetermined position.

The control part may receive a command requesting the dispensing of the pouch type medicine B4110 from an external device, and may control the rotational movement of the medicine receiving part B4100, when the requesting command is received. That is, the control part may control the driving of the rotational force providing part B4230 which provides the power for the rotational movement of the medicine receiving part B4100, and the pouch type medicines B4110 received in the medicine receiving part B4100 may be moved in the dispensing direction B4120 and then located at the predetermined position.

Further, if it is determined by the sensing part that one of the plurality of pouch type medicines B4110 received in the medicine receiving part B4100 is located at the predetermined position, the control part may control the rotation of the medicine dispensing part B450 so that the pouch type medicine B4110 located at the predetermined position is dispensed to the outer side. That is, the control part may control the driving of the power providing part B4130 providing the power for the rotation of the medicine dispensing part B450, and also may control so that the medicine dispensing part B450 is rotated at the predetermined angle by the rotation of the power providing part B4130, and thus the dispensing space B455 provided by the medicine dispensing part B450 is in communicated with the outer side.

Therefore, the pouch type medicines B4110 located at the predetermined position may be dispensed one by one to the outer side through the dispensing space B455.

Here, the control part may control the driving of the medicine dispensing part B450 and the medicine receiving part B4100 at the same time or in turn. Further, if it is determined by the sensing part that one of the plurality of pouch type medicines B4110 received in the medicine receiving part B4100 is located at the predetermined position, the control part may control the driving of the rotating part B4210 due to the rotational force providing part B4230 to be stopped, and may simultaneously control the medicine dispensing part B450 so that the pouch type medicine B4110 located at the predetermined position is immediately dispensed.

In other words, the control part controls only one of the plurality of pouch type medicines B4110 received in the medicine receiving part B4100 to be located at the predetermined position corresponding to a distal end in the dispensing direction B4120, such that the pouch type medicines B4110 received in the medicine receiving part B4100 may be dispensed one by one.

Meanwhile, as described above, the medicine receiving part B4100 may be driven by the power supplied from an inner side, i.e., the rotational force providing part B4230, and the medicine dispensing part B450 may be selectively driven by the power supplied from the outer side.

The supplying of the external power supplied to the medicine dispensing part B450 may be determined by the sensing part which determines whether one of the pouch type medicines B4110 received in the medicine receiving part B4100 is located at the predetermined position corresponding to the distal end in the dispensing direction B4120.

That is, if it is determined by the sensing part that one of the pouch type medicines received in the medicine receiving part B4100 is located at the predetermined position, the control part may control the power providing part B4130 providing the power for the rotation of the medicine dispensing part B450 to be driven.

Until now, the configurations and characteristics of the present invention have been described on the basis of the embodiments according to the present invention, but the present invention is not limited thereto. Various modifications or changes within the spirit of the invention would be obvious to those skilled in the art. Therefore, the modifications or changes belong to the claims.

For example, the power providing part B4130 and the rotation providing part B4150 may be configured with gears, such that the medicine dispensing part B450 may be rotated from the housing B410, but are not limited thereto. The power providing part B4130 and the rotation providing part B4150 may be configured with belts, chains, or the like.

Until now, the main construction elements of the first medicine dispensing device 100, and the medicine dispensing containers D100, BOX1, BOX2, BOX3, and BOX4 which are designed so as to be installed in the first medicine dispensing device 100 and to automatically dispense the various types of medicines have been described.

Hereinafter, the second medicine dispensing device 200 will be described.

5. Second Medicine Dispensing Device

FIG. 117 is a schematic perspective view illustrating the second medicine dispensing device according to the present invention, and FIGS. 118 and 119 are schematic perspective views illustrating a packed medicine dispensing means and a packed medicine dispensing means moving part provided at the second medicine dispensing device according to the present invention.

Referring to FIGS. 117 to 119, the second medicine dispensing device 200 according to the present invention may include a packed medicine dispensing container M4 which receives at least one packed medicine, a cartridge M6 for installing the packed medicine dispensing container (hereinafter called a "cartridge"), which allows the packed medicine dispensing container M4 to be installed in the second medicine dispensing device 200, a packed medicine dispensing means M8 which dispenses the packed medicines received in the packed medicine dispensing container M4, and a packed medicine dispensing means moving part M10 which moves the packed medicine dispensing means M8 to each layer in the second medicine dispensing device 200.

In the aspect of a basic function, the packed medicine dispensing container M4 which may be installed in the second medicine dispensing device 200 according to present invention, and the various medicine dispensing containers D100 which may be installed in the first medicine dispensing device 100 perform a similar function of storing the medicines and dispensing the stored medicines using the external power provided from the outer side.

Further, in the aspect of the basic function, the cartridge M6 for installing the packed medicine dispensing container, which is provided at the second medicine dispensing device 200 according to present invention, and the cartridge D200 which is provided at the first medicine dispensing device 100 perform a similar function of allowing the packed medicine dispensing container M4 or the medicine dispensing container D100 to be installed in the second medicine dispensing device 200 or the first medicine dispensing device 100.

Also, in the aspect of the basic function, the packed medicine dispensing means M8 provided at the second medicine dispensing device 200 according to present invention, and the medicine dispensing driving means D300 provided at the first medicine dispensing device 100 perform a similar function which provides the external power to dispense the medicines stored in the packed medicine dispensing container M4 or the medicine dispensing container D100.

Also, in the aspect of the basic function, the packed medicine dispensing means moving part M10 provided at the second medicine dispensing device 200 according to present invention, and the medicine dispensing driving means moving part D400 provided at the first medicine dispensing device 100 perform a similar function of allowing the interlayer movement of the packed medicine dispensing means M8 or the medicine dispensing driving means D300.

However, the second medicine dispensing device 200 may have a different structure from the first medicine dispensing device 100 in an aspect that will be described below.

Hereinafter, the detailed configuration of the second medicine dispensing device 200 will be described.

In the second medicine dispensing device 200 according to the present invention, the plurality of packed medicine dispensing containers M4 may be installed on the cartridge M6, and the cartridge M6 may be provided at each layer of the second medicine dispensing device 200.

At least one cartridge M6 may be installed at each layer of the second medicine dispensing device 200, and the number of packed medicine dispensing containers M4 installed in one cartridge M6 may be variously changed according to intentions of those skilled in the art.

Here, the second medicine dispensing device 200 may allow the withdrawing of the medicine receiving part M12 of the packed medicine dispensing container M4 receiving at least one packed medicine, and the dispensing of the packed medicine by the packed medicine dispensing means M8. The packed medicine dispensing container M4 may be removably inserted and installed in the cartridge M6.

The packed medicine dispensing means M8 may apply a withdrawing external force to the packed medicine dispensing container M4 fixed to a predetermined position on the cartridge M6, may expose at least one of the packed medicines, and may apply a dispensing external force to the exposed packed medicine and dispense the exposed packed medicine to an outer side.

The packed medicine dispensed to the outer side may be seated on the conveyor part M16 of the packed medicine dispensing means M8, may be displaced by a rotational movement of a belt of the conveyor part M16, and then may be gathered in a predetermined external space.

Meanwhile, an interlayer movement of the packed medicine dispensing means M8 may be performed by the packed medicine dispensing means moving part M10, and the packed medicine dispensing means moving part M10 may move the packed medicine dispensing means M8 to a layer in which the packed medicine dispensing container M4 receiving the necessary packed medicines is disposed according to an external signal.

In other words, when a signal according to a prescription for a patient is applied to the second medicine dispensing device 200 according to the present invention, the packed medicine dispensing means moving part M10 moves the packed medicine dispensing means M8 to the desired layer according to the signal, and then the necessary packed medicine may be dispensed from the packed medicine dispensing container M4 by the withdrawing external force and the dispensing external force due to the packed medicine dispensing means M8.

The dispensed packed medicine may be seated on the conveyor part M16, and the conveyor part M16 on which the packed medicine is seated, i.e., the packed medicine dispensing means M8, is moved to a position corresponding to a preset dispensing space MS1 by the packed medicine dispensing means moving part M10, and thus the seated packed medicine may be gathered in the predetermined external space by the rotational movement of the belt of the conveyor part M16.

However, the rotational movement of the belt of the conveyor part M16 is not limited to a state in which the rotational movement is performed after the conveyor part M16 is moved to the position corresponding to the preset dispensing space MS1. The rotational movement may be performed before the conveyor part M16 is moved to the position corresponding to the preset dispensing space MS1.

Meanwhile, when the packed medicines according to the prescription for the patient are received in the plurality of packed medicine dispensing containers M4 disposed in each layer and the plurality of packed medicine dispensing containers M4 disposed in multiple layers, the packed medicine dispensing means M8 may be moved to a certain layer by the packed medicine dispensing means moving part M10 and may dispense the packed medicines in turn from the plurality of packed medicine dispensing containers M4 disposed at the corresponding layer. When the dispensing in the layer is completed, the packed medicine dispensing means M8 may be moved to another layer, and then may perform the dispensing of the packed medicine again.

If the dispensing of the packed medicines from the plurality of packed medicine dispensing containers M4 according to the prescription for the patient is completed, the conveyor part M16 on which the plurality of packed medicines are seated, i.e., the packed medicine dispensing means M8, is finally moved to a position corresponding to the preset dispensing space MS1 by the packed medicine dispensing means moving part M10, and the plurality of seated packed medicines may be gathered in the predetermined external space by the rotational movement of the belt of the conveyor part M16.

5-1. Dispensing Principle of Packed Medicine from Packed Medicine Dispensing Container by Packed Medicine Dispensing Means FIGS. 120 to 126 are schematic perspective views illustrating an operation relationship between the packed medicine dispensing means and the packed medicine dispensing means moving part provided at the second medicine dispensing device according to the present invention.

Referring to FIG. 120, the dispensing of the packed medicine from the packed medicine dispensing container M4 may be performed by the dispensing external force due to a dispensing external force applying part M20, after the medicine receiving part M12 of the packed medicine dispensing container M4 is dispensed by a withdrawing external force applying part M18 of the packed medicine dispensing means M8.

Specifically, when the signal according to the prescription for the patient is applied to the second medicine dispensing device 200 according to the present invention, the packed medicine dispensing means moving part M10 moves the packed medicine dispensing means M8 including the withdrawing external force applying part M18, the dispensing external force applying part M20 and the conveyor part M16 to the desired layer according to the signal.

In the layer to which the packed medicine dispensing means M8 is moved, at least one packed medicine dispensing container M4 may be installed and arranged on at least one cartridge M6, and the withdrawing external force applying part M18 of the packed medicine dispensing means M8 is moved to a position corresponding to one of the packed medicine dispensing containers M4 receiving the necessary medicine.

When the withdrawing external force applying part M18 is completely moved to the position corresponding to one of the packed medicine dispensing containers M4, the withdrawing external force applying part M18 is slid along a separation preventing guide part M22 and moved toward the packed medicine dispensing container M4.

Meanwhile, the withdrawing external force applying part M18 may have an attractive force with the packed medicine dispensing container M4, and may include an electromagnet which is magnetized according to a current flow so that the attractive force may be controlled.

Here, the medicine receiving part M12 of the packed medicine dispensing container M4 may have a front surface part M24 reacting to magnetism of the withdrawing external force applying part M18, such that the attractive force is generated between the withdrawing external force applying part M18 and the packed medicine dispensing container M4. The withdrawing external force applying part M18 and the medicine receiving part M12 may be interlocked and moved together by the attractive force acting between the withdrawing external force applying part M18 and the packed medicine dispensing container M4.

Eventually, the withdrawing external force applying part M18 moved toward the front surface part M24 of the packed medicine dispensing container M4 may be returned to its original position while the attractive force with the medicine receiving part M12 is applied thereto, and thus may withdraw the medicine receiving part M12 from a supporting part M14.

Meanwhile, in the packed medicine dispensing container M4, at least one packed medicine MT may be exposed to an outer side by the withdrawing of the medicine receiving part M12, and the exposed packed medicine MT is maintained in a standby state to be dispensed to the conveyor part M16.

The packed medicine MT exposed to the outer side may receive the dispensing external force due to a movement of the dispensing external force applying part M20 of the packed medicine dispensing means M8, and may be finally dispensed to the conveyor part M16 by the dispensing external force due to the dispensing external force applying part M20.

Here, the packed medicine MT dispensed to the conveyor part M16 by the dispensing external force of the dispensing external force applying part M20 may be a packed medicine MT which is located at a frontmost side of the packed medicines received in the medicine receiving part M12. If the packed medicine MT located at the frontmost side is dispensed by the movement of the dispensing external force applying part M20, another packed medicine may be automatically disposed at the position.

Therefore, if one packed medicine is dispensed to the conveyor part M16, the medicines in the medicine receiving part M12 may be automatically arranged in turn from the frontmost side, and then may be repeatedly dispensed by the movement of the dispensing external force applying part M20.

Here, the packed medicine MT seated on the conveyor part M16 may be moved up and down by the packed medicine dispensing means moving part M10, and also may be gathered in the predetermined external space by the rotational movement of the belt of the conveyor part M16.

Meanwhile, when it is necessary to dispense two or more packed medicines from one packed medicine dispensing container M4, one packed medicine is dispensed by the movement of the dispensing external force applying part M20, and then other packed medicines may be dispensed by the repeated movement of the dispensing external force applying part M20, while the medicine receiving part M12 of the packed medicine dispensing container M4 is withdrawn.

The dispensing of the two or more packed medicines through the repeated movement of the dispensing external force applying part M20 may be realized by automatically moving the packed medicines in the medicine receiving part M12 toward the frontmost side.

Hereinafter, the packed medicine dispensing container M4, the packed medicine dispensing means M8 and the cartridge M6 for installing the packed medicine dispensing container will be described in detail.

5-2. Packed Medicine Dispensing Container

FIGS. 127 and 128 are schematic perspective views illustrating the packed medicine dispensing container provided at the second medicine dispensing device according to the present invention, FIG. 129 is a partial exploded perspective view illustrating the packed medicine dispensing container provided at the second medicine dispensing device according to the present invention, and FIG. 130 is a schematic perspective view illustrating a state after the medicine receiving part of the packed medicine dispensing container provided at the second medicine dispensing device according to the present invention is withdrawn.

Referring to FIGS. 127 to 130, the packed medicine dispensing container M4 provided at the second medicine dispensing device 200 according to the present invention may include the medicine receiving part M12 having a predetermined internal space MS2 receiving at least one packed medicine, and the supporting part M14 supporting the medicine receiving part M12.

Here, the supporting part M14 may be a construction element installed at the cartridge M6, and the medicine receiving part M12 may be seated on the supporting part M14 to be withdrawn.

In other words, the medicine receiving part M12 may be moved from the supporting part M14 in a withdrawing direction so that at least one of the one or more packed medicines arranged in the internal space to be dispensed is exposed to the outer side, and this may be performed by the withdrawing external force due to the withdrawing external force applying part M18 of the packed medicine dispensing means M8.

That is, the withdrawing external force may be provided by the withdrawing external force applying part M18 including the electromagnet which is magnetized according to the current flow. The medicine receiving part M12 may have the front surface part M24 which reacts to the magnetism of the electromagnet and generates the attractive force with the electromagnet, and thus may be interlocked and moved with the withdrawing external force applying part M18.

When the movement of the medicine receiving part M12 in the withdrawing direction by the withdrawing external force due to the withdrawing external force applying part M18 is completed, and at least one of the packed medicines is dispensed to the outer side, the medicine receiving part M12 may be automatically returned to its original position by removing the withdrawing external force.

Here, the cutting-off of the attractive force acting between the medicine receiving part M12 and the withdrawing external force applying part M18 by the removing of the withdrawing external force may be performed by cutting off the current applied to the medicine receiving part M12 including the electromagnet. The automatic returning of the medicine receiving part M12 may be performed by an elastic member or an attractive force of a magnet provided at the medicine receiving part M12 and the supporting part M14.

However, the returning of the medicine receiving part M12 is not limited to being performed by removing the withdrawing external force. When the movement due to the withdrawing external force is completed, and at least one of the packed medicines is dispensed to the outer side, the medicine receiving part M12 may be returned to its original position by a directional change of the withdrawing external force.

The medicine receiving part M12 may be slid from the supporting part M14 by the withdrawing external force due to the withdrawing external force applying part M18 and may be moved in the withdrawing direction. For smooth sliding movement thereof, the medicine receiving part M12 and the supporting part M14 may have a movement guide part M26 and a rotating part M28, respectively.

The movement guide part M26 may be a kind of ball bearing, and may be rotatably coupled to an extending part M30 formed to extend from a lower end of a side wall of the medicine receiving part M12 toward a side surface of the supporting part M14.

Here, as illustrated in the drawings, a single movement guide part M26 may be coupled to a single extending part M30, but the present invention is not limited thereto. At least one movement guide part M26 may be provided according to intentions of those skilled in the art.

The movement guide part M26 may be moved along the side surface of the supporting part M4 so as to guide the movement of the medicine receiving part M12 in the withdrawing direction. The side surface of the supporting part M14 may have a movement guide corresponding part M32 which is inserted into the movement guide part M26 and recessed in the withdrawing direction to provide a moving route of the movement guide part M26.

Therefore, when the medicine receiving part M12 is withdrawn from the supporting part M14 by the withdrawing external force due to the withdrawing external force applying part M18, the movement guide part M26 serves as a kind of wheel in the movement guide corresponding part M32, and thus the medicine receiving part M12 may be smoothly withdrawn.

Meanwhile, the withdrawing of the medicine receiving part M12 from the supporting part M14 may be more smoothly performed by the rotating part M28 which is a kind of ball bearing. The rotating part M28 may be provided at the supporting part M14.

That is, the rotating part M28 may be coupled with the supporting part M14 to be in contact with a lower surface of the medicine receiving part M12 and to be rotated at a predetermined position, such that the movement of the medicine receiving part M12 in the withdrawing direction is guided.

Here, like the movement guide part M26, the number of rotating parts M28 is not limited to only one, and one or more rotating parts may be provided according to intentions of those skilled in the art.

The sliding withdrawal of the medicine receiving part M12 from the supporting part M14 due to the withdrawing external force applying part M18 may be performed by the rotational movement of the movement guide part M26 in the movement guide corresponding part M32 and the rotation of the rotating part M28 at the predetermined position. The movement guide part M26 and the rotating part M28 may be configured with a means other than the ball bearing.

FIG. 131 is a schematic perspective view illustrating an inner side of the packed medicine dispensing container provided at the second medicine dispensing device according to the present invention, and FIG. 132 is a schematic exploded perspective view illustrating the inner side of the packed medicine dispensing container provided at the second medicine dispensing device according to the present invention.

Referring to FIGS. 131 and 132, as described above, at least one packed medicine may be arranged in the medicine receiving part M12, and at least one of the packed medicines arranged in the internal space MS2 may be exposed to the outer side by the withdrawing of the medicine receiving part M12 from the supporting part M14.

The at least one exposed packed medicine may be dispensed to the conveyor part M16 by the movement of the dispensing external force applying part M20. When the dispensing is completed, the packed medicines arranged in the medicine receiving part M12 may be automatically displaced to be arranged in turn from the front most side.

Here, to smoothly move the packed medicine in the medicine receiving part M12, a frictional force generated between the packed medicine and the medicine receiving part M12 by the position change should be reduced, and this may be realized by at least one seating part M34 having a concavo-convex surface.

The seating part M34 may be a kind of bottom wall in the medicine receiving part M12 on which the packed medicine is seated, and a contact surface area with the packed medicine in the internal space MS3 may be reduced by a concavo-convex shape continuously formed in the withdrawing directing, and thus the packed medicine may be moved smoothly.

Meanwhile, in the seating part M34, the supporting part M may be configured with a removal part M36 formed to extend downward and removably inserted into a removal corresponding part M38 formed on the supporting part M14. One of the removal part M36 and the removal corresponding part M38 may be formed in a protrusion shape, and the other may be formed in a groove or hole shape.

If the removal part M36 is inserted into the removal corresponding part M38, a predetermined spacing space MS3 may be formed between the seating part M34 and another seating part M34, and the spacing space MS3 may provide a moving route in which a pressing part M40 to be described later is moved in the withdrawing direction.

FIGS. 133 and 134 are internal configuration views for explaining an operation principle of the pressing part of the packed medicine dispensing container provided at the second medicine dispensing device according to the present invention.

Referring to FIGS. 133 and 134, a position movement of the packed medicine MT in the medicine receiving part M12 may be performed by the pressing part M40 which provides a forward pressing force to the packed medicine MT received in the internal space MS2, and a pressing source part M42 which is connected to the pressing part M40 to provide a forward restoring force to the pressing part M40 and thus to generate the pressing force.

The pressing source part M42 may be formed of a rubber material which is elastically deformed, and may move the pressing part M40 in the withdrawing direction using a restoring force with respect to the elastic deformation thereof.

The pressing part M40 may be formed to protrude above the seating part M34 of the medicine receiving part M12, and may be moved in the withdrawing direction along the spacing space MS3 formed between the seating part M34 and another seating part M34.

Here, the pressing part M40 may include a pressing movement part M44 which is disposed under the seating part M34 to be connected with the pressing source part M42, and a pressing force providing part M46 which is coupled with the pressing movement part M44 to extend above the seating part M34 and to directly provide the pressing force to the packed medicine.

The pressing movement part M44 may have a groove corresponding to part of an outer surface of the pressing source part M42 so that the pressing source part M42 is stably wound, and may be moved in the withdrawing direction by the restoring force of the pressing source part M42.

Meanwhile, the medicine receiving part M12 corresponding to a lower side of the seating part M34 may have at least one protrusion fixing part M48 which protrudes so that the pressing source part M42 is wound thereon. As illustrated in the drawings, one pair of protrusion fixing parts M48 may be formed to be biased to a front side thereof.

In other words, the protrusion fixing part M48 may have the groove corresponding to part of the outer surface of the pressing source part M42 so that the pressing source part M42 is stably wound, and the pressing source part M42 may include a first pressing source part M41 and a second pressing source part M43.

The first pressing source part M41 and the second pressing source part M43 may respectively have one fixing end which is connected to the medicine receiving part M12, and the other free end which extends from the one fixing end to be elastically deformed, to be wound on the at least one protrusion fixing part M48 and then to be connected to the pressing part M40. Each of the other free ends may be integrally connected with each other and wound on the pressing part M40.

Eventually, as illustrated in the drawings, the pressing source part M42 may be a single elastic rubber member, one side end thereof may be fixed to a rear side of the medicine receiving part M12, and the other side end thereof may be elastically deformed, wound on the protrusion fixing part M48 formed at a front side thereof, wound on the pressing movement part M44, wound again on the protrusion fixing part M48 formed at the front side thereof, and then finally fixed to a rear side.

Therefore, when the packed medicine located at the frontmost side of the medicine receiving part M12 is dispensed to the conveyor part M16 by the dispensing external force applying part M20, the pressing part M40 may be automatically moved in the withdrawing direction by the restoring force of the pressing source part M42, and thus the packed medicines may be arranged in turn from the frontmost side.

FIGS. 135 to 145 are schematic views illustrating modified examples of the pressing source part of the packed medicine dispensing container provided at the second medicine dispensing device according to the present invention.

Referring to FIG. 135, a pressing source part M42a may have one fixing end which is connected to a front side, and the other free end which is connected to the pressing part M40 to be elastically deformed toward a rear side.

Here, the number of pressing source parts M42a is not limited to only one, and one or more pressing source parts may be provided according to intentions of those skilled in the art.

Referring to FIGS. 136 to 139, a pressing source part M42b may have a first pressing source part M42b1 and a second pressing source part M42b2, and in each of the first pressing source part M42b1 and the second pressing source part M42b2, the other free ends thereof are integrally connected with each other and wound on the pressing part M40.

Referring to FIGS. 140 and 141, a pressing source part M42c may be wound on a single protrusion forming part M48 formed at a front side of the medicine receiving part M12, and then may be elastically deformed toward a rear side thereof, and one free end and the other free end may be connected to the pressing part M40.

Meanwhile, as illustrated in FIG. 141, the one free end and the other free end may be integrally connected with each other, and wound on the pressing part M40.

Here, the number of pressing source parts M42c and the number of protrusion forming parts M48 are not limited to only one, and one or more pressing source parts and one or more protrusion forming parts may be provided according to intentions of those skilled in the art.

Referring to FIGS. 142 and 143, a pressing source part M42d may have a first pressing source part M42d1 and a second pressing source part M42d2, and each of the first pressing source part M42d1 and the second pressing source part M42d2 may have one free end which is connected with the medicine receiving part M12, and the other free end which extends from the one free end to be elastically deformed, is wound on the at least one protrusion fixing part M48, and then connected to the pressing part M40.

Here, the other free end of the first pressing source part M42d1 and the other free end of the second pressing source part M42d2 may be connected with each other and wound on the pressing part M40.

Referring to FIGS. 144 and 145, a pressing source part M42*e* may include a rack gear M42*e*1 and a pinion gear M42*e*2, and a spiral elastic member M42*e*3 which is coupled to a rotating shaft of the pinion gear M42*e*2, and the pressing part M40 may be coupled to the rotating shaft.

Therefore, a restoring force in the withdrawing direction may be generated by the spiral elastic member M42*e*3, and thus the pressing part M40 may be moved in the withdrawing direction by the rotation of the pinion gear M42*e*2 on the rack gear M42*e*1.

FIGS. 146 and 147 are a schematic perspective view and a partial view explaining a principle of detecting a movement of the packed medicine dispensing container provided at the second medicine dispensing device according to the present invention.

Referring to FIGS. 146 and 147, the packed medicine dispensing container M4 may have a movement detecting sensor M50 which detects whether the medicine receiving part M12 is moved from the supporting part M14, i.e., whether the withdrawing is performed.

Here, the movement detecting sensor M50 may be provided on one of the supporting part M14 and the medicine receiving part M12, and the other of the supporting part M14 and the medicine receiving part M12 on which the movement detecting sensor M50 is not provided may have a magnetic field generating part M52 which generates a magnetic field.

Here, the movement detecting sensor M50 may be a magnetic sensor which measures an intensity and a direction of the magnetic field or magnetic line of force. The movement detecting sensor M50 may detect the intensity or the direction of the magnetic field and thus may detect whether the medicine receiving part M12 is withdrawn.

As an example, as illustrated in the drawings, the magnetic field generating part M52 may be disposed as a kind of magnet at an upper surface of the rear side of the supporting part M14, and the movement detecting sensor M50 which is the magnetic sensor for detecting the magnetic field of the magnetic field generating part M52 may be disposed at a lower surface of the rear side of medicine receiving part M12.

Therefore, when the medicine receiving part M12 is withdrawn, the movement detecting sensor M50 may detect whether the medicine receiving part M12 is moved by a change of a distance between the movement detecting sensor M50 and the magnetic field generating part M52. To enhance detection accuracy, a position of the magnetic field generating part M52 may be varied.

That is, a detecting ability of the movement detecting sensor M50 may be slightly changed according to its environment. To compensate for this problem, the position of the magnetic field generating part M52 may be moved, and thus the accuracy may be ensured.

Meanwhile, the supporting part M14 may have an interference preventing space MS4 which is continuously formed in a moving direction of the medicine receiving part M12 to prevent interference with the movement detecting sensor M50 or the magnetic field generating part M52 provided at the medicine receiving part M12 and the supporting part M14 when the medicine receiving part M12 is moved.

Therefore, due to the interference preventing space MS4, the magnetic field generating part M52 disposed at the lower surface of the rear side of the medicine receiving part M12 may be stably moved in the withdrawing direction without the interference with the supporting part M14.

FIGS. 148 and 149 are partial views explaining a principle of increasing and reducing an external communication space of the packed medicine dispensing container provided at the second medicine dispensing device 200 according to the present invention.

Referring to FIGS. 148 and 149, the medicine receiving part M12 may have the external communication space MS5 corresponding to the dispensed packed medicine so as to prevent interference between the dispensed packed medicine and a side wall M54 defining the internal space when the medicine receiving part M12 receiving at least one packed medicine is withdrawn by the withdrawing external force due to the withdrawing external force applying part M18, and one packed medicine is dispensed.

Here, the external communication space MS5 may have a variable size due to a plurality of removable communication space adjusting parts M56. A size of the communication space adjusting part M56 may correspond to a width of the packed medicine received in the internal space.

In other words, various kinds of packed medicines may be received in the medicine receiving part M12 of the packed medicine dispensing container M4, and thus the packed medicines may have various widths.

In the case of the packed medicine having a relatively small width, even though the external communication space MS5 has a small size corresponding to the small width, there is no problem in withdrawing the medicine receiving part M12 and then dispensing the packed medicine through the external communication space MS5. However, in the case of the packed medicine having a greater width than the external communication space MS5, it is necessary to adjust the external communication space MS5.

Therefore, the external communication space MS5 may be adjusted by whether at least one communication space controlling part M56 is installed or removed. Therefore, the adjustment may be performed by controlling the number of installed communication space controlling parts M56 according to the width of the packed medicine.

FIGS. 150 to 152 are partial views explaining an operation principle of an aligning part of the packed medicine dispensing container provided at the second medicine dispensing device according to the present invention.

Referring to FIGS. 150 to 152, the medicine receiving part M12 may have the aligning part M58 which is movable in the internal space to press the packed medicines in one direction and thus to align the packed medicines received in the internal space MS2.

Here, the aligning part M58 may be coupled to a rotating part M60 which is rotatably coupled so as to load the new packed medicines into the internal space. Due to the aligning part M58, the packed medicines may be stably disposed in the internal space.

That is, since the packed medicines may have various sizes, the aligning part M58 which presses the packed medicines toward one side wall in one direction is required to prevent the movement of the packed medicines in the internal space.

The aligning part M58 may include a first aligning part M58*a* which is coupled to the rotating part M60 to be moved in a direction inclined at a predetermined angle with respect to the withdrawing direction, and a second aligning part M58*b* which is coupled to the first aligning part M58*a* to be moved in the same direction as the withdrawing direction.

Specifically, the first aligning part M58*a* may be moved in a direction vertical to the withdrawing direction, and thus may press the packed medicines to the one side wall, and the second aligning part M58*b* may be moved in the same direction as the withdrawing direction based on the first aligning part M58a, and thus may stably dispense the packed medicine located at the frontmost side.

The aligning part M58 may press all of the packed medicines received in the internal space except for the packed medicine located at the frontmost side toward the one side wall, and thus may stably arrange the packed medicines in the internal space. The aligning part M58 should be spaced from the packed medicine located at the frontmost side so as to apply the dispensing external force to the packed medicine arranged at the frontmost side of the dispensing external force applying part M20.

In other words, since the packed medicines received in the medicine receiving part M12 may not have a constant size, and may have various widths and sizes according to the kind of the packed medicines, the first aligning part M58a and the second aligning part M58b are movably provided in the rotating part M60, and thus all of the above-mentioned reasons may be satisfied.

FIGS. 153 to 156 are schematic views explaining an operating principle of a dispensing space increasing part of the packed medicine dispensing container provided at the second medicine dispensing device according to the present invention.

Referring to FIGS. 153 to 156, the packed medicine dispensing container M4 may include the medicine receiving part M12 and the supporting part M14 which supports the medicine receiving part M12, and may further include a passing part M62 through which the medicine receiving part M12 passes when the medicine receiving part M12 is withdrawn from the supporting part M14 by the withdrawing external force due to the withdrawing external force applying part M18.

Specifically, the passing part M62 may be coupled to the supporting part M14, and may be a structure which surrounds at least part of a side wall of the medicine receiving part M12 before the medicine receiving part M12 is moved from the supporting part M14, and through which the medicine receiving part M12 passes when the medicine receiving part M12 is moved in the withdrawing direction.

Here, the packed medicine dispensing container M4 according to the present invention may include the dispensing space increasing part M64 which is coupled to the medicine receiving part M12 so as to increase a dispensing space MS6 through which the dispensing external force applying part M20 passes when the medicine receiving part M12 passes the passing part M62 and is moved in the withdrawing direction, and then the packed medicine located at the frontmost side among the packed medicines received in the internal space is dispensed by the dispensing external force due to the dispensing external force applying part M20.

The front side of the medicine receiving part M12 may have the predetermined dispensing space MS6 formed between the front surface part M24 before the medicine receiving part is moved from the supporting part M14 in the withdrawing direction. The dispensing space increasing part M64 may increase the dispensing space MS6 when the medicine receiving part M12 is withdrawn.

That is, the dispensing space increasing part M64 is in contact with the passing part M62 before the medicine receiving part M12 passes the passing part M62, and thus a movement thereof is blocked. When the medicine receiving part M12 passes the passing part M62, the dispensing space increasing part M64 may be moved by the restoring force and thus may increase the dispensing space MS6.

In other words, when the medicine receiving part M12 passes the passing part M62, the dispensing space increasing part M64 may be moved upward by the restoring force of a restoring member M66 which is a kind of spring, and thus may increase the dispensing space MS6. Due to the increase of the dispensing space M56, the dispensing external force applying part M20 which provides the dispensing external force may be moved smoothly.

Specifically, the dispensing space increasing part M64 may include a fixing part M64a which is coupled to the medicine receiving part M12, one pair of intermediation parts M64b which are rotatably coupled to the fixing part M64a, and an elevating part M64c which is coupled to the intermediation parts M64b to be elevated by rotation of the intermediation parts M64b.

Here, the increasing of the dispensing space MS6 may be performed by an upward movement of the elevating part M64c. The upward movement of the elevating part M64c may be interlocked with the rotation of the pair of intermediation parts M64b which are rotated in the fixing part M64a.

That is, if the medicine receiving part M12 passes the passing part M62, the elevating part M64c is moved upward by the restoring force of the restoring member M66 which is coupled with the fixing part M64a to provide the restoring force to the elevating part M64c in an upward moving direction, and the intermediation parts M64b are rotated at a predetermined angle from the fixing part M64a at the same time with the upward movement.

Meanwhile, the restoring member M66 may be inserted into a restoring member fixing part M64a1 which is formed to extend from one edge of a withdrawing direction side of the fixing part M64a to approximately a center, and may also be received in a receiving groove M64c which is formed at the elevating part M64c to receive the restoring member fixing part M64a1, and thus may be stably fixed at a predetermined position.

However, the restoring member M66 is not limited to the elastic member such as the spring, and may be configured with a magnet which generates a repulsive force.

Here, the upward movement of the elevating part M64c may be effectively performed by an elevation guide part M68a and an elevation guide corresponding part M68b which is slidably inserted into the elevation guide part M68a.

Specifically, the elevation guide part M68a may be formed at one of the medicine receiving part M12 and the elevating part M64c to be recessed in an elevating direction. The elevation guide corresponding part M68b may be formed at the other one to protrude correspondingly to the elevation guide part M68a, and thus may be slid with respect to the elevation guide part M68a.

Eventually, the elevating of the elevating part M64 may be performed by sliding the elevation guide corresponding part M68b along the elevation guide part M68a. In the elevating process, separation of the elevating part M64c may be prevented in advance.

FIGS. 157 to 160 are schematic views explaining an operation principle of a withdrawal realizing part and a movement blocking part of the packed medicine dispensing container provided at the second medicine dispensing device according to the present invention.

Referring to FIGS. 157 to 160, the supporting part M14 of the packed medicine dispensing container M4 may include the movement blocking part M72 of which a position is moved by a withdrawal allowing part M70 of the cartridge M6 in which the supporting part M14 is installed. A position movement of the movement blocking part M72 may be performed by an elastic member M74.

Here, the medicine receiving part M12 may include a withdrawal realizing part M76 of which a hooked state with the movement blocking part M72 is released by the position movement of the movement blocking part M72 due to the withdrawal allowing part M70 so as to allow a movement in the withdrawing direction.

Specifically, the withdrawal realizing part M76 may be formed to protrude downward from the lower surface of the medicine receiving part M12, and a groove in which the movement blocking part M72 is hooked is formed at one side of a rear portion of the withdrawal realizing part M76.

The movement blocking part M72 may be movably fixed to an upper surface of the rear side of the supporting part M14 by a covering part M78, and may always be hooked in the groove of the withdrawal realizing part M76 by the restoring force of the elastic member M74, thereby preventing the movement of the withdrawal realizing part M76, i.e., an abnormal withdrawal of the medicine receiving part M12, in advance.

In other words, the packed medicine dispensing container M4 according to the present invention is maintained in a state in which the withdrawal realizing part M76 is hooked in the movement blocking part M72 before being installed at the cartridge M6, and the withdrawal of the medicine receiving part M12 may be prevented. However, at the moment at which the packed medicine dispensing container M4 is installed at the cartridge M6, the movement blocking part M72 is pushed by the withdrawal allowing part M70, and the withdrawal realizing part M76 may become freely movable.

Eventually, if the packed medicine dispensing container M4 is installed at the cartridge M6, the withdrawal of the medicine receiving part M12 by the withdrawing external force applying part M18 may be performed. However, if the packed medicine dispensing container M4 is not installed at the cartridge M6, the withdrawal of the medicine receiving part may be prevented.

FIGS. 161 and 162 are schematic views explaining an operation principle of a locking part of the packed medicine dispensing container provided at the second medicine dispensing device according to the present invention.

Referring to FIGS. 161 and 162, the packed medicine dispensing container M4 may include the rotating part M60 which is rotatably coupled so as to allow the loading of the new packed medicines. The rotation of the rotating part M60 may be realized by the locking part M78 formed at the rear side of the medicine receiving part M12.

Here, when all of the packed medicines received in the packed medicine dispensing container M4 are dispensed by the withdrawing external force applying part M18 and the dispensing external force applying part M20, the new packed medicines may be loaded in the packed medicine dispensing container M4. In this case, the rotating part M60 should be rotated.

The locking part M78 may include a locking intermediation part M78a of which a position is varied by a separate locking release member. The rotating part M60 may have a catching part M60a which is removably coupled to the locking intermediation part M78a so that a catching operation thereof is determined by a movement of the locking intermediation part M78a.

Meanwhile, in order to rotate the rotating part M60 and to load the new packed medicines in the medicine receiving part M12, the locking intermediation part M78a of the locking part M78 may be rotated using the separate locking release member. If the locking intermediation part M78a of the locking part M78 is rotated using the separate locking release member, the catching part M60a of the rotating part M60 is separated from the locking intermediation part M78a, and thus the rotation of the rotating part M60 may be performed.

Here, the locking release member is configured with a kind of key which is inserted into the locking part M78 to rotate the rotating part M60 when necessary. However, for the sake of specialized medications and to prevent medication accidents, a separate refill station with a key may be used.

That is, when the new packed medicines are loaded in the medicine receiving part M12 of the packed medicine dispensing container M4, the packed medicine dispensing container M4 is separated from the cartridge M6, and then inserted into the refill station, and thus the locking part M78 may be rotated.

At this time, the key provided as the releasing member at the refill station is automatically inserted into the locking part M78 to rotate the locking part M78.

Therefore, use of the refill station to rotate the locking part M78 may enhance safety more than use of the locking release member configured with only the existing key, and medication accidents due to loading of wrong medicines may be prevented in advance.

FIG. 163 is a schematic view explaining a principle of installing the packed medicine dispensing container provided at the second medicine dispensing device according to the present invention to the cartridge.

Referring to FIG. 163, the supporting part M14 may have a position fixing corresponding part M84 which is formed to be recessed from the lower surface thereof, such that a position fixing part M82 formed at the cartridge M6 in which the supporting part M14 is installed is inserted and thus a position thereof is fixed on the cartridge M6.

When the packed medicine dispensing container M4 is inserted and installed in the cartridge M6, the position fixing part M82 formed at the cartridge M6 to be moved up and down is inserted into the position fixing corresponding part M84, and thus the packed medicine dispensing container M4 may be fixed. Therefore, if the position fixing part M82 is not moved down, the packed medicine dispensing container M4 may not be separated from the cartridge M6.

Meanwhile, when the packed medicine dispensing container M4 is inserted into the cartridge M6, an insertion guide protrusion M88 formed at the cartridge M6 may be inserted into an insertion guide groove M86 which is continuously formed at lower sides of both side surfaces of the supporting part M14 in an insertion direction, and thus the supporting part M14 may be smoothly inserted into the cartridge M6.

That is, the insertion of the packed medicine dispensing container M4 into the cartridge M6 may be guided by the insertion guide protrusion M88 and the insertion guide groove M86.

Meanwhile, a separation detection corresponding part M80 configured with a kind of magnet generating a magnetic field may be coupled to the lower surface of the supporting part M4. The separation detection corresponding part M80 may operate a separation detecting sensor M90 provided at the cartridge M6, and thus may detect whether the supporting part M14 is abnormally separated from the cartridge M6.

5-3. Packed Medicine Dispensing Means

FIGS. 164 to 167 are schematic views explaining an operation principle of the withdrawing external force of the packed medicine dispensing means provided at the second medicine dispensing device according to the present invention to the cartridge, and FIGS. 168 to 173 are schematic views explaining an operation principle of the packed medicine dispensing means provided at the second medicine dispensing device according to the present invention to the cartridge.

Referring to FIGS. 164 to 173, the packed medicine dispensing means M8 may be a kind of external force applying device which applies the withdrawing external force to the packed medicine dispensing container M4 fixed to the predetermined position to receive at least one packed medicine, exposes at least one of the packed medicines, and applies the withdrawing force to the exposed packed medicine to be dispensed to the outer side.

Here, the withdrawing external force may be provided by the withdrawing external force applying part M18 which is movably coupled on a supporting frame M92, and a withdrawing external force driving power providing part M94 which is connected with the withdrawing external force applying part M18 to provide driving power for a movement of the withdrawing external force applying part M18 in the withdrawing direction.

Specifically, the withdrawing external force applying part M18 may apply the withdrawing external force to the packed medicine dispensing container M4 so as to withdraw the packed medicine dispensing container M4 installed at the cartridge M6 and to expose at least one of the packed medicines to the outer side. The withdrawing external force driving power providing part M94 may be connected with the withdrawing external force applying part M18, and may generate the driving power to move the withdrawing external force applying part M18 and to generate the withdrawing external force.

The withdrawing external force applying part M18 may be movably coupled to the supporting frame M92, and may be moved to a position corresponding to one of the packed medicine dispensing containers M4 disposed at different positions from each other. This may be performed by applying the signal according to the prescription for the patient to the second medicine dispensing device 200.

That is, in the layer to which the packed medicine dispensing means M8 is moved by the signal, at least one packed medicine dispensing container M4 may be arranged at at least one cartridge M6. The withdrawing external force applying part M18 of the packed medicine dispensing means M8 is moved on the supporting frame M92 and disposed at a position corresponding to the corresponding packed medicine dispensing container M4 receiving the necessary packed medicine.

If the withdrawing external force applying part M18 is moved at the position corresponding to the corresponding packed medicine dispensing container M4, the withdrawing external force applying part M18 is slid along the separation preventing guide part M22, and moved toward the packed medicine dispensing container M4.

The separation preventing guide part M22 may prevent the withdrawing external force applying part M18 from being separated while the withdrawing external force applying part M18 is moved to the packed medicine dispensing container M4, and may be coupled with the withdrawing external force applying part M18 so that the withdrawing external force applying part M18 is slid.

The separation preventing guide part M22 may have at least one separation preventing guide groove M22a which is continuously formed in a moving direction of the withdrawing external force applying part M1. The withdrawing external force applying part M18 may have a separation preventing guide protrusion M22b formed to correspond to the separation preventing guide groove M22a and inserted into the separation preventing guide groove M22a.

Therefore, since the movement of the withdrawing external force applying part M18 toward the packed medicine dispensing container M4 is performed while the separation preventing guide protrusion M22b is inserted into the separation preventing guide groove M22a, stable sliding may be realized.

Here, the withdrawing external force by the withdrawing external force applying part M18 may be achieved by an attractive force acting between the withdrawing external force applying part M18 and the packed medicine dispensing container M4. Specifically, the attractive force may be a force acting between the withdrawing external force applying part M18 and the front surface part M24.

The attractive force may be generated by the electromagnet which is magnetized according to the current flow, and the withdrawing external force applying part M18 may control the generation of the attractive force and the electromagnet.

The withdrawing external force applying part M18 may be moved toward the packed medicine dispensing container M4 by the driving power due to the withdrawing external force driving power providing part M94, and may provide the attractive force as the withdrawing external force to the packed medicine dispensing container M4. Further, the withdrawing external force applying part M18 may be returned to its original position by the driving power due to the withdrawing external force driving power providing part M94 while the attractive force with the packed medicine dispensing container M4 acts, and may allow the withdrawal of the medicine receiving part M12 of the packed medicine dispensing container M4.

When the medicine receiving part M12 is withdrawn by the withdrawing external force due to the withdrawing external force applying part M18, one of the packed medicines may be dispensed to the conveyor part M16 by the dispensing external force applying part M20, and the position of the packed medicine seated on the conveyor part M16 may be varied by the rotation of the belt of the conveyor part M16.

The movement of the withdrawing external force applying part M18 may be performed by the rotation of the withdrawing external force driving power providing part M94, and a moving direction of the withdrawing external force applying part M18 may be determined according to a rotational direction of the withdrawing external force driving power providing part M94.

That is, the driving force due to the withdrawing external force driving power providing part M94 may be transmitted to a withdrawing external force transmitting part M96 by the bevel gear. The withdrawing external force transmitting part M96 may include a first chain pulley part M96a, a second chain pulley part M96b and a chain part M96c.

Here, the withdrawing external force transmitting part M96 may be a kind of driving power transmitting structure which is connected with the withdrawing external force driving power providing part M94 and the withdrawing external force applying part M18 and transmits the driving power due to the withdrawing external force driving power providing part M94 to the withdrawing external force applying part M18.

The withdrawing external force driving power providing part M94 may rotate the bevel gear, and the driving power generated by the rotation may be provided to at least one of the first chain pulley part M96a and the second chain pulley part M96b. The chain part M96c may be engaged with the first chain pulley part M96a and the second chain pulley part M96b, and may be moved by the rotation of the first chain pulley part M96a and the second chain pulley part M96b.

The withdrawing external force applying part M18 may be connected with the chain part M96c to be interlocked with the movement of the chain part M96c, and may be moved toward the packed medicine dispensing container M4 or reversely. Finally, the rotational direction of the first chain pulley part M96a and the second chain pulley part M96b is changed according to the rotational direction of the withdrawing external force driving power providing part M94, and thus the moving direction of the withdrawing external force applying part M18 may also be changed.

Meanwhile, when the withdrawing external force applying part M18 is moved by the withdrawing external force driving power providing part M94, the movement of the withdrawing external force applying part M18 may be detected by a withdrawal detecting sensor M98. The withdrawal detecting sensor M98 may be coupled to a sensor seating part M100 coupled to one side surface of the separation preventing guide part M22.

A coupling position of the withdrawal detecting sensor M98 may be an initial position of the withdrawing external force applying part M18 on the sensor seating part M100 or a position corresponding to a finally disposed position, but is not limited thereto. The coupling position may be variously changed according to intentions of those skilled in the art.

Further, the number of withdrawal detecting sensors M98 may be variously changed.

If the withdrawing external force applying part M18 withdraws the medicine receiving part M12 of the packed medicine dispensing containers M4 in which the dispensing of the packed medicine will be performed, at least one packed medicine may be exposed to the outer side, and one of the exposed packed medicines may be dispensed to the conveyor part M16 by the dispensing external force due to the dispensing external force applying part M20.

Specifically, the dispensing external force applying part M20 may be disposed around the withdrawing external force applying part M18 on the supporting frame M92, may apply the dispensing external force according to the movement, and thus may dispense at least one of the packed medicines received in the packed medicine dispensing container M4 to the conveyor part M16.

Here, the dispensing external force due to the dispensing external force applying part M20 may be provided by moving the dispensing external force applying part M20 from one side of the packed medicine dispensing container M4 withdrawn by the withdrawing external force applying part M18 toward the other side thereof. The dispensing external force applying part M20 may be moved from the one side thereof to the other side thereof, and then may be moved again to the one side thereof so that another dispensing external force may be applied.

Meanwhile, the movement of the dispensing external force applying part M20 on the supporting frame M92 and the movement of the withdrawing external force applying part M18 to a position corresponding to one of the packed medicine dispensing containers disposed at another position may each be performed by different driving power. Motors M102 and 104 providing each driving power may be coupled to the supporting frame M92.

When the packed medicine is dispensed from the packed medicine dispensing container M4 by the dispensing external force due to the dispensing external force applying part M20 and then seated on the conveyor part M16, it may be detected by a stacking detection sensor M106 whether the packed medicine is dispensed or whether the packed medicine is stacked and seated on the conveyor part M16.

That is, the stacking detection sensor M106 may be disposed adjacent to the withdrawing external force applying part M18, and may detect whether the packed medicine is dispensed or whether the dispensed packed medicine is stacked.

In other words, in the second medicine dispensing device 200, the packed medicine dispensing means M8 may be moved to the layer in which the packed medicine dispensing container M4 receiving the necessary packed medicine is disposed by the packed medicine dispensing means moving part M10 according to the prescription for the patient, and the necessary packed medicine may be dispensed from the packed medicine dispensing container M4 by the withdrawing external force and the dispensing external force.

When the dispensing of the packed medicine is completed, the packed medicine dispensing means M8 may be moved to another layer according to the prescription for the patient, and may perform the dispensing of another packed medicine through repetitive operations.

Here, when the packed medicine arranged in another layer is dispensed, the different packed medicines may be received in the packed medicine dispensing containers M4 located in the different layers but the same position. In this process, there is a possibility of the different packed medicines being dispensed at the same position of the conveyor part M16.

In this case, the different packed medicines may be seated on about the same position, and thus may be seated while stacked atop one another.

Stacking of the different packed medicines may cause a problem in the movement of the withdrawing external force applying part M18 and the dispensing external force applying part M20. A means for detecting this problem is the stacking detection sensor M106.

Therefore, if stacking of the packed medicines is detected by the stacking detection sensor M106, the stacking may be removed by the rotational movement and vibration of the belt of the conveyor part M16.

However, to prevent the stacking of the different packed medicines, the rotation of the belt of the conveyor part M16 may be performed upon the interlayer movement of the packed medicine dispensing means M8.

5-4. Cartridge for Installing Packed Medicine Dispensing Container

FIGS. 174 and 175 are schematic perspective views illustrating a cartridge for installing the packed medicine dispensing container provided at the second medicine dispensing device according to the present invention.

Referring to FIGS. 174 and 175, the cartridge M6 may be a kind of packed medicine dispensing container installing structure which is provided at each layer of the second medicine dispensing device 200 and in which the packed medicine dispensing container M4 is removably inserted.

Specifically, the cartridge M6 may include a cartridge housing M108 which supports the packed medicine dispensing container M4 while restricting the packed medicine dispensing container M4 from entering over a predetermined distance, and the withdrawal allowing part M70 which protrudes from the cartridge housing M108 and allows the withdrawal of the medicine receiving part M12 of the packed medicine dispensing container M4.

When the packed medicine dispensing container M4 is inserted into the cartridge housing M108, the withdrawal allowing part M70 may be inserted into an inner side of the supporting part M14 of the packed medicine dispensing container M4, may separate the withdrawal realizing part M76 from the movement blocking part M72, and may allow the medicine receiving part M12 to be withdrawn by the withdrawing external force applying part M18.

Here, before the packed medicine dispensing container M4 is installed at the cartridge M6, the packed medicine dispensing container M4 may be maintained in a state in which the withdrawal realizing part M76 is hooked in the movement blocking part M72, and thus the withdrawal of the medicine receiving part M12 is prevented. However, at the moment at which the packed medicine dispensing container M4 is installed at the cartridge M6, the movement blocking part M72 is pushed by the withdrawal allowing part M70 of the cartridge M6, and the withdrawal realizing part M76 may become freely movable from the movement blocking part M72.

The cartridge housing M108 may include a seating housing M110 on which the packed medicine dispensing container M4 is seated, and a restricting housing M112 which is coupled to one side end of the seating housing M110 to define an entering range of the packed medicine dispensing container M4. The restricting housing M112 may be in contact with a rear side wall of the packed medicine dispensing container M4, The restricting housing M112 of the cartridge housing M108 may have a data transmitting and receiving terminal which is connected with the packed medicine dispensing container M4 so as to transmit and receive data. The cartridge housing M108 may transmit and receive information on the packed medicine to/from the packed medicine dispensing container M4 through the data transmitting and receiving terminal M114.

Meanwhile, the withdrawal allowing part M70 may protrude from the restricting housing M112 and may be formed to be parallel with the seating housing M110.

The withdrawal allowing part M70 is formed so that a width of one side end thereof is smaller than that of the other side end directed to the restricting housing M112. Therefore, when the withdrawal allowing part M70 is inserted into the supporting part M14 of the packed medicine dispensing container M4, the withdrawal allowing part M70 may smoothly push the movement blocking part M72, and thus may separate the withdrawal realizing part M76 from the movement blocking part M72.

To this end, a width of the withdrawal allowing part M70 may be linearly or non-linearly reduced after a predetermined distance from the restricting housing M112. In another aspect, one side surface of the withdrawal allowing part M70 may be formed to be inclined toward the other side surface after the predetermined distance from the restricting housing M112.

FIGS. 176 to 182 are schematic views explaining an operation principle of the position fixing part of the cartridge for installing the packed medicine dispensing container provided at the second medicine dispensing device according to the present invention.

Referring to FIGS. 176 to 182, the cartridge M6 may include the position fixing part M82 which is inserted into the position fixing corresponding part M84 formed to be recessed from the lower surface thereof, such that the position of the packed medicine dispensing container M4 is fixed. The position fixing part M82 may be installed at the seating housing M110 to be moved up and down.

The position fixing part M82 may be formed at a front side of the seating housing M110, may be moved down by a moving-down source part M116, and may be automatically moved up by a restoring force after the downward movement.

Specifically, when the position fixing part M82 is inserted into the position fixing corresponding part M84 of the packed medicine dispensing container M4, and then the dispensing of the necessary packed medicine is completed, or when the packed medicine dispensing container M4 is separated from the cartridge M6, the moving-down source part M116 moves the position fixing part M82 down, and thus the packed medicine dispensing container M4 is withdrawn from the cartridge housing M108. The moving-down force which moves the position fixing part M82 down may be provided by a contact surface with the position fixing part M82.

That is, the contact surface between the moving-down source part M116 and the position fixing part M82 is formed to be inclined with respect to the position movement direction of the moving-down source part M116 toward the restricting housing M112. When the moving-down source part M116 is moved to the restricting housing M112, the position fixing part M82 may be naturally moved down by the inclined contact surface.

Here, the moving-down source part M116 and the position fixing part M82 may be automatically returned to their original positions after the position movement of the moving-down source part M116 toward the restrict housing M112. This may be performed by a first restoring member M118 disposed between the moving-down source part M116 and the seating housing M110 and a second restoring member M120 disposed between the position fixing part M82 and the seating housing M110.

The first restoring member M118 may be a spring serving as an elastic body disposed between both side ends of the moving-down source part M116 and the seating housing M110, and the second restoring member M120 may be a spring serving as an elastic body disposed between a lower surface of the position fixing part M82 and the seating housing M110.

Here, the number of first restoring members M118 and second restoring members M120 may not be separately determined, and may be variously changed according to intentions of those skilled in the art.

The first restoring members M118 and the second restoring members M120 are not limited to the elastic bodies such as the spring, and may be configured with magnets which generate a repulsive force.

Meanwhile, when the moving-down source part M116 is moved toward the restricting housing M112, a moving range of the moving-down source part M116 toward the restricting housing M112 may be restricted by a stopper M122 disposed under the moving-down source part M116. The stopper M122 may be coupled to an upper surface of the seating housing M110.

The stopper M122 may include a buffer part which restricts the moving range through contact with the moving-down source part M116, and absorbs an impact generated at a contacting portion thereof by contact.

The buffer part may be a kind of elastic body such as a rubber material.

Meanwhile, the separation of the position fixing part M82 may be prevented by an up and down movement guide protrusion M124 and an up and down movement guide groove M126 in which the up and down movement guide protrusion M124 is inserted when the moving-down source part M116 is moved down toward the restricting housing M112 and moved up by the restoring force.

The up and down movement guide protrusion M124 may be formed to protrude from one of one side surface of the position fixing part M82 and one surface of the seating housing M110 opposite to the one side surface, and the up and down movement guide groove M126 may be formed to be recessed in the other one.

Specifically, the up and down movement guide protrusion M124 may be formed to continuously protrude from both side surfaces of the position fixing part M82 in an upward and downward moving direction. The up and down movement guide groove M126 may be formed to be continuously recessed in the upward and downward moving direction, such that the up and down movement guide protrusion M124 is moved up and down therein.

Therefore, since the up and down movement guide protrusion M124 is slid along the up and down movement guide groove M126, the upward and downward movement of the position fixing part M82 due to the position movement of the moving-down source part M116 may be stably performed.

Meanwhile, the seating housing M110 may have an insertion guide part M128 which guides an insertion of the packed medicine dispensing container M4, when the packed medicine dispensing container is inserted. The insertion guide part M128 may be disposed to correspond to a width of the packed medicine dispensing container M4.

Here, the insertion guide part M128 may have an insertion guide protrusion M88 which is inserted into an insertion guide groove M86 formed in lower sides of both side surfaces of the packed medicine dispensing container M4. The insertion guide protrusion M88 may be formed to correspond to the insertion guide groove M86.

One pair of insertion guide protrusions M88 may be formed at both sides of one insertion guide part M128, and one insertion guide protrusion M88 and another insertion guide protrusion M88 of another insertion guide part M128 may be simultaneously inserted into the pair of insertion guide grooves M86 of one packed medicine dispensing container M4.

Therefore, since the insertion guide protrusion M88 is inserted and slid in the insertion guide groove M86, the insertion of the packed medicine dispensing container M4 into the cartridge M6 may be stably performed.

FIG. 183 is a schematic view explaining an operation principle of the separation detecting sensor of the cartridge for installing the packed medicine dispensing container provided at the second medicine dispensing device according to the present invention.

Referring to FIG. 183, the separation detecting sensor M90 which detects whether the packed medicine dispensing container M4 is separated from the cartridge housing M108 may be installed at the cartridge housing M108. The separation detecting sensor M90 may detect the separation detection corresponding part M80 which is coupled to the lower surface of the supporting part M14 of the packed medicine dispensing container M4 to generate the magnetic field.

Therefore, the separation detecting sensor M90 may detect whether the packed medicine dispensing container M4 is abnormally separated from the cartridge M6, and thus may prevent the packed medicine dispensing container M4 from being withdrawn by a third person in advance.

6. Controlling Method of Medicine Dispensing System

Hereinafter, a method of controlling the medicine dispensing system according to one embodiment of the present invention will be described in detail with reference to the drawings.

The method of controlling the medicine dispensing system according to one embodiment of the present invention may be performed in the environment described with reference to FIG. 1.

Further, the method of controlling the medicine dispensing system according to one embodiment of the present invention may be performed by the medicine dispensing system 1 configured by a combination of the medicine dispensing devices 100 and 200 described with reference to FIGS. 2 to 183 and the medicine gathering device 300. However, hereinafter, for convenience of explanation, it is assumed that the medicine dispensing system 1 is configured with one first medicine dispensing device 100 and one medicine gathering device 300 (referring to FIG. 2). Further, for example, a case in which the first medicine dispensing device 100 is located at a left side of the medicine gathering device 300 will be described. That is, a left side in the first medicine dispensing device 100 is located farther from the first medicine dispensing device 100, and a right side is located closer to the first medicine dispensing device 100.

Further, hereinafter, for convenience of explanation, the control part 318 provided at the medicine gathering device 300 may control all of the operations of the medicine gathering device 300 and the medicine dispensing device 100 or 200 of the medicine dispensing system 1. However, it is not necessary that the medicine dispensing device 100 or 200 be controlled by the control part 318 of the medicine gathering device 300, and each medicine dispensing device 100 or 200 may have a separate control part which performs a necessary controlling operation.

Also, hereinafter, for example, the medicine gathering device to be described includes the same construction elements as those in the medicine gathering device 300 which was described with reference to FIGS. 7 and 8. However, it is not necessary that the method of controlling the medicine dispensing system according to one embodiment of the present invention be realized by the medicine gathering device 300 described with reference to FIGS. 7 and 8. That is, the method may be realized by a medicine gathering device including more construction elements or fewer construction elements.

FIG. 184 is a flow chart explaining the method of controlling the medicine dispensing system according to one embodiment of the present invention.

Referring to FIG. 184, the method of controlling the medicine dispensing system according to one embodiment of the present invention may include a process S10 of receiving at least one prescription, a process S12 of storing the received prescription, a process S14 of selecting at least one prescription, a process S16 of dispensing a medicine according to the prescription, and a process S18 of storing information on the dispensed medicine. Hereinafter, each process will be described in detail.

The communication part 302 may receive at least one prescription from the server 2 (S10).

The prescription may correspond to a certain patient. The prescription may include information on a kind of medicine, the number of medicines, an administration method, an administration time, or the like.

The prescription may be transmitted by the server 2 in real time, and the transmitted prescription may be received by the communication part 302 in real time, and may be received through the above-mentioned network N.

Further, the communication part 302 may receive a variety of information on the patient to whom the prescription corresponds together with the prescription. As described above, the variety of information on the patient may be personal information such as the patient's name, sex and age, medical history information such as the patient's medical records, information on a rendering physician, information on a rendering nurse, information on an inpatient clinic, information on an inpatient room, or the like. For example, the information indicating that a physician of a patient A is 'B,' his or her nurse is 'C,' and that the patient A is being hospitalized in 'Room 300' of a cancer ward may be received together with a prescription for patient A.

The memory part 308 may store the prescription received by the communication part 302 (S12).

At this time, the memory part 308 may store the variety of information on the patient corresponding to the prescription received in the process S10.

The memory part 308 may categorize and store the received prescription on the basis of the variety of information on the patient to whom the received prescription corresponds.

The category may include a rendering physician, a rendering nurse, an inpatient clinic, an inpatient room, or the like. The memory part 308 may store the received prescription in association with one of the categories.

For example, when a first prescription for patient C who has a physician A and a nurse B and is being hospitalized in room 300 of a pediatric ward, and a second prescription for patient D who has a physician A' and the nurse B and is being hospitalized in room 200 of the pediatric ward are received, the first prescription may be stored in a category of physician A, and the second prescription may be stored in a category of physician A'. Further, the first and second prescriptions may be stored in a category of nurse B. Further, the first and second prescriptions may be stored in a category of 'pediatric ward.' The first prescription may be stored in a category of 'room 300' of the pediatric ward, and the second prescription may be stored in a category of 'room 200' of the pediatric ward.

The control part 318 may select at least one prescription (hereinafter called 'at least one selected prescription') of the at least one received prescriptions (S14).

The control part 318 may automatically select the at least one selected prescription according to a predetermined algorithm, or may select at least one prescription according to a user's input.

Hereinafter, the case in which the at least one prescription is selected according to the predetermined algorithm will be described.

The control part 318 may select the prescription according to various events.

As an example, the control part 318 may select a different prescription according to a user logged in to the medicine dispensing system 1. That is, when the nurse A logs in to the medicine dispensing system 1, the control part 318 may select the prescriptions corresponding to the patients under the nurse A's care. If the nurse B logs in, the prescriptions corresponding to the patients under the nurse B's care may be selected.

As another example, the control part 318 may select different prescriptions in consideration of the administration time included in the prescriptions. That is, based on a current time, the prescriptions which prescribe that medicine be taken within a predetermined time range may be selected. That is, when the administration time is 2 p.m. in the first prescription and the administration time is 3 p.m. in the second prescription, if the current time is about 2 p.m., the control part 318 may select the first prescription, but may not select the second prescription. The predetermined time range may be changed by a user's setting, or may be preset.

For example, when the predetermined time range is +30 minutes, the prescriptions corresponding to a time range in which 30 minutes are added to the current time may be selected (in consideration of the administration time prescribed in the prescriptions). When the predetermined time range is −15 minutes to +20 minutes, the prescriptions corresponding to a time range from a time 15 minutes before the current time to a time 20 minutes after the current time may be selected.

Next, the case in which at least one prescription is selected according to the user's input will be described.

The control part 318 may provide at least one user interface to receive the user's input for selecting the at least one prescription.

As an example, the control part 318 may output a prescription list through an output part 310 so as to allow the user to separately select the prescription corresponding to each patient. Therefore, the user may select the necessary prescriptions (according to which medicines are required to be dispensed) from the prescription list. For example, the user may select the prescription corresponding to the 'patient A' and/or the 'patient B' from the prescription list displayed on an image output part 312.

As another example, the control part 318 may provide a first user interface including an image or text so as to allow the user to select at least one prescription based on the categories stored in the memory part 308. The image or the text may correspond to the ward, the inpatient room, the rendering physician, the rendering nurse, or the like, and the user may select the category necessary to select the prescriptions using the image or the text. For example, the user may select an image corresponding to the 'ward' in the categories displayed on the first user interface. Then, the control part 318 may provide a second user interface so as to allow the user to select a sub-category corresponding to the category selected by the user. For example, when the user selects the category of 'ward' through the first user interface, the control part 318 may provide the second user interface to allow the user to select at least one of the plurality of wards. Therefore, the user may select the image or the text corresponding to at least one (e.g., 'pediatric ward') of the plurality of wards (e.g., 'pediatric ward,' 'cancer ward' or the like). As described above, according to the user's selected input, the control part 318 may select at least one prescription corresponding to the patient hospitalized in the 'pediatric ward' on the basis of the variety of information on the patient stored in the memory part 308.

The control part 318 may control a medicine dispensing operation to dispense the medicine (hereinafter called 'medicine included in the prescription') included in the at least one selected prescription (S16).

The control part 318 may transmit a medicine dispensing operation request to the first medicine dispensing device 100 including at least one medicine dispensing container D100 storing the medicine included in the prescription.

The medicine dispensing operation request may include information for dispensing particular medicines included in the prescription from the at least one medicine dispensing container D100. For example, the medicine dispensing operation request may include at least one of prescription information (e.g., the kind and the number of prescribed medicines, or the like), information on the medicine dispensing container D100 storing the medicine included in the prescription (e.g., information on a stock of the medicine, expiration date of the medicine, and a position of the container), selection information of the medicine dispensing container D100 storing the medicine included in the prescription, and dispensing order information of the selected medicine dispensing container D100. Information necessary for the medicine dispensing operation (e.g., selection information and dispensing order information of the medicine dispensing container D100) will be described later in detail.

The kind of information included in the medicine dispensing operation request may be determined by role sharing between the medicine gathering device 300 and the first medicine dispensing device 100.

For example, the medicine gathering device 300 may determine all matters necessary for the medicine dispensing operation, and the first medicine dispensing device 100 may receive the determined matters and may perform only the dispensing operation. In this case, the control part 318 transmits the selection information and the dispensing order information of the medicine dispensing container D100 to the first medicine dispensing device 100, and the first medicine dispensing device 100 may control an operation of the at least one medicine dispensing container D100 to dispense the medicine included in the prescription according to the received selection information of the medicine dispensing container D100 and the dispensing order of the selected medicine dispensing container D100. Meanwhile, information on the number of medicines to be dispensed may also be transmitted and received.

As another example, the medicine gathering device 300 may transmit minimum matters necessary for the medicine dispensing operation, and the first medicine dispensing device 100 may determine all of the matters necessary for the medicine dispensing operation and may perform the dispensing operation. In this case, the control part 318 may transmit only the selected prescription information to the first medicine dispensing device 100, and the first medicine dispensing device 100 may select the medicine dispensing container D100 in consideration of the other necessary matters, may determine the dispensing order of the selected medicine dispensing container D100, and then may control the operation of the at least one medicine dispensing container D100 to dispense the medicine included in the prescription according to the determined order.

As still another example, the medicine gathering device 300 may determine and transmit some of the matters necessary for the medicine dispensing operation, and the first medicine dispensing device 100 may determine other matters necessary for the medicine dispensing operation and may perform the dispensing operation. In this case, based on the prescription or the like, the control part 318 may select the medicine dispensing container D100 and may transmit the selected information to the first medicine dispensing device 100. Based on the received selection information, the first medicine dispensing device 100 may determine the dispensing order in consideration of the other necessary matters (e.g., the position of the selected medicine dispensing container D100, or the like), and may control the operation of the at least one medicine dispensing container D100 to dispense the medicine included in the prescription according to the determined order.

The detailed controlling method of the medicine dispensing operation by the control part 318 and/or the first medicine dispensing device 100 will be described later in each related part.

The memory part 308 may store medicine dispensing information corresponding to the at least one selected prescription (S18).

The medicine dispensing information may be information on whether the medicine included in the prescription is dispensed normally according to the medicine dispensing operation request in the process S16. That is, the memory part 308 may store the dispensing information of a case in which some or all of the medicines included in the received prescription are dispensed, or a case in which some or all of the medicines included in the received prescription are not dispensed.

The memory part 308 may store the medicine dispensing information separately from the prescription stored in the process S12, or in association with the prescription. For example, the medicine dispensing information may be stored in a separate file, or the medicine dispensing information may be stored to be included in the prescription.

According to the medicine dispensing system 1 according to one embodiment of the present invention, since the medicine dispensing information is stored, the medicine corresponding to the prescription may be precisely dispensed and delivered to the patient, and a medication accident occurring when the same medicine that has already been dispensed is dispensed again and delivered to the patient may be prevented.

6-1. Controlling Method of Dispensing Operation—First Embodiment

Hereinafter, in the medicine dispensing system according to one embodiment of the present invention, a detailed method of controlling the medicine dispensing operation will be described in detail with reference to the related drawings. That is, a detailed controlling method of the process S16 of controlling the dispensing operation will be described in detail.

FIG. 185 is a flow chart explaining an operation state in which the medicine is dispensed in the medicine dispensing system according to one embodiment of the present invention, and FIG. 186 is a view explaining a method of selecting the medicine dispensing container in the medicine dispensing system according to one embodiment of the present invention.

Referring to FIG. 185, the method of controlling the medicine dispensing operation in the medicine dispensing system according to one embodiment of the present invention may include a process S40 of confirming the medicine to be dispensed on the basis of the prescription, a process S42 of confirming information on the medicine dispensing container D100 receiving the medicine to be dispensed, a process S44 of selecting the medicine dispensing container from which the medicine is dispensed, a process S46 of determining the dispensing order of the selected container, and a process S48 of controlling an operation of the medicine conveying part and the medicine dispensing container D100 according to the determined order.

As described above with reference to FIG. 184, the control part 318 may select at least one of the prescriptions received from the server 2 (S14). At this time, the control part 318 may confirm the medicine to be dispensed on the basis of the selected prescription (S40). In other words, the control part 318 may confirm the information on the kind of the medicine to be dispensed, the number of medicines, or the like, based on the prescription information included in the selected prescription.

As described above, the medicine dispensing container D100 may include at least one of the packaging type medicine dispensing container BOX1, the blister-packed medicine dispensing container BOX2, the ampoule type medicine dispensing container BOX3 and the pouch type medicine dispensing container BOX4. As described above, the packaging type medicine dispensing container BOX1, the blister-packed medicine dispensing container BOX2, the ampoule type medicine dispensing container BOX3 and the pouch type medicine dispensing container BOX4 may be disposed in the first medicine dispensing device 100.

The information on the medicine dispensing container D100 may be the information on the kind, the stock and the expiration date of the medicine, and the position of the medicine dispensing container D100.

Further, the information on the medicine dispensing container D100 may be manually input by the user, and the input information may be stored in the memory part 308. Alternatively, the information on the medicine dispensing container D100 may be separately stored in a memory included in the medicine dispensing container D100.

The control part 318 may confirm the information on the medicine dispensing container D100 receiving the medicine to be dispensed, based on the information on the medicine dispensing container D100 stored in the memory part 308.

Alternatively, the control part 318 may request the information on the medicine dispensing container D100 to the first medicine dispensing device 100.

The memory part 318 may obtain the information on the medicine dispensing container from the separate memory provided at the medicine dispensing container D100 receiving the medicine to be dispensed. Alternatively, the control part 318 may obtain the information on the medicine dispensing container receiving the medicine to be dispensed, based on the information on the medicine dispensing container previously stored by a separate memory means provided at the first medicine dispensing device 100.

Therefore, when the plurality of medicines are included in the prescription, the control part 318 may confirm each container storing the plurality of medicines among the plurality of medicine dispensing containers D100 included in the medicine dispensing system 1, and may confirm the information on the stock and the expiration date of the medicine received in the confirmed medicine dispensing container D100 and the position of the confirmed medicine dispensing container D100.

<Selection of Medicine Dispensing Container>

The control part 318 may select the container from which the medicine is dispensed based on the information on the confirmed medicine dispensing container D100 and the prescription (S44).

If the number of medicine dispensing containers D100 including one of the plurality of medicines included in the prescription is one, the control part 318 may select the one medicine dispensing container.

Meanwhile, when it is confirmed that one of the plurality of medicines included in the prescription is stored in two or more medicine dispensing containers D100 of the plurality of medicine dispensing containers D100 included in the medicine dispensing system 1, the control part 318 may select at least one medicine dispensing container D100 of the two or more medicine dispensing containers D100. At this time, in selecting the medicine dispensing container D100 of the two or more medicine dispensing containers D100, from which the medicine is actually dispensed, the control part 318 may consider at least one of the position information of the medicine dispensing container D100, and the stock and the expiration date of the medicine received in the medicine dispensing container D100.

The control part 318 may select the medicine dispensing container D100 from which the medicine is dispensed according to a predetermined order of priority of the stock, the expiration date and the position information. The control part 318 may select the medicine dispensing container D100 from which the medicine is dispensed according to a previously given weighted value with respect to at least one of the stock, the expiration date and the position information. That is, when the order of priority of the stock, the expiration date and the position information is established in an order of the expiration date→the stock→the position information, firstly, in consideration of the expiration date, the medicine dispensing container D100 from which the medicine is dispensed may be selected.

Hereinafter, a method in which the control part 318 selects at least one medicine dispensing container D100 in consideration of at least one of the stock, the expiration date and the position information will be described in detail.

Further, in the following description it will be assumed that 5 A medicines and 2 B medicines are included in a first prescription for patient A, and as illustrated in FIG. 186, a first medicine dispensing container A1, D100 storing the A medicine, a second medicine dispensing container A2, D100 storing the A medicine and a third medicine dispensing container B, D100 storing the B medicine are arranged in the first medicine dispensing device 100, for convenience of explanation.

[Expiration Date]

When it is confirmed that the A medicine is stored in A1 and A2 medicine dispensing containers A1, A2, D100 (S42), the control part 318 may preferentially select one of the A1 medicine dispensing container A1, D100 and the A2 medicine dispensing container A2, D100, which stores the A medicine having a closer expiration date. For example, when the medicine included in the A1 medicine dispensing container A1, D100 expires in one month, and the medicine included in the A2 medicine dispensing container A2, D100 expires in two months, the control part 318 may select the A medicine to be dispensed from the A1 medicine dispensing container A1, D100.

Meanwhile, in selecting the medicine dispensing container D100 from which the medicine is dispensed in consideration of the expiration date, the control part 318 may establish a critical range with respect to the expiration date, and may not consider the expiration date when the expiration date of the medicine is beyond the critical range. For example, when all of the A1 medicine dispensing container A1, D100 and the A2 medicine dispensing container A2, D100 expire in six months or more, there may be no order of priority with respect to the expiration date between the A1 medicine dispensing container A1, D100 and the A2 medicine dispensing container A2, D100. In this case, the control part 318 may select the medicine dispensing container D100 from which the medicine is dispensed in consideration of another factor having a lower priority.

[Stock]

When it is confirmed that the A medicine is stored in the A1 and A2 medicine dispensing container A2, D100 (S42), the control part 318 may preferentially select one of the A1 medicine dispensing container A1, D100 and the A2 medicine dispensing container A2, D100 that stores a smaller stock of the A medicine. For example, when the stock of the medicine included in the A1 medicine dispensing container A1, D100 is 8, and the stock of the medicine included in the A2 medicine dispensing container A2, D100 is 14, the control part 318 may select the A medicine to be dispensed from the A1 medicine dispensing container A1, D100.

However, if the stock of the medicine included in the A1 medicine dispensing container A1, D100 is smaller than the number of A medicines included in the prescription information (for example, the stock in the A1 medicine dispensing container is 3), the control part 318 may select the medicine dispensing container from which the medicine is dispensed, as follows.

The control part 318 may select all of the A1 medicine dispensing container A1, D100 and the A2 medicine dispensing container A2, D100. That is, when it is necessary to dispense a total of 5 A medicines, as prescribed in the prescription, the control part 318 may select all of the A1 medicine dispensing container A1, D100 and the A2 medicine dispensing container A2, D100, such that 3 A medicines are dispensed from the A1 medicine dispensing container A1, D100, and the remaining 2 A medicines are dispensed from the A2 medicine dispensing container A2, D100.

Alternatively, the control part 318 may preferentially select the medicine dispensing container D100 from which the entire number of medicines may be dispensed. For example, when the prescribed number is 5, and the stock in one medicine dispensing container D100 is 3, and the stock in another medicine dispensing container D100 is 10, the control part 318 may select the medicine dispensing container D100 in which the stock of the medicines is 10, such that the medicines are dispensed from the medicine dispensing container in which the stock of the medicines is 10.

Alternatively, the control part 318 may select the medicine dispensing container D100 from which the A medicine is dispensed in consideration of a factor other than the stock. In particular, the control part 318 may select the medicine dispensing container D100 from which the A medicine is dispensed in consideration of another factor having a lower priority than the stock. For example, when the A1 medicine dispensing container A1, D100 is located in a different layer from that in which the B medicine dispensing container D100 storing the B medicine is located, and the A2 medicine dispensing container A2, D100 is located in the same layer as that that in which the B medicine dispensing container D100 storing the B medicine is located, the control part 318 may select the A2 medicine dispensing container A2, D100 in consideration of a factor such as a medicine dispensing speed, such that the A medicine is dispensed from the A2 medicine dispensing container A2, D100.

[Position Relation #1—Vertical Position]

When it is confirmed that the A medicine is stored in the A1, A2 and A3 medicine dispensing containers A1, A2, A3, D100 (S42), the control part 318 may preferentially select one of the A1 medicine dispensing container A1, D100, the A2 medicine dispensing container A2, D100 and the A3 medicine dispensing container A3, D100 that is located at the highest or lowest position. For example, when the A1 medicine dispensing container A1, D100 is located at the highest position, the A3 medicine dispensing container A3, D100 is located at the lowest position, and the A2 medicine dispensing container A2, D100 is located at the middle position, the control part 318 may select the A medicine to be dispensed from the A1 medicine dispensing container A1, D100 or the A3 medicine dispensing container A3, D100.

Meanwhile, the control part 318 may consider a relative vertical distance with respect to the medicine feeding port 320 (referring to FIG. 8) before an absolute height of the medicine dispensing container D100 in the first medicine dispensing device 100. That is, the medicine dispensing container D100 which has a longer or shorter vertical distance from the medicine feeding port 320 of the medicine gathering device 300 may be selected.

Alternatively, the control part 318 may determine the medicine dispensing container D100 from which the medicine is dispensed in consideration of the relative vertical distance between the medicine dispensing container D100 and the medicine conveying part D500 in the first medicine dispensing device 100.

[Position Relation #2—Horizontal Position]

When it is confirmed that the A medicine is stored in the A1 and A2 medicine dispensing containers A1, A2, D100 (S42), the control part 318 may select one of the A1 medicine dispensing container A1, D100 and the A2 medicine dispensing container A2, D100 that is located closer to the medicine feeding port 320. For example, when one medicine gathering device 300 is included in the medicine dispensing system 1, the medicine dispensing container which is located closer to the medicine feeding port 320 of the medicine gathering device 300 may be selected. When two or more medicine gathering devices 300 are included in the medicine dispensing system 1, one medicine gathering device 300 which gathers the dispensed medicine is selected, and then the medicine dispensing container which is located closer to the medicine feeding port 320 of the selected medicine gathering device 300 may be selected.

[Position Relation #3—Relative Position Relation with Another Container]

When it is confirmed that the A medicine is stored in the A1, A2 and A3 medicine dispensing containers A1, A2, A3, D100 (S42), the control part 318 may preferentially select one of the A1 medicine dispensing container A1, D100, the A2 medicine dispensing container A2, D100 and the A3 medicine dispensing container A3, D100, which is located in the same layer as that in which the medicine dispensing container D100 which may dispense the different medicine is located. For example, when the A1 and A3 medicine dispensing containers A1, A3, D100 are located in a different layer from that in which the B medicine dispensing container B, D100 storing the B medicine is located, and the A2 medicine dispensing container A2, D100 is located in the same layer as that in which the B medicine dispensing container B, D100 storing the B medicine is located, the control part 318 may select the A2 medicine dispensing container A2, D100, such that the A medicine is dispensed from the A2 medicine dispensing container A2, D100.

Hereinafter, for more detailed description, a reference for selecting at least one medicine dispensing container D100 from which the medicine is dispensed among the plurality of medicine dispensing containers D100 will be described exemplarily.

[Expiration Date Vs. Stock]

For example, when it is assumed that the stock of the A medicine received in the A1 medicine dispensing container A1, D100 is 10 and the A medicine expires in three months, and the stock of the A medicine received in the A2 medicine dispensing container A2, D100 is 4 and the A medicine expires in one year, and 5 A medicines are prescribed in the prescription, the control part 318 may select the A1 medicine dispensing container A1, D100, which has the closer expiration date, preferentially considering the expiration date (order of priority: expiration date>stock).

However, preferentially considering the stock (order of priority: stock>expiration date), the control part 318 may select the A2 medicine dispensing container A2, D100 in preferential consideration of the stock regardless of the expiration date.

[Expiration Date Vs. Position Information]

As another example, as illustrated in FIG. 186, when it is assumed that the A1 medicine dispensing container A1, D100 storing the A medicine is disposed in the first layer of the first medicine dispensing device 100, the A2 medicine dispensing container A2, D100 storing the A medicine and the B medicine dispensing container B, D100 storing the B medicine are disposed in the second layer thereof, the A medicine stored in the A1 medicine dispensing container A1, D100 expires in three months, and the A medicine stored in the A2 medicine dispensing container A2, D100 expires in one year, the control part 318 may select the A1 medicine dispensing container A1, D100, which has the closer expiration date, preferentially considering the expiration date (order of priority: expiration date>position information).

However, preferentially considering the position information (order of priority: position information>expiration date), the control part 318 may preferentially consider the position information regardless of the expiration date. In the case as illustrated in FIG. 186, the control part 138 may select the A2 medicine dispensing container A2, D100, which is disposed in the same layer as that in which the B medicine dispensing container B, D100 is disposed, even though the A medicine stored in the A1 medicine dispensing container A, D100 has the closer expiration date.

[Stock Vs. Position Information]

As still another example, as illustrated in FIG. 186, when it is assumed that the A1 medicine dispensing container A1, D100 storing the A medicine is disposed in the first layer of the first medicine dispensing device 100, the A2 medicine dispensing container A2, D100 storing the A medicine and the B medicine dispensing container B, D100 storing the B medicine are disposed in the second layer thereof, the stock of the A medicine stored in the A1 medicine dispensing container A1, D100 is 6, and the stock of the A medicine stored in the A2 medicine dispensing container A2, D100 is 10, the control part 318 may select the A1 medicine dispensing container A1, D100, which has the smaller stock, preferentially considering the stock (order of priority: stock>position information). Alternatively, the A2 medicine dispensing container A2, D100 of which the stock is sufficient to dispense all of the number of medicines according to the prescription may be selected.

However, preferentially considering the position information (order of priority: position information>stock), the control part 318 may preferentially consider the position information regardless of the stock. Therefore, the control part 138 may preferentially consider the position relation with the B medicine dispensing container B, D100 storing the B medicine. The control part 138 may select the A2 medicine dispensing container A2, D100 which is disposed in the same layer as that in which the B medicine dispensing container B, D100 is disposed. This is because, when the medicine dispensing container located at the same layer as that in which another medicine dispensing container D100 is disposed is selected, the dispensing may be simultaneously performed at the two containers. Therefore, the dispensing of the medicine may be more rapidly performed than when the medicine is dispensed from the medicine dispensing container located in another layer.

<Determination of Medicine Dispensing Order>

The control part 318 may determine a medicine dispensing order by which the medicines are dispensed, in turn, from the selected medicine dispensing containers D100 (S46).

Hereinafter, the description will be provided with reference to FIG. 187. FIG. 187 is a view explaining the medicine dispensing order according to one embodiment of the present invention.

For example, it is assumed that A medicine is determined to be dispensed from a first medicine dispensing container 1B, D100, and B medicine is determined to be dispensed from a second medicine dispensing container 2B, D100, and C medicine is determined to be dispensed from a third medicine dispensing container 3B, D100, and D medicine is determined to be dispensed from a fourth medicine dispensing container 4B, D100.

In this case, the control part 138 may determine what order the medicines are dispensed from the first to fourth medicine containers 1B, 2B, 3B, 4B, D100.

Basically, in determining the medicine dispensing order, the factor to be considered may be a time for dispensing the medicine or a movement distance (e.g., a vertical movement distance) of the medicine conveying part D500 necessary for dispensing the medicine.

Alternatively, in determining the medicine dispensing order, the factor to be considered may be existence of a fragile medicine among the medicines and the number of the fragile medicines.

The fragile medicine is a medicine which is easily damaged or broken while the plurality of medicines are dispensed together. For example, the fragile medicine may be the ampoule type medicine.

Meanwhile, the fragile medicine is a relative concept among the medicines to be dispensed. A medicine which is regarded as the fragile medicine among the medicines included in a prescription may be regarded as a breakage-causing medicine among the medicines included in another prescription (the breakage-causing medicine means a medicine which easily breaks or destroys the fragile medicine).

For example, when the plurality of ampoule type medicines are included in a plurality of medicines to be dispensed, an ampoule type medicine having a larger volume (or a heavier weight) may be regarded as the breakage-causing medicine, and another ampoule type medicine having a smaller volume (or a lighter weight) may be regarded as the fragile medicine. Further, in the same condition, when the ampoule type medicine is formed of a more fragile material, it may be regarded as the fragile medicine, and when the ampoule type medicine is formed of a less fragile material, it may be regarded as the breakage-causing medicine.

Hereinafter, for more detailed explanation, a reference for determining the medicine dispensing order of the plurality of medicine dispensing containers D100 in various conditions will be described exemplarily.

The control part 318 may determine the dispensing order such that a moving route of the medicine conveying part D500 for conveying the medicine dispensed from the selected medicine dispensing container D100 to the medicine gathering device 300 has the shortest distance or a time for dispensing the medicine becomes the shortest. Hereinafter, the shorted moving route of the medicine conveying part D500 is referred to as the shortest route condition, and the shortest time for dispensing the medicine is referred to as the shortest time condition.

When the medicine dispensing containers D100 from which the medicines are dispensed are separately located over the plurality of layers, in order to achieve the shortest route condition or the shortest time condition, the control part 318 may determine one of the medicine dispensing container D100 located at the highest position and the medicine dispensing container D100 located at the lowest position as the medicine dispensing container D100 having the highest priority, and also may determine the other one as the medicine dispensing container D100 having the lowest priority. At this time, the rest containers other than the medicine dispensing containers D100 located at the highest position and at the lowest position may respectively have a higher priority, as located closer to the medicine dispensing container D100 having the highest priority. That is, as illustrated in FIG. 187, when the first medicine dispensing container 1B, D100 is located at the highest position, and the second medicine dispensing container 2B, D100 is located at the next highest position, and the third medicine dispensing container 3B, D100 is located at the further next highest position, and the fourth medicine dispensing container 4B, D100 is located at the lowest position, the control part 318 may determine one of the first medicine dispensing container 1B, D100 and the fourth medicine dispensing container 4B, D100 as the medicine dispensing container having the highest priority. At this time, if the first medicine dispensing container 1B, D100 is determined to have the highest priority, the second medicine dispensing container 2B, D100 may have a second priority, and the third medicine dispensing container 3B, D100 may have a third priority, and the fourth medicine dispensing container 4B, D100 may have the lowest priority. However, if the fourth medicine dispensing container 4B, D100 is determined to have the highest priority, the third medicine dispensing container 3B, D100 may have the second priority, and the second medicine dispensing container 2B, D100 may have the third priority, and the first medicine dispensing container 4B, D100 may have the lowest priority.

The control part 318 may determine the dispensing order in consideration of the existence of the fragile medicine among the medicines dispensed from the selected medicine dispensing container D100 and/or the number of the fragile medicines, such that the fragile medicines are not damaged.

The control part 318 may determine the existence of the fragile medicine among the medicines to be dispensed. For example, whether the ampoule type medicine is included in the medicines to be dispensed may be determined.

When the fragile medicine is not included in the medicines to be dispensed may be determined, the control part 318 may determine the dispensing order according to the shortest route condition or the shortest time condition.

Meanwhile, when the fragile medicine is included in the medicines to be dispensed, the control part 318 may determine the existence of the fragile medicine among the medicines to be dispensed.

If the fragile medicine is included in the medicines to be dispensed, but the breakage-causing medicine is not included, the control part 318 may determine the dispensing order according to the shortest route condition or the shortest time condition. In this case, since the breakage-causing medicine which may break the fragile medicine is not included, there is not possibility that the fragile medicine is damaged, eve when any medicine is firstly dispensed.

Meanwhile, when all of the fragile medicine and the breakage-causing medicine are included in the medicines to be dispensed, the control part 318 may determine the dispensing order so that the breakage-causing medicine is dispensed earlier than the fragile medicine. For example, when an ampoule type medicine having an X size and another ampoule type medicine having an Y size (Y is larger than X) are included in the medicines to be dispensed, the ampoule type medicine having the Y size is regarded as the breakage-causing medicine, and the ampoule type medicine having the X size is regarded as the fragile medicine. In this case, the control part 318 may determine the dispensing order so that the ampoule type medicine having the Y size, as a breakage-causing medicine, is dispensed earlier.

When all of the fragile medicine and the breakage-causing medicine are included, the reason why the breakage-causing medicine is dispensed earlier is as follows.

Firstly, in a process in which the medicines which may be dispensed in a unit of prescription are dispensed by the first medicine dispensing device 100 and conveyed to the medicine gathering device 300, the dispensed medicines may be continuously moved by the operation of the medicine conveying part D500. In this conveying process, in the case in which the fragile medicine is dispensed earlier and located at a position adjacent to the medicine dispensing container D100 storing the breakage-causing medicine, if the breakage-causing medicine free-falls on the conveying part D500, there is high possibility that the fragile medicine is damaged.

Secondly, in a process in which the medicines dispensed by the first medicine dispensing device 100 are conveyed to the medicine gathering device 300, the medicines which are gathered in the unit of prescription at one end of the medicine conveying part D500 may free-fall all at once into a medicine gathering space (not shown) of the medicine gathering device 300. If the fragile medicine firstly falls down, and then the breakage-causing medicine free-falls into the medicine gathering space, there is high possibility that the fragile medicine is damaged.

Hereinafter, the determining of the dispensing order under more specific conditions will be described with reference to FIGS. 187 and 188.

FIG. 187 illustrates a case in which the medicine dispensing containers 1B, 2B, 3B, 4B, D100 from which the medicines are dispensed are selected, and all of the selected medicine dispensing containers 1B, 2B, 3B, 4B, D100 are disposed in different layers from each other.

FIG. 188 illustrates a case in which, unlike FIG. 187, in the positions of the first to fourth medicine dispensing containers 1B, 2B, 3B, 4B, D100, the first and second medicine dispensing containers 1B, 2B, D100 are located in the same layer.

Firstly, referring to FIG. 187, it is assumed that all of the selected medicine dispensing containers 1B, 2B, 3B, 4B, D100 are disposed in different layers from each other.

At this time, when it is assumed that the breakage-causing medicine is stored in the second medicine dispensing container 2B, D100, and the fragile medicine is stored in the third medicine dispensing container 3B, D100, the control part 318 should determine the dispensing order so that the breakage-causing medicine is dispensed earlier than the fragile medicine. For example, the dispensing order, such as 2B>3B>B>4B, 2B>3B>4B>1B, 1B>2B>3B>4B, 4B>1B>2B>3B, 2B>1B>4B>3B and 2B>1B>3B>4B, may be variously determined, as long as the medicine (breakage-causing medicine) of the second medicine dispensing container 2B, D100 is dispensed earlier than the medicine (fragile medicine) of the third medicine dispensing container 3B, D100. However, the dispensing order should not be selected by the combination, such as 3B>2B>1B>4B, 3B>1B>4B>2B and 3B>1B>2B>4B, in which the medicine (breakage-causing medicine) of the second medicine dispensing container 2B, D100 is dispensed later than the medicine (fragile medicine) of the third medicine dispensing container 3B, D100. Meanwhile, in this situation, the control part 318 may determine the dispensing order by selecting the combinations that best fit the shortest route condition or the shorted time condition, among the combinations of the dispensing order in which the breakage-causing medicine is dispensed earlier than the fragile medicine. For example, the dispensing order of 1B>2B>3B>4B is the combination in which the shortest route condition or the shorted time condition is satisfied, and also the breakage-causing medicine is dispensed earlier than the fragile medicine, and thus the control part 318 may determine the dispensing order of 1B>2B>3B>4B.

However, when it is assumed that the fragile medicine is stored in the second medicine dispensing container 2B, D100, and the breakage-causing medicine is stored in the third medicine dispensing container 3B, D100, the control part 318 may determine the dispensing order of 4B>3B>2B>1B, in which the breakage-causing medicine C is dispensed earlier than the fragile medicine B, and also the shortest route condition or the shorted time condition is satisfied.

Meanwhile, when it is assumed that the fragile medicine is stored in the first medicine dispensing container 1B, D100, and the breakage-causing medicine is stored in the third medicine dispensing container 3B, D100, the control part 318 may determine the dispensing order of 4B>3B>2B>1B, in which the breakage-causing medicine is dispensed earlier than the fragile medicine, and also the shortest route condition or the shorted time condition is satisfied.

As illustrated in FIG. 188, it is assumed that the medicine dispensing containers 1B, 2B, 3B, 4B, D100 from which the medicines are dispensed are selected, and part of the selected medicine dispensing containers 1B, 2B, 3B, 4B, D100 are disposed in the same layer. Meanwhile, like the above-mentioned example, it is also assumed that the A medicine is stored in the first medicine dispensing container 1B, D100, and the B medicine is stored in the second medicine dispensing container 2B, D100, and the C medicine is stored in the third medicine dispensing container 3B, D100, and the D medicine is stored in the fourth medicine dispensing container 4B.

At this time, it is assumed that the breakage-causing medicine is stored in the second medicine dispensing container 2B, D100, and the fragile medicine stored in the first medicine dispensing container 1B, D100. Even in this case, as described in the above example, the control part 318 should determine the dispensing order so that the breakage-causing medicine is dispensed earlier than the fragile medicine. For example, the dispensing order, such as 2B>3B>1B>4B, 2B>3B>4B>1B, 1B>2B>3B>4B, 4B>1B>2B>3B, 2B>1B>4B>3B and 2B>1B>3B>4B, may be variously determined, as long as the medicine (breakage-causing medicine) of the second medicine dispensing container 2B, D100 is dispensed earlier than the medicine (fragile medicine) of the first medicine dispensing container 1B, D100. However, as illustrated in FIG. 188, since the first medicine dispensing container 1B, D100 and the second medicine dispensing container 2B, D100 are disposed in the same layer, the dispensing order is preferably determined from one of 2B>1B>3B>4B and 4B>3B>2B>1B to satisfy the shortest route condition or the shortest time condition. In this case, as described above, the medicine dispensing driving means D300 of the first medicine dispensing device 100 may be operated so that the medicines are simultaneously dispensed from the first medicine dispensing container 1B, D100 and the second medicine dispensing container 2B, D100. However, when the B medicine is the breakage-causing medicine and the A medicine is the fragile medicine, the control part 318 may control the medicine dispensing driving means D300 and each medicine dispensing container 1B, 2B, D100, such that the medicine is firstly dispensed from the second medicine dispensing container 2B, D100, before the medicine is dispensed from the first medicine dispensing container 1B, D100.

Meanwhile, in controlling the medicine dispensing operation timing of the first medicine dispensing container 1B, D100, the control part 318 may detect whether the medicine is actually dispensed from the second medicine dispensing container 2B, D100, and may control the timing so that the medicine is dispensed from the first medicine dispensing container 1B, D100, after the medicine is actually dispensed from the second medicine dispensing container 2B, D100. In this case, preferably, a sensor which detects the dispensing of the medicine is provided at the dispensing part provided at each medicine dispensing container 1B, 2B D100.

Alternatively, in controlling the medicine dispensing operation timing of the first medicine dispensing container 1B, D100, the control part 318 may control a time interval between the dispensing timing of the first medicine dispensing container 1B, D100 and the dispensing timing of the second medicine dispensing container 2B, D100, such that the medicine is dispensed from the first medicine dispensing container 1B, D100, after the medicine is actually dispensed from the second medicine dispensing container 2B, D100. That is, in this case, it is not necessary to provide the separate sensor which detects the dispensing of the medicine.

Meanwhile, it is assumed that the fragile medicine is stored in the second medicine dispensing container 2B, D100, and the breakage-causing medicine stored in the first medicine dispensing container 1B, D100. In this case, the control part 318 may determine the dispensing order of 1B>2B>3B>4B or 4B>3B>1B>2B. However, in this case, even though the breakage-causing medicine is firstly dispensed from the first medicine dispensing container 1B, D100, and then the fragile medicine is dispensed in the second medicine dispensing container 2B, if a distance between the first medicine dispensing container 1B, D100 and the second medicine dispensing container 2B is long, the fragile medicine may be actually dispensed before the breakage-causing medicine, and may be seated on the medicine conveying part D500. In this case, as described later, the operation timing of the medicine conveying part D500, the medicine dispensing driving means D300 and the medicine dispensing container D100 may be controlled to prevent the damage of the fragile medicine.

The control part 318 may control the operation of the medicine conveying part D500 and the selected medicine dispensing container D100 according to the determined medicine dispensing order (S48).

As described above, the control part 318 may control the medicine conveying part D500 to be moved up and down between the layers of the first medicine dispensing device 100 according to the determined medicine dispensing order. That is, as described above, when the medicine dispensing containers 1B, 2B, 3B, 4B, D100 are selected as the medicine dispensing containers from which the medicines are dispensed, the control part 318 may control the medicine conveying part D500 to be moved up and down to the layer corresponding to each of the medicine dispensing containers 1B, 2B, 3B, 4B, D100. That is, the interlayer movement of the medicine conveying part D500 may be performed by the medicine dispensing driving means moving part D400 described above with reference to FIG. 9. The control part 318 may transmit the medicine dispensing operation request including the medicine dispensing order to the first medicine dispensing device 100, and the medicine dispensing driving means moving part D400 may be driven according to the medicine dispensing order included in the medicine dispensing operation request. Therefore, the medicine dispensing driving means moving part D400 may move the medicine conveying part D500 to the corresponding layer in turn according to the medicine dispensing order.

Meanwhile, as illustrated in FIG. 189, the control part 318 may the medicine dispensing timing between the medicine dispensing containers D100 located in the same layer. FIG. 189 is a view explaining a method of controlling the medicine dispensing timing of the medicine dispensing containers according to one embodiment of the present invention.

As illustrated in FIG. 189, when fifth and sixth medicine dispensing containers 5B, 6B are selected as the medicine dispensing containers from which the medicines are dispensed, the control part 318 may control the medicine conveying part D500, such that an a medicine a dispensed from the fifth medicine dispensing container 5B, D100 is conveyed to one end of the medicine conveying part D500 during a time interval between a first time point t1 at which the medicine is dispensed from the fifth medicine dispensing container 5B, 100 and a second time point t2 at which the medicine is dispensed from the sixth medicine dispensing container 6B, D100. That is, when the medicines are dispensed according to the determined dispensing order, the medicine conveying part D500 may be controlled to be continuously rotated and moved, while the dispensing of the medicine is performed from the selected medicine dispensing container. Therefore, as illustrated in FIG. 189, the a medicine a may be continuously moved by the medicine conveying part D500, until the a medicine a is dispensed at the first time point t1 from the fifth medicine dispensing container 5B, D100 and seated on the medicine conveying part D500, and then the b medicine b is dispensed at the second time point t2 from the sixth medicine dispensing container 6B, D100.

A conveying speed (i.e., a rotating speed) of the medicine conveying part D500 may be constant or variable.

A conveying direction of the medicine conveying part D500 may be a direction toward the medicine gathering device 300. That is, the conveying direction of the medicine conveying part D500 may be a direction toward one end in which the medicine seated on the medicine conveying part D500 is closer to the medicine feeding port 320 of the medicine gathering device 300.

The reason why the medicine conveying part D500 is configured to be continuously rotated is to reduce the possibility that the medicine already seated on the medicine conveying part D500 and the medicine falling to the medicine conveying part D500 collide with each other and then are damaged, while the medicines dispensed at certain positions fall down and are seated on the medicine conveying part D500. Further, the medicines seated on the medicine conveying part D500 should be eventually discharged to the medicine gathering device 300 in the unit of prescription. At this time, if the medicine conveying part D500 is rotated toward the medicine feeding port 320 provided at the medicine gathering device 300, when the gathered medicines are discharged to the medicine gathering device 300, the medicines may be further rapidly discharged. Meanwhile, a gate (not shown) which may be opened and closed may be provided at the one end of the medicine conveying part D500, such that the medicines may be gathered at the one end of the medicine conveying part D500, and the medicines may be separated from the medicine conveying part D500 at only a position in which the position of the medicine conveying part D500 corresponds to the position of the medicine feeding portion 320. That is, the gate (medicine discharge blocking gate) may be closed when the medicine conveying part D500 is moved to gather the medicines dispensed from the medicine dispensing containers D100, and may be opened to convey the medicines gathered in the unit of prescription to the medicine gathering device 300, when the one end of the medicine conveying part D500 is moved to the position corresponding to the position of the medicine feeding portion 320. At this time, since the gate (medicine discharge blocking gate) which prevents the gathered medicines from being separated (discharged) from the medicine conveying part D500 is opened, the medicines may be conveyed to the medicine feeding port 320 by the operation of the medicine conveying part D500 which is continuously rotated.

Meanwhile, as described above, after all of the medicines included in one prescription are dispensed from the medicine dispensing containers D100, and then conveyed to the medicine gathering device 300 through the discharging port, the first medicine dispensing device 100 may gather and dispense the medicines included in the next prescription in the same manner.

At this time, after all of the medicines included in a first prescription are dispensed, the conveying operation of the medicine conveying part may be stopped during a period of time before the medicines to be firstly dispensed, among the medicines included in a second prescription, are dispensed from the medicine dispensing container D100.

For example, when a q medicine and an r medicine are included in the first prescription, and a k medicine and an l medicine are included in the second prescription, and the dispensing order is determined so that the k medicine is dispensed earlier than the l medicine, all of the q medicine and the r medicine are conveyed to the medicine gathering device 300, and then the conveying operation of the medicine conveying part D500 may be stopped. Then, to dispense the k medicine included in the second prescription, the medicine conveying part D500 may be moved to a layer in which the medicine dispensing container D100 storing the k medicine is located. By this time, the conveying operation of the medicine conveying part D500 may be stopped. However, at a time when the k medicine is dispensed from the medicine dispensing container to the medicine conveying part D500, the conveying operation of the medicine conveying part D500 may be resumed.

As described above, the conveying operation of the medicine conveying part D500 is to more rapidly gather and dispense the medicines. After all of the medicines included in one prescription are gathered and discharged, it is not necessary to continuously maintain the conveying operation until a point of time before the medicines included in another prescription are gathered.

As described above, while the medicine conveying part D500 is controlled to continuously perform the conveying operation, the conveying operation of the medicine conveying part D500 may be selectively stopped between the one prescription and the other prescription, and unnecessary power loss may be prevented.

However, when the medicine dispensing container D100 storing the medicine which is determined to be firstly dispensed among the medicines included in the second prescription is located at the same layer as that in which the discharging port is located, the operation of the medicine conveying part D500 is not stopped, and the medicines included in the second prescription may be immediately dispensed.

As described above, when the medicine conveying part D500 is located at the layer in which the medicine dispensing container D100 storing the medicines to be dispensed, based on the determined dispensing order, the control part 318 may control the selected medicine dispensing container D100 so that the selected medicine dispensing container D100 dispenses the medicine according to the determined medicine dispensing order. The medicine dispensing operation of the medicine dispensing container D100 may be performed by the medicine dispensing driving means D300. That is, the medicine dispensing driving means D300 may drive the at least one selected medicine dispensing container D100 so that the medicine according to the prescription is dispensed from the medicine dispensing container D100.

At this time, as described above, in the case of the medicine dispensing container D100 required to be maintained in a state in which the medicine may be dispensed from the medicine dispensing container D100 by the medicine dispensing driving means D300, the medicine dispensing container D100 may perform a preparing operation for dispensing the medicine before or at the same time as the operation of the medicine dispensing driving means D300. For example, an operation such as a process B3S10 illustrated in FIG. 105 may be the preparing operation for dispensing the medicine. As another example, as described with reference to FIG. 116, the operation in which the pouch type medicine B4110 is allowed to be located at the predetermined position (e.g., a distal end of the dispensing direction) by the rotation of the medicine receiving part B4100 may be the preparing operation for dispensing the medicine. Even in the case of other type of medicine dispensing container D100, when the preparing operation for dispensing the medicine is needed, each medicine dispensing container D100 may previously perform the preparing operation, and thus the medicine may be immediately dispensed by the driving of the medicine dispensing driving means D300.

The medicines included in the prescription may be dispensed in turn from the selected medicine dispensing container D100 according to the close interaction of the movement of the medicine conveying part D500, the medicine dispensing driving means D300 and the medicine dispensing container D100.

At this time, as described above, to prevent the damage of the fragile medicine, the medicine dispensing order is determined, and thus the damage of the medicine is prevented. However, to achieve the object which prevents the damage of the medicine by controlling the dispensing order, it is necessary to more precisely control the operation timing of the medicine dispensing container.

It is assumed that the medicine storing container D100 including the breakage-causing medicine and the medicine storing container D100 including the fragile medicine are located in the same layer, and particularly, the first medicine storing container 1B, D100 including the breakage-causing medicine is located farther from the medicine feeding port 320 than the second medicine storing container 2B, D100 including the fragile medicine, as illustrated in FIG. 188.

In this case, even though the breakage-causing medicine is firstly dispensed from the container, there is still the possibility that the fragile medicine is damaged. This is because, even though the breakage-causing medicine is firstly dispensed from the first medicine storing container 1B, D100, the medicine conveying part D500 continuously performs the rotational operation (conveying operation), and thus the firstly dispensed breakage-causing medicine is continuously moved toward the medicine feeding port 320, and the moving breakage-causing medicine may collide with the fragile medicine, when the fragile medicine is dispensed from the second medicine dispensing container 2B, D100 and seated on the medicine conveying part D500, and thus the fragile medicine may be damaged.

Therefore, in this case, the control part 318 may control the medicine dispensing operation, as follows.

Firstly, the control part 318 may control the medicine dispensing driving means D300 to dispense the fragile medicine after a point of time when it is determined that the breakage-causing medicine is conveyed by the conveying operation of the medicine conveying part D500 and passes the second medicine dispensing container 2B, D100 in consideration of a distance between the first medicine dispensing container 1B, D100 storing the breakage-causing medicine and the second medicine dispensing container 2B, D100 storing the fragile medicine and the rotational speed (conveying speed) of the medicine conveying part D500. That is, a time interval between a point of time when the breakage-causing medicine is dispensed and a point of time when the fragile medicine is dispensed may be changed according to a distance between the first medicine dispensing container 1B, D100 storing the breakage-causing medicine and the second medicine dispensing container 2B, D100 (it is assumed that the conveying speed of the medicine conveying part is constant).

Secondly, the control part 318 may establish a sufficiently long predetermined time to prevent a collision between the breakage-causing medicine and the fragile medicine, and then may control the medicine dispensing driving means D300 or the like, such that the fragile medicine is dispensed at a point of time when the predetermined time passed after the breakage-causing medicine is dispensed. That is, the time interval between the point of time when the breakage-causing medicine is dispensed and the point of time when the fragile medicine is dispensed may be not changed according to the distance between the first medicine dispensing container 1B, D100 storing the breakage-causing medicine and the second medicine dispensing container 2B, D100 storing the fragile medicine, but may be constant.

Thirdly, the control part 318 may control the medicine dispensing driving means D300 or the like, such that the fragile medicine is dispensed after whether the conveying of the breakage-causing medicine to the one end of the medicine conveying part D500 is completed is detected using a sensor provided at one end (i.e., one end in which the operable gate is located) of the medicine conveying part D500.

Also, by another method different from the above-mentioned method, the control part 318 may control the medicine dispensing timing to prevent the collision between the breakage-causing medicine and the fragile medicine and thus the damage of the fragile medicine.

Until now, the method of controlling the medicine dispensing operation according to one embodiment of the present invention has been described. In the method of controlling the dispensing operation, a way of determining the medicine dispensing order is used to achieve the objects of preventing the damage of the fragile medicine and/or enhancing the medicine dispensing efficiency. Hereinafter, another embodiment for the method of controlling the dispensing operation will be described.

6-2. Controlling Method of Dispensing Operation—Second Embodiment

A method of controlling a dispensing operation in the medicine dispensing system according to one embodiment of the present invention will be described. That is, another embodiment for the specific controlling method in the process S16 of controlling the dispensing operation will be described later in detail.

FIG. 190 is a flow chart explaining a method of controlling the dispensing operation in the medicine dispensing system according to another embodiment of the present invention.

As illustrated in FIG. 190, the method of controlling the dispensing operation according to another embodiment of the present invention may be performed by including at least one of a process S50 of confirming a medicine to be dispensed on the basis of a prescription, a process S52 of confirming information of a medicine dispensing container receiving the medicine to be dispensed, a process S54 of selecting the medicine dispensing container from which the medicine is dispensed, a process S56 of determining a dispensing order of the selected medicine dispensing container, a process S58 of controlling a vertical moving speed and/or a horizontal conveying speed of a medicine conveying part, and a process S60 of controlling a dispensing operation of the medicine dispensing container. At this time, since the processes S50, S52, S54 and S56 are the same as or similar to the above-mentioned processes S40, S42, S44 and S46, the description thereof will be omitted. Hereinafter, the processes S58 and S60 will be described in detail.

The control part 138 may control at least one of the vertical moving speed and the horizontal conveying speed of the medicine conveying part based on at least one of information obtained by the processes S50 to S56, such as the information of the medicine to be dispensed, the information of the selected medicine dispensing container D100 and the information of the medicine dispensing order (S58).

Of course, as basically described in the above-mentioned method of controlling the medicine dispensing operation according the present invention, the control part 318 may control the medicine conveying part D500 to be moved up and down between the layers of the first medicine dispensing device 100 according to the determined medicine dispensing order. Further, when the medicine is dispensed according to the determined medicine dispensing order, the control part 318 may control the medicine conveying part D500 to be continuously rotated and moved, while the medicine dispensing operation from the selected medicine dispensing container is performed. Further, as described above, when the medicine conveying part D500 is located in the layer in which the medicine dispensing container D100 storing the medicine to be dispensed is located, based on the determined dispensing order, the control part 318 may control the selected medicine dispensing container D100, such that the selected medicine dispensing container D100 dispenses the medicine according to the determined medicine dispensing order. In the case of the medicine dispensing container D100 required to be maintained in a state in which the medicine may be dispensed from the medicine dispensing container D100, the medicine dispensing container D100 may perform a preparing operation for dispensing the medicine before or at the same time as the operation of the medicine dispensing driving means D300. That is, the medicines included in the prescription may be dispensed in turn from the selected medicine dispensing container D100 according to the close interaction of the movement of the medicine conveying part D500, the medicine dispensing driving means D300 and the medicine dispensing container D100.

Since this has been already described in the method of controlling the medicine dispensing operation according to one embodiment of the present invention, the detailed description thereof will be omitted. Hereinafter, a method of controlling the vertical moving speed and the horizontal conveying speed of the medicine conveying part D500 by the control part 318 will be mainly described.

The control part 318 may control at least one of the vertical moving speed and the horizontal conveying speed of the medicine conveying part D500 in consideration of some factors.

For example, the control part 318 may control at least one of the vertical moving speed and the horizontal conveying speed of the medicine conveying part D500 based on whether the fragile medicine is included in the medicine to be dispensed and/or whether the breakage-causing medicine is included therein.

As another example, the control part 318 may control at least one of the vertical moving speed and the horizontal conveying speed of the medicine conveying part D500 based on a position relation between the medicine dispensing containers D100 storing the medicines to be dispensed. That is, in a first medicine dispensing container D100 storing a first medicine and a second medicine dispensing container D100 storing a second medicine, when the first medicine dispensing container D100 is located in a N-th row of a P-th layer, and the second medicine dispensing container D100 is located in a M-th row of a Q-th layer, at least one of the vertical moving speed and the horizontal conveying speed of the medicine conveying part D500 may be controlled based on a vertical distance Dv between the P-th layer and the Q-th layer and a horizontal distance Dh between the N-th row and M-th row.

Firstly, a method of controlling at least one of the vertical moving speed and the horizontal conveying speed of the medicine conveying part based on whether the fragile medicine is included in the medicine to be dispensed and/or whether the breakage-causing medicine is included therein will be described.

When the fragile medicine is not included in the medicine to be dispensed, the control part 318 may not change the vertical moving speed and the horizontal conveying speed of the medicine conveying part D500. That is, the medicine dispensing driving means moving part D400 and the driving roll CB14 of the medicine conveying part D500 may be controlled so that the medicine conveying part D500 is operated on the basis of a predetermined basic vertical moving speed and a predetermined basic horizontal conveying speed. However, if necessary, even when the fragile medicine is not included, the vertical moving speed and the horizontal conveying speed of the medicine conveying part D500 may be controlled in consideration of the position relation between the medicine dispensing containers D100 which will be described later.

Meanwhile, when the fragile medicine is included in the medicine to be dispensed, the control part 318 may determine whether the breakage-causing medicine is included in the medicine to be dispensed.

When the fragile medicine is included in the medicine to be dispensed, but the breakage-causing medicine is not included, as described above, the control part 318 may control the driving roll CB14 of the medicine conveying part D500 and the medicine dispensing driving means moving part D400 on the basis of the predetermined basic vertical moving speed and the predetermined basic horizontal conveying speed. At this time, also, the vertical moving speed and the horizontal conveying speed of the medicine conveying part D500 may be controlled in consideration of the position relation between the medicine dispensing containers D100.

Meanwhile, when all of the fragile medicine and the breakage-causing medicine are included in the medicines to be dispensed, the control part 318 may control the vertical moving speed and the horizontal conveying speed of the medicine conveying part D500 in consideration of the position relation between the medicine dispensing containers D100, as described below. That is, the predetermined vertical moving speed of the medicine conveying part and the predetermined horizontal conveying speed of the medicine conveying part may be changed by the control part 318.

As described above, to prevent the damage of the fragile medicine, the control part 318 determines the medicine dispensing order and thus prevents the damage of the medicine. However, to achieve the object which prevents the damage of the medicine by controlling the dispensing order, it is necessary to more precisely control at least one of the vertical moving speed and the horizontal conveying speed of the medicine conveying part D500.

It is assumed that the medicine storing container D100 including the breakage-causing medicine and the medicine storing container D100 including the fragile medicine are located in the same layer, and particularly, the first medicine storing container 1B, D100 including the breakage-causing medicine is located farther from the medicine feeding port 320 than the second medicine storing container 2B, D100 including the fragile medicine, as illustrated in FIG. 188.

In this case, even though the breakage-causing medicine is firstly dispensed from the container, there is still the possibility that the fragile medicine is damaged. This is because, even though the breakage-causing medicine is firstly dispensed from the first medicine storing container 1B, D100, the medicine conveying part D500 continuously performs the rotational operation (conveying operation), and thus the firstly dispensed breakage-causing medicine is continuously moved to the medicine feeding port 320, and the moving breakage-causing medicine may collide with the fragile medicine, when the fragile medicine is dispensed from the second medicine dispensing container 2B, D100 and seated on the medicine conveying part D500, and thus the fragile medicine may be damaged.

Therefore, in this case, the control part 318 may control the medicine dispensing operation, as follows.

FIGS. 191 and 192 are views explaining a method of controlling the dispensing timing of the medicine dispensing containers according to another embodiment of the present invention. Hereinafter, the medicine dispensing operation of the control part 318 will be described with reference to FIGS. 191 and 192.

Firstly, the control part 318 may control the vertical moving speed of the medicine conveying part D500 such that, after the breakage-causing medicine is dispensed, the breakage-causing medicine passes the row in which the medicine dispensing container storing the fragile medicine is located, before the medicine conveying part D500 is moved to the layer in which the medicine dispensing container storing the fragile medicine is located, in consideration of a vertical distance (e.g., a distance between the layers in which each container is disposed) and a horizontal distance (e.g., a distance between the rows in which each container is disposed) between the first medicine dispensing container 1B, D100 storing the breakage-causing medicine a and the second medicine dispensing container 2B, D100 storing the fragile medicine b.

For example, in moving the medicine conveying part D500 to the layer in which the medicine dispensing container B storing the fragile medicine b is located, after the breakage-causing medicine a is dispensed, as illustrated in FIG. 191(*a*), when the medicine conveying part D500 is moved at a vertical moving speed Vv1, the breakage-causing medicine a may be located at a further rear side than the fragile medicine b. In this case, as described above, the possibility that the fragile medicine b is damaged by the breakage-causing medicine a, while the dispensed medicines are conveyed to the medicine gathering device 300, is increased.

Therefore, in this case, as illustrated in FIG. 191(*b*), if the medicine conveying part D500 is moved vertically at a vertical moving speed Vv2 which is faster than the vertical moving speed Vv1, the fragile medicine b may be located at a further front side than the breakage-causing medicine a, and thus the possibility that the fragile medicine b is damaged may be reduced.

Meanwhile, when the vertical distance between the first medicine dispensing container 1B, D100 storing the breakage-causing medicine a and the second medicine dispensing container 2B, D100 storing the fragile medicine b is sufficiently long, the breakage-causing medicine a may be located at a further front side than the fragile medicine b, even though the vertical moving speed of the medicine conveying part D500 is not controlled. In this case, the control part 318 may not change the vertical moving speed of the medicine moving part D500.

Further, when the horizontal distance between the first medicine dispensing container 1B, D100 storing the breakage-causing medicine a and the second medicine dispensing container 2B, D100 storing the fragile medicine b is sufficiently short, the breakage-causing medicine a may be located at the further front side than the fragile medicine b, even though the vertical moving speed of the medicine conveying part D500 is not controlled. In this case, the control part 318 may not change the vertical moving speed of the medicine moving part D500.

Further, when the horizontal conveying speed Vh of the medicine conveying part D500 is sufficiently fast, the breakage-causing medicine a may be located at the further front side than the fragile medicine b, even though the vertical moving speed of the medicine conveying part D500 is not controlled. In this case, the control part 318 may not change the vertical moving speed of the medicine moving part D500.

That is, the control part 318 may control the vertical moving speed of the medicine conveying part D500 in consideration of the horizontal distance and the vertical distance between the medicine dispensing containers 1B, 2B and the horizontal conveying speed of the medicine conveying part D500.

Secondly, the control part 318 may control the horizontal conveying speed of the medicine conveying part D500 such that, after the breakage-causing medicine is dispensed, the breakage-causing medicine passes the row in which the medicine dispensing container storing the fragile medicine is located, before the medicine conveying part D500 is moved to the layer in which the medicine dispensing container storing the fragile medicine is located, in consideration of the vertical distance (e.g., the distance between the layers in which each container is disposed) and the horizontal distance (e.g., a distance between the rows in which each container is disposed) between the first medicine dispensing container 1B, D100 storing the breakage-causing medicine and the second medicine dispensing container 2B, D100 storing the fragile medicine.

For example, in moving the medicine conveying part D500 to the layer in which the second medicine dispensing container 2B, D100 storing the fragile medicine b is located, after the breakage-causing medicine a is dispensed, as illustrated in FIG. 192(*a*), when the horizontal conveying speed of the medicine conveying part D500 is Vh1, the breakage-causing medicine a may be located at a further rear side than the fragile medicine b. In this case, as described above, the possibility that the fragile medicine b is damaged by the breakage-causing medicine a, while the dispensed medicines are conveyed to the medicine gathering device 300, is increased. Therefore, in this case, as illustrated in FIG. 192(b), if the medicine is moved vertically at a horizontal conveying speed Vh2 which is faster than the horizontal conveying Vv1, the fragile medicine b may be located at a further front side than the breakage-causing medicine a, and thus the possibility that the fragile medicine b is damaged may be reduced.

Meanwhile, when the vertical distance between the first medicine dispensing container 1B, D100 storing the breakage-causing medicine a and the second medicine dispensing container 2B, D100 storing the fragile medicine b is sufficiently long, or when the horizontal distance between the first medicine dispensing container 1B, D100 storing the breakage-causing medicine a and the second medicine dispensing container 2B, D100 storing the fragile medicine b is sufficiently short, or when the vertical moving speed Vv of the medicine conveying part D500 is sufficiently small, the breakage-causing medicine a may be located at the further front side than the fragile medicine b, even though the vertical moving speed of the medicine conveying part D500 is not controlled. Therefore, the control part 318 may not change the horizontal conveying speed of the medicine moving part D500.

That is, the control part 318 may control the horizontal conveying speed of the medicine conveying part D500 in consideration of the horizontal distance and the vertical distance between the medicine dispensing containers 1B, 2B and the vertical moving speed of the medicine conveying part D500.

Thirdly, the control part 318 may control all of the vertical moving speed and the horizontal conveying speed of the medicine conveying part D500 such that, after the breakage-causing medicine is dispensed, the breakage-causing medicine passes the row in which the medicine dispensing container storing the fragile medicine is located, before the medicine conveying part D500 is moved to the layer in which the medicine dispensing container storing the fragile medicine is located, in consideration of the vertical distance (e.g., the distance between the layers in which each container is disposed) and the horizontal distance (e.g., a distance between the rows in which each container is disposed) between the first medicine dispensing container 1B, D100 storing the breakage-causing medicine and the second medicine dispensing container 2B, D100 storing the fragile medicine.

Eventually, according to the method of controlling the medicine dispensing operation according to another embodiment of the present invention, when the vertical distance between the medicine dispensing container D100 storing the breakage-causing medicine and the medicine dispensing container D100 storing the fragile medicine is H, and the horizontal distance therebetween is S, and the vertical moving speed of the medicine conveying part D500 is Vv, and the horizontal conveying speed of the medicine conveying part D500 is Vh, and particularly, when the medicine dispensing container D100 storing the breakage-causing medicine is located farther from the medicine feeding port 320 than and the medicine dispensing container D100 storing the fragile medicine, the control part 318 may control the Vv and/or the Vh to satisfy an equation of $S/Vh < H/Vv$ or a modified equation therefrom.

Until now, the method of controlling the medicine dispensing operation according to another embodiment of the present invention has been described.

As described in the methods of controlling the medicine dispensing operation according to one embodiment and another embodiment of the present invention, the method of controlling the medicine dispensing operation according to one embodiment of the present invention may achieve some objects of the present invention by controlling the timing for dispensing the medicine from the medicine dispensing container B100 to the medicine conveying part D500 rather than controlling the moving speed and/or the conveying speed of the medicine conveying part D500, and the method of controlling the medicine dispensing operation according to another embodiment of the present invention may achieve some objects of the present invention by controlling the moving speed and/or the conveying speed of the medicine conveying part D500 rather than controlling the timing for dispensing the medicine from the medicine dispensing container B100 to the medicine conveying part D500.

However, even though the method of controlling the medicine dispensing operation according to one embodiment of the present invention is different from the method of controlling the medicine dispensing operation according to another embodiment of the present invention in the specific controlling method thereof, the controlling methods are not excluded from each other, but maintain the complementary relation, and thus the two embodiments may be combined with each other.

For example, when the medicine dispensing container D100 from which the medicine is dispensed is selected, and the medicine dispensing order is determined, the control part 318 may control the moving speed and/or the conveying speed of the medicine conveying part D500 and may simultaneously control the timing for dispensing the medicine from the medicine dispensing container D100 to the medicine conveying part D500.

7. Other Modified Example

Hereinafter, an additional operation controlling method of the medicine dispensing system 1 and/or various modified examples of the controlling method of the medicine dispensing system 1 will be described.

7-1. Modified Example of Medicine Conveying Part—a Plurality of Medicine Conveying Parts Hereinafter, in the case in which the first medicine dispensing device 100 includes two or more medicine conveying parts, a controlling operation according to the process S48 will be described with reference to the related drawings.

FIGS. 193 to 196 are views explaining a method of controlling the medicine conveying part when two or more medicine conveying parts are provided to the medicine dispensing device according to one embodiment of the present invention.

Referring to FIG. 193, the first medicine dispensing device 100 may include a first medicine conveying part D500-1 and a second medicine conveying part D500-2. At this time, the first medicine conveying part D500-1 and the second medicine conveying part D500-2 may be driven to have each assigned area in the first medicine dispensing device 100. When the medicines are dispensed from the medicine dispensing containers D100, the medicine conveying part D500 is moved to the layer in which the corresponding medicine dispensing container D100 is located. The assigned area may mean an area in which each medicine conveying part D500-1, D500-2 may be moved, when the medicine is dispensed from the medicine dispensing container D100. At this time, as described above, since the medicine conveying part D500 may be moved up and down in the first medicine dispensing device 100, the assigned area of each medicine conveying part D500-1, D500-2 may be referred to as an up and down moving range of each medicine conveying part D500-1, D500-2.

The assigned area may be a predetermined fixed area, or may be a variable area determined by the control part 318.

Firstly, the case in which assigned area is the predetermined fixed area will be described.

For example, referring to FIG. 193, a first assigned area CR1 of the first medicine conveying part D500-1 may be established to an upper side of the first medicine dispensing device 100, and a second assigned area CR2 of the second medicine conveying part D500-2 may be established to a lower side of the first medicine dispensing device 100.

At this time, the assigned areas of the first medicine conveying part D500-1 and the second medicine conveying part D500-2 may be determined by a first up and down moving rail coupled to the first medicine conveying part D500-1 and a second up and down moving rail coupled to the second medicine conveying part D500-2. That is, the first up and down moving rail and the second up and down moving rail may be physically separated from each other. Since the first medicine conveying part D500-1 may be movable on the first up and down moving rail, and the second medicine conveying part D500-2 may be movable on the second up and down moving rail, the first assigned area CR1 may be determined by a length of the first up and down moving rail, and the second assigned area CR2 may be determined by a length of the second up and down moving rail.

Meanwhile, the assigned areas of the first medicine conveying part D500-1 and the second medicine conveying part D500-2 may be logically determined. That is, as described above, even though the first medicine conveying part D500-1 and the second medicine conveying part D500-2 are coupled to a common up and down moving rail, instead of the up and down moving rails physically separated from each other, the first assigned area CR1 of the first medicine conveying part D500-1 and the second assigned area CR2 of the second medicine conveying part D500-2 may be established as illustrated in the drawings.

The control part 318 may confirm a position in which at least one medicine dispensing container D100 selected in the process S44 is arranged in the medicine dispensing device 100, may confirm whether the confirmed position is located in the first assigned area CR1 of the first medicine conveying part D500-1 or the second assigned area CR2 of the second medicine conveying part D500-2, and may control each of the first medicine conveying part D500-1 and the second medicine conveying part D500-2 so that the medicine is dispensed from the medicine dispensing container D100 located in each assigned area. That is, if the medicine dispensing container D100 from which the medicine is dispensed is determined, the control part 318 may assign the medicine dispensing container D100 to each medicine conveying part D500-1, D500-2 in consideration of each assigned area CR1, CR2 of each medicine conveying part D500-1, D500-2. Each medicine conveying part D500-1 and D500-2 may separately perform the medicine dispensing operation. Here, the fact that each medicine conveying part D500-1 and D500-2 may separately perform the medicine dispensing operation means that the operation of each medicine conveying part D500-1, D500-2 may be controlled at the same time rather than that the operation of the first medicine conveying part D500-1 is controlled to dispense the medicine, and then the operation of the second medicine conveying part D500-2 is controlled to dispense the medicine. Although the operation of each medicine conveying part D500-1, D500-2 may be controlled at the same time, if necessary, for example, when the medicine dispensing order is determined in consideration of the fragile medicine and the breakage-causing medicine, the control part 318 may properly control the operation timing of the first medicine conveying part D500-1 and the second medicine conveying part D500-2.

And the case in which the assigned area is variable will be described.

Whenever the medicine dispensing containers D100 storing the medicines, which should be conveyed to the medicine gathering device 300 at once, are selected, the control part 318 may determine the assigned area of each medicine conveying part D500-1, D500-2 in consideration of positions of the selected medicine dispensing containers D100.

For example, FIG. 194(a) illustrates a case in which all of the medicine dispensing containers A, B and C from which the medicines are dispensed are located at the upper side of the first medicine dispensing device 100. In this case, the control part 318 may determine a layer, in which the medicine dispensing containers A and B are located, as a third assigned area CR3 of the first medicine conveying part D500-1, and may determine a layer, in which the medicine dispensing container C is located, as a fourth assigned area CR4 of the second medicine dispensing part D500-2.

As another example, FIG. 194(b) illustrates a case in which all of the medicine dispensing containers A, B and C from which the medicines are dispensed are located at the lower side of the first medicine dispensing device 100. Even in this case, the control part 318 may determine a layer, in which the medicine dispensing containers A and B are located, as a fifth assigned area CR5 of the first medicine conveying part D500-1, and may determine a layer, in which the medicine dispensing container C is located, as a sixth assigned area CR6 of the second medicine dispensing part D500-2.

In determining the assigned areas of each medicine conveying part D500-1, D500-2, the control part 318 may determine the assigned areas so that a time for dispensing the medicines which should be dispensed at once is minimized.

When the two or more medicine conveying parts D500 are provided at the first medicine dispensing device 100, the number of the medicine feeing ports 320 through which the medicine is delivered from the first medicine dispensing device 100 to the medicine gathering device 300 may be the same as the number of the medicine conveying parts D500. That is, when the number of the medicine conveying parts D500 is 2, two medicine feeding ports 320 may be provided.

Meanwhile, although two or more medicine conveying parts D500-1, D500-2 are provided at the first medicine dispensing device 100, only one medicine feeding port 320 may be provided, as illustrated in FIG. 195. At this time, the medicine feeding port 320 is preferably provided at about a middle height of the medicine gathering device 300.

As illustrated in FIG. 195, even though the two or more medicine conveying parts D500-1, D500-2 are provided, when one medicine feeding port 320 is provided, the control part 318 may differently control a first delivering timing when the first medicine conveying part D500-1 delivers the medicines to the medicine gathering device 300 and a second delivering timing when the second medicine conveying part D500-2 delivers the medicines to the medicine gathering device 300.

For example, as illustrated in FIG. 196, the control part 318 may control the first medicine conveying part D500-1 to be located at a height corresponding to the medicine feeding port 320 and to deliver the medicine, and then may control the second medicine conveying part D500-2 to located at a height corresponding to the medicine feeding port 320 and to deliver the medicine.

At this time, the control part 318 may determine the medicine conveying part D500 which is firstly controlled to deliver the medicine to the medicine gathering device 300 in consideration of the time for dispensing the medicines which should be dispensed at once, or the medicine conveying part D500 on which the fragile medicine and/or the breakage-causing medicine are seated.

7-2. Stock Management Method in Medicine Dispensing Container

A method of managing the stock in the medicine dispensing container according to one embodiment of the present invention will be described.

As described above, various kinds of medicines may be stored in the medicine dispensing container D100. To load the medicines into the medicine dispensing container D100, a user may install the medicine dispensing container D100 at a separate refill station. If the medicine dispensing container D100 is installed at the refill station, the medicine dispensing container D100 is maintained in a state in which new medicines may be loaded therein. For example, as described in the description of the blister-packed medicine dispensing container BOX2, when the blister-packed medicine dispensing container BOX2 is installed at the refill station, the locking part B2L is rotated so that the rotating part B2102 is allowed to be rotated, and thus the new medicines may be loaded into the medicine receiving part B2110.

In the state in which the medicine storing container D100 is filled with the medicines, the medicine storing container D100 is installed at the first medicine dispensing device 100. Then, as described above, the medicines stored in each medicine storing container D100 are dispensed in turn according the medicine dispensing operation based on the prescription. Therefore, the stock of the medicines stored in the medicine storing container D100 is gradually reduced.

The medicine dispensing system 1 according to one embodiment of the present invention may establish a stock shortage warning value for each medicine storing container D100. The control part 318 may monitor the stock in each medicine storing container D100, and may inform the stock shortage to the user, if the stock in a certain medicine storing container D100 is the same as or less than the stock shortage warning value established in the corresponding medicine dispensing container D100.

For example, in the case in which the stock shortage warning value established in the medicine dispensing container D100 is 5, if the number of the medicines stored in the medicine dispensing container D100 is reduced to 5 or less through the medicine dispensing operation, the control part 318 may inform the stock shortage in the medicine dispensing container D100 to the user.

Meanwhile, the stock shortage warning value for one medicine dispensing container D100 may be established to 5, while the stock shortage warning value for another medicine dispensing container D100 is established to 8. Like this, since the stock shortage warning value for each medicine dispensing container D100 may be established differently, the stock management for each medicine may be effectively performed. The stock shortage warning value for each medicine dispensing container D100 may be separately established by the user.

The medicine dispensing system 1 may inform the stock shortage to the user in various manners.

For example, the control part 318 may inform the stock shortage to the user through the output part 310 in a visual or acoustic manner.

As another example, a plurality of lamps corresponding to the medicine dispensing containers D100 and the number thereof may be provided on a front or rear surface of the first medicine dispensing device 100, and the lamp corresponding to the medicine dispensing container D100 which is determined in a stock shortage state may be tuned on. Therefore, the user may recognize the medicine dispensing container D100 which is in the stock shortage state.

As still another example, the lamps corresponding to the medicine dispensing containers D100 may be provided at the cartridge D200 in which the medicine dispensing containers D100 are installed, and the lamp corresponding to the medicine dispensing container D100 which is determined in the stock shortage state may be tuned on.

7-3. Modified Example of Prescription Selecting Method

Hereinafter, a method in which the user or the like may more easily select the prescription for dispensing the medicine using a terminal 3 will be described. That is, another embodiment of the process S14 of selecting at least one prescription described with reference to FIG. 184 will be described.

Hereinafter, it is assumed that the terminal 3 used by the user or the like is a smart phone. However, the terminal 3 used by the user or the like is not limited to the smart phone, and may be a mobile terminal which is manufactured for special purposes and used in a hospital or the like.

Further, it is assumed that the terminal 3 used by the user or the like is provided individually.

Further, hereinafter, a term 'proximity tagging" means an action in which the user or the like is located within a distance in which a reader and a tag defined by a near field communication (NFC) technology, a radio frequency identification (RFID) technology, or the like may perform communication according to a predetermined protocol. That is, when an NFC reader or an RFID reader is located in the medicine gathering system 1, and an NFC tag or an RFID tag is located in the terminal 3 used by the user, the 'proximity tagging' may be an action in which the user takes the terminal 3 to an installation position of the reader of the medicine gathering system 1. If the user performs the 'proximity tagging', the NFC reader and/or the RFID reader and the NFC tag and/or the RFID tag detect the 'proximity tagging' state, and then starts a communication procedure defined by an NFC communication protocol and/or an RFID communication protocol. Therefore, the NFC reader and/or the RFID reader and the NFC tag and/or the RFID tag may transmit and receive necessary information to/from each other.

Further, the terminal 3 described in the present invention may have a control part which controls each construction element of the terminal 3 and an operation of the terminal 3, and may also include an output part which outputs the necessary information or the like for the operation of the terminal 3.

Hereinafter, the detailed description thereof will be provided with reference to FIGS. 197 and 198. FIG. 197 is a flowchart explaining the method of selecting the prescription according to one embodiment of the present invention, and FIG. 198 is an exemplary view explaining the method of selecting the prescription according to one embodiment of the present invention.

Referring to FIG. 197, the method of selecting the prescription according to one embodiment of the present invention may include a process S70 in which the terminal 3 receives information of the prescription, a process S72 of selecting at least part of the received prescription, a process S74 in which the terminal 3 transmits first identification information and the medicine dispensing system 1 receives the first identification information when the terminal 3 is proximity-tagged to the medicine dispensing system 1, a process S76 in which the medicine dispensing system 1 provides a user authentication interface for user authentication, and a process S78 of performing a prescription dispensing operation when user information confirmed through the user authentication interface coincides with previously stored user authentication information. Hereinafter, each process will be specifically described.

The terminal 3 may receive information of the prescription through a communication part provided at the terminal 3 (S70). The terminal 3 may be individually provided to the users. For example, a first terminal 3 may be provided to a first nurse, and a second terminal 3 may be provided to a second nurse 2.

At this time, a server 2 or the medicine dispensing system 1 may match and store first terminal identification information for the first terminal 3 with user information of the first nurse, and second terminal identification information for the second terminal 3 with user information of the second nurse. Alternatively, the first terminal 3 may store the user information for the first nurse, and the second terminal 3 may store the user information for the second nurse.

A doctor may treat a patient and then may issue the prescription for each patient. The prescription may be input through the terminal 3 such as a computer used by the doctor. The input prescription may be transmitted to the server 2. When the server 2 receives the prescription from the doctor's terminal, the server 2 confirms patient information on the prescription, and may confirm information of the terminal 3 of the nurse corresponding to the patient. That is, the server 2 may confirm whether the first nurse or the second nurse is in charge of the patient for the issued prescription, and also may confirm information (e.g., a number assigned to the smart phone, a serial number of the smart phone, or the like) of the terminal assigned to the nurse in charge. Then, the server 2 may transmit prescription information to the terminal 3, and thus the terminal 3 may receive the prescription information. The information received from the server 2 may be the prescription itself, or may be a notice of prescription issuance.

In the first terminal 3 assigned to the first nurse, the first terminal 3 may receive the information of the corresponding prescription, when the prescription for each patient is issued. At this time, the first nurse may be in charge of a plurality of patients, and thus a plurality of pieces of information of the prescriptions may be received in the first terminal 3.

Meanwhile, when the information of the prescription is received, the terminal 3 may output an alarm for informing the user that information related to the prescription is received.

Further, when the administration time recorded in the received prescription arrives, the terminal 3 may output an alarm for informing that the administration time arrives.

And the terminal 3 may select at least part of the received prescriptions (S72).

In order to select at least part of the received prescriptions, the terminal 3 may receive an input for the selection. For example, as illustrated in FIG. 198, the terminal 3 may visually display a list of the received prescriptions to select at least part of the received prescriptions, and thus the user may select the prescription which needs the dispensing of the medicine. A user interface which is provided to the user to select part of the prescriptions may be designed in various manners.

Alternatively, the terminal 3 may select at least part of the received prescriptions according to a predetermined algorithm.

For example, only the prescriptions corresponding to a standard predetermined in consideration of the administration time in the received prescription may be selected. For example, in consideration of the current time and the administration time in the prescription, only the prescriptions in which the administration time within a predetermined time range (e.g., within 30 minutes) from the current time has already arrived or will arrive may be selected.

Meanwhile, when the user interface for selecting the prescription is provided to the user but the input for the selection is not received from the user, the terminal 3 may select all of the received prescriptions.

And when the terminal 3 is proximity-tagged to the medicine dispensing system 1, the terminal 3 may transmit the first identification information, and the medicine dispensing system 1 may receive the first identification information (S74). That is, when the user takes the terminal 3 to the medicine dispensing system 1 and performs the proximity tagging, the near field communication between near field communication modules (e.g., when using NFC communication, an NFC communication module installed in the terminal 3 and an NFC communication module installed in the medicine dispensing system 1) installed in the terminal 3 and the medicine dispensing system 1 may be started, and the first identification information may be transmitted and received through the near field communication.

The first identification information may be the serial number of the first terminal.

Alternatively, the first identification information may be the user information (e.g., a name, an employee identification number, a resident registration number, or the like of the nurse) of the first nurse stored in the first terminal which is owned by the first nurse.

Meanwhile, the terminal 3 may transmit the information of the prescription selected by the process S72 to the medicine dispensing system 1 through the near field communication modules at the same time as the process S74 or separately from the process S74.

Meanwhile, the near field communication module may be a module which is separately provided from the communication part for receiving the information of the prescription. For example, the communication part for receiving the information of the prescription may be a module for WiFi communication or a module for performing the communication through a mobile communication network (e.g., an LTE network), and the near field communication module may be a module for the NFC communication or the RFID communication.

Meanwhile, when the terminal 3 is proximity-tagged to the medicine dispensing system 1, the medicine dispensing system 1 may provide a user authentication interface for the user authentication (S76).

For example, the medicine dispensing system 1 may provide the user authentication interface which may receive from the user an ID and password of the user, a registration number, an accredited certificate, and biometric information such as fingerprint information, face recognition information, voice recognition information, and iris recognition information.

When the user authentication information is received through the user authentication interface, the medicine dispensing system 1 may compare user authentication information corresponding to the first identification information received in the process S74. That is, when the user authentication information received in the process S76 is a user password, the medicine dispensing system 1 may compare whether the password stored to correspond to the first identification information received from the terminal 3 coincides with the password input by the user. Alternatively, when the user authentication information is a fingerprint, the medicine dispensing system 1 may compare whether the fingerprint information stored to correspond to the received first identification information coincides with the fingerprint information input by the user.

At this time, the medicine dispensing system 1 may have a separate input means for receiving the user authentication information from the user. For example, a device for the user authentication, such as a fingerprint recognition device, an iris input device and a face recognition device may be provided at the medicine dispensing device 1.

When the user information confirmed through the user authentication interface coincides with the previously stored user authentication information, the medicine dispensing system 1 may perform the prescription dispensing operation (S78).

At this time, the medicine dispensing system 1 may perform the medicine dispensing operation based on the prescription selection information received through the process S74 or separately from the process S74. That is, the medicine dispensing system 1 may perform the medicine dispensing operation for at least part of the prescriptions selected by the terminal 3 among the prescriptions received in the terminal 3.

Meanwhile, before performing the medicine dispensing operation, the medicine dispensing system 1 may perform an operation in which the user confirms the prescriptions selected in the terminal 3. For example, a list of the prescriptions selected in the terminal 3 may be output through the output part 310 such as an image output part 312, and the user may confirm the output list of the selected prescriptions (in which the medicine dispensing operation is performed), may perform a confirmation input, may exclude part of the prescriptions from the list, or may further add non-selected prescriptions.

Since the medicine dispensing operation is already described, the detailed description thereof will be omitted.

Until now, the method of controlling the medicine dispensing system according to some embodiments of the present invention has been described. In describing the method of controlling the medicine dispensing system, it was assumed that the medicine dispensing system 1 was configured with the combination of the first medicine dispensing device 100 and the medicine gathering device 300.

However, the medicine dispensing system 1 configured with the combination of the second medicine dispensing device 200 and the medicine gathering device 300 may be also operated in the similar method.

However, unlike the medicine dispensing driving means D300 which may simultaneously dispense the medicines from the plurality of medicine dispensing containers D100 located in one layer, the second medicine dispensing device 200 has the packed medicine dispensing means M8 which transmits the driving force to dispense the medicine from only one packed medicine dispensing container M4 located in one layer. Therefore, there may be some differences in the controlling method thereof due to such a difference.

Meanwhile, when the medicine dispensing system 1 is configured with the combination of the first medicine dispensing device 100, the second medicine dispensing device 200, and the medicine gathering device 300, the first medicine dispensing device 100 and the second medicine dispensing device 200 may be independently controlled.

However, when the medicine dispensing system 1 includes a plurality of first medicine dispensing devices 100, the control part 318 may control the plurality of first medicine dispensing devices 100 so that the medicine dispensing operation between the first medicine dispensing devices 100 is performed through mutual close cooperation, for example, the dispensing operation is performed according to the medicine dispensing order. Even when the medicine dispensing system 1 includes a plurality of second medicine dispensing devices 200, it may be equally applied.

Further, for convenience of explanation, the medicine container installed in the first medicine dispensing device 100 was referred to as the medicine dispensing container D100, and the medicine container installed in the second medicine dispensing device 200 was referred to as the packed medicine dispensing container M4. However, all of the medicine dispensing container D100 and the packed medicine dispensing container M4 may be referred to the medicine dispensing container.

7-4. Medicine Dispensing System in which Medicine Dispensing Device is Integrally Formed with Medicine Gathering Device Hereinafter, an integral medicine dispensing system having functions which are the same as or similar to the functions applied to the medicine dispensing device and the medicine gathering device will be described. Here, for convenience of explanation, the integral medicine dispensing system may be distinguishably referred to as a drug supplying apparatus or a drug storing and supplying apparatus.

FIG. 199 is a block diagram of a medicine integrated management system using a medicine storing and supplying device according to one embodiment of the present invention, and FIG. 200 is a perspective view of a main device and a sub device illustrated in FIG. 199.

And FIG. 201 is a perspective view of the main device illustrated in FIG. 200, FIG. 202 is a perspective view of a first storage part illustrated in FIG. 201, FIG. 203 is a partially-enlarged perspective view of a second storage part illustrated in FIG. 201, FIG. 204 is a partially-enlarged perspective view of the second storage part illustrated in FIG. 203, and FIG. 205 is a perspective view of a medicine cartridge illustrated in FIG. 203.

Further, FIG. 206 is a perspective view of a medicine discharge part illustrated in FIG. 201, and FIG. 207 is an enlarged perspective view of a main portion of the medicine discharge part illustrated in FIG. 206.

FIG. 208 is a perspective view of a collection container illustrated in FIG. 201, and FIG. 209 is an operation state diagram illustrating a medicine discharging action.

As illustrated in FIGS. 199 and 200, the medicine integrated management system using the medicine storing and supplying device according to one embodiment of the present invention includes a main medicine storing and supplying device (hereinafter, called as "main device") E110 which stores various types of medicines such as injections and tablets and discharges the stored medicine according to an administrator's request, a sub medicine storing and supplying device (hereinafter, called as "sub device") E120 which is communicably connected with the main device E110 to discharge the medicine stored therein, and a hospital server E130 which communicates with the main device E110 to transmit prescription information of a prescription to the main device E110 and to manage the stock of the medicine stored in the main device E110 and the sub device E120.

Also, the medicine integrated management system using the medicine storing and supplying device according to one embodiment of the present invention further includes a medicine refill device E140 which refills the medicine into each cartridge of a medicine storage part E114 provided at the main device E110 and the sub device E120.

The medicine refill device E140 performs confirmation which confirms an administrator having an access authority through communication with the hospital server E130, and opens a door provided at each cartridge to refill the medicine only when the confirmed administrator is accessed.

As illustrated in FIG. 200, the main device E110 and the sub device 120 are formed to have the same configuration. However, the sub device E120 is configured with only the medicine storage part and performs a medicine storing and supplying operation according to a control signal transmitted from a control part E117 of the main device E110.

FIG. 200 illustrates that the medicine integrated management system has one main device E110 and three sub devices E120. However, the present invention is not limited thereto.

For example, the present invention may be modified so that a plurality of sub devices E120 connected with one main device E110 are provided in a large hospital in which many kinds and a great number of medicines are prescribed to the patients, and only one main device E110 is provided or one or two sub devices E120 are provided in a small pharmacy.

Therefore, in the present invention, one main device is communicably connected with the sub devices, and the medicines are stored in the plurality of sub devices, and thus the corresponding medicine may be precisely dispensed and then supplied to the administrator according to the prescription information of the prescription through the main device.

As illustrated in FIGS. 200 and 201, the main device E110 includes a display part E111 which displays various menus and operation states to perform the medicine storing and supplying operation, an input part E112 which receives a command for performing a desired operation by selecting the menu displayed on the display part E111, an authenticating means E113 which confirms the administrator having an authorization, the medicine storage part E114 which individually stores the plurality of medicines, a medicine discharge part E115 which discharges and supplies the medicine from the medicine storage part E114 to the administrator, a communication module E116 which communicates with the hospital server E130 and the sub device E120, and the control part E117 which manages stock information of the medicines stored in the medicine storage part E114 and controls the medicine storage part E114 and the medicine discharge part E115 to discharge the medicine to the confirmed administrator on the basis of the prescription received through the communication module E116.

Also, the main device E110 further includes a memory part E118 which stores various programs for performing the medicine storing and supplying operation, stock information and discharge information of the medicines stored in the medicine storage part E114, access information of the administrator, or the like.

The display part E111 and the input part E112 may be configured with a touch panel which displays various menus on a screen, receives an administrator's command according to a touch operation of the administrator, and displays an operation state according to the corresponding command, thereby performing input and display functions at the same time.

Of course, the display part E111 may be configured with a display device such as a liquid crystal display E1 and a light emitting diode panel E1, and the input part E112 may be configured with a separate input device such as a keyboard.

The authenticating means E113 includes a recognition device which recognizes biometric information of the administrator, such as a fingerprint and iris, to confirm a predetermined access right.

Of course, the authenticating means E113 may be modified to confirm the access right of the administrator using the ID and password of the administrator or selectively using the recognition information such as an ID, fingerprint and iris.

The medicine storage part E114 includes a first storage part E150 and a second storage part E160 which are manufactured according to a shape, a size, and a supplying manner of the medicine.

The configuration of the medicine storage part E114 will be described in detail with reference to FIGS. 201 to 204.

The medicine discharge part E115 is a part which gathers the medicines discharged from the first storage part E160 of the medicine storage part E114 and discharges the medicines to the administrator.

The configuration of the medicine discharge part E115 will be described in detail with reference to FIG. 205.

The control part E17 controls each unit provided at the main device E110 and the sub device E120.

That is, the control part E117 communicates with the hospital server E130 through the communication module E116, transmits the recognition information or the administrator information input through the authenticating means E113 to the hospital server E130, and then receives the prescription information of the prescription from the hospital server E130 when the access right is authenticated.

And the control part E117 controls an operation of the display part E111 to display the received prescription information on the screen, and controls an operation of the medicine storage part E114 and the medicine discharge part E115 provided at the main device E110 and/or the sub device E120 to discharge the medicines corresponding to the prescription information according to an operation of the administrator input through the input part E112.

The control part E117 stores the stock information of each medicine stored in the medicine storage part E114, the kind and the number of the discharged medicine, information of the administrator who dispenses the medicine, or the like, and simultaneously transmits the information to the hospital server E130 through the communication module E116.

Therefore, according to the present invention, since the medicine is discharged to the administrator having the authenticated access right for the corresponding medicine according to the prescription information of the prescription transmitted from the hospital server, the medicine may be safely prescribed, prepared, and administered.

Next, the configuration of the main device will be described in detail with reference with FIGS. 201 to 204.

As illustrated in FIG. 201, the main device E110 includes a cabinet E1100 forming an exterior, and eight storage containers E1101 to E1108 which are installed at left and right sides of the cabinet E1100 on four levels, respectively.

Each of the storage containers E1101 to E1108 are removably installed to be slid to a front side in the cabinet E1100, i.e., an installation space in which each part of the main device E110 is installed.

Preferably, a locking means is installed at each of the storage containers E1101 to E1108, such that only the administrator having the access right slides and opens each storage container.

In particular, each of the storage containers E1101 to E1108 is manufactured to have a unit size, and thus to be selectively installed in a space provided at the cabinet E1100.

In the present invention, since the storage containers formed in different internal shapes according to the stored medicines are formed in the same unit size, the storage containers may be selectively installed and used in the cabinets of the main device and the sub device, and medicine storing efficiency may be enhanced.

Further, as illustrated in FIG. 203, each of the storage containers E1101 to E1108 includes a horizontal frame E164 and a vertical frame 165 which are arranged longitudinally and transversely to form a shelf structure for storing the plurality of medicines.

For example, as illustrated in FIG. 201, the display part E11, the input part E112, the communication module E116, and the control part E117 are provided at a second storage container E1102 from the right top of the cabinet E1100 to allow the administrator to easily use.

The first storage part E150 of the medicine storage part E114 is provided at both lower portions of the cabinet E1100, i.e., at third and fourth storage containers E1107 and E1108 from the left top and at a fourth storage container E1104 from the right top, and the second storage part E160 is provided at first and second storage containers E1101, E1102, E1105, and E1106 from the both tops of the cabinet E1100.

In particular, the second storage part E160 is installed at the first and second storage containers E1101, E1102, E1105, and E1106 from the both tops of the cabinet E1100 to be opposite to each other, and thus the plurality medicines may be efficiently stored.

Meanwhile, the main device E110 may further include a wrapper providing part E1110 which provides a wrapper packing the discharged medicines, a printing part E1120 which prints a notice indicating an administration method of the discharged medicines on a sticker, a collection container E1130 which collects erroneously discharged medicines, and a bar code recognition part E1140 which recognizes information of the collected medicine.

The wrapper providing part E1110 and the collection container E1130 are provided at a front surface of the second storage container E1106 from the left top of the cabinet E1100, and the printing part E1120 and the bar code recognition part E1140 are provided at a third storage container E1103 from the right top of the cabinet E1100.

As illustrated in FIG. 202, the first storage part E150 is formed in a drawer structure and removably installed in the cabinet E1100.

In the embodiment, for convenience for explanation, the first storage part E150 is exemplarily provided at the third storage container E1107 from the left top of the cabinet E1100. However, each storage container E1104, E1107, E1108 in which the first storage part E150 is provided has the same structure.

That is, the first storage part E150 includes a drawer E151 in which a medicine storage case E152 having a different shape according to the type of medicine is received, and a drawer installing part E153 in which the drawers E151 arranged on a plurality of levels are installed.

The drawer E151 is formed in a drawer shape which has a receiving space therein to receive the medicine storage case E152, and a sliding member E1511 is installed at both side surfaces of the drawer E151 so that the administrator slides forwardly the drawer E151 from an inner side of the drawer installing part E153 and withdraws the drawer E151.

That is, after the access right of the administrator is confirmed by the authenticating means E113, the administrator grasps and pulls a handle E1512 provided at a front surface of the drawer E151, and thus the drawer E151 is slid forwardly without a separate driving device.

The medicine storage case E152 has a plurality of cells which may store various kinds of tablet type medicines.

An upper surface of each cell is opened, and a door E1521 is provided at the opened upper surface of the cell.

Here, a size and a shape of each cell may be variously changed according to the tablet type medicines to be received.

A memory chip (not shown) which stores a serial number provided when being firstly manufactured and information of the medicine received in each cell is installed at each cell.

Here, the memory chip is preferably configured with a read-only-memory to prevent initially stored information from being deleted or changed.

The medicine storage case E152 includes a door opening/closing part (not shown) which is opens and closes the door E1521 according to a control signal transmitted from the control part E117.

The door opening/closing part may selectively release a coupling between a hooking portion formed at the door E1521 and a hooking member connected to a solenoid using the solenoid operated according to the control signal of the control part E117.

In particular, the door E1521 of each cell is opened only when all of the cells of the medicine storage case E152 are withdrawn to an outer side of the drawer installing part E153.

To this end, a withdrawal detecting part (not shown) which detects a withdrawing state of the drawer E151 is preferably installed at a rear end of the drawer E151 or a front surface of the drawer installing part E153.

A door detecting part (not shown) which detects whether the door E1521 is opened is installed at each cell of the medicine storage case E152, and a fixing means (not shown) which fixes the drawer E151 in a completely withdrawn state is installed at the front surface of the drawer installing part E153.

For example, the fixing means protrudes only when the drawer E151 is completely opened, and fixes the rear end of the drawer E151 to a front end of the drawer installing part E153.

That is, the control part E117 generates a control signal controlling an operation of the fixing means, such that the door E1521 of the cell provided at the medicine storage case E152 is opened when the drawer E151 is completely withdrawn from the drawer installing part E153, and the drawer E151 is inserted into the drawer installing part E153 only when the all of the doors E1521 are closed.

When the administrator having the authenticated access right withdraws tablets from the first storage part E150, the control part E117 generates a control signal so as to open the door E1521 of the cell storing the medicine to be withdrawn according to the prescription information of the prescription.

Therefore, the present invention may prevent a breakdown and a damage of the medicine storage case due to collision between the drawer installing part and the door provided at each cell of the medicine storage case, while the drawer is slid.

And in the present invention, when the administrator having the authenticated access right withdraws the drawer, the door of the cell storing the corresponding medicine is opened, and when the administrator withdraws the medicine and then closes all doors, the fixing means is released and thus the drawer may be inserted.

Eventually, in the present invention, only the medicines prescribed to the patient may be provided to the corresponding patient, and thus accidents due to administration of wrong medicine may be prevented.

A loading space in which a plurality of drawers, e.g., four drawers E151 are loaded is formed in the drawer installing part E153, and an opening is formed in the front surface of the drawer installing part E153 so that the each drawer E151 may be slid forwardly.

The drawer installing part E153 is configured with one storage container E1107 and thus may be forwardly slid from the inner side of the cabinet E1100.

Therefore, when a problem occurs in the drawer E151 or the medicine storage case E152, an administrator who is in charge of the breakdown and repair of the medicine storing and supplying device may slide the entire drawer installing part E153, and then may easily perform a checking and repairing operation without space restriction.

Also, the drawer installing part E153 has a locking means (not shown) which selectively locks and releases each drawer E151 loaded in the loading space.

Therefore, in the present invention, the administrator may discharge only the corresponding medicines included the prescription information of the prescription, and thus the accidents due to the administration of the wrong medicines may be prevented.

As illustrated in FIGS. 203 and 204, the second storage part E160 includes a plurality of medicine cartridges E161 storing injections and a cartridge installing part E162 in which the plurality of medicine cartridges E161 are installed on a plurality of levels to be parallel with each.

In the embodiment, the cartridge installing parts E162 are disposed in two rows at the storage containers E1101, E1102, E1105, and E1106 provided at the both tops of the cabinet E1100 to be opposite to each other, and installing spaces E1621 are formed at each cartridge installing part E162 on three levels-three for each level, and the medicine cartridge E161 is installed at each installing space E1621 of the cartridge installing part E162.

The medicine cartridge E161 is formed in a rectangular parallelepiped of which an upper portion is opened, and a cover E1611 is installed at an upper surface of the medicine cartridge E161.

Here, when all of the injections stored in the medicine cartridge E161 are discharged, and it is necessary to refill the injections, the cover E1611 coupled to the medicine refill device E140 is opened only when the administrator having the authorization is authenticated.

To this end, a locking means (not shown) which locks and releases the cover E1611 is provided at a rear side of the medicine cartridge E161. As illustrated in FIG. 205, a coupling hole E1612 in which a key member (not shown) provided at the medicine refill device E140 is coupled, when the medicine cartridge E161 is coupled to the medicine refill device E140, is formed in a rear surface of the locking means.

Also, a memory chip E1613 which stores a serial number of the medicine cartridge E161 and information of the medicine received in the medicine cartridge E161 is installed at a rear surface of the medicine cartridge E161, and a locking member E1614 which is coupled to the installing space E1621 of the cartridge installing part E162 is formed to protrude from a rear side thereof.

Like the memory chip installed at the medicine cartridge E161, the memory chip E1613 is preferably configured with a read-only-memory to prevent initially stored information from being deleted or changed.

A discharging port E1615 which discharges the stored medicine is formed in a lower surface of a front part of the medicine cartridge E161, and a discharging port opening/closing part E1616 which performs an opening/closing operation by an opening/closing driving part E1622 of the cartridge installing part E162 is installed at the discharging port E1615.

A discharging port opening/closing locking part E1 (not shown), which locks the discharging port opening/closing part E1616 and then releases the discharging port opening/closing part E1616 when being installed at the cartridge installing part E162 so that a locking release member E1627 installed at a front surface of the cartridge installing part E162 is inserted therein, is provided in the medicine cartridge E161.

To this end, an insertion hole E1619, in which the locking release member E1627 is inserted, is formed in the rear surface of the medicine cartridge E161.

Preferably, as illustrated in FIG. 6, a guide groove E1618 is formed at both side surfaces of a lower portion of the medicine cartridge E161 to be recessed inwardly, and a plurality of guide ribs E1626 which are inserted into the guide groove E1618 are formed at the cartridge installing part E162.

Referring to FIGS. 203 and 204 again, at the cartridge installing part E162, a memory recognition part E1623 is installed at a position corresponding to the memory chip E1613 of the medicine cartridge E161, and a coupling hole E1624 is formed at a position corresponding to the locking member E1614.

Also, a cartridge installation locking part (not shown) which releases the coupling of the locking member E1614 coupled through the coupling hole E1624 is installed at an inner side of the coupling hole E1624 of the cartridge installing part E162.

The opening/closing driving part E1622 of the cartridge installing part E162 is rotated by a driving force of a motor installed therein so as to open and close the discharging port opening/closing part E1616 of the medicine cartridge E161.

Meanwhile, a guide piece E1617 which guides the injection discharged from the medicine cartridge D161 to the medicine discharge part E115 is provided at an upper portion of a front surface of the medicine cartridge E161.

That is, in the present invention, the cartridge installing part is installed on multiple levels to install the plurality of medicine cartridges, and thus in order to prevent the injection formed of a glass container from being broken when the injection is discharged downwardly, the guide piece is formed to extend from an upper surface of the medicine cartridge and to be downwardly inclined toward the medicine discharge part.

Also, as illustrated in FIG. 203, an installation hole E1625 is formed in a front frame E1628 of the cartridge installing part E162, such that a removal guide piece E163 which is separately manufactured from the medicine cartridge E161 may be installed therein.

That is, in the present invention, the removal guide piece E163 is installed at the installation hole E1625 of the front frame E1628 located above the installation space E1621, in which the medicine cartridge E162 is not installed, among the plurality of installation spaces E1621 provided in the cartridge installing part E162, and thus the injection is safely delivered to the medicine discharge part E117.

In the present invention, since the guide piece is provided at the medicine cartridge, or the removal guide piece is installed at the cartridge installing part, the injection may be safely discharged to the medicine discharge part.

Meanwhile, the cartridge E161 provided at the second storage part E160 to store the injection may be provided to have a shape and/or a function the same as or similar to the ampoule type medicine dispensing container BOX3, other than the shape and/or the function described with reference to FIGS. 203 to 205.

Further, the second storage part E160 may have different kinds of cartridges which have shapes and/or functions the same as or similar to the packaging type medicine dispensing container BOX1, the blister-packed medicine dispensing container BOX2, and the pouch type medicine dispensing container BOX4, other than the cartridge E161 storing the injection.

Further, the cartridge installing part E162 may be provided to have a shape and/or a function the same as or similar to the cartridge D200 described with reference to FIG. 9 or the like, other than the shape and/or the function described with reference to FIGS. 203 to 205. The configuration of the medicine discharge part will be described in detail with reference to FIG. 206.

As illustrated in FIGS. 206 and 207, the medicine discharge part E115 includes a conveying part E170 which is moved up and down between the second storage parts E160 provided at both sides of the cabinet E1100 so as to convey the medicine discharged from the second storage parts E160 to a front side of the cabinet E1100, a gathering part E171 which gathers the medicines conveyed by the conveying part E170, a take-out container E172 which has a take-out shutter E1721 installed at one side thereof in contact with the gathering part E171 and which receives the medicines gathered at the gathering part E171 when the take-out shutter E1721 is opened and then delivers the medicines to the administrator, and a shutter opening/closing part E173 which opens and closes the take-out shutter E1721.

The conveying part E170 includes a conveyor belt E1701 which conveys the medicine discharged from the medicine cartridge E161 toward the front surface of the cabinet D1100, and an up and down moving part E1702 which moves up and down the conveyor belt E1701.

In particular, when the injection formed of the glass container is stored, a seat guide E1703 is installed at both sides of the conveyor belt E1701 to safely convey the injection discharged from the medicine cartridge E161 to the conveyor belt E1701 and to seat the injection on the conveyor belt E1701.

The seat guide E1703 is formed to be inclined and thus to extend to the guide piece E1617 provided at the medicine cartridge E161 or the removal guide piece E163 provided at the cartridge installing part E162.

Preferably, a buffer member (not shown) is provided on an upper surface of the seat guide E1703 to prevent the damage of the injection.

Also, a buffer member (not shown) may be formed on an outer surface of the conveyor belt E1701 in a silicon coating manner so as to minimize a shock when the injection is seated thereon and thus to prevent the damage or the breaking of the injection.

The gathering part E171 is formed in a hopper shape to gather the injections, and a bottom surface of the gather part E171 is formed to be inclined, such that the gathered injections are moved to the gathering container E172.

A rear surface of the gathering part E171 is formed to be opened and thus to receive the injection from the conveyor belt E1701, and one side surface of the gathering part E171, e.g., a right surface thereof in FIG. 207 is opened to transmit the injection gathered therein to the take-out container E172, and a transmitting shutter E1711 is installed at the opening right surface.

As illustrated in FIG. 5, the take-out shutter E1721 is installed at the take-out container E172.

A bottom surface of one side of the take-out container E172, to which the take-out shutter E1721 is installed to receive the injection from the gathering part E171, is formed to be inclined, such that the injection is moved to the one side and then taken out at once, and also a bottom buffer member E1722 may be attached to a lower surface of the other side thereof to prevent the damage and the breaking of the injection.

Since the bottom surface of the take-out container E172 is formed to extend at the same angle as the bottom surface of the gathering part E171, the present invention may safely receive the injection from the gathering part.

The take-out container E172 is installed to be forwardly slid to the front side, such that the administrator may easily take out the medicine.

Here, a locking means (not shown) may be installed at the take-out container E172 so that only the administrator having the authorized access right may take out the medicine.

The shutter opening/closing part E173 includes a motor E1731 and a rotating arm E1732 which is rotated by the driving force of the motor E1731 to open and close the transmitting shutter E1711.

Therefore, the transmitting shutter E1711 presses and opens the take-out shutter E1721, while performing an opening operation due to the rotating arm E1732.

As illustrated in FIGS. 201 and 208, the collection container E130 is hinged to a front surface of the second storage container E1102 from the left top of the cabinet E1100 to be rotated toward a front side thereof about a hinge shaft coupled to both sides of a lower end thereof.

The collection container E1130 is formed in an approximately rectangular parallelepiped shape of which a rear surface is opened, and a blocking door E1131 hinged to both inner surfaces of the collection container E1130 is installed at the opened rear surface thereof.

A collecting port E1132 which collects the medicine is formed at the blocking door E1131, and a rotational member E1133 which is hinged to both inner surfaces of the collection container E1130 so as to be rotated and thus to open the collecting port E1132 is installed at an inner side of the collecting port E1132.

The rotational member E1133 is formed in a pipe shape of which one side is opened, and the opening of the rotational member E1133 has the same size as the collecting port E1132.

When the medicine is put into the collecting port E1132, the rotational member E1133 is rotated so as to transmit the medicine to an inner side of the collection container E1130, and then returned to its original position so as to prevent the medicine put into the collection container E1130 from being discharged to an outer side through the collecting port E1132.

A first locking part which locks and releases the collection container E1130 to/from the storage container E1102 is installed at a front surface of the collection container E1130 (E1, referring to FIG. 201), and a second locking part E1134 which locks and releases the blocking door E1131 to/from the collection container E1130 is installed at the blocking door E1131.

In the present invention, since the first and second locking parts are installed at the front and rear sides of the collection container, only the administrator having the authorized access right is allowed to put the medicine into the collection container, and also to take out the medicines collected in the collection container by releasing the first and second locking parts and then opening the blocking door.

Further in the present invention, since the rotational member is installed at the inner side of the collecting port of the collection container, the collected medicine is prevented from being discharged to the outer side through the collecting port.

Next, an operation of the medicine storing and supplying device according to the preferred embodiment of the present invention will be described in detail.

Firstly, when power is supplied to the main device E1110 and the server device E120, the control part E117 of the main device E110 executes a program stored in the memory part E118 to display various menus on the display part E111 and also to display an image confirming the access right of the administrator.

The input part E112 receives the ID and the password from the administrator, or the confirming means E113 recognizes the biometric information such as the fingerprint and the iris and then transmits the information to the control part E117.

Then, the control part E117 transmits the input information through the communication module E116 to the hospital server E130, and then controls the display part E117 to receive the prescription information of the prescription which will is treated by the administrator and then to display the information on the screen, when the confirmation of the access right of the administrator is completed.

Therefore, when the administrator selects the prescription information to be treated and then inputs a preparing command through the input part E112, the control part E117 controls the operation of the medicine storage part E114 and the medicine discharge part E115 to discharge the corresponding medicine among the medicines stored in the medicine storage part E114 to the administrator.

Then, a medicine discharging operation of the medicine storing and supplying device according to the preferred embodiment of the present invention will be described in detail.

When the medicine stored in the medicine storage case E152 is discharged, the control part E117 controls the locking means installed at each drawer E151 of the drawer installing part E153 to be released, such that the drawer E151 storing the corresponding medicine, among the plurality of drawers E151 provided at the first storage part E150, is opened to the front side thereof.

When the locking means is released, the administrator may grasp the handle E1512 and may slide the corresponding drawer E151 toward the front side.

At this time, when a detecting signal indicating that the drawer E151 is completely withdrawn from the drawer installing part E153 is transmitted from the withdrawal detecting sensor installed at the rear end of the drawer E151 or the front part of the drawer installing part E153, the control part E117 controls the door opening/closing part to open the door E1521 of the corresponding cell storing the medicine to be discharged, among the cells provided at the medicine storage case E152.

Then, when all of the medicines is completely discharged, and a detecting signal indicating that all doors E1521 is closed is transmitted from the door detecting part, the control part E117 controls the fixing means to be released, such that the drawer E151 may be slid into the drawer installing part E153.

When the medicine stored in the medicine cartridge E161 is discharged, the control part E117 controls an operation of the up and down moving part E1702, such that the conveyor belt E1701 is moved to a position corresponding to the medicine cartridge E161 storing the medicine to be discharged.

Therefore, as illustrated in FIG. 209, the up and down moving part E1702 moves up the conveyor belt E1701 to a position corresponding to a lower end of the guide piece E1617 of the medicine cartridge E161 from which the medicine is discharged.

The medicine discharged from the medicine cartridge E161 is seated on the conveyor belt E1701 along the guide piece E1617 of the medicine cartridge E161 installed in the installation space E1621 or the removal guide piece E163 installed at the front frame E1628 of the cartridge installing part E162 when the medicine cartridge is not installed, and the seat guide E1703.

Then, the up and down moving part E1702 moves down the conveyor belt E1701 so that the transmitting shutter E1711 installed at one side of the gathering part E171 coupled to a front end of the conveyor belt E1701 is in contact with the take-out shutter E1721 of the take-out container E172.

At this time, the conveyor belt E1701 conveys the seated medicine to the gathering part E172, and the shutter opening/closing part E173 rotates the rotating arm E1732 using the driving force of the motor E1731 to open the transmitting shutter E1711.

Then, the take-out shutter E172 located at one side of the transmitting shutter E1711 is opened together by the opening operation of the transmitting shutter.

Therefore, the medicine gathered in the gathering part E171 is transmitted to the take-out container E172 along the inclined bottom surface.

Meanwhile, the present invention has a double structure having the gathering part which primarily gathers the medicine conveyed by the conveying part, and the take-out container which secondarily gathers the medicine discharged when the take-out shutter of the gathering part is opened.

Therefore, the present invention may safely discharge the medicine such as injection formed of the glass container, and may allow only the administrator having the just access right to take out the medicine, and thus may previously prevent the accidents due to erroneous administration to a wrong patient or a discharge and a loss of the medicine by the user who does not the just access right.

The medicine discharged through the above-mentioned processes is packed by the administrator using the wrapper provided from the wrapper providing part E1110, and the sticker on which the administration method is printed by the printing part E1120 is attached to the wrapper, and then the packed medicine is delivered and administered to the corresponding patient.

In this discharging process of the medicine, the control part E117 stores the information of the discharged medicine in the memory part E118 and simultaneously transmits the information to the hospital server E130 through the communication module E116, and thus the integrated management of the stock information of the medicine is enabled.

Meanwhile, when the administrator checks the taken-out medicine, and it is found that the medicine is erroneously discharged, the collection container E1130 collects the erroneously discharged medicine, and only the administrator having the just access right is allowed to discharge the medicine collected in the collection container E1130.

At this time, the bar code recognition part E1140 recognizes the information of the collected medicine and transmits the recognized information to the control part E117, and the control part E117 stores the information of the collected medicine and simultaneously stores the information to the hospital server E130 through the communication module E116.

Through the above-mentioned process, the present invention may store various types of medicines such as injection and tablets, may allow only the administrator having the just access right to take out the medicine, thereby allowing the safe administration, and may manage the stock of the medicine and the discharge information, thereby enhancing efficiency of the medicine management.

Hereinafter, the medicine cartridge E161 will be described in detail with reference to FIGS. 203 to 205.

FIG. 210 is another perspective view of the cartridge installing part and the medicine cartridge illustrated in FIG. 203, FIG. 211 is a perspective view illustrating a state in which the cover is opened from the medicine cartridge illustrated in FIG. 210 to show an internal configuration, FIG. 212 is a plane view illustrating a state in which the inclined member and the cover are removed in FIG. 211 to show the internal configuration, FIG. 213 is an operation state illustrating a state in which the medicine cartridge illustrated in FIG. 212 is installed at the cartridge installing part, FIG. 214 is an operation state illustrating an operation state of an opening/closing blocking part when the locking release part illustrated in FIG. 212 is coupled, and FIG. 215 is an enlarged perspective view of a main portion of the cartridge installing part illustrated in FIG. 210.

As illustrated in FIGS. 210 to 213, the medicine cartridge E161 includes a cartridge body E121 which is formed in the rectangular parallelepiped shape of which the upper portion is opened and in which the space storing the medicine is provided, the cover E1611 installed at the opened upper surface, and the discharging port opening/closing part E1616 which receives the driving force from the opening/closing driving part E1622 provided at the cartridge installing part E162 and opens and closes the discharging port E1615 formed at a lower surface of a front side of the cartridge body E121.

In FIG. 120, the discharging port E1615 which discharges the medicine is formed the lower surface of the front side of the cartridge body E121, and the guide groove E1618 in which the guide rib E1626 provided at the cartridge installing part E162 is formed at lower portions of the both side surface of the cartridge body E121 to extend long.

A hooking member E1221 is formed at a lower surface of the rear side of the cover E1611 to be engaged with a hooking portion provided at a cover locking part E1126 when the cover is closed.

The cover E1611 may be formed of a transparent material to easily check a state of the medicine stored therein. When the medicine to be stored is a specific medicine, the cover E161 may be formed of an obscured material to preclude the check of the medicine stored therein.

Particularly, in the present invention, the cover E1611 is opened only when being coupled to the medicine refill device (not shown) separately manufactured from the medicine supplying device.

Therefore, in the present invention, only the administrator having the confirmed access right is allowed to refill the medicine into the medicine cartridge using the medicine refill device, and thus the erroneous administration may be prevented.

Meanwhile, when the medicine, such as injection, which is formed in a cylindrical shape is stored, the medicine cartridge E161 further includes an inclined member E124 which is installed to be inclined toward the discharging port E1615 and thus to move the medicine stored therein toward the discharging port E1615, and a guide part E125 which fixes the medicine stored in the body E121 to prevent a movement thereof.

In FIG. 211, the inclined member E124 is formed to be inclined toward the discharging port E1615, such that the medicine stored in the cartridge body E121 and having the cylindrical shape may be naturally moved to the discharging port E1615.

A moving slit E1241 is formed in the upper surface of the inclined member E124 so that a first guide E1251 provided at the guide part E125 is coupled therein and moved therealong, and a moving groove 242 is provided at a rear end of the inclined member E124 so that a second guide E1252 provided at the guide part E125 is coupled therein and moved therealong.

The guide part E125 serves to prevent the damage or the breaking of the injection type medicine, while the medicine is refilled into the cartridge body E161 through the medicine refill device, and then installed at the body E121.

To this end, the guide part E125 includes a first guide E1251 which allows the medicine stored in the cartridge body E121 to be pushed toward the discharging port E1615 side, and a second guide E1252 which allows the medicine to be pushed toward one inner side surface of the cartridge body E121, e.g., an upper surface in FIG. 211.

The first guide E1251 is formed to be inclined toward an upper side of the discharging port E1615, and a lower portion of the first guide E1251 has an approximately "工"-shaped cross section to be coupled to the moving slit E1241 of the inclined member E124 and to be moved along the moving slit E1241.

The second guide E1252 is formed to have a width corresponding to a width of an internal space of the cartridge body E121, and a lower end of a rear side of the second guide E1252 has an approximately "⊏"-shaped cross section to to be moved along the moving groove E1242 of the inclined member E124.

A hooking member E1253 is installed at a rear end of the second guide E1252, so that the user may hook his/her finger and easily move it.

Therefore, in the present invention, the second guide is moved according to a height of the medicine stored in the medicine cartridge, such that the medicine is pushed toward one side, and thus the medicine is prevented from being damaged or broken, and also the medicines having various sizes may be safely stored.

As illustrated in FIGS. 212 and 213, the medicine cartridge E161 further includes the cover locking part E1126 which locks and releases the cover E1611, the memory chip E1127 which stores the serial number of the medicine cartridge E161 and the information of the medicine received in the medicine cartridge E161, the locking member E1614 which protrudes toward a rear side to be coupled with the cartridge installing part E162, and the opening/closing blocking part E126 which blocks the opening and closing operation of the discharging port opening/closing part E1616 according to the coupling of the locking release member E1627 provided at the cartridge installing part E162 through the rear surface of the cartridge body E121.

To this end, the installation space in which the cover locking part E126 and the memory chip E27 are installed is formed at the rear surface of the cartridge body E121, and also a rear cover E1213 which covers the installation space is coupled to the rear surface of the cartridge body E121.

As illustrated in FIG. 212, a coupling hole (not shown), in which the locking member E1614 protruding to a rear side and a key member of the medicine refill device separately manufacture from the medicine supplying device are coupled, is formed at the rear cover E1213.

Further, the insertion hole E1619, in which the locking release member E1627 is inserted when the cartridge body E121 is installed at the cartridge installing part E162, is formed at a rear end of the cartridge body E121.

Here, the insertion hole E1619 also serves as a guide which guides the locking release member E1627, such that the medicine cartridge E161 may be exactly installed to the cartridge installing part E162.

In FIGS. 212 and 213, the discharging port opening/closing part E1616 includes an opening/closing member E1232 which reciprocates forwardly and backwardly to open and close the discharging port E1615, and a protruding part E1231 in which a plurality of protrusions are formed at a lower surface of the opening/closing member E1232 to pass through the lower surface of the cartridge body E121, to protrude downwardly, and thus to be engaged with a gear member E1322 provided at the opening/closing driving part E1622 of the cartridge installing part E162.

An elastic member E1233 which provides a restoring force to the opening/closing member E1232 is provided between a rear end of one side of the opening/closing member E1232 and an inner surface of the rear side of the cartridge body E121.

One end of the elastic member E1233 is coupled to an outer circumferential surface of a protruding bar E1215 which is formed at an inner surface of the rear side of the cartridge body E121 to protrude.

Although not illustrated, the cover locking part E126 includes a lock member which is rotated in a state that the key member provided at the medicine refill device is coupled to a position corresponding to the coupling hole of the rear cover E1213, a moving member which is moved to one side by the rotation of the lock member, and a locking member which is coupled to an upper portion of the moving member and has a catching portion formed at an upper end of one side thereof to be engaged with the hooking member E1221 of the cover E1611.

The memory chip E127 is preferably configured with a read-only-memory to prevent initially stored information from being deleted or changed.

As illustrated in FIGS. 212 and 214, the opening/closing blocking part E129 includes a hinge rotating member E1291 which is hinged to the bottom surface of the cartridge body E121 and of which one end (hereinafter, called as "pressing end") is in contact with the locking release member E1627, and the other end (hereinafter, called as "engaging end") is engaged with a short step E1234 formed at a distal front end of one side of the opening/closing member E1232, a fixing member E1292 which is located between both ends of the hinge rotating member E1291 and fixed to the bottom surface of the cartridge body E121, and an elastic spring E1293 which is installed between the fixing member E1292 and the pressing end of the hinge rotating member E1291 in contact with the locking release member E1627.

That is, as illustrated in FIG. 214, when the medicine cartridge E161 is installed at the cartridge installing part E162, the locking release member E1627 is inserted through the insertion hole E1619 of the cartridge body E121 to press the pressing end of the hinge rotating member E1291.

Then, the hinge rotating member E1291 is rotated in an arrow direction illustrated in FIG. 124, and the engaging between the engaging end of the hinge rotating member E1291 and the short step E1234 of the opening/closing member E1232 is released.

Therefore, in the present invention, only when the medicine cartridge is installed at the cartridge installing part, the locking state of the discharging port opening/closing part is released using the locking release member, and the discharging port is opened and closed.

Further, in the present invention, when the medicine cartridge is separate from the cartridge installing part, the opening/closing member is fixed using the opening/closing blocking part, and thus the discharging port is always closed. Therefore, the erroneous discharge of the medicine due to vibration generated in a moving process may be previously prevented.

As illustrated in FIGS. 210 and 213, the cartridge installing part E162 includes the opening/closing driving part E1622 which drives the discharging port opening/closing part E1616 of the medicine cartridge E161, the locking release member E1627 which is inserted through the insertion hole E169 of the medicine cartridge E161, the memory recognition part E1623 which is installed at a position corresponding to the memory chip E127 of the medicine cartridge E161, and a locking part E135 which is engaged with and released from the locking member E1614 coupling through the coupling hole E1624 formed at a position corresponding to the locking member E1614.

As illustrated in FIG. 213, the opening/closing driving part E1622 includes the motor E1321 generating the driving force, and the gear member E1322 which is connected with a gear coupled to a rotating shaft of the motor E1321 through a belt to linearly reciprocate the protruding part E1231 of the discharging port opening/closing part E1616 using the driving force transmitted from the motor E1321.

Meanwhile, in the present invention, as described above, the cartridge installing part is installed on multiple levels to install the plurality of medicine cartridges, and thus in order to prevent the injection formed of a glass container from be broken when the injection is discharged downwardly, the guide piece is formed to extend from an upper surface of the medicine cartridge and to be downwardly inclined toward the medicine discharge part.

If the medicine cartridge E161 is not installed at part of the plurality of installation spaces E1621 provided at the cartridge installing part E162, the installation hole E1625 is formed in the lower surface of the front frame E1637 of the cartridge installing part E162 so as to install the removal guide pieces E163 separately manufactured from the medicine cartridge E161.

As illustrated in FIG. 215, a fixing rib E1361 is formed at both side end of the installation hole E1625, and a fixing groove E1362 is formed at a center of the fixing rib E1361.

The removal guide piece E163 is formed in a plate shape which is inclined approximately downwardly, and an installation plate E1151 having a shape corresponding to the installation hole E1625 is coupled to a rear surface of the removal guide piece E163.

An installation part E1152 which is in contact with both ends of the installation hole E1625 is formed at a lower surface of the installation plate E11511, and a protrusion E1153 inserted into the fixing groove E1362 formed at the fixing rib E1361 is formed at both side ends of the installation part E1152.

As described above, in the present invention, since the guide piece is provided at the medicine cartridge, or the removal guide piece is installed at the cartridge installing part, the medicine such as injection which is easily damaged may be safely discharged to the medicine discharge part.

A method of operating the medicine supplying device according to the preferred embodiment of the present will be described in detail.

Firstly, the medicine cartridge E161 is installed at the separately manufactured medicine refill device (not shown) to confirm the access right of the administrator, and the cover E1611 provided at an upper portion of the cartridge body E121 is opened to put the medicine into the cartridge body E121 and to store the medicine therein.

At this time, the key member (not shown) provided at the medicine refill device is rotated so that the lock member is rotated to be arranged long left and right, and the moving member and the locking member are horizontally moved to one side, and thus the locking member E1221 of the cover E1611 is separated from the catching portion formed at the upper end of one side of the locking member, and the cover E1611 is opened.

Then, the administrator may put the medicine into the cartridge body E121.

Meanwhile, when the medicine stored in the medicine cartridge E161, in order to prevent the injection from being damaged while the injection is moved from the medicine refill device to the medicine supplying device, the injection is pushed toward the discharging port E1615 side and the one inner side surface of the cartridge body E121 using the guide part E125.

That is, the first guide E1251 is moved along the moving slit E1241 formed at the inclined member E124 in a lengthwise direction of the body E121 to push the injection toward the discharging port E1615 side, and the second guide E1252 is moved along the moving groove 242 formed at the rear end of the inclined member E124 in a width direction of the body E121 to push the injection toward the one inner side surface of the cartridge body E121, e.g., the upper surface in FIG. 211.

Then, when the refill of the medicine is completed, and the cover E161 is closed by the administrator, the key member is rotated in an opposite direction to the rotational direction when the cover E121 is opened, and the lock member of the cover locking part E126 is rotated to be arranged long up and down.

As the locking member and the moving member is horizontally moved in the opposite direction to the moving direction when the cover E121 is opened, the catching portion of the locking member is engaged with the hooking member E1221 of the cover E121, and the cover E1611 is locked not to be opened.

Through this process, the medicine cartridge E161 storing the medicine is installed at the installation space E1621 provided at the cartridge installing part E162.

In the detailed description of the installation process of the medicine cartridge E161, the guide groove E1618 formed at both side surfaces of the medicine cartridge E161 positions the medicine cartridge to correspond to one pair of guide ribs E1626 provided at the cartridge installing part E162, and then moves the medicine cartridge toward the inner side of the installation space E1621 of the cartridge installation part E162.

Then, while the medicine cartridge E161 is moved, the guide groove E1618 is guided by the guide rib E1626, and thus the medicine cartridge E161 is stably installed at the cartridge installing part E162.

The locking release member E1627 provided at the cartridge installing part E162 is inserted through the insertion hole E1619 formed in the rear surface of the medicine cartridge E161.

The locking member E16114 formed at the rear surface of the medicine cartridge E161 passes through the coupling hole E1624 of the cartridge installing part E162 and is engaged with the locking part E135.

At this time, as illustrated in FIG. 24, while the engaging end of the hinge rotating member E1291 provided at the opening/closing blocking part E129 is engaged with the short step E1234 formed at the distal end of one side of the opening/closing member E1232, the locking release member E1627 presses the pressing end of the hinge rotating member E1291, and thus the hinge rotating member E1291 is rotated and released from the short step E1234 of the opening/closing member E1232.

Therefore, the opening/closing member E1232 may be reciprocated by the driving force transmitted from the opening/closing driving part E1622.

When the installation of the medicine cartridge E161 is completed, the memory recognition part E1623 of the cartridge installing part E162 and the memory chip E127 of the medicine cartridge E161 are electrically connected with each other, and the memory recognition part E1623 recognizes the serial number and the medicine information stored in the memory chip E127.

Therefore, the control part of the medicine supplying device controls the operation of the medicine cartridge E161, the cartridge installing part E162 and the medicine discharge part E170 to receive the serial number and the medicine information stored in the memory chip E127 from the memory recognition part E1623, to perform the stock management of the medicine, to confirm the access right of the administrator and then to discharge the medicine according to the prescription information assigned to the corresponding administrator.

In detailed description of the medicine discharging process, the opening/closing driving part E1622 is driven according to the control signal of the control part.

That is, when the motor E1321 of the opening/closing driving part E1622 is rotated in one direction, the gear member E1322 connected to the rotating shaft of the motor E1321 through the belt is also rotated, and thus the opening/closing member E1232 engaged with the protruding part E1231 formed at the lower side of the gear member E1322 is moved.

Thus, the medicine is discharged through the discharging port E1615 of the medicine cartridge E161 and the discharging space E1301, the medicine is naturally moved along the inclined surface of the inclined member E124 to the discharging port E1615 without the separate driving device.

Since the present invention does not need the separate driving device to move the medicine in the medicine cartridge, the manufacturing cost of the medicine cartridge may be reduced, and the workability may be also increased.

If all of the medicines are discharged, and the control signal for closing the discharging port E1615 is transmitted from the control part, the motor E1321 of the opening/closing driving part E1622 is rotated in the opposite direction to the rotating direction in the opening operation, and the opening/closing member E1232 engaged with the gear member E1322 is moved in the opposite direction to the moving direction in opening operation, and thus the discharging port E1615 is closed.

When a releasing command for releasing the medicine cartridge E161 is input by the administrator to refill the medicine, the hook member is rotated by the motor of the locking part E135, and the locking member E1614 is separated from the locking part E135.

And, if the medicine cartridge E161 is separated from the cartridge installing part E162, the hinge rotating member E1291 of the opening/closing blocking part E129 is rotated to its original position by the restoring force of the elastic spring E1293, as the locking release member E1627 is separated. And the engaging end of the hinge rotating member E1291 is engaged again with the short step E1234 formed at the distal end of one side of the opening/closing part E1616.

In the present invention, since the discharging port opening/closing part is fixed not to perform the opening/closing operation by the opening/closing blocking part, the erroneous discharge of the medicine in the moving process of the medicine cartridge may be previously prevented.

Therefore, the administrator slides the storage container, in which the corresponding medicine cartridge is installed, toward the front side, separates only the corresponding medicine cartridge, and refills the medicine using the medicine supplying device.

Through the above-mentioned process, the medicine cartridge storing the medicine such as injection may be easily installed and removed to/from the cartridge installing part, and thus the medicine may be stably supplied.

Hereinafter, a production management part and a hospital management part which may be further provided to the hospital server E130 or may be connected to the hospital server E130 will be described, and an operating method between the production management part and/or the hospital management part and the medicine dispensing system according to one embodiment of the present invention will be described in detail.

Further, the medicine supplying device described below is at least one of the medicine dispensing system 1, the main device E10 and the subs device E120 or the combination thereof. However, hereinafter, for convenience of explanation, the operation of the main device E110 described with reference to FIG. 199 will be exemplarily described.

FIG. 216 is a block diagram of the production management part according to one embodiment of the present invention, and FIG. 217 is a block diagram of the hospital management part according to one embodiment of the present invention. Hereinafter, for convenience of explanation, the medicine dispensing container BOX1, BOX2, BOX3, BOX4, the packed medicine dispensing container M4 and the medicine cartridge E161 or the like may be referred to as "medicine receiving container".

A medicine management system according to the preferred embodiment of the present invention includes a production management part E250 which produces a medicine receiving container, registers inherent identification information for each medicine receiving container to confirm a genuine product, a hospital management part E240 which communicated with the production management part to request a genuine product certification of the medicine receiving container and to transmit medicine discharge information to the production management part E250, a medicine supplying device E2100 in which the plurality of medicine receiving containers are installed to discharge the medicine stored in the medicine receiving container according to the prescription information transmitted from the hospital management part E240, and a medicine refill device E230 which opens a cover installed at the medicine receiving container to refill the medicine into the medicine receiving container and transmits information of the medicine refilled in the medicine receiving container to the hospital management part E240.

As illustrated in FIG. 216, the production management part E250 includes a production side information communication part E251 which receives medicine receiving container identification information registered to the medicine receiving container from the hospital management part E240, performs the genuine product certification of the medicine receiving container, and transmits the certification result, a production information management control part E252 which manages medicine receiving container identification information according to an order and a production of the medicine receiving container based on a result of communicating with the hospital management part E240 and the medicine supplying device E2100 using the production side information communication part E251, an identification information generation part E253 which generates the medicine receiving container identification information according to a control of the production information management control part E252, an identification information registration part E254 which registers the medicine receiving container identification information in a memory in the medicine receiving container, a production information storage part E255 which stores medicine receiving container identification information and history information according to the production of the medicine receiving container, a production information search part E256 which searches production information of the medicine receiving container using the medicine receiving container identification information, a genuine product certification part E257 which certifies the medicine receiving container as a genuine product according to a result of the search of the production information search part E256, and a medicine consumption analysis part E288 which analyzes a consumption state for each medicine using information related to medicine discharge of the medicine receiving container.

The production side information communication part E251 also performs a function of receiving the information related to the medicine discharge of the medicine receiving container from the hospital management part E240.

Here, the medicine receiving container identification information is inherent identification information which identifies each medicine receiving container, is configured with a hexadecimal number of 16 figures, generated from the identification information generation part E253, and stored and managed in the production information storage part E255.

The genuine product certification part E257 performs the genuine product certification of the medicine receiving container according to a request for the genuine product certification of the medicine receiving container transmitted from the hospital management part E240.

In the present invention, the genuine product certification of the corresponding medicine receiving container is performed using the medicine receiving container identification information and the history information which are provided at each medicine receiving container by a producer, and thus an unjustifiable use of the medicine receiving container may be prevented.

In the present invention, the kind and the consumption state of the medicine received in the medicine receiving container may be variously analyzed by hospitals, regional groups and lengths of time using the medicine consumption analysis part, may be reflected to the medicine production, and thus efficiency in the production and the stock management of the medicine may be enhanced.

As illustrated in FIG. 217, the hospital management part E240 includes a hospital side information communication part E241 which communicates with the production management part E250, a medicine information management control part E242 which confirms whether the medicine receiving container is a genuine product using the communication of the hospital side information communication part E241, and manages a discharge state of the medicine receiving container according to the information of the medicine stored in the medicine receiving container and the prescription information, an identification information recognition part E243 which recognizes the medicine receiving container identification information registered to the medicine receiving container, a medicine information storage part E244 which stores the medicine receiving container identification information and the information of the medicine stored in the medicine receiving container according to a control of the medicine information management control part E242, a medicine information input part E245 which inputs the information of the medicine put into the medicine receiving container, and a prescription information management part E246 which receives and manages the prescription information from a terminal of a medical team.

The hospital side information communication part E241 transmits the medicine receiving container identification information supplied to the hospital and the medicine discharge state information of the medicine receiving container to the production management part E250, and receives an identified result of the medicine receiving container from the production management part E250.

The information of the medicine may include a name of the medicine, a manufacturer, the number of the medicines, expiration date information, or the like.

Meanwhile, the medicine supplying device E2100 or the hospital management part E240 may further include a reader (not shown) which recognizes information of an identification means such as a radio frequency identification (hereinafter, called as 'RFID') which is attached to each kind of medicine supplied from the medicine storage part E214 of the medicine supplying device E2100 to the administrator.

That is, in the present invention, the identification means is attached to each kind of medicine, and the reader is installed at the medicine supplying device or the hospital management part, and the medicine discharged from the medicine supplying device may be precisely counted, and thus the stock of the medicine may be managed in real time.

Therefore, in the present invention, the medication accidents due to the loss or the erroneous discharge of the medicine may be previously prevented, and thus efficiency in the stock management of the medicine may be enhanced.

Next, a method of controlling the medicine management system according to the preferred embodiment of the present invention will be described in detail with reference to FIG. 218.

FIG. 218 is a flow chart explaining the method of controlling each process of the medicine management system according to one embodiment of the present invention.

Firstly, the production management part E210 produces the medicine receiving container in a process E2S10.

At this time, the production side information communication part E251 communicates with the hospital side information communication part E241 of the hospital management part E240, receives the order information of the medicine receiving container (E2S11), and the identification information generation part E253 generates the medicine receiving container identification information corresponding to the number of ordered medicine receiving containers (E2S 12).

Then, the identification information registration part E254 registers the medicine receiving container identification information generated from the identification information generation part E253 in the memory chip built in the medicine receiving container (E2S13), and the production information storage part E255 stores the medicine receiving container identification information and the production history information (E2S14).

If the medicine receiving container of which the medicine receiving container identification information is registered through these procedures is delivered, the hospital management part E240 performs a process of identifying whether the medicine receiving container is a genuine product.

That is, the identification information recognition part E243 recognizes the medicine receiving container identification information registered in the memory chip of the medicine receiving container (E2S15), and the hospital side information communication part E241 transmits the medicine receiving container identification information recognized from the identification information recognition part E243 to the production management part E250, and requests the genuine product certification (E2S16).

Then, the production information search part E256 searches the medicine receiving container identification information stored in the production information storage part E255 (E2S17), and the genuine product certification part E257 compares the searched medicine receiving container identification information with the received medicine receiving container identification information, identifies whether the medicine receiving container is a genuine product through the registered history information and the compared result, and the production side information communication part E251 transmits the identified result to the hospital management part E240 (E2S18).

And the hospital side information communication part E241 receives the identified result, and transmits it to the medicine information management control part E242.

If it is failed to obtain the genuine product certification in the process E2S18, the medicine information management control part E242 informs the administration about prohibition of use of the corresponding medicine receiving container.

On the contrary, if the genuine product certification of the medicine receiving container is completed (E2S19), the medicine refill device E230 identifies the access right of the administrator to put the medicine into the medicine receiving container, and then releases the cover locking part of the medicine receiving container in order to open the cover of the medicine receiving container (E2S20).

Therefore, the medicine receiving container receives and stores the medicine therein.

At this time, the medicine information input part E245 receives the information of the medicine stored in the medicine receiving container from the administrator, and transmits the information to the medicine information management control part E242 (E2S21), and the medicine information management control part E242 controls the medicine information storage part E244 to store the input information of the medicine and the medicine receiving container identification information (E2S22).

The medicine receiving container receiving the medicine through these procedures is installed at the cartridge installing part E162 installed at the medicine storage part E114 (E2S23).

At this time, the memory recognition part of the cartridge installing part E162 recognizes the information stored in the memory chip of the medicine receiving container (E2S24), and the communication module (E116) of the medicine supplying device E2100 transmits a position of the medicine receiving container to the hospital management part E240 using the ID according to the information recognized from the memory recognition part and an installation position of the cartridge installing part E162 (E2S25).

And, the communication module E16 receives the identified result of the access right of the administrator and the prescription information from the hospital management part E240 (E2S26). The control part E117 controls the driving of the medicine receiving container and the cartridge installing part E162 to discharge the medicine stored in the medicine receiving container according to the prescription information (E2S27).

At this time, the reader provided at the medicine supplying device E2100 or the hospital management part E240 recognizes the identification information of the identification means attached to each kind of discharged medicine, and precisely counts the name and the number of the discharged medicine (E2S28).

Then, the control part E217 transmits the discharge state information of the medicine stored in the medicine receiving container to the hospital management part E240 through the communication module E216, and the medicine information management control part E242 of the hospital management part E240 transmits the discharge state information of the medicine stored in the medicine receiving container to the production management part E250 through the hospital side information communication part E241 (E2S29).

And the medicine consumption analysis part E258 of the production management part E250 may variously analyze the medicine consumption information by hospitals, regional groups and lengths of time (E2530).

Therefore, in the present invention, the analyzed information of the medicine consumption may be reflected to the medicine production operation, and thus efficiency in the production and the stock management of the medicine may be enhanced.

Through above-mentioned procedures, the present invention stores the medicine, provides the identification to the medicine receiving container from which the medicine is discharged according to the prescription information, and thus easily manages the medicine and the medicine receiving container, and also prevents an unjustifiable use of the medicine receiving container and the medicine.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A medicine dispensing device comprising:
    a medicine storage part configured to store a medicine;
    wherein the medicine storage part includes a plurality of medicine dispensing containers;
    a medicine discharge part configured to discharge the medicine stored in the medicine storage part;
    a communication module configured to communicate with a hospital server; and
    a control part configured to:
        select at least one of the medicine dispensing containers based on prescription information of a prescription received from the hospital server through the communication module,
        determine, based on at least one of a volume size information of the medicine, a weight information of the medicine, a type information of the medicine, a position information of the medicine dispensing container, a route to the medicine dispensing container which has a minimized length and a minimized time to dispense the medicine, at least one of the medicine dispensing containers to be dispensed prior to other medicine dispensing containers of the at least one selected medicine dispensing container, wherein the medicine discharge part comprises a conveying part which is moved up and down and wherein the conveying part is configured to receive the medicine dispensed from the medicine dispensing container and convey the medicine dispensed to a predetermined discharge position of the medicine dispensing device, and
        control an operation of the medicine storage part, the medicine discharge part and the conveying part to discharge the medicine of the determined medicine dispensing container.

2. The medicine dispensing device of claim 1, further comprising an identification means configured to verify an access authorization of an administrator and to allow the administrator having the verified access authorization to access the prescription information of the prescription to discharge the medicine stored.

3. The medicine dispensing device of claim 2, further comprising:
    a display part configured to display an operation state and various menus for performing a medicine storing operation and a supplying operation,
    an input part configured to input a command to select a menu displayed on the display part and to perform a desired operation, and
    a memory part configured to discharge information and store stock information of the medicine stored in the medicine storage part, and access information of the administrator.

4. The medicine dispensing device of claim 3, wherein the medicine dispensing device is communicably connected with one or more sub devices having the medicine storage part therein.

5. The medicine dispensing device of claim 1, wherein each medicine dispensing container is removably installed to be slid forwardly from a cabinet forming an exterior of the medicine dispensing device.

6. The medicine dispensing device of claim 1, further comprising
    a wrapper providing part configured to provide a wrapper packing the discharged medicine,
    a printing part configured to print a notice informing an administration method of the discharged medicine on a sticker,
    a collection container configured to collect erroneously discharged medicine, and
    a bar code recognition part configured to recognize information of the collected medicine.

7. The medicine dispensing device of claim 1, wherein the medicine storage part comprises a medicine cartridge formed in a box shape of which an upper portion is opened to store the medicine therein and having a discharging port through which the medicine is discharged, and a cartridge installing part having a plurality of installation spaces in which the medicine cartridge is installed, and the medicine cartridge is removably installed in an installation space of the cartridge installing part to be stacked, and comprises a discharging portion opening/closing part provided at a lower side thereof to open and close the discharging port.

8. The medicine dispensing device of claim 7, wherein the medicine cartridge comprises a cover installed at an opened upper surface to perform an opening/closing operation, a locking means installed at a rear surface of the medicine cartridge to lock and release the cover, and a discharging port opening/closing locking part configured to lock the discharging port opening/closing part and to release the discharging port opening/closing part when being installed at the cartridge installing part so that a locking release member installed at a front surface of the cartridge installing part is inserted therein, and an insertion hole in which the locking release member is inserted is formed in the rear surface of the medicine cartridge.

9. The medicine dispensing device of claim 8, wherein the medicine cartridge further comprises a locking member configured to pass through a coupling hole formed in the cartridge installing part and to be coupled to a cartridge installation locking part provided at the cartridge installing part.

10. The medicine dispensing device of claim 8, further comprising a medicine refill device separately manufactured from the medicine dispensing device, and configured to open the cover of the medicine cartridge after the valid access authorization of the administrator is verified, when it is necessary to refill the medicine into the medicine cartridge, wherein the locking means performs a locking release operation only when installed in the medicine refill device.

11. The medicine dispensing device of claim 7, wherein the medicine cartridge has a memory chip configured to store a serial number assigned when the medicine cartridge was first manufactured and information of the stored medicine, and the cartridge installing part has a memory recognition part installed at a position corresponding to the memory chip of the medicine cartridge, and the memory chip has a read-only-memory to prevent initially stored information from being deleted or changed.

12. The medicine dispensing device of claim 1, wherein the medicine discharge part comprises a gathering part configured to primarily gather the medicine conveyed by the conveying part, a take-out container configured to deliver the medicine delivered from the gathering part to an administrator, and a shutter opening/closing part configured to open and close a shutter, wherein the conveying part comprises a conveyor belt configured to convey the medicine discharged from a medicine cartridge of the medicine storage part toward the gathering part, and an up and down moving part which moves up and down the conveyor belt, and wherein a seat guide is installed at both sides of the conveyor belt to guide the medicine discharged from the medicine cartridge and to seat the medicine on the conveyor belt.

13. The medicine dispensing device of claim 12, wherein a buffer member is provided at at least one of an upper surface of the seat guide and an upper surface of the conveyor belt.

14. The medicine dispensing device of claim 12, wherein an opening is formed at one side surface of the gathering part to receive the medicine from the conveyor belt and to deliver the medicine into the take-out container, and a transmitting shutter configured to perform an opening/closing operation by the shutter opening/closing part is installed at the opened one side surface of the gathering part, and a take-out shutter configured to perform an opening/closing operation together with the opening/closing operation of the transmitting shutter is installed at one side of the take-out container.

15. The medicine dispensing device of claim 1, wherein the medicine storage part comprises a drawer in which medicine storage cases having different shapes according to types of the medicine are received, and a drawer installing part having a loading space in which the drawers are arranged on a plurality of levels to be stacked.

16. The medicine dispensing device of claim 15, wherein a plurality of cells formed according to a shape of the received medicine are provided at the medicine storage case, and the plurality of cells comprise a door installed at an upper surface of each cell to selectively open and close the upper surface, a door detecting part configured to detect whether the door is opened, a door opening/closing part installed at each cell to open and close the door, and a memory chip configured to store a serial number assigned to each cell when the cell was first manufactured and information of the medicine stored therein, the memory chip has a read-only-memory to prevent initially stored information from being deleted or changed.

17. The medicine dispensing device of claim 16, wherein a withdrawal detecting part configured to detect a withdrawing state of the drawer is installed at a rear end of the drawer or a front surface of the drawer installing part, and a fixing means configured to fix the drawer in a withdrawn state is installed at the front surface of the drawer installing part, and the control part controls the door opening/closing part to open the door of the cell storing the medicine to be discharged, among the cells provided at the medicine storage case according to a detecting signal of the withdrawal detecting part, and controls the fixing means so that the drawer is slid into the drawer installing part, only when all of the doors are closed.

18. The medicine dispensing device of claim 16, further comprising a medicine refill device separately manufactured from the medicine dispensing device, and configured to open a door provided at each cell of the medicine storage case after the valid access authorization of the administrator is verified, when it is necessary to refill the medicine into the medicine cartridge.

* * * * *